United States Patent
Mills et al.

(10) Patent No.: US 12,098,144 B2
(45) Date of Patent: Sep. 24, 2024

(54) PIPERAZINE INDAZOLE GLUCOCORTICOID RECEPTOR ANTAGONISTS

(71) Applicant: Corcept Therapeutics Incorporated, Menlo Park, CA (US)

(72) Inventors: Mark Mills, Nottingham (GB); Andrew William Phillips, Nottingham (GB); Bohdan Waszkowycz, Macclesfield (GB); Hazel Joan Hunt, West Sussex (GB); Angus Morrison, Scotland (GB); Angelo Pugliese, Scotland (GB); Jonathan Gillespie, Scotland (GB); Euan Fordyce, Scotland (GB)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

(21) Appl. No.: 18/068,902

(22) Filed: Dec. 20, 2022

(65) Prior Publication Data

US 2023/0192666 A1   Jun. 22, 2023

Related U.S. Application Data

(60) Provisional application No. 63/368,413, filed on Jul. 14, 2022, provisional application No. 63/292,104, filed on Dec. 21, 2021.

(51) Int. Cl.
| | | |
|---|---|---|
| C07D 403/14 | (2006.01) | |
| A61P 43/00 | (2006.01) | |
| C07D 401/14 | (2006.01) | |
| C07D 403/04 | (2006.01) | |
| C07D 405/14 | (2006.01) | |
| C07D 413/14 | (2006.01) | |
| C07D 417/14 | (2006.01) | |

(52) U.S. Cl.
CPC .......... *C07D 403/14* (2013.01); *A61P 43/00* (2018.01); *C07D 401/14* (2013.01); *C07D 403/04* (2013.01); *C07D 405/14* (2013.01); *C07D 413/14* (2013.01); *C07D 417/14* (2013.01)

(58) Field of Classification Search
CPC .. C07D 403/14; C07D 401/14; C07D 403/04; C07D 405/14; C07D 413/14; C07D 417/14; C07D 471/04; C07D 487/04; C07D 519/00; A61P 43/00
See application file for complete search history.

(56) References Cited

U.S. PATENT DOCUMENTS

| | | | |
|---|---|---|---|
| 7,238,696 B2 | 7/2007 | Bernotas | |
| 7,678,813 B2 | 3/2010 | Clark et al. | |
| 7,928,237 B2 | 4/2011 | Clark et al. | |
| 8,324,203 B2 | 12/2012 | Clark et al. | |
| 8,557,839 B2 | 10/2013 | Williams et al. | |
| 8,598,154 B2 | 12/2013 | Clark et al. | |
| 8,658,637 B2 | 2/2014 | Kuzmich | |
| 8,859,774 B2 | 10/2014 | Hunt et al. | |
| 9,273,047 B2 | 3/2016 | Hunt et al. | |
| 9,707,223 B2 | 7/2017 | Hunt et al. | |
| 9,956,216 B2 | 5/2018 | Hunt et al. | |
| 10,047,082 B2 | 8/2018 | Hunt et al. | |
| 10,323,034 B2 | 6/2019 | Hunt et al. | |
| 10,456,392 B2 | 10/2019 | Hunt et al. | |
| 10,464,927 B2 | 11/2019 | Zheng | |
| 10,787,449 B2 | 9/2020 | Hunt et al. | |
| 10,793,576 B2 | 10/2020 | Li | |
| 10,973,813 B2 | 4/2021 | Hunt et al. | |
| 11,370,789 B2 | 6/2022 | Hunt et al. | |
| 11,787,780 B2 * | 10/2023 | Hunt ................... | C07D 401/14 514/252.06 |
| 2004/0138286 A1 | 7/2004 | Imazaki et al. | |
| 2007/0142438 A1 | 6/2007 | Arista | |
| 2012/0165320 A1 | 6/2012 | Jain | |
| 2015/0291604 A1 | 10/2015 | Chen | |
| 2018/0093991 A1 | 4/2018 | Thompson et al. | |
| 2018/0228776 A1 | 8/2018 | Saitoh et al. | |
| 2019/0016721 A1 | 1/2019 | Chen et al. | |
| 2019/0185470 A1 | 6/2019 | Jakob et al. | |
| 2021/0169872 A1 | 6/2021 | Hunt et al. | |
| 2021/0369701 A1 | 12/2021 | Hunt et al. | |
| 2023/0032612 A1 | 2/2023 | Hunt et al. | |

FOREIGN PATENT DOCUMENTS

| | | |
|---|---|---|
| WO | 2009115427 A1 | 9/2009 |
| WO | 2019121611 | 6/2019 |
| WO | 2020254552 A2 | 12/2020 |
| WO | 2021262587 | 12/2021 |
| WO | 2022072512 | 4/2022 |
| WO | 2023122594 | 6/2023 |

OTHER PUBLICATIONS

Zhang et al., "Recent Advances in Indazole-Containing Derivatives: Synthesis and Biological Perspectives", Molecules 2018, 23(11):2783.
Clark et al., "Glucocorticoid Receptor Antagonists", Curr Top Med Chem 2008; 8(9), 813-838.
International Search Report and Written Opinion for PCT/US2022/082027, mailed Apr. 17, 2023, 16 pages.
International Search Report and Written Opinion for PCT/US2022/082034, mailed Apr. 26, 2023, 12 pages.

(Continued)

*Primary Examiner* — Juliet C Switzer
*Assistant Examiner* — Dawanna Shar-Day White
(74) *Attorney, Agent, or Firm* — Mintz, Levin, Cohn, Ferris, Glovsky and Popeo, P.C.

(57) ABSTRACT

Provided are piperazine substituted fused azadecalin compounds of Formula J, I, Ia, Ib, Ib-1, Ib-2, Ic and Id for use in pharmaceutical formulations, and for modulating glucocorticoid receptors.

28 Claims, No Drawings

(56) References Cited

OTHER PUBLICATIONS

Clark et al., "1H-Pyrazolo[3,4-g]hexahydro-isoquinolines as selective glucocorticoid receptor antagonists with high functional activity", Bioorg Med Chem Lett 2008, 18(4), pp. 1312-1317.

Clark et al., "2-Benzenesulfonyl-8a-benzyl-hexahydro-2H-isoquinolin-6-ones as selective glucocorticoid receptor antagonists", Bioorg Med Chem Lett 2007, 17(20), pp. 5704-5708.

Hunt et al., "1H-Pyrazolo[3,4-g]hexahydro-isoquinolines as potent GR antagonists with reduced hERG inhibition and an improved pharmacokinetic profile", Bioorg Med Chem Lett 2015, 25(24), pp. 5720-5725.

Hunt et al., "Identification of the Clinical Candidate (R)-(1-(4-Fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor (GR) Antagonist", J Med Chem 2017, 60(8), pp. 3405-3421.

International Search Report and Written Opinion for PCT/US2021/038218, mailed Oct. 12, 2021, 10 pages.

* cited by examiner

PIPERAZINE INDAZOLE GLUCOCORTICOID RECEPTOR ANTAGONISTS

CROSS-REFERENCES TO RELATED APPLICATIONS

This application claims priority to U.S. Provisional Application Nos. 63/368,413, filed Jul. 14, 2022, and 63/292,104, filed Dec. 21, 2021, each of which is incorporated herein in its entirety.

BACKGROUND OF THE INVENTION

In most species, including man, the physiological glucocorticoid is cortisol (hydrocortisone). In rodents, the physiological glucocorticoid is corticosterone. Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these residues include the ligand binding domain, GR-beta is unable to bind the natural ligand, and is constitutively localized in the nucleus.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

Cortisol (and corticosterone) also bind to the mineralocorticoid receptor, MR. Cortisol has higher affinity for MR than it does for GR, and MR is usually considered to be fully occupied under normal physiological conditions. Under conditions of stress, cortisol concentrations are increased and GR becomes occupied. MR also binds to the mineralocorticoid aldosterone, and aldosterone and cortisol have similar affinity for MR. However, glucocorticoids circulate at roughly 100 times the level of mineralocorticoids. An enzyme (11-β hydroxsteroid dehydrogenase 1), which deactivates cortisol (and corticosterone) exists in mineralocorticoid target tissues to prevent overstimulation by glucocorticoids.

When administered to subjects in need thereof, steroids can provide both intended therapeutic effects as well as negative side effects. What is needed in the art are new compositions and methods for selectively modulating GR. Surprisingly, the present invention meets these and other needs.

BRIEF SUMMARY OF THE INVENTION

In one embodiment, the present invention provides a compound of Formula J:

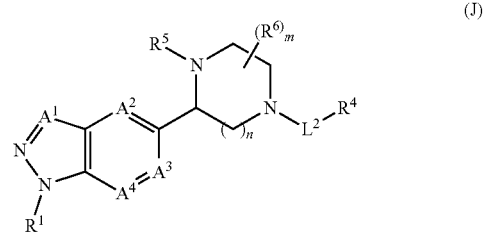

(J)

or a pharmaceutically acceptable salt thereof, wherein $R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;

each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =$CR^2$— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

$L^2$ is —C(O)—, —C(O)O—, —C(O)N($R^3$)—, —S(O)$_2$— or —S(O)$_2$N($R^3$)—;

$R^3$ is hydrogen, or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein the cycloalkyl, heterocycloalkyl, aryl and heteroaryl are each independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2$$R^{4b}$, —S(O)$_2$N($R^{4b}$)($R^{4c}$), —N($R^{4b}$)S(O)$_2$$R^{4c}$, $C_{3-8}$ cycloalkyl, $C_{1-6}$ alkyl-$C_{3-8}$ cycloalkyl, heterocycloalkyl, $C_{1-6}$alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

$R^5$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{1-6}$ alkyl-$OR^{5a}$, —$C(O)R^{5a}$, $C_{1-6}$ alkyl-$C(O)R^{5a}$, —$C(O)OR^{5a}$, —$C(O)N(R^{5a})(R^{5b})$, —$S(O)_2R^{5a}$, —$S(O)_2N(R^{5a})(R^{5b})$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —OH, —$C(O)R^{5c1}$, —$C(O)OR^{5c1}$, —$OC(O)R^{5c1}$, —$OC(O)OR^{5c1}$, —$C(O)N(R^{5c1})(R^{5c2})$, —$N(R^{5c1})C(O)R^{5c2}$, —$OC(O)N(R^{5c1})(R^{5c2})$, —$N(R^{5c1})C(O)OR^{5c2}$, —$S(O)_2R^{5c1}$, —$S(O)_2N(R^{5c1})(R^{5c2})$, —$N(R^{5c1})S(O)_2R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently hydrogen, $C_{1-6}$ alkyl, halogen, $C_{1-6}$ haloalkyl, or oxo;

subscript m is 0, 1, 2, 3, 4, or 5; and subscript n is 1 or 2.

In another embodiment, the present invention provides a compound of Formula I:

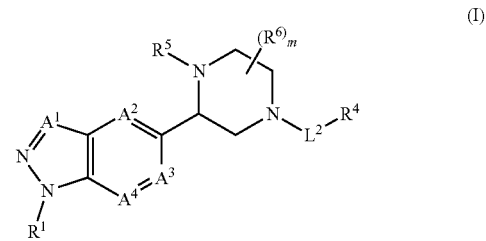

(I)

or a pharmaceutically acceptable salt thereof, wherein $R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;

each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —$C(O)N(R^{1b})(R^{1c})$, $C_{3-10}$ cycloalkyl, or heterocycloalkyl having 3 to 12 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR²— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

$L^2$ is —C(O)—, —C(O)O—, —C(O)N(R³)—, —S(O)₂— or —S(O)₂N(R³)—;

$R^3$ is hydrogen, or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and
wherein the cycloalkyl, heterocycloalkyl, aryl and heteroaryl are each independently substituted with 0 to 5 $R^{4a}$ groups;
alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;
each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2R^{4b}$, —S(O)$_2$N($R^{4b}$)($R^{4c}$), —N($R^{4b}$)S(O)$_2R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;
each $R^{4b}$ and $R^{4c}$ is hydrogen or $C_{1-6}$ alkyl;
$R^5$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{1-6}$ alkyl-O$R^{5a}$, —C(O)$R^{5a}$, $C_{1-6}$ alkyl-C(O)$R^{5a}$, —C(O)O$R^{5a}$, —C(O)N($R^{5a}$)($R^{5b}$), —S(O)$_2R^{5a}$, —S(O)$_2$N($R^{5a}$)($R^{5b}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl,
wherein each heterocycloalkyl independently has 3 to 12 ring members and 1 to 3 heteroatoms each independently N, O or S,
wherein each heteroaryl independently has 5 to 10 ring members and 1 to 4 heteroatoms each independently N, O or S, and
wherein each cycloalkyl, heterocycloalkyl, aryl and heteroaryl is independently substituted with 0 to 4 $R^{5c}$ groups;
each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;
alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)$_2R^{5c1}$, —S(O)$_2$N($R^{5c1}$)($R^{5c2}$), —N($R^{5c1}$)S(O)$_2R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;
each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;
alternatively, $R^{5c1}$ and $R^{5c2}$ are combined with the atoms to which they are attached to form a heterocycloalkyl having 3 to 12 ring members and 1 to 3 heteroatoms each independently N, O or S, wherein the heterocycloalkyl is substituted with 0, 1 or 2 $C_{1-6}$ alkyl groups;
each $R^{5d}$ is independently $C_{1-6}$ alkyl or halogen;
each $R^6$ is independently hydrogen, $C_{1-6}$ alkyl, halogen, $C_{1-6}$ haloalkyl, or oxo; and
subscript m is 0, 1, 2, 3, 4, or 5.
In another embodiment, the present invention provides a compound of Formula I:

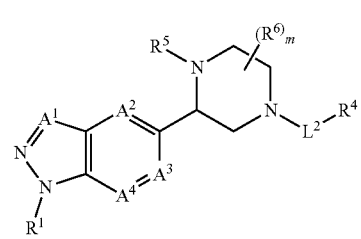

(I)

or a pharmaceutically acceptable salt thereof, wherein
$R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;
each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;
each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR²— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

$L^2$ is —C(O)—, —C(O)O—, —C(O)N($R^3$)—, —S(O)$_2$— or —S(O)$_2$N($R^3$)—;

$R^3$ is hydrogen, or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein the cycloalkyl, heterocycloalkyl, aryl and heteroaryl are each independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2$$R^{4b}$, —S(O)$_2$N($R^{4b}$)($R^{4c}$), —N($R^{4b}$)S(O)$_2$$R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

$R^5$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{1-6}$ alkyl-O$R^{5a}$, —C(O)$R^{5a}$, —C(O)O$R^{5a}$, —C(O)N($R^{5a}$)($R^{5b}$), —S(O)$_2$$R^{5a}$, —S(O)$_2$N($R^{5a}$)($R^{5b}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)$_2$$R^{5c1}$, —S(O)$_2$N($R^{5c1}$)($R^{5c2}$), —N($R^{5c1}$)S(O)$_2$$R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently hydrogen, $C_{1-6}$ alkyl, halogen, $C_{1-6}$ haloalkyl, or oxo; and subscript m is 0, 1, 2, 3, 4, or 5.

In another embodiment, the present invention provides a pharmaceutical composition comprising a compound of the present invention and a pharmaceutically acceptable excipient.

In another embodiment, the present invention provides a method of treating a disorder or condition through modulating a glucocorticoid receptor, the method comprising administering to a subject in need of such treatment, a therapeutically effective amount of a compound or a pharmaceutical composition of the present invention, thereby treating the disorder or condition.

In another embodiment, the present invention provides a method of treating a disorder or condition through antagonizing a glucocorticoid receptor, the method comprising administering to a subject in need of such treatment, an effective amount of the compound or a pharmaceutical composition of the present invention.

In another embodiment, the present invention provides a compound or pharmaceutical composition for use in a method of treating a disorder or condition through modulating a glucocorticoid receptor.

In another embodiment, the present invention provides a compound or pharmaceutical composition for use in a method of treating a disorder or condition through antagonizing the glucocorticoid receptor.

In another embodiment, the present invention provides use of a compound or pharmaceutical composition of the present invention in the manufacture of a medicament for treating a disorder or condition through modulating a glucocorticoid receptor.

In another embodiment, the present invention provides a use of a compound or pharmaceutical composition of the present invention in the manufacture of a medicament for treating a disorder or condition through antagonizing a glucocorticoid receptor.

DETAILED DESCRIPTION OF THE INVENTION

I. General

The present invention provides compounds of Formula J, I, Ia, Ib, Ib-1, Ib-2, Ic or Id capable of modulating and/or antagonizing a glucocorticoid receptor, and thereby providing beneficial therapeutic effects. The present invention also provides methods of treating disorders and conditions by modulating a glucocorticoid receptor or by antagonizing a glucocorticoid receptor. The present invention also provides use of a compound of the present invention in the manufacture of a medicament for treating a disorder or condition through modulating a glucocorticoid receptor, agonizing a glucocorticoid receptor or antagonizing a glucocorticoid receptor.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated (i.e., $C_{1-6}$ means one to six carbons), and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$, where n is 1, 2, 3, 4, 5 or 6. Representative $C_{1-4}$ alkylene groups include, but are not limited to, methylene, ethylene, propylene, isopropylene, butylene, isobutylene, and sec-butylene.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Deuteroalkyl" refers to an alkyl group, as defined above, where at least one of the hydrogen atoms is replaced with a deuterium. As for the alkyl group, deuteroalkyl groups can have any suitable number of carbon atoms, such as $C_{1-6}$. Exemplary $C_{1-4}$ deuteroalkyl groups include, but are not limited to, $-CH_2D$, $-CHD_2$, $-CD_3$, $-CH_2CH_2D$, $-CH_2CHD_2$, $-CH_2CD_3$, and the like.

"Alkoxy" refers to an alkyl group having an oxygen atom that connects the alkyl group to the point of attachment: alkyl-O—. As for alkyl groups, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_{1-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The alkoxy component is as defined above. Examples of the alkyl-alkoxy group include, but are not limited to, 2-ethoxy-ethyl and methoxymethyl.

"Hydroxyalkyl" or "alkylhydroxy" refers to an alkyl group, as defined above, where at least one of the hydrogen atoms is replaced with a hydroxy group. As for the alkyl group, hydroxyalkyl or alkylhydroxy groups can have any suitable number of carbon atoms, such as $C_{1-6}$. Exemplary $C_{1-4}$ hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), 1,2-dihydroxyethyl, and the like.

"Halogen" refers to fluorine, chlorine, bromine and iodine.

"Haloalkyl" refers to alkyl, as defined above, where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Amino" refers to an —$N(R)_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Oxo" refers to a carbonyl group, =O.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-6}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocycloalkyl" or "heterocyclyl" refers to a saturated ring system having from 3 to 12 ring members and from 1 to 5 heteroatoms of N, O and S. The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, 4, or 5, or 1 to 2, 1 to 3, 1 to 4, 1 to 5, 2 to 3, 2 to 4, 2 to 5, 3 to 4 or 3 to 5. The heterocycloalkyl group can include any number of carbons, such as $C_{3-6}$, $C_{4-6}$, $C_{5-6}$, $C_{3-8}$, $C_{4-8}$, $C_{5-8}$, $C_{6-5}$, $C_{3-9}$, $C_{3-10}$, $C_{3-11}$, and $C_{3-12}$. The heterocycloalkyl group can include groups such as aziridine, azetidine, pyrrolidine, piperidine, azepane, diazepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. The heterocycloalkyl groups can also form spiro structures such as, but not limited to, diazabicycloheptane, diazabicyclooctane, diazaspirooctane or diazaspirononane. Heterocycloalkyl groups can be unsubstituted or substituted. For example, heterocycloalkyl groups can be substituted with $C_{1-6}$ alkyl or oxo (=O), among many others. Heterocycloalkyl groups can also include a double bond or a triple bond, such as, but not limited to dihydropyridine or 1,2,3,6-tetrahydropyridine.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heterocycloalkyl component is as defined above. Alkyl-heterocycloalkyl groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Examples of alkyl-aryl groups include, but are not limited to, benzyl and ethyl-benzene. Alkyl-aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. The heteroatoms can also be oxidized, such as, but not limited to, —N(O)—, —S(O)— and —S(O)$_2$—. Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heteroaryl component is as defined within. Alkyl-heteroaryl groups can be substituted or unsubstituted.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, surfactants, coatings, sweeteners, flavors and colors. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Therapeutically effective amount" refers to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

A cortisol receptor is a glucocorticoid receptor (GR), specifically the type II GR, which specifically binds cortisol and/or cortisol analogs such as dexamethasone (See, e.g., Turner & Muller, J. Mol. Endocrinol. Oct. 1, 2005 35 283-292).

"Mineralocorticoid receptor" (MR) refers to a type I glucocorticoid receptor (GR I), which is activated by aldosterone in humans.

"Glucocorticoid receptor modulator" (GRM) refers to any compound which modulates any biological response associated with the binding of a glucocorticoid receptor to an agonist. As used herein, with respect to a GRM, the glucocorticoid receptor may be GR. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, inhibits the agonist-induced increase in the activity of tyrosine aminotransferase (TAT) in HepG2 cells. TAT activity can be measured as outlined in the literature by A. Ali et al., J. Med. Chem., 2004, 47, 2441-2452.

"Glucocorticoid receptor antagonist" (GRA) refers to any compound which inhibits any biological response associated with the binding of a glucocorticoid receptor to an agonist. As used herein, with respect to a GRA, the glucocorticoid receptor may be GR. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. An inhibitor is a compound with an IC$_{50}$ (half maximal inhibition concentration) of less than 10 micromolar. See Example 1 of U.S. Pat. No. 8,685,973, the entire contents of which is hereby incorporated by reference in its entirety.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Antagonize' and "antagonizing" refer to inhibiting the binding of an agonist at a receptor molecule or to inhibiting the signal produced by a receptor-agonist. A receptor antagonist inhibits or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulators of the present invention. In some embodiments, examples of disorders or conditions include, but are not limited to, Alzheimer's disease, amyotrophic lateral sclerosis (ALS), antipsychotic induced weight gain, cancer, Cushing Disease, Cushing's Syndrome, major psychotic depression, Nonalcoholic steatohepatitis, and obesity. In some embodiments, the disorders or conditions include nonalcoholic liver disease and/or nonalcoholic steatohepatitis. In some embodiments, the disorders or conditions include cancer.

"Medicament" refers to a composition or substance used for treatment of a disease or condition.

"Subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

III. Compounds

The present invention provides compounds of Formula J, I, Ia, Ib, Ib-1, Ib-2, Ic, and Id, or a pharmaceutically acceptable salt thereof. In some embodiments, the present invention provides a compound of Formula J:

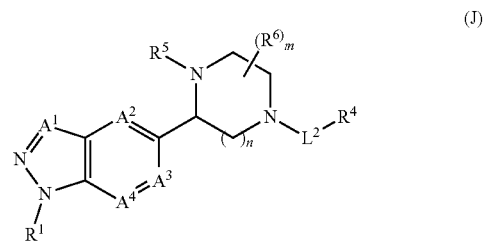

or a pharmaceutically acceptable salt thereof, wherein $R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;

each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR²— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

$L^2$ is —C(O)—, —C(O)O—, —C(O)N($R^3$)—, —S(O)₂— or —S(O)₂N($R^3$)—;

$R^3$ is hydrogen, or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl,
wherein each heterocycloalkyl independently has 3 to 12 ring members and 1 to 3 heteroatoms each independently N, O or S,
wherein each heteroaryl independently has 5 to 10 ring members and 1 to 4 heteroatoms each independently N, O or S, and
wherein the cycloalkyl, heterocycloalkyl, aryl and heteroaryl are each independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)₂$R^{4b}$, —S(O)₂N($R^{4b}$)($R^{4c}$), —N($R^{4b}$)S(O)₂$R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

$R^5$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{1-6}$ alkyl-O$R^{5a}$, —C(O)$R^{5a}$, $C_{1-6}$ alkyl-C(O)$R^{5a}$, —C(O)O$R^{5a}$, —C(O)N($R^{5a}$)($R^{5b}$), —S(O)₂$R^{5a}$, —S(O)₂N($R^{5a}$)($R^{5b}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl,
wherein each heterocycloalkyl independently has 3 to 12 ring members and 1 to 3 heteroatoms each independently N, O or S,
wherein each heteroaryl independently has 5 to 10 ring members and 1 to 4 heteroatoms each independently N, O or S, and
wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl,
wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)₂$R^{5c1}$, —S(O)₂N($R^{5c1}$)($R^{5c2}$), —N($R^{5c1}$)S(O)₂$R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently hydrogen, $C_{1-6}$ alkyl, halogen, $C_{1-6}$ haloalkyl, or oxo;
subscript m is 0, 1, 2, 3, 4, or 5; and
subscript n is 1 or 2.

In some embodiments, the present invention provides a compound of Formula I:

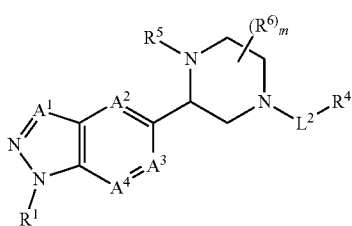

(I)

or a pharmaceutically acceptable salt thereof, wherein
$R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;
each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;
each $R^{1b}$ and $R^{1c}$ is independently hydrogen, $C_{1-6}$ alkyl or a 3 to 8 membered heterocycloalkyl having 1 to 3 heteroatoms each independently N, O or S;
$A^1$, $A^2$, $A^3$ and $A^4$ are each independently =CR$^2$— or =N—;
each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;
$L^2$ is —C(O)—, —C(O)O—, —C(O)N($R^3$)—, —S(O)$_2$— or —S(O)$_2$N($R^3$)—;
$R^3$ is hydrogen, or $C_{1-6}$ alkyl;
$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl,
  wherein each heterocycloalkyl independently has 3 to 12 ring members and 1 to 3 heteroatoms each independently N, O or S,
  wherein each heteroaryl independently has 5 to 10 ring members and 1 to 4 heteroatoms each independently N, O or S, and
  wherein the cycloalkyl, heterocycloalkyl, aryl and heteroaryl are each independently substituted with 0 to 5 $R^{4a}$ groups;
alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;
each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2$$R^{4b}$, —S(O)$_2$N($R^{4b}$)($R^{4c}$), —N($R^{4b}$)S(O)$_2$$R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;
each $R^{4b}$ and $R^{4c}$ is hydrogen or $C_{1-6}$ alkyl;
$R^5$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{1-6}$ alkyl-OR$^{5a}$, —C(O)$R^{5a}$, $C_{1-6}$ alkyl-C(O)$R^{5a}$, —C(O)O$R^{5a}$, —C(O)N($R^{5a}$)($R^{5b}$), —S(O)$_2$$R^{5a}$, —S(O)$_2$N($R^{5a}$)($R^{5b}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl,
  wherein each heterocycloalkyl independently has 3 to 12 ring members and 1 to 3 heteroatoms each independently N, O or S,
  wherein each heteroaryl independently has 5 to 10 ring members and 1 to 4 heteroatoms each independently N, O or S, and
  wherein each cycloalkyl, heterocycloalkyl, aryl and heteroaryl is independently substituted with 0 to 4 $R^{5c}$ groups;
each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl,
  wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;
alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;
each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)$_2$$R^{5c1}$, —S(O)$_2$N($R^{5c1}$)($R^{5c2}$), —N($R^{5c1}$)S(O)$_2$$R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently hydrogen, $C_{1-6}$ alkyl, halogen, $C_{1-6}$ haloalkyl, or oxo; and subscript m is 0, 1, 2, 3, 4, or 5.

In some embodiments, the present invention provides a compound of Formula I:

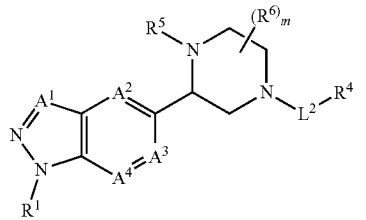

(I)

or a pharmaceutically acceptable salt thereof, wherein $R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;

each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR$^2$— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

$L^2$ is —C(O)—, —C(O)O—, —C(O)N($R^3$)—, —S(O)$_2$— or —S(O)$_2$N($R^3$)—;

$R^3$ is hydrogen, or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein the cycloalkyl, heterocycloalkyl, aryl and heteroaryl are each independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)R$^{4b}$, —C(O)OR$^{4b}$, —OC(O)R$^{4b}$, —OC(O)OR$^{4b}$, —C(O)N(R$^{4b}$)(R$^{4c}$), —N(R$^{4b}$)C(O)R$^{4c}$, —OC(O)N(R$^{4b}$)(R$^{4c}$), —N(R$^{4b}$)C(O)OR$^{4c}$, —S(O)$_2$R$^{4b}$, —S(O)$_2$N(R$^{4b}$)(R$^{4c}$), —N(R$^{4b}$)S(O)$_2$R$^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

$R^5$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{1-6}$ alkyl-OR$^{5a}$, —C(O)R$^{5a}$, —C(O)OR$^{5a}$, —C(O)N(R$^{5a}$)(R$^{5b}$), —S(O)$_2$R$^{5a}$, —S(O)$_2$N(R$^{5a}$)(R$^{5b}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —OH, —C(O)R$^{5c1}$, —C(O)OR$^{5c1}$, —OC(O)R$^{5c1}$, —OC(O)OR$^{5c1}$, —C(O)N(R$^{5c1}$)(R$^{5c2}$), —N(R$^{5c1}$)C(O)R$^{5c2}$, —OC(O)N(R$^{5c1}$)(R$^{5c2}$), —N(R$^{5c1}$)C(O)OR$^{5c2}$, —S(O)$_2$R$^{5c1}$, —S(O)$_2$N(R$^{5c1}$)(R$^{5c2}$), —N(R$^{5c1}$)S(O)$_2$R$^{5c2}$, C$_{3-8}$ cycloalkyl, C$_{1-6}$ alkyl-C$_{3-8}$ cycloalkyl, heterocycloalkyl, C$_{1-6}$ alkyl-heterocycloalkyl, C$_{6-12}$ aryl, C$_{1-6}$ alkyl-C$_{6-12}$ aryl, heteroaryl, or C$_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 C$_{1-6}$ alkyl groups;

each R$^{5c1}$ and R$^{5c2}$ is independently hydrogen, C$_{1-6}$ alkyl, C$_{2-6}$ alkenyl, C$_{2-6}$ alkynyl, C$_{2-6}$ alkoxyalkyl, C$_{1-6}$ hydroxyalkyl, C$_{1-6}$ haloalkyl, C$_{3-8}$ cycloalkyl, C$_{1-6}$ alkyl-C$_{3-8}$ cycloalkyl, heterocycloalkyl, C$_{1-6}$ alkyl-heterocycloalkyl, C$_{6-12}$ aryl, C$_{1-6}$ alkyl-C$_{6-12}$ aryl, heteroaryl, or C$_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 C$_{1-6}$ alkyl groups; alternatively, R$^{5c1}$ and R$^{5c2}$ are combined with the atoms to which they are attached to form a heterocycloalkyl having 3 to 12 ring members and 1 to 3 heteroatoms each independently N, O or S, wherein the heterocycloalkyl is substituted with 0, 1 or 2 C$_{1-6}$ alkyl groups;

each R$^{5d}$ is independently C$_{1-6}$ alkyl or halogen;

each R$^6$ is independently hydrogen, C$_{1-6}$ alkyl, halogen, C$_{1-6}$ haloalkyl, or oxo; and subscript m is 0, 1, 2, 3, 4, or 5.

In some embodiments, the compound of Formula J, I, Ia, Ib, Ib-1, Ib-2, Ic, or Id, or the pharmaceutically acceptable salt thereof, is the compound wherein R$^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 R$^{1a}$ groups; each R$^{1a}$ is independently C$_{1-6}$ alkyl, C$_{1-6}$ alkoxy, C$_{1-6}$ alkoxyalkyl, C$_{1-6}$ hydroxyalkyl, halogen, C$_{1-6}$ haloalkyl, C$_{1-6}$ haloalkoxy, —OH, oxo, —CN, —C(O)N(R$^{1b}$)(R$^{1c}$), C$_{3-10}$ cycloalkyl, or heterocycloalkyl having 3 to 12 ring members and 1 to 4 heteroatoms each N, O or S; and each R$^{1b}$ and R$^{1c}$ is independently hydrogen, C$_{1-6}$ alkyl or a 3 to 8 membered heterocycloalkyl having 1 to 3 heteroatoms each independently N, O or S.

In some embodiments, the compound of Formula J, I, Ia, Ib, Ib-1, Ib-2, Ic, or Id, or the pharmaceutically acceptable salt thereof, is the compound wherein R$^1$ is phenyl or heteroaryl having 5 to 6 ring members and 1 to 3 heteroatoms each N, each independently substituted with 0 to 3 R$^{1a}$ groups; each R$^{1a}$ is independently C$_{1-6}$ alkyl, C$_{1-6}$ alkoxy, C$_{1-6}$ hydroxyalkyl, halogen, C$_{1-6}$ haloalkyl, —OH, oxo, or —CN; and each Rib and R$^{1c}$ is independently hydrogen or C$_{1-6}$ alkyl. In some embodiments, the compound of Formula J, I, Ia, Ib, Ib-1, Ib-2, Ic, or Id, or the pharmaceutically acceptable salt thereof, is the compound wherein R$^1$ is phenyl, pyrrole, pyrazole, imidazole, pyridine, pyrazine, pyrimidine, or pyridazine, each independently substituted with 0 to 3 R$^{1a}$ groups; and each R$^{1a}$ is independently methyl, ethyl, n-propyl, isopropyl, —OMe, —CH$_2$OH, fluoro, chloro, bromo, —CHF$_2$, —OH, oxo, or —CN. In some embodiments, the compound of Formula J, I, Ia, Ib, Ib-1, Ib-2, Ic, or Id, or the pharmaceutically acceptable salt thereof, is the compound wherein R$^1$ is phenyl, substituted with 0 to 2 R$^{1a}$ groups each independently methyl, —CH$_2$OH, fluoro, —CHF$_2$, or —CN, pyridyl, substituted with 0 to 3 R$^{1a}$ groups each independently methyl, —OMe, F, —OH or oxo, pyrazole, substituted with 1 to 2 R$^{1a}$ groups each independently methyl, pyridazine, substituted with 1 to 3 R$^{1a}$ groups each independently methyl or oxo, or pyrazine, substituted with 1 to 2 R$^{1a}$ groups each methyl. In some embodiments, the compound of Formula J, I, Ia, Ib, Ib-1, Ib-2, Ic, or Id, or the pharmaceutically acceptable salt thereof, is the compound wherein R$^1$ is

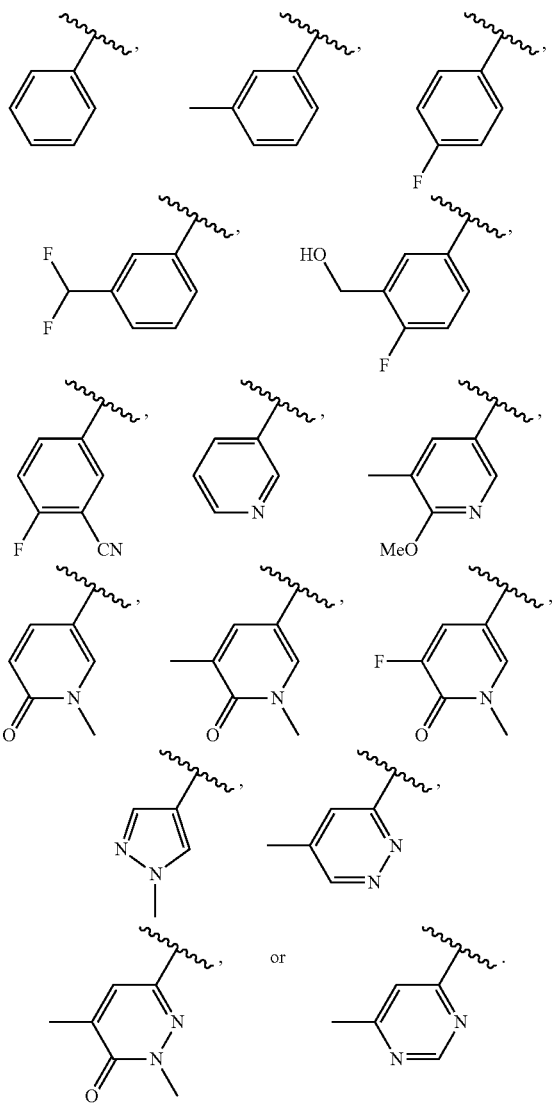

In some embodiments, the compound of Formula J, I, Ia, Ib, Ib-1, Ib-2, Ic, or Id, or the pharmaceutically acceptable salt thereof, is the compound wherein R$^1$ is phenyl or heteroaryl having 5 to 6 ring members and 1 to 3 heteroatoms each N, each independently substituted with 0 to 3 R$^{1a}$ groups; and each R$^{1a}$ is independently C$_{1-6}$ alkyl, halogen, —OH, oxo, or —CN. In some embodiments, the compound of Formula J, I, Ia, Ib, Ib-1, Ib-2, Ic, or Id, or the pharmaceutically acceptable salt thereof, is the compound wherein R$^1$ is phenyl, pyrrole, pyrazole, imidazole, pyridine, pyrazine, pyrimidine, or pyridazine, each independently substituted with 0 to 3 $R^{1a}$ groups; and each $R^{1a}$ is independently methyl, ethyl, n-propyl, isopropyl, fluoro, chloro, bromo, —OH, oxo, or —CN. In some embodiments, the compound of Formula J, I, Ia, Ib, Ib-1, Ib-2, Ic, or Id, or the pharmaceutically acceptable salt thereof, is the compound wherein $R^1$ is phenyl, substituted with 1 to 2 $R^{1a}$ groups each independently fluoro or —CN, pyridyl, substituted with 0 to 3 $R^{1a}$ groups each independently methyl, —OH or oxo, or pyrazole, substituted with 1 to 2 $R^{1a}$ groups each independently methyl. In some embodiments, the compound of Formula J, I, Ia, Ib, Ib-1, Ib-2, Ic, or Id, or the pharmaceutically acceptable salt thereof, is the compound wherein $R^1$ is

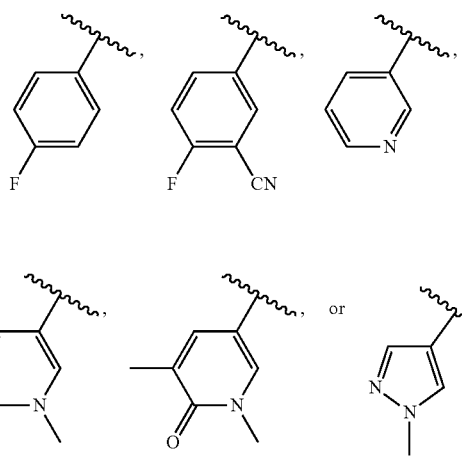

In some embodiments, the compound of Formula J, I, Ia, Ib, Ib-1, Ib-2, Ic, or Id, or the pharmaceutically acceptable salt thereof, is the compound wherein $R^1$ is

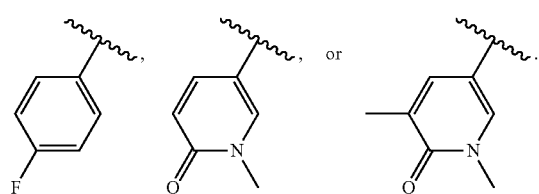

In some embodiments, the compound of Formula J, I, Ia, Ib, Ib-1, Ib-2, Ic, or Id, or the pharmaceutically acceptable salt thereof, is the compound wherein $R^1$ is phenyl substituted with halogen. In some embodiments, the compound of Formula J, I, Ia, Ib, Ib-1, Ib-2, Ic, or Id, or the pharmaceutically acceptable salt thereof, is the compound wherein $R^1$ is

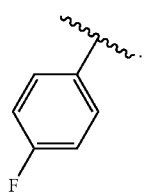

In some embodiments, the compound of Formula J, I, or the pharmaceutically acceptable salt thereof, is the compound wherein $A^1$, $A^2$, $A^3$ and $A^4$ are each independently =$CR^2$— or =N—; and each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN.

In some embodiments, the compound of Formula J, I, or the pharmaceutically acceptable salt thereof, is the compound wherein each of $A^1$, $A^2$, $A^3$, and $A^4$ is =$CR^2$—. In some embodiments, the compound of Formula J, I, or the pharmaceutically acceptable salt thereof, is the compound wherein at least one $R^2$ is $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN.

In some embodiments, the compound of Formula J, I, Ia, Ib, Ib-1, Ib-2, Ic, or Id, or the pharmaceutically acceptable salt thereof, is the compound wherein each $R^2$ is independently hydrogen, $C_{1-6}$ alkyl, $C_{1-6}$ alkoxy, halogen or $C_{1-6}$ haloalkyl. In some embodiments, the compound of Formula J, I, Ia, Ib, Ib-1, Ib-2, Ic, or Id, or the pharmaceutically acceptable salt thereof, is the compound wherein each $R^2$ is independently hydrogen, $C_{1-6}$ alkyl, $C_{1-6}$ alkoxy or halogen. In some embodiments, the compound of Formula J, I, Ia, Ib, Ib-1, Ib-2, Ic, or Id, or the pharmaceutically acceptable salt thereof, is the compound wherein each $R^2$ is independently hydrogen, methyl, ethyl, n-propyl, iso-propyl, methoxy, ethoxy, n-propoxy, iso-propoxy, fluoro, chloro, bromo, —$CH_2F$, —$CHF_2$, —$CF_3$, —$CH_2CH_2F$, —$CH_2CHF_2$, or —$CH_2CF_3$. In some embodiments, the compound of Formula J, I, Ia, Ib, Ib-1, Ib-2, Ic, or Id, or the pharmaceutically acceptable salt thereof, is the compound wherein each $R^2$ is independently hydrogen, methyl, ethyl, n-propyl, iso-propyl, methoxy, ethoxy, n-propoxy, iso-propoxy, fluoro, chloro or bromo. In some embodiments, the compound of Formula J, I, Ia, Ib, Ib-1, Ib-2, Ic, or Id, or the pharmaceutically acceptable salt thereof, is the compound wherein each $R^2$ is independently hydrogen, methyl, methoxy, fluoro, chloro, or $CF_3$. In some embodiments, the compound of Formula J, I, Ia, Ib, Ib-1, Ib-2, Ic, or Id, or the pharmaceutically acceptable salt thereof, is the compound wherein each $R^2$ is independently hydrogen, methyl, methoxy, or chloro. In some embodiments, the compound of Formula J, I, Ia, Ib, Ib-1, Ib-2, Ic, or Id, or the pharmaceutically acceptable salt thereof, is the compound wherein each $R^2$ is hydrogen or methyl.

In some embodiments, the compound of Formula J, I, Ia, Ib, Ib-1, Ib-2, Ic, or Id, or the pharmaceutically acceptable salt thereof, is the compound wherein $R^2$ is hydrogen or methyl. In some embodiments, the compound of Formula J, I, Ia, Ib, Ib-1, Ib-2, Ic, or Id, or the pharmaceutically acceptable salt thereof, is the compound wherein $R^2$ is methyl.

In some embodiments, the compound of Formula J, I, Ia, Ib, Ib-1, Ib-2, Ic, or Id, or the pharmaceutically acceptable salt thereof, is the compound wherein $A^1$, $A^2$ and $A^4$ are each =CH—; and $A^3$ is =C(Me)-, =C(OMe)-, =C(F)—, =C(Cl)—, or =C($CF_3$)—. In some embodiments, the compound of Formula J, I, or the pharmaceutically acceptable salt thereof, is the compound wherein $A^1$, $A^2$ and $A^4$ are each =CH—; and $A^3$ is =C(Me)-, =C(OMe)- or =C(Cl)—. In some embodiments, the compound of Formula J, I, or the pharmaceutically acceptable salt thereof, is the compound wherein $A^1$, $A^2$ and $A^4$ are each =CH—; and $A^3$ is =C(Me)-.

Each embodiment of $A^1$, $A^2$, $A^3$, $A^4$ and $R^2$ described herein can be combined with each embodiment of $R^1$ described herein.

In some embodiments, the compound of Formula J, I, Ia, Ib, Ib-1, Ib-2, Ic, or Id, or the pharmaceutically acceptable salt thereof, is the compound wherein subscript n is 2. In some embodiments, the compound of Formula J, I, Ia, Ib, Ib-1, Ib-2, Ic, or Id, or the pharmaceutically acceptable salt thereof, is the compound wherein subscript n is 1.

Each embodiment of subscript n described herein can be combined with each embodiment of $R^1$, $A^1$, $A^2$, $A^3$, $A^4$, and $R^2$ described herein.

In some embodiments, the compound of Formula J, I, or the pharmaceutically acceptable salt thereof, is the compound having the structure of Formula Ia:

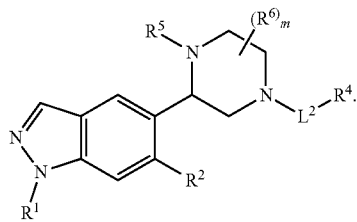

(Ia)

In some embodiments, the compound of Formula J, I, or Ia, or the pharmaceutically acceptable salt thereof, is the compound having the structure of Formula Ib:

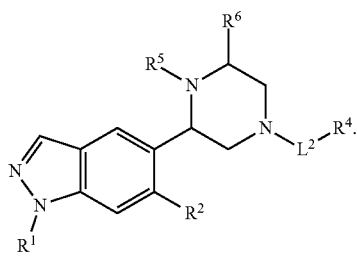

(Ib)

In some embodiments, the compound of Formula J, I, Ia, or Ib, or the pharmaceutically acceptable salt thereof, is the compound having the structure of Formula Ib-1:

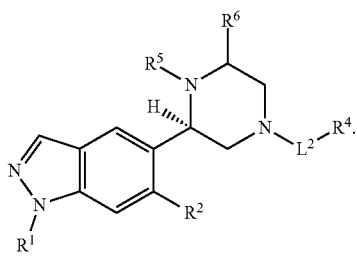

(Ib-1)

In some embodiments, the compound of Formula J, I, Ia, or Ib, or the pharmaceutically acceptable salt thereof, is the compound having the structure of Formula Ib-2:

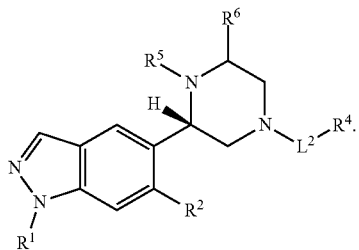

(Ib-2)

In some embodiments, the compound of Formula J, I, Ia, Ib, Ib-1, or Ib-2, or the pharmaceutically acceptable salt thereof, is the compound wherein $L^2$ is —C(O)—, —C(O)O—, —C(O)N($R^3$)—, —S(O)$_2$— or —S(O)$_2$N($R^3$)—; and $R^3$ is hydrogen, or $C_{1-6}$ alkyl. In some embodiments, the compound of Formula J, I, Ia, Ib, Ib-1, or Ib-2, or the pharmaceutically acceptable salt thereof, is the compound wherein $L^2$ is —C(O)—, —S(O)$_2$— or —S(O)$_2$N($R^3$)—; and $R^3$ is $C_{1-6}$ alkyl. In some embodiments, the compound of Formula J, I, Ia, Ib, Ib-1, or Ib-2, or the pharmaceutically acceptable salt thereof, is the compound wherein $L^2$ is —C(O)—, —S(O)$_2$— or —S(O)$_2$N(Me)-. In some embodiments, the compound of Formula J, I, Ia, Ib, Ib-1, or Ib-2, or the pharmaceutically acceptable salt thereof, is the compound wherein $L^2$ is —C(O)—, or —S(O)$_2$—. In some embodiments, the compound of Formula J, I, Ia, Ib, Ib-1, or Ib-2, or the pharmaceutically acceptable salt thereof, is the compound wherein $L^2$ is —S(O)$_2$—.

Each embodiment of $L^2$ and $R^3$ described herein can be combined with each embodiment of $R^1$, $A^1$, $A^2$, $A^3$, $A^4$, $R^2$ and subscript n described herein.

In some embodiments, the compound of Formula J, I, Ia, or Ib, or the pharmaceutically acceptable salt thereof, is the compound having the structure of Formula Ic or Formula Id:

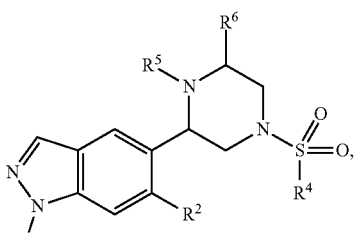

(Ic)

or

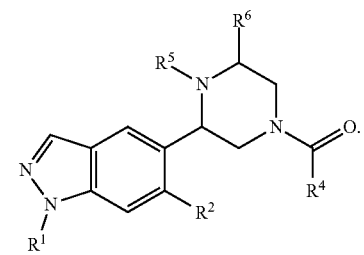

(Id)

In some embodiments, the compound of Formula J, I, Ia, or Ib, or the pharmaceutically acceptable salt thereof, is the compound having the structure of Formula Ic:

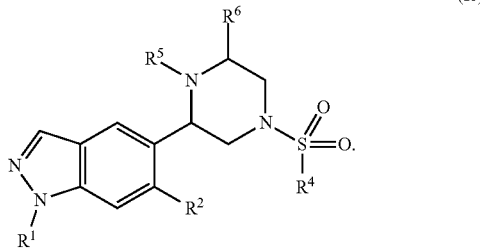

(Ic)

In some embodiments, the compound of Formula J, I, Ia, Ib, Ib-1, Ib-2, Ic, or Id, or the pharmaceutically acceptable salt thereof, is the compound wherein
- $R^4$ is $C_{1-6}$ alkyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 6 ring members and 1 to 3 heteroatoms each independently N, O or S, wherein each heteroaryl independently has 5 to 6 ring members and 1 to 4 heteroatoms each independently N, O or S, and wherein the cycloalkyl, heterocycloalkyl, aryl and heteroaryl are each independently substituted with 0 to 5 $R^{4a}$ groups;
- alternatively, $R^3$ and $R^4$ are combined with the atoms to which they are attached to form a heterocycloalkyl having 5 to 6 ring members and 1 additional heteroatom N, O or S; and
- each $R^{4a}$ is independently $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 6 ring members and 1 to 3 heteroatoms each independently N, O or S, wherein each heteroaryl independently has 5 to 6 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups.

In some embodiments, the compound of Formula J, I, Ia, Ib, Ib-1, Ib-2, Ic or Id, or the pharmaceutically acceptable salt thereof, is the compound wherein
- $R^4$ is $C_{1-6}$ alkyl, $C_{2-6}$ alkoxyalkyl, $C_{1-6}$ hydroxyalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 6 ring members and 1 to 3 heteroatoms each independently N, O or S, wherein each heteroaryl independently has 5 to 6 ring members and 1 to 4 heteroatoms each independently N, O or S, and wherein the cycloalkyl, heterocycloalkyl, aryl and heteroaryl are each independently substituted with 0 to 5 $R^{4a}$ groups;
- alternatively, $R^3$ and $R^4$ are combined with the atoms to which they are attached to form a heterocycloalkyl having 5 to 6 ring members and 1 additional heteroatom N, O or S; and
- each $R^{4a}$ is independently $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 6 ring members and 1 to 3 heteroatoms each independently N, O or S, wherein each heteroaryl independently has 5 to 6 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups.

In some embodiments, the compound of Formula J, I, Ia, Ib, Ib-1, Ib-2, Ic, or Id, or the pharmaceutically acceptable salt thereof, is the compound wherein
- $R^4$ is $C_{1-6}$ alkyl, $C_{2-3}$ alkoxyalkyl, $C_{1-3}$ hydroxyalkyl, $C_{1-6}$ haloalkyl, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-aryl, heteroaryl, or $C_{1-2}$ alkyl-heteroaryl, wherein each heterocycloalkyl independently has 5 to 6 ring members and 1 to 3 heteroatoms each independently N or O, wherein each heteroaryl independently has 5 to 6 ring members and 1 to 3 heteroatoms each independently N, O or S, and wherein the cycloalkyl, heterocycloalkyl, aryl, and heteroaryl are each independently substituted with 0 to 3 $R^{4a}$ groups; and
- each $R^{4a}$ is independently $C_{1-3}$ alkyl, $C_{1-3}$ alkoxy, $C_{2-3}$ alkoxyalkyl, halogen, $C_{1-3}$ haloalkyl, —CN, or heterocycloalkyl, wherein each heterocycloalkyl independently has 5 to 6 ring members and 1 to 2 heteroatoms each independently N or O.

In some embodiments, the compound of Formula J, I, Ia, Ib, Ib-1, Ib-2, Ic or Id, or the pharmaceutically acceptable salt thereof, is the compound wherein
- $R^4$ is $C_{1-6}$ alkyl, $C_{2-3}$ alkoxyalkyl, $C_{1-3}$ hydroxyalkyl, $C_{3-6}$ cycloalkyl, $C_{1-2}$ alkyl-$C_{3-6}$ cycloalkyl, heterocycloalkyl, or heteroaryl, wherein each heterocycloalkyl independently has 5 to 6 ring members and 1 to 3 heteroatoms each independently N or O, wherein each heteroaryl independently has 5 to 6 ring members and 1 to 3 heteroatoms each independently N, O or S, and wherein the cycloalkyl, heterocycloalkyl, and heteroaryl are each independently substituted with 0 to 2 $R^{4a}$ groups; and
- each $R^{4a}$ is independently $C_{1-3}$ alkyl, $C_{2-3}$ alkoxyalkyl, halogen, $C_{1-3}$ haloalkyl, or heterocycloalkyl, wherein each heterocycloalkyl independently has 5 to 6 ring members and 1 to 2 heteroatoms each independently N or O.

In some embodiments, the compound of Formula J, I, Ia, Ib, Ib-1, Ib-2, Ic, or Id, or the pharmaceutically acceptable salt thereof, is the compound wherein
- $R^4$ is methyl, ethyl, n-propyl, iso-propyl, n-butyl, iso-butyl, sec-butyl, methoxymethyl, methoxyethyl, iso-propoxyethyl, hydroxymethyl, 1-hydroxyethyl, 2-hydroxyethyl, —CH$_2$F, —CHF$_2$, —CF$_3$, —CH$_2$CH$_2$F, —CH$_2$CHF$_2$, —CH$_2$CF$_3$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or heteroaryl, wherein each cycloalkyl is cyclopropyl, cyclobutyl, cyclopentyl, or cyclohexyl, where each heterocycloalkyl is oxetane, tetrahydrofuran, pyrrolidine, tetrahydropyran, piperidine, or morpholine, wherein each aryl is phenyl,
wherein each heteroaryl is pyrrole, pyridine, pyrazole, imidazole, pyridazine, pyrimidine, pyrazine, isoxazole, oxazole, isothiazole, thiazole, or triazole,
wherein the cycloalkyl, heterocycloalkyl, aryl, and heteroaryl are each independently substituted with 0 to 3 $R^{4a}$ groups; and
$R^{4a}$ is independently methyl, ethyl, n-propyl, iso-propyl, methoxy, ethoxy, isopropoxy, methoxymethyl, methoxyethyl, ethoxymethyl, fluoro, chloro, bromo, —CH$_2$F, —CHF$_2$, —CF$_3$, —CH$_2$CH$_2$F, —CH$_2$CHF$_2$, —CH$_2$CF$_3$, —CN, tetrahydrofuran, pyrrolidine, tetrahydropyran, piperidine, or morpholine.

In some embodiments, the compound of Formula J, I, Ia, Ib, Ib-1, Ib-2, Ic or Id, or the pharmaceutically acceptable salt thereof, is the compound wherein
$R^4$ is methyl, ethyl, n-propyl, iso-propyl, n-butyl, iso-butyl, sec-butyl, methoxymethyl, methoxyethyl, hydroxymethyl, 1-hydroxyethyl, 2-hydroxyethyl, $C_{3-6}$ cycloalkyl, $C_{1-2}$ alkyl-$C_{3-6}$ cycloalkyl, heterocycloalkyl, or heteroaryl,
wherein each cycloalkyl is cyclopropyl, cyclobutyl, cyclopentyl, or cyclohexyl, where each heterocycloalkyl is tetrahydrofuran, pyrrolidine, tetrahydropyran, piperidine, or morpholine,
wherein each heteroaryl is pyrrole, pyridine, pyrazole, imidazole, pyridazine, pyrimidine, pyrazine, isoxazole, oxazole, isothiazole, thiazole, or triazole, and
wherein the cycloalkyl, heterocycloalkyl, and heteroaryl are each independently substituted with 0 to 2 $R^{4a}$ groups; and
each $R^{4a}$ is independently methyl, ethyl, n-propyl, iso-propyl, methoxymethyl, methoxyethyl, ethoxymethyl, fluoro, chloro, bromo, —CH$_2$F, —CHF$_2$, —CF$_3$, —CH$_2$CF$_3$, tetrahydrofuran, pyrrolidine, tetrahydropyran, piperidine, or morpholine.

In some embodiments, the compound of Formula J, I, Ia, Ib, Ib-1, Ib-2, Ic, or Id, or the pharmaceutically acceptable salt thereof, is the compound wherein
$R^4$ is methyl, n-propyl, iso-butyl, —CH(OH)CH$_3$, methoxyethyl, isopropoxyethyl, CH$_2$CF$_3$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or heteroaryl,
wherein each cycloalkyl is cyclopropyl or cyclobutyl, where each heterocycloalkyl is oxetane, tetrahydrofuran or morpholine,
wherein each aryl is phenyl,
wherein each heteroaryl is pyridine, pyrazole, isoxazole, thiazole, or triazole, wherein the heteroaryl is substituted with 0 to 2 $R^{4a}$ groups; and
each $R^{4a}$ is independently methyl, ethyl, n-propyl, iso-propyl, methoxy, methoxyethyl, fluoro, —CHF$_2$, —CF$_3$, —CH$_2$CHF$_2$, —CH$_2$CF$_3$, —CN, or tetrahydropyran.

In some embodiments, the compound of Formula J, I, Ia, Ib, Ib-1, Ib-2, Ic or Id, or the pharmaceutically acceptable salt thereof, is the compound wherein
$R^4$ is methyl, n-propyl, iso-butyl, —CH(OH)CH$_3$, methoxyethyl, $C_{3-6}$ cycloalkyl, $C_{1-2}$ alkyl-$C_{3-6}$ cycloalkyl, heterocycloalkyl, or heteroaryl,
wherein each cycloalkyl is cyclopropyl,
where each heterocycloalkyl is tetrahydrofuran or morpholine,
wherein each heteroaryl is pyridine, pyrazole, isoxazole, thiazole, or triazole, wherein the heteroaryl is substituted with 0 to 2 $R^{4a}$ groups; and each $R^{4a}$ is independently methyl, ethyl, n-propyl, iso-propyl, methoxyethyl, fluoro, —CHF$_2$, or tetrahydropyran.

In some embodiments, the compound of Formula J, I, Ia, Ib, Ib-1, Ib-2, Ic, or Id, or the pharmaceutically acceptable salt thereof, is the compound wherein $R^4$ is pyridine, pyrazole, thiazole, or triazole, each substituted with 0 to 2 $R^{4a}$ groups; and each $R^{4a}$ is independently methyl, ethyl, n-propyl, iso-propyl, methoxy, methoxyethyl, fluoro, —CHF$_2$, —CF$_3$, —CH$_2$CHF$_2$, —CH$_2$CF$_3$, —CN, or tetrahydropyran.

In some embodiments, the compound of Formula J, I, Ia, Ib, Ib-1, Ib-2, Ic, or Id, or the pharmaceutically acceptable salt thereof, is the compound wherein $R^4$ is methyl, n-propyl, iso-butyl, —CH(OH)CH$_3$, methoxyethyl, isopropoxyethyl, CH$_2$CF$_3$,

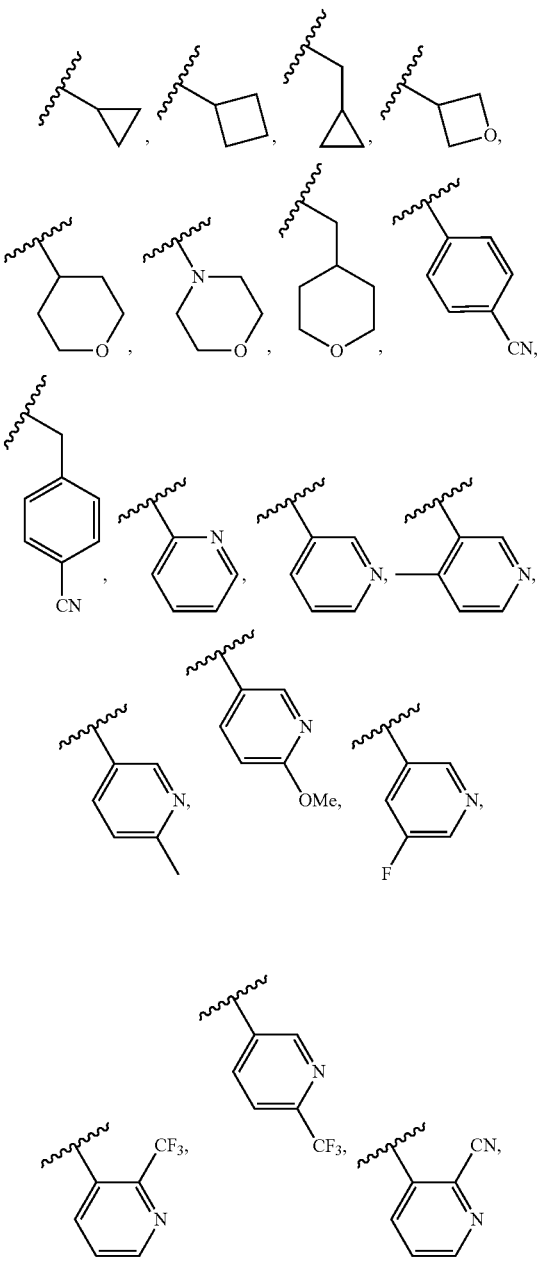

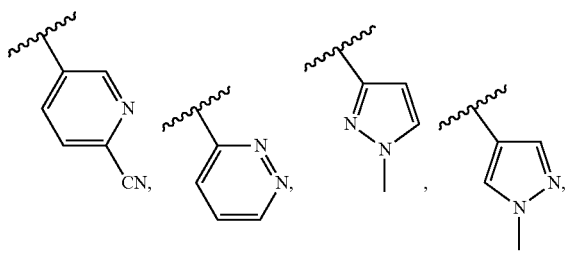
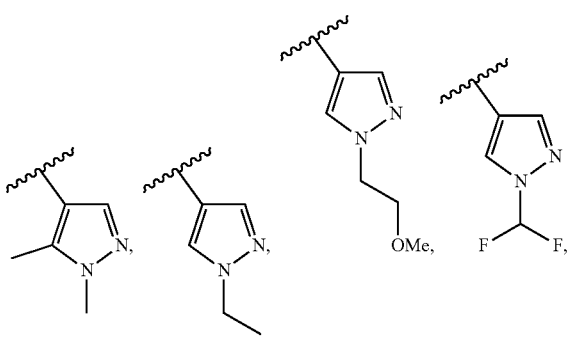
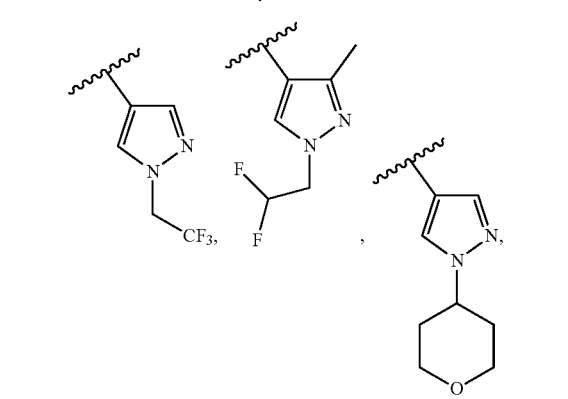
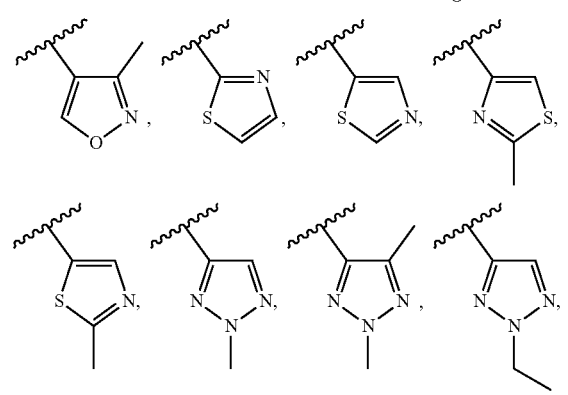
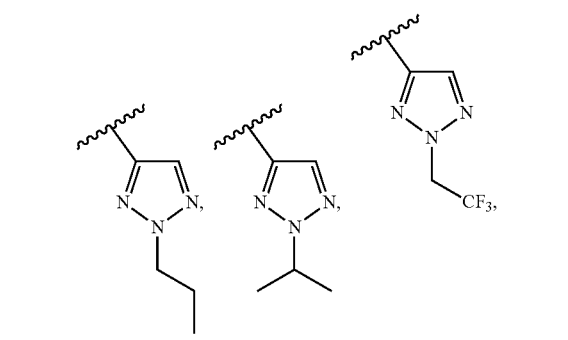
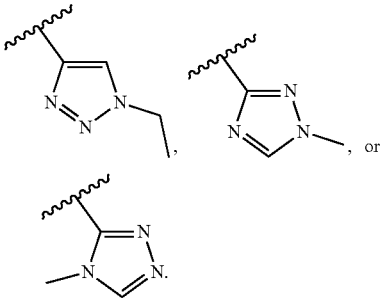
In some embodiments, the compound of Formula J, I, Ia, Ib, Ib-1, Ib-2, Ic, or Id, or the pharmaceutically acceptable salt thereof, is the compound wherein
$R^4$ is methyl, n-propyl, iso-butyl, —CH(OH)CH$_3$, methoxyethyl, isopropoxyethyl, CH$_2$CF$_3$,
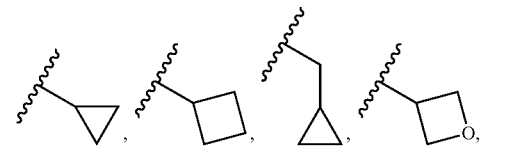
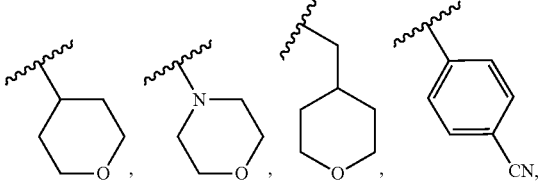
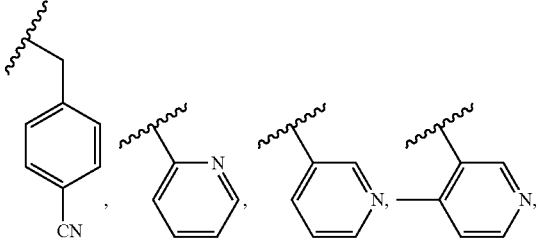
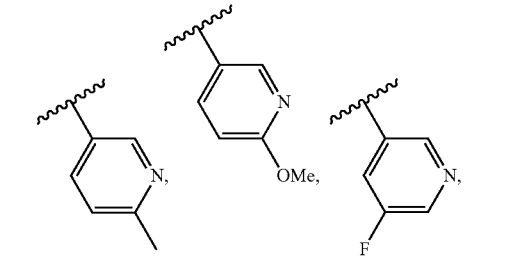
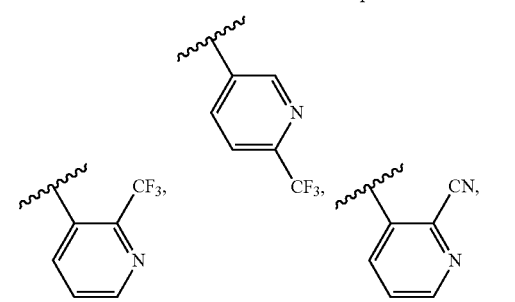

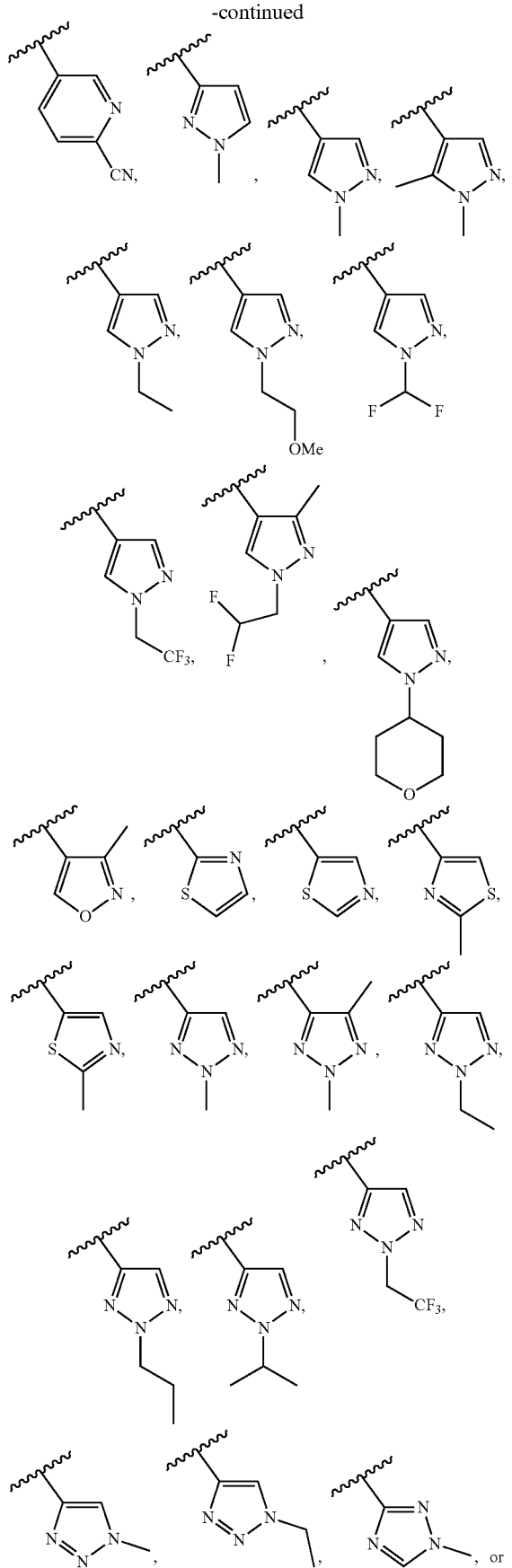
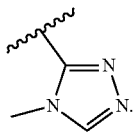
In some embodiments, the compound of Formula J, I, Ia, Ib, Ib-1, Ib-2, Ic or Id, or the pharmaceutically acceptable salt thereof, is the compound wherein
$R^4$ is methyl, n-propyl, iso-butyl, —CH(OH)CH$_3$, methoxyethyl,
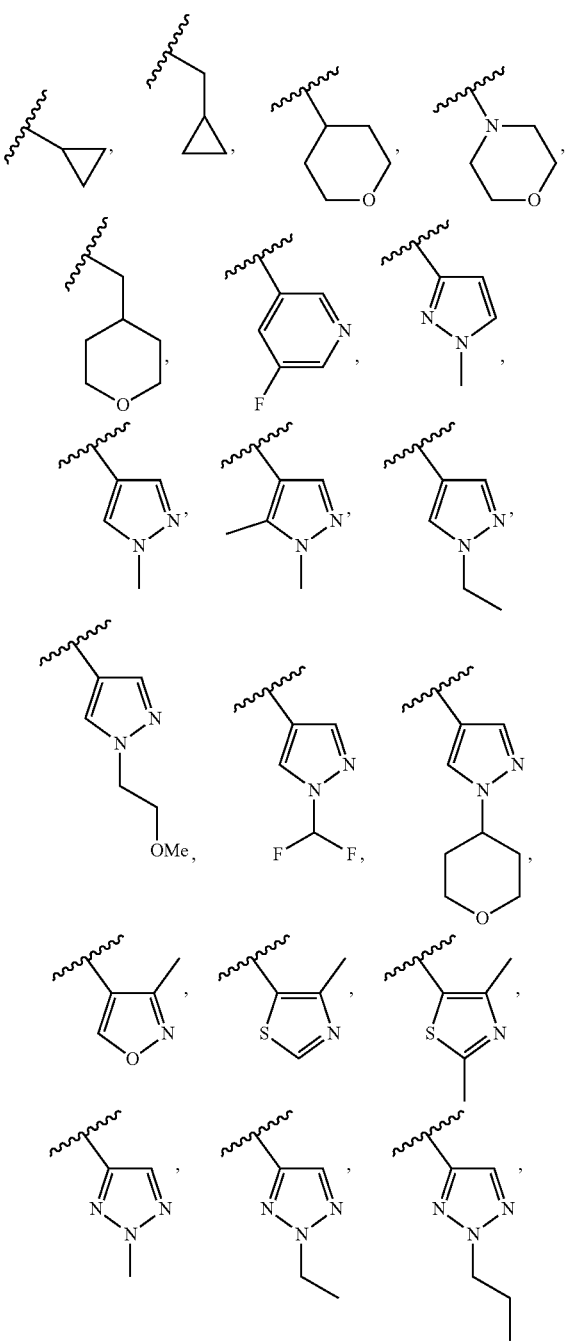

-continued

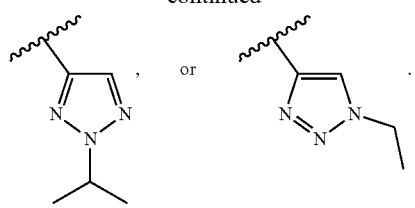

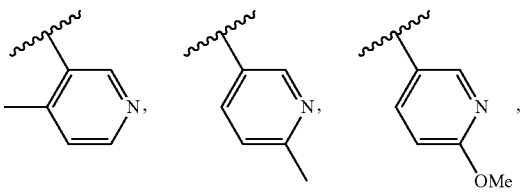

Each embodiment of $R^4$, $R^{4a}$, $R^{4b}$, and $R^{4c}$ described herein can be combined with each embodiment of $R^1$, $A^1$, $A^2$, $A^3$, $A^4$, $R^2$, subscript n, $L^2$ and $R^3$ described herein.

In some embodiments, the compound of Formula J, I, Ia, Ib, Ib-1, Ib-2, or Id, or the pharmaceutically acceptable salt thereof, is the compound wherein $L^2$ is —C(O)—; and
$R^4$ is methyl, —CH(OH)CH$_3$, or

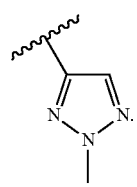 [SMILES: *c1cnn(C)n1]

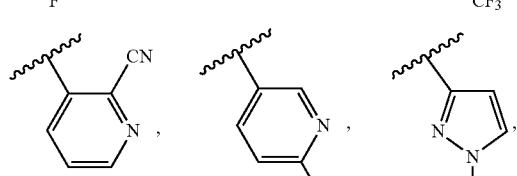

In some embodiments, the compound of Formula J, I, Ia, Ib, Ib-1, Ib-2, Ic, or Id, or the pharmaceutically acceptable salt thereof, is the compound wherein $L^2$ is —S(O)$_2$—; and
$R^4$ is methyl, n-propyl, iso-butyl, -methoxyethyl, iso-propoxyethyl, CH$_2$CF$_3$,

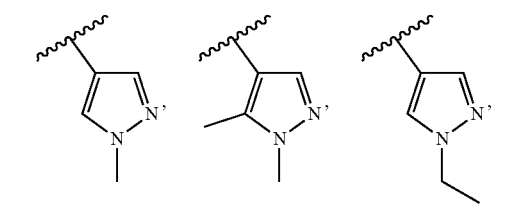

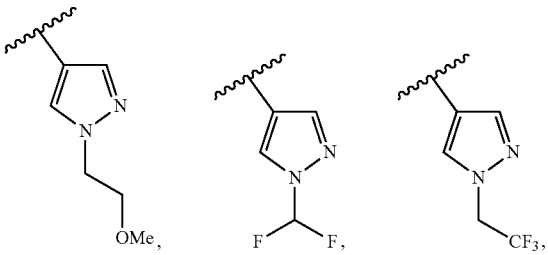

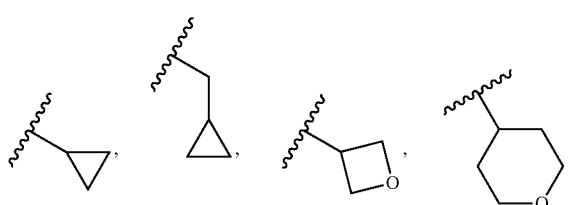

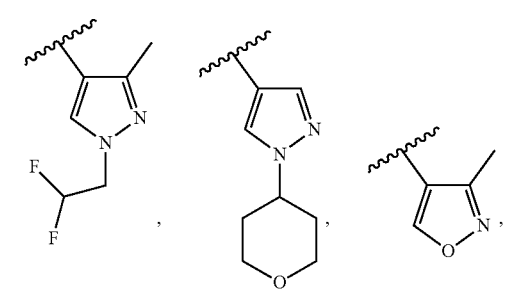

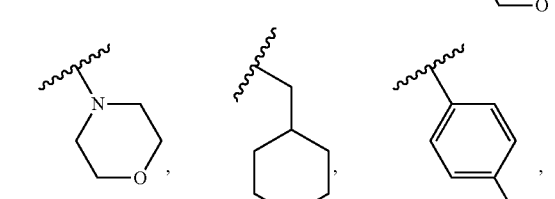

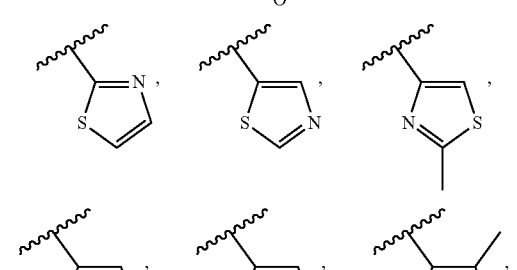

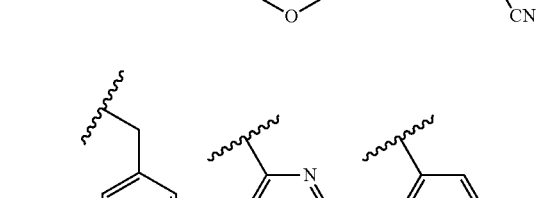

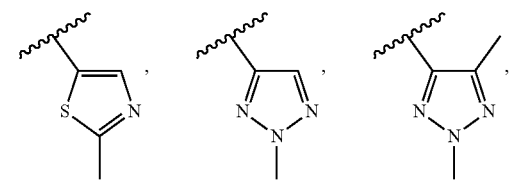

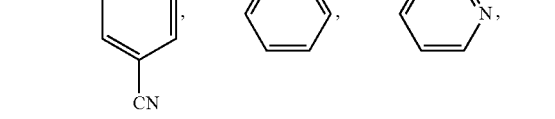

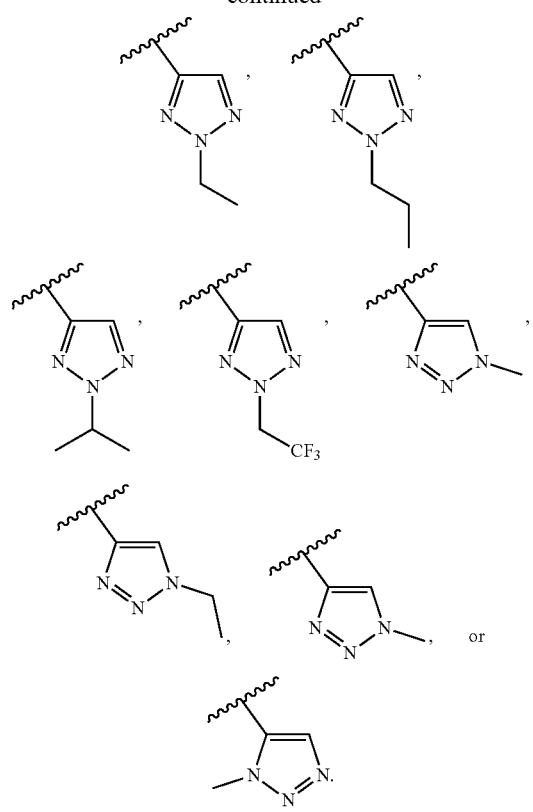

In some embodiments, the compound of Formula J, I, Ia, Ib, Ib-1, Ib-2, or Ic, or the pharmaceutically acceptable salt thereof, is the compound wherein L² is —S(O)₂—; and R⁴ is methyl, n-propyl, iso-butyl, —CH₂CH₂OCH₃

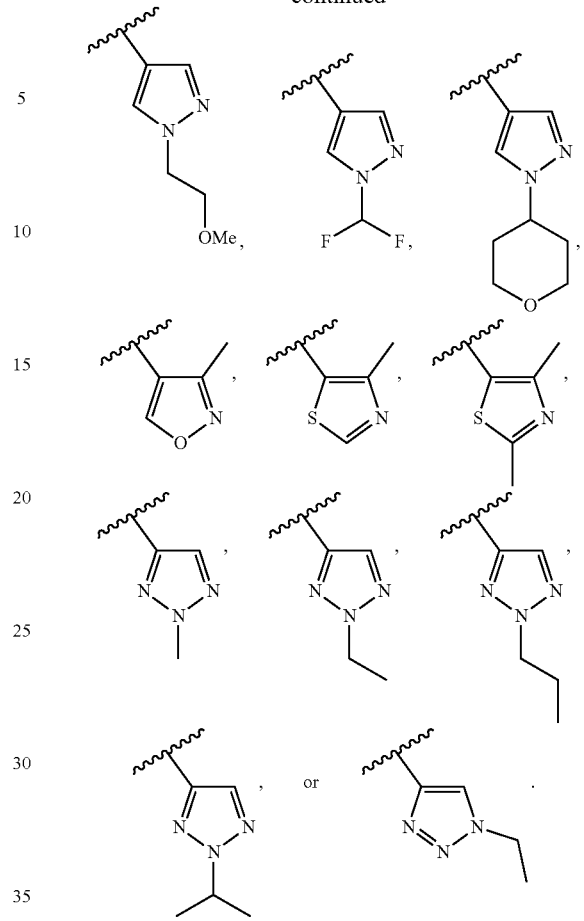

In some embodiments, the compound of Formula J, I, Ia, Ib, Ib-1, or Ib-2, or the pharmaceutically acceptable salt thereof, is the compound wherein L² is —S(O)N(Me)-; and R⁴ is methyl, or

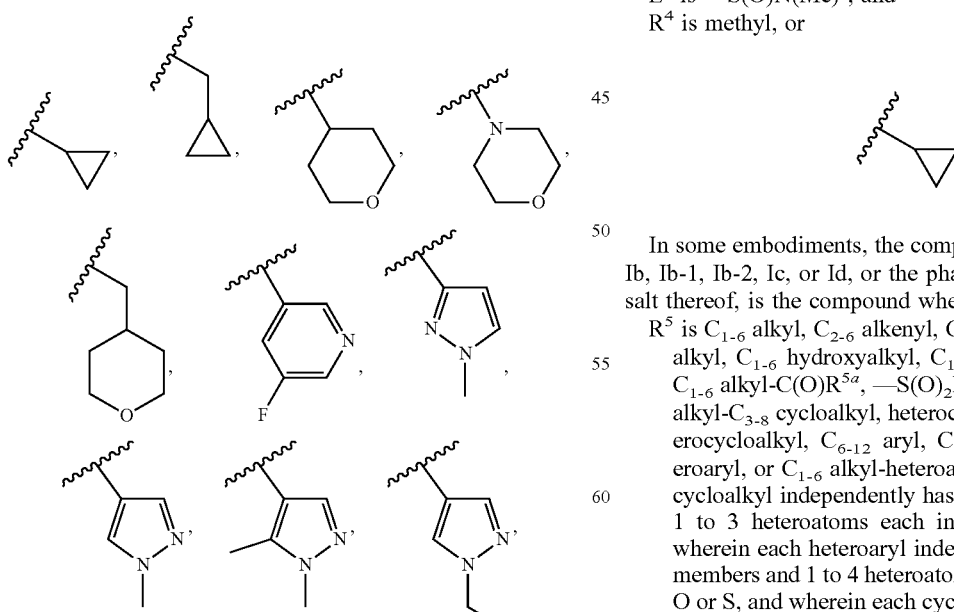

In some embodiments, the compound of Formula J, I, Ia, Ib, Ib-1, Ib-2, Ic, or Id, or the pharmaceutically acceptable salt thereof, is the compound wherein R⁵ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, —C(O)R$^{5a}$, $C_{1-6}$ alkyl-C(O)R$^{5a}$, —S(O)₂R$^{5a}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 6 ring members and 1 to 3 heteroatoms each independently N, O or S, wherein each heteroaryl independently has 5 to 6 ring members and 1 to 4 heteroatoms each independently N, O or S, and wherein each cycloalkyl, heterocycloalkyl, aryl and heteroaryl is independently substituted with 0 to 4 R$^{5c}$ groups;

each R$^{5a}$ and R$^{5b}$ is independently hydrogen or $C_{1-6}$ alkyl;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups; and each $R^{5c}$ is independently $C_{1-6}$ alkyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo or —OH.

In some embodiments, the compound of Formula J, I, Ia, Ib, Ib-1, Ib-2, Ic or Id, or the pharmaceutically acceptable salt thereof, is the compound wherein $R^5$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, —C(O)$R^{5a}$, —S(O)$_2R^{5a}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 6 ring members and 1 to 3 heteroatoms each independently N, O or S, wherein each heteroaryl independently has 5 to 6 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen or $C_{1-6}$ alkyl; alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups; and each $R^{5c}$ is independently $C_{1-6}$ alkyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, or —CN.

In some embodiments, the compound of Formula J, I, Ia, Ib, Ib-1, Ib-2, Ic, or Id, or the pharmaceutically acceptable salt thereof, is the compound wherein $R^5$ is $C_{1-6}$ alkyl, $C_{2-6}$ alkenyl, $C_{1-6}$ hydroxyalkyl, $C_{1-6}$ haloalkyl, —C(O)$R^{5a}$, $C_{1-2}$ alkyl-C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each heterocycloalkyl independently has 3 to 6 ring members and 1 to 2 heteroatoms each independently N or O, wherein each heteroaryl independently has 5 to 6 ring members and 1 to 3 heteroatoms each independently N, O or S, and wherein each cycloalkyl, heterocycloalkyl, aryl and heteroaryl is independently substituted with 0 to 2 $R^{5c}$ groups;

each $R^{5a}$ is independently $C_{1-6}$ alkyl; and each $R^{5c}$ is independently $C_{1-3}$ alkyl, $C_{1-3}$ alkoxy, halogen, $C_{1-3}$ haloalkyl, —CN, oxo or —OH.

In some embodiments, the compound of Formula J, I, Ia, Ib, Ib-1, Ib-2, Ic, or Id, or the pharmaceutically acceptable salt thereof, is the compound wherein $R^5$ is $C_{1-6}$ alkyl, $C_{2-6}$ alkenyl, $C_{1-6}$ hydroxyalkyl, $C_{1-6}$ haloalkyl, —C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each heterocycloalkyl independently has 3 to 6 ring members and 1 to 2 heteroatoms each independently N or O, wherein each heteroaryl independently has 5 to 6 ring members and 1 to 3 heteroatoms each independently N, O or S, and wherein each cycloalkyl, heterocycloalkyl, aryl and heteroaryl is independently substituted with 0 to 2 $R^{5c}$ groups;

each $R^{5a}$ is independently $C_{1-6}$ alkyl; and each $R^{5c}$ is independently $C_{1-3}$ alkyl, $C_{1-3}$ alkoxy, halogen, $C_{1-3}$ haloalkyl, or —CN.

In some embodiments, the compound of Formula J, I, Ia, Ib, Ib-1, Ib-2, Ic, or Id, or the pharmaceutically acceptable salt thereof, is the compound wherein $R^5$ is $C_{1-6}$ alkyl, $C_{1-6}$ haloalkyl, or $C_{1-2}$ alkyl-$C_{3-6}$ cycloalkyl, wherein each cycloalkyl is independently substituted with 0 to 2 $R^{5c}$ groups; and each $R^{5c}$ is independently $C_{1-3}$ alkyl, $C_{1-3}$ alkoxy, halogen, $C_{1-3}$ haloalkyl, —CN, oxo or —OH. In some embodiments, the compound of Formula J, I, Ia, Ib, Ib-1, Ib-2, Ic, or Id, or the pharmaceutically acceptable salt thereof, is the compound wherein $R^5$ is $C_{1-6}$ alkyl. In some embodiments, the compound of Formula J, I, Ia, Ib, Ib-1, Ib-2, Ic, or Id, or the pharmaceutically acceptable salt thereof, is the compound wherein $R^5$ is $C_{1-6}$ haloalkyl. In some embodiments, the compound of Formula J, I, Ia, Ib, Ib-1, Ib-2, Ic, or Id, or the pharmaceutically acceptable salt thereof, is the compound wherein $R^5$ is $C_{1-2}$ alkyl-$C_{3-6}$ cycloalkyl, wherein each cycloalkyl is independently substituted with 0 to 2 $R^{5c}$ groups; and each $R^{5c}$ is independently $C_{1-3}$ alkyl, $C_{1-3}$ alkoxy, halogen, $C_{1-3}$ haloalkyl, —CN, oxo or —OH.

In some embodiments, the compound of Formula J, I, Ia, Ib, Ib-1, Ib-2, Ic, or Id, or the pharmaceutically acceptable salt thereof, is the compound wherein $R^5$ is methyl, ethyl, n-propyl, iso-propyl, n-butyl, iso-butyl, sec-butyl, $C_{4-6}$ alkenyl, $C_{4-6}$ hydroxyalkyl, —CH$_2$F, —CHF$_2$, —CF$_3$, —CH$_2$CH$_2$F, —CH$_2$CHF$_2$, —CH$_2$CF$_3$, —CH$_2$CHFCH$_3$, —CH$_2$CF$_2$CH$_3$, —CH$_2$CH$_2$CF$_3$, —CH$_2$CF(CH$_3$)$_2$, —CH$_2$CH$_2$CH$_2$CF$_3$, —CH$_2$CH(CH$_3$)(CF$_3$), —CH$_2$C(CH$_3$)$_2$(CF$_3$), —C(O)$R^{5a}$, $C_{1-2}$ alkyl-C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each cycloalkyl is cyclopropyl, cyclobutyl, cyclopentyl, or cyclohexyl, wherein each heterocycloalkyl is oxetane, tetrahydrofuran, or tetrahydropyran, wherein each aryl is phenyl, wherein each heteroaryl is pyrrole, pyridine, pyrazole, imidazole, pyridazine, pyrimidine, pyrazine, isoxazole, oxazole, isothiazole, thiazole, or triazole, and wherein each cycloalkyl, aryl and heteroaryl is independently substituted with 0 to 2 $R^{5c}$ groups;

each $R^{5a}$ is independently methyl, ethyl, n-propyl or iso-propyl; and each $R^{5c}$ is independently methyl, ethyl, n-propyl, iso-propyl, methoxy, ethoxy, n-propoxy, iso-propoxy, fluoro, chloro, bromo, —CH$_2$F, —CHF$_2$, —CF$_3$, —CH$_2$CF$_3$, —CN, oxo or —OH.

In some embodiments, the compound of Formula J, I, Ia, Ib, Ib-1, Ib-2, Ic or Id, or the pharmaceutically acceptable salt thereof, is the compound wherein $R^5$ is methyl, ethyl, n-propyl, iso-propyl, n-butyl, iso-butyl, sec-butyl, $C_{4-6}$ alkenyl, $C_{4-6}$ hydroxyalkyl, —CH$_2$F, —CHF$_2$, —CF$_3$, —CH$_2$CF$_3$, —CH$_2$CH$_2$CF$_3$, —CH$_2$CH$_2$CH$_2$CF$_3$, —CH$_2$CH(CH$_3$)(CF$_3$), —C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each cycloalkyl is cyclopropyl, cyclobutyl, cyclopentyl, or cyclohexyl, wherein each heterocycloalkyl is oxetane, tetrahydrofuran, or tetrahydropyran, wherein each aryl is phenyl, wherein each heteroaryl is pyrrole, pyridine, pyrazole, imidazole, pyridazine, pyrimidine, pyrazine, isoxazole, oxazole, isothiazole, thiazole, or triazole, and wherein each cycloalkyl, aryl and heteroaryl is independently substituted with 0 to 2 $R^{5c}$ groups;

each $R^{5a}$ is independently methyl, ethyl, n-propyl or iso-propyl; and each $R^{5c}$ is independently methyl, ethyl, n-propyl, iso-propyl, methoxy, ethoxy, n-propoxy, iso-propoxy, fluoro, chloro, bromo, —CH$_2$F, —CHF$_2$, —CF$_3$, —CH$_2$CF$_3$, or —CN.

In some embodiments, the compound of Formula J, I, Ia, Ib, Ib-1, Ib-2, Ic, or Id, or the pharmaceutically acceptable salt thereof, is the compound wherein $R^5$ is ethyl, iso-propyl, iso-butyl,

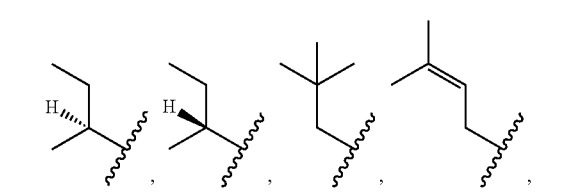

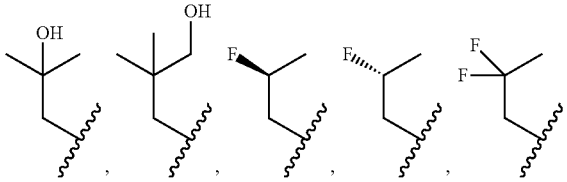

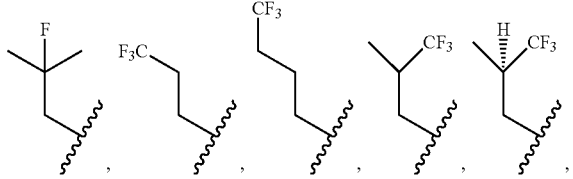

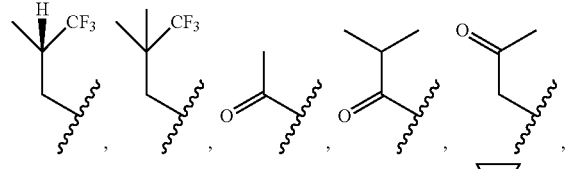

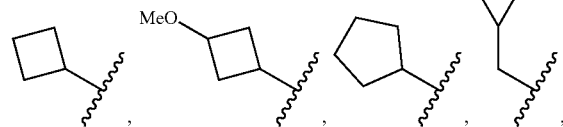

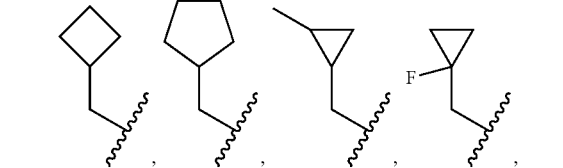

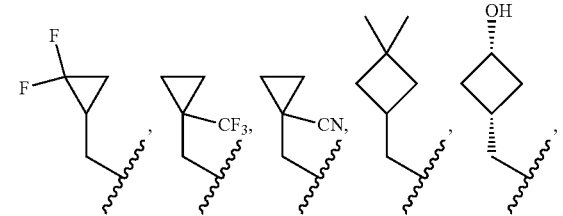

-continued

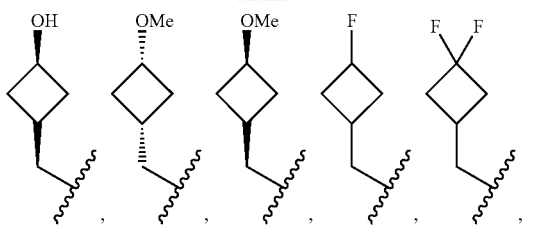

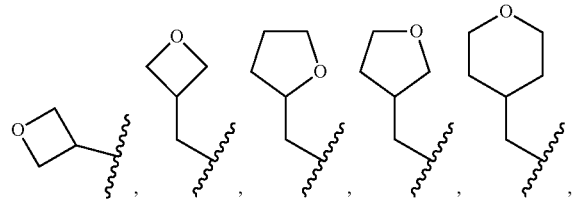

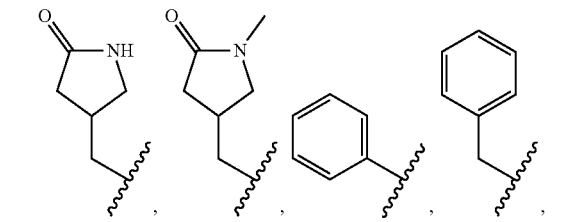

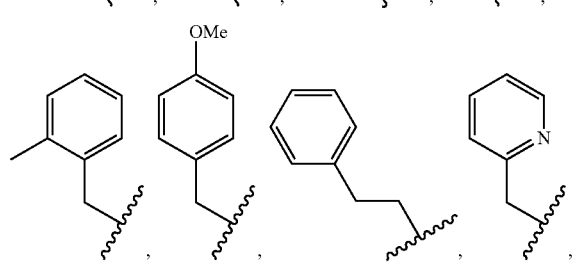

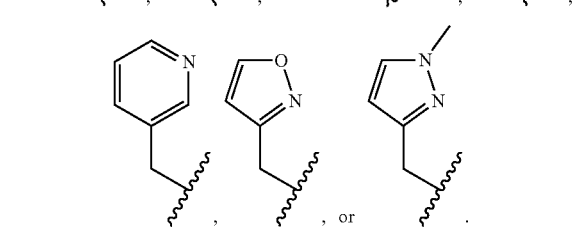

In some embodiments, the compound of Formula J, I, Ia, Ib, Ib-1, Ib-2, Ic or Id, or the pharmaceutically acceptable salt thereof, is the compound wherein $R^5$ is ethyl, iso-propyl, iso-butyl,

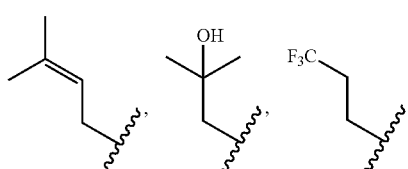

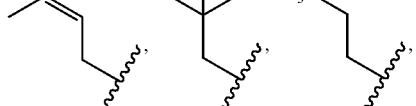

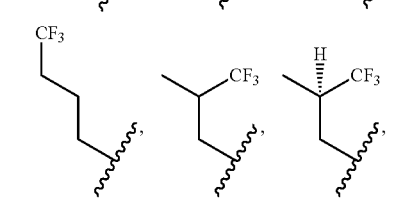

-continued

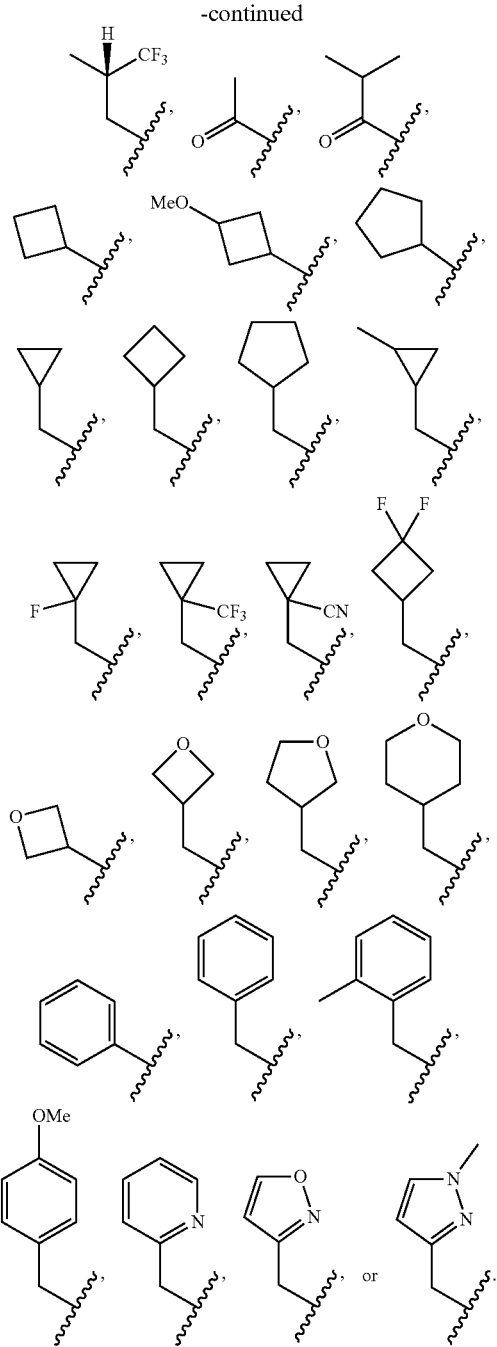

Each embodiment of $R^5$, $R^{5a}$, $R^{5b}$, $R^{5c}$, $R^{5c1}$, $R^{5c2}$, and $R^{5d}$ described herein can be combined with each embodiment of $R^1$, $A^1$, $A^2$, $A^3$, $A^4$, $R^2$, subscript n, $L^2$, $R^3$, $R^4$, $R^{4a}$, $R^{4b}$, and $R^{4c}$ described herein.

In some embodiments, the compound of Formula J, I, Ia, Ib, Ib-1, Ib-2, Ic, or Id, or the pharmaceutically acceptable salt thereof, is the compound wherein $R^6$ is hydrogen, $C_{1-6}$ alkyl or oxo; and subscript m is 0, 1 or 2. In some embodiments, the compound of Formula J, I, Ia, Ib, Ib-1, Ib-2, Ic or Id, or the pharmaceutically acceptable salt thereof, is the compound wherein $R^6$ is hydrogen or $C_{1-6}$ alkyl; and subscript m is 0 or 1. In some embodiments, the compound of Formula J, I, Ia, Ib, Ib-1, Ib-2, Ic or Id, or the pharmaceutically acceptable salt thereof, is the compound wherein $R^6$ is hydrogen or methyl; and subscript m is 0 or 1. In some embodiments, the compound of Formula J, I, Ia, Ib, Ib-1, Ib-2, Ic, or Id, or the pharmaceutically acceptable salt thereof, is the compound wherein $R^6$ is hydrogen, methyl, or oxo; and subscript m is 0, 1 or 2. In some embodiments, the compound of Formula J, I, Ia, Ib, Ib-1, Ib-2, Ic or Id, or the pharmaceutically acceptable salt thereof, is the compound wherein subscript m is 0.

Each embodiment of $R^6$ and subscript m described herein can be combined with each embodiment of $R^1$, $A^1$, $A^2$, $A^3$, $A^4$, $R^2$, subscript n, $L^2$, $R^3$, $R^4$, $R^{4a}$, $R^{4b}$, $R^{4c}$, $R^5$, $R^{5a}$, $R^{5b}$, $R^{5c}$, $R^{5c1}$, $R^{5c2}$, and $R^{5d}$ described herein.

In some embodiments, the compound of Formula J, I, Ia, Ib, Ib-1, Ib-2, Ic, or Id, or the pharmaceutically acceptable salt thereof, is the compound wherein
   $R^1$ is phenyl or heteroaryl having 5 to 6 ring members and 1 to 3 heteroatoms each N, each independently substituted with 0 to 3 $R^{1a}$ groups; each $R^{1a}$ is independently $C_{1-6}$ alkyl, $C_{1-6}$ alkoxy, $C_{1-6}$ hydroxyalkyl, halogen, $C_{1-6}$ haloalkyl, —OH, oxo, or —CN;
   each $R^{1b}$ and $R^{1c}$ is independently hydrogen or $C_{1-6}$ alkyl;
   $A^1$, $A^2$ and $A^4$ are each =CH—;
   $A^3$ is =C(Me)-, =C(OMe)-, =C(F)—, =C(Cl)—, or =C(CF_3)—; and
   subscript n is 1.

In some embodiments, the compound of Formula J, I, Ia, Ib, Ib-1, Ib-2, Ic, or Id, or the pharmaceutically acceptable salt thereof, is the compound wherein
   $R^1$ is phenyl or heteroaryl having 5 to 6 ring members and 1 to 3 heteroatoms each N, each independently substituted with 0 to 3 $R^{1a}$ groups; each $R^{1a}$ is independently $C_{1-6}$ alkyl, $C_{1-6}$ alkoxy, $C_{1-6}$ hydroxyalkyl, halogen, $C_{1-6}$ haloalkyl, —OH, oxo, or —CN;
   each $R^{1b}$ and $R^{1c}$ is independently hydrogen or $C_{1-6}$ alkyl;
   $A^1$, $A^2$ and $A^4$ are each =CH—;
   $A^3$ is =C(Me)-, =C(OMe)-, =C(F)—, =C(Cl)—, or =C(CF_3)—;
   subscript n is 1;
   $L^2$ is —C(O)—, —S(O)_2— or —S(O)_2N(R^3)—;
   $R^3$ is $C_{1-6}$ alkyl;
   $R^4$ is $C_{1-6}$ alkyl, $C_{2-3}$ alkoxyalkyl, $C_{1-3}$ hydroxyalkyl, $C_{3-6}$ cycloalkyl, $C_{1-2}$ alkyl-$C_{3-6}$ cycloalkyl, heterocycloalkyl, or heteroaryl, wherein each heterocycloalkyl independently has 5 to 6 ring members and 1 to 3 heteroatoms each independently N or O, wherein each heteroaryl independently has 5 to 6 ring members and 1 to 3 heteroatoms each independently N, O or S, and wherein the cycloalkyl, heterocycloalkyl, and heteroaryl are each independently substituted with 0 to 2 $R^{4a}$ groups; and
   each $R^{4a}$ is independently $C_{1-3}$ alkyl, $C_{2-3}$ alkoxyalkyl, halogen, $C_{1-3}$ haloalkyl, or heterocycloalkyl, wherein each heterocycloalkyl independently has 5 to 6 ring members and 1 to 2 heteroatoms each independently N or O.

In some embodiments, the compound of Formula J, I, Ia, Ib, Ib-1, Ib-2, Ic, or Id, or the pharmaceutically acceptable salt thereof, is the compound wherein
   $R^1$ is phenyl or heteroaryl having 5 to 6 ring members and 1 to 3 heteroatoms each N, each independently substituted with 0 to 3 $R^{1a}$ groups; each $R^{1a}$ is independently $C_{1-6}$ alkyl, $C_{1-6}$ alkoxy, $C_{1-6}$ hydroxyalkyl, halogen, $C_{1-6}$ haloalkyl, —OH, oxo, or —CN;
   each $R^{1b}$ and $R^{1c}$ is independently hydrogen or $C_{1-6}$ alkyl;
   $A^1$, $A^2$ and $A^4$ are each =CH—;
   $A^3$ is =C(Me)-, =C(OMe)-, =C(F)—, =C(Cl)—, or =C(CF_3)—;

subscript n is 1;
L² is —C(O)—, —S(O)₂— or —S(O)₂N(R³)—;
R³ is $C_{1-6}$ alkyl;
R⁴ is $C_{1-6}$ alkyl, $C_{2-3}$ alkoxyalkyl, $C_{1-3}$ hydroxyalkyl, $C_{3-6}$ cycloalkyl, $C_{1-2}$ alkyl-$C_{3-6}$ cycloalkyl, heterocycloalkyl, or heteroaryl, wherein each heterocycloalkyl independently has 5 to 6 ring members and 1 to 3 heteroatoms each independently N or O, wherein each heteroaryl independently has 5 to 6 ring members and 1 to 3 heteroatoms each independently N, O or S, and wherein the cycloalkyl, heterocycloalkyl, and heteroaryl are each independently substituted with 0 to 2 $R^{4a}$ groups;
each $R^{4a}$ is independently $C_{1-3}$ alkyl, $C_{2-3}$ alkoxyalkyl, halogen, $C_{1-3}$ haloalkyl, or heterocycloalkyl, wherein each heterocycloalkyl independently has 5 to 6 ring members and 1 to 2 heteroatoms each independently N or O;
R⁵ is $C_{1-6}$ alkyl, $C_{2-6}$ alkenyl, $C_{1-6}$ hydroxyalkyl, $C_{1-6}$ haloalkyl, —C(O)$R^{5a}$, $C_{1-2}$ alkyl-C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each heterocycloalkyl independently has 3 to 6 ring members and 1 to 2 heteroatoms each independently N or O, wherein each heteroaryl independently has 5 to 6 ring members and 1 to 3 heteroatoms each independently N, O or S, and wherein each cycloalkyl, heterocycloalkyl, aryl and heteroaryl is independently substituted with 0 to 2 $R^{5c}$ groups;
each $R^{5a}$ is independently $C_{1-6}$ alkyl;
each $R^{5c}$ is independently $C_{1-3}$ alkyl, $C_{1-3}$ alkoxy, halogen, $C_{1-3}$ haloalkyl, —CN, oxo or —OH; and
subscript m is 0.

In some embodiments, the compound of Formula J, I, Ia, Ib, Ib-1, Ib-2, Ic, or Id, or the pharmaceutically acceptable salt thereof, is the compound wherein
R¹ is phenyl, substituted with 0 to 2 $R^{1a}$ groups each independently methyl, —CH₂OH, fluoro, —CHF₂, or —CN, pyridyl, substituted with 0 to 3 $R^{1a}$ groups each independently methyl, —OMe, F, —OH or oxo, pyrazole, substituted with 1 to 2 $R^{1a}$ groups each independently methyl, pyridazine, substituted with 1 to 2 $R^{1a}$ groups each independently methyl or oxo, or pyrazine, substituted with 1 to 2 $R^{1a}$ groups each methyl;
A¹, A² and A⁴ are each =CH—;
A³ is =C(Me)-, =C(OMe)-, =C(F)—, =C(Cl)—, or =C(CF₃)—;
L² is —C(O)—, —S(O)₂— or —S(O)₂N(Me)-;
R⁴ is $C_{1-6}$ alkyl, $C_{2-3}$ alkoxyalkyl, $C_{1-3}$ hydroxyalkyl, $C_{1-6}$ haloalkyl, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-aryl, heteroaryl, or $C_{1-2}$ alkyl-heteroaryl, wherein each heterocycloalkyl independently has 5 to 6 ring members and 1 to 3 heteroatoms each independently N or O, wherein each heteroaryl independently has 5 to 6 ring members and 1 to 3 heteroatoms each independently N, O or S, and wherein the cycloalkyl, heterocycloalkyl, aryl, and heteroaryl are each independently substituted with 0 to 3 $R^{4a}$ groups;
each $R^{4a}$ is independently $C_{1-3}$ alkyl, $C_{1-3}$ alkoxy, $C_{2-3}$ alkoxyalkyl, halogen, $C_{1-3}$ haloalkyl, —CN, or heterocycloalkyl, wherein each heterocycloalkyl independently has 5 to 6 ring members and 1 to 2 heteroatoms each independently N or O;
R⁵ is $C_{1-6}$ alkyl, $C_{2-6}$ alkenyl, $C_{1-6}$ hydroxyalkyl, $C_{1-6}$ haloalkyl, —C(O)$R^{5a}$, $C_{1-2}$ alkyl-C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each heterocycloalkyl independently has 3 to 6 ring members and 1 to 2 heteroatoms each independently N or O, wherein each heteroaryl independently has 5 to 6 ring members and 1 to 3 heteroatoms each independently N, O or S, and wherein each cycloalkyl, heterocycloalkyl, aryl and heteroaryl is independently substituted with 0 to 2 $R^{5c}$ groups;
each $R^{5a}$ is independently $C_{1-6}$ alkyl;
each $R^{5c}$ is independently $C_{1-3}$ alkyl, $C_{1-3}$ alkoxy, halogen, $C_{1-3}$ haloalkyl, —CN, oxo or —OH;
R⁶ is hydrogen, methyl, or oxo;
subscript m is 0, 1 or 2; and
subscript n is 1.

In some embodiments, the compound of Formula J, I, Ia, Ib, Ib-1, Ib-2, Ic, or Id, or the pharmaceutically acceptable salt thereof, is the compound wherein
R¹ is phenyl, substituted with 1 to 2 $R^{1a}$ groups each independently fluoro or —CN, pyridyl, substituted with 0 to 3 $R^{1a}$ groups each independently methyl, —OH or oxo, or pyrazole, substituted with 1 to 2 $R^{1a}$ groups each independently methyl;
A¹, A² and A⁴ are each =CH—;
A³ is =C(Me)-, =C(OMe)-, =C(F)—, =C(Cl)—, or =C(CF₃)—;
L² is —C(O)—, —S(O)₂— or —S(O)₂N(Me)-;
R⁴ is $C_{1-6}$ alkyl, $C_{2-3}$ alkoxyalkyl, $C_{1-3}$ hydroxyalkyl, $C_{1-6}$ haloalkyl, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-aryl, heteroaryl, or $C_{1-2}$ alkyl-heteroaryl, wherein each heterocycloalkyl independently has 5 to 6 ring members and 1 to 3 heteroatoms each independently N or O, wherein each heteroaryl independently has 5 to 6 ring members and 1 to 3 heteroatoms each independently N, O or S, and wherein the cycloalkyl, heterocycloalkyl, aryl, and heteroaryl are each independently substituted with 0 to 3 $R^{4a}$ groups;
each $R^{4a}$ is independently $C_{1-3}$ alkyl, $C_{1-3}$ alkoxy, $C_{2-3}$ alkoxyalkyl, halogen, $C_{1-3}$ haloalkyl, —CN, or heterocycloalkyl, wherein each heterocycloalkyl independently has 5 to 6 ring members and 1 to 2 heteroatoms each independently N or O;
R⁵ is $C_{1-6}$ alkyl, $C_{2-6}$ alkenyl, $C_{1-6}$ hydroxyalkyl, $C_{1-6}$ haloalkyl, —C(O)$R^{5a}$, $C_{1-2}$ alkyl-C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each heterocycloalkyl independently has 3 to 6 ring members and 1 to 2 heteroatoms each independently N or O, wherein each heteroaryl independently has 5 to 6 ring members and 1 to 3 heteroatoms each independently N, O or S, and wherein each cycloalkyl, heterocycloalkyl, aryl and heteroaryl is independently substituted with 0 to 2 $R^{5c}$ groups;
each $R^{5a}$ is independently $C_{1-6}$ alkyl;
each $R^{5c}$ is independently $C_{1-3}$ alkyl, $C_{1-3}$ alkoxy, halogen, $C_{1-3}$ haloalkyl, —CN, oxo or —OH;
R⁶ is hydrogen, methyl, or oxo; and
subscript m is 0, 1 or 2.

In some embodiments, the compound of Formula J, I, Ia, Ib, Ib-1, Ib-2, Ic or Id, or the pharmaceutically acceptable salt thereof, is the compound wherein
R¹ is phenyl substituted with halogen;
A¹, A² and A⁴ are each =CH—;
A³ is =C(Me)-, =C(OMe)- or =C(Cl)—;
L² is —C(O)—, —S(O)₂— or —S(O)₂N(Me)-;

R⁴ is $C_{1-6}$ alkyl, $C_{2-3}$ alkoxyalkyl, $C_{1-3}$ hydroxyalkyl, $C_{3-6}$ cycloalkyl, $C_{1-2}$ alkyl-$C_{3-6}$ cycloalkyl, heterocycloalkyl, or heteroaryl, wherein each heterocycloalkyl independently has 5 to 6 ring members and 1 to 3 heteroatoms each independently N or O, wherein each heteroaryl independently has 5 to 6 ring members and 1 to 3 heteroatoms each independently N, O or S, and wherein the cycloalkyl, heterocycloalkyl, and heteroaryl are each independently substituted with 0 to 2 $R^{4a}$ groups;

each $R^{4a}$ is independently $C_{1-3}$ alkyl, $C_{2-3}$ alkoxyalkyl, halogen, $C_{1-3}$ haloalkyl, or heterocycloalkyl, wherein each heterocycloalkyl independently has 5 to 6 ring members and 1 to 2 heteroatoms each independently N or O;

R⁵ is $C_{1-6}$ alkyl, $C_{2-6}$ alkenyl, $C_{1-6}$ hydroxyalkyl, $C_{1-6}$ haloalkyl, —C(O)$R^{5a}$, $C_{3-6}$ cycloalkyl, $C_{1-2}$ alkyl-$C_{3-6}$ cycloalkyl, heterocycloalkyl, $C_{1-2}$ alkyl-heterocycloalkyl, $C_{6-12}$ aryl, $C_{1-2}$ alkyl-$C_{6-12}$ aryl, or $C_{1-2}$ alkyl-heteroaryl, wherein each heterocycloalkyl independently has 3 to 6 ring members and 1 to 2 heteroatoms each independently N or O, wherein each heteroaryl independently has 5 to 6 ring members and 1 to 3 heteroatoms each independently N, O or S, and wherein each cycloalkyl, heterocycloalkyl, aryl and heteroaryl is independently substituted with 0 to 2 $R^{5c}$ groups;

each $R^{5a}$ is independently $C_{1-6}$ alkyl;

each $R^{5c}$ is independently $C_{1-3}$ alkyl, $C_{1-3}$ alkoxy, halogen, $C_{1-3}$ haloalkyl, or —CN;

R⁶ is hydrogen or methyl; and subscript m is 0 or 1.

In some embodiments, the compound of Formula J, I, Ia, Ib, Ib-1, Ib-2, Ic, or Id, or the pharmaceutically acceptable salt thereof, is the compound wherein R¹ is phenyl or heteroaryl having 5 to 6 ring members and 1 to 3 heteroatoms each N, each independently substituted with 0 to 3 $R^{1a}$ groups;

each $R^{1a}$ is independently $C_{1-6}$ alkyl, $C_{1-6}$ alkoxy, $C_{1-6}$ hydroxyalkyl, halogen, $C_{1-6}$ haloalkyl, —OH, oxo, —CN, or $C_{1-6}$ alkyl-C(O)N($R^{1b}$)($R^{1c}$);

each $R^{1b}$ and $R^{1c}$ is independently hydrogen or $C_{1-6}$ alkyl;

A¹, A² and A⁴ are each =CH—;

A³ is =C(Me)-, =C(OMe)-, =C(F)—, =C(Cl)—, or =C(CF₃)—;

R⁴ is heteroaryl, having 5 to 6 ring members and 1 to 3 heteroatoms each independently N, O or S, and substituted with 0 to 3 $R^{4a}$ groups;

each $R^{4a}$ is independently $C_{1-3}$ alkyl, $C_{1-3}$ alkoxy, $C_{2-3}$ alkoxyalkyl, halogen, $C_{1-3}$ haloalkyl, —CN, or heterocycloalkyl, wherein each heterocycloalkyl independently has 5 to 6 ring members and 1 to 2 heteroatoms each independently N or O;

R⁵ is $C_{1-6}$ alkyl, $C_{1-6}$ haloalkyl, or $C_{1-2}$ alkyl-$C_{3-6}$ cycloalkyl, wherein each cycloalkyl is independently substituted with 0 to 2 $R^{5c}$ groups;

each $R^{5c}$ is independently $C_{1-3}$ alkyl, $C_{1-3}$ alkoxy, halogen, $C_{1-3}$ haloalkyl, —CN, oxo or —OH;

subscript m is 0; and subscript n is 1.

In some embodiments, the compound of Formula J, I, Ia, Ib, Ib-1, Ib-2, Ic, or Id, or the pharmaceutically acceptable salt thereof, is the compound wherein R¹ is

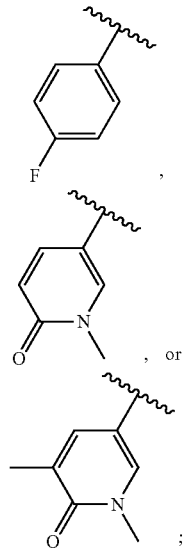

A¹, A² and A⁴ are each =CH—;

A³ is =C(Me)-;

L² is —S(O)₂—;

R⁴ is pyridine, pyrazole, thiazole, or triazole, each substituted with 0 to 2 $R^{4a}$ groups;

each $R^{4a}$ is independently methyl, ethyl, n-propyl, iso-propyl, methoxy, methoxyethyl, fluoro, —CHF₂, —CF₃, —CH₂CHF₂, —CH₂CF₃, —CN, or tetrahydropyran;

R⁵ is $C_{1-6}$ alkyl, $C_{1-6}$ haloalkyl, or $C_{1-2}$ alkyl-$C_{3-6}$ cycloalkyl, wherein each cycloalkyl is independently substituted with 0 to 2 $R^{5c}$ groups;

each $R^{5c}$ is independently $C_{1-3}$ alkyl, $C_{1-3}$ alkoxy, halogen, $C_{1-3}$ haloalkyl, —CN, oxo or —OH;

subscript m is 0; and subscript n is 1.

In some embodiments, the compound of Formula J, I, Ia, Ib, Ib-1, Ib-2, Ic, or Id, or the pharmaceutically acceptable salt thereof, is the compound wherein R¹ is

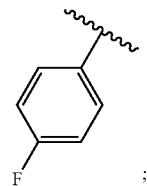

A¹, A² and A⁴ are each =CH—;

A³ is =C(Me)-;

L² is —S(O)₂—;

R⁴ is pyrazole or triazole, each substituted with 1 $R^{4a}$ groups;

$R^{4a}$ is methyl, ethyl, n-propyl, or iso-propyl;

R⁵ is $C_{1-6}$ haloalkyl;

subscript m is 0; and subscript n is 1.

In some embodiments, the compound of Formula J, I, Ia, Ib, Ib-1, Ib-2, Ic, or Id, or the pharmaceutically acceptable salt thereof, is the compound wherein
R[1] is
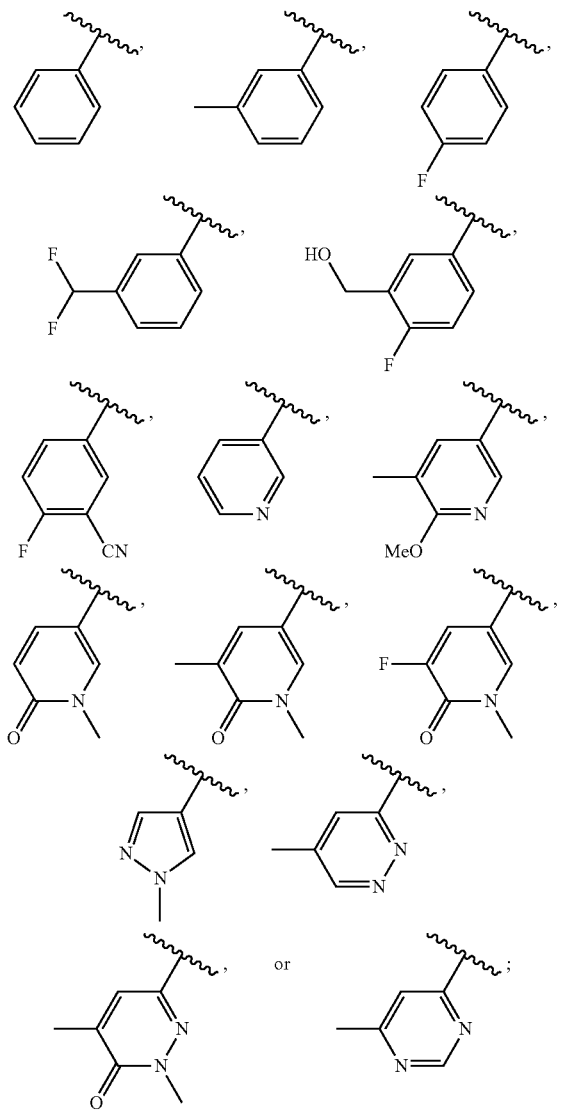
A[1], A[2] and A[4] are each =CH—;
A[3] is =C(Me)-, =C(OMe)-, =C(F)—, =C(Cl)—, or =C(CF$_3$)—;
L[2] is —C(O)—, —S(O)$_2$— or —S(O)$_2$N(Me)-;
R[4] is methyl, n-propyl, iso-butyl, —CH(OH)CH$_3$, methoxyethyl, isopropoxyethyl, CH$_2$CF$_3$, -continued
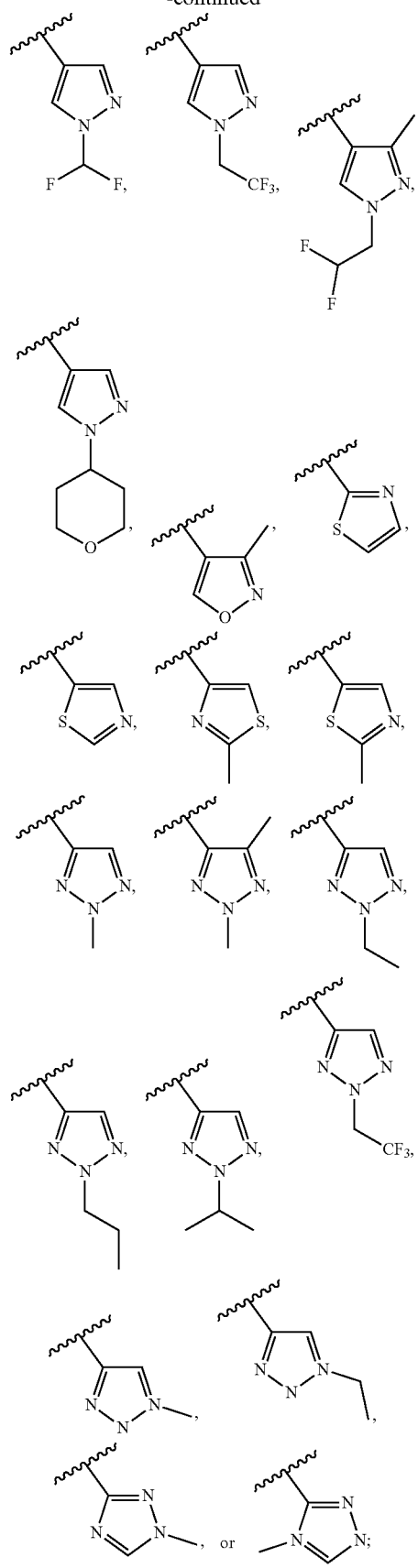
$R^5$ is ethyl, iso-propyl, iso-butyl,
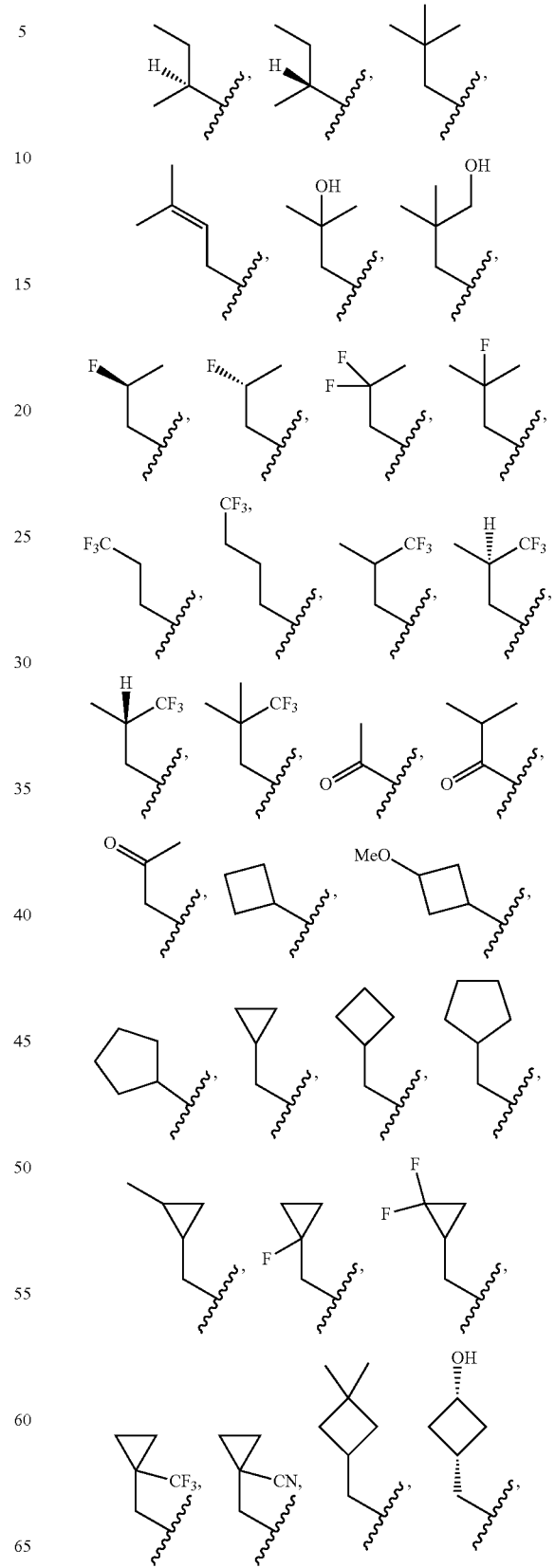

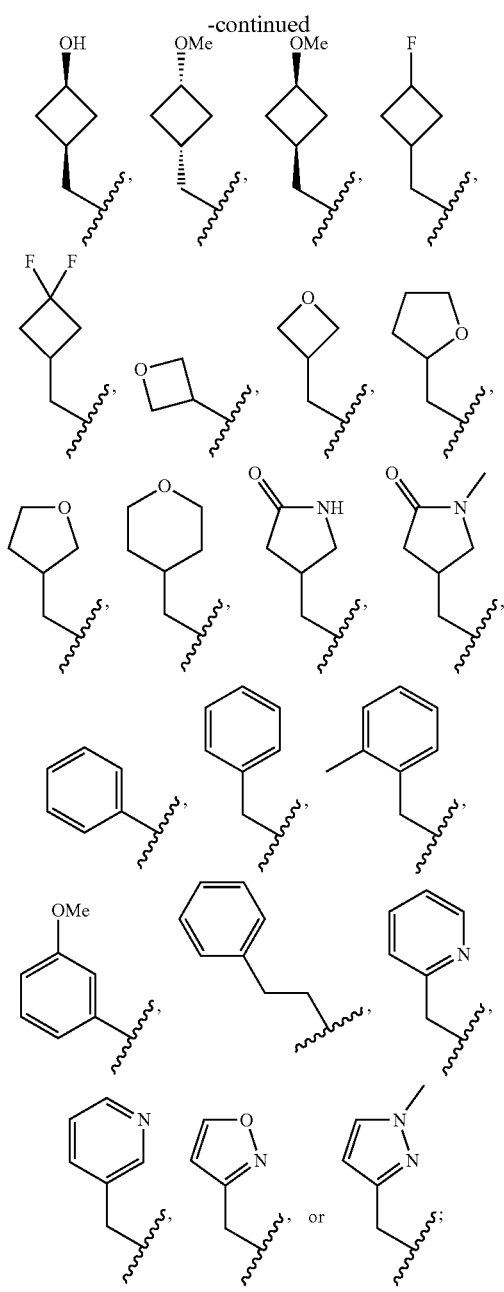

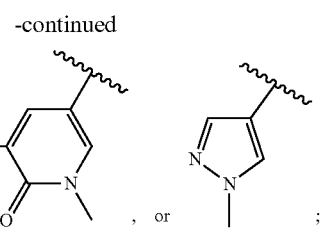

$A^1$, $A^2$ and $A^4$ are each =CH—;

$A^3$ is =C(Me)-, =C(OMe)-, =C(F)—, =C(Cl)—, or =C(CF$_3$)—;

$L^2$ is —C(O)—, —S(O)$_2$— or —S(O)$_2$N(Me)-;

$R^4$ is methyl, n-propyl, iso-butyl, —CH(OH)CH$_3$, methoxyethyl, isopropoxyethyl, CH$_2$CF$_3$,

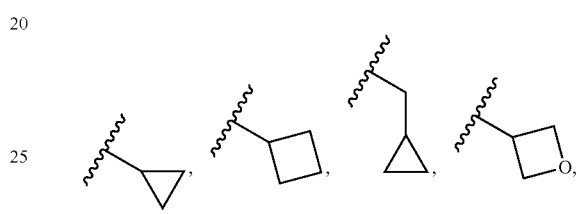

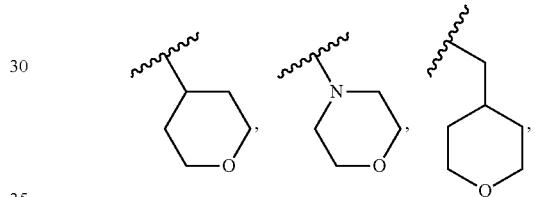

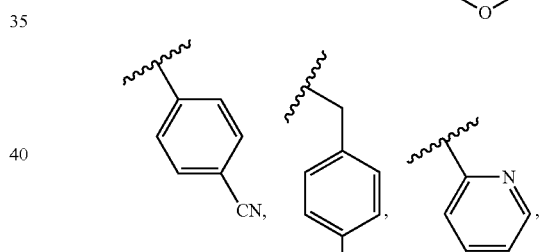

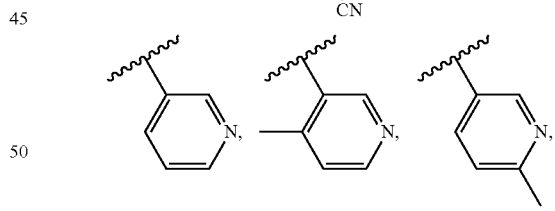

$R^6$ is hydrogen, methyl, or oxo; and subscript m is 0, 1 or 2.

In some embodiments, the compound of Formula J, I, Ia, Ib, Ib-1, Ib-2, Ic, or Id, or the pharmaceutically acceptable salt thereof, is the compound wherein $R^1$ is

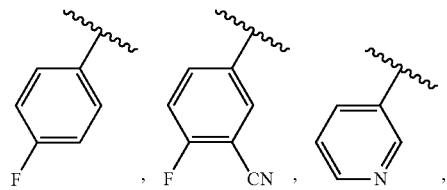

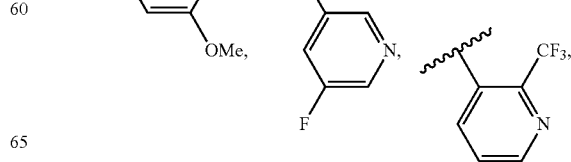

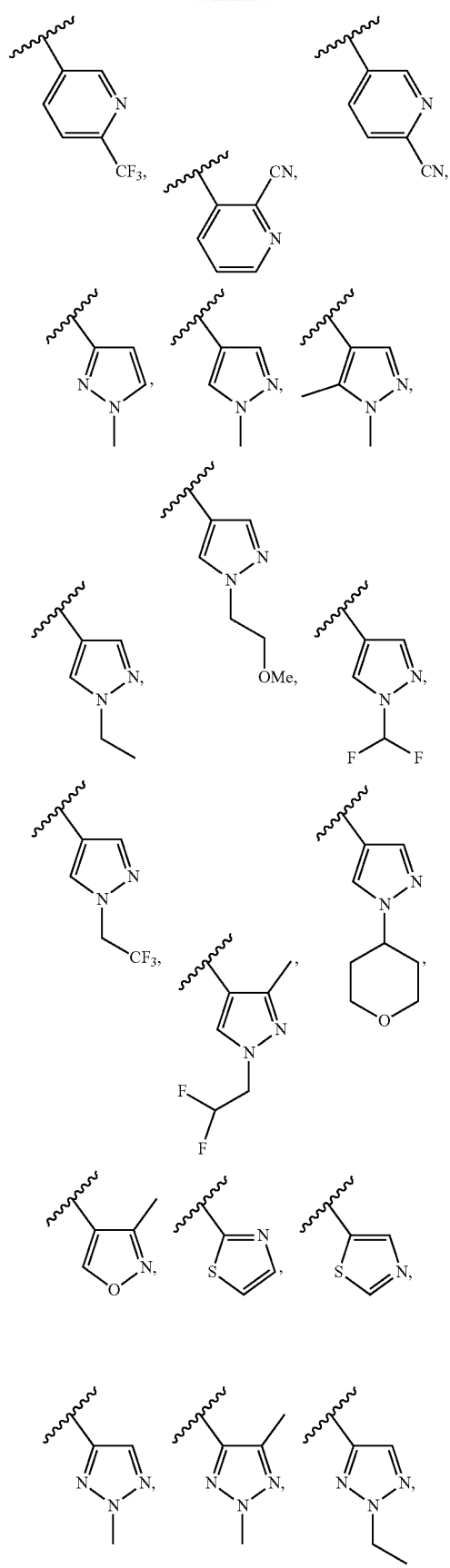
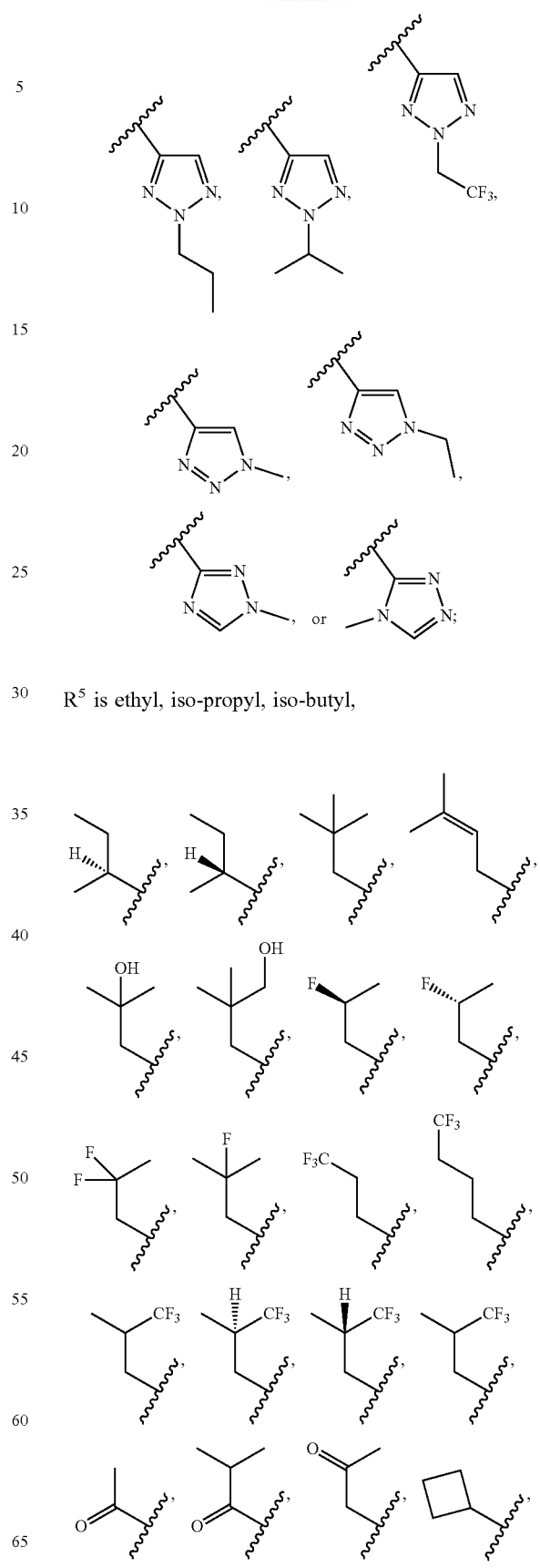
R[5] is ethyl, iso-propyl, iso-butyl,

-continued
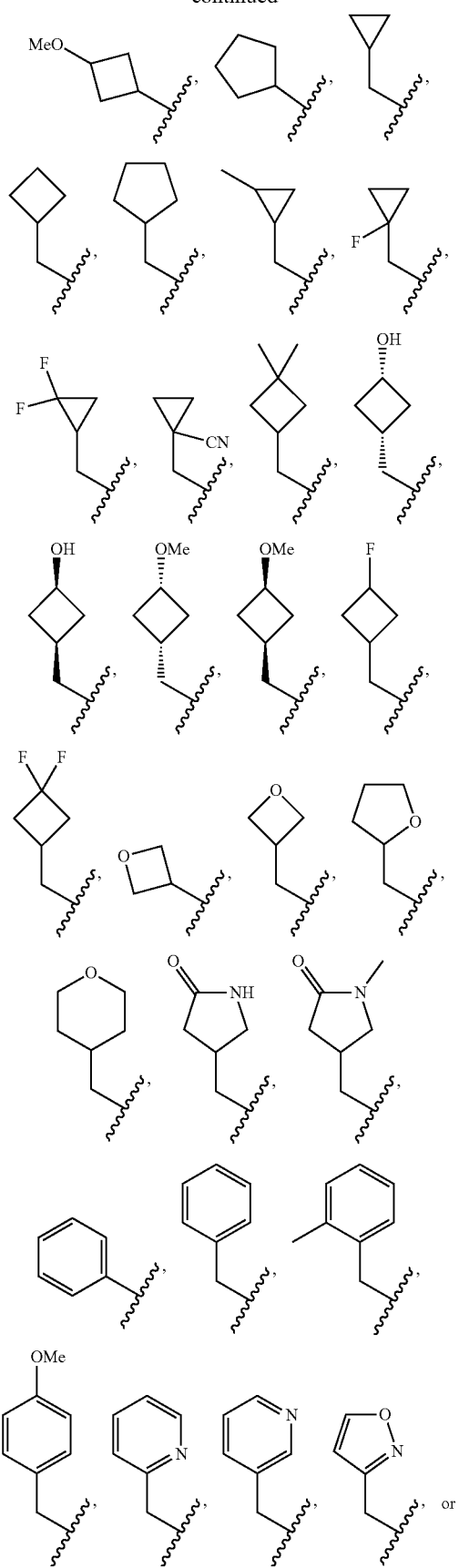
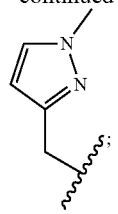
$R^6$ is hydrogen, methyl, or oxo; and
subscript m is 0, 1 or 2.
In some embodiments, the compound of Formula J, I, Ia, Ib, Ib-1, Ib-2, Ic or Id, or the pharmaceutically acceptable salt thereof, is the compound wherein
$R^1$ is
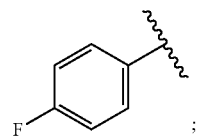 [SMILES: *c1ccc(F)cc1]
$A^1$, $A^2$ and $A^4$ are each =CH—;
$A^3$ is =C(Me)-, =C(OMe)- or =C(Cl)—;
$L^2$ is —C(O)—, —S(O)$_2$— or —S(O)$_2$N(Me)-;
$R^4$ is methyl, n-propyl, iso-butyl, —CH(OH)CH$_3$, methoxyethyl,
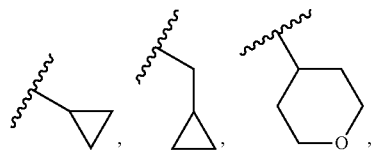
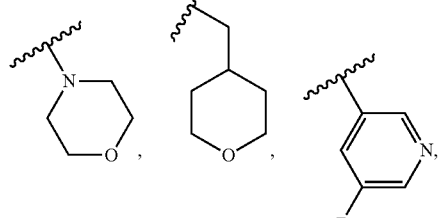
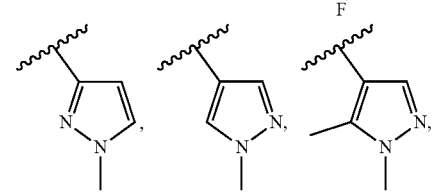
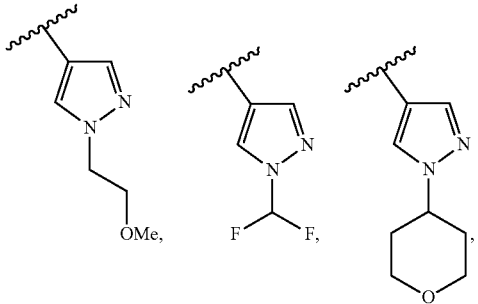

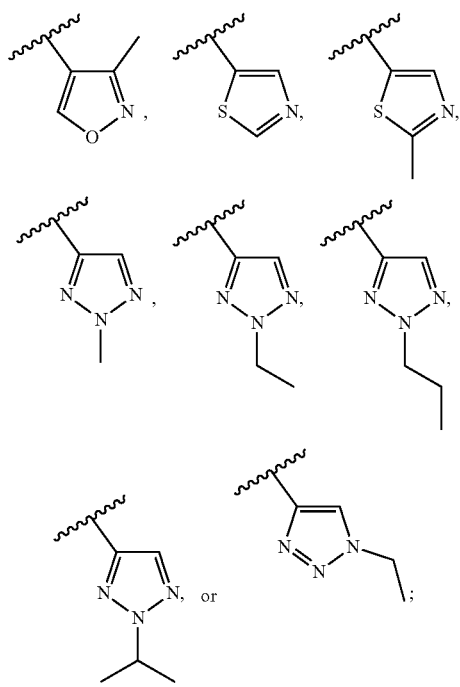
$R^5$ is ethyl, iso-propyl, iso-butyl,
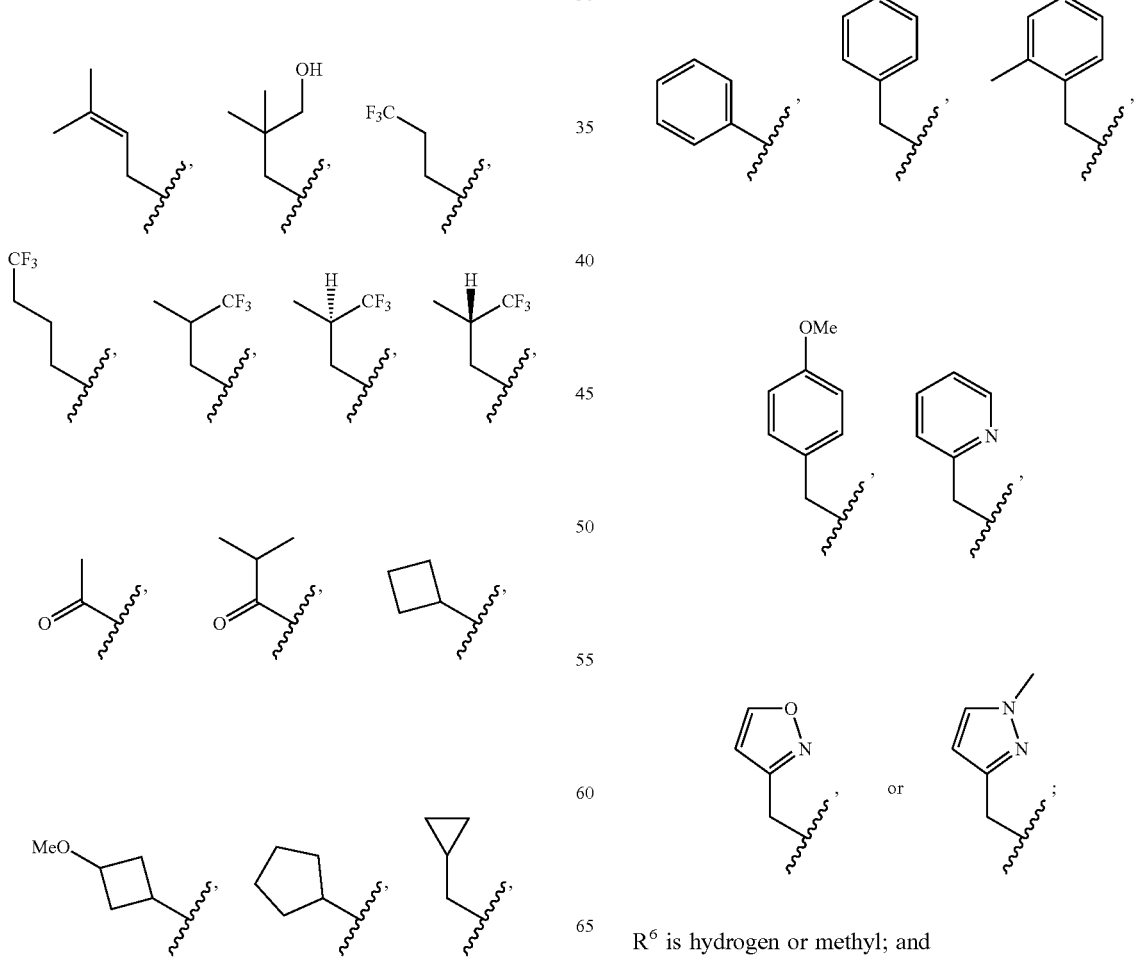
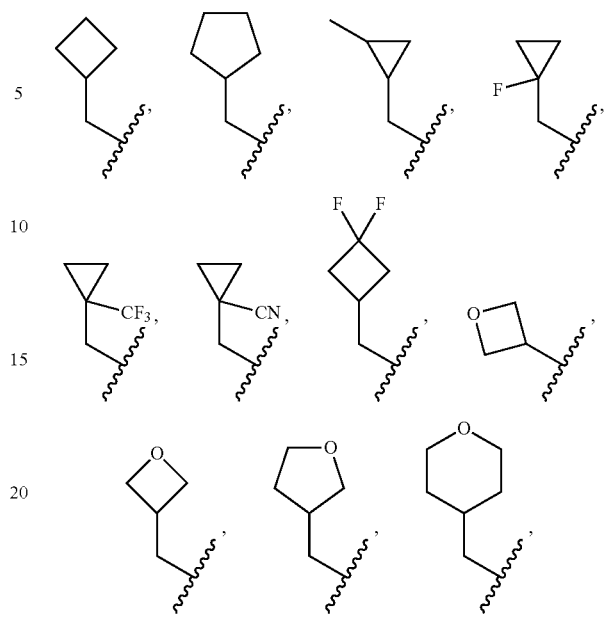
$R^6$ is hydrogen or methyl; and subscript m is 0 or 1.

In some embodiments, the compound of Formula J, I, Ia, Ib, Ib-1, Ib-2, Ic or Id, or the pharmaceutically acceptable salt thereof, is a compound of Table 1A.
TABLE 1A
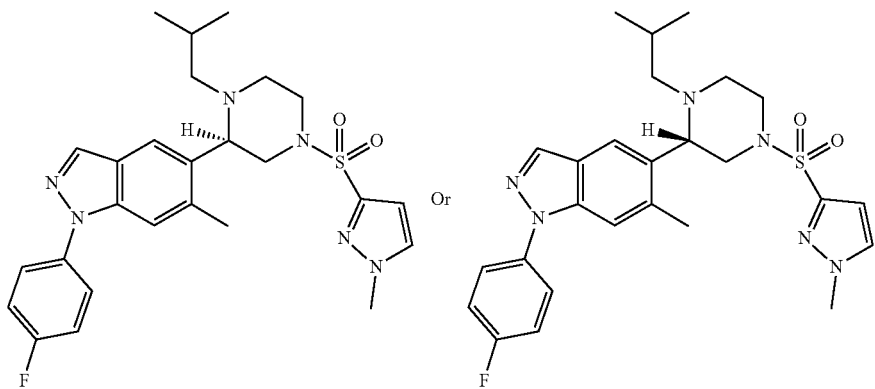 [SMILES: Cc1cc2c(cnn2-c2ccc(F)cc2)cc1[C@@H]1CN(S(=O)(=O)c2ccn(C)n2)CCN1CC(C)C ; Cc1cc2c(cnn2-c2ccc(F)cc2)cc1[C@H]1CN(S(=O)(=O)c2ccn(C)n2)CCN1CC(C)C]
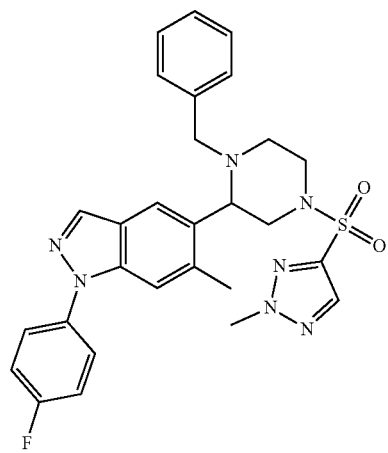 [SMILES: Cc1cc2c(cnn2-c2ccc(F)cc2)cc1C1CN(S(=O)(=O)c2cnn(C)n2)CCN1Cc1ccccc1]
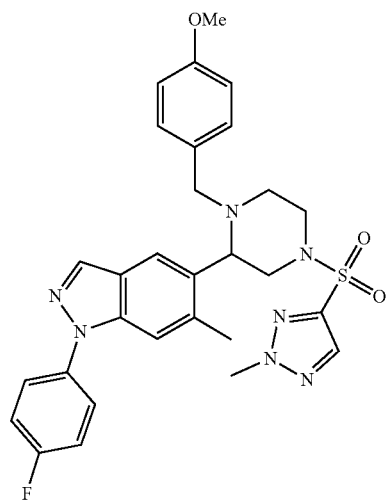 [SMILES: COc1ccc(CN2CCN(S(=O)(=O)c3cnn(C)n3)CC2c2cc3cnn(-c4ccc(F)cc4)c3cc2C)cc1]

TABLE 1A-continued
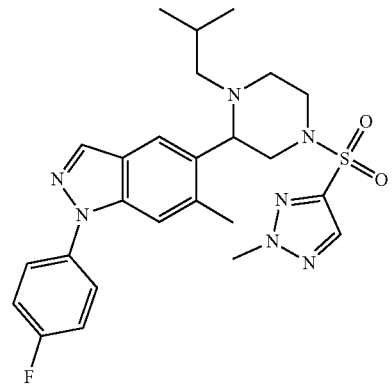 [SMILES: Cc1cc2c(cnn2-c2ccc(F)cc2)cc1C1CN(S(=O)(=O)c2cnn(C)n2)CCN1CC(C)C]
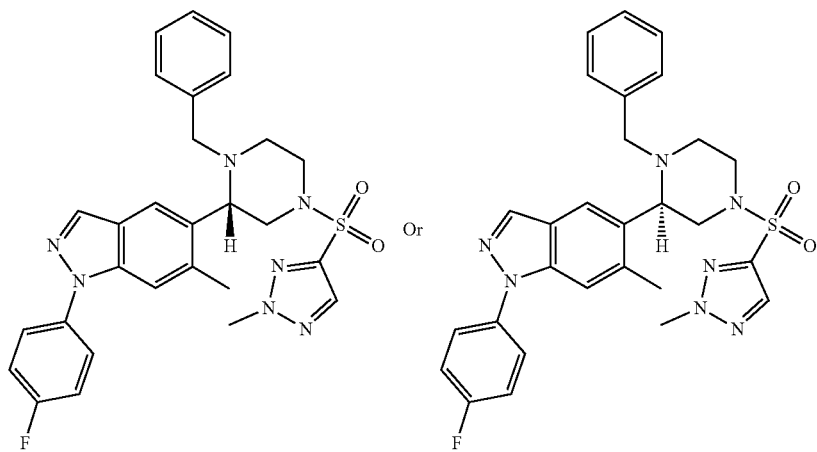 [SMILES: Cc1cc2c(cnn2-c2ccc(F)cc2)cc1[C@H]1CN(S(=O)(=O)c2cnn(C)n2)CCN1Cc1ccccc1 ; Cc1cc2c(cnn2-c2ccc(F)cc2)cc1[C@@H]1CN(S(=O)(=O)c2cnn(C)n2)CCN1Cc1ccccc1]
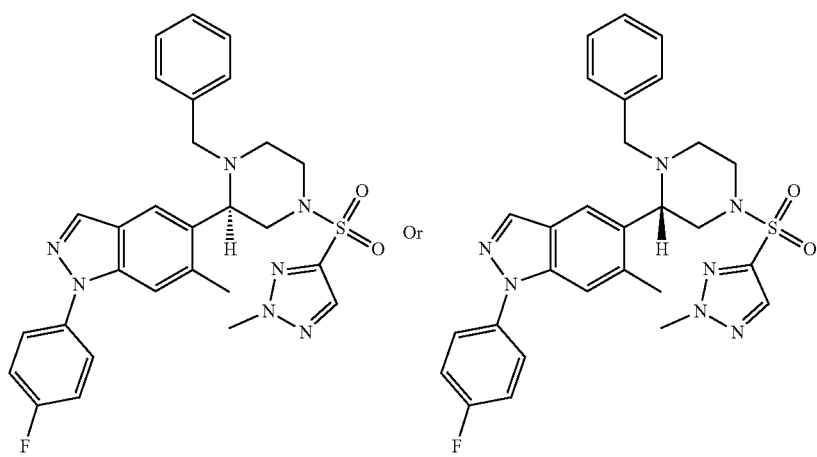 [SMILES: Cc1cc2c(cnn2-c2ccc(F)cc2)cc1[C@@H]1CN(S(=O)(=O)c2cnn(C)n2)CCN1Cc1ccccc1 ; Cc1cc2c(cnn2-c2ccc(F)cc2)cc1[C@H]1CN(S(=O)(=O)c2cnn(C)n2)CCN1Cc1ccccc1]

TABLE 1A-continued
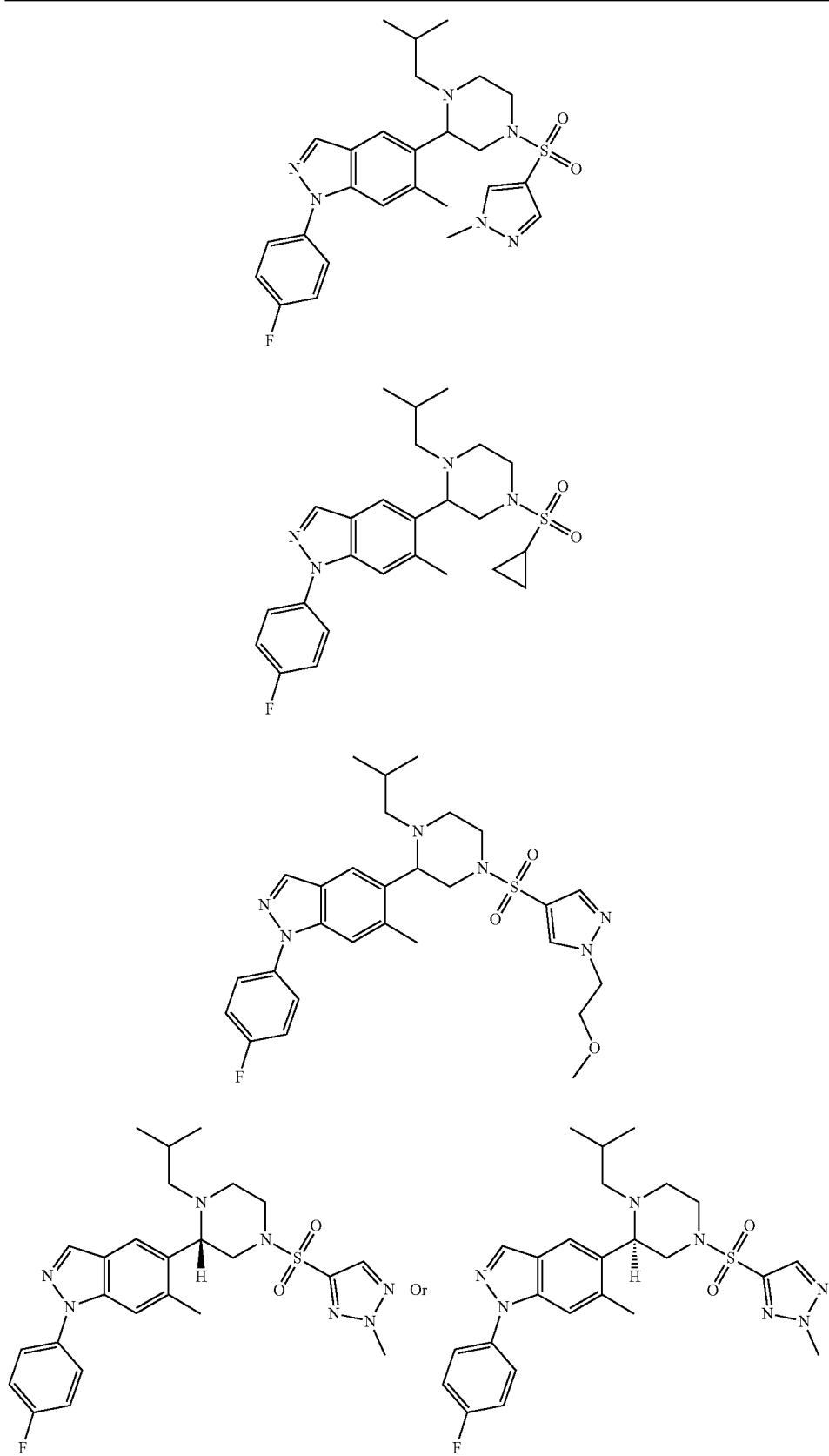

TABLE 1A-continued
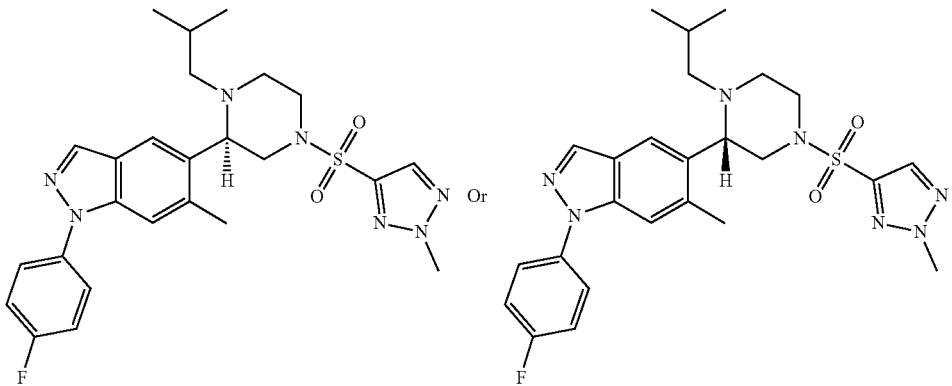 [SMILES: Cc1cc2c(cnn2-c2ccc(F)cc2)cc1[C@@H]1CN(S(=O)(=O)c2cnn(C)n2)CCN1CC(C)C ; Cc1cc2c(cnn2-c2ccc(F)cc2)cc1[C@H]1CN(S(=O)(=O)c2cnn(C)n2)CCN1CC(C)C]
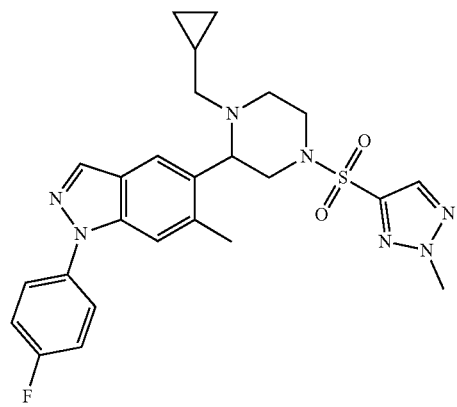 [SMILES: Cc1cc2c(cnn2-c2ccc(F)cc2)cc1C1CN(S(=O)(=O)c2cnn(C)n2)CCN1CC1CC1]
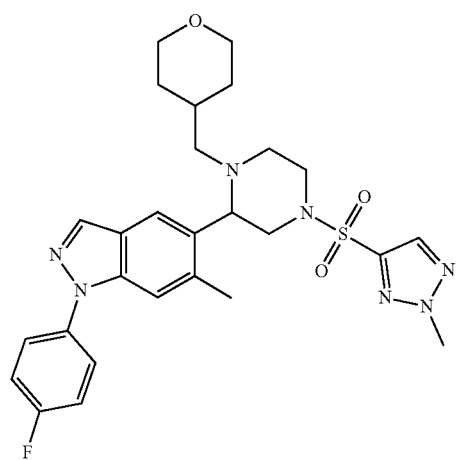 [SMILES: Cc1cc2c(cnn2-c2ccc(F)cc2)cc1C1CN(S(=O)(=O)c2cnn(C)n2)CCN1CC1CCOCC1]

TABLE 1A-continued
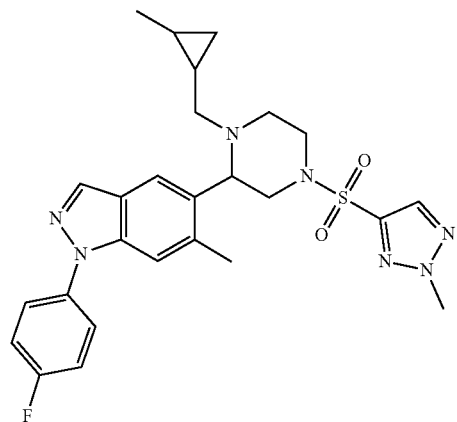 [SMILES: Cc1cc2c(cnn2-c2ccc(F)cc2)cc1C1CN(S(=O)(=O)c2cnn(C)n2)CCN1CC1CC1C]
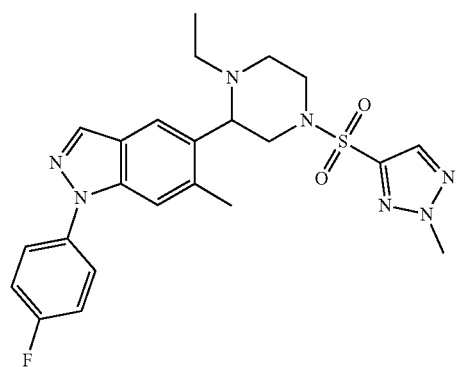 [SMILES: CCN1CCN(S(=O)(=O)c2cnn(C)n2)CC1c1cc2cnn(-c3ccc(F)cc3)c2cc1C]
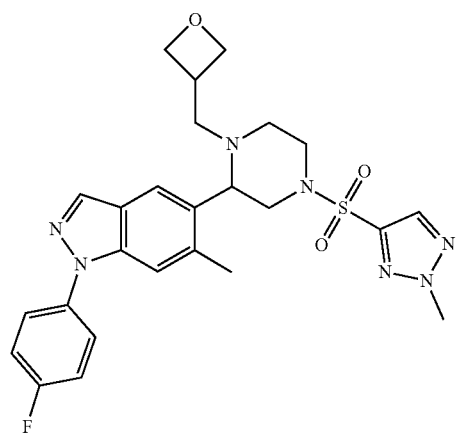 [SMILES: Cc1cc2c(cnn2-c2ccc(F)cc2)cc1C1CN(S(=O)(=O)c2cnn(C)n2)CCN1CC1COC1]
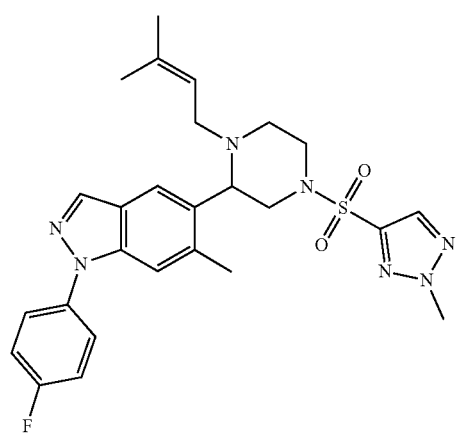 [SMILES: CC(C)=CCN1CCN(S(=O)(=O)c2cnn(C)n2)CC1c1cc2cnn(-c3ccc(F)cc3)c2cc1C]

TABLE 1A-continued
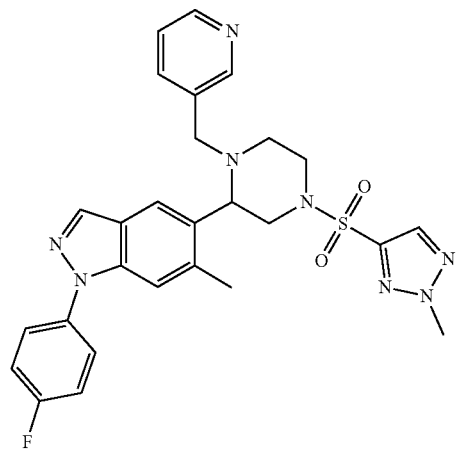 [SMILES: Cc1cc2c(cnn2-c2ccc(F)cc2)cc1C1CN(S(=O)(=O)c2cnn(C)n2)CCN1Cc1cccnc1]
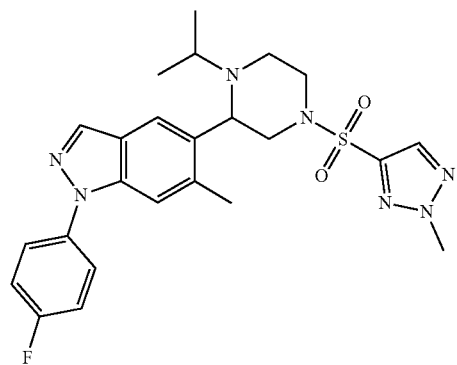 [SMILES: Cc1cc2c(cnn2-c2ccc(F)cc2)cc1C1CN(S(=O)(=O)c2cnn(C)n2)CCN1C(C)C]
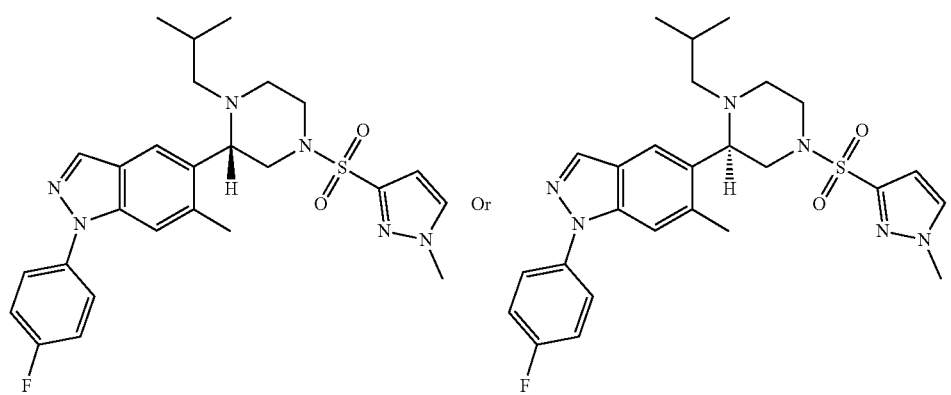 [SMILES: Cc1cc2c(cnn2-c2ccc(F)cc2)cc1[C@H]1CN(S(=O)(=O)c2ccn(C)n2)CCN1CC(C)C ; Cc1cc2c(cnn2-c2ccc(F)cc2)cc1[C@@H]1CN(S(=O)(=O)c2ccn(C)n2)CCN1CC(C)C]

In some embodiments, the compound of Formula J, I, Ia, Ib, Ib-1, Ib-2, Ic or Id, or the pharmaceutically acceptable salt thereof, is a compound of Table 1B.
TABLE 1B
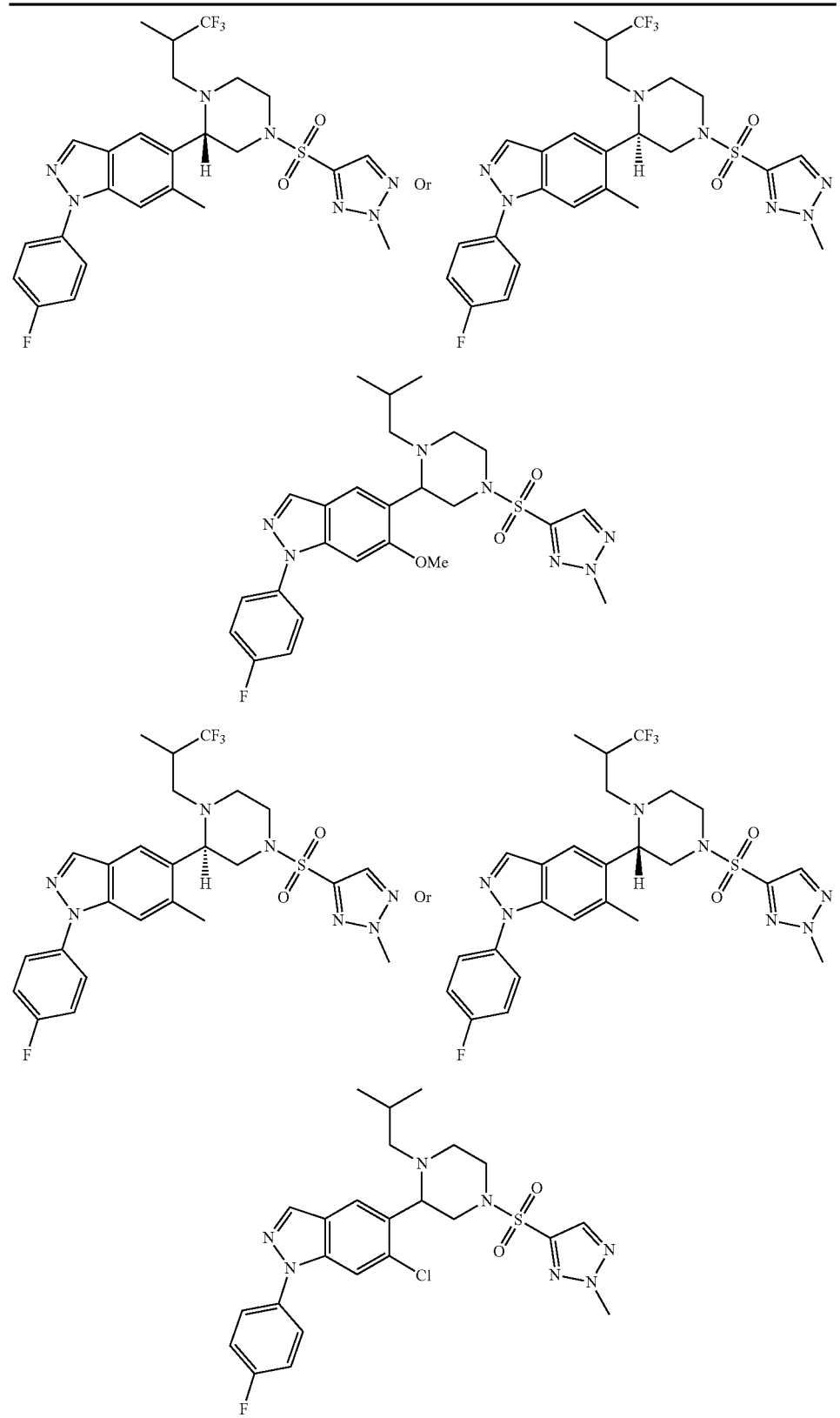

TABLE 1B-continued
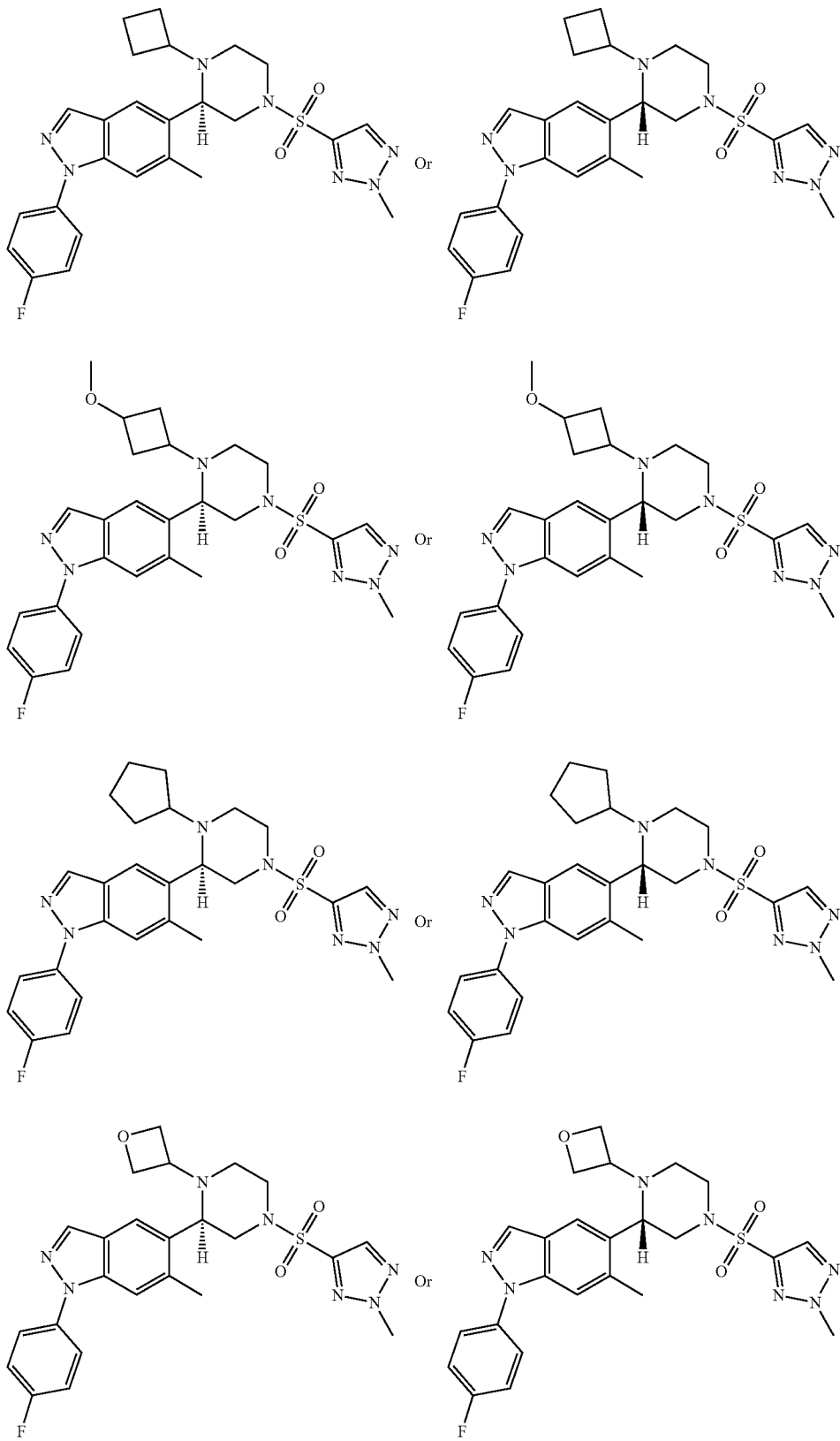

TABLE 1B-continued
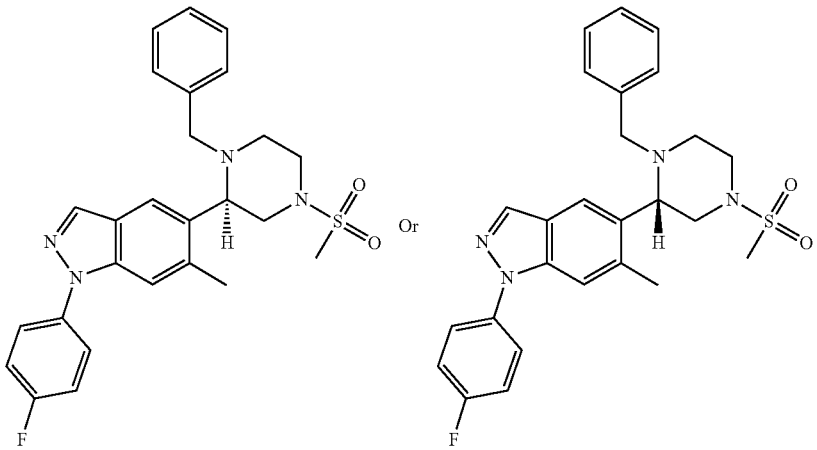
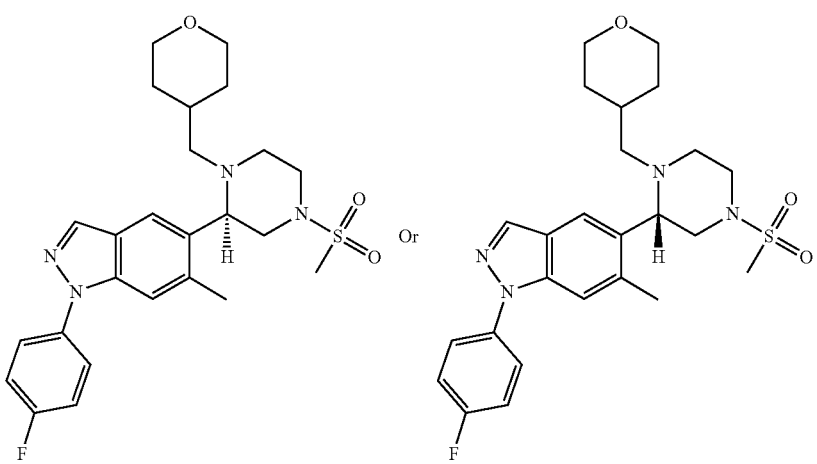
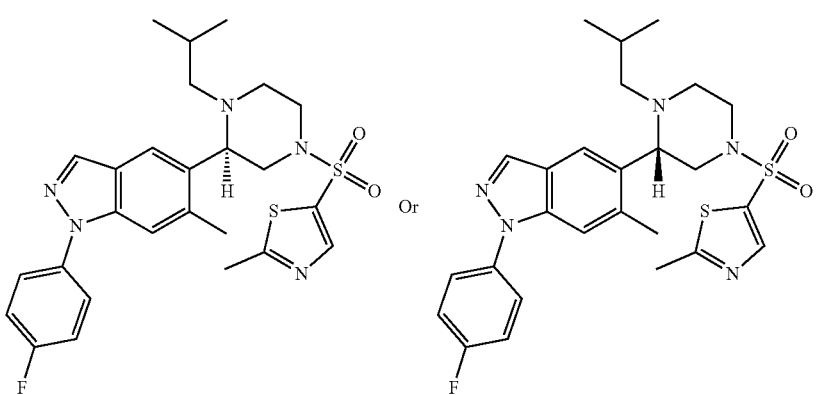

TABLE 1B-continued
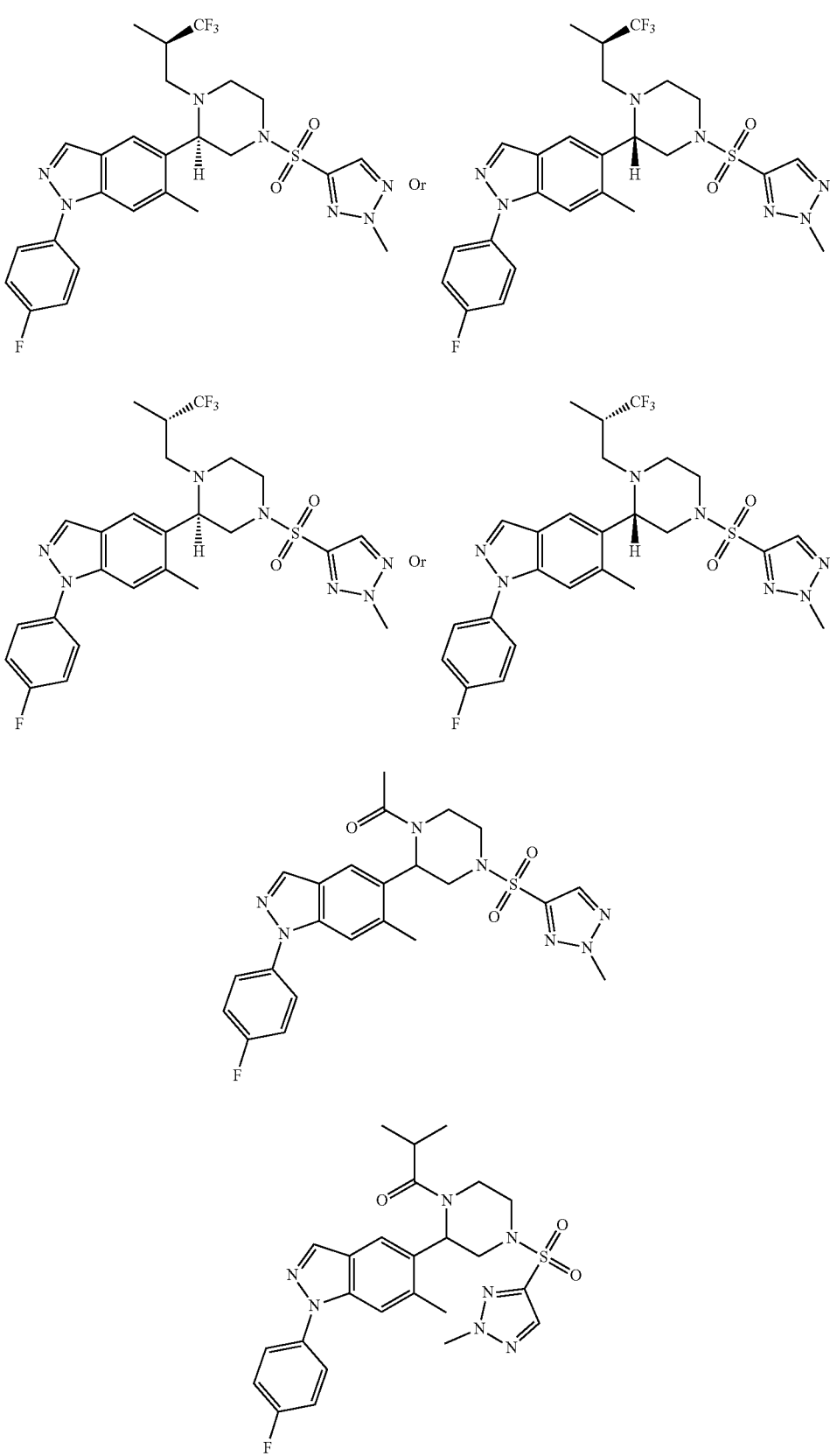

TABLE 1B-continued
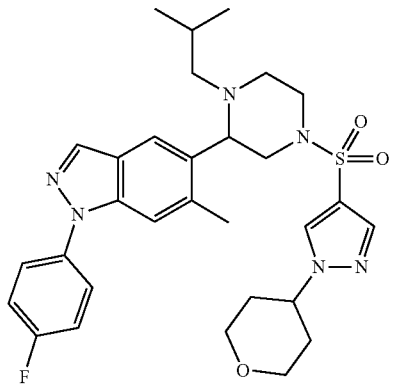
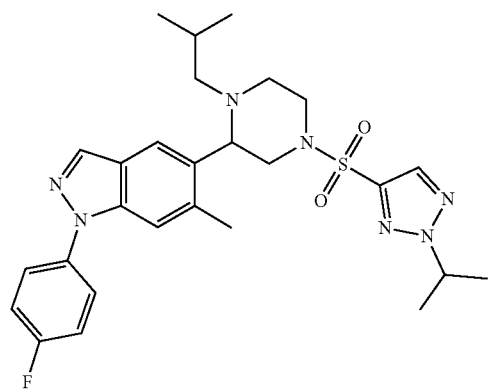
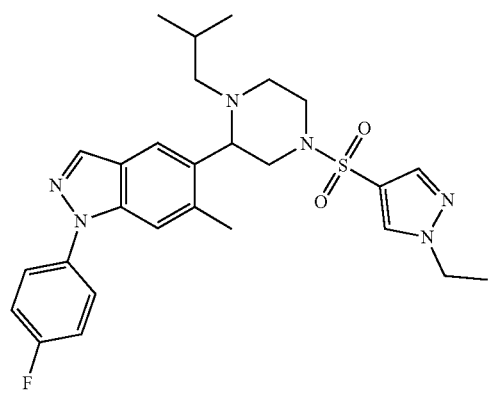
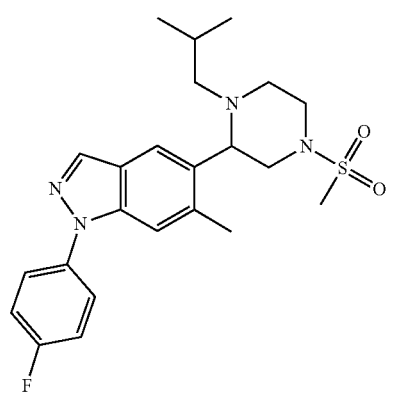

TABLE 1B-continued
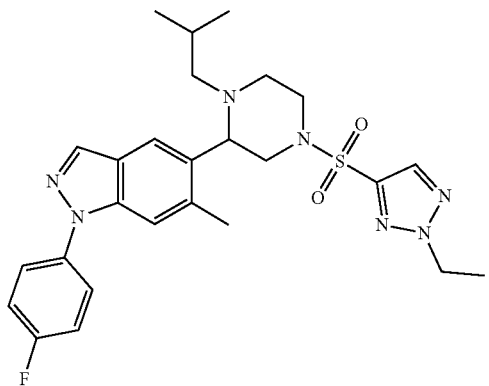
In some embodiments, the compound of Formula J, I, Ia, Ib, Ib-1, Ib-2, Ic or Id, or the pharmaceutically acceptable salt thereof, is a compound of Table 1C.
TABLE 1C
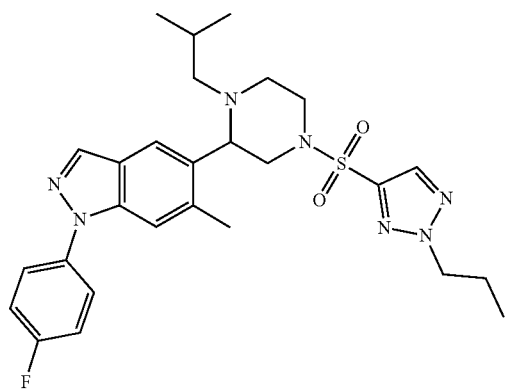
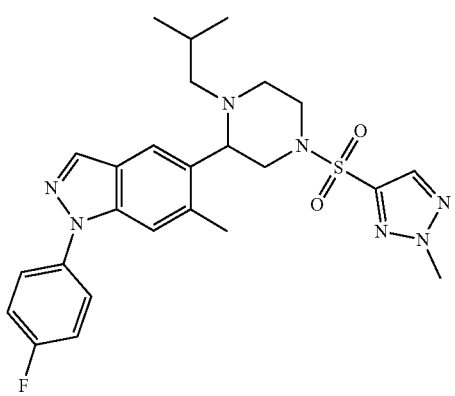

TABLE 1C-continued
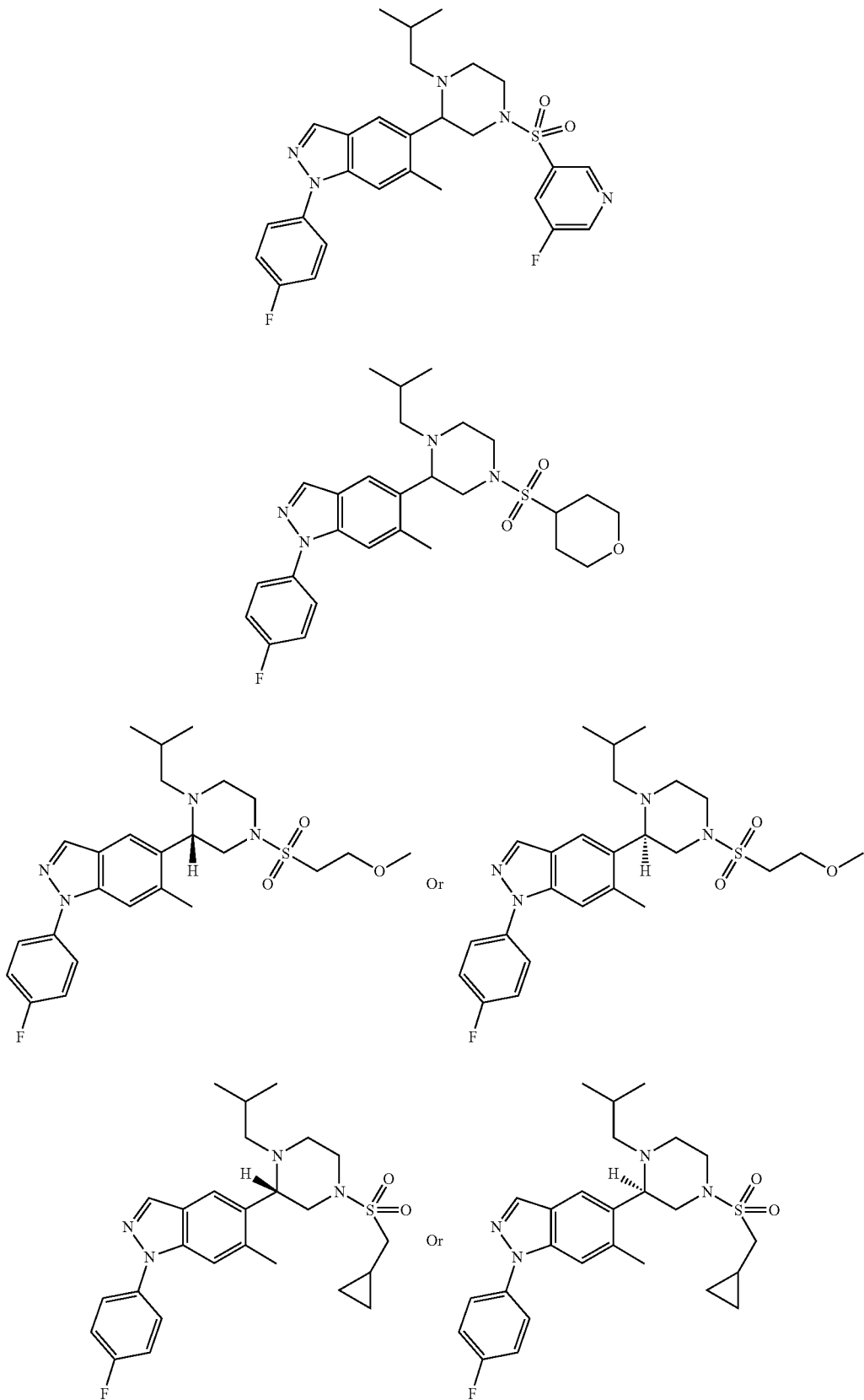

TABLE 1C-continued
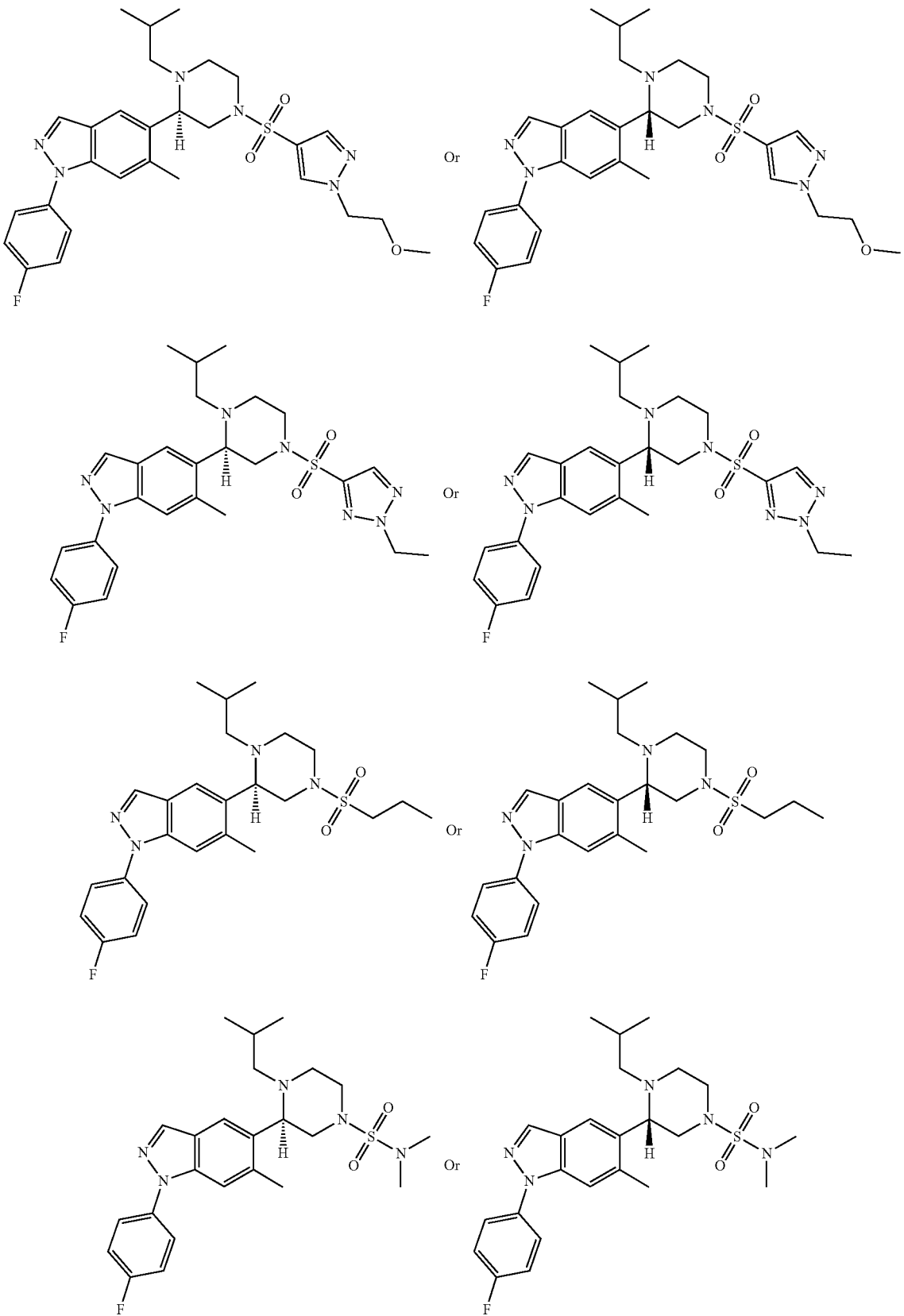

TABLE 1C-continued
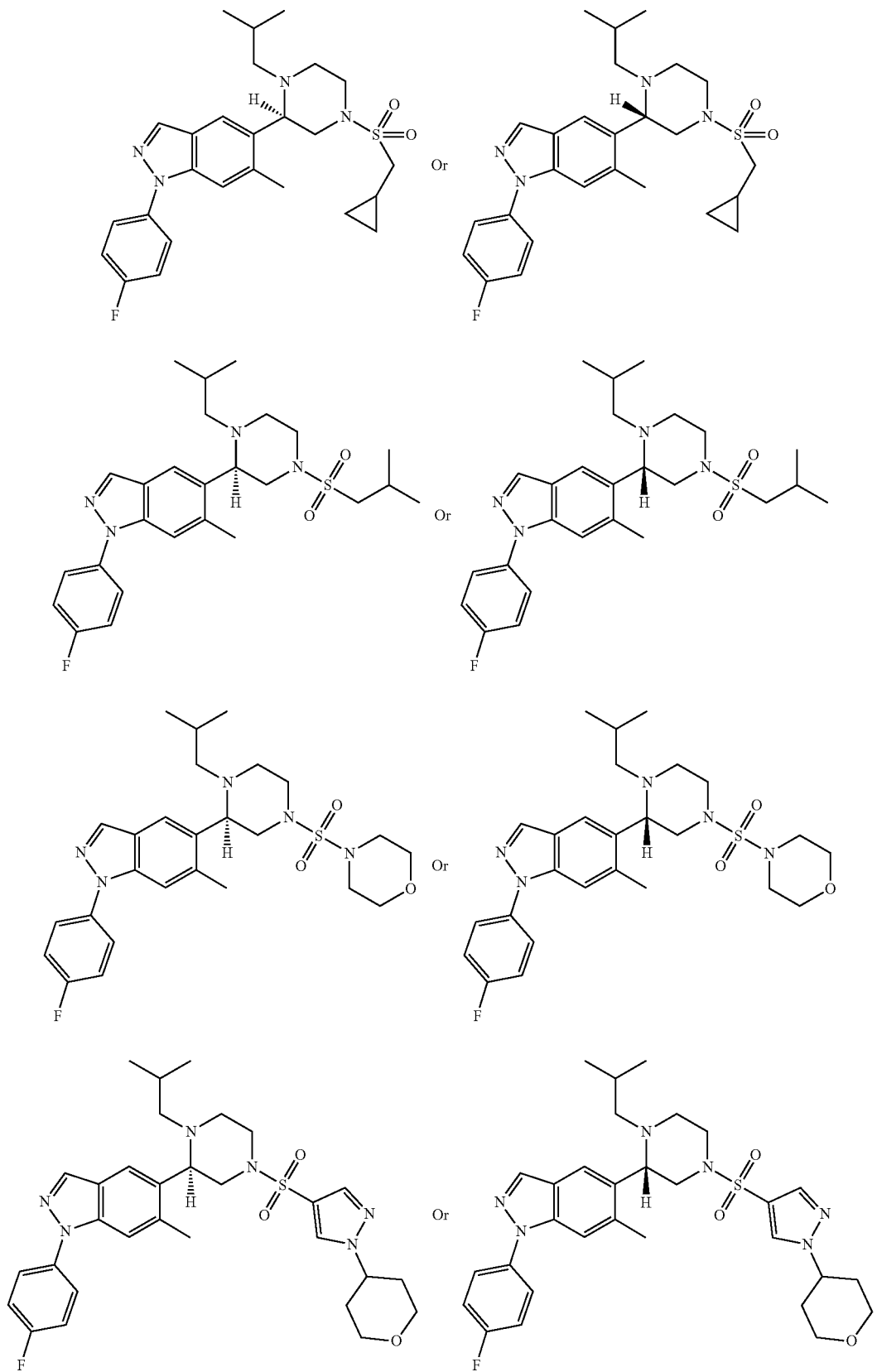

TABLE 1C-continued
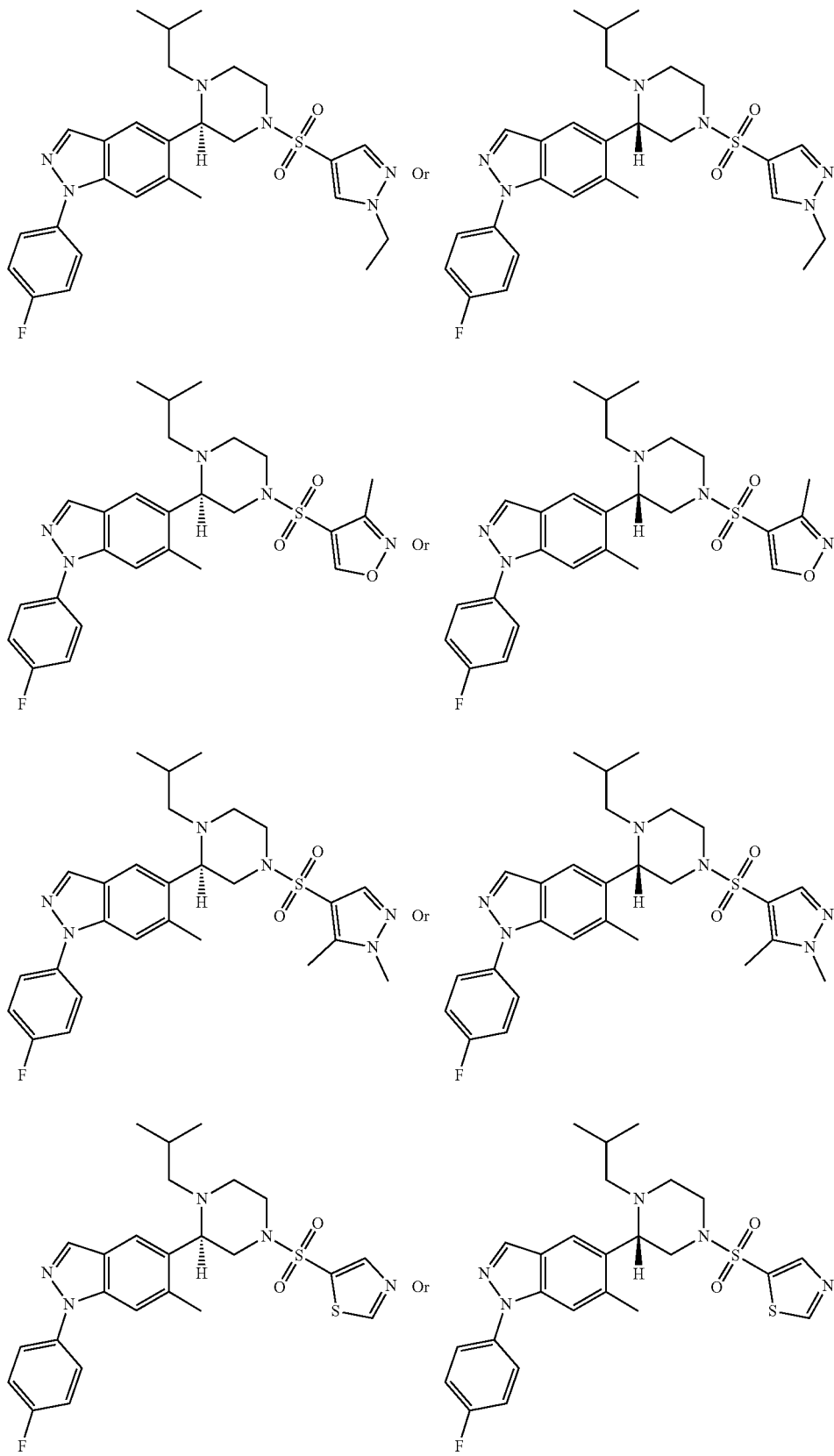

TABLE 1C-continued
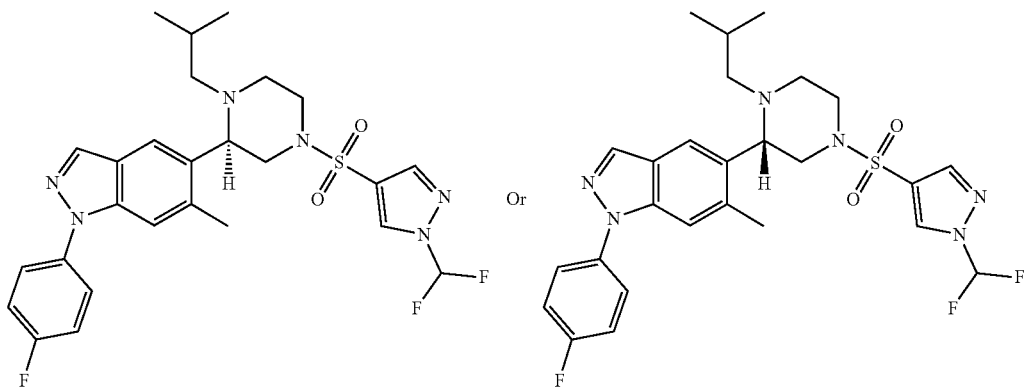
In some embodiments, the compound of Formula J, I, Ia, Ib, Ib-1, Ib-2, Ic or Id, or the pharmaceutically acceptable salt thereof, is a compound of Table 1D.
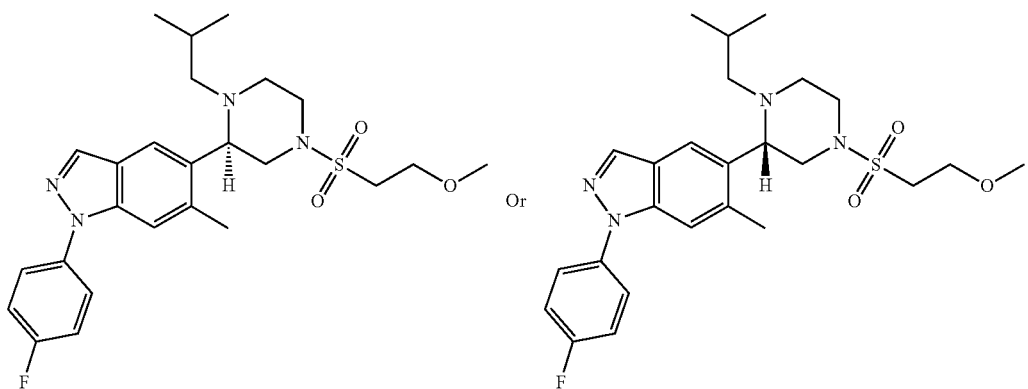
TABLE 1D
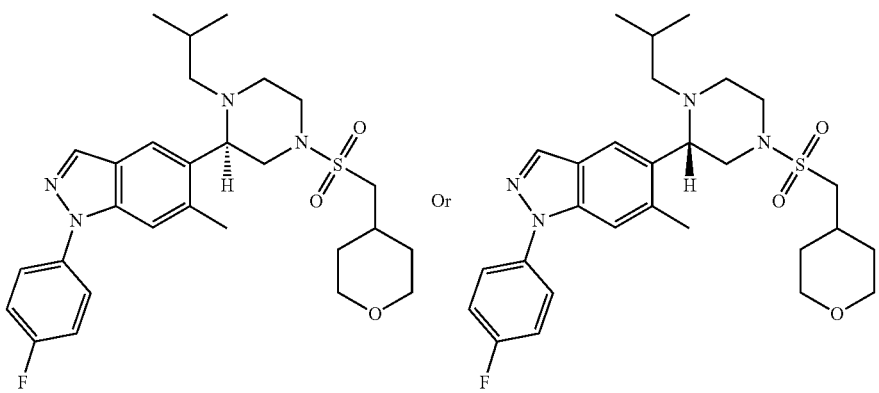

TABLE 1D-continued
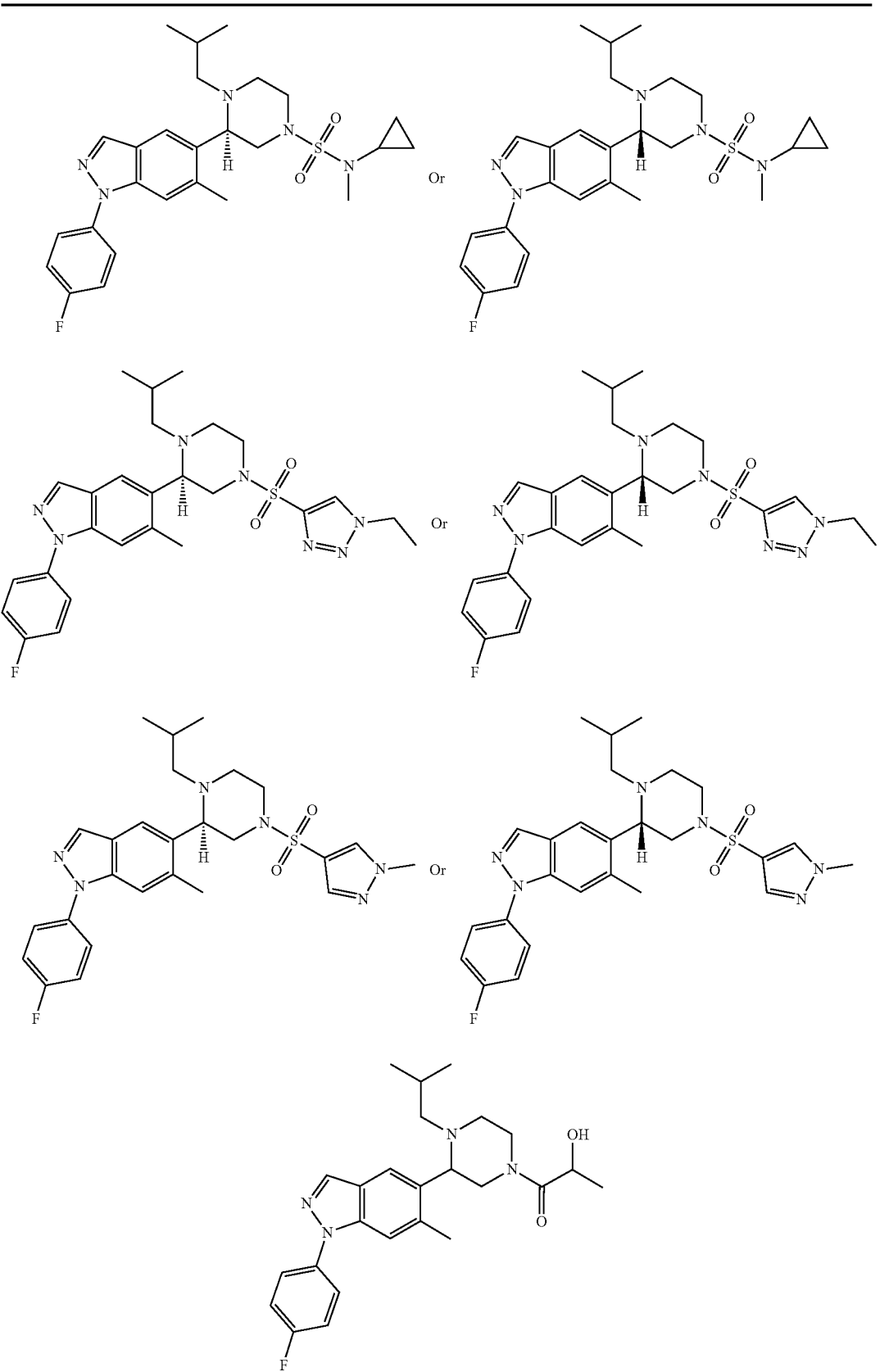

TABLE 1D-continued
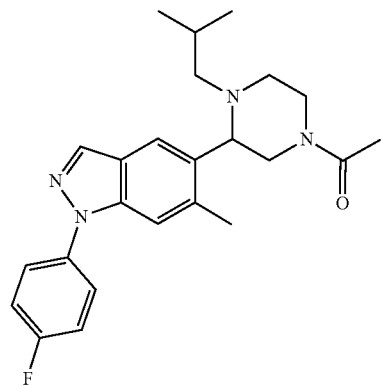
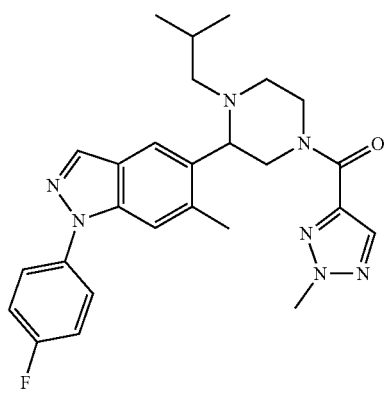
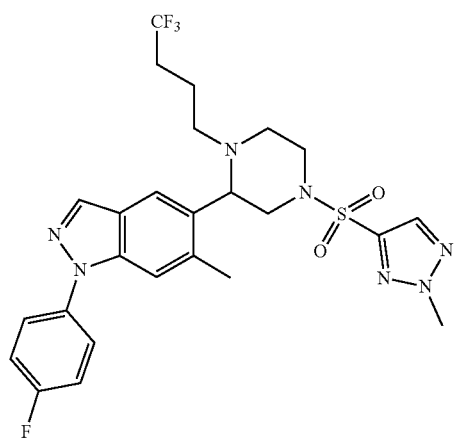
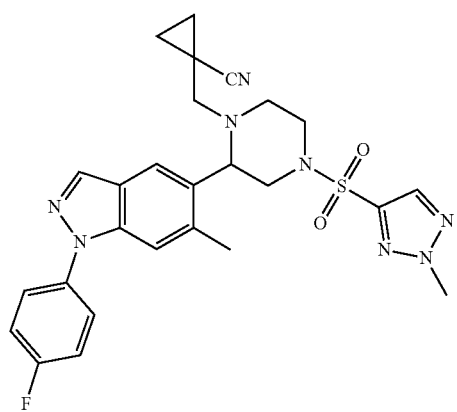

TABLE 1D-continued
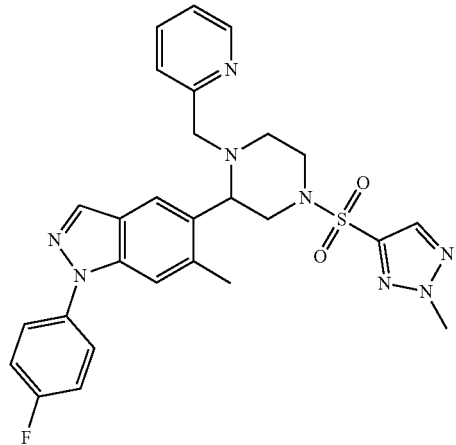
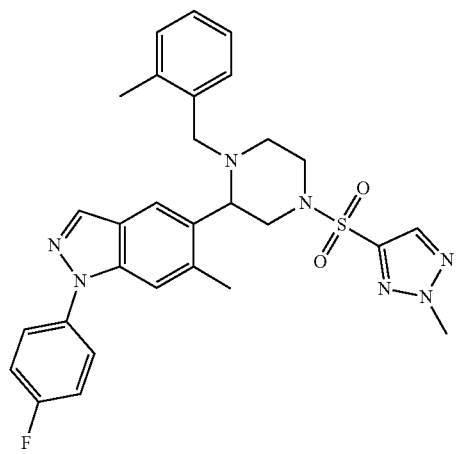
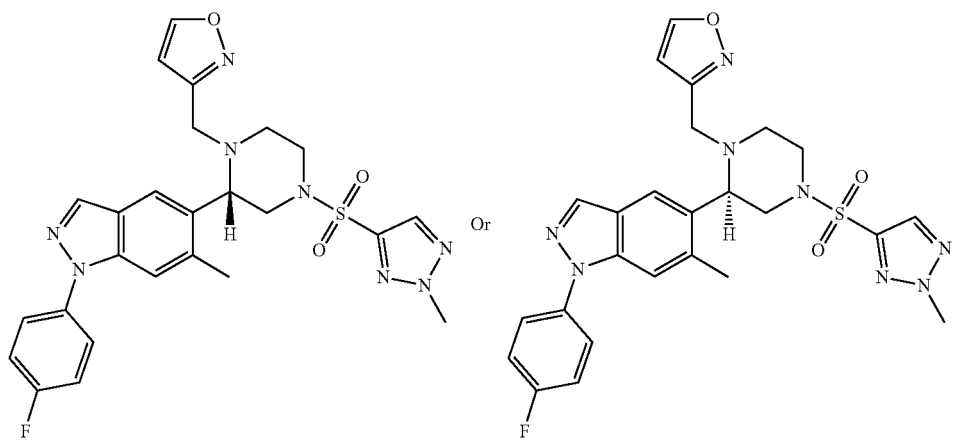

TABLE 1D-continued
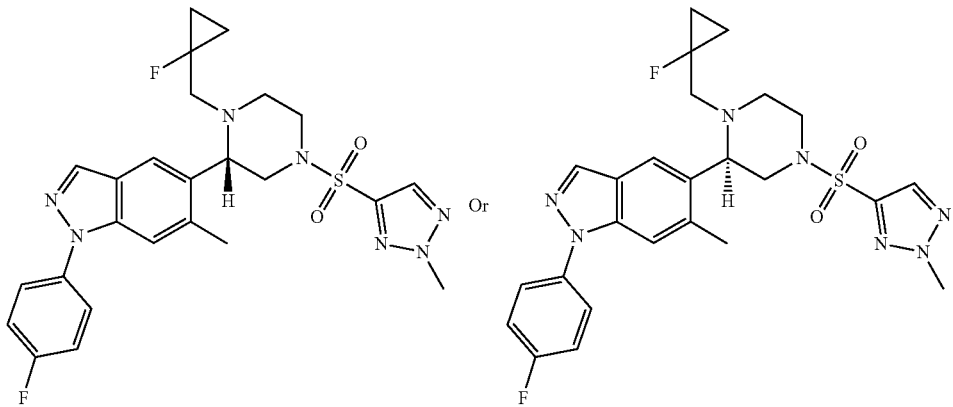
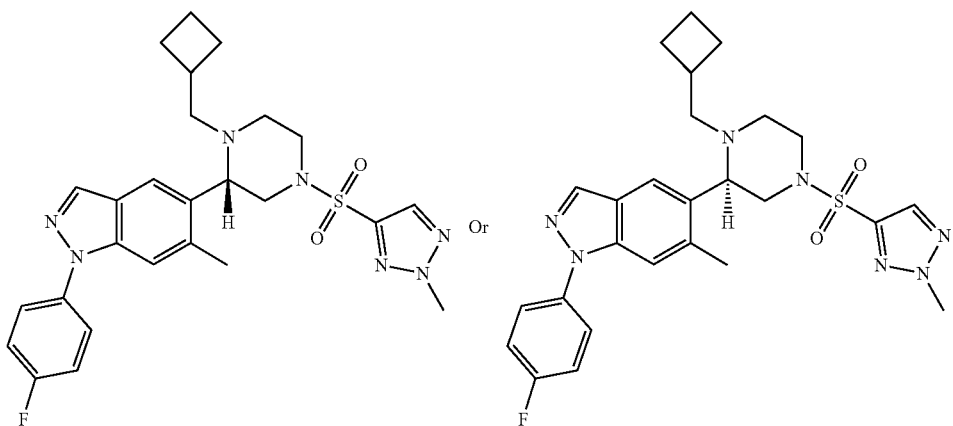
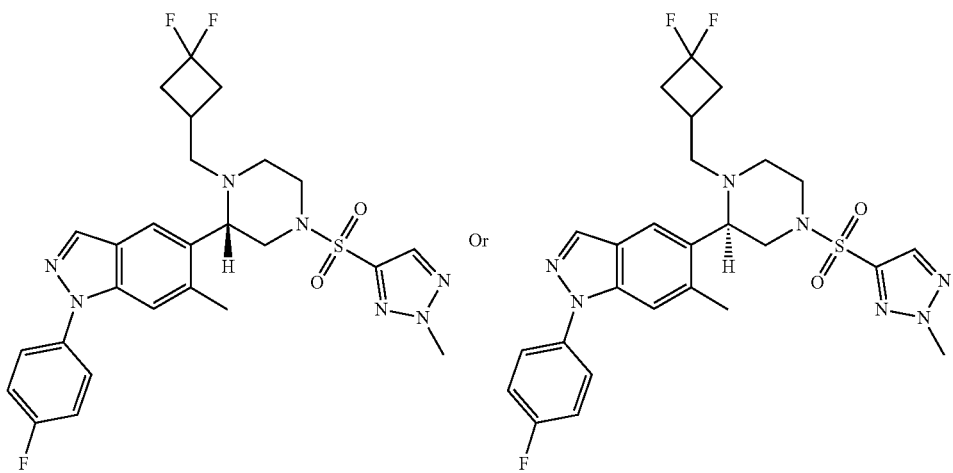

TABLE 1D-continued
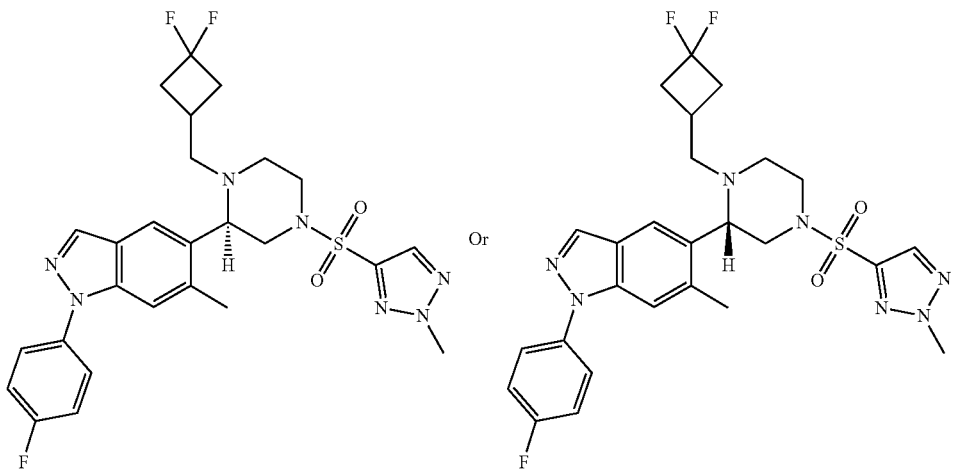
Or
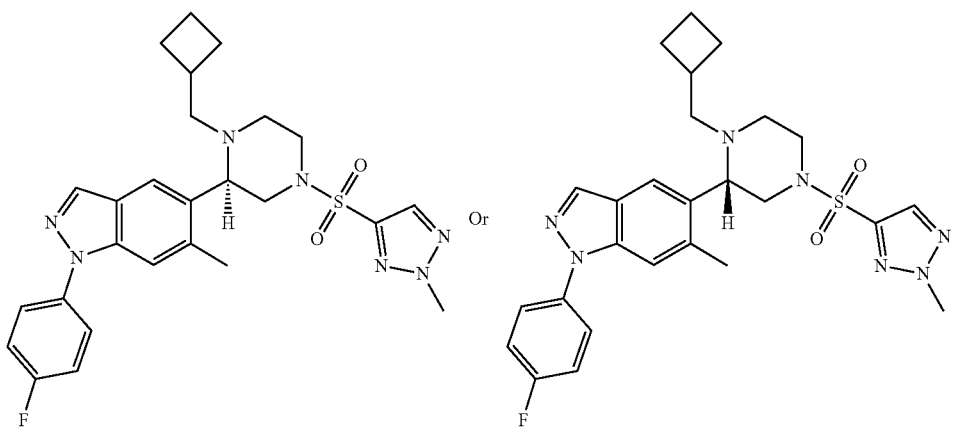
Or
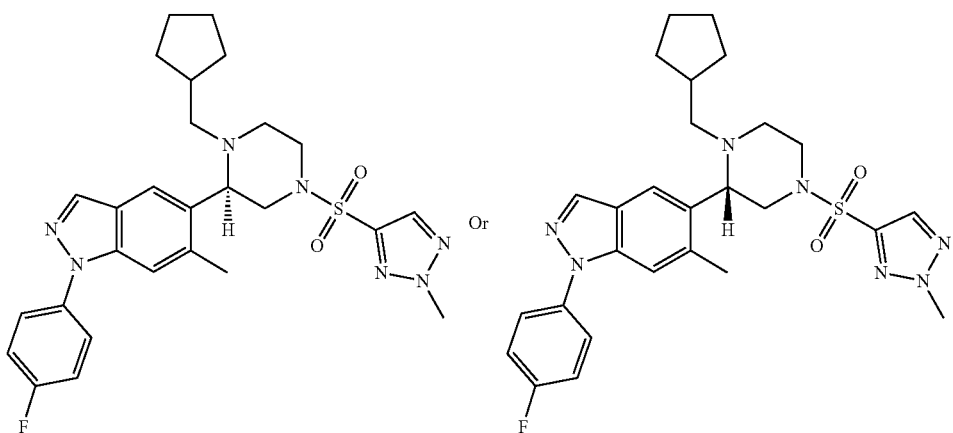
Or

TABLE 1D-continued
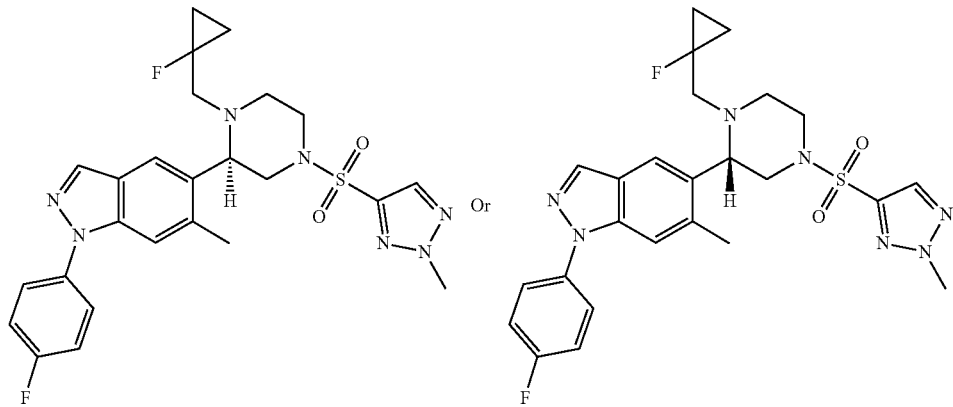
Or
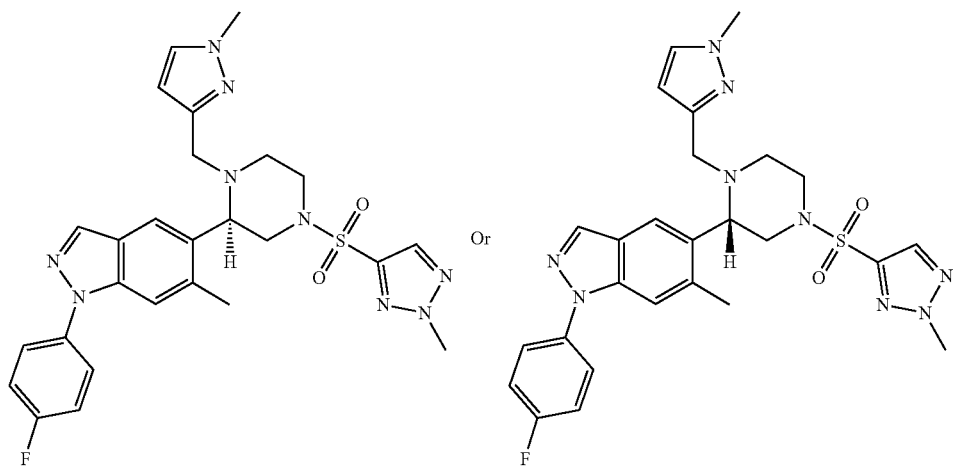
Or
In some embodiments, the compound of Formula J, I, Ia, Ib, Ib-1, Ib-2, Ic or Id, or the pharmaceutically acceptable salt thereof, is a compound of Table 1E.
TABLE 1E
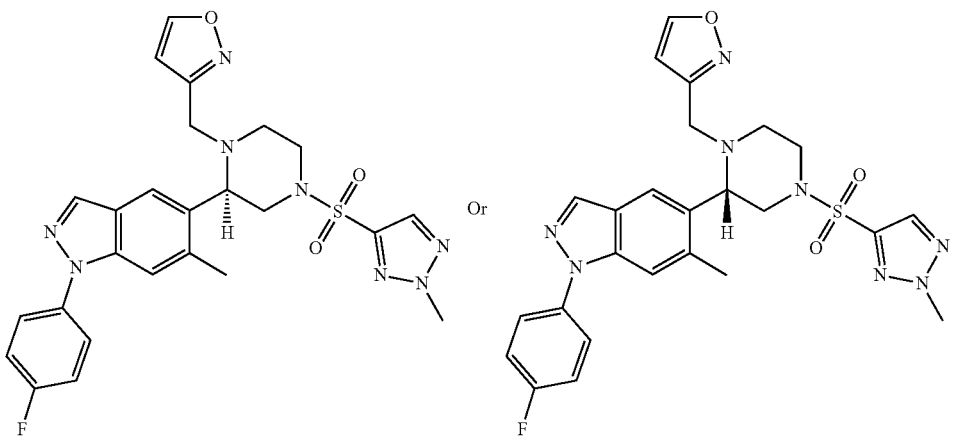
Or TABLE 1E-continued
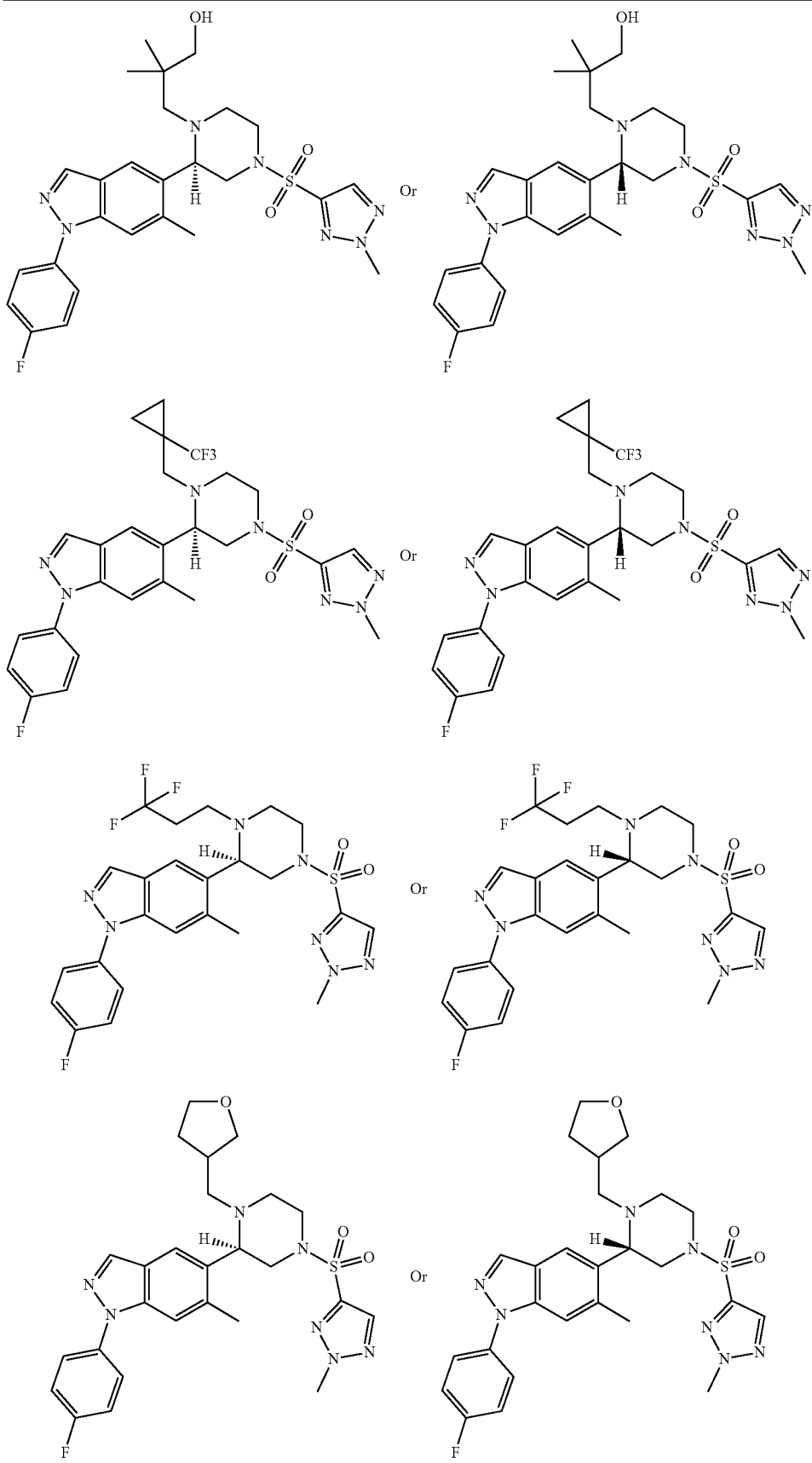

TABLE 1E-continued
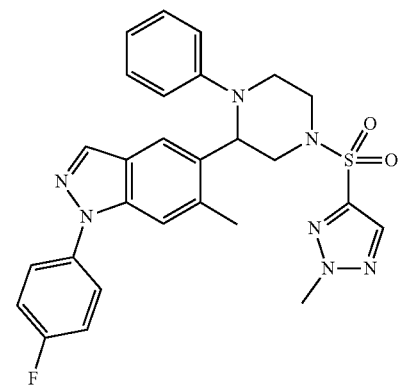
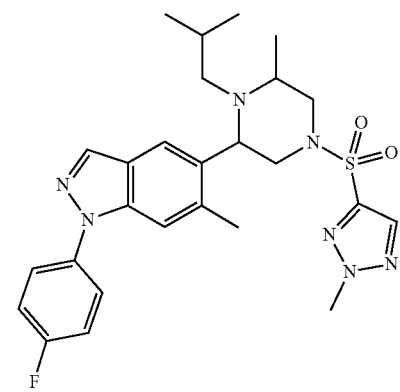
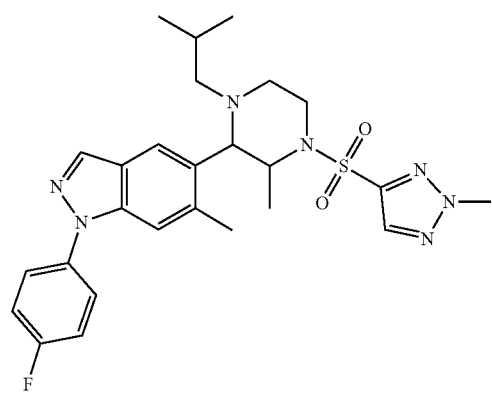 [SMILES: Cc1cc2c(cnn2-c2ccc(F)cc2)cc1C1C(C)N(S(=O)(=O)c2cnn(C)n2)CCN1CC(C)C]
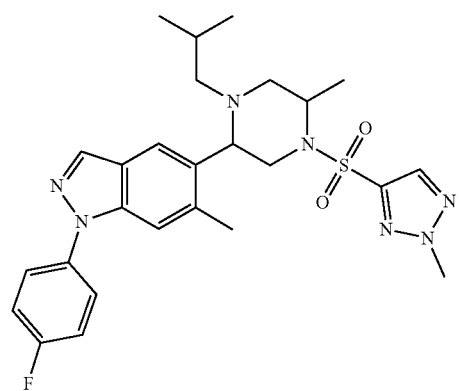 [SMILES: Cc1cc2c(cnn2-c2ccc(F)cc2)cc1C1CN(S(=O)(=O)c2cnn(C)n2)C(C)CN1CC(C)C]

In some embodiments, the compound of Formula J, I, Ia, Ib, Ib-1, Ib-2, Ic or Id, or the pharmaceutically acceptable salt thereof, is a compound of Table 1F.
TABLE 1F
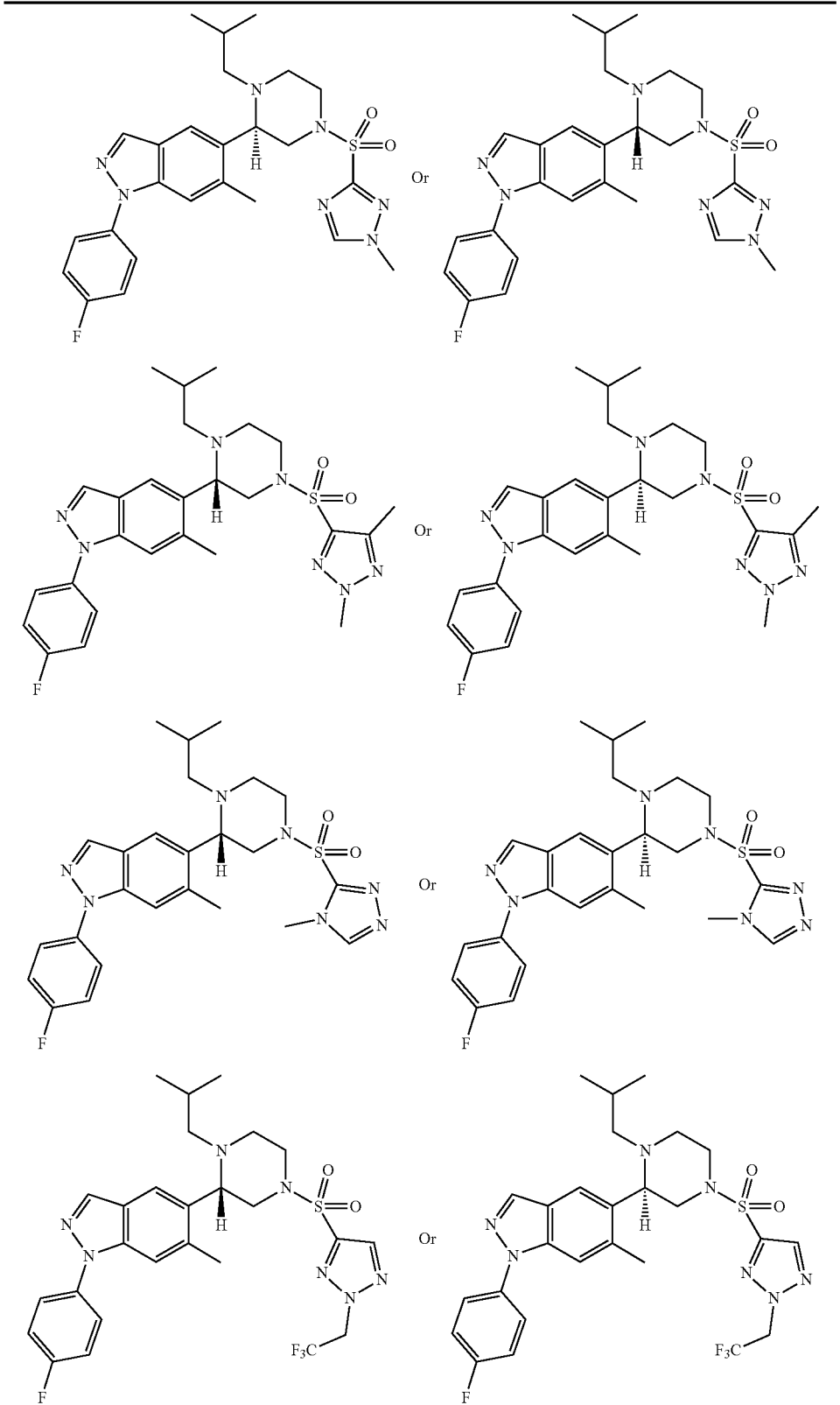

TABLE 1F-continued
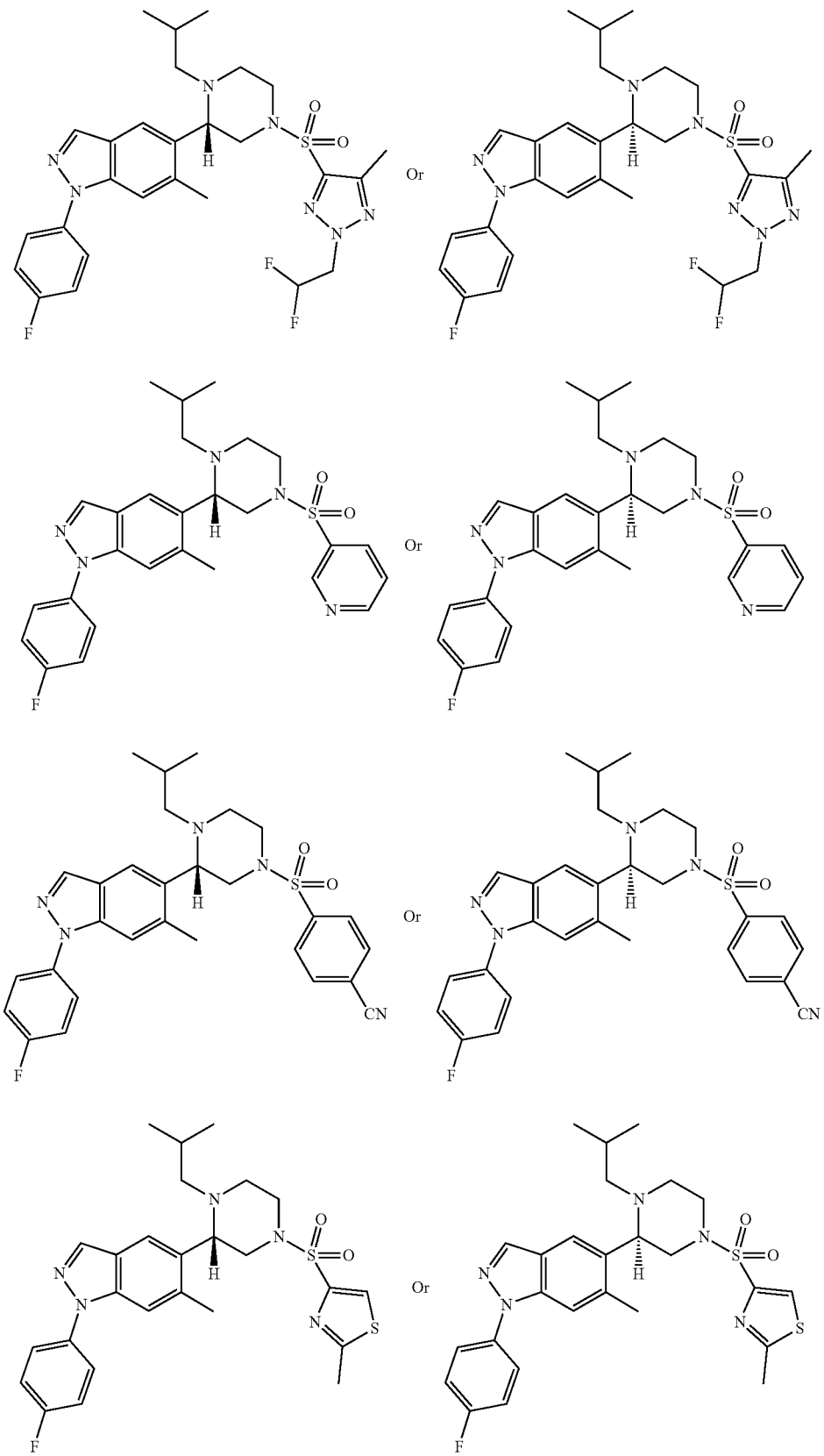

TABLE 1F-continued
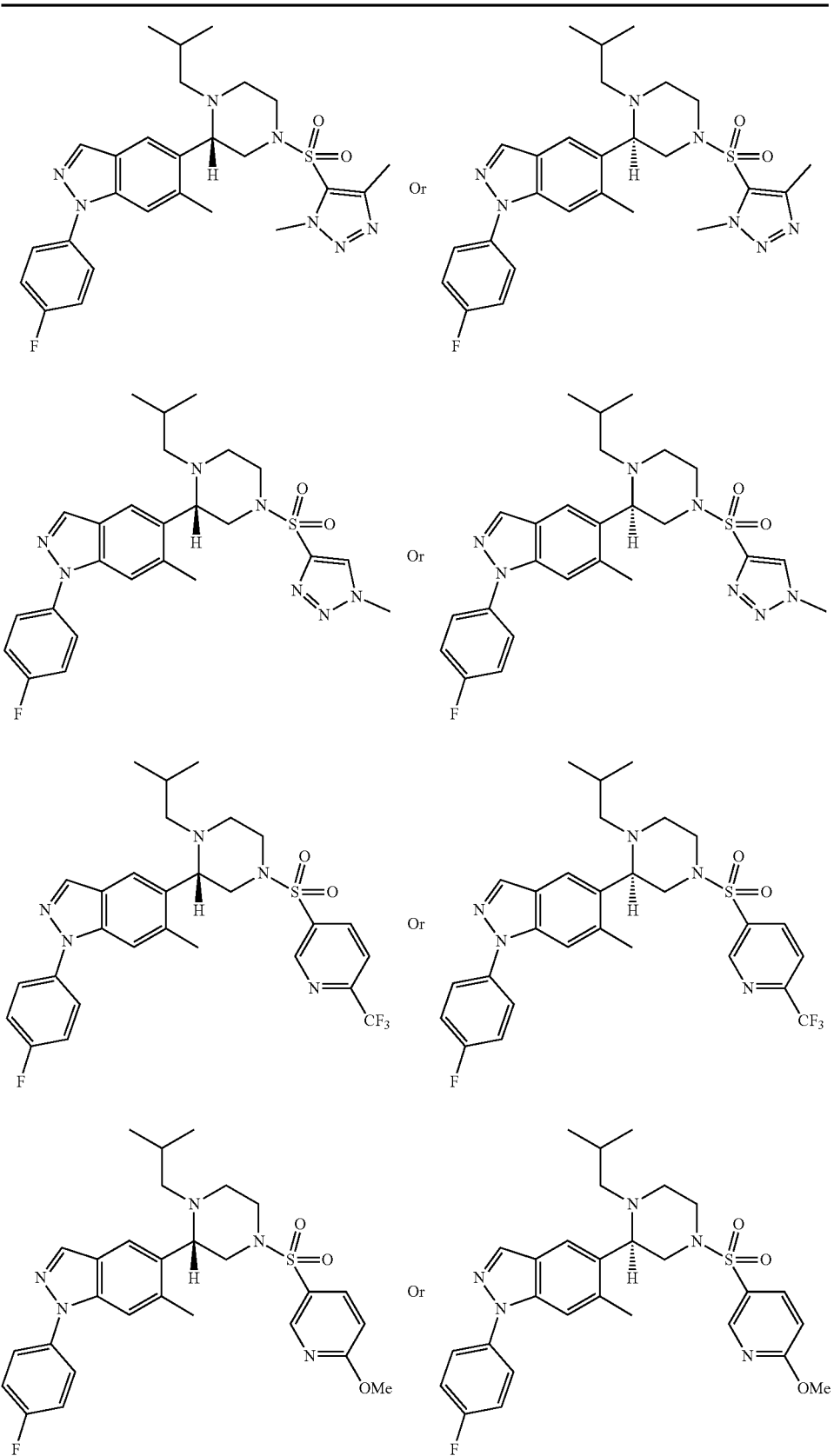

TABLE 1F-continued
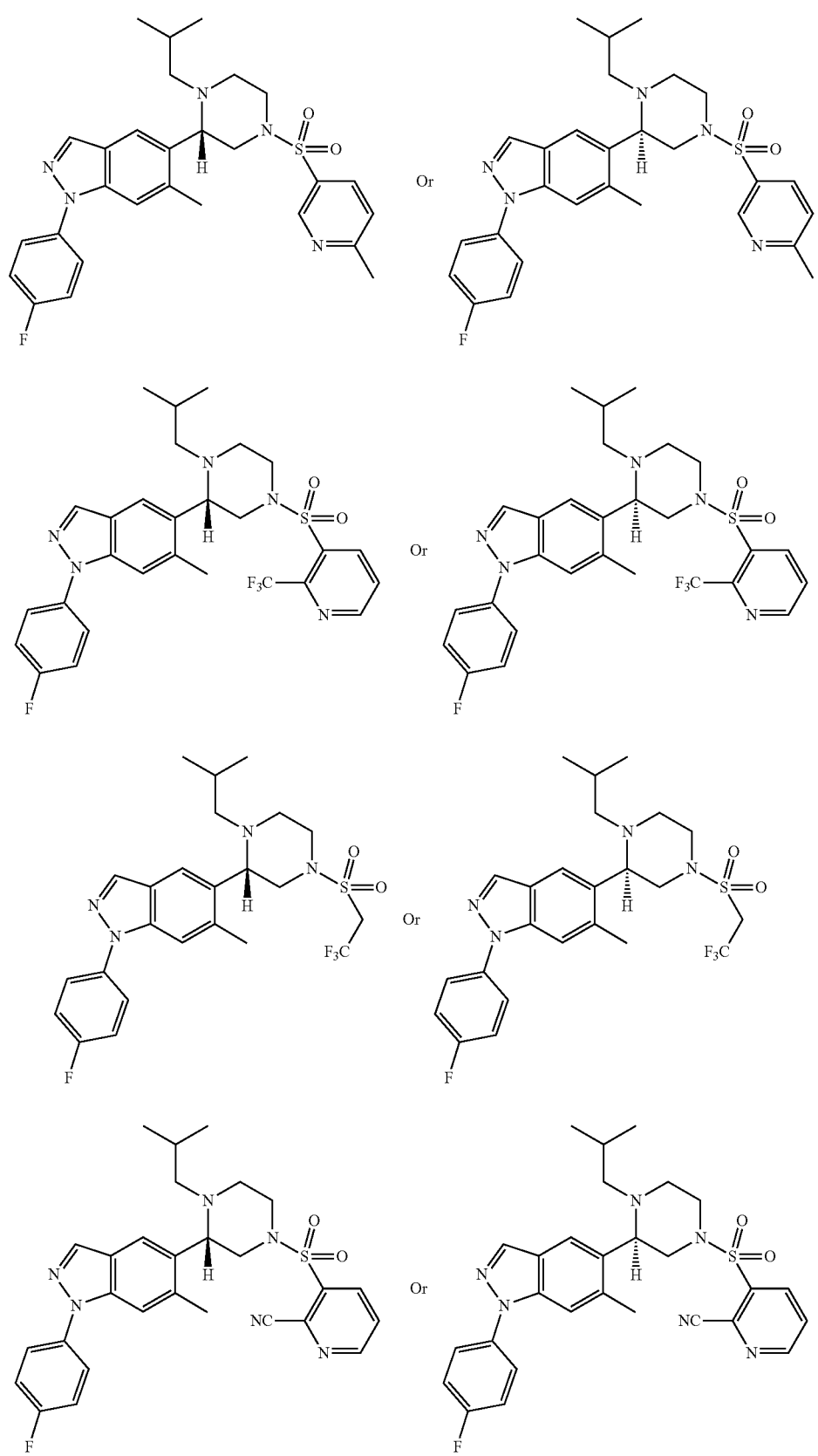

TABLE 1F-continued
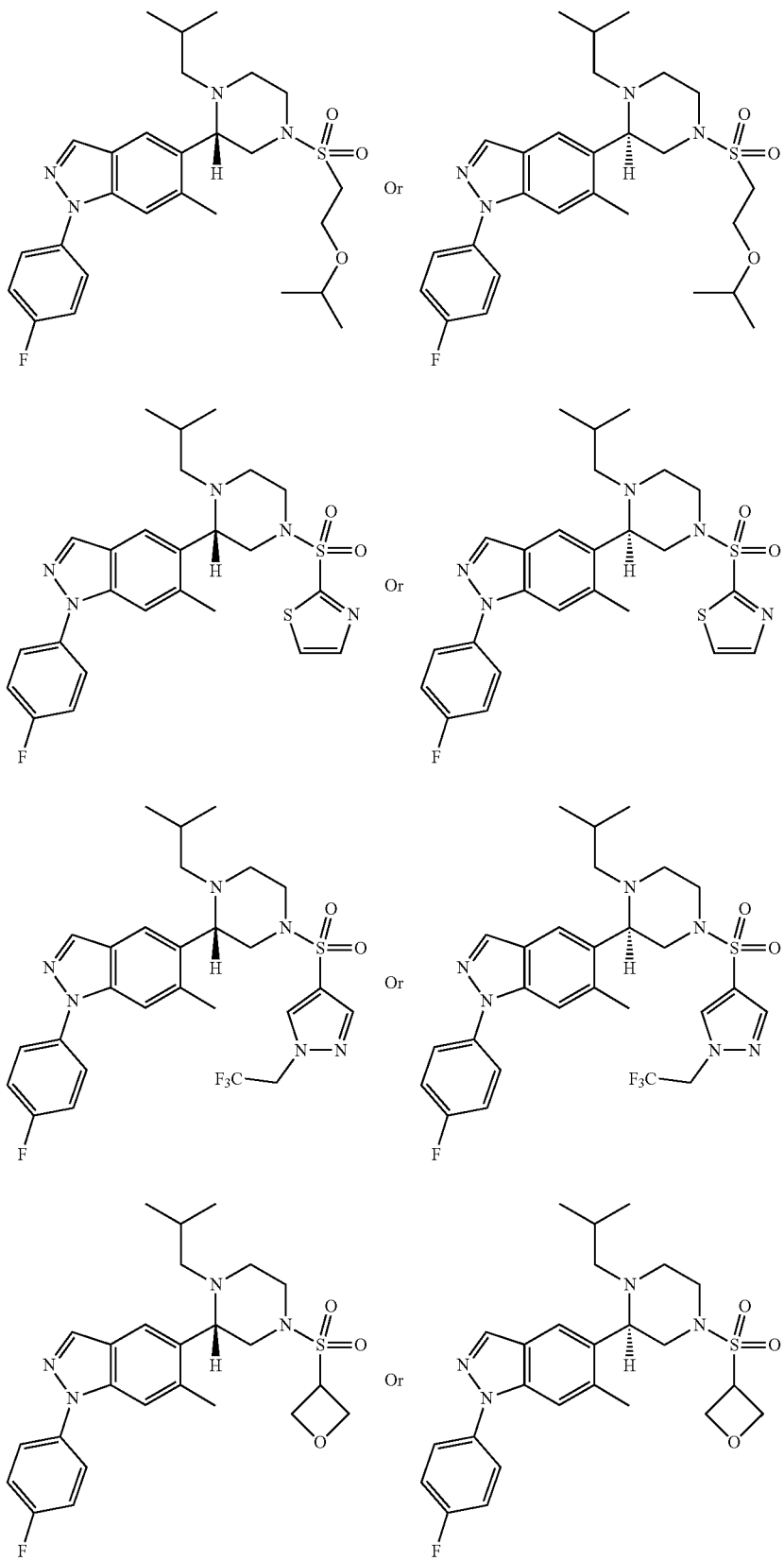

In some embodiments, the compound of Formula J, I, Ia, Ib, Ib-1, Ib-2, Ic or Id, or the pharmaceutically acceptable salt thereof, is a compound of Table 1G.
TABLE 1G
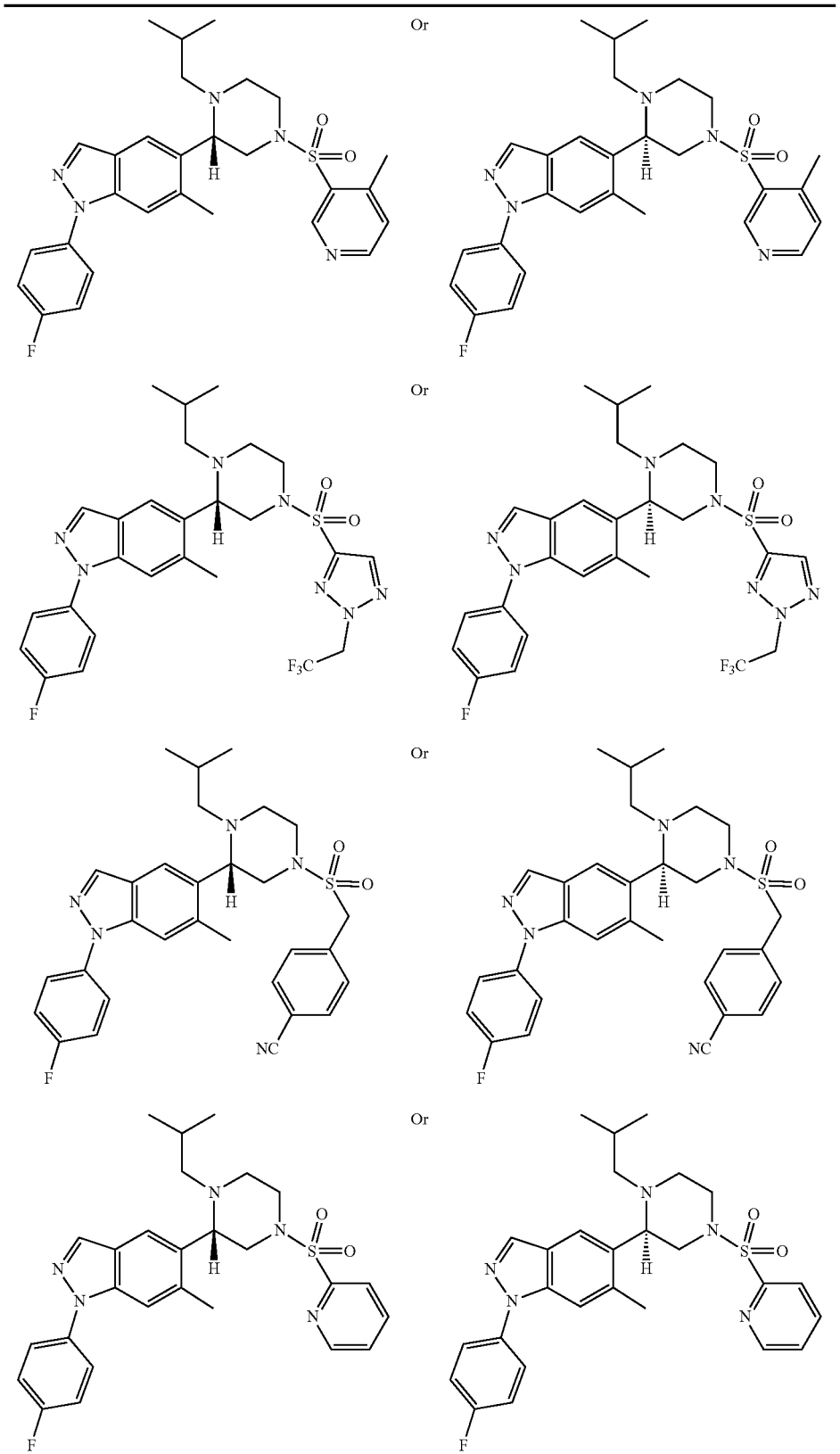

TABLE 1G-continued
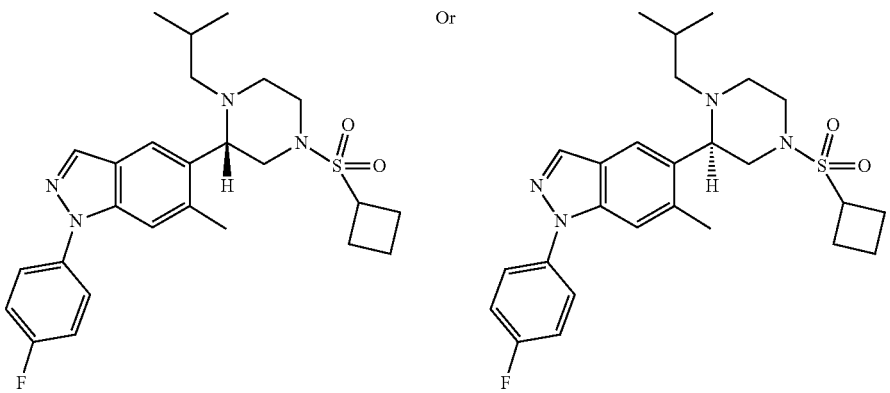
Or
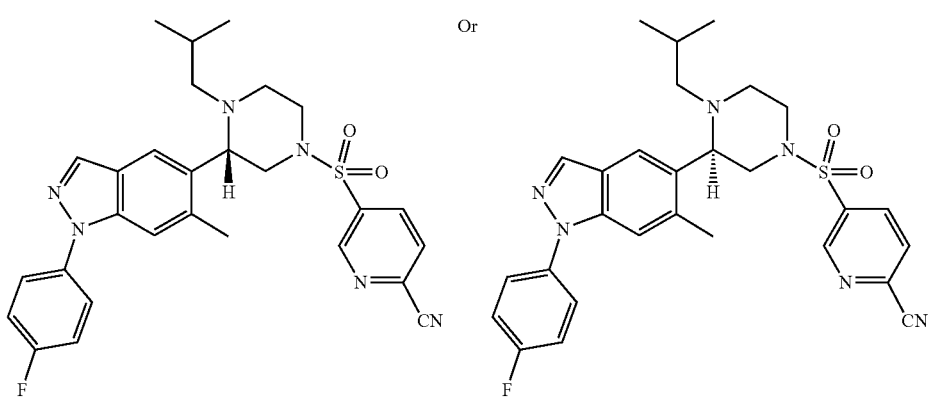
Or
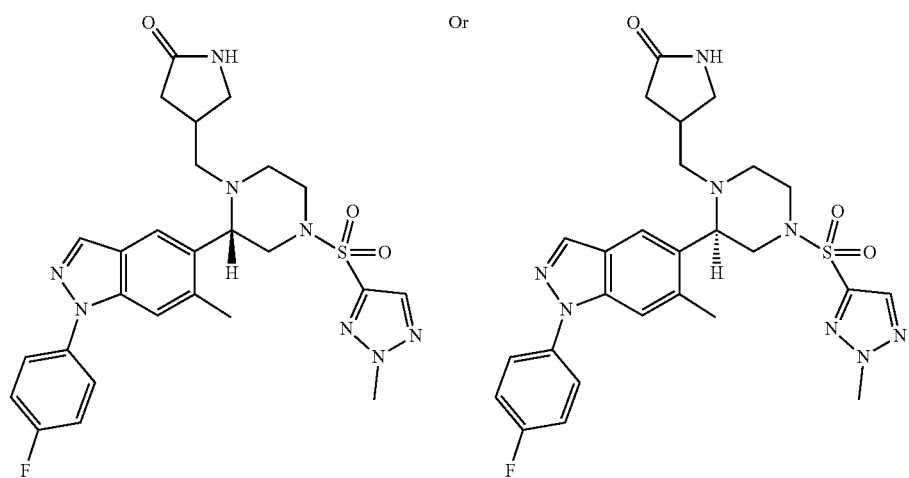
Or

TABLE 1G-continued
Or
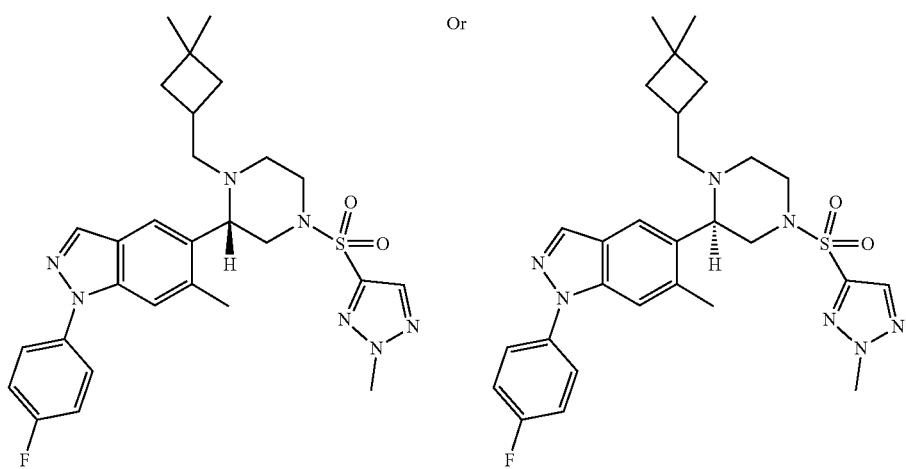
Or
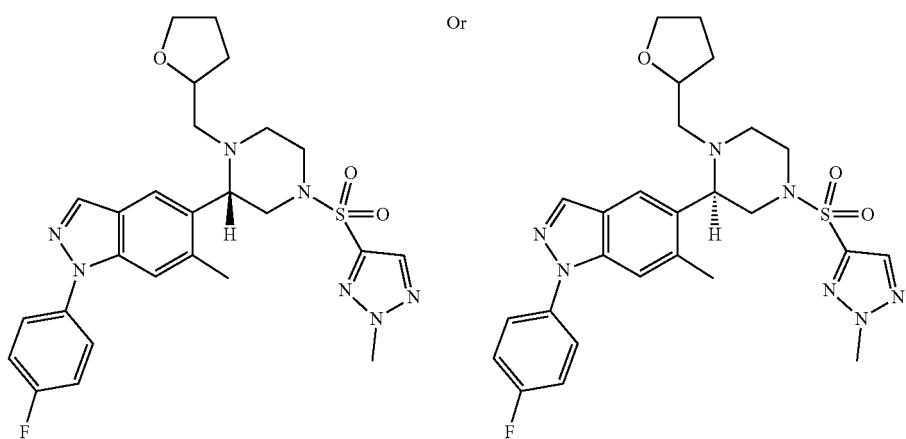
Or
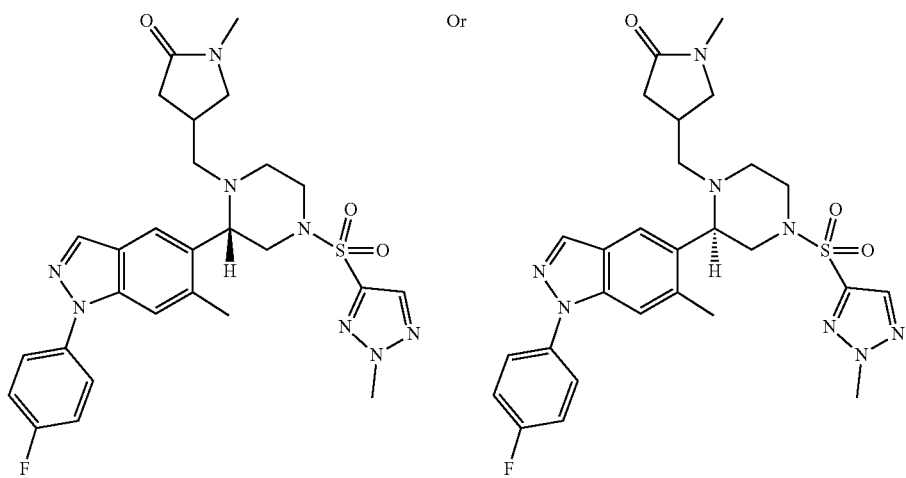

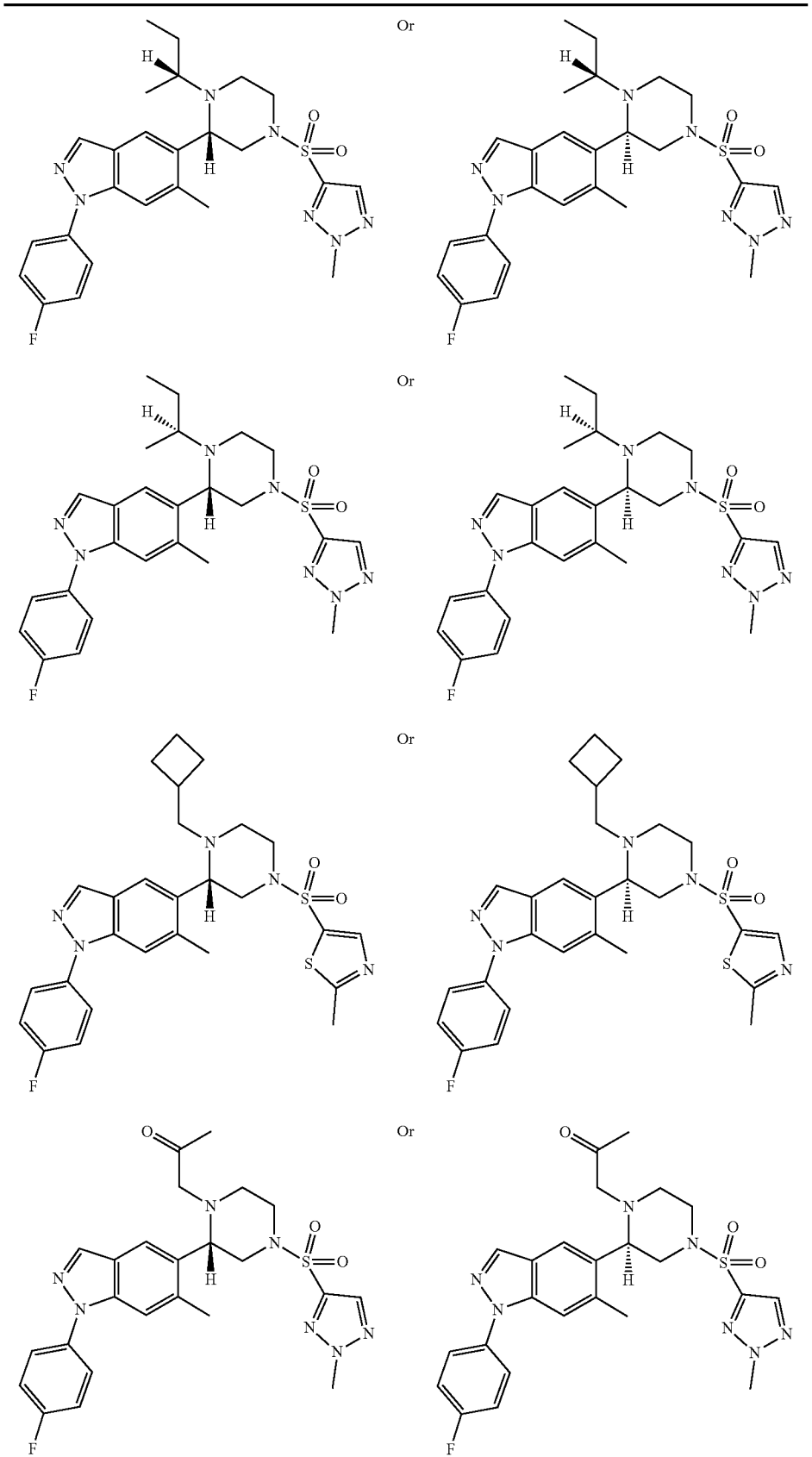

TABLE 1G-continued
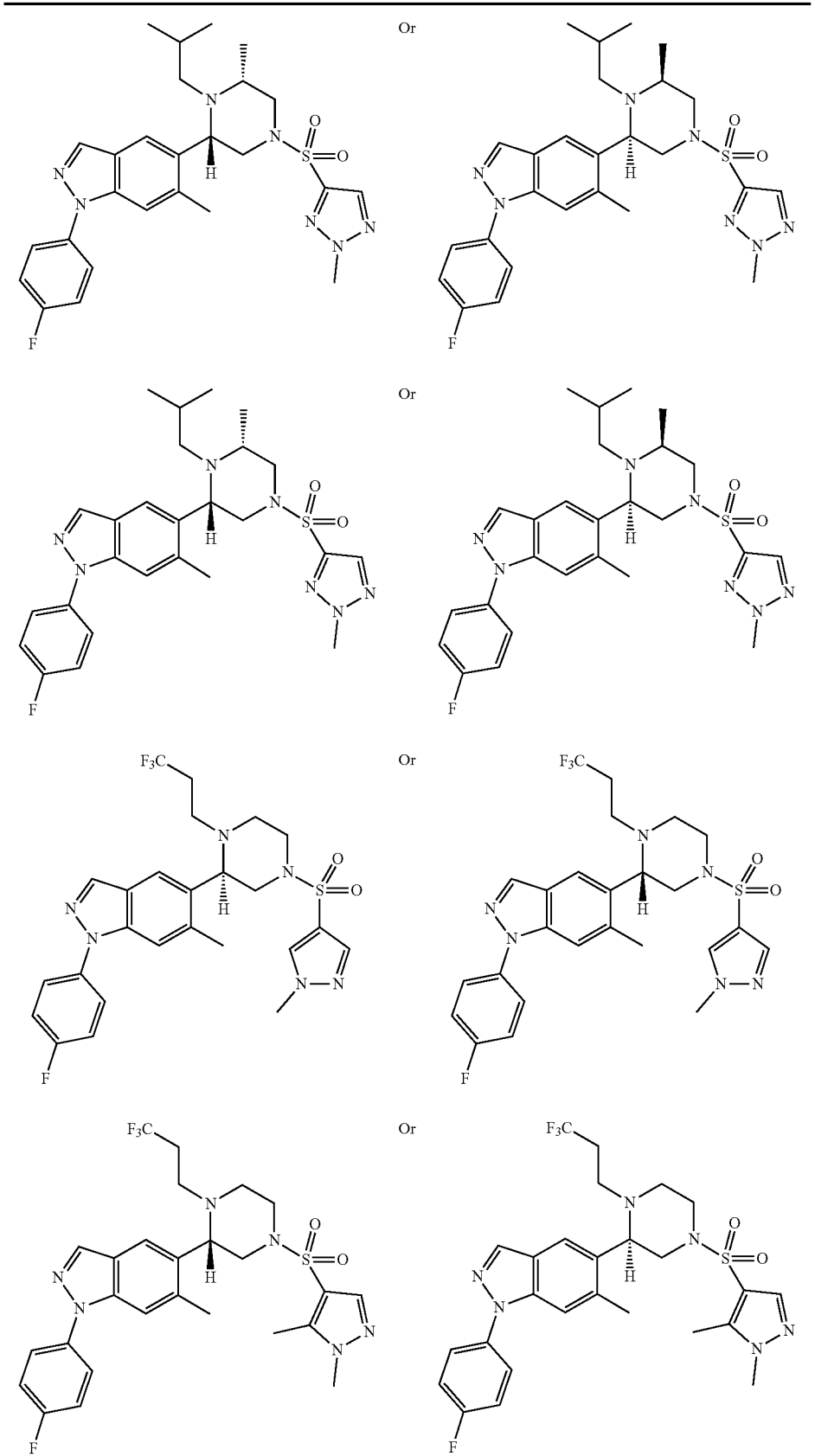

TABLE 1G-continued
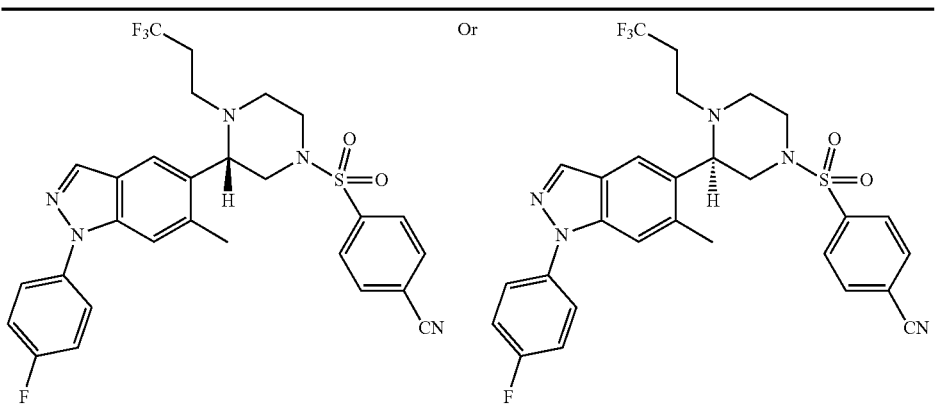
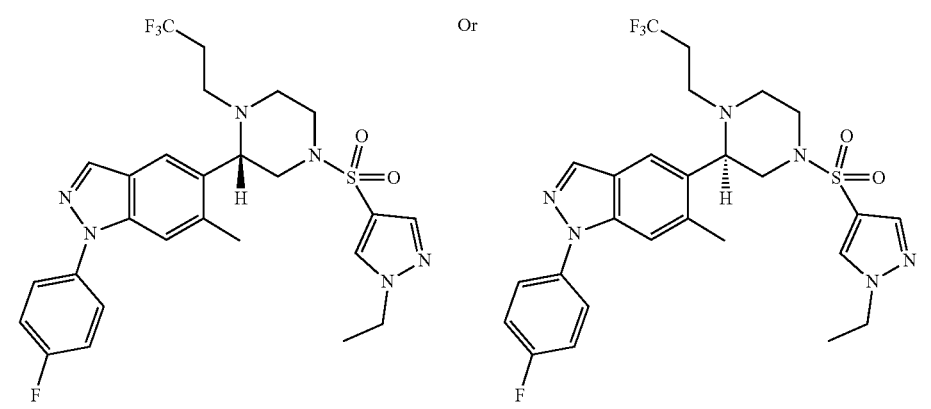
In some embodiments, the compound of Formula J, 1, Ia, Ib, Ib-1, Ib-2, Ic or Id, or the pharmaceutically acceptable salt thereof, is a compound of Table 1H.
TABLE 1H1
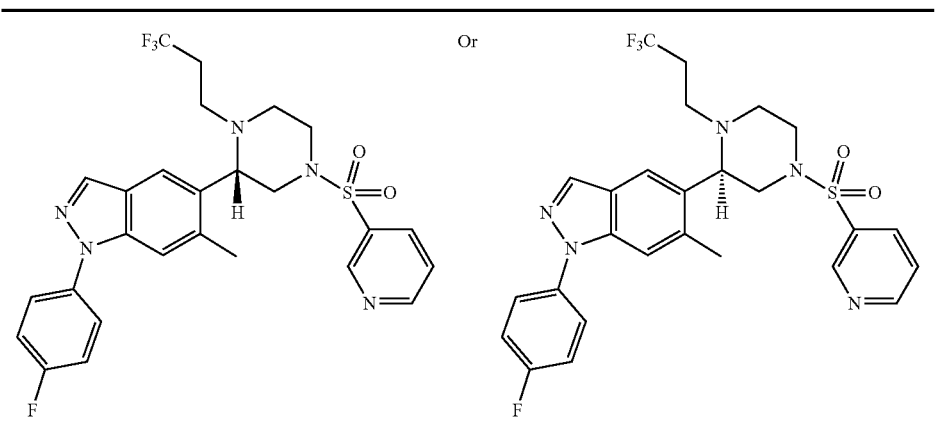

TABLE 1H1-continued
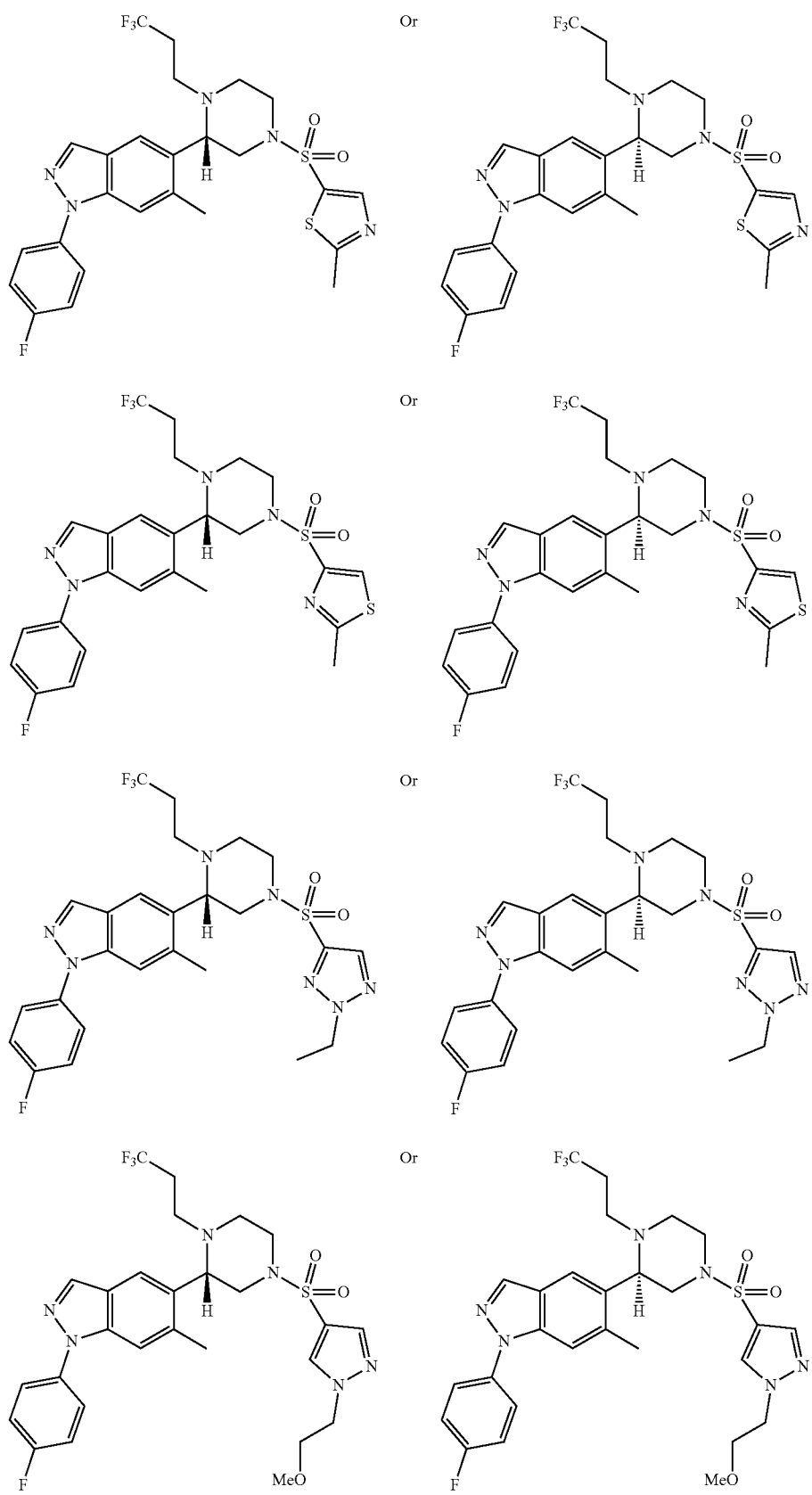

TABLE 1H1-continued
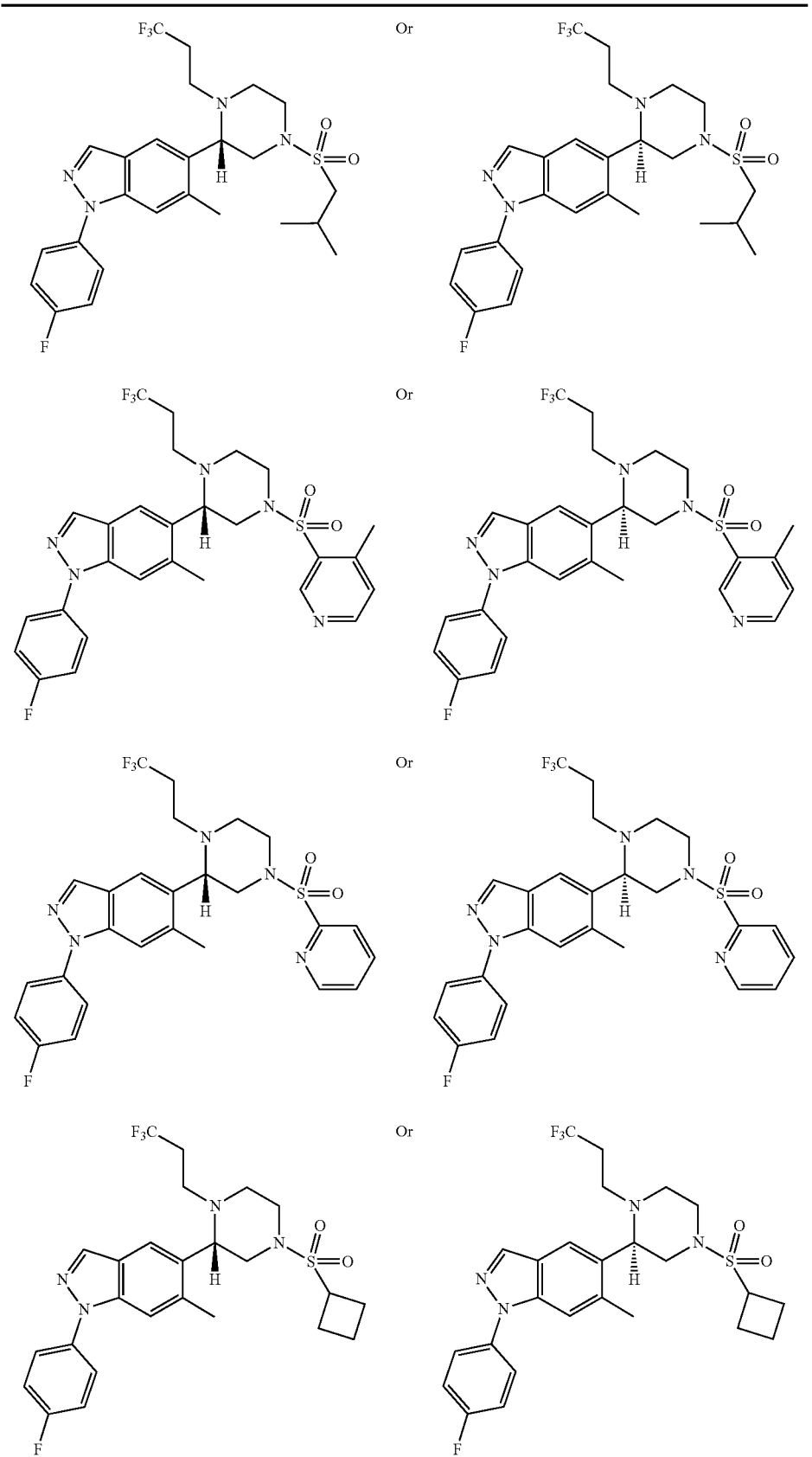

TABLE 1H1-continued
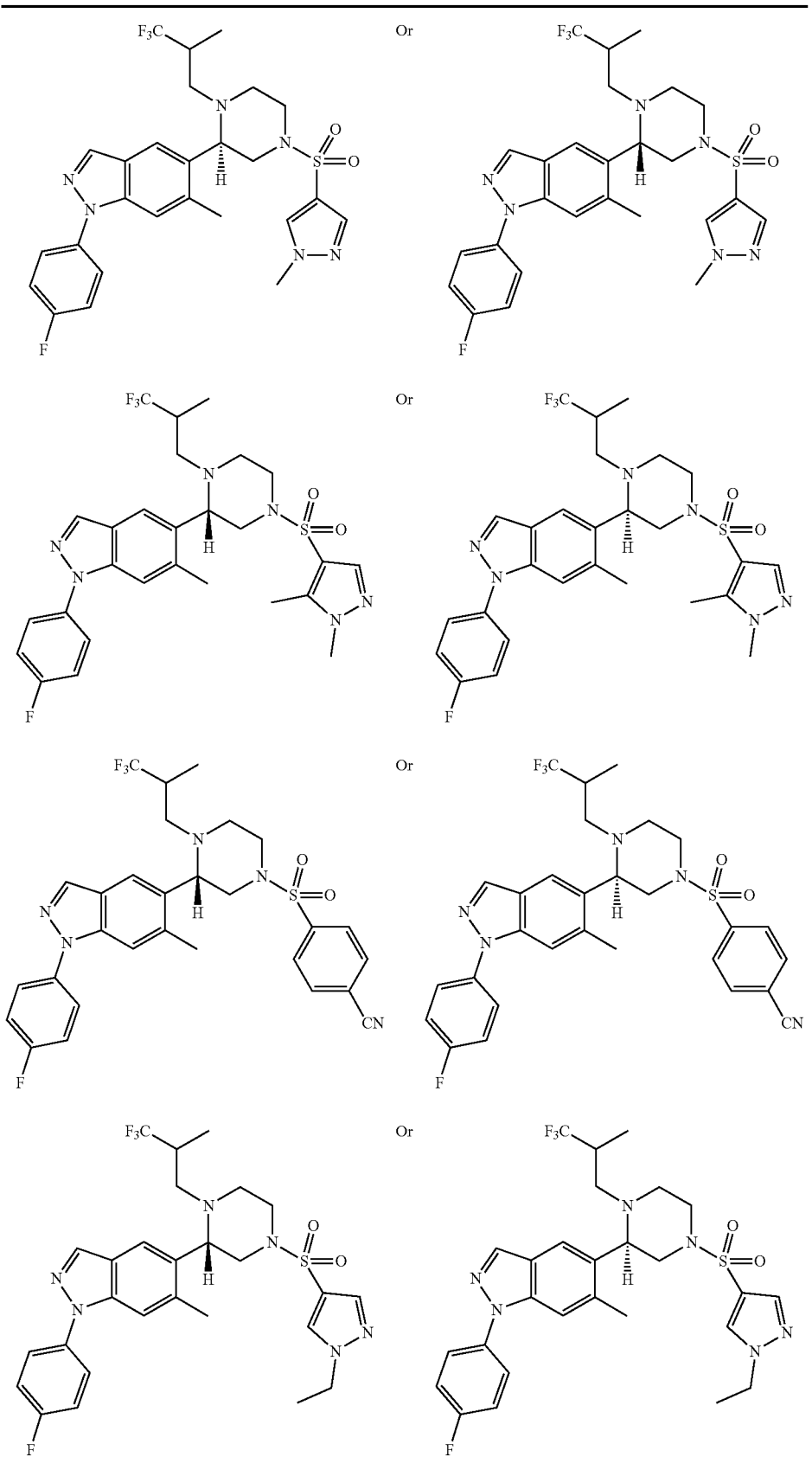

TABLE 1H1-continued
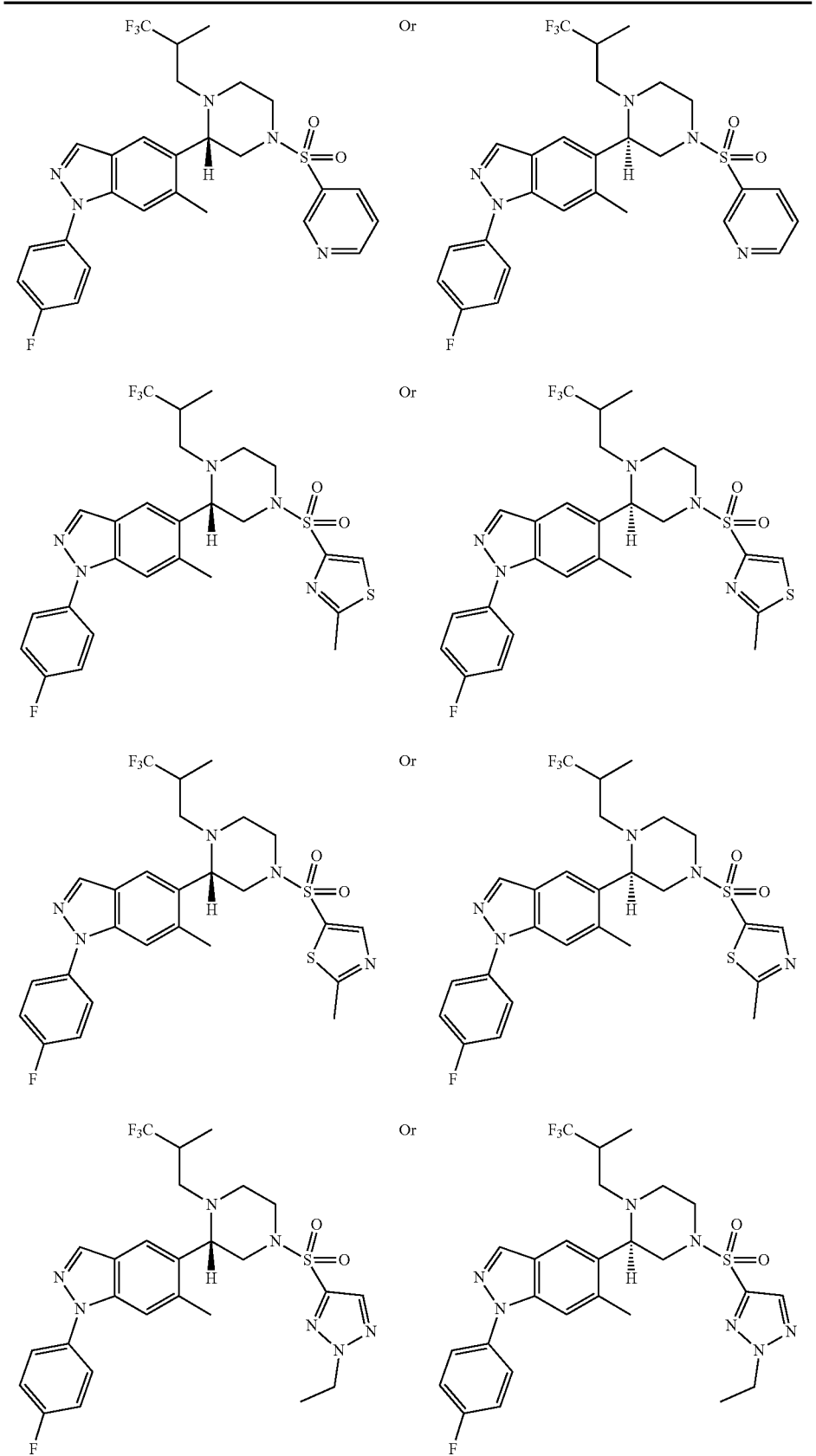

TABLE 1H1-continued
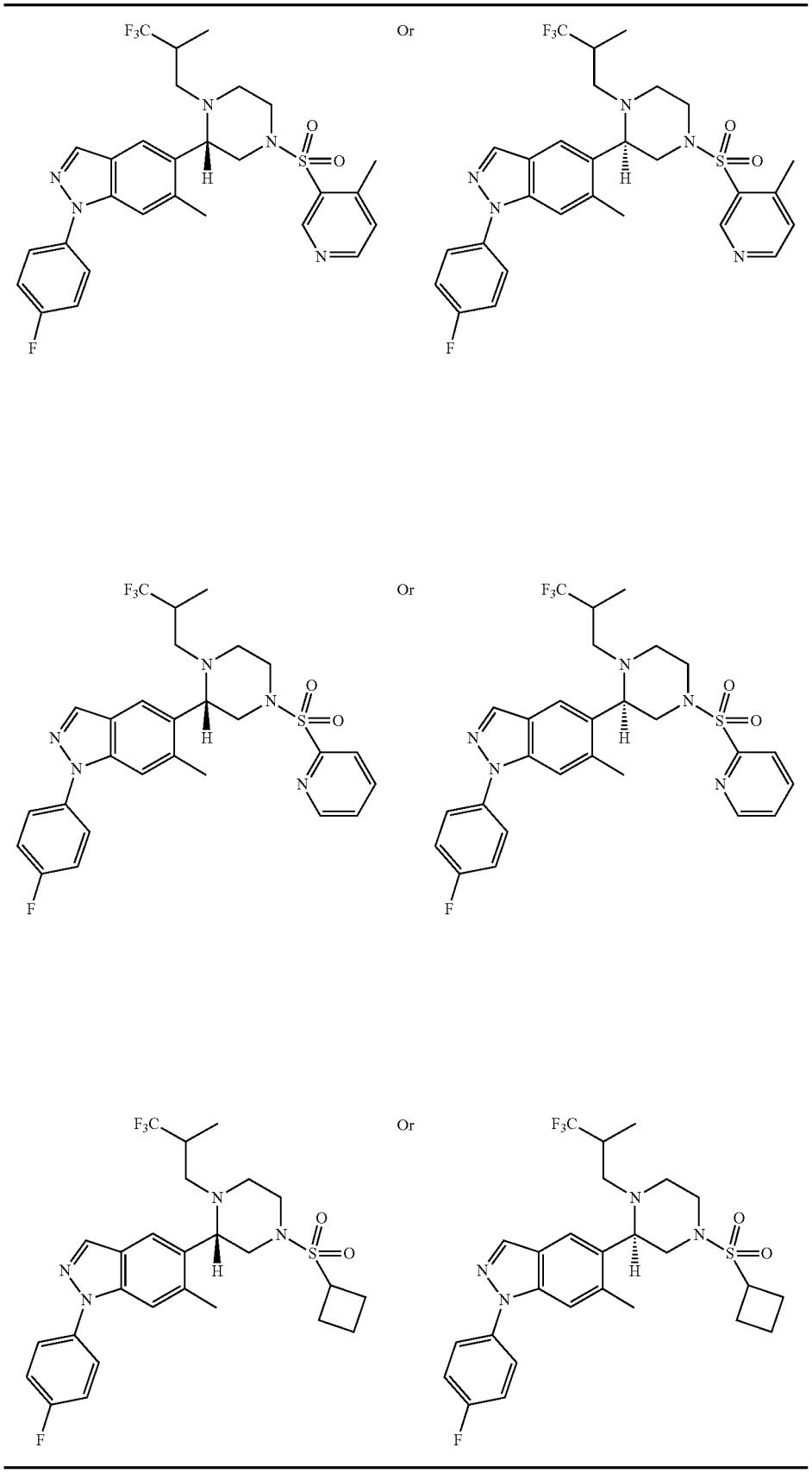

In some embodiments, the compound of Formula J, I, Ia, Ib, Ib-1, Ib-2, Ic or Id, or the pharmaceutically acceptable salt thereof, is a compound of Table 1I.
TABLE 1I
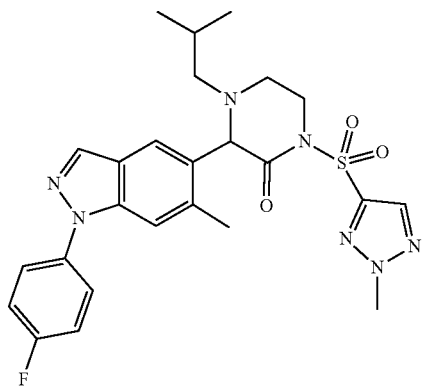 [SMILES: Cc1cc2c(cnn2-c2ccc(F)cc2)cc1C1C(=O)N(S(=O)(=O)c2cnn(C)n2)CCN1CC(C)C]
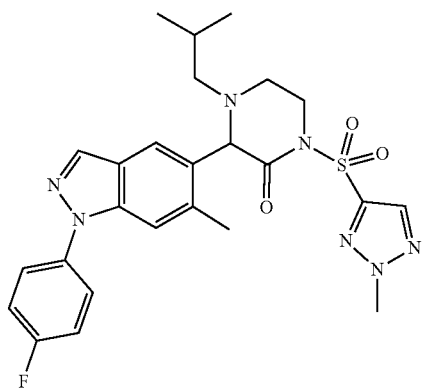 [SMILES: Cc1cc2c(cnn2-c2ccc(F)cc2)cc1C1C(=O)N(S(=O)(=O)c2cnn(C)n2)CCN1CC(C)C]
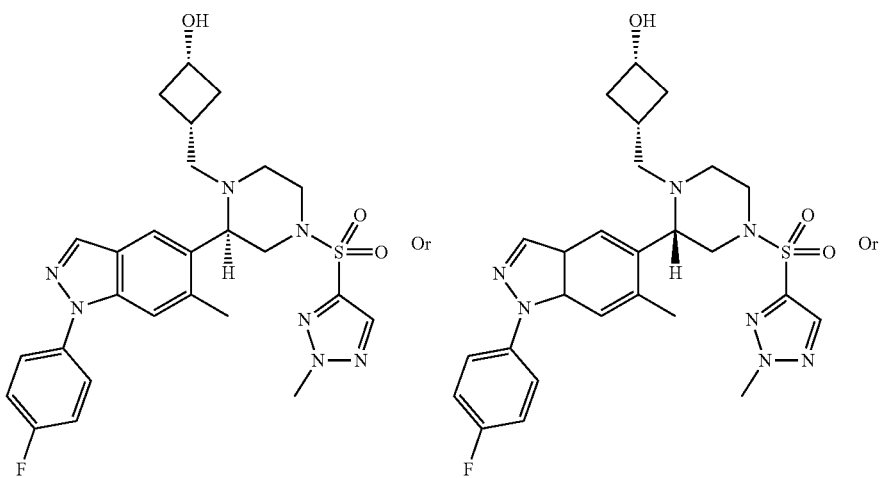 [SMILES: Cc1cc2c(cnn2-c2ccc(F)cc2)cc1[C@@H]1CN(S(=O)(=O)c2cnn(C)n2)CCN1C[C@H]1C[C@@H](O)C1 ; CC1=CC2C(C=NN2c2ccc(F)cc2)C=C1[C@H]1CN(S(=O)(=O)c2cnn(C)n2)CCN1C[C@H]1C[C@@H](O)C1]

TABLE 1I-continued
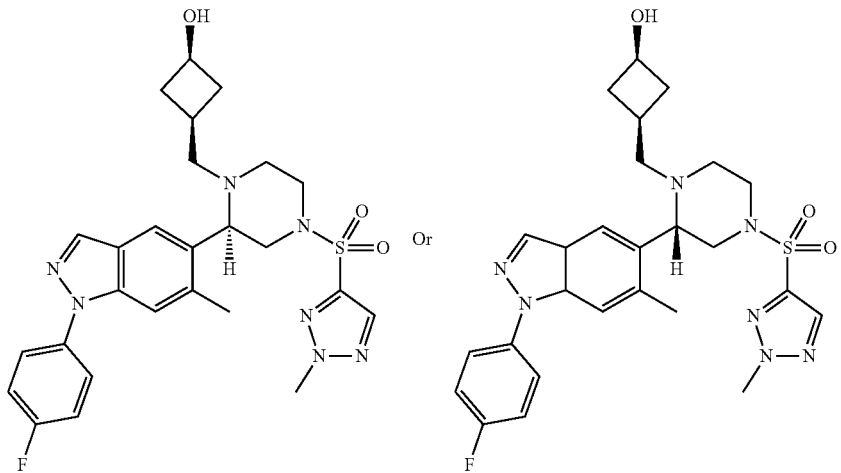 [SMILES: Cc1cc2c(cnn2-c2ccc(F)cc2)cc1[C@@H]1CN(S(=O)(=O)c2cnn(C)n2)CCN1C[C@H]1C[C@@H](O)C1 ; CC1=CC2C(C=NN2c2ccc(F)cc2)C=C1[C@H]1CN(S(=O)(=O)c2cnn(C)n2)CCN1C[C@H]1C[C@@H](O)C1]
Or
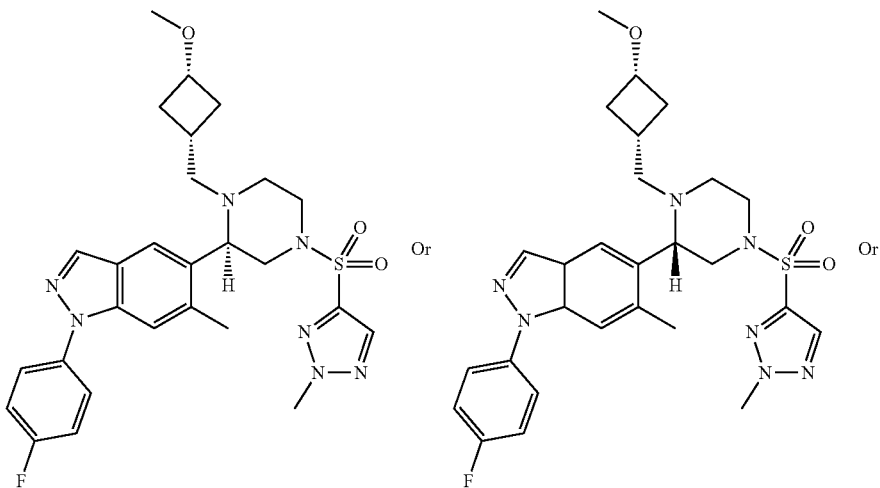 [SMILES: CO[C@H]1C[C@@H](CN2CCN(S(=O)(=O)c3cnn(C)n3)C[C@H]2c2cc3cnn(-c4ccc(F)cc4)c3cc2C)C1 ; CO[C@H]1C[C@@H](CN2CCN(S(=O)(=O)c3cnn(C)n3)C[C@@H]2C2=CC3C=NN(c4ccc(F)cc4)C3C=C2C)C1]
Or
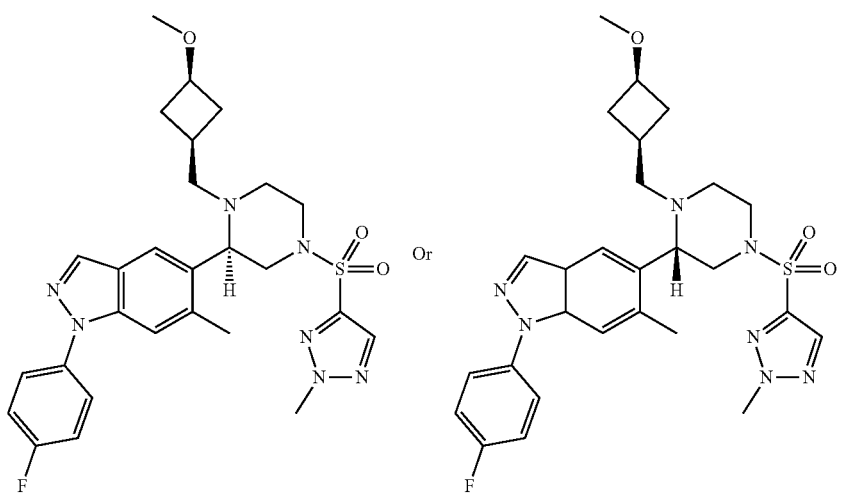 [SMILES: CO[C@H]1C[C@@H](CN2CCN(S(=O)(=O)c3cnn(C)n3)C[C@H]2c2cc3cnn(-c4ccc(F)cc4)c3cc2C)C1 ; CO[C@H]1C[C@@H](CN2CCN(S(=O)(=O)c3cnn(C)n3)C[C@@H]2C2=CC3C=NN(c4ccc(F)cc4)C3C=C2C)C1]
Or

TABLE 1I-continued
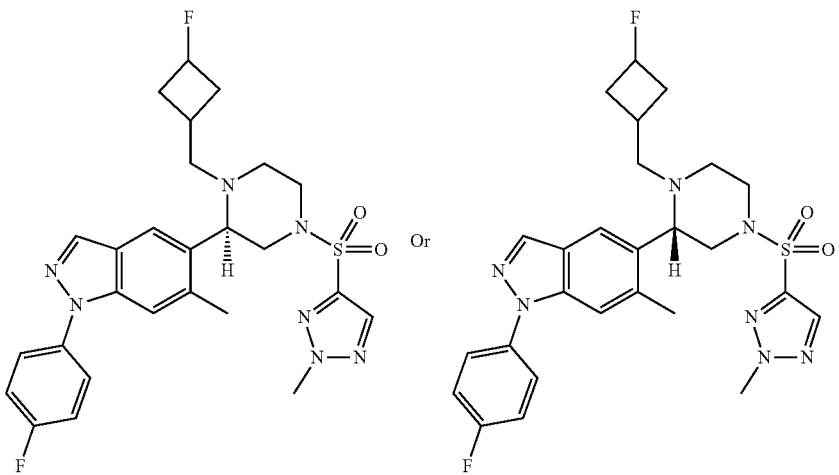 [SMILES: Cc1cc2c(cnn2-c2ccc(F)cc2)cc1[C@@H]1CN(S(=O)(=O)c2cnn(C)n2)CCN1CC1CC(F)C1 ; Cc1cc2c(cnn2-c2ccc(F)cc2)cc1[C@H]1CN(S(=O)(=O)c2cnn(C)n2)CCN1CC1CC(F)C1]
Or
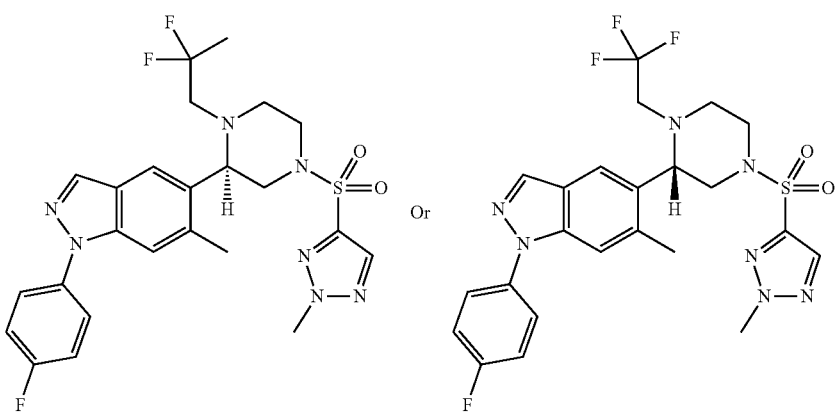 [SMILES: Cc1cc2c(cnn2-c2ccc(F)cc2)cc1[C@@H]1CN(S(=O)(=O)c2cnn(C)n2)CCN1CC(C)(F)F ; Cc1cc2c(cnn2-c2ccc(F)cc2)cc1[C@H]1CN(S(=O)(=O)c2cnn(C)n2)CCN1CC(F)(F)F]
Or
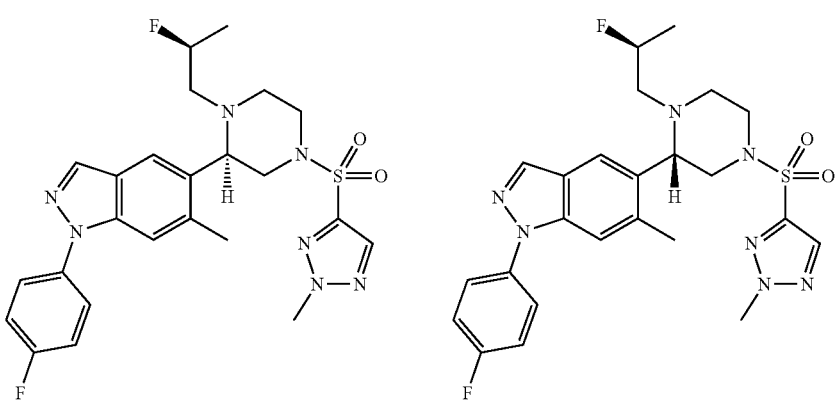 [SMILES: Cc1cc2c(cnn2-c2ccc(F)cc2)cc1[C@@H]1CN(S(=O)(=O)c2cnn(C)n2)CCN1C[C@H](C)F ; Cc1cc2c(cnn2-c2ccc(F)cc2)cc1[C@H]1CN(S(=O)(=O)c2cnn(C)n2)CCN1C[C@H](C)F]

TABLE 1I-continued
And | Or | And
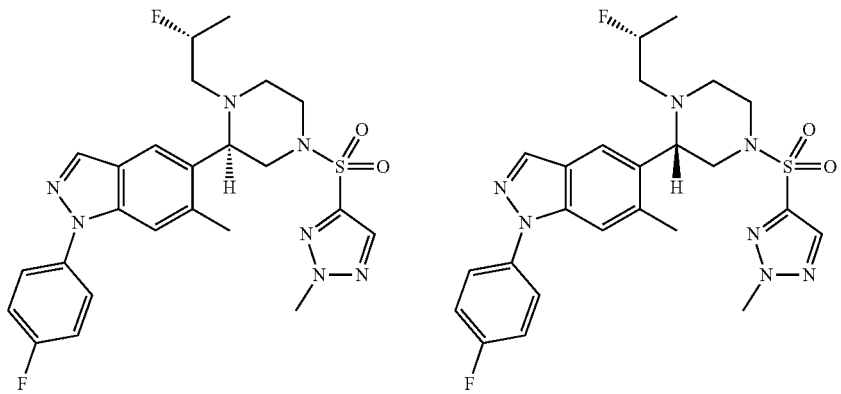 [SMILES: Cc1cc2c(cnn2-c2ccc(F)cc2)cc1[C@@H]1CN(S(=O)(=O)c2cnn(C)n2)CCN1C[C@@H](C)F ; Cc1cc2c(cnn2-c2ccc(F)cc2)cc1[C@H]1CN(S(=O)(=O)c2cnn(C)n2)CCN1C[C@@H](C)F]
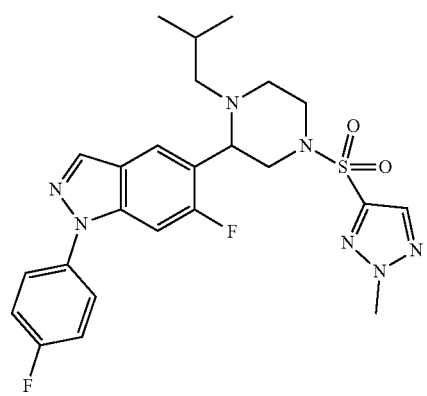
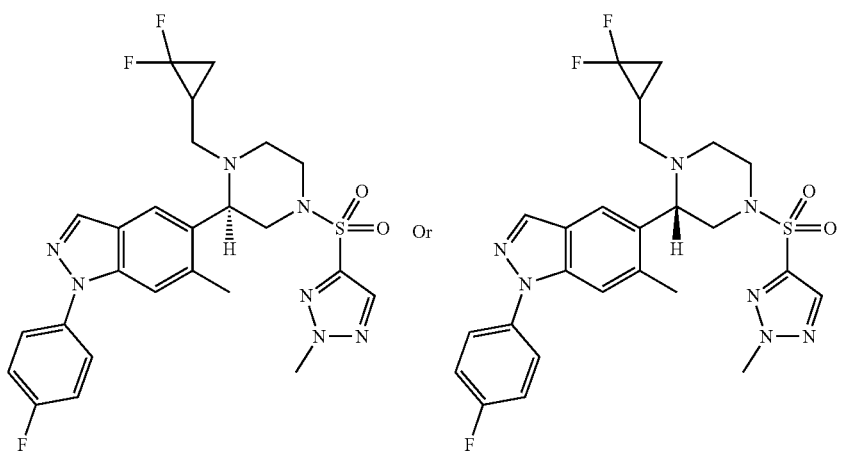 [SMILES: Cc1cc2c(cnn2-c2ccc(F)cc2)cc1[C@@H]1CN(S(=O)(=O)c2cnn(C)n2)CCN1CC1CC1(F)F ; Cc1cc2c(cnn2-c2ccc(F)cc2)cc1[C@H]1CN(S(=O)(=O)c2cnn(C)n2)CCN1CC1CC1(F)F]
Or

TABLE 1I-continued
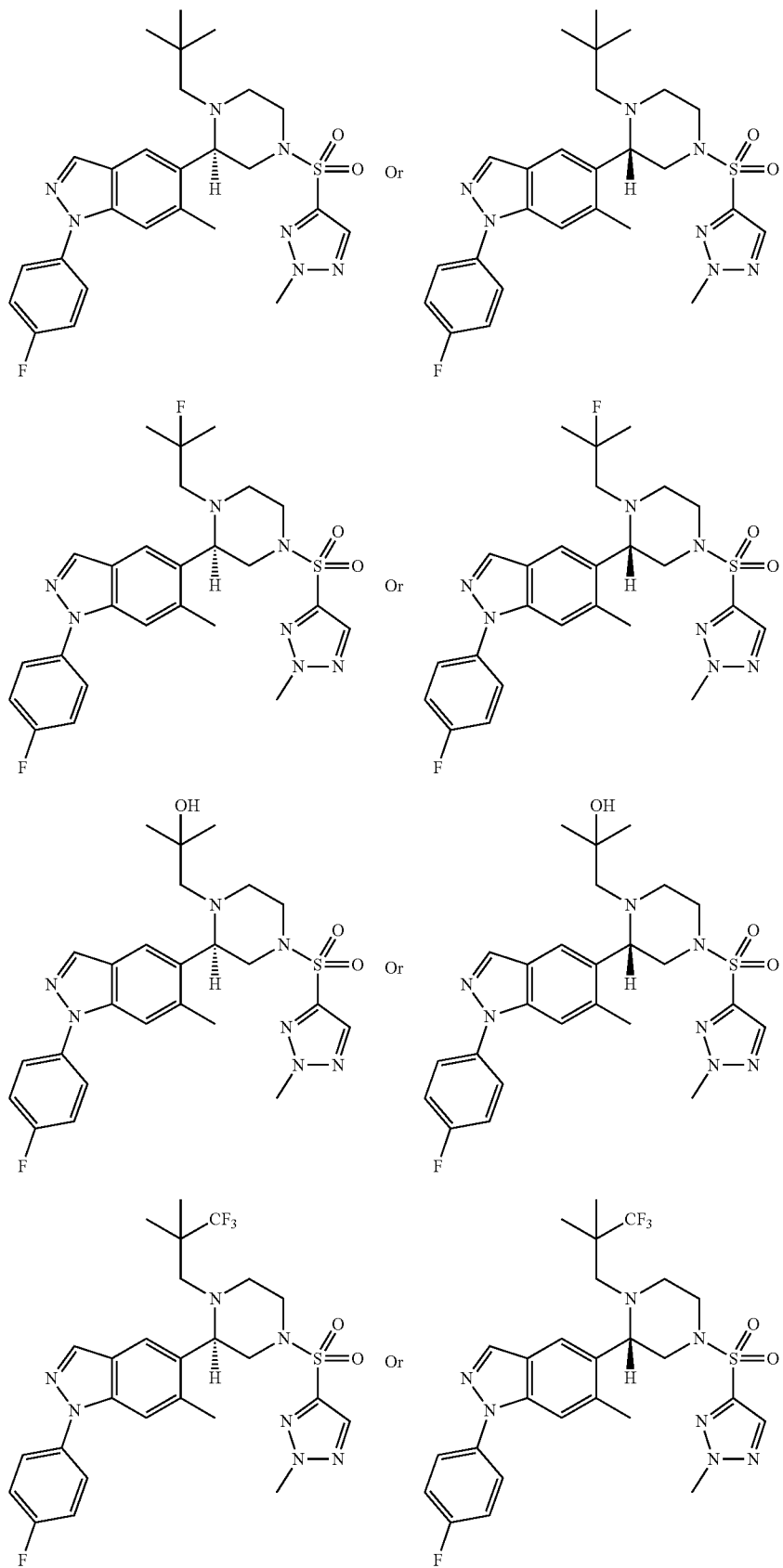

TABLE 1I-continued
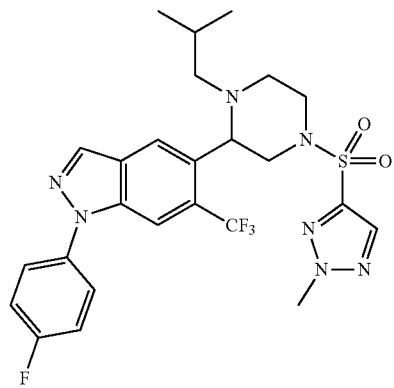 [SMILES: CC(C)CN1CCN(S(=O)(=O)c2cnn(C)n2)CC1c1cc2cnn(-c3ccc(F)cc3)c2cc1C(F)(F)F]
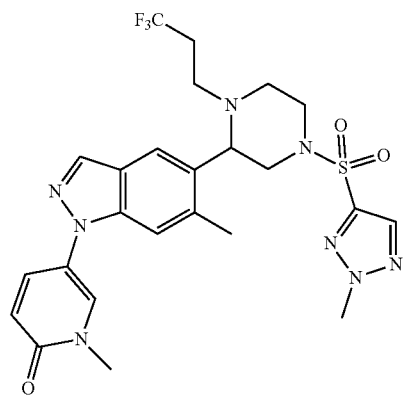 [SMILES: Cc1cc2c(cnn2-c2ccc(=O)n(C)c2)cc1C1CN(S(=O)(=O)c2cnn(C)n2)CCN1CCC(F)(F)F]
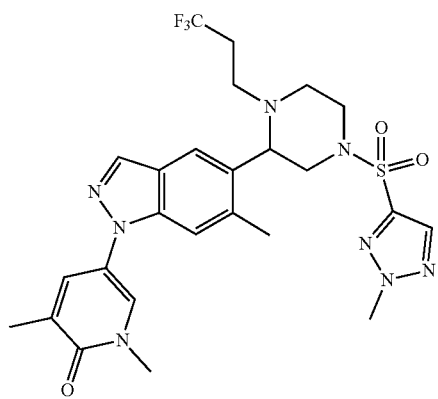
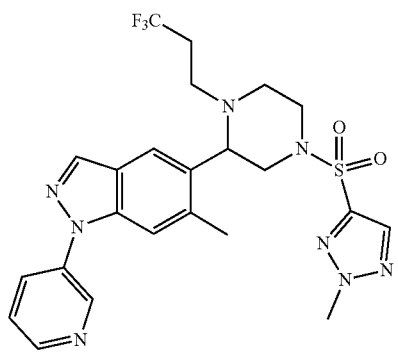

TABLE 1I-continued
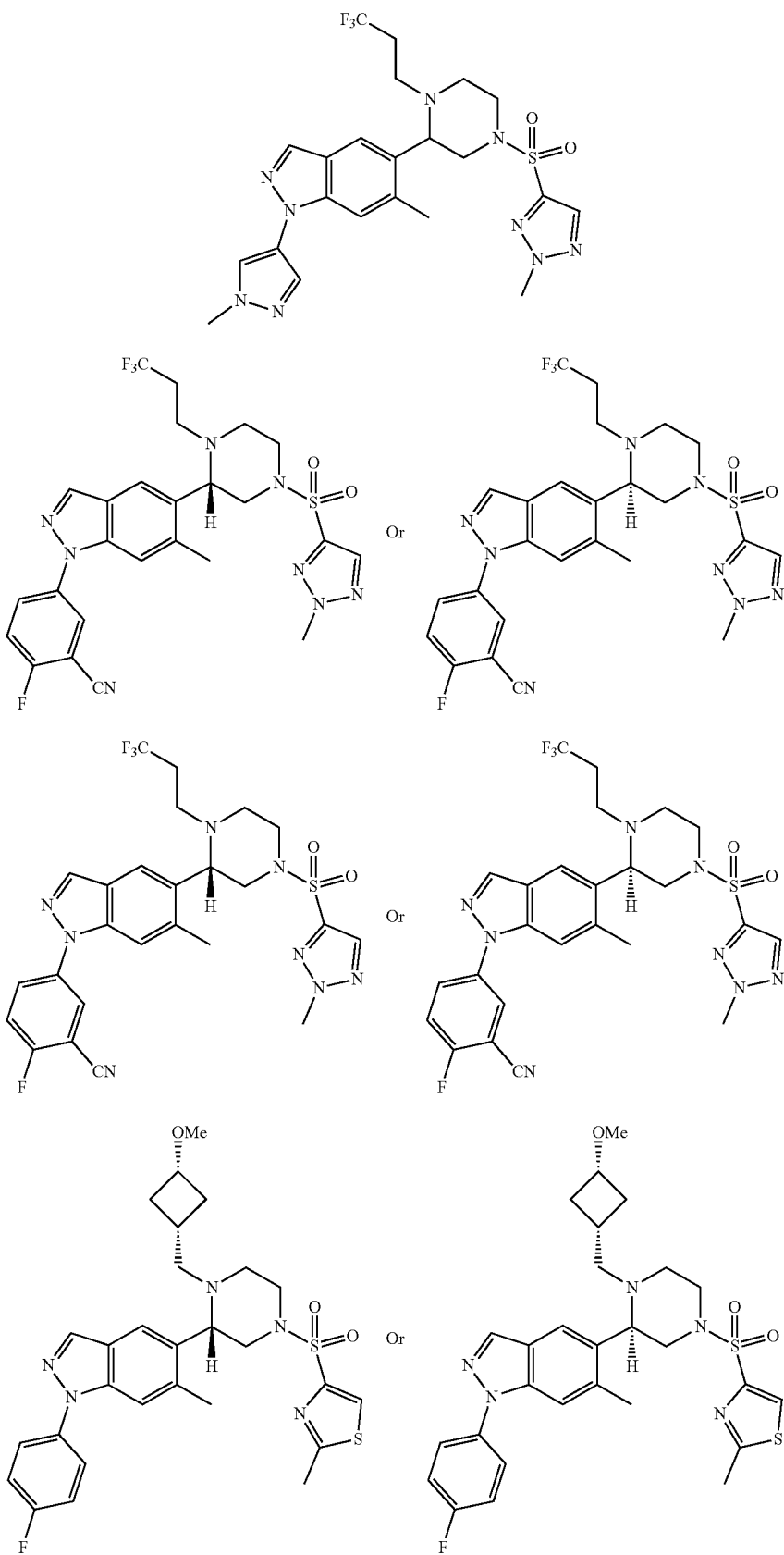

TABLE 1I-continued
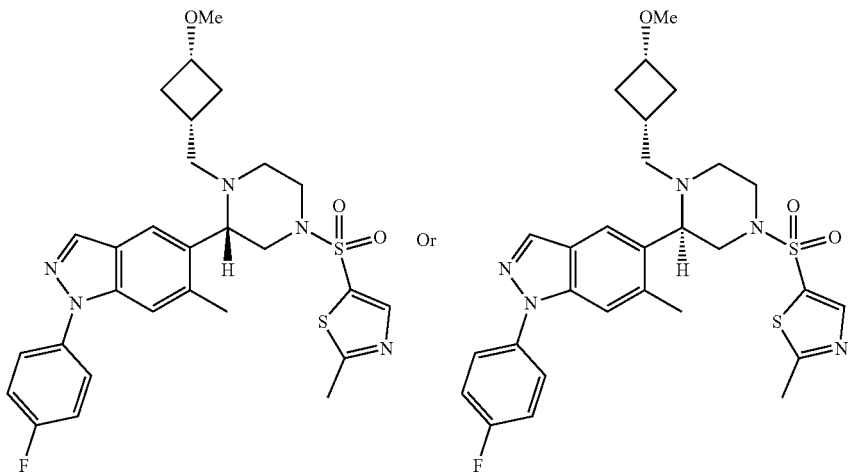 [SMILES: CO[C@H]1C[C@@H](CN2CCN(S(=O)(=O)c3cnc(C)s3)C[C@@H]2c2cc3cnn(-c4ccc(F)cc4)c3cc2C)C1 ; CO[C@H]1C[C@@H](CN2CCN(S(=O)(=O)c3cnc(C)s3)C[C@H]2c2cc3cnn(-c4ccc(F)cc4)c3cc2C)C1]
In some embodiments, the compound of Formula J, I, Ia, Ib, Ib-1, Ib-2, Ic or Id, or the pharmaceutically acceptable salt thereof, is a compound of Table 1J.
TABLE 1J
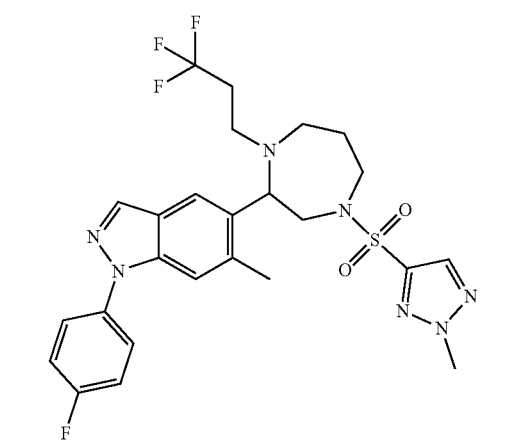 [SMILES: Cc1cc2c(cnn2-c2ccc(F)cc2)cc1C1CN(S(=O)(=O)c2cnn(C)n2)CCCN1CCC(F)(F)F]
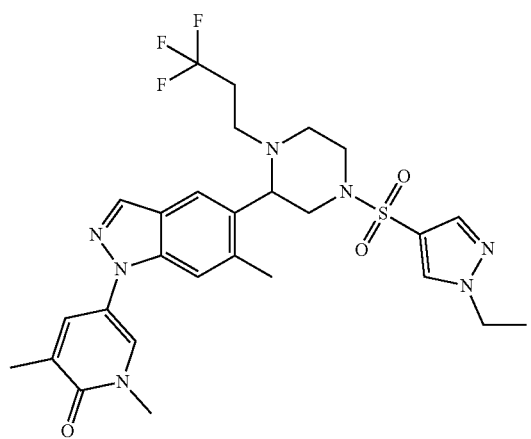 [SMILES: CCn1cc(S(=O)(=O)N2CCN(CCC(F)(F)F)C(c3cc4cnn(-c5cc(C)c(=O)n(C)c5)c4cc3C)C2)cn1]

TABLE 1J-continued
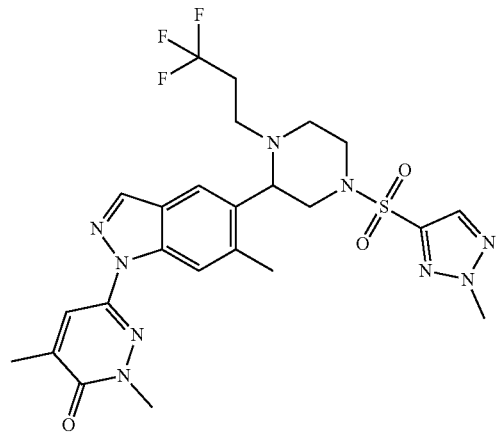 [SMILES: Cc1cc2c(cnn2-c2cc(C)c(=O)n(C)n2)cc1C1CN(S(=O)(=O)c2cnn(C)n2)CCN1CCC(F)(F)F]
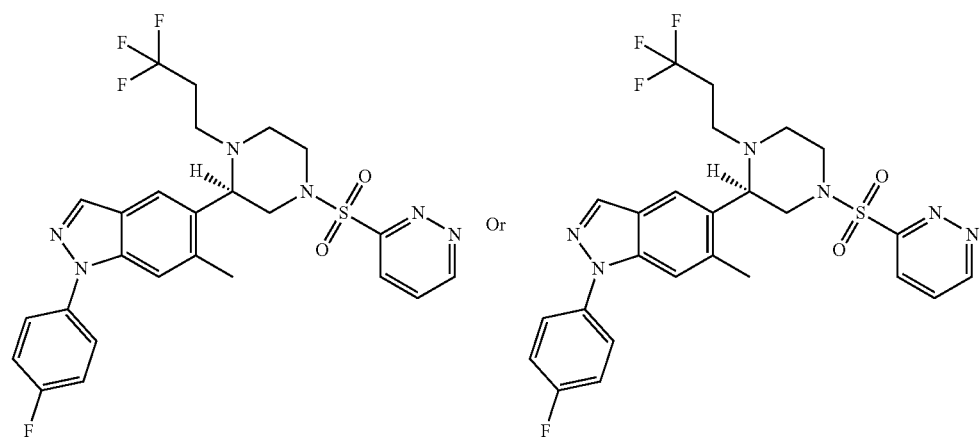 [SMILES: Cc1cc2c(cnn2-c2ccc(F)cc2)cc1[C@@H]1CN(S(=O)(=O)c2cccnn2)CCN1CCC(F)(F)F ; Cc1cc2c(cnn2-c2ccc(F)cc2)cc1[C@@H]1CN(S(=O)(=O)c2cccnn2)CCN1CCC(F)(F)F]
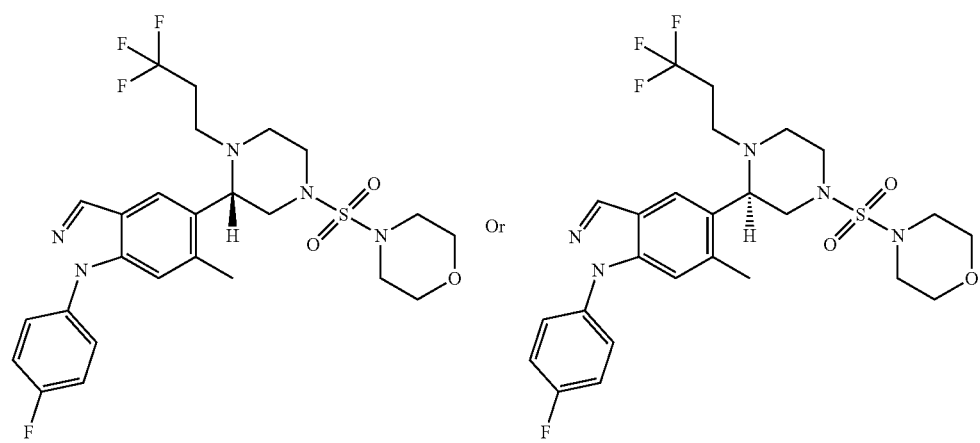 [SMILES: Cc1cc(Nc2ccc(F)cc2)c(C=N)cc1[C@H]1CN(S(=O)(=O)N2CCOCC2)CCN1CCC(F)(F)F ; Cc1cc(Nc2ccc(F)cc2)c(C=N)cc1[C@@H]1CN(S(=O)(=O)N2CCOCC2)CCN1CCC(F)(F)F]

TABLE 1J-continued
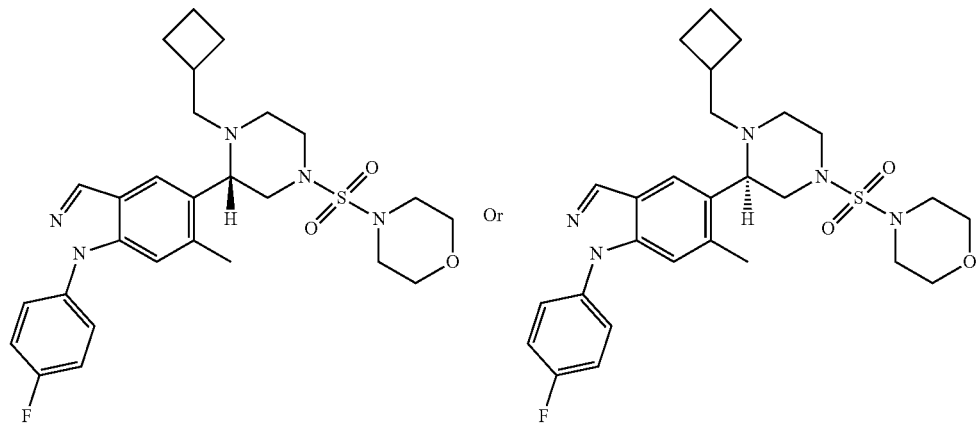 [SMILES: Cc1cc(Nc2ccc(F)cc2)c(C=N)cc1[C@H]1CN(S(=O)(=O)N2CCOCC2)CCN1CC1CCC1 ; Cc1cc(Nc2ccc(F)cc2)c(C=N)cc1[C@@H]1CN(S(=O)(=O)N2CCOCC2)CCN1CC1CCC1]
Or
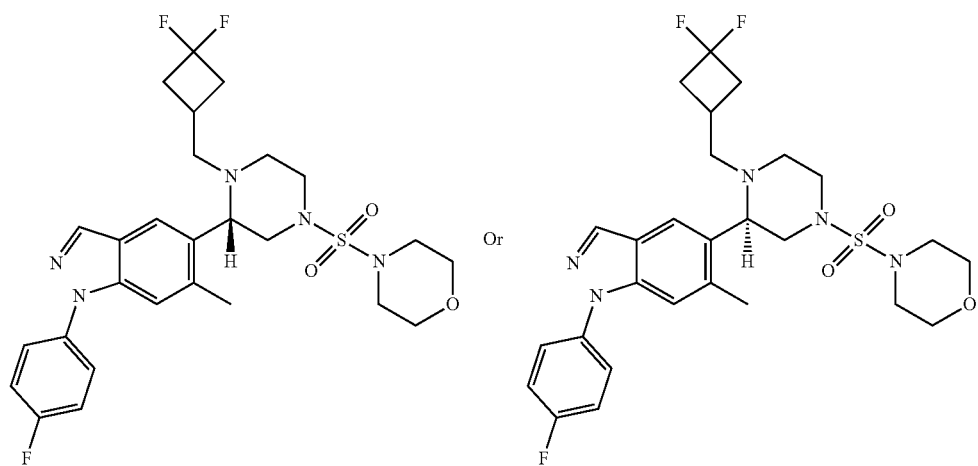 [SMILES: Cc1cc(Nc2ccc(F)cc2)c(C=N)cc1[C@H]1CN(S(=O)(=O)N2CCOCC2)CCN1CC1CC(F)(F)C1 ; Cc1cc(Nc2ccc(F)cc2)c(C=N)cc1[C@@H]1CN(S(=O)(=O)N2CCOCC2)CCN1CC1CC(F)(F)C1]
Or
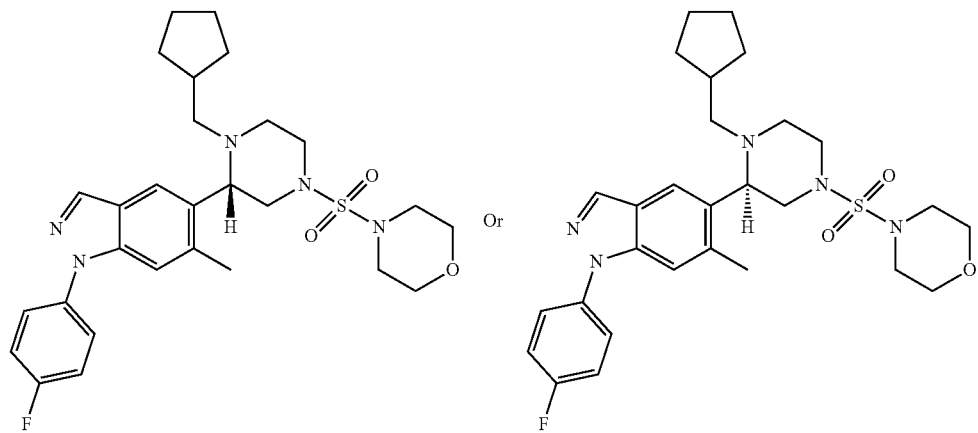 [SMILES: Cc1cc(Nc2ccc(F)cc2)c(C=N)cc1[C@H]1CN(S(=O)(=O)N2CCOCC2)CCN1CC1CCCC1 ; Cc1cc(Nc2ccc(F)cc2)c(C=N)cc1[C@@H]1CN(S(=O)(=O)N2CCOCC2)CCN1CC1CCCC1]
Or

TABLE 1J-continued
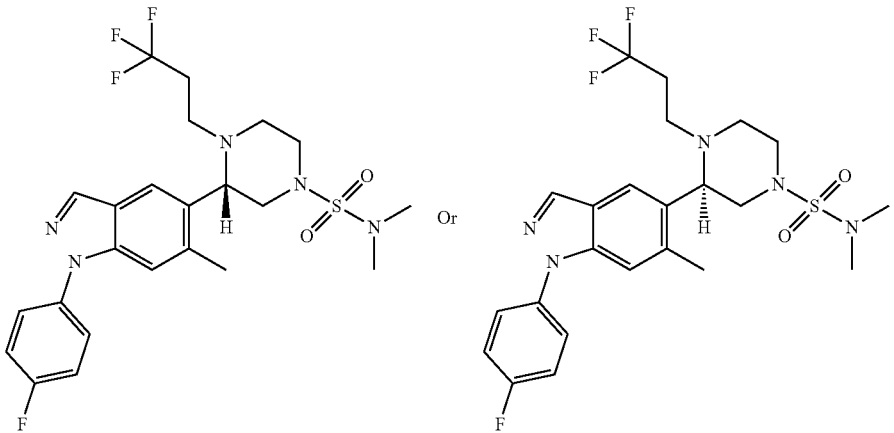 [SMILES: Cc1cc(Nc2ccc(F)cc2)c(C=N)cc1[C@H]1CN(S(=O)(=O)N(C)C)CCN1CCC(F)(F)F ; Cc1cc(Nc2ccc(F)cc2)c(C=N)cc1[C@@H]1CN(S(=O)(=O)N(C)C)CCN1CCC(F)(F)F]
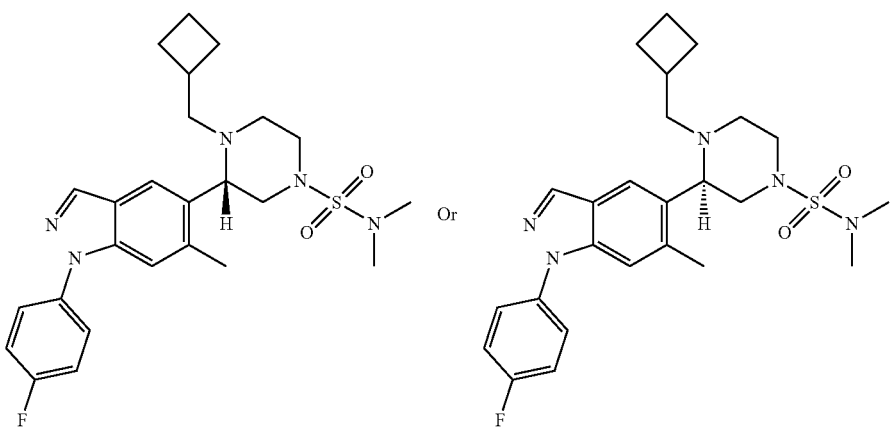 [SMILES: Cc1cc(Nc2ccc(F)cc2)c(C=N)cc1[C@H]1CN(S(=O)(=O)N(C)C)CCN1CC1CCC1 ; Cc1cc(Nc2ccc(F)cc2)c(C=N)cc1[C@@H]1CN(S(=O)(=O)N(C)C)CCN1CC1CCC1]
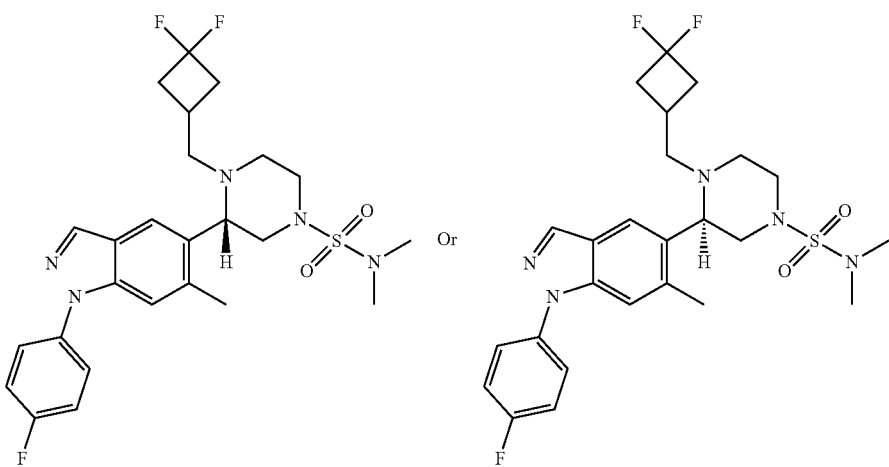 [SMILES: Cc1cc(Nc2ccc(F)cc2)c(C=N)cc1[C@H]1CN(S(=O)(=O)N(C)C)CCN1CC1CC(F)(F)C1 ; Cc1cc(Nc2ccc(F)cc2)c(C=N)cc1[C@@H]1CN(S(=O)(=O)N(C)C)CCN1CC1CC(F)(F)C1]

TABLE 1J-continued
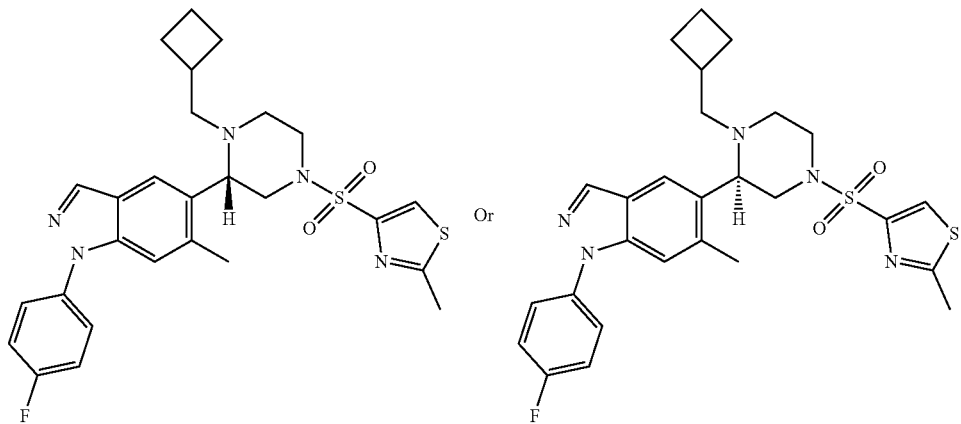 [SMILES: Cc1nc(S(=O)(=O)N2CCN(CC3CCC3)[C@@H](c3cc(C=N)c(Nc4ccc(F)cc4)cc3C)C2)cs1 ; Cc1nc(S(=O)(=O)N2CCN(CC3CCC3)[C@H](c3cc(C=N)c(Nc4ccc(F)cc4)cc3C)C2)cs1]
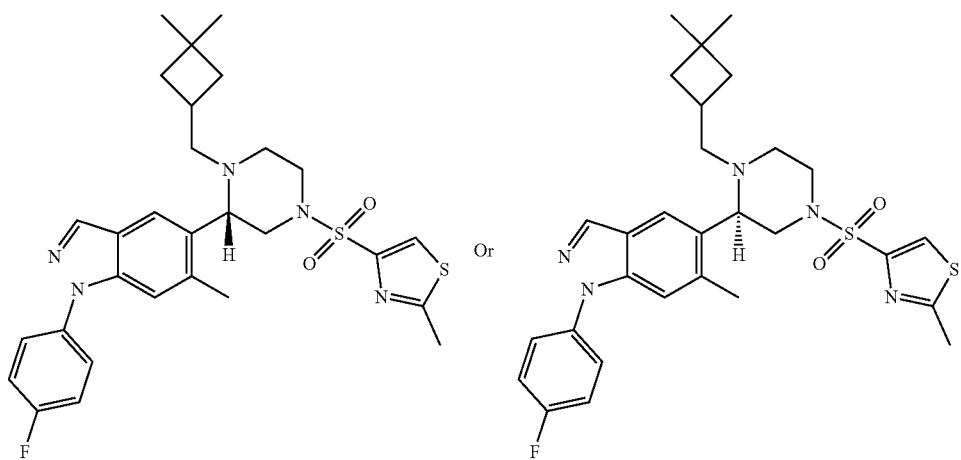 [SMILES: Cc1nc(S(=O)(=O)N2CCN(CC3CC(C)(C)C3)[C@@H](c3cc(C=N)c(Nc4ccc(F)cc4)cc3C)C2)cs1 ; Cc1nc(S(=O)(=O)N2CCN(CC3CC(C)(C)C3)[C@H](c3cc(C=N)c(Nc4ccc(F)cc4)cc3C)C2)cs1]
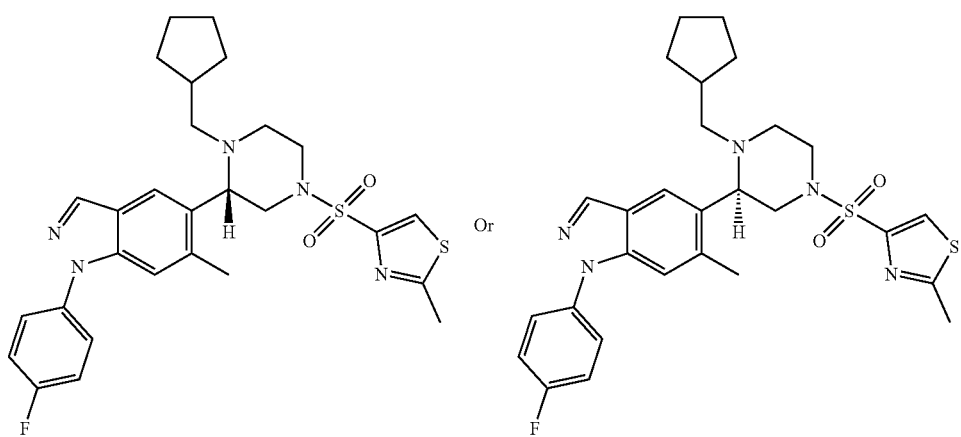 [SMILES: Cc1nc(S(=O)(=O)N2CCN(CC3CCCC3)[C@@H](c3cc(C=N)c(Nc4ccc(F)cc4)cc3C)C2)cs1 ; Cc1nc(S(=O)(=O)N2CCN(CC3CCCC3)[C@H](c3cc(C=N)c(Nc4ccc(F)cc4)cc3C)C2)cs1]

TABLE 1J-continued
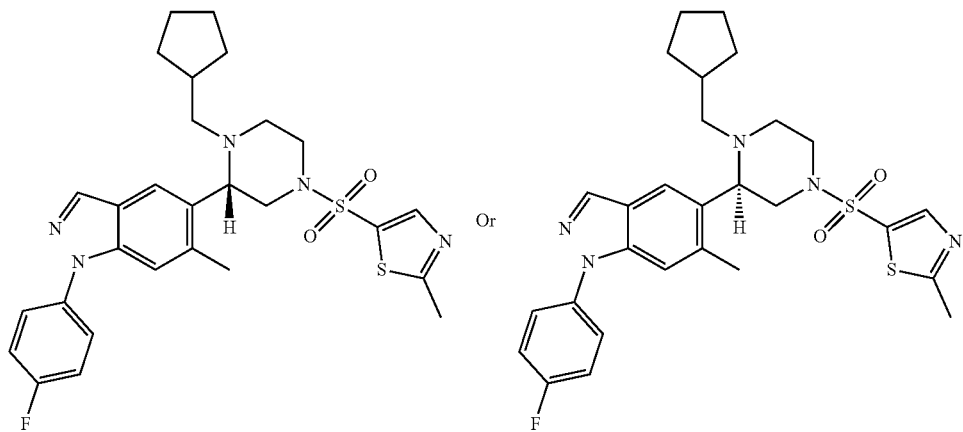 [SMILES: Cc1ncc(S(=O)(=O)N2CCN(CC3CCCC3)[C@@H](c3cc(C=N)c(Nc4ccc(F)cc4)cc3C)C2)s1 ; Cc1ncc(S(=O)(=O)N2CCN(CC3CCCC3)[C@H](c3cc(C=N)c(Nc4ccc(F)cc4)cc3C)C2)s1]
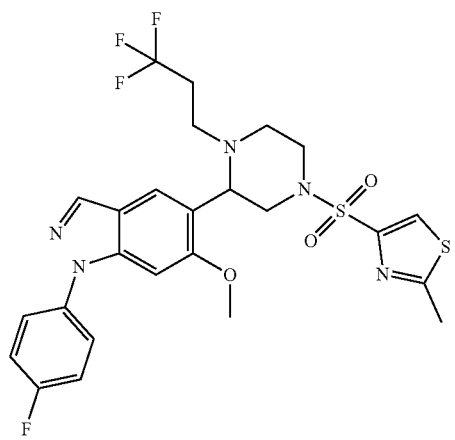 [SMILES: COc1cc(Nc2ccc(F)cc2)c(C=N)cc1C1CN(S(=O)(=O)c2csc(C)n2)CCN1CCC(F)(F)F]
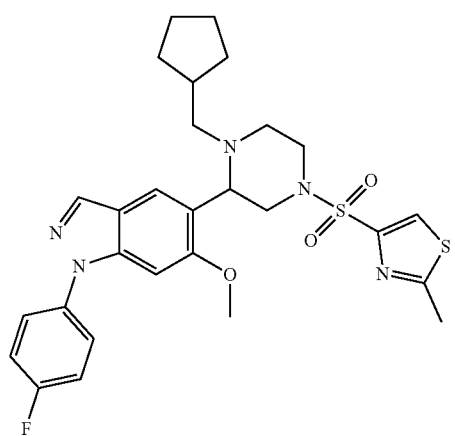 [SMILES: COc1cc(Nc2ccc(F)cc2)c(C=N)cc1C1CN(S(=O)(=O)c2csc(C)n2)CCN1CC1CCCC1]

TABLE 1J-continued
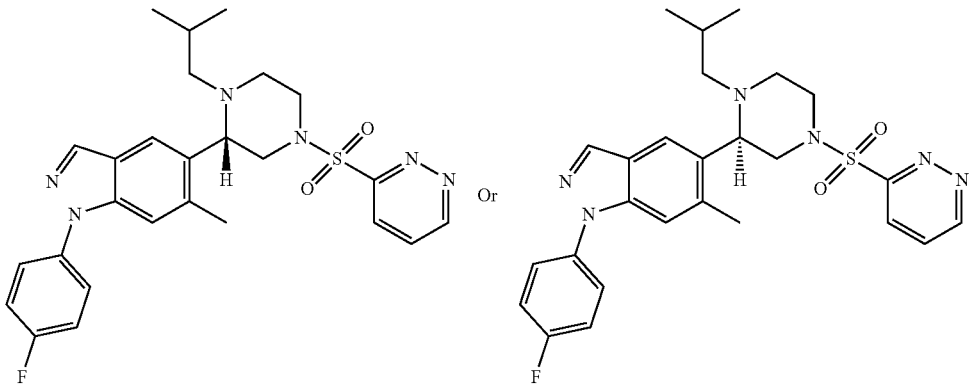 [SMILES: Cc1cc(Nc2ccc(F)cc2)c(C=N)cc1[C@H]1CN(S(=O)(=O)c2cccnn2)CCN1CC(C)C ; Cc1cc(Nc2ccc(F)cc2)c(C=N)cc1[C@@H]1CN(S(=O)(=O)c2cccnn2)CCN1CC(C)C]
Or
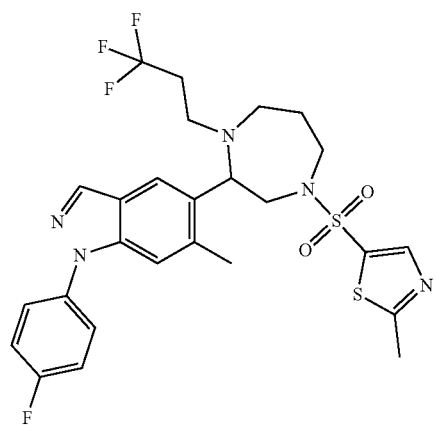 [SMILES: Cc1ncc(S(=O)(=O)N2CCCN(CCC(F)(F)F)C(c3cc(C=N)c(Nc4ccc(F)cc4)cc3C)C2)s1]
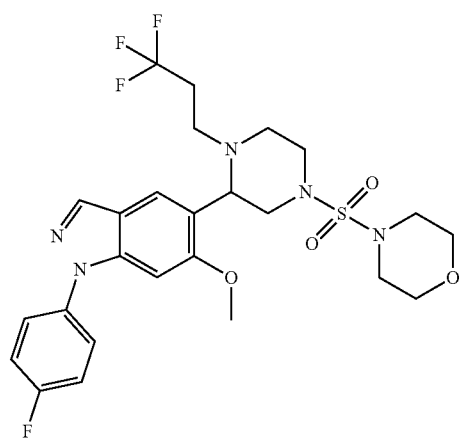 [SMILES: COc1cc(Nc2ccc(F)cc2)c(C=N)cc1C1CN(S(=O)(=O)N2CCOCC2)CCN1CCC(F)(F)F]

In some embodiments, the compound of Formula J, I, Ia, Ib, Ib-1, Ib-2, Ic or Id, or the pharmaceutically acceptable salt thereof, is a compound of Table 1K.
TABLE 1K
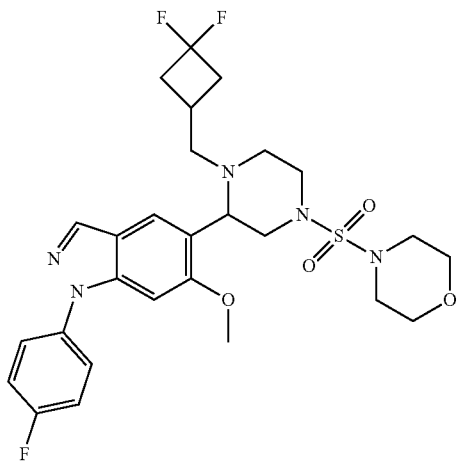 [SMILES: COc1cc(Nc2ccc(F)cc2)c(C=N)cc1C1CN(S(=O)(=O)N2CCOCC2)CCN1CC1CC(F)(F)C1]
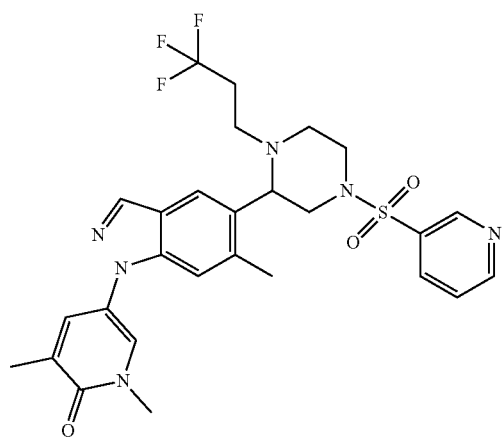 [SMILES: Cc1cc(Nc2cc(C)c(=O)n(C)c2)c(C=N)cc1C1CN(S(=O)(=O)c2cccnc2)CCN1CCC(F)(F)F]
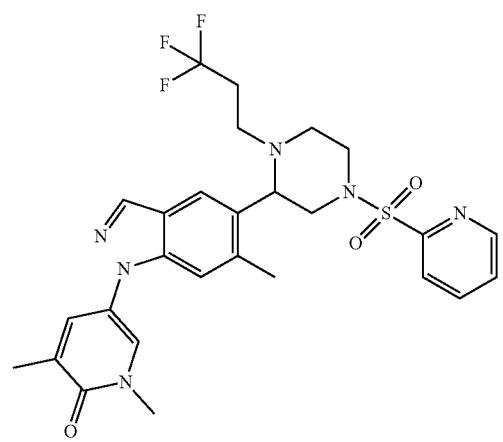 [SMILES: Cc1cc(Nc2cc(C)c(=O)n(C)c2)c(C=N)cc1C1CN(S(=O)(=O)c2ccccn2)CCN1CCC(F)(F)F]

TABLE 1K-continued
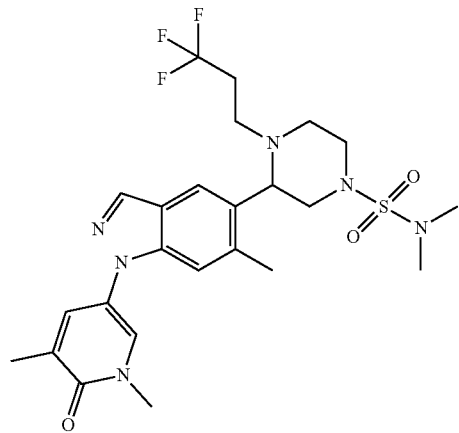
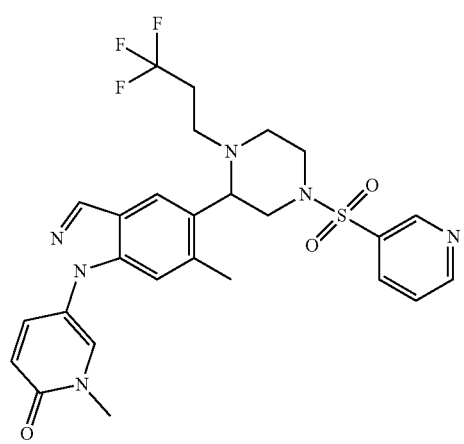 [SMILES: Cc1cc(Nc2ccc(=O)n(C)c2)c(C=N)cc1C1CN(S(=O)(=O)c2cccnc2)CCN1CCC(F)(F)F]
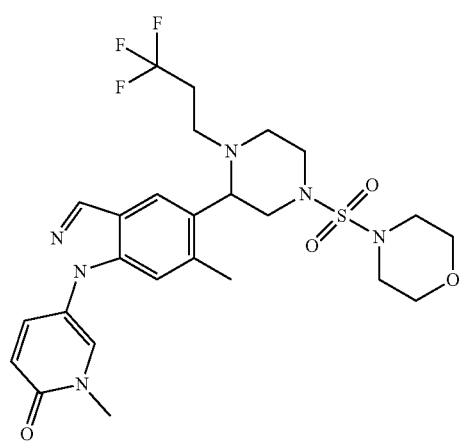 [SMILES: Cc1cc(Nc2ccc(=O)n(C)c2)c(C=N)cc1C1CN(S(=O)(=O)N2CCOCC2)CCN1CCC(F)(F)F]

TABLE 1K-continued
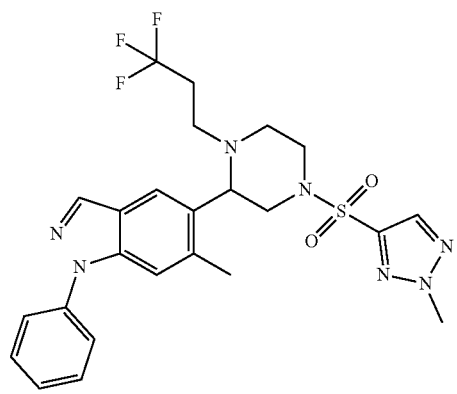 [SMILES: Cc1cc(Nc2ccccc2)c(C=N)cc1C1CN(S(=O)(=O)c2cnn(C)n2)CCN1CCC(F)(F)F]
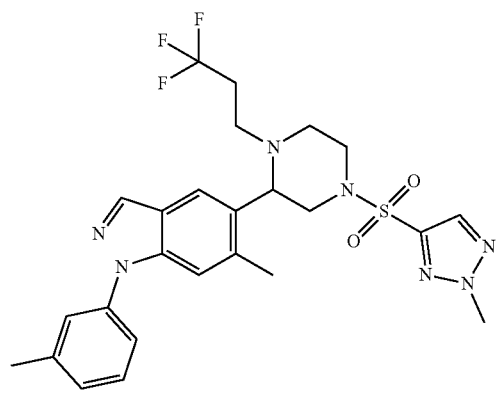 [SMILES: Cc1cccc(Nc2cc(C)c(C3CN(S(=O)(=O)c4cnn(C)n4)CCN3CCC(F)(F)F)cc2C=N)c1]
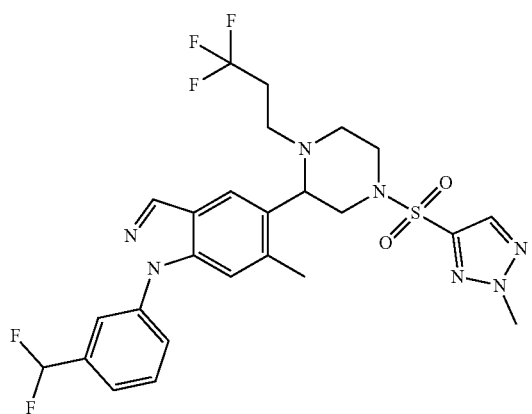 [SMILES: Cc1cc(Nc2cccc(C(F)F)c2)c(C=N)cc1C1CN(S(=O)(=O)c2cnn(C)n2)CCN1CCC(F)(F)F]
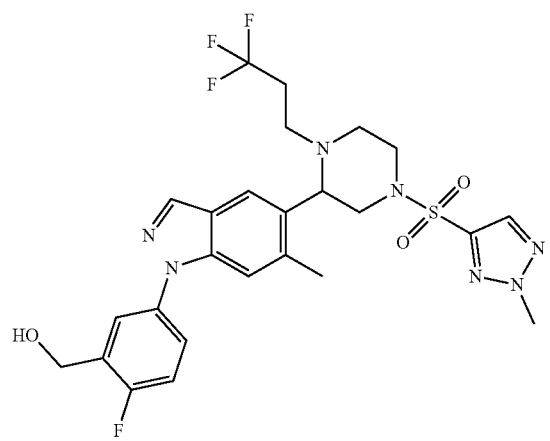 [SMILES: Cc1cc(Nc2ccc(F)c(CO)c2)c(C=N)cc1C1CN(S(=O)(=O)c2cnn(C)n2)CCN1CCC(F)(F)F]

TABLE 1K-continued
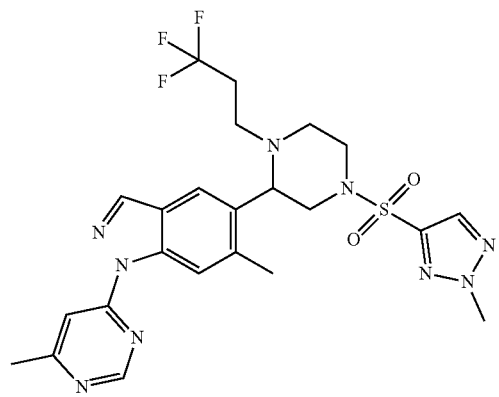 [SMILES: Cc1cc(Nc2cc(C)c(C3CN(S(=O)(=O)c4cnn(C)n4)CCN3CCC(F)(F)F)cc2C=N)ncn1]
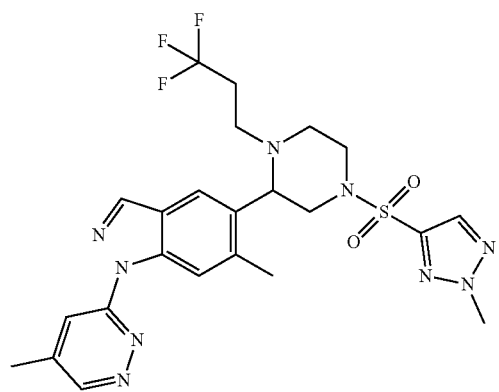 [SMILES: Cc1cnnc(Nc2cc(C)c(C3CN(S(=O)(=O)c4cnn(C)n4)CCN3CCC(F)(F)F)cc2C=N)c1]
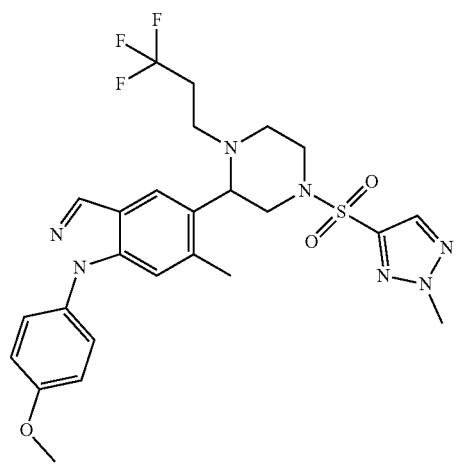 [SMILES: COc1ccc(Nc2cc(C)c(C3CN(S(=O)(=O)c4cnn(C)n4)CCN3CCC(F)(F)F)cc2C=N)cc1]

TABLE 1K-continued
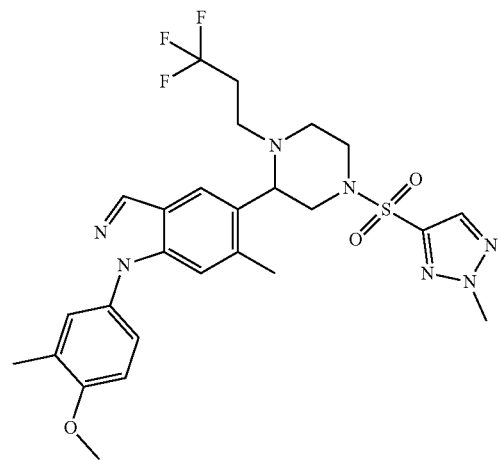 [SMILES: COc1ccc(Nc2cc(C)c(C3CN(S(=O)(=O)c4cnn(C)n4)CCN3CCC(F)(F)F)cc2C=N)cc1C]
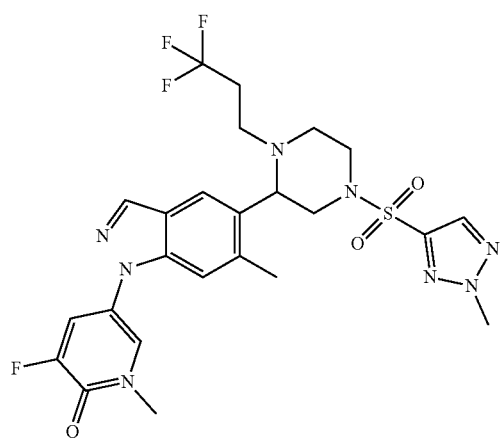
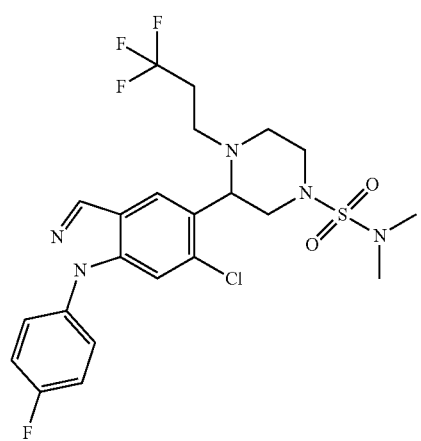 [SMILES: CN(C)S(=O)(=O)N1CCN(CCC(F)(F)F)C(c2cc(C=N)c(Nc3ccc(F)cc3)cc2Cl)C1]

TABLE 1K-continued
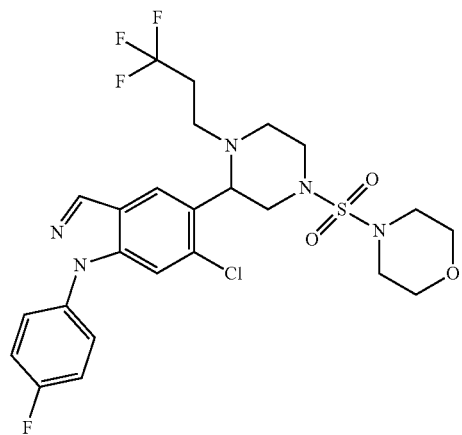 [SMILES: N=Cc1cc(C2CN(S(=O)(=O)N3CCOCC3)CCN2CCC(F)(F)F)c(Cl)cc1Nc1ccc(F)cc1]
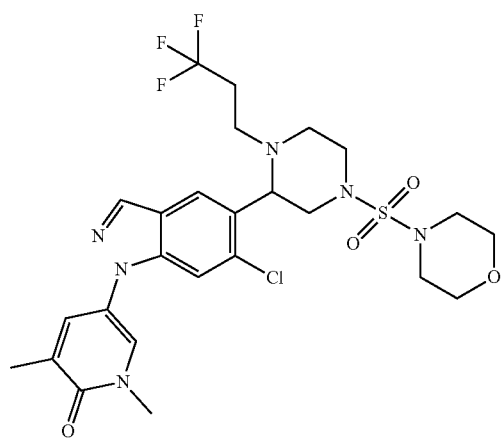 [SMILES: Cc1cc(Nc2cc(Cl)c(C3CN(S(=O)(=O)N4CCOCC4)CCN3CCC(F)(F)F)cc2C=N)cn(C)c1=O]
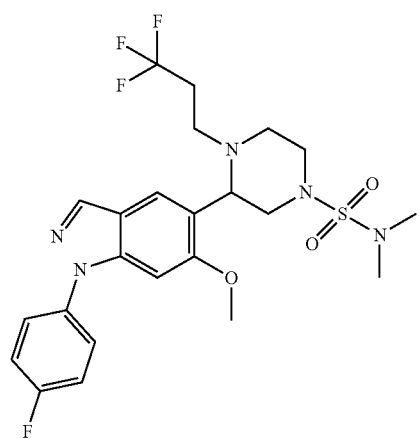 [SMILES: COc1cc(Nc2ccc(F)cc2)c(C=N)cc1C1CN(S(=O)(=O)N(C)C)CCN1CCC(F)(F)F]

TABLE 1K-continued

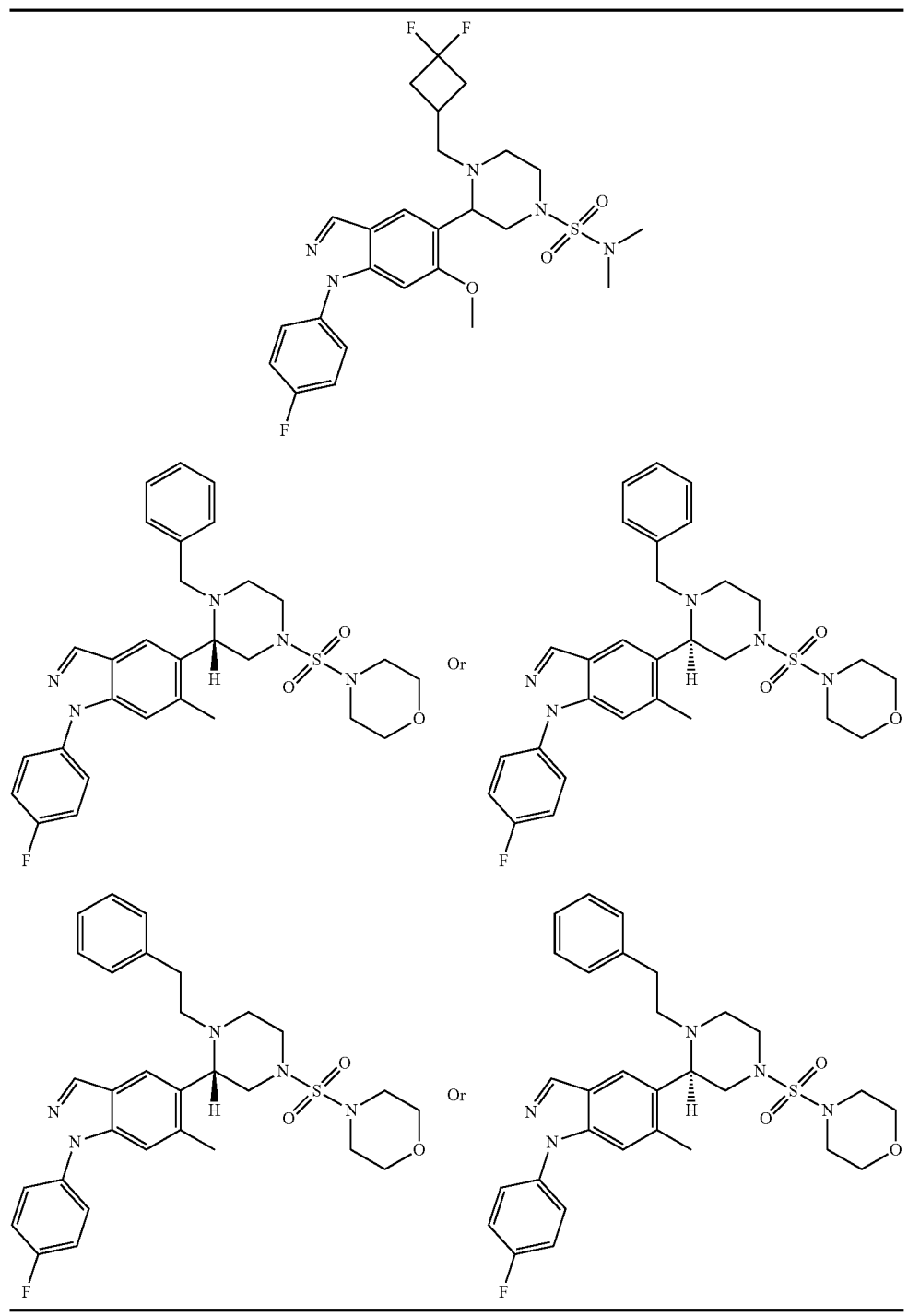

In some embodiments, the compound of Formula J, I, Ia, Ib, Ib-1, Ib-2, Ic or Id, or the pharmaceutically acceptable salt thereof, is a compound of Table 1A, Table 1B, Table 1C, Table 1D, Table 1E, Table 1F, Table 1G, Table 1H, Table 1I, Table 1J, or Table 1K. In some embodiments, the compound of Formula J, I, Ia, Ib, Ib-1, Ib-2, Ic or Id, or the pharmaceutically acceptable salt thereof, is a compound of Table 1A, Table 1B, Table 1C, Table 1D, Table 1E, Table 1F, Table 1G, Table 1H, or Table 1I. In some embodiments, the compound of Formula J, I, Ia, Ib, Ib-1, Ib-2, Ic or Id, or the pharmaceutically acceptable salt thereof, is a compound of Table 1A, Table 1B, Table 1C, Table 1D or Table 1E. In some embodiments, the compound of Formula J, I, Ia, Ib, Ib-1, Ib-2, Ic or Id, or the pharmaceutically acceptable salt thereof, is a compound of Table 1F, Table 1G, Table 1H, or Table 1I. In some embodiments, the compound of Formula J, I, Ia, Ib, Ib-1, Ib-2, Ic or Id, or the pharmaceutically acceptable salt thereof, is a compound of Table 1J, or Table 1K. In some embodiments, the compound of Formula J, I, Ia, Ib, Ib-1, Ib-2, Ic or Id, or the pharmaceutically acceptable salt thereof, is a compound of Table 1A. In some embodiments, the compound of Formula J, I, Ia, Ib, Ib-1, Ib-2, Ic or Id, or the pharmaceutically acceptable salt thereof, is a compound of Table 1B. In some embodiments, the compound of Formula J, I, Ia, Ib, Ib-1, Ib-2, Ic or Id, or the pharmaceutically acceptable salt thereof, is a compound of Table 1C. In some embodiments, the compound of Formula J, I, Ia, Ib, Ib-1, Ib-2, Ic or Id, or the pharmaceutically acceptable salt thereof, is a compound of Table 1D. In some embodiments, the compound of Formula J, I, Ia, Ib, Ib-1, Ib-2, Ic or Id, or the pharmaceutically acceptable salt thereof, is a compound of Table 1E. In some embodiments, the compound of Formula J, I, Ia, Ib, Ib-1, Ib-2, Ic or Id, or the pharmaceutically acceptable salt thereof, is a compound of Table 1F. In some embodiments, the compound of Formula J, I, Ia, Ib, Ib-1, Ib-2, Ic or Id, or the pharmaceutically acceptable salt thereof, is a compound of Table 1G. In some embodiments, the compound of Formula J, I, Ia, Ib, Ib-1, Ib-2, Ic or Id, or the pharmaceutically acceptable salt thereof, is a compound of Table 1H. In some embodiments, the compound of Formula J, I, Ia, Ib, Ib-1, Ib-2, Ic or Id, or the pharmaceutically acceptable salt thereof, is a compound of Table 1I. In some embodiments, the compound of Formula J, I, Ia, Ib, Ib-1, Ib-2, Ic or Id, or the pharmaceutically acceptable salt thereof, is a compound of Table 1J. In some embodiments, the compound of Formula J, I, Ia, Ib, Ib-1, Ib-2, Ic or Id, or the pharmaceutically acceptable salt thereof, is a compound of Table 1K.

In some embodiments, the compound of Formula J, I, Ia, Ib, Ib-1, Ib-2, Ic or Id, is a compound of Table 1A, Table 1B, Table 1C, Table 1D, Table 1E, Table 1F, Table 1G, Table 1H, Table 1I, Table 1J, or Table 1K. In some embodiments, the compound of Formula J, I, Ia, Ib, Ib-1, Ib-2, Ic or Id is a compound of Table 1A, Table 1B, Table 1C, Table 1D, Table 1E, Table 1F, Table 1G, Table 1H, or Table 1I. In some embodiments, the compound of Formula J, I, Ia, Ib, Ib-1, Ib-2, Ic or Id is a compound of Table 1A, Table 1B, Table 1C, Table 1D or Table 1E. In some embodiments, the compound of Formula J, I, Ia, Ib, Ib-1, Ib-2, Ic or Id is a compound of Table 1F, Table 1G, Table 1H, or Table 1I. In some embodiments, the compound of Formula J, I, Ia, Ib, Ib-1, Ib-2, Ic or Id, is a compound of Table 1J, or Table 1K. In some embodiments, the compound of Formula J, I, Ia, Ib, Ib-1, Ib-2, Ic or Id is a compound of Table 1A. In some embodiments, the compound of Formula J, I, Ia, Ib, Ib-1, Ib-2, Ic or Id is a compound of Table 1B. In some embodiments, the compound of Formula J, I, Ia, Ib, Ib-1, Ib-2, Ic or Id is a compound of Table 1C. In some embodiments, the compound of Formula J, I, Ia, Ib, Ib-1, Ib-2, Ic or Id is a compound of Table 1D. In some embodiments, the compound of Formula J, I, Ia, Ib, Ib-1, Ib-2, Ic or Id is a compound of Table 1E. In some embodiments, the compound of Formula J, I, Ia, Ib, Ib-1, Ib-2, Ic or Id is a compound of Table 1F. In some embodiments, the compound of Formula J, I, Ia, Ib, Ib-1, Ib-2, Ic or Id is a compound of Table 1G. In some embodiments, the compound of Formula J, I, Ia, Ib, Ib-1, Ib-2, Ic or Id is a compound of Table 1H. In some embodiments, the compound of Formula J, I, Ia, Ib, Ib-1, Ib-2, Ic or Id is a compound of Table 1I. In some embodiments, the compound of Formula J, I, Ia, Ib, Ib-1, Ib-2, Ic or Id, is a compound of Table 1J. In some embodiments, the compound of Formula J, I, Ia, Ib, Ib-1, Ib-2, Ic or Id, is a compound of Table 1K.

In some embodiments, the compound of Formula J, I, Ia, Ib, Ib-1, Ib-2, Ic or Id, or the pharmaceutically acceptable salt thereof, is the compound having the structure:

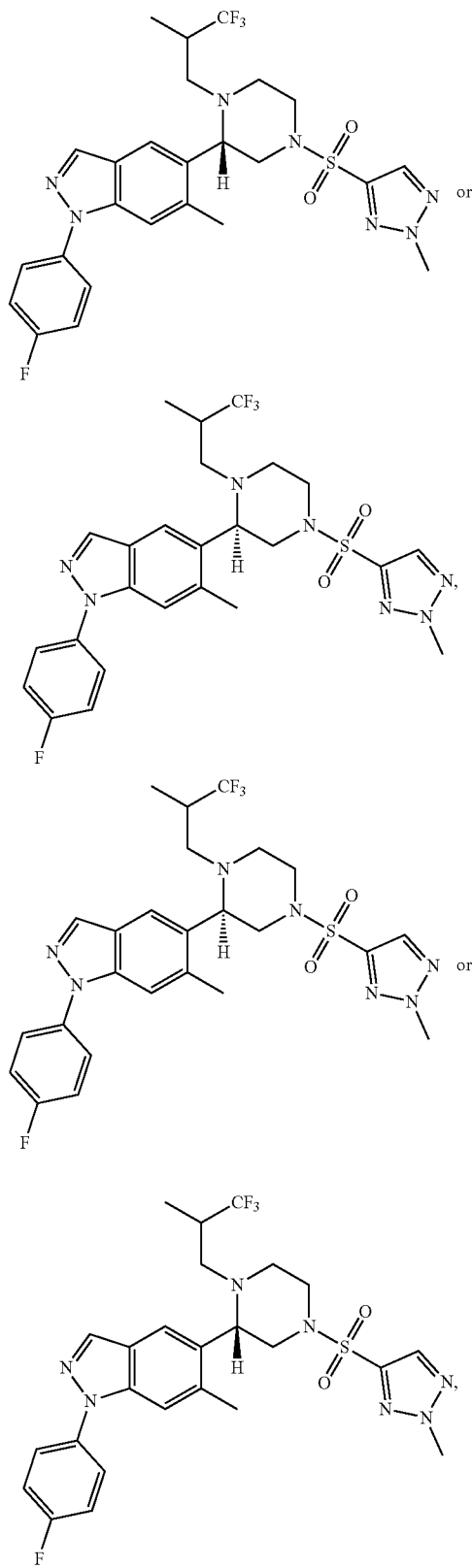

189
-continued
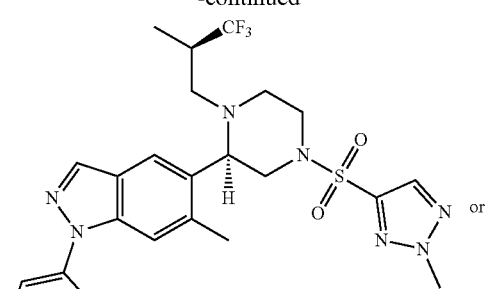
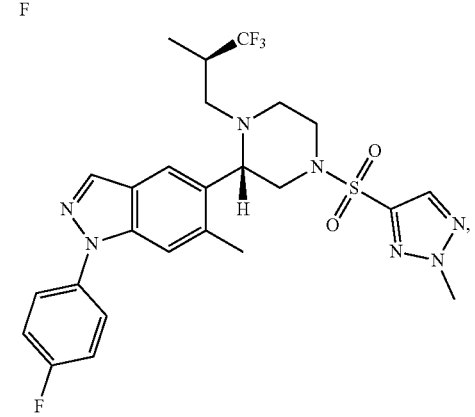
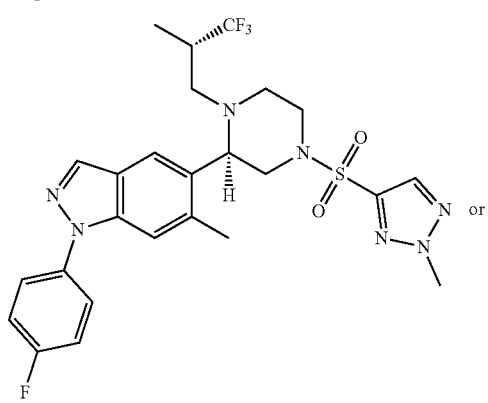
or
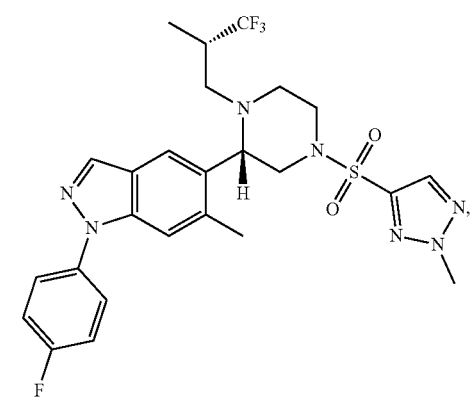
190
-continued
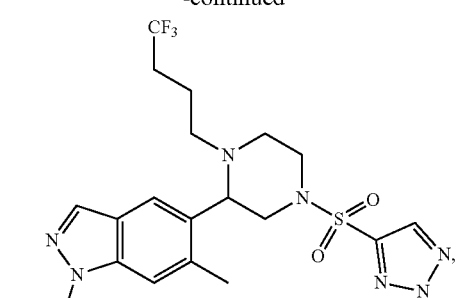
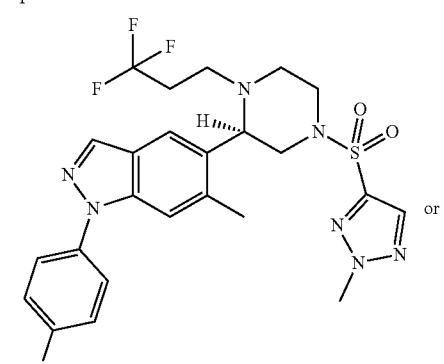
or
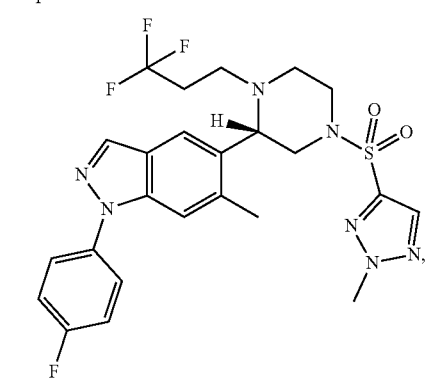
or
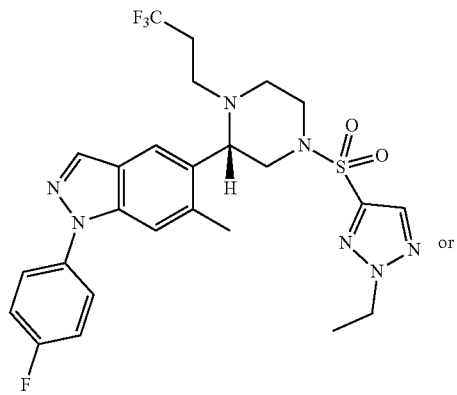
or 191
-continued
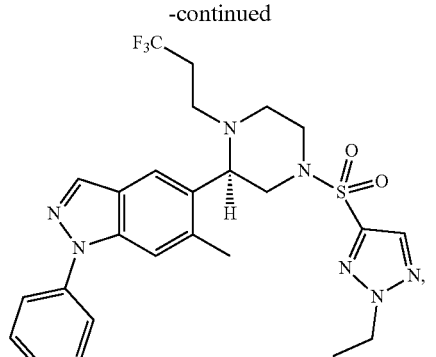
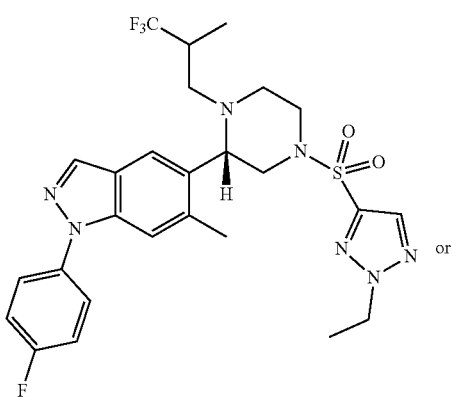
or
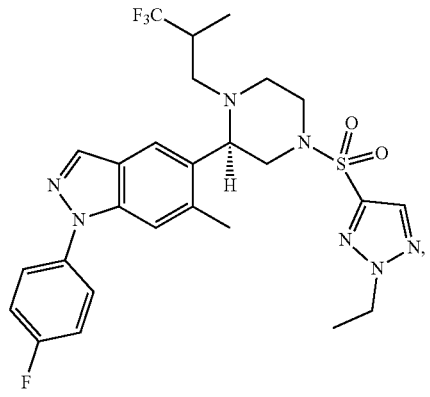
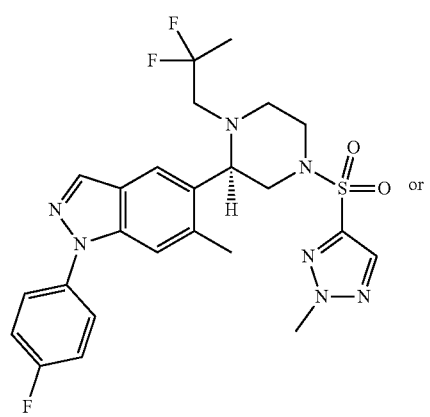
or
192
-continued
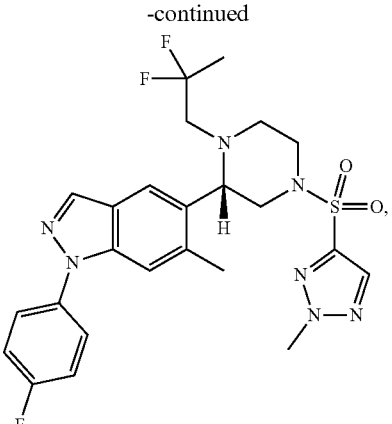
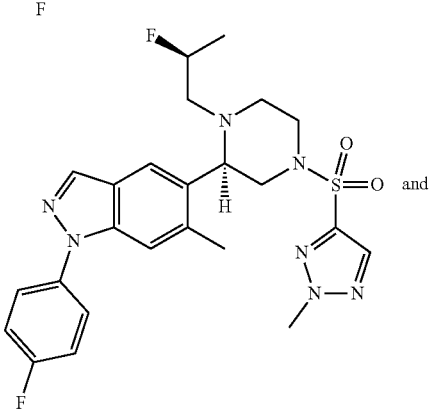
and
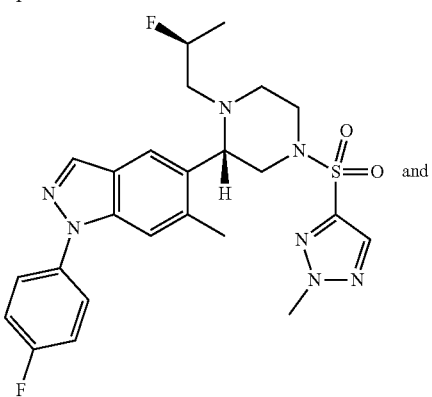
and
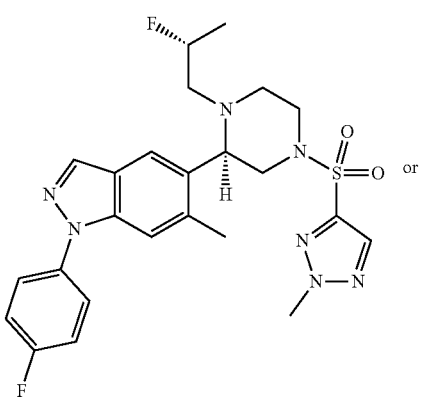
or 193
-continued
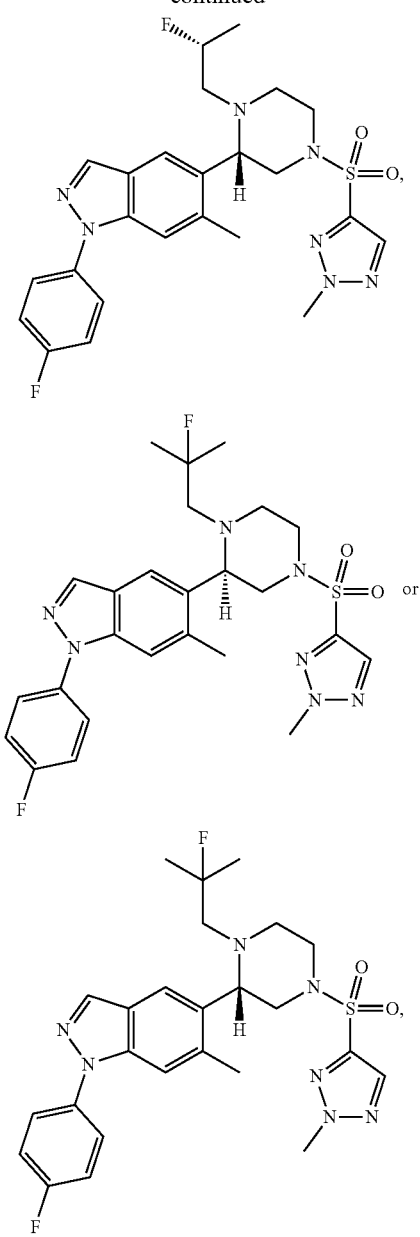
194
-continued
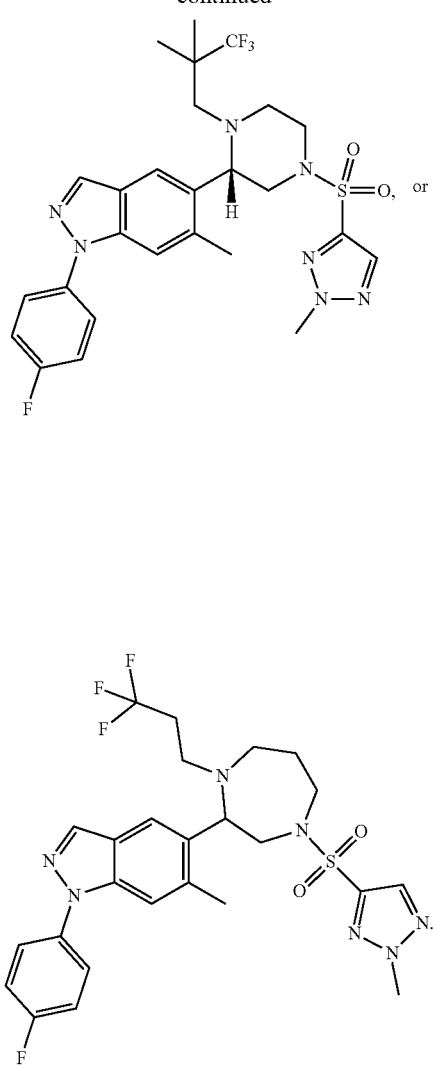
In some embodiments, the compound of Formula J, I, Ia, Ib, Ib-1, Ib-2, Ic or Id, or the pharmaceutically acceptable salt thereof, is the compound having the structure
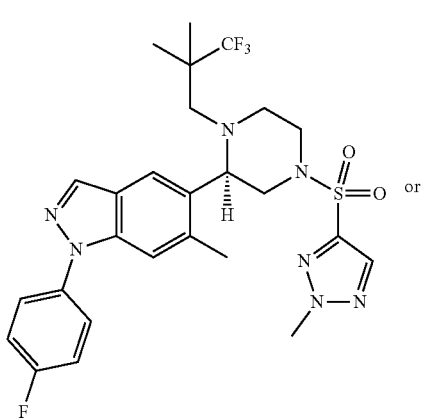
or
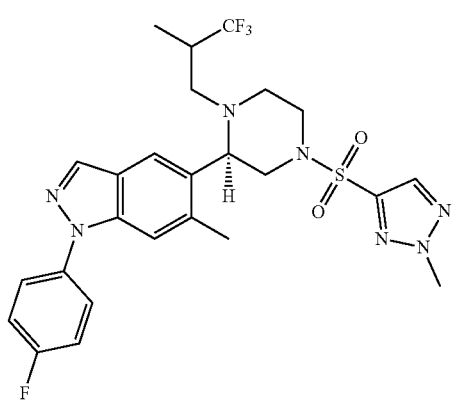
or -continued

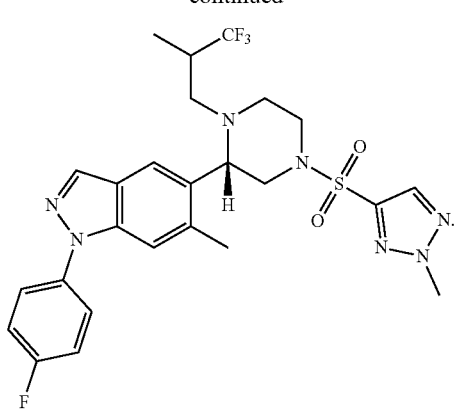

In some embodiments, the compound of Formula J, I, Ia, Ib, Ib-1, Ib-2, Ic or Id, or the pharmaceutically acceptable salt thereof, is the compound having the structure

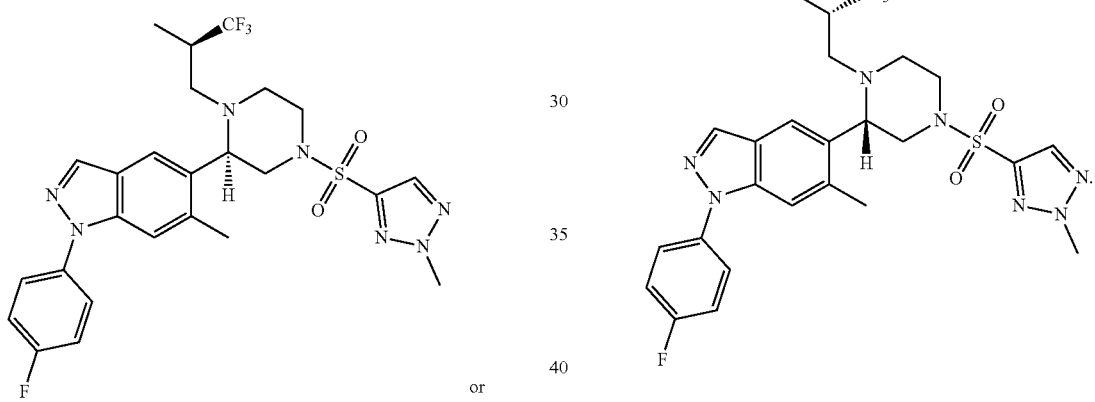

or

In some embodiments, the compound of Formula J, I, Ia, Ib, Ib-1, Ib-2, Ic or Id, or the pharmaceutically acceptable salt thereof, is the compound having the structure

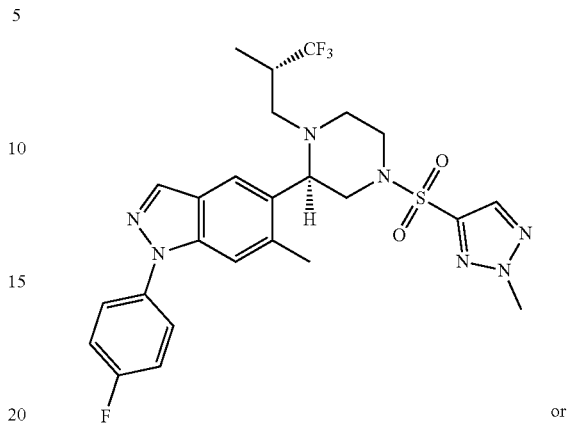

or

In some embodiments, the compound of Formula J, I, Ia, Ib, Ib-1, Ib-2, Ic or Id, or the pharmaceutically acceptable salt thereof, is the compound having the structure

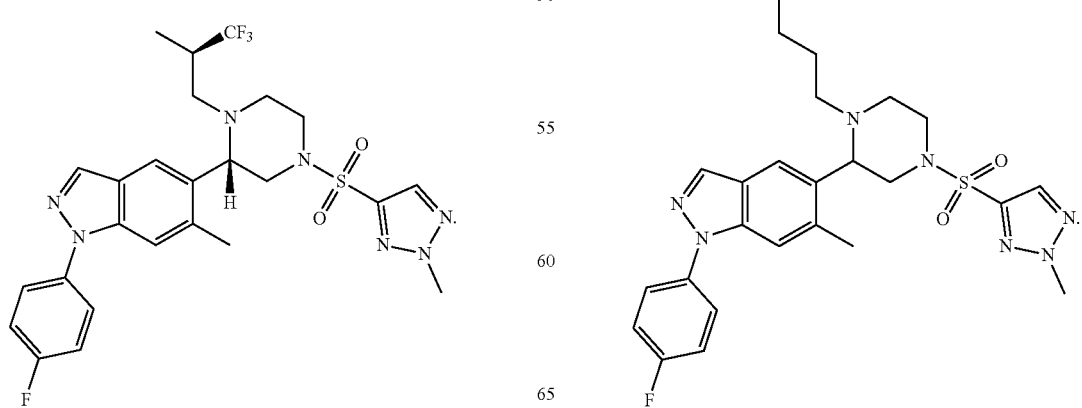

In some embodiments, the compound of Formula J, I, Ia, Ib, Ib-1, Ib-2, Ic or Id, or the pharmaceutically acceptable salt thereof, is the compound having the structure

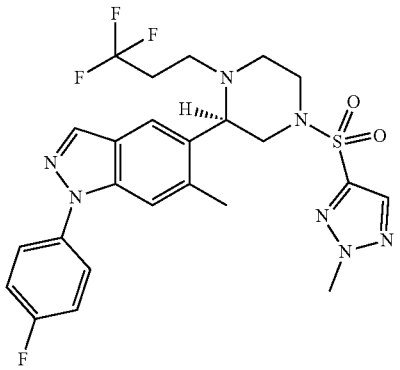

or

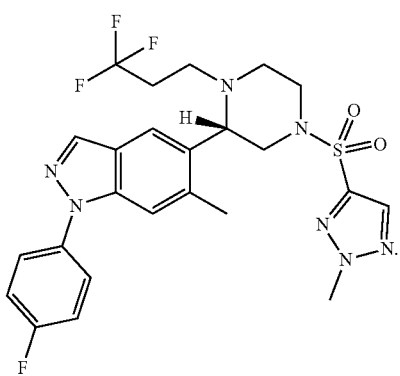

In some embodiments, the compound of Formula J, I, Ia, Ib, Ib-1, Ib-2, Ic or Id, or the pharmaceutically acceptable salt thereof, is the compound having the structure

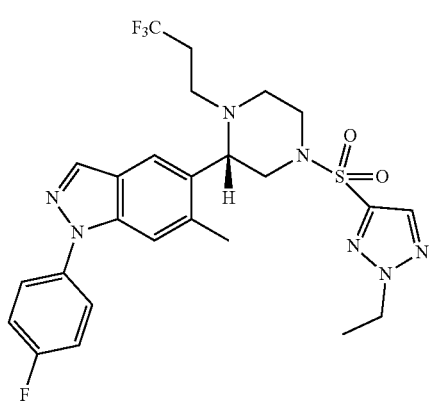

or

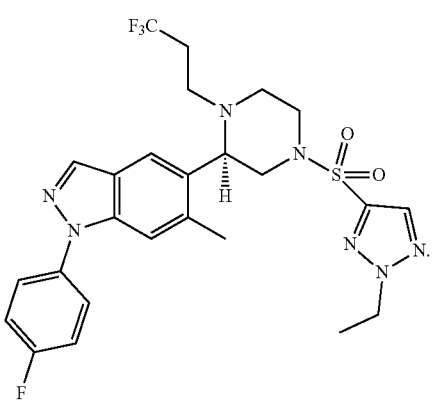

In some embodiments, the compound of Formula J, I, Ia, Ib, Ib-1, Ib-2, Ic or Id, or the pharmaceutically acceptable salt thereof, is the compound having the structure

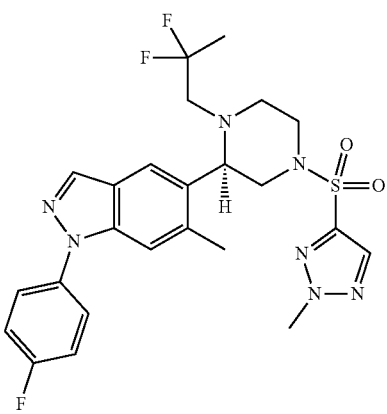

or

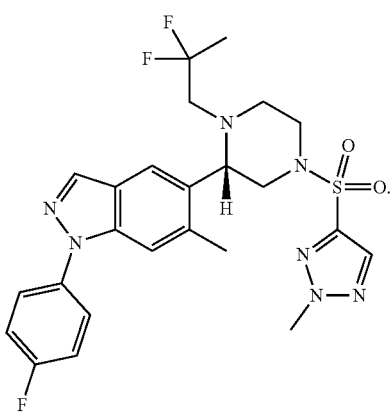

In some embodiments, the compound of Formula J, I, Ia, Ib, Ib-1, Ib-2, Ic or Id, or the pharmaceutically acceptable salt thereof, is the compound having the structure

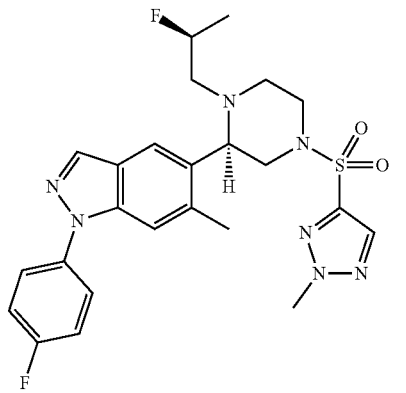

And

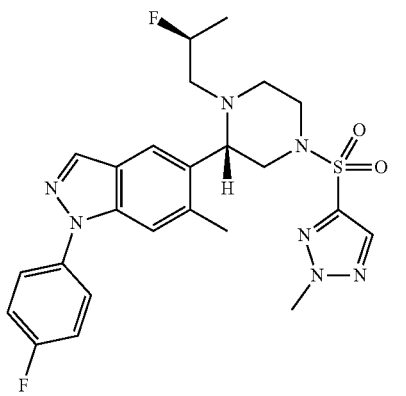

And

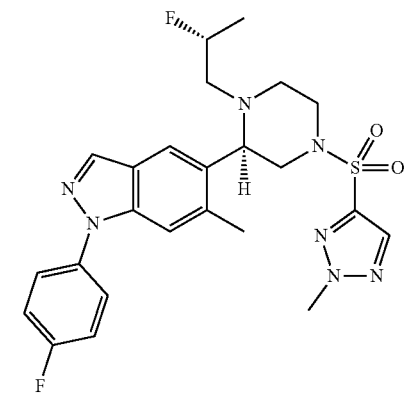

Or

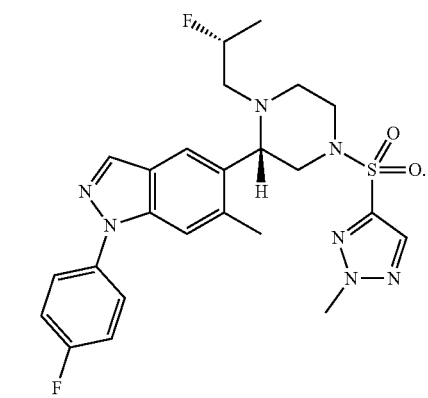

In some embodiments, the compound of Formula J, I, Ia, Ib, Ib-1, Ib-2, Ic or Id, or the pharmaceutically acceptable salt thereof, is the compound having the structure

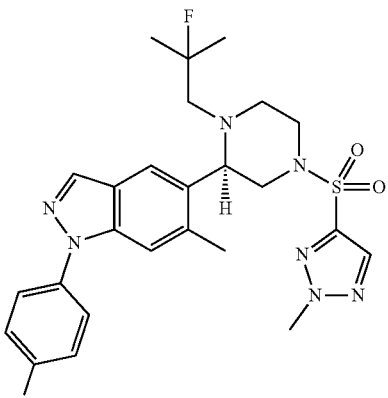

Or

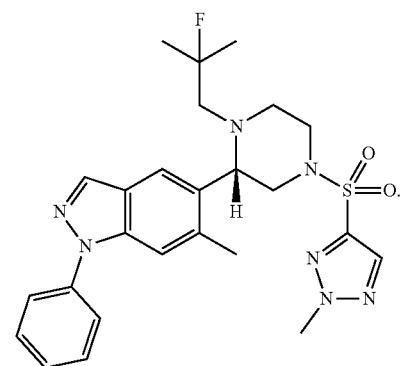

In some embodiments, the compound of Formula J, I, Ia, Ib, Ib-1, Ib-2, Ic or Id, or the pharmaceutically acceptable salt thereof, is the compound having the structure

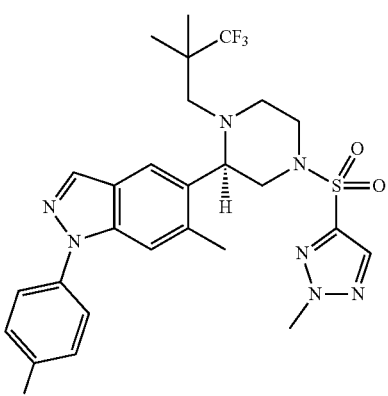

Or

-continued

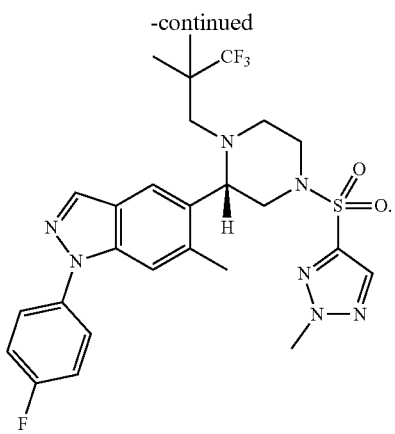

In some embodiments, the compound of Formula J, I, Ia, Ib, Ib-1, Ib-2, Ic or Id, or the pharmaceutically acceptable salt thereof, is the compound having the structure

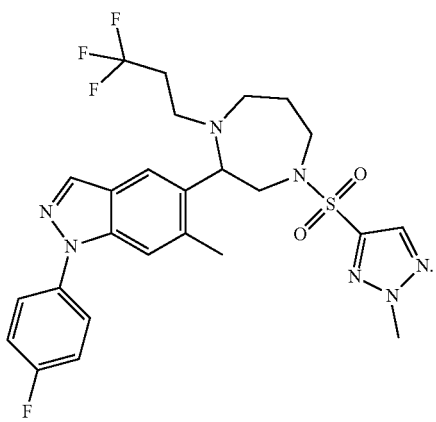 [SMILES: Cc1cc2c(cnn2-c2ccc(F)cc2)cc1C1CN(S(=O)(=O)c2cnn(C)n2)CCCN1CCC(F)(F)F]

The compounds of the present invention may exist as salts. The present invention includes such salts, which can be pharmaceutically acceptable salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms.

Certain compounds of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17 ($^{17}$O), oxygen-18 ($^{18}$O), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Compositions

In some embodiments, the present invention provides a pharmaceutical composition comprising a compound of any one of the compounds of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of Formula J, I, Ia, Ib, Ib-1, Ib-2, Ic and Id of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including one or more pharmaceutically acceptable carriers and/or excipients and either a compound of Formula J, I, Ia, Ib, Ib-1, Ib-2, Ic and Id, or a pharmaceutically acceptable salt thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, surfactants, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties and additional excipients as required in suitable proportions and compacted in the shape and size desired.

The powders, capsules and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other excipients, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers including, but not limited to sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of Formula J, I, Ia, Ib, Ib-1, Ib-2, Ic and Id mixed with a filler or binders such as lactose or starches, lubricants such as talc or magnesium stearate, and, optionally, stabilizers. In soft capsules, the compounds of Formula J, I, Ia, Ib, Ib-1, Ib-2, Ic and Id may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of Formula J, I, Ia, Ib, Ib-1, Ib-2, Ic and Id in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of Formula J, I, Ia, Ib, Ib-1, Ib-2, Ic and Id of the invention can be delivered by transdermally, by a topical route, formulated as applicator sticks, solutions, suspensions, emulsions, gels, creams, ointments, pastes, jellies, paints, powders, and aerosols.

The compounds of Formula J, I, Ia, Ib, Ib-1, Ib-2, Ic and Id and compositions of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the compounds of Formula J, I, Ia, Ib, Ib-1, Ib-2, Ic and Id of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The pharmaceutical formulations of the compounds of Formula J, I, Ia, Ib, Ib-1, Ib-2, Ic and Id of the invention can be provided as a salt and can be formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

In some embodiments, the formulations of the compounds of Formula J, I, Ia, Ib, Ib-1, Ib-2, Ic and Id of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR and/or MR modulator and disease or condition treated.

Single or multiple administrations of the compound of Formula J, I, Ia, Ib, Ib-1, Ib-2, Ic and Id formulations can be administered depending on the dosage and frequency as required and tolerated by the patient. The formulations should provide a sufficient quantity of active agent to effectively treat the disease state. Thus, in one embodiment, the pharmaceutical formulations for oral administration of the compound of Formula J, I, Ia, Ib, Ib-1, Ib-2, Ic and Id is in a daily amount of between about 0.5 to about 30 mg per kilogram of body weight per day. In an alternative embodiment, dosages are from about 1 mg to about 20 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing formulations including the compound of Formula J, I, Ia, Ib, Ib-1, Ib-2, Ic and Id for parenteral administration are known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a pharmaceutical composition including a compound of Formula J, I, Ia, Ib, Ib-1, Ib-2, Ic and Id of the invention has been formulated in one or more acceptable carriers, it can be placed in an appropriate container and labeled for treatment of an indicated condition. For administration of the compounds of Formula J, I, Ia, Ib, Ib-1, Ib-2, Ic and Id, such labeling would include, e.g., instructions concerning the amount, frequency and method of administration.

In some embodiments, the compositions of the present invention are useful for parenteral administration, such as intravenous (IV) administration or administration into a body cavity or lumen of an organ. The formulations for administration will commonly comprise a solution of the compositions of the present invention dissolved in one or more pharmaceutically acceptable carriers. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, tonicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

V. Methods & Use

In some embodiments, the present invention provides a method of treating a disorder or condition through modulating a glucocorticoid receptor, the method comprising administering to a subject in need of such treatment, a therapeutically effective amount of any one of the compounds of the present invention, or a pharmaceutical composition of the present invention, thereby treating the disorder or condition.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In some embodiments, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR), aldosterone receptor (AR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR). In another exemplary embodiment, the specific glucocorticoid antagonist binds preferentially to GR rather than to the aldosterone receptor (AR).

In some embodiments, the specific glucocorticoid receptor antagonist binds to the GR with an association constant (Kd) that is at least 10-fold less than the Kd for any other NR. In some embodiments, the specific glucocorticoid receptor antagonist binds to the GR with an association constant (Kd) that is at least 100-fold less than the Kd for any other NR. In some embodiments, the specific glucocorticoid receptor antagonist binds to the GR with an association constant (Kd) that is at least 1000-fold less than the Kd for any other NR.

In some embodiments, the present invention provides a method of treating a disorder or condition through antagonizing a glucocorticoid receptor, the method comprising administering to a subject in need of such treatment, an effective amount of any one of the compounds of the present invention, or a pharmaceutical composition of the present invention.

In some embodiments, the disorder or condition is selected from the group consisting of Alzheimer's disease, amyotrophic lateral sclerosis (ALS), antipsychotic induced weight gain, cancer, Cushing Disease, Cushing's Syndrome, major psychotic depression, Nonalcoholic steatohepatitis, and obesity. In some embodiments, the disorder or condition can be ovarian cancer, breast cancer, non-small cell lung cancer or prostate cancer.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in modulating a glucocorticoid receptor. In some embodiments, the second agent is an agent for treating Alzheimer's disease, amyotrophic lateral sclerosis (ALS), antipsychotic induced weight gain, cancer, Cushing Disease, Cushing's Syndrome, major psychotic depression, Nonalcoholic steatohepatitis, and obesity. In some embodiments, the second agent is an agent for treating major psychotic depression, stress disorders or antipsychotic induced weight gain. In some embodiments, the second agent is an agent for treating nonalcoholic fatty liver disease and/or nonalcoholic steatohepatitis. In some embodiments, the second agent is an agent for treating cancer. In some embodiments, the second agent is an anti-cancer agent. In some embodiments, the second agent is a chemotherapeutic.

In some embodiments, any one of the compounds of the present invention, or a pharmaceutical composition of the present invention can be used for a method of treating a disorder or condition through modulating a glucocorticoid receptor.

In some embodiments, any one of the compounds of the present invention, or a pharmaceutical composition of the present invention can be used for a method of treating a disorder or condition through antagonizing a glucocorticoid receptor.

In some embodiments, any one of the compounds of the present invention, or a pharmaceutical composition of the present invention, can be used in the manufacture of a medicament for treating a disorder or condition through modulating a glucocorticoid receptor.

In some embodiments, any one of the compounds of the present invention, or a pharmaceutical composition of the present invention, can be used in the manufacture of a medicament for treating a disorder or condition through antagonizing a glucocorticoid receptor.

VI. Compound Examples

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

Column chromatography was performed on pre-packed silica (230-400 mesh, 40-63 μm) cartridges using the amount indicated. SCX was purchased from Supelco and treated with 1 M hydrochloric acid prior to use. Flash column chromatography was preformed using prepacked Biotage SFär silica columns or RediSep Silver normal-phase silica flash columns using either a Biotage Isolera (Uppsala, Sweden) or CombiFlash NextGen 300+ (Thousand Oaks, California) purification system. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH or 0.7 M $NH_3$ in MeOH.

Preparative Reverse Phase High Performance Liquid Chromatography. Prep HPLC was performed using UV detection at 215 and 254 nm with either a Waters X-Select Prep-C18, 5 μm, 19×50 mm column eluting with a $H_2O$-MeCN gradient containing 0.1% v/v formic acid over 10 min (Method A), or a Waters X-Bridge Prep-C18, 5 μm, 19×50 mm column eluting with a $H_2O$-MeCN gradient containing 0.1% ammonium bicarbonate over 10 min (Method B).

Preparative Reverse phase High Performance Liquid Chromatography. Preparative HPLC was carried out on a Teledyne ACCQPrep HP150 Prep HPLC System with 200-400 nm UV variable wavelength detector, ACCQPrep HP150 AS 2×2—AutoSampler using a Waters XBridge BEH C18 OBD Prep column, 5 μM 19 mm×50 mm i.d. column and a flow rate of 24 mL/minute eluting with $H_2O$/MeCN containing 0.1% $NH_4OH$ (Method AA) or 0.1% formic acid (Method BB) over 10 minutes using UV detection at 254 nm. Gradient information: 0.0-1.0 min, 10% MeCN; 1.0-9.0 min, ramped from 10% MeCN to 100% MeCN; 9.0-10.0 min, held at 100% MeCN.

4-(benzylthio)-2-methyl-2H-1,2,3-triazole

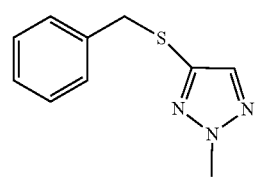

Preparation of 4-(benzylthio)-2-methyl-2H-1,2,3-triazole was performed according to the procedure described for Example 1 in U.S. Pat. No. 10,494,349, which is incorporated herein in its entirety for all purposes.

2-methyl-2H-1,2,3-triazole-4-sulfonyl chloride

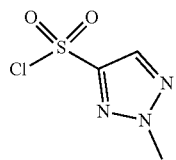

Preparation of 2-methyl-2H-1,2,3-triazole-4-sulfonyl chloride was performed according to the procedure described for Intermediate 5A in U.S. Pat. No. 10,047,082, which is incorporated herein in its entirety for all purposes.

4-(benzylthio)-2-isopropyl-2H-1,2,3-triazole

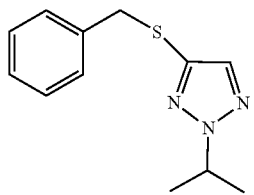 [SMILES: CC(C)n1ncc(SCc2ccccc2)n1]

Preparation of 4-(benzylthio)-2-isopropyl-2H-1,2,3-triazole was performed according to the procedure described for Example 2 in U.S. Pat. No. 10,494,349, which is incorporated herein in its entirety for all purposes.

2-isopropyl-2H-1,2,3-triazol-4-yl)sulfonyl

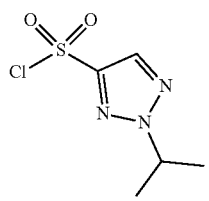

Preparation of 2-isopropyl-2H-1,2,3-triazole-4-sulfonyl chloride was performed according to the procedure described for Intermediate 5D in U.S. Pat. No. 10,494,349, which is incorporated herein in its entirety for all purposes.

Analytical Methods

Reverse Phase High Performance Liquid Chromatography. Method 1: Waters XSelect CSH UPLC C18 1.7 μm (2.1×30 mm) at 40° C.; flow rate 0.77 mL·min$^{-1}$ eluted with a H$_2$O-MeCN gradient containing 0.1% v/v formic acid over 3 min employing UV detection between 210 and 400 nm. Gradient information: 0-0.11 min, held at 95% H$_2$O-5% MeCN, 0.11-2.15 min ramped from 95% H$_2$O-5% MeCN to 5% H$_2$O-95% MeCN; 2.15-2.49 min, held at 5% H$_2$O-95% MeCN, 2.49-2.56 min, ramped from 5% H$_2$O-95% MeCN to 95% H$_2$O-5% MeCN; 2.56-3.00 min, held at 95% H$_2$O-5% MeCN.

Method 2: Apparatus: Agilent 1260; Quaternary Pump, HiP Sampler, Column Compartment, DAD: 260+/−90 nm, G6150 MSD: ESI; Column: Waters Cortecs C18, 30×2.1 mm, 2.7 μm, Temp: 40° C., Flow: 1.35 mL/min, Gradient: t0=5% B, t2.5 min=100% B, t3.0 min=100% B, Eluent A: 0.1% Formic in water, Eluent B: acetonitrile.

Method 3: Apparatus: Agilent 1260; Quaternery Pump, HiP Sampler, Column Compartment, DAD: 260+/−90 nm, G6150 MSD: ESI; Column: Waters XBridge C18, 30×2.1 mm, 2.5 μm, Temp: 40° C., Flow: 1.35 mL/min, Gradient: t0=5% B, t2.5 min=100% B, t3.0 min=100% B, Eluent A: 0.1% NH3 in water, Eluent B: acetonitrile.

Method 4: Apparatus: Agilent 1260; Quaternary Pump, HiP Sampler, Column Compartment, DAD: 260+/−90 nm, G6150 MSD: ESI; Column: Waters Cortecs C18, 30×2.1 mm, 2.7 μm, Temp: 40° C., Flow: 1.35 mL/min, Gradient: t0=5% B, t2.5 min=100% B, t3.0 min=100% B, Eluent A: 0.1% Formic in water, Eluent B: Acetonitrile.

Method 5: Apparatus: Waters HClass; Binary Solvent Pump, SM-FTN, CMA, PDA: 210-400 nm, QDa: ACQ-QDa ESI; Column: Waters BEH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% NH3 in water, Eluent B: Acetonitrile.

Method 6: Apparatus: Waters HClass; Quaternary Solvent Pump, SM-FTN, CMA, PDA: 210-400 nm, QDa: ACQ-QDa ESI; Column: Waters CSH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% Formic acid in water, Eluent B: acetonitrile Method 7: Waters HClass; Quaternary Solvent Pump, SM-FTN, CMA, PDA: 210-400 nm, QDa: ACQ-QDa ESI; Column: Waters CSH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% Formic acid in water, Eluent B: acetonitrile.

Method 8: UPLC_Basic, Apparatus: Waters HClass; Binary Solvent Pump, SM-FTN, CMA, PDA: 210-400 nm, QDa: ACQ-QDa ESI; Column: Waters BEH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% NH3 in water, Eluent B: Acetonitrile.

Method 9: LCMS_Acidic, Apparatus: Agilent 1260; Binary Pump, HiP Sampler, Column Compartment, DAD: 260+/−90 nm, G6150 MSD: ESI; Column: Waters Cortecs C18, 30×2.1 mm, 2.7 μm, Temp: 40° C., Flow: 1.35 mL/min, Gradient: t0=5% B, t2.5 min=100% B, t3.0 min=100% B, Eluent A: 0.1% Formic in water, Eluent B: acetonitrile.

Method 11: Phenomenex Luna® C18 2.5 μm (2.0×50 mm) at 45° C.; flow rate 1.0 mL·min$^{-1}$ eluted with a H$_2$O-MeCN gradient containing 0.1% v/v formic acid over 5.50 min employing UV detection at 254 nm. Gradient information: 0-0.50 min, held at 99% H$_2$O-1% MeCN; 0.50-3.50 min ramped from 99% H$_2$O-1% MeCN to 0% H$_2$O-100% MeCN; 3.50-4.25 min, held at 0% H$_2$O-100% MeCN; 4.25-5.00 min, ramped from 0% H$_2$O-100% MeCN to 99% H$_2$O-1% MeCN; 5.00-5.50 min, held at 99% H$_2$O-1% MeCN.

Method 12: Phenomenex Luna® C18 2.5 μm (2.0×50 mm) at 45° C.; flow rate 1.0 mL·min-1 eluted with a H$_2$O-MeCN gradient containing 0.1% v/v formic acid over 3.75 min employing UV detection at 254 nm. Gradient information: 0-0.50 min, held at 99% H$_2$O-1% MeCN; 0.50-2.00 min ramped from 99% H$_2$O-1% MeCN to 0% H$_2$O-100% MeCN; 2.00-3.25 min, held at 0% H$_2$O-100% MeCN; 3.25-3.26 min, ramped from 0% H$_2$O-100% MeCN to 99% H$_2$O-1% MeCN; 3.26-3.75 min, held at 99% H$_2$O-1% MeCN.

NMR spectra were recorded using either a Bruker Avance III HD 500 MHz instrument or a Bruker Avance Neo 400 MHz, using either residual non-deuterated solvent, or tetra-methylsilane as reference or Varian Y 400 MHz instrument, using tetra-methylsilane as reference, or a QOne AS400 400 MHz spectrometer using either residual non-deuterated solvent, or tetra-methylsilane as reference.

All chemical names have been generated using ChemDraw.

Abbreviations

DCM=dichloromethane
DIBAL-H—diisobutylaluminium hydride
DIPEA=diisopropylethylamine
DMF=dimethylformamide
DMSO=dimethyl sulfoxide
EtOAc=ethyl acetate
EtOH=ethanol
H, hr, HR, Hr=hours
MeCN=acetonitrile
MeOH=methanol
min=minutes
$MgSO_4$=magnesium sulfate
$NaHCO_3$=sodium hydrogen carbonate
NaOH=sodium hydroxide
$Na_2SO_4$=sodium sulfate
$NH_4Cl$=ammonium chloride
RT, rt=room temperature
sat.=saturated
SFC=supercritical fluid chromatography
TBME=t-butylmethylether
THF=tetrahydrofuran
Wt=weight

Example 1: 1-(4-fluorophenyl)-5-(1-isobutyl-4-((1-methyl-1H-pyrazol-3-yl)sulfonyl)piperazin-2-yl)-6-methyl-1H-indazole

Intermediate ZA: 5-bromo-1-(4-fluorophenyl)-6-methyl-1H-indazole

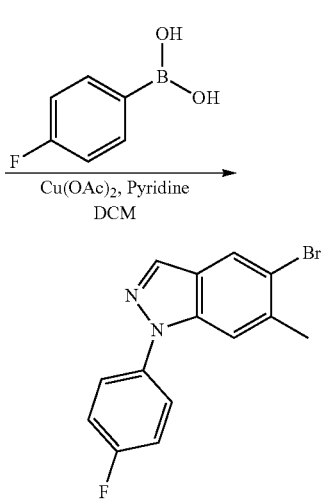

Pyridine (18.7 g, 19.1 mL, 237 mmol) was added to a solution of 5-bromo-6-methyl-1H-indazole (25.0 g, 118 mmol), (4-fluorophenyl)boronic acid (33.1 g, 237 mmol) and copper (II) acetate (21.5 g, 118 mmol) in DCM (500 mL). The reaction mixture was stirred at 20° C. for 21 hours. The reaction mixture was concentrated under reduced pressure, redissolved in EtOAc (500 mL) and washed with water (200 mL), 1N HCl (200 mL), saturated sodium hydrogen carbonate (2×200 mL) and brine (100 mL). The organic layer was concentrated, dried using $MgSO_4$, filtered, and the filtrate was concentrated under reduced pressure. The crude product was purified by chromatography on silica gel (330 g cartridge, 0-10% EtOAc/isohexane) to afford 5-bromo-1-(4-fluorophenyl)-6-methyl-1H-indazole (Intermediate ZA) (34.2 g, 0.11 mol, 81% yield) as a yellow solid; $R^t$ 2.33 min (Method 7); m/z 305.3 and 307.5 $(M+H)^+$ $(ES^+)$; $\delta_H$ (DMSO-d6, 400 MHz) δ 8.30 (d, J=0.9 Hz, 1H), 8.16 (s, 1H), 7.81 (s, 1H), 7.80-7.76 (m, 2H), 7.50-7.38 (m, 2H), 2.50 (s, 3H).

Alternatively, 5-bromo-1-(4-fluorophenyl)-6-methyl-1H-indazole can be prepared according to the method for Intermediate C in PCT Publication No. WO2021/262587.

Intermediate A: 1-(4-fluorophenyl)-6-methyl-5-(pyrazin-2-yl)-1H-indazole

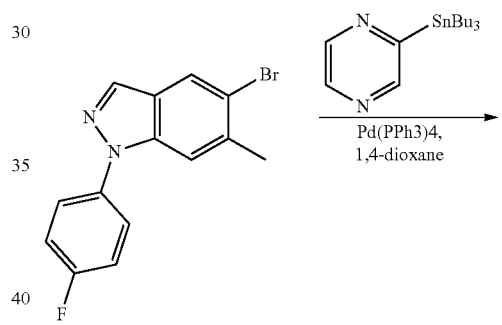

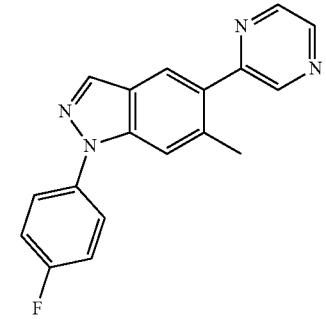

A solution of 5-bromo-1-(4-fluorophenyl)-6-methyl-1H-indazole (7.98 g, 26.2 mmol) and 2-(tributylstannyl)pyrazine (10.0 g, 8.55 mL, 27.1 mmol) in 1,4-dioxane (200 mL) was degassed (bubbling nitrogen) for 20 mins. Tetrakis(triphenylphosphine palladium(0)) (1.51 g, 1.31 mmol) was then added and the reaction mixture stirred at 90° C. for 18 hours. Tetrakis(triphenylphosphine palladium(0)) (604 mg, 523 µmol) was added and the reaction mixture stirred at 90° C. for 4 days. The reaction mixture was cooled to rt and concentrated in vacuo. The crude product was purified by chromatography on silica gel (220 g cartridge, 0-100% EtOAc/isohexane) to afford the product as a pale yellow solid. The solid triturated with EtOAc (3×50 mL) to afford 1-(4-fluorophenyl)-6-methyl-5-(pyrazin-2-yl)-1H-indazole (5.20 g, 17.1 mmol, 65.3%) as an off white solid; R$^t$ 0.19 min (Method 4); m/z 305.0 (M+H)$^+$ (ES$^+$).

Intermediate B: 1-(4-fluorophenyl)-6-methyl-5-(piperazin-2-yl)-1H-indazole

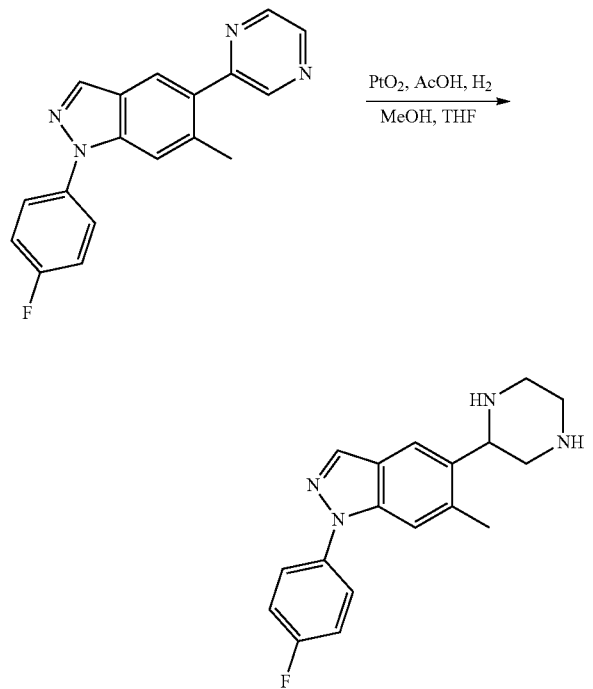

1-(4-Fluorophenyl)-6-methyl-5-(pyrazin-2-yl)-1H-indazole (4.00 g, 13.1 mmol) was partially dissolved in MeOH (150 mL) and THF (150 mL) and then treated with acetic acid (7.89 g, 7.81 mL, 131 mmol) and platinum (IV) oxide (149 mg, 657 µmol). The reaction mixture was then stirred at 60° C. for 40 hours under an atmosphere of hydrogen (5 bar). After cooling to rt, the reaction mixture was filtered through a glass microfibre pad, washing with MeOH (20 mL). The filtrate was concentrated in vacuo to a yellow oil, before being taken up in DCM (100 mL) and washed with sat. aqueous NaHCO$_3$ (2×80 mL). The organics were dried over MgSO$_4$ and concentrated in vacuo. The crude product was purified by chromatography on silica gel (80 g cartridge, 0-10% (0.7 M Ammonia/MeOH)/DCM, then isocratic 10% (0.7 M Ammonia/MeOH)/DCM to afford 1-(4-fluorophenyl)-6-methyl-5-(piperazin-2-yl)-1H-indazole (2.63 g, 8.3 mmol, 63%) as a white solid; R$^t$ 0.25 min (Method 4); m/z 311.2 (M+H)$^+$ (ES$^+$). δH NMR (400 MHz, DMSO) δ 8.26 (d, J=0.9 Hz, 1H), 8.00 (s, 1H), 7.91-7.69 (m, 2H), 7.57 (s, 1H), 7.41 (t, J=8.8 Hz, 2H), 3.87 (dd, J=9.8, 2.6 Hz, 1H), 2.98-2.87 (m, 2H), 2.86-2.76 (m, 2H), 2.65 (td, J=12.2, 3.2 Hz, 1H), 2.48 (s, 3H), 2.34 (dd, J=12.0, 9.8 Hz, 1H).

Intermediate C: 1-(4-fluorophenyl)-6-methyl-5-(piperazin-2-yl)-1H-indazole isomer 1

Intermediate D: 1-(4-fluorophenyl)-6-methyl-5-(piperazin-2-yl)-1H-indazole isomer 2

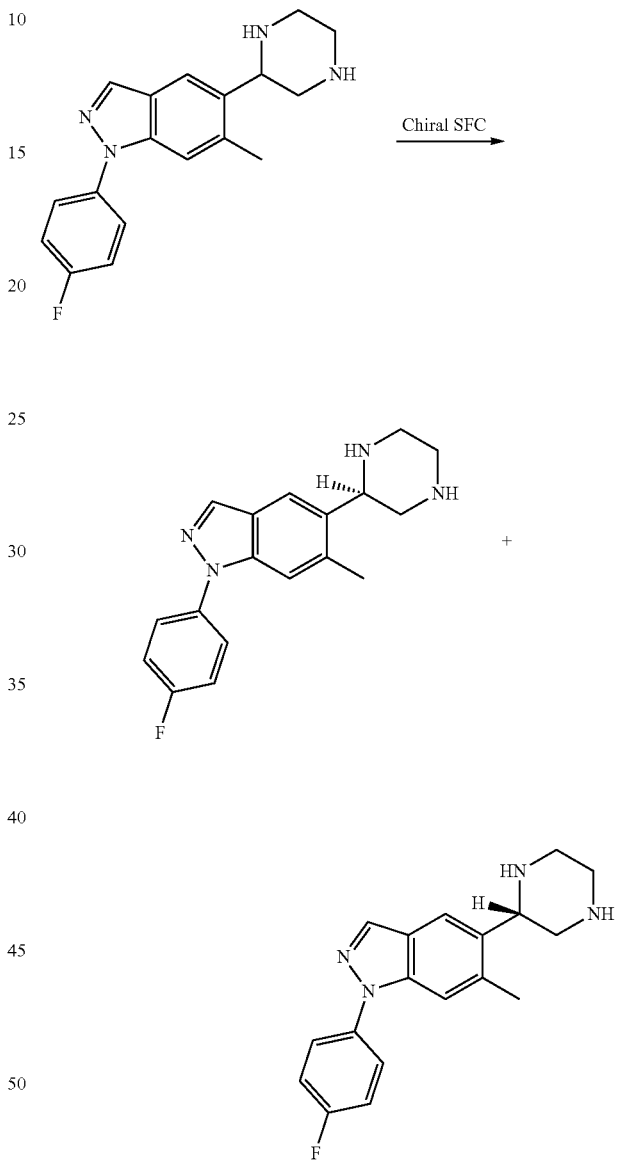

1-(4-Fluorophenyl)-6-methyl-5-(piperazin-2-yl)-1H-indazole (2.63 g, 8.3 mmol) was dissolved to 100 mg/mL in MeOH, filtered and was then separated by chiral SFC on a Waters prep 100 with UV detection across all wavelengths with PDA as well as a QDA, 40° C., 120 bar. The column was a Phenomenex Lux® 5 µM Cellulose-4, LC Column 250×21 mm, AXIA™ packed} flow rate 65 mL/min of 45%, 55% CO$_2$ to give the separated stereoisomers 1-(4-fluorophenyl)-6-methyl-5-(piperazin-2-yl)-1H-indazole (1.45 g, isomer 1) (Intermediate C). and 1-(4-fluorophenyl)-6-methyl-5-(piperazin-2-yl)-1H-indazole (1.48 g isomer 2) (Intermediate D). Data identical to Intermediate B.

Intermediate E: 1-(4-fluorophenyl)-6-methyl-5-(4-((1-methyl-1H-pyrazol-3-yl)sulfonyl)piperazin-2-yl)-1H-indazole

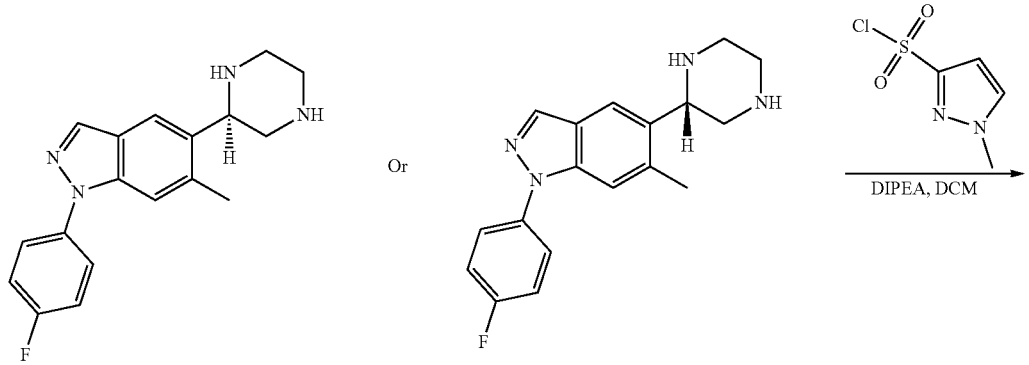

To a solution of 1-(4-fluorophenyl)-6-methyl-5-(piperazin-2-yl)-1H-indazole (250 mg, 556 µmol) in DCM (6 mL) were added N-ethyl-N-isopropylpropan-2-amine (215 mg, 290 µL, 1.67 mmol) and 1-methyl-1H-pyrazole-3-sulfonyl chloride (110 mg, 611 µmol). The reaction mixture was stirred at rt for 90 mins before being quenched with NaHCO₃ (5 mL). The layers were separated, and the aqueous layer extracted with DCM (3×5 mL). Combined organic extracts were dried over MgSO₄ and concentrated in vacuo. The crude product was purified by chromatography on silica gel (12 g cartridge, 0-10% (0.7 M Ammonia/MeOH)/DCM) to afford 1-(4-fluorophenyl)-6-methyl-5-(4-((1-methyl-1H-pyrazol-3-yl)sulfonyl)piperazin-2-yl)-1H-indazole (153 mg, 0.32 mmol, 58%) as a flocculent white solid; $R^t$ 1.31 min (Method 4); m/z 455.0 (M+H)⁺ (ES⁺). δH NMR (400 MHz, DMSO) δ 8.26 (d, J=0.9 Hz, 1H), 7.95-7.90 (m, 2H), 7.83-7.73 (m, 2H), 7.63 (s, 1H), 7.48-7.36 (m, 2H), 6.66 (d, J=2.3 Hz, 1H), 3.99 (d, J=10.0 Hz, 1H), 3.93 (s, 3H), 3.64-3.49 (m, 2H), 3.09 (d, J=11.9 Hz, 1H), 2.86 (m, 2H), 2.58-2.52 (m, 1H), 2.18 (t, J=10.9 Hz, 1H).

Example 1: 1-(4-fluorophenyl)-5-(1-isobutyl-4-((1-methyl-1H-pyrazol-3-yl)sulfonyl)piperazin-2-yl)-6-methyl-1H-indazole

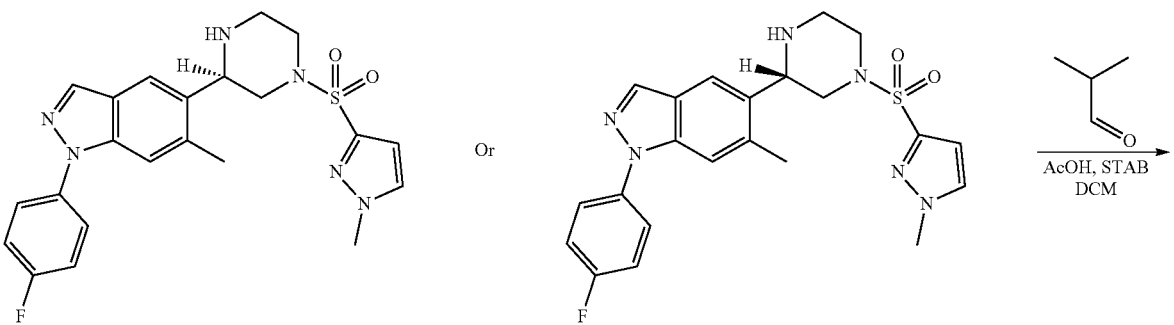

219                  220

-continued

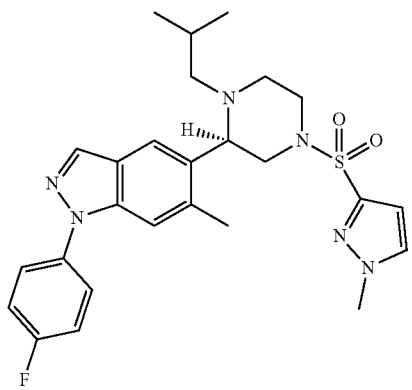 Or 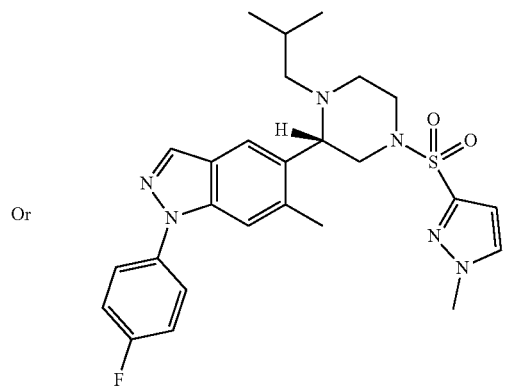

To a solution of 1-(4-fluorophenyl)-6-methyl-5-(4-((1-methyl-1H-pyrazol-3-yl)sulfonyl)piperazin-2-yl)-1H-indazole (153 mg, 337 μmol) in DCM (4.00 mL) were added isobutyraldehyde (36.4 mg, 46 μL, 505 μmol) and acetic acid. The reaction mixture was stirred at rt for 45 mins before the addition of sodium triacetoxyborohydride (214 mg, 1.01 mmol). The reaction mixture was then stirred for a further 3 days at rt before being quenched with sat. aqueous NaHCO$_3$ (6 mL). The layers were separated, and the aqueous layer extracted with DCM (3×5 mL). The combined organic extracts were dried over MgSO$_4$ and concentrated in vacuo. The crude product was purified by chromatography on silica gel (12 g cartridge, 0-60% EtOAc/isohexane) to afford 1-(4-fluorophenyl)-5-(1-isobutyl-4-((1-methyl-1H-pyrazol-3-yl)sulfonyl)piperazin-2-yl)-6-methyl-1H-indazole (122 mg, 0.23 mmol, 67%) as a white solid; R$^t$ 1.84 min (Method 4); m/z 511.2 (M+H)$^+$ (ES$^+$). δH NMR (400 MHz, DMSO) δ 8.28 (d, J=0.9 Hz, 1H), 7.94 (d, J=2.3 Hz, 1H), 7.85-7.75 (m, 3H), 7.63 (s, 1H), 7.50-7.37 (m, 2H), 6.65 (d, J=2.3 Hz, 1H), 3.93 (s, 3H), 3.68 (d, J=11.6 Hz, 1H), 3.56 (dd, J=10.5, 3.2 Hz, 1H), 3.47-3.39 (m, 1H), 3.21 (d, J=11.8 Hz, 1H), 2.73-2.63 (m, 1H), 2.48 (s, 3H), 2.33 (m, 1H), 2.19 (t, J=11.7 Hz, 1H), 2.02 (t, J=12.2 Hz, 1H), 1.77 (d, J=10.2 Hz, 2H), 0.80 (d, J=6.3 Hz, 3H), 0.64 (d, J=6.3 Hz, 3H).

Examples 2-22

TABLE 2

The examples shown in the table below were prepared by similar methods to those described for Example 1

| Example | Structure | LC-MS analysis |
|---|---|---|
| 2 | 5-(1-benzyl-4-((2-methyl-2H-1,2,3-triazol-4-yl)sulfonyl)piperazin-2-yl)-1-(4-fluorophenyl)-6-methyl-1H-indazole | R$^t$ 2.31 min (Method 9); m/z 546.2 (M + H)$^+$ (ES$^+$) |

TABLE 2-continued

The examples shown in the table below were prepared by similar methods to those described for Example 1

| Example | Structure | LC-MS analysis |
|---|---|---|
| 3 | 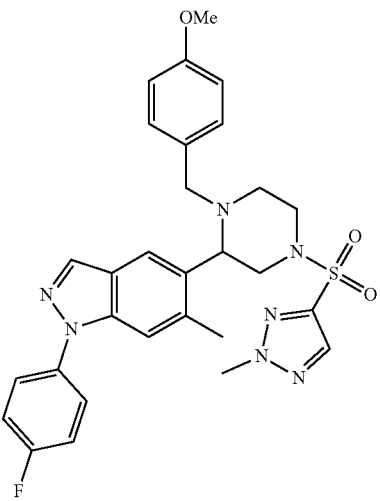 [SMILES: COc1ccc(CN2CCN(S(=O)(=O)c3cnn(C)n3)CC2c2cc3cnn(-c4ccc(F)cc4)c3cc2C)cc1]<br>1-(4-fluorophenyl)-5-(1-(4-methoxybenzyl)-4-((2-methyl-2H-1,2,3-triazol-4-yl)sulfonyl)piperazin-2-yl)-6-methyl-1H-indazole | $R^t$ 2.15 min (Method 9); m/z 576.2 $(M + H)^+$ $(ES^+)$ |
| 4 | 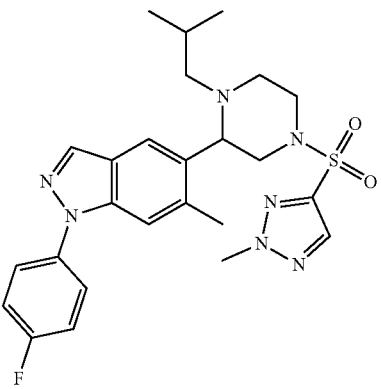 [SMILES: Cc1cc2c(cnn2-c2ccc(F)cc2)cc1C1CN(S(=O)(=O)c2cnn(C)n2)CCN1CC(C)C]<br>1-(4-fluorophenyl)-5-(1-isobutyl-4-((2-methyl-2H-1,2,3-triazol-4-yl)sulfonyl)piperazin-2-yl)-6-methyl-1H-indazole | $R^t$ 2.02 min (Method 9); m/z 512.2 $(M + H)^+$ $(ES^+)$ |

TABLE 2-continued
The examples shown in the table below were prepared by similar methods to those described for Example 1
| Example | Structure | LC-MS analysis |
|---|---|---|
| 5 | 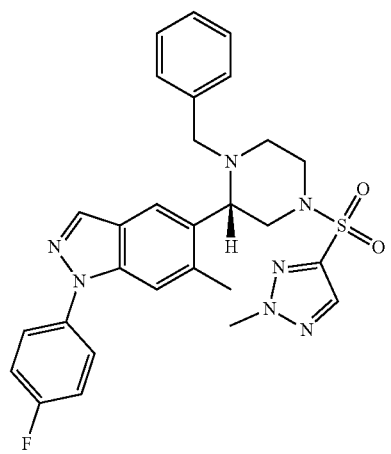 Or 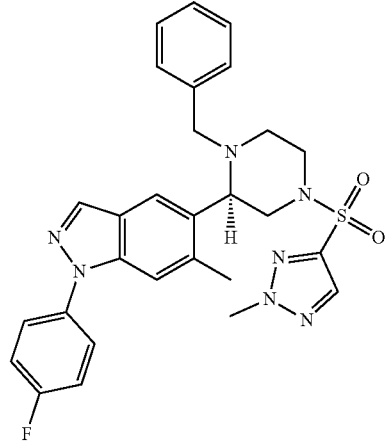 [SMILES: Cc1cc2c(cnn2-c2ccc(F)cc2)cc1[C@@H]1CN(S(=O)(=O)c2cnn(C)n2)CCN1Cc1ccccc1]  5-(1-benzyl-4-((2-methyl-2H-1,2,3-triazol-4-yl)sulfonyl)piperazin-2-yl)-1-(4-fluorophenyl)-6-methyl-1H-indazole | $R^t$ 2.28 min (Method 9); m/z 546.2 (M + H)$^+$ (ES$^+$) |
| 6 | 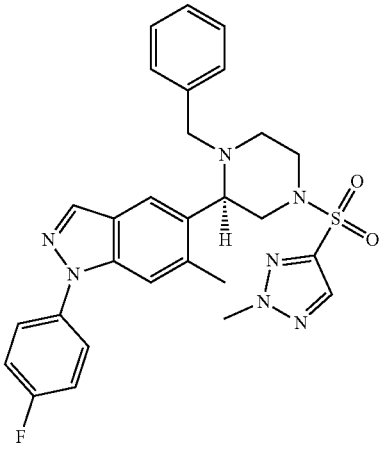 Or | $R^t$ 2.28 min (Method 7); m/z 546.2 (M + H)$^+$ (ES$^+$) |

TABLE 2-continued

The examples shown in the table below were prepared by similar methods to those described for Example 1

| Example | Structure | LC-MS analysis |
|---|---|---|
| | 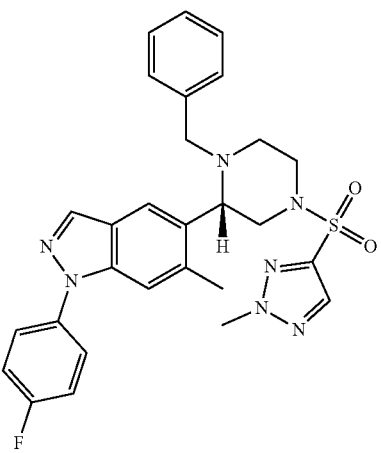 [SMILES: Cc1cc2c(cnn2-c2ccc(F)cc2)cc1[C@H]1CN(S(=O)(=O)c2cnn(C)n2)CCN1Cc1ccccc1]<br>5-(1-benzyl-4-((2-methyl-2H-1,2,3-triazol-4-yl)sulfonyl)piperazin-2-yl)-1-(4-fluorophenyl)-6-methyl-1H-indazole | |
| 7 | 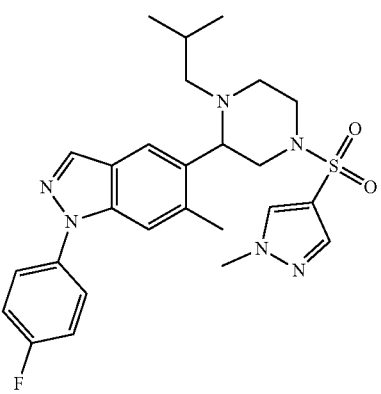 [SMILES: Cc1cc2c(cnn2-c2ccc(F)cc2)cc1C1CN(S(=O)(=O)c2cnn(C)c2)CCN1CC(C)C]<br>1-(4-fluorophenyl)-5-(1-isobutyl-4-((1-methyl-1H-pyrazol-4-yl)sulfonyl)piperazin-2-yl)-6-methyl-1H-indazole | R$^t$ 1.85 min (Method 9); m/z 511.4 (M + H)$^+$ (ES$^+$) |
| 8 | 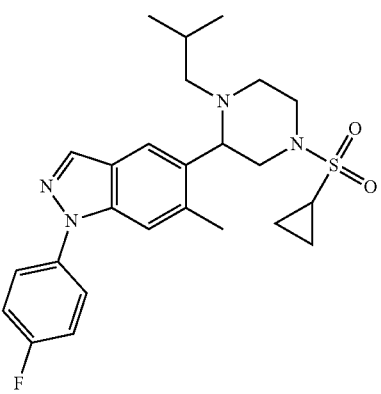 [SMILES: Cc1cc2c(cnn2-c2ccc(F)cc2)cc1C1CN(S(=O)(=O)C2CC2)CCN1CC(C)C]<br>5-(4-(cyclopropylsulfonyl)-1-isobutylpiperazin-2-yl)-1-(4-fluorophenyl)-6-methyl-1H-indazole | R$^t$ 1.80 min (Method 6); m/z 471.3 (M + H)$^+$ (ES$^+$) |

TABLE 2-continued

The examples shown in the table below were prepared by similar methods to those described for Example 1

| Example | Structure | LC-MS analysis |
|---|---|---|
| 9 | 1-(4-fluorophenyl)-5-(1-isobutyl-4-((1-(2-methoxyethyl)-1H-pyrazol-4-yl)sulfonyl)piperazin-2-yl)-6-methyl-1H-indazole | $R^t$ 1.84 min (Method 9); m/z 555.2 $(M + H)^+$ $(ES^+)$ |
| 10 | 1-(4-fluorophenyl)-5-(1-isobutyl-4-((2-methyl-2H-1,2,3-triazol-4-yl)sulfonyl)piperazin-2-yl)-6-methyl-1H-indazole | $R^t$ 1.65 min (Method 9); m/z 512.1 $(M + H)^+$ $(ES^+)$ |

Or

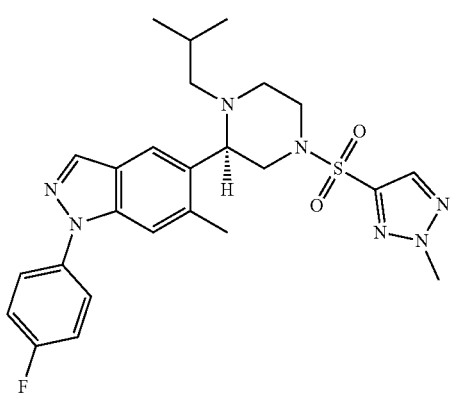 [SMILES: Cc1cc2c(cnn2-c2ccc(F)cc2)cc1[C@@H]1CN(S(=O)(=O)c2cnn(C)n2)CCN1CC(C)C]

TABLE 2-continued

The examples shown in the table below were prepared by similar methods to those described for Example 1

| Example | Structure | LC-MS analysis |
|---|---|---|
| 11 | 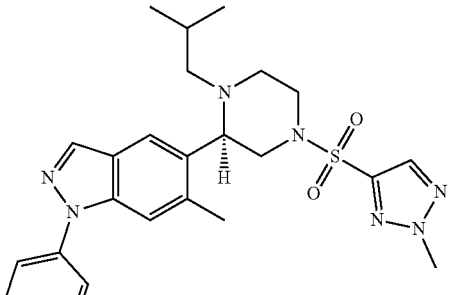 1-(4-fluorophenyl)-5-(1-isobutyl-4-((2-methyl-2H-1,2,3-triazol-4-yl)sulfonyl)piperazin-2-yl)-6-methyl-1H-indazole | R$^t$ 1.64 min (Method 9); m/z 511.2 (M + H)$^+$ (ES$^+$) |
| 12 | 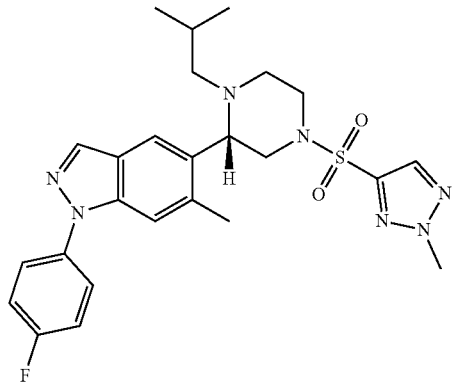 [SMILES: Cc1cc2c(cnn2-c2ccc(F)cc2)cc1[C@H]1CN(S(=O)(=O)c2cnn(C)n2)CCN1CC(C)C] 5-(1-(cyclopropylmethyl)-4-((2-methyl-2H-1,2,3-triazol-4-yl)sulfonyl)piperazin-2-yl)-1-(4-fluorophenyl)-6-methyl-1H-indazole | R$^t$ 1.61 min (Method 9); m/z 510.2 (M + H)$^+$ (ES$^+$) |

TABLE 2-continued

The examples shown in the table below were prepared by similar methods to those described for Example 1

| Example | Structure | LC-MS analysis |
|---------|-----------|----------------|
| 13 | 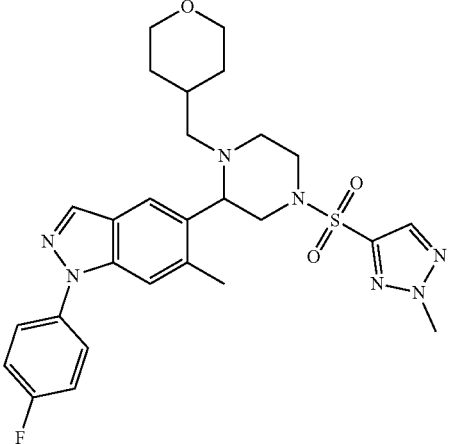 [SMILES: Cc1cc2c(cnn2-c2ccc(F)cc2)cc1C1CN(S(=O)(=O)c2cnn(C)n2)CCN1CC1CCOCC1] 1-(4-fluorophenyl)-6-methyl-5-(4-((2-methyl-2H-1,2,3-triazol-4-yl)sulfonyl)-1-((tetrahydro-2H-pyran-4-yl)methyl)piperazin-2-yl)-1H-indazole | $R^t$ 1.85 min (Method 9); m/z 554.2 $(M + H)^+$ $(ES^+)$ |
| 14 | 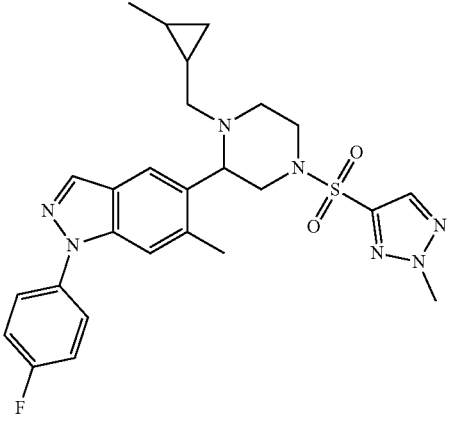 [SMILES: Cc1cc2c(cnn2-c2ccc(F)cc2)cc1C1CN(S(=O)(=O)c2cnn(C)n2)CCN1CC1CC1C] 1-(4-fluorophenyl)-6-methyl-5-(4-((2-methyl-2H-1,2,3-triazol-4-yl)sulfonyl)-1-((2-methylcyclopropyl)methyl)piperazin-2-yl)-1H-indazole | $R^t$ 1.72 min (Method 9); m/z 524.2 $(M + H)^+$ $(ES^+)$ |
| 15 | 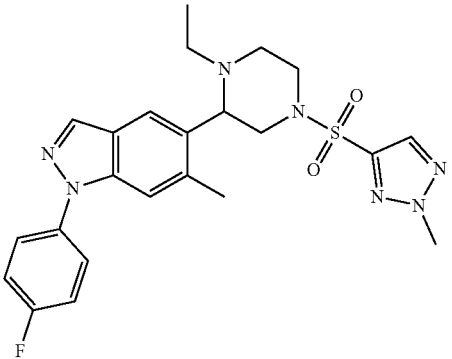 [SMILES: CCN1CCN(S(=O)(=O)c2cnn(C)n2)CC1c1cc2cnn(-c3ccc(F)cc3)c2cc1C] 5-(1-ethyl-4-((2-methyl-2H-1,2,3-triazol-4-yl)sulfonyl)piperazin-2-yl)-1-(4-fluorophenyl)-6-methyl-1H-indazole | $R^t$ 1.50 min (Method 7); m/z 484.2 $(M + H)^+$ $(ES^+)$ |

TABLE 2-continued

The examples shown in the table below were prepared by similar methods to those described for Example 1

| Example | Structure | LC-MS analysis |
|---|---|---|
| 16 | 1-(4-fluorophenyl)-6-methyl-5-(4-((2-methyl-2H-1,2,3-triazol-4-yl)sulfonyl)-1-(oxetan-3-ylmethyl)piperazin-2-yl)-1H-indazole | R$^t$ 1.74 min (Method 9); m/z 526.2 (M + H)$^+$ (ES$^+$) |
| 17 | 1-(4-fluorophenyl)-6-methyl-5-(4-((2-methyl-2H-1,2,3-triazol-4-yl)sulfonyl)-1-(3-methylbut-2-en-1-yl)piperazin-2-yl)-1H-indazole | R$^t$ 1.75 min (Method 7); m/z 524.3 (M + H)$^+$ (ES$^+$) |
| 18 | 1-(4-fluorophenyl)-6-methyl-5-(4-((2-methyl-2H-1,2,3-triazol-4-yl)sulfonyl)-1-(pyridin-3-ylmethyl)piperazin-2-yl)-1H-indazole | R$^t$ 1.69 min (Method 9); m/z 547.2 (M + H)$^+$ (ES$^+$) |

TABLE 2-continued

The examples shown in the table below were prepared by similar methods to those described for Example 1

| Example | Structure | LC-MS analysis |
|---|---|---|
| 19 | 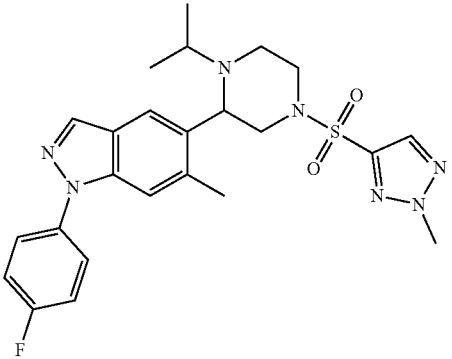 [SMILES: Cc1cc2c(cnn2-c2ccc(F)cc2)cc1C1CN(S(=O)(=O)c2cnn(C)n2)CCN1C(C)C] 1-(4-fluorophenyl)-5-(1-isopropyl-4-((2-methyl-2H-1,2,3-triazol-4-yl)sulfonyl)piperazin-2-yl)-6-methyl-1H-indazole | $R^t$ 1.56 min (Method 9); m/z 498.2 (M + H)$^+$ (ES$^+$) |
| 20 | 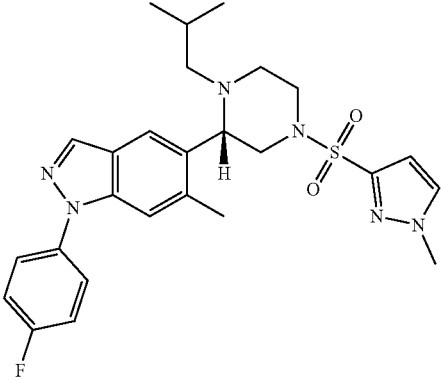 Or 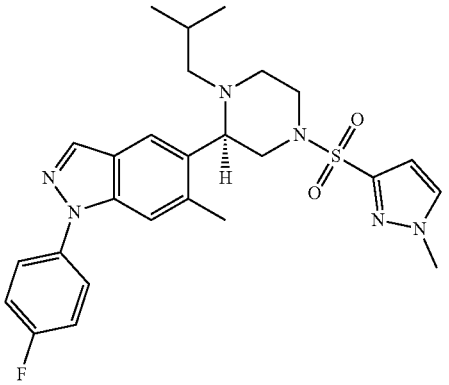 [SMILES: Cc1cc2c(cnn2-c2ccc(F)cc2)cc1[C@@H]1CN(S(=O)(=O)c2ccn(C)n2)CCN1CC(C)C] 1-(4-fluorophenyl)-5-(1-isobutyl-4-((1-methyl-1H-pyrazol-3-yl)sulfonyl)piperazin-2-yl)-6-methyl-1H-indazole | $R^t$ 1.85 min (Method 9); m/z 511.2 (M + H)$^+$ (ES$^+$) |

TABLE 2-continued

The examples shown in the table below were prepared by similar methods to those described for Example 1

| Example | Structure | LC-MS analysis |
|---------|-----------|----------------|
| 21 | | R$^t$ 2.31 and 2.34 min (Method 9); m/z 566.2 (M + H)$^+$ (ES$^+$) |

Or 1-(4-fluorophenyl)-6-methyl-5-(4-((2-methyl-2H-1,2,3-triazol-4-yl)sulfonyl)-1-(3,3,3-trifluoro-2-methylpropyl)piperazin-2-yl)-1H-indazole (enantiomer of Example 23)

| 22 | | R$^t$ 1.64 min (Method 9); m/z 528.2 (M + H)$^+$ (ES$^+$) |

1-(4-fluorophenyl)-5-(1-isobutyl-4-((2-methyl-2H-1,2,3-triazol-4-yl)sulfonyl)piperazin-2-yl)-6-methoxy-1H-indazole

Example 23: 1-(4-fluorophenyl)-6-methyl-5-((2R)-4-((2-methyl-2H-1,2,3-triazol-4-yl)sulfonyl)-1-(3,3,3-trifluoro-2-methylpropyl)piperazin-2-yl)-1H-indazole (Enantiomer of Example 21)

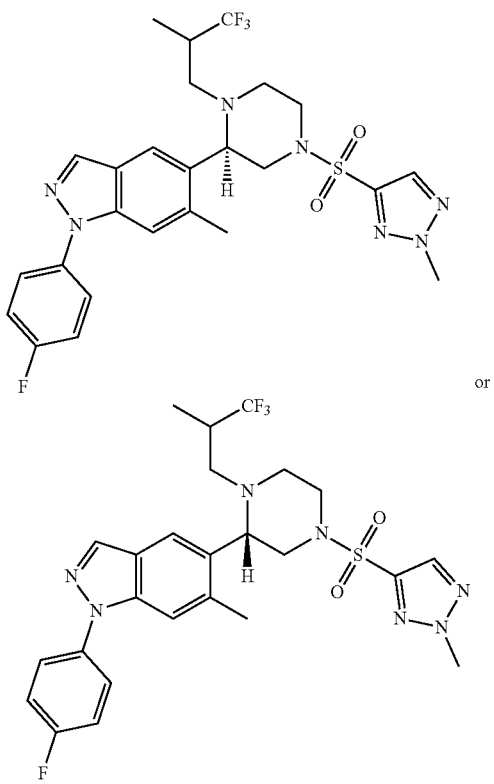

To a solution of 3,3,3-trifluoro-2-methylpropanal (2.81 g, 2.03 Eq, 22.3 mmol) in DCM (120 mL) were added 4 Å MS (activated with heat gun under vacuum for 10 mins) and the mixture stirred for 15 mins at rt. Acetic acid (1.32 g, 1.31 mL, 2 Eq, 22.0 mmol) was then added and the mixture stirred for a further 30 mins. (R)-1-(4-fluorophenyl)-6-methyl-5-(4-((2-methyl-2H-1,2,3-triazol-4-yl)sulfonyl)piperazin-2-yl)-1H-indazole (5.00 g, 1 Eq, 11.0 mmol) was then added and the reaction mixture stirred at rt for 15 hours. Sodium triacetoxyhydroborate (6.98 g, 3 Eq, 32.9 mmol) was then added and the reaction mixture stirred for a further 5 hours. The reaction mixture was quenched with MeOH (30 mL) and sat. aq. NaHCO$_3$ (200 mL). The molecular sieves were filtered off and the layers separated. The aqueous layer was extracted with DCM (3×100 mL). Combined organic extracts were dried over MgSO$_4$ and concentrated in vacuo. The crude product was purified by chromatography on silica gel (120 g cartridge, 0-60% EtOAc/isohexane) to afford 1-(4-fluorophenyl)-6-methyl-5-((2R)-4-((2-methyl-2H-1,2,3-triazol-4-yl)sulfonyl)-1-(3,3,3-trifluoro-2-methylpropyl)piperazin-2-yl)-1H-indazole (4.02 g, 7.11 mmol, 64.8%) as a flocculent white solid. The product was analysed by UPLC (CSH C18 Column, 130 Å, 1.7 μm, 2.1 mm×30 mm, 3 min method, 0.1% Formic acid, 2-100% MeCN/water): 3289-390-col, m/z 566.4 (M+H)$^+$ (ES$^+$); no ion (M−H)− (ES−), at 2.313 and 2.342 min, 98.71% purity 210-400 nm. $^1$H NMR in DMSO-d6 3289-390-rd was consistent with product structure at 98% purity. Indazole CH3 obscured under DMSO. $^1$H NMR (400 MHz, DMSO) δ 8.32-8.24 (m, 2H), 7.87-7.75 (m, 3H), 7.66 (t, J=1.6 Hz, 1H), 7.49-7.38 (m, 2H), 4.27 (d, J=1.6 Hz, 3H), 3.68 (m, 2H), 3.48 (dd, J=12.4, 9.7 Hz, 1H), 3.35-3.26 (obscured m, 1H), 2.81-2.58 (m, 3H), 2.47-1.90 (m, 3H), 0.99-0.87 (m 3H). R$^t$ 2.31 and 2.34 min (Method 9).

Examples 24-31

TABLE 3

The examples shown in the table below were prepared by similar methods to those described for Example 1

| Example | Structure | LC-MS analysis |
|---|---|---|
| 24 | 6-chloro-1-(4-fluorophenyl)-5-(1-isobutyl-4-((2-methyl-2H-1,2,3-triazol-4-yl)sulfonyl)piperazin-2-yl)-1H-indazole | R$^t$ 2.38 min (Method 9); m/z 532.2/534.0 (M + H)$^+$ (ES$^+$) |

TABLE 3-continued
The examples shown in the table below were prepared by similar methods to those described for Example 1
| Example | Structure | LC-MS analysis |
|---|---|---|
| 25 | 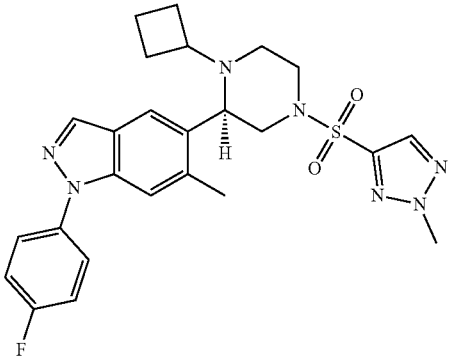 Or 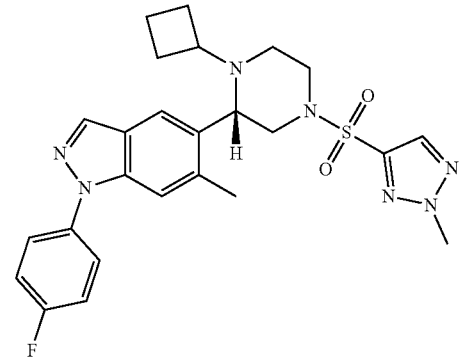 5-(1-cyclobutyl-4-((2-methyl-2H-1,2,3-triazol-4-yl)sulfonyl)piperazin-2-yl)-1-(4-fluorophenyl)-6-methyl-1H-indazole | $R^t$ 1.50 min (Method 7); m/z 510.4 $(M + H)^+$ $(ES^+)$ |
| 26 | 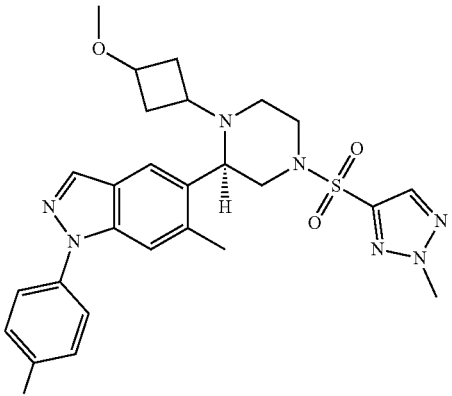 Or | $R^t$ 1.73 min (Method 8); m/z 540.3 $(M + H)^+$ $(ES^+)$ |

TABLE 3-continued

The examples shown in the table below were prepared by similar methods to those described for Example 1

| Example | Structure | LC-MS analysis |
|---|---|---|
| | 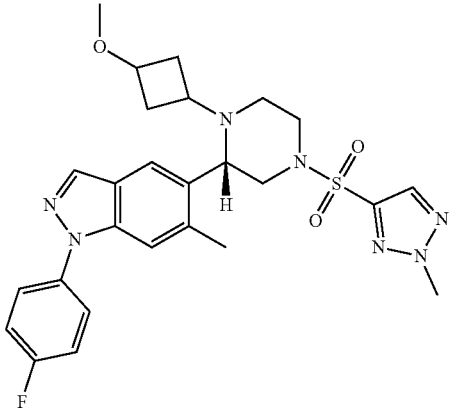 [SMILES: COC1CC(N2CCN(S(=O)(=O)c3cnn(C)n3)C[C@@H]2c2cc3cnn(-c4ccc(F)cc4)c3cc2C)C1]

1-(4-fluorophenyl)-5-(1-(3-methoxycyclobutyl)-4-((2-methyl-2H-1,2,3-triazol-4-yl)sulfonyl)piperazin-2-yl)-6-methyl-1H-indazole | |
| 27 | 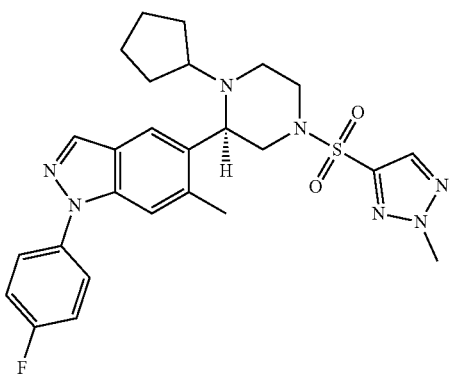

Or

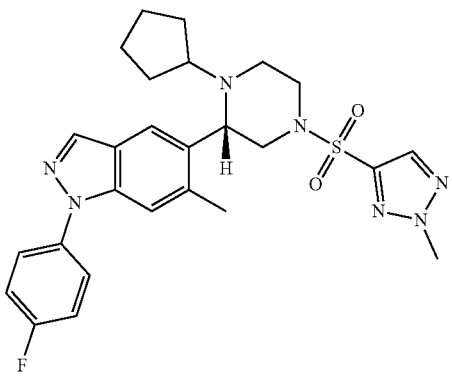 [SMILES: Cc1cc2c(cnn2-c2ccc(F)cc2)cc1[C@H]1CN(S(=O)(=O)c2cnn(C)n2)CCN1C1CCCC1]

5-(1-cyclopentyl-4-((2-methyl-2H-1,2,3-triazol-4-yl)sulfonyl)piperazin-2-yl)-1-(4-fluorophenyl)-6-methyl-1H-indazole | $R^t$ 1.62 min (Method 7); m/z 524.4 (M + H)$^+$ (ES$^+$) |

TABLE 3-continued
The examples shown in the table below were prepared by similar methods to those described for Example 1
| Example | Structure | LC-MS analysis |
|---|---|---|
| 28 | 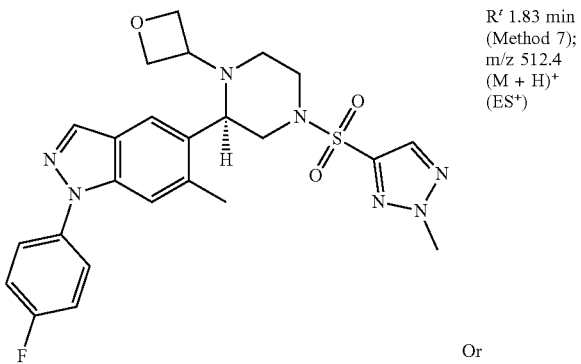<br><br>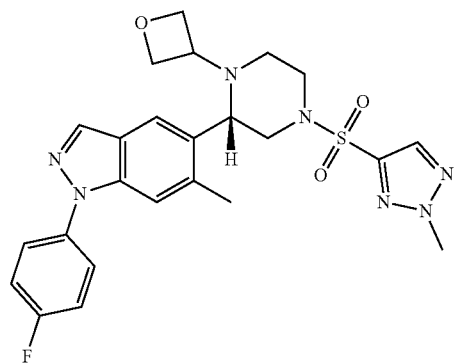 [SMILES: Cc1cc2c(cnn2-c2ccc(F)cc2)cc1[C@H]1CN(S(=O)(=O)c2cnn(C)n2)CCN1C1COC1]<br><br>1-(4-fluorophenyl)-6-methyl-5-(4-((2-methyl-2H-1,2,3-triazol-4-yl)sulfonyl)-1-(oxetan-3-yl)piperazin-2-yl)-1H-indazole | $R^t$ 1.83 min (Method 7); m/z 512.4 (M + H)$^+$ (ES$^+$) |
| 29 | 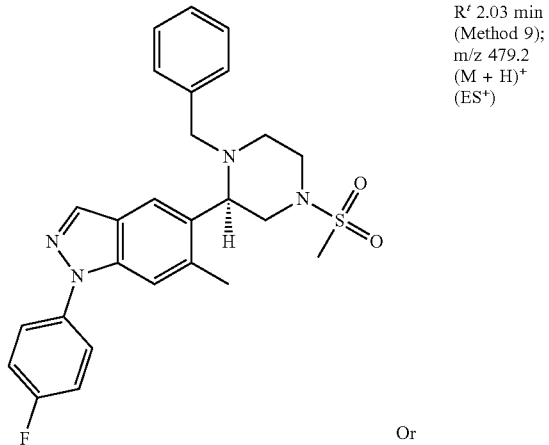 | $R^t$ 2.03 min (Method 9); m/z 479.2 (M + H)$^+$ (ES$^+$) |
Or
Or TABLE 3-continued
The examples shown in the table below were prepared by similar methods to those described for Example 1
| Example | Structure | LC-MS analysis |
|---------|-----------|----------------|
| | 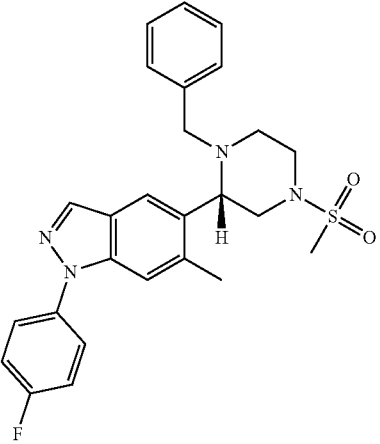 [SMILES: Cc1cc2c(cnn2-c2ccc(F)cc2)cc1[C@H]1CN(S(C)(=O)=O)CCN1Cc1ccccc1] 5-(1-benzyl-4-(methylsulfonyl)piperazin-2-yl)-1-(4-fluorophenyl)-6-methyl-1H-indazole | |
| 30 | 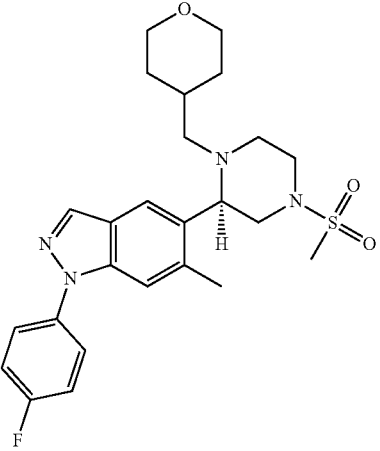 [SMILES: Cc1cc2c(cnn2-c2ccc(F)cc2)cc1[C@H]1CN(S(C)(=O)=O)CCN1CC1CCOCC1] Or 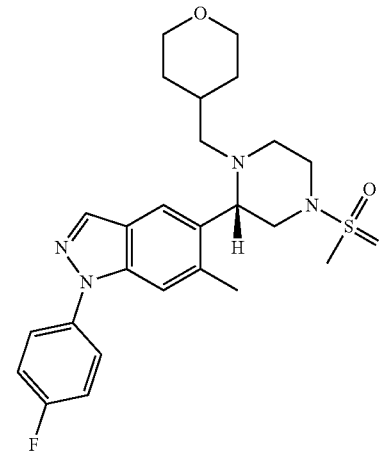 1-(4-fluorophenyl)-6-methyl-5-(4-(methylsulfonyl)-1-((tetrahydro-2H-pyran-4-yl)methyl)piperazin-2-yl)-1H-indazole | $R^t$ 1.56 min (Method 9); m/z 487.2 $(M + H)^+$ $(ES^+)$ |

TABLE 3-continued

The examples shown in the table below were prepared by similar methods to those described for Example 1

| Example | Structure | LC-MS analysis |
|---|---|---|
| 31 | 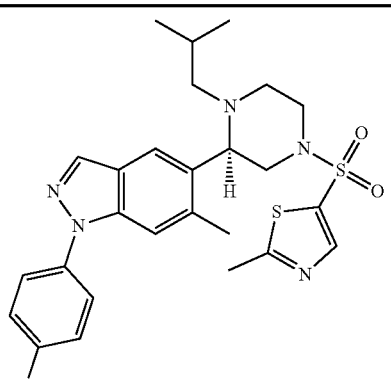<br>5-((3-(1-(4-fluorophenyl)-6-methyl-1H-indazol-5-yl)-4-isobutylpiperazin-1-yl)sulfonyl)-2-methylthiazole | R$^t$ 2.20 min (Method 9); m/z 528.2 (M + H)$^+$ (ES$^+$) |

Example 32: 1-(4-fluorophenyl)-6-methyl-5-(4-((2-methyl-2H-1,2,3-triazol-4-yl)sulfonyl)-1-(3,3,3-trifluoro-2-methylpropyl)piperazin-2-yl)-1H-indazole Example 33: 1-(4-fluorophenyl)-6-methyl-5-(4-((2-methyl-2H-1,2,3-triazol-4-yl)sulfonyl)-1-(3,3,3-trifluoro-2-methylpropyl)piperazin-2-yl)-1H-indazole

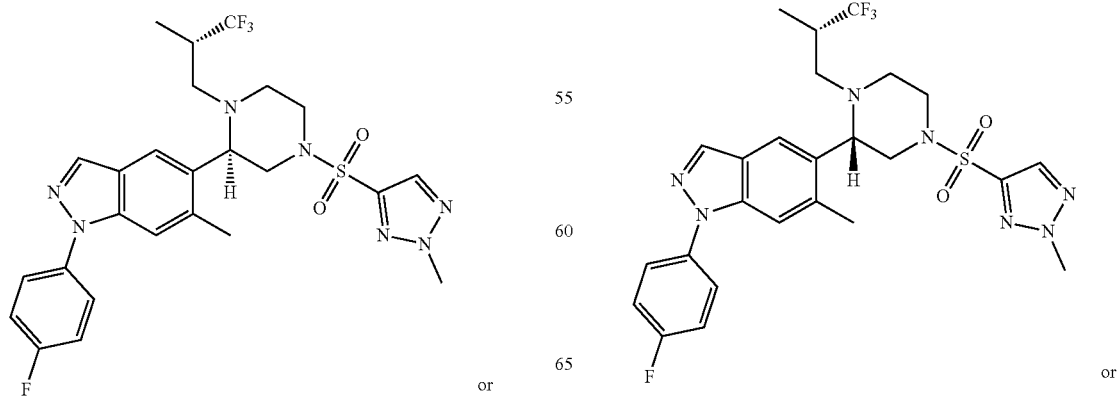

251

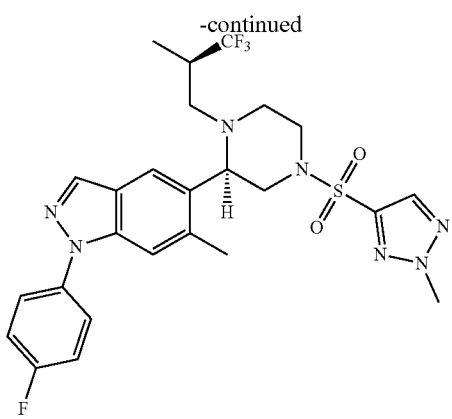

or

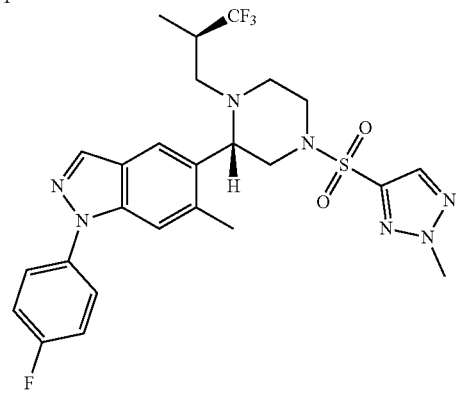

1-(4-Fluorophenyl)-6-methyl-5-(4-((2-methyl-2H-1,2,3-triazol-4-yl)sulfonyl)-1-(3,3,3-trifluoro-2-methylpropyl)piperazin-2-yl)-1H-indazole (48.8 mg, 0.083 mmol) was dissolved in 1 mL DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH C18 ODB prep column, 130 Å, 5 μm, 30 mm×100 mm, flow rate 40 mL min-1 eluting with a 0.1% Formic acid in water-MeCN gradient over 17.5 mins using UV across all wavelengths with PDA as well as a QDA and ELS detector. At-column dilution pump gives 2 mL min-1 Methanol over the entire method, which is included in the following MeCN percentages. Gradient information: 0.0-0.5 min, 55% MeCN; 0.5-21.0 min, ramped from 55% MeCN to 85% MeCN; 21.0-21.2 min, ramped from 85% MeCN to 100% MeCN; 21.2-24.0 min, held at 100% MeCN. The clean fractions were evaporated in a Genevac affording 1-(4-fluorophenyl)-6-methyl-5-((R)-4-((2-methyl-2H-1,2,3-triazol-4-yl)sulfonyl)-1-((R)-3,3,3-trifluoro-2-methylpropyl)piperazin-2-yl)-1H-indazole (14.2 mg, 24 μmol, 57%, 95% Purity) (Example 32) as a clear colourless solid; R$^t$ 2.18 min (Method 9); m/z 566.4 (M+H)$^+$ (ES$^+$); δH NMR (400 MHz, MeOD) δ 8.16 (d, J=0.9 Hz, 1H), 8.05 (s, 1H), 7.92 (s, 1H), 7.84-7.71 (m, 2H), 7.59 (s, 1H), 7.36 (t, J=8.7 Hz, 2H), 4.31 (s, 3H), 3.93-3.81 (m, 1H), 3.73 (dd, J=10.3, 3.2 Hz, 1H), 3.66 (dd, J=12.0, 2.8 Hz, 1H), 2.90 (td, J=11.8, 2.8 Hz, 1H), 2.79 (dd, J=13.4, 8.8 Hz, 1H), 2.70-2.35 (m, 7H), 1.99 (dd, J=13.3, 4.7 Hz, 1H), 0.98 (d, J=7.0 Hz, 3H), and 1-(4-fluorophenyl)-6-methyl-5-((R)-4-((2-methyl-2H-1,2,3-triazol-4-yl)sulfonyl)-1-((S)-3,3,3-trifluoro-2-methylpropyl)piperazin-2-yl)-1H-indazole (13.8 mg, 23 μmol, 56%, 95% Purity) (Example 33) as a clear colourless solid; R$^t$ 2.35 min (Method 9); m/z 566.4

252

(M+H)$^+$ (ES$^+$); δH NMR (400 MHz, MeOD) δ 8.19 (d, J=0.9 Hz, 1H), 8.05 (s, 1H), 7.93 (s, 1H), 7.82-7.72 (m, 2H), 7.64-7.57 (m, 1H), 7.36 (dd, J=9.5, 7.8 Hz, 2H), 4.31 (s, 3H), 3.89 (dd, J=11.8, 2.7 Hz, 1H), 3.78 (dd, J=10.5, 3.2 Hz, 1H), 3.71-3.64 (m, 1H), 3.28 (d, J=11.8 Hz, 1H), 2.91 (td, J=11.9, 2.8 Hz, 1H), 2.74-2.51 (m, 5H), 2.50-2.29 (m, 2H), 2.22 (dd, J=12.1, 3.1 Hz, 1H), 1.08 (d, J=6.8 Hz, 3H).

Example 34: 1-(2-(1-(4-fluorophenyl)-6-methyl-1H-indazol-5-yl)-4-((2-methyl-2H-1,2,3-triazol-4-yl)sulfonyl)piperazin-1-yl)ethan-1-one

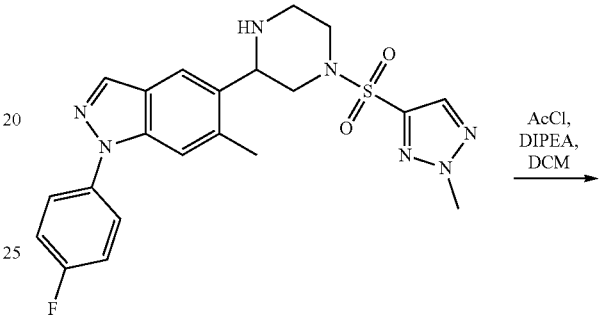

To a solution of 1-(4-fluorophenyl)-6-methyl-5-(4-((2-methyl-2H-1,2,3-triazol-4-yl)sulfonyl)piperazin-2-yl)-1H-indazole (25 mg, 55 μmol) in DCM (1.00 mL) were added N-ethyl-N-isopropylpropan-2-amine (35 mg, 48 μL, 0.27 mmol) and acetyl chloride (8.6 mg, 7.8 μL, 0.11 mmol). The reaction mixture was stirred for 45 mins at rt before being quenched with sat. aqueous NaHCO₃ (3 mL). The organics were extracted with DCM (3×3 mL), with the aid of a phase separator and then concentrated onto silica gel. The crude product was purified by chromatography on silica gel (4 g cartridge, 0-100% 3:1 EtOAc-EtOH/isohexane) to afford 1-(2-(1-(4-fluorophenyl)-6-methyl-1H-indazol-5-yl)-4-((2-methyl-2H-1,2,3-triazol-4-yl)sulfonyl)piperazin-1-yl)ethan-1-one (24 ng, 46 μmol, 83%) as a pale yellow solid; R$^t$ 1.84 min (Method 4); m/z 511.2 (M+H)$^+$ (ES$^+$); δH NMR (400 MHz, DMSO) δ 8.25 (d, J=0.9 Hz, 1H), 8.16 (s, 1H), 7.90 (s, 1H), 7.83-7.72 (m, 2H), 7.59 (q, J=1.0 Hz, 1H), 7.44-7.35 (m, 2H), 5.57 (t, J=5.1 Hz, 1H), 4.22 (s, 3H), 4.11 (d, J=14.0 Hz, 1H), 3.83 (ddd, J=13.3, 5.1, 1.1 Hz, 1H), 3.78-3.57 (m, 2H), 3.42 (dd, J=13.3, 5.1 Hz, 1H), 3.16 (td, J=10.9, 4.5 Hz, 1H), 2.47 (d, J=0.9 Hz, 3H), 1.96 (d, J=3.3 Hz, 3H).

Example 35: 1-(2-(1-(4-fluorophenyl)-6-methyl-1H-indazol-5-yl)-4-((2-methyl-2H-1,2,3-triazol-4-yl)sulfonyl)piperazin-1-yl)-2-methylpropan-1-one

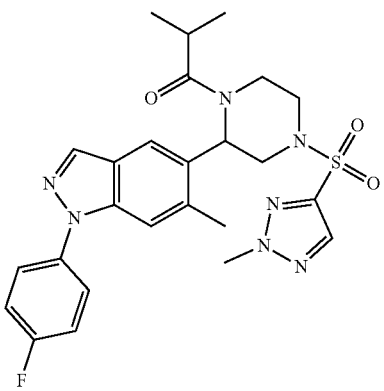 [SMILES: Cc1cc2c(cnn2-c2ccc(F)cc2)cc1C1CN(S(=O)(=O)c2cnn(C)n2)CCN1C(=O)C(C)C]

The compound was prepared by similar methods to those described for Example 34; Rt 1.97 min (Method 1); m/z 526.4 (M+H)⁺ (ES⁺). δH 8.24 (d, J=0.9 Hz, 1H), 8.16 (s, 1H), 7.87 (s, 1H), 7.83-7.74 (m, 2H), 7.59 (d, J=1.3 Hz, 1H), 7.44-7.34 (m, 2H), 5.60 (t, J=5.3 Hz, 1H), 4.21 (s, 3H), 4.17 (d, J=4.9 Hz, 1H), 3.82 (dd, J=13.3, 5.5 Hz, 1H), 3.76-3.65 (m, 2H), 3.43 (obsc m, 1H), 3.14 (m, 1H), 2.79 (p, J=6.7 Hz, 1H), 2.46 (d, J=0.8 Hz, 3H), 0.99 (d, J=6.7 Hz, 3H), 0.91 (d, J=6.6 Hz, 3H).

Example 36: 1-(4-fluorophenyl)-5-(1-isobutyl-4-((1-(tetrahydro-2H-pyran-4-yl)-1H-pyrazol-4-yl)sulfonyl)piperazin-2-yl)-6-methyl-1H-indazole Intermediate F: tert-butyl 3-(1-(4-fluorophenyl)-6-methyl-1H-indazol-5-yl)piperazine-1-carboxylate

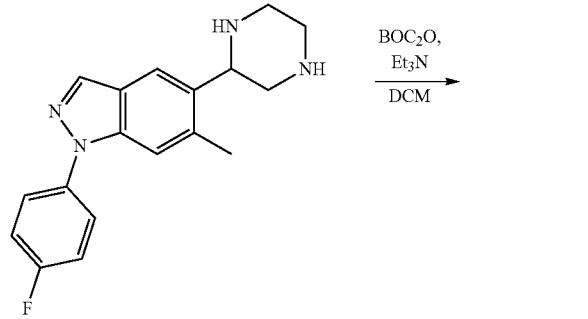

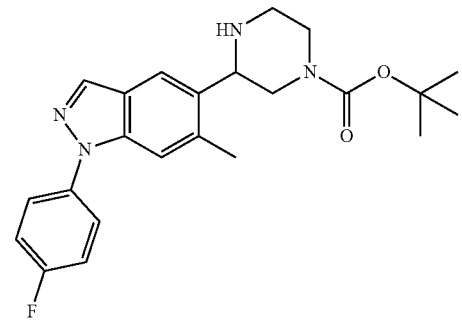

To a solution of 1-(4-fluorophenyl)-6-methyl-5-(piperazin-2-yl)-1H-indazole (3.30 g, 10.6 mmol) [Intermediate B] in DCM (100 mL) were added triethylamine (1.29 g, 1.77 mL, 12.8 mmol) and di-tert-butyl dicarbonate (2.32 g, 10.6 mmol) and the reaction mixture stirred at rt overnight. The reaction mixture was quenched with water (40 mL) and the layers separated. The aqueous layer was extracted with DCM (2×20 mL). Combined organic extracts were dried over MgSO₄ and concentrated in vacuo. The crude product was purified by chromatography on silica gel (80 g cartridge, 0-10% (0.7 M Ammonia/MeOH)/DCM) to afford tert-butyl 3-(1-(4-fluorophenyl)-6-methyl-1H-indazol-5-yl)piperazine-1-carboxylate (3.83 g, 8.9 mmol, 83%) as a pale yellow solid; Rt 1.41 min (Method 4); m/z 355.2 (M+H)+(ES⁺).

Intermediate G: tert-butyl 3-(1-(4-fluorophenyl)-6-methyl-1H-indazol-5-yl)-4-isobutylpiperazine-1-carboxylate

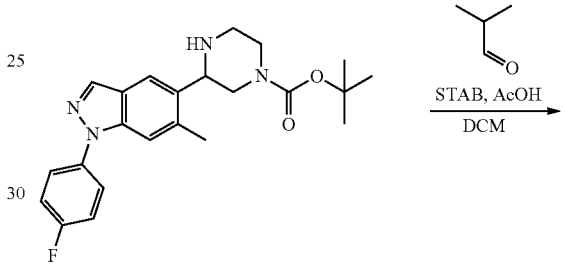

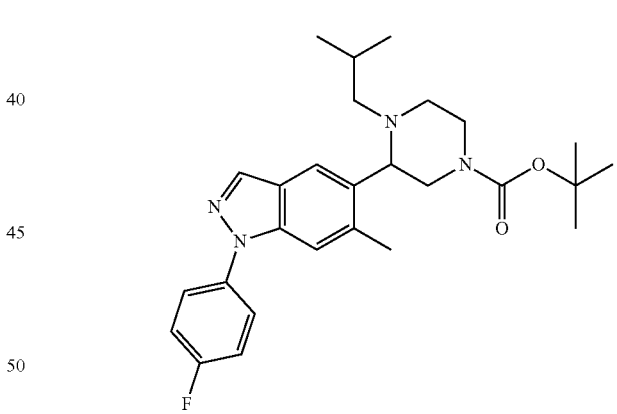

The compound was prepared by similar methods to those described for Example 1 to give tert-butyl 3-(1-(4-fluorophenyl)-6-methyl-1H-indazol-5-yl)-4-isobutylpiperazine-1-carboxylate (2.4 g, 63%); Rt 1.82 min (Method 1); m/z 467.2 (M+H)⁺ (ES⁺); δH NMR (400 MHz, DMSO) δ 8.30 (d, J=0.9 Hz, 1H), 7.93 (s, 1H), 7.86-7.74 (m, 2H), 7.63 (s, 1H), 7.46-7.38 (m, 2H), 3.96 (d, J=13.0 Hz, 1H), 3.77 (s, 1H), 3.13 (d, J=11.8 Hz, 1H), 3.01 (s, 1H), 2.69 (d, J=19.9 Hz, 1H), 2.13-1.91 (m, 2H), 1.77 (ddd, J=22.8, 12.0, 5.6 Hz, 2H), 1.40 (s, 9H), 1.24 (s, 2H), 0.94-0.79 (m, 4H), 0.65 (d, J=6.5 Hz, 3H)

255

Intermediate H: 1-(4-fluorophenyl)-5-(1-isobutylpiperazin-2-yl)-6-methyl-1H-indazole

256

Example 36: 1-(4-fluorophenyl)-5-(1-isobutyl-4-((1-(tetrahydro-2H-pyran-4-yl)-1H-pyrazol-4-yl)sulfonyl)piperazin-2-yl)-6-methyl-1H-indazole

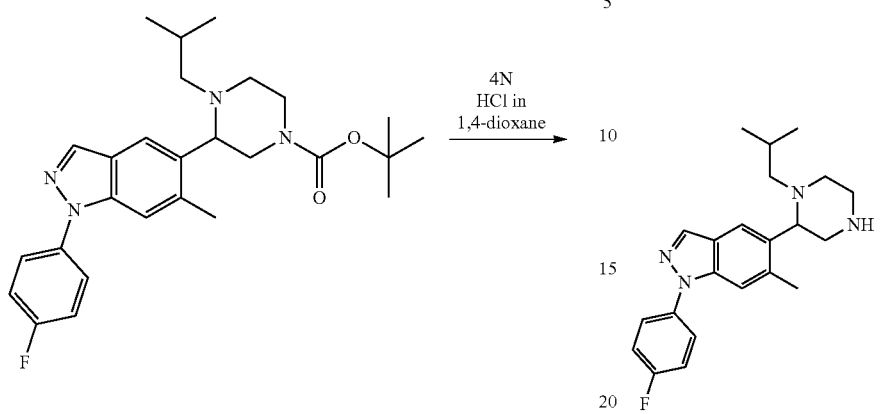

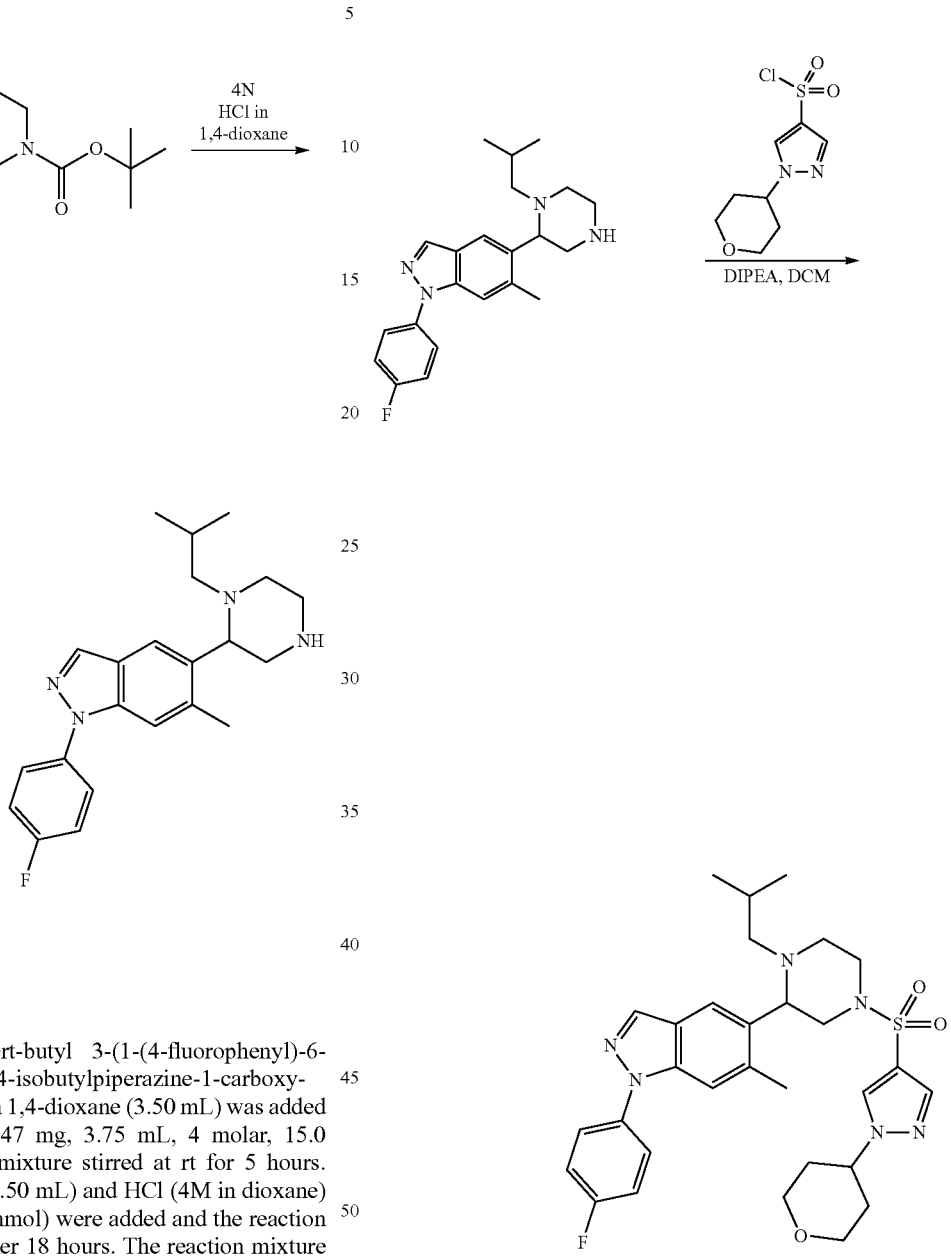

To a solution of tert-butyl 3-(1-(4-fluorophenyl)-6-methyl-1H-indazol-5-yl)-4-isobutylpiperazine-1-carboxylate (350 mg, 750 μmol) in 1,4-dioxane (3.50 mL) was added HCl (4M in dioxane) (547 mg, 3.75 mL, 4 molar, 15.0 mmol) and the reaction mixture stirred at rt for 5 hours. Additional 1,4-dioxane (3.50 mL) and HCl (4M in dioxane) (547 mg, 3.75 mL, 15.0 mmol) were added and the reaction mixture stirred for a further 18 hours. The reaction mixture was then concentrated to a white solid and the residue redissolved in DCM (10 mL). Sat. aqueous NaHCO$_3$ (10 mL) was added, and the layers separated. The aqueous was extracted with DCM (2×5 mL). Combined organic extracts were dried over MgSO$_4$ and concentrated in vacuo to afford 1-(4-fluorophenyl)-5-(1-isobutylpiperazin-2-yl)-6-methyl-1H-indazole (268 mg, 0.69 mmol, 93%) as a pale tan solid, which was used without further purification; Rt 1.48 min (Method 4); m/z 367.2 (M+H)+ (ES+); δH NMR (400 MHz, DMSO) δ 8.31-8.23 (m, 1H), 7.91 (s, 1H), 7.79 (m, 2H), 7.58 (d, J=3.9 Hz, 1H), 7.42 (m, 2H), 3.57 (dd, J=3.6, 1.6 Hz, 1H), 3.06 (d, J=11.4 Hz, 1H), 2.93 (d, J=12.5 Hz, 1H), 2.80 (d, J=12.4 Hz, 2H), 2.47 (obs s, 4H), 2.00 (t, J=10.6 Hz, 2H), 1.80 (s, 1H), 1.72 (d, J=12.1 Hz, 1H), 0.92-0.74 (m, 3H), 0.72-0.50 (m, 3H).

The compound was prepared by similar methods to those described for Example 1; Rt 1.94 min (Method 4); m/z 581.2 (M+H)$^+$ (ES$^+$); δH NMR (400 MHz, DMSO) δ 8.41 (s, 1H), 8.27 (d, J=0.9 Hz, 1H), 7.89-7.73 (m, 4H), 7.64 (s, 1H), 7.50-7.35 (m, 2H), 4.48 (tt, J=10.4, 5.1 Hz, 1H), 3.94 (d, J=12.2 Hz, 2H), 3.69-3.52 (m, 2H), 3.42 (ddd, J=14.9, 9.2, 3.1 Hz, 3H), 3.23 (d, J=11.8 Hz, 1H), 2.47 (m, 4H), 2.22 (dd, J=29.0, 17.1 Hz, 2H), 2.04-1.85 (m, 5H), 1.84-1.70 (m, 2H), 0.78 (d, J=6.2 Hz, 3H), 0.64 (d, J=6.3 Hz, 3H).

Examples 37-64

TABLE 4

The examples shown in the table below were prepared by similar methods to those described for Example 36

| Example | Structure | LC-MS analysis |
|---|---|---|
| 37 | 1-(4-fluorophenyl)-5-(1-isobutyl-4-((2-isopropyl-2H-1,2,3-triazol-4-yl)sulfonyl)piperazin-2-yl)-6-methyl-1H-indazole | $R^t$ 2.38 min (Method 7); m/z 540.0 (M + H)$^+$ (ES$^+$) |
| 38 | 5-(4-((1-ethyl-1H-pyrazol-4-yl)sulfonyl)-1-isobutylpiperazin-2-yl)-1-(4-fluorophenyl)-6-methyl-1H-indazole | $R^t$ 1.98 min (Method 7); m/z 525.4 (M + H)$^+$ (ES$^+$) |
| 39 | 1-(4-fluorophenyl)-5-(1-isobutyl-4-(methylsulfonyl)piperazin-2-yl)-6-methyl-1H-indazole | $R^t$ 1.67 min (Method 7); m/z 445.4 (M + H)$^+$ (ES$^+$) |

TABLE 4-continued

The examples shown in the table below were prepared by similar methods to those described for Example 36

| Example | Structure | LC-MS analysis |
|---|---|---|
| 40 | 5-(4-((2-ethyl-2H-1,2,3-triazol-4-yl)sulfonyl)-1-isobutylpiperazin-2-yl)-1-(4-fluorophenyl)-6-methyl-1H-indazole | $R^t$ 2.21 min (Method 7); m/z 526.5 $(M + H)^+$ $(ES^+)$ |
| 41 | 1-(4-fluorophenyl)-5-(1-isobutyl-4-((2-propyl-2H-1,2,3-triazol-4-yl)sulfonyl)piperazin-2-yl)-6-methyl-1H-indazole | $R^t$ 2.39 min (Method 7); m/z 540.2 $(M + H)^+$ $(ES^+)$ |
| 42 | 1-(4-fluorophenyl)-5-(1-isobutyl-4-((1-methyl-1H-pyrazol-3-yl)sulfonyl)piperazin-2-yl)-6-methyl-1H-indazole | $R^t$ 1.86 min (Method 9); m/z 511.4 $(M + H)^+$ $(ES^+)$ |

TABLE 4-continued

The examples shown in the table below were prepared by similar methods to those described for Example 36

| Example | Structure | LC-MS analysis |
|---|---|---|
| 43 | 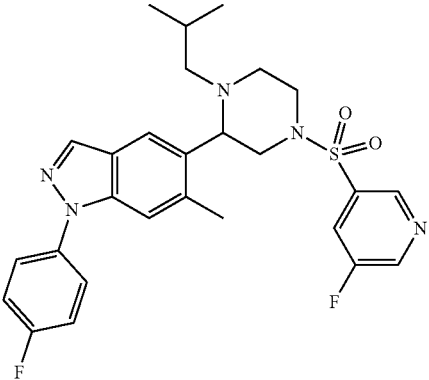 1-(4-fluorophenyl)-5-(4-((5-fluoropyridin-3-yl)sulfonyl)-1-isobutylpiperazin-2-yl)-6-methyl-1H-indazole | R$^t$ 2.18 min (Method 9); m/z 526.2 (M + H)$^+$ (ES$^+$) |
| 44 | 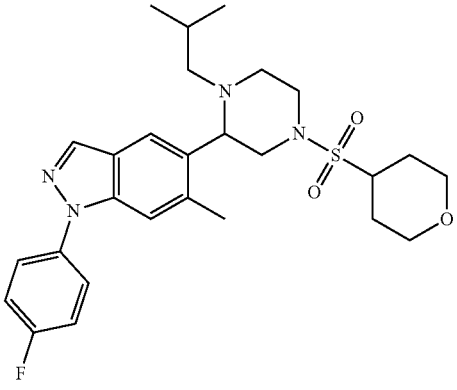 [SMILES: Cc1cc2c(cnn2-c2ccc(F)cc2)cc1C1CN(S(=O)(=O)C2CCOCC2)CCN1CC(C)C] 1-(4-fluorophenyl)-5-(1-isobutyl-4-((tetrahydro-2H-pyran-4-yl)sulfonyl)piperazin-2-yl)-6-methyl-1H-indazole | R$^t$ 1.74 min (Method 9); m/z 515.2 (M + H)$^+$ (ES$^+$) |
| 45 | 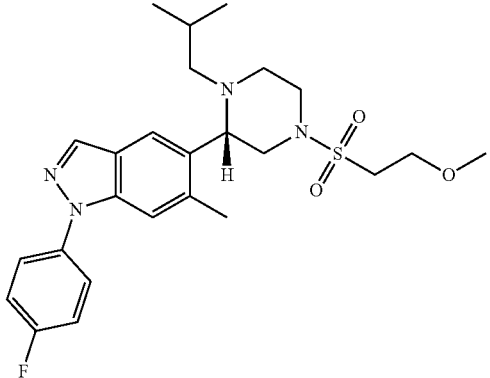 | R$^t$ 1.68 min (Method 7); m/z 489.5 (M + H)$^+$ (ES$^+$) |

Or

TABLE 4-continued

The examples shown in the table below were prepared by similar methods to those described for Example 36

| Example | Structure | LC-MS analysis |
|---|---|---|
|  | 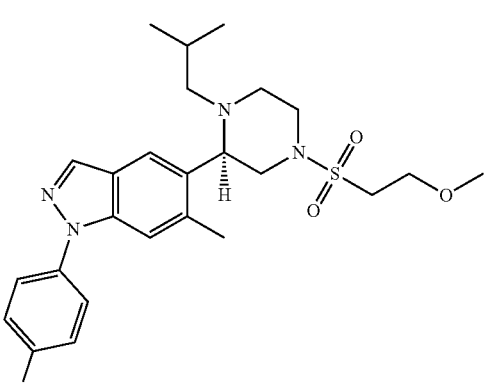<br>1-(4-fluorophenyl)-5-(1-isobutyl-4-((2-methoxyethyl)sulfonyl)piperazin-2-yl)-6-methyl-1H-indazole |  |
| 46 | 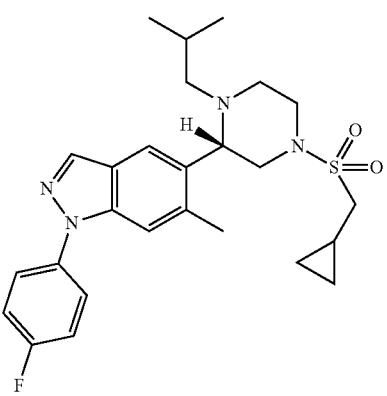<br>Or<br>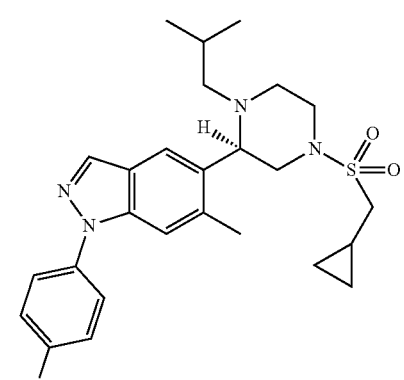<br>5-(4-((cyclopropylmethyl)sulfonyl)-1-isobutylpiperazin-2-yl)-1-(4-fluorophenyl)-6-methyl-1H-indazole | $R^t$ 1.84 min (Method 7); m/z 485.4 (M + H)$^+$ (ES$^+$) |

TABLE 4-continued
The examples shown in the table below were prepared by similar methods to those described for Example 36
| Example | Structure | LC-MS analysis |
|---|---|---|
| 47 | 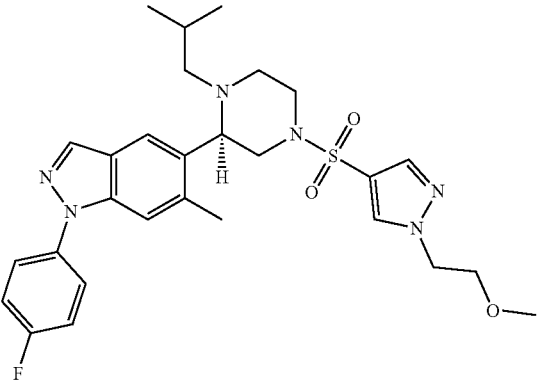 1-(4-fluorophenyl)-5-(1-isobutyl-4-((1-(2-methoxyethyl)-1H-pyrazol-4-yl)sulfonyl)piperazin-2-yl)-6-methyl-1H-indazole | R$^t$ 1.89 min (Method 9); m/z 555.2 (M + H)$^+$ (ES$^+$) |
| 48 | 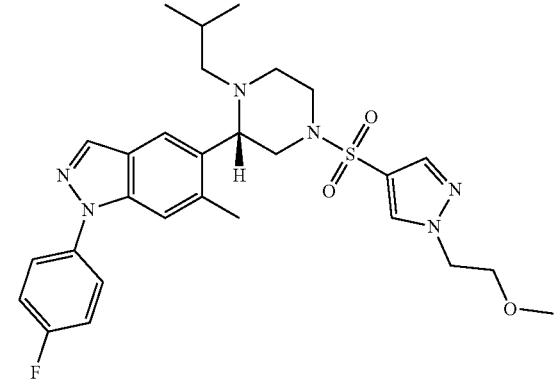 | R$^t$ 2.15 min (Method 9); m/z 526.2 (M + H)$^+$ (ES$^+$) |

TABLE 4-continued

The examples shown in the table below were prepared by similar methods to those described for Example 36

| Example | Structure | LC-MS analysis |
|---|---|---|
|  | 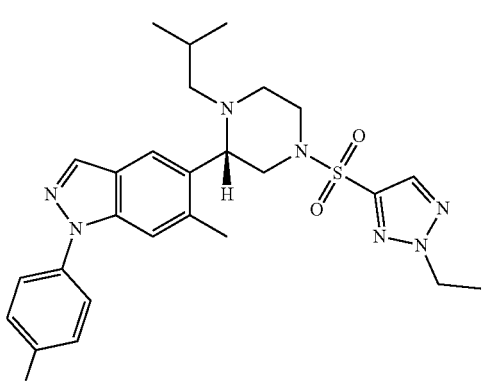<br>5-(4-((2-ethyl-2H-1,2,3-triazol-4-yl)sulfonyl)-1-isobutylpiperazin-2-yl)-1-(4-fluorophenyl)-6-methyl-1H-indazole |  |
| 49 | 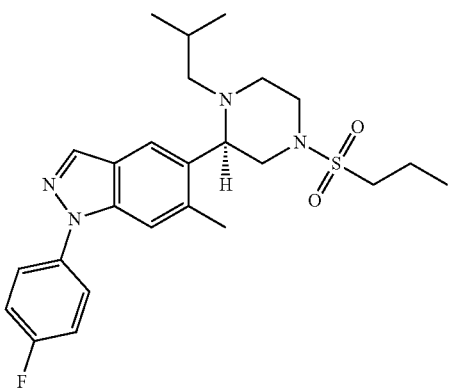 [SMILES: CCCS(=O)(=O)N1CCN(CC(C)C)[C@@H](c2cc3cnn(-c4ccc(F)cc4)c3cc2C)C1]<br>Or<br>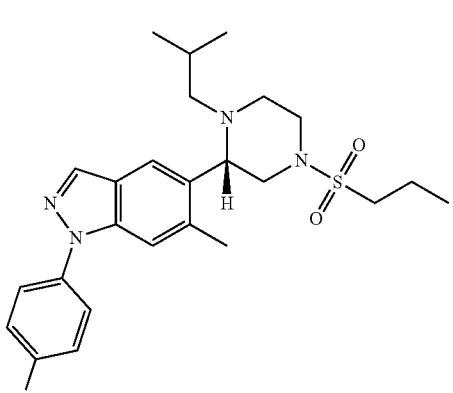<br>1-(4-fluorophenyl)-5-(1-isobutyl-4-(propylsulfonyl)piperazin-2-yl)-6-methyl-1H-indazole | $R^t$ 1.72 min (Method 9); m/z 473.2 (M + H)$^+$ (ES$^+$) |

TABLE 4-continued
The examples shown in the table below were prepared by similar methods to those described for Example 36
| Example | Structure | LC-MS analysis |
|---|---|---|
| 50 | 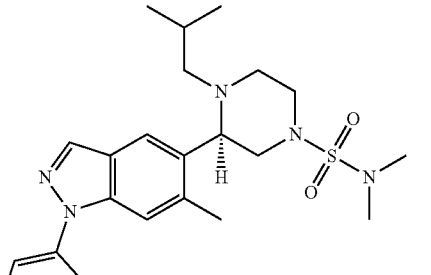<br>Or<br>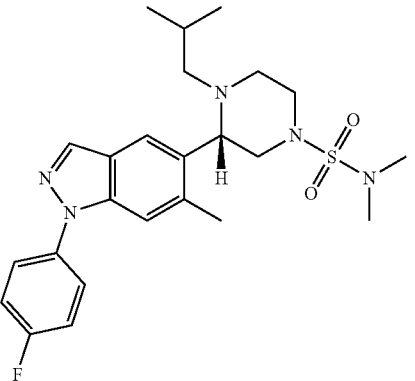 [SMILES: Cc1cc2c(cnn2-c2ccc(F)cc2)cc1[C@H]1CN(S(=O)(=O)N(C)C)CCN1CC(C)C]<br>3-(1-(4-fluorophenyl)-6-methyl-1H-indazol-5-yl)-4-isobutyl-N,N-dimethylpiperazine-1-sulfonamide | R' 1.62 min (Method 9); m/z 474.2 (M + H)+ (ES+) |
| 51 | 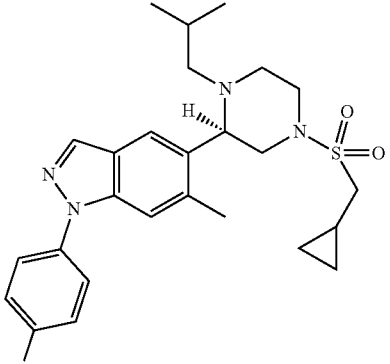<br>Or | R' 1.73 min (Method 9); m/z 485.2 (M + H)+ (ES+) |

TABLE 4-continued
The examples shown in the table below were prepared by similar methods to those described for Example 36
| Example | Structure | LC-MS analysis |
|---|---|---|
| | 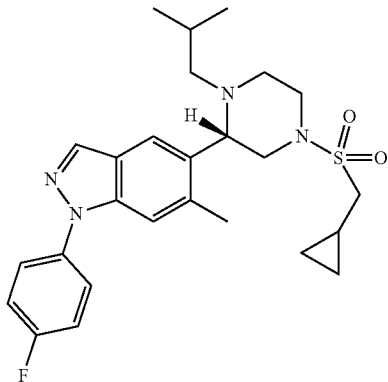 [SMILES: Cc1cc2c(cnn2-c2ccc(F)cc2)cc1[C@H]1CN(S(=O)(=O)CC2CC2)CCN1CC(C)C]
5-(4-((cyclopropylmethyl)sulfonyl)-1-isobutylpiperazin-2-yl)-1-(4-fluorophenyl)-6-methyl-1H-indazole | |
| 52 | 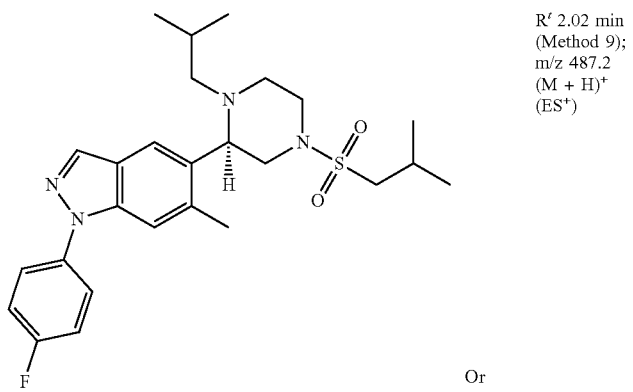
Or
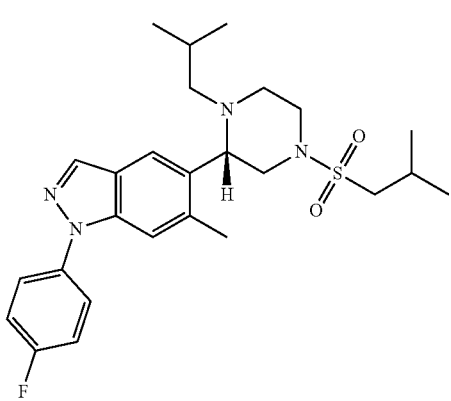 [SMILES: Cc1cc2c(cnn2-c2ccc(F)cc2)cc1[C@H]1CN(S(=O)(=O)CC(C)C)CCN1CC(C)C]
1-(4-fluorophenyl)-5-(1-isobutyl-4-(isobutylsulfonyl)piperazin-2-yl)-6-methyl-1H-indazole | R$^t$ 2.02 min (Method 9); m/z 487.2 (M + H)$^+$ (ES$^+$) |

TABLE 4-continued
The examples shown in the table below were prepared by similar methods to those described for Example 36
| Example | Structure | LC-MS analysis |
|---|---|---|
| 53 | 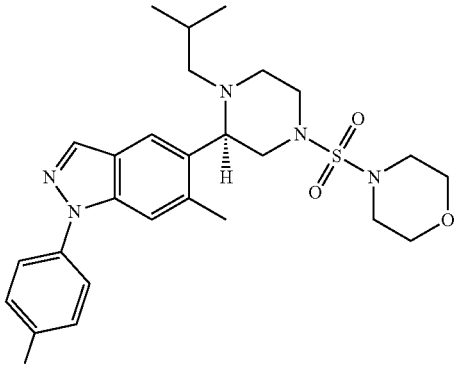 Or 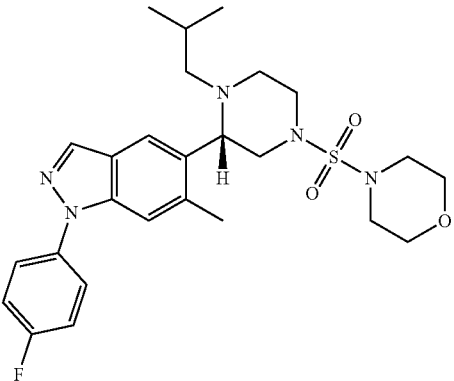 [SMILES: Cc1cc2c(cnn2-c2ccc(F)cc2)cc1[C@H]1CN(S(=O)(=O)N2CCOCC2)CCN1CC(C)C] 4-((3-(1-(4-fluorophenyl)-6-methyl-1H-indazol-5-yl)-4-isobutylpiperazin-1-yl)sulfonyl)morpholine | R$^t$ 1.78 min (Method 9); m/z 516.2 (M + H)$^+$ (ES$^+$) |
| 54 | 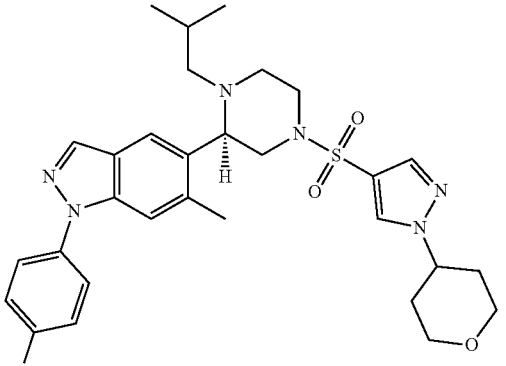 Or | R$^t$ 1.93 min (Method 9); m/z 581.2 (M + H)$^+$ (ES$^+$) |

TABLE 4-continued

The examples shown in the table below were prepared by similar methods to those described for Example 36

| Example | Structure | LC-MS analysis |
|---|---|---|
|  | 1-(4-fluorophenyl)-5-(1-isobutyl-4-((1-(tetrahydro-2H-pyran-4-yl)-1H-pyrazol-4-yl)sulfonyl)piperazin-2-yl)-6-methyl-1H-indazole |  |
| 55 | 5-(4-((1-ethyl-1H-pyrazol-4-yl)sulfonyl)-1-isobutylpiperazin-2-yl)-1-(4-fluorophenyl)-6-methyl-1H-indazole<br><br>Or | R$^t$ 1.94 min (Method 9); m/z 525.2 (M + H)$^+$ (ES$^+$) |

TABLE 4-continued
The examples shown in the table below were prepared by similar methods to those described for Example 36
| Example | Structure | LC-MS analysis |
|---|---|---|
| 56 | 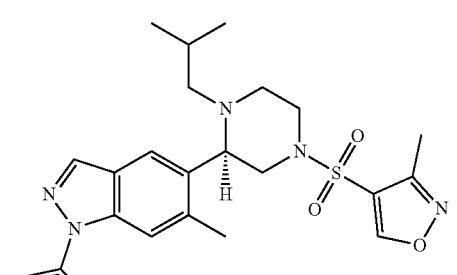 4-((3-(1-(4-fluorophenyl)-6-methyl-1H-indazol-5-yl)-4-isobutylpiperazin-1-yl)sulfonyl)-3-methylisoxazole | $R^t$ 2.15 min (Method 9); m/z 512.2 (M + H)$^+$ (ES$^+$) |
| 57 | 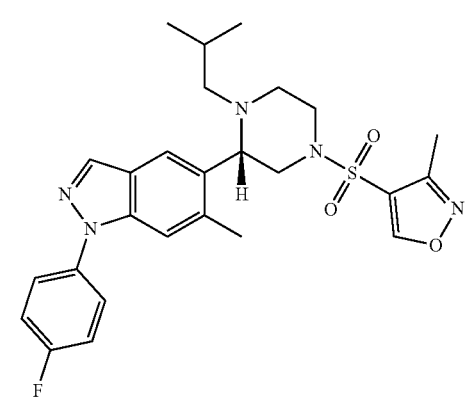 | $R^t$ 1.86 min (Method 9); m/z 525.2 (M + H)$^+$ (ES$^+$) |
Or
Or TABLE 4-continued The examples shown in the table below were prepared by similar methods to those described for Example 36

| Example | Structure | LC-MS analysis |
|---|---|---|
|  | 5-(4-((1,5-dimethyl-1H-pyrazol-4-yl)sulfonyl)-1-isobutylpiperazin-2-yl)-1-(4-fluorophenyl)-6-methyl-1H-indazole |  |
| 58 | Or<br><br>5-((3-(1-(4-fluorophenyl)-6-methyl-1H-indazol-5-yl)-4-isobutylpiperazin-1-yl)sulfonyl)thiazole | $R^t$ 2.11 min (Method 9); m/z 514.2 (M + H)$^+$ (ES$^+$) |

TABLE 4-continued
The examples shown in the table below were prepared by similar methods to those described for Example 36
| Example | Structure | LC-MS analysis |
|---|---|---|
| 59 | <br>5-(4-((1-(difluoromethyl)-1H-pyrazol-4-yl)sulfonyl)-1-isobutylpiperazin-2-yl)-1-(4-fluorophenyl)-6-methyl-1H-indazole | $R^t$ 2.09 min (Method 9); m/z 547.2 (M + H)$^+$ (ES$^+$) |
| 60 | 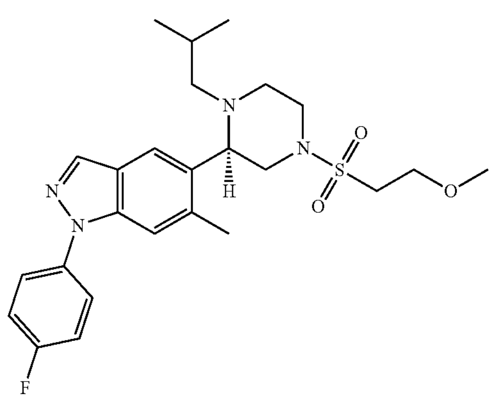 | $R^t$ 1.80 min (Method 9); m/z 488.6 (M + H)$^+$ (ES$^+$) |

TABLE 4-continued

The examples shown in the table below were prepared by similar methods to those described for Example 36

| Example | Structure | LC-MS analysis |
|---|---|---|
| | 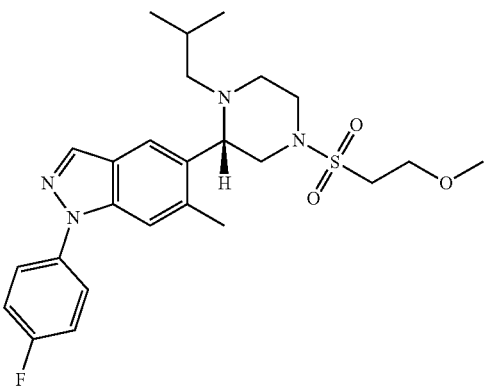 [SMILES: COCCS(=O)(=O)N1CCN(CC(C)C)[C@@H](c2cc3cnn(-c4ccc(F)cc4)c3cc2C)C1]<br>1-(4-fluorophenyl)-5-(1-isobutyl-4-((2-methoxyethyl)sulfonyl)piperazin-2-yl)-6-methyl-1H-indazole | |
| 61 | 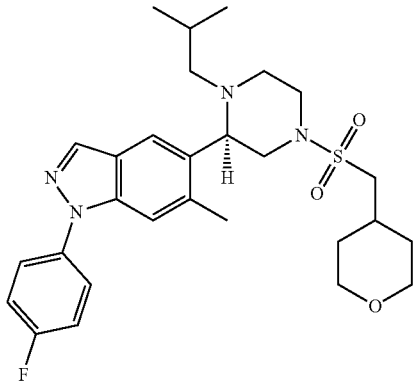<br>Or<br>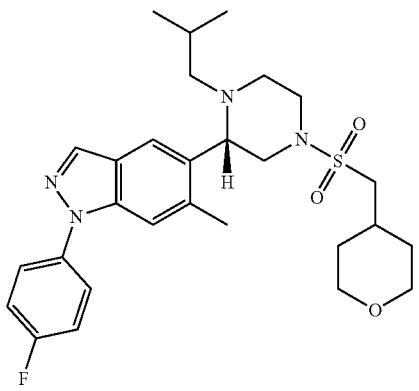 [SMILES: Cc1cc2c(cnn2-c2ccc(F)cc2)cc1[C@H]1CN(S(=O)(=O)CC2CCOCC2)CCN1CC(C)C]<br>1-(4-fluorophenyl)-5-(1-isobutyl-4-(((tetrahydro-2H-pyran-4-yl)methyl)sulfonyl)piperazin-2-yl)-6-methyl-1H-indazole | $R^t$ 1.90 min (Method 9); m/z 529.2 $(M + H)^+$ $(ES^+)$ |

TABLE 4-continued
The examples shown in the table below were prepared by similar methods to those described for Example 36
| Example | Structure | LC-MS analysis |
|---------|-----------|----------------|
| 62 | 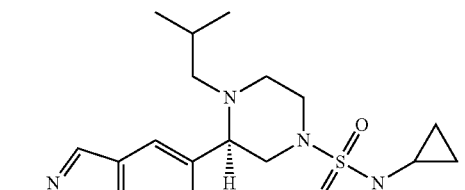 <br> Or <br> 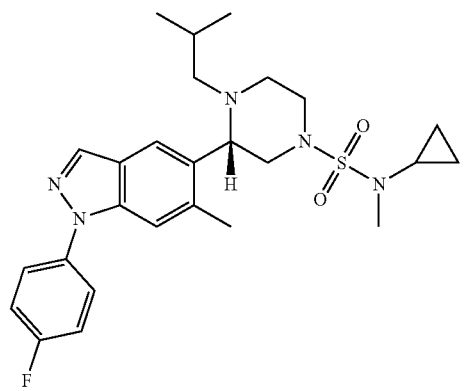 [SMILES: Cc1cc2c(cnn2-c2ccc(F)cc2)cc1[C@H]1CN(S(=O)(=O)N(C)C2CC2)CCN1CC(C)C] <br> N-cyclopropyl-3-(1-(4-fluorophenyl)-6-methyl-1H-indazol-5-yl)-4-isobutyl-N-methylpiperazine-1-sulfonamide | $R^t$ 1.94 min (Method 9); m/z 500.2 (M + H)$^+$ (ES$^+$) |
| 63 | 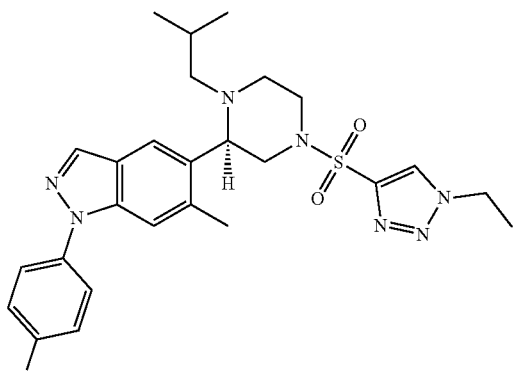 <br> Or | $R^t$ 1.95 min (Method 9); m/z 526.2 (M + H)$^+$ (ES$^+$) |

TABLE 4-continued

The examples shown in the table below were prepared by similar methods to those described for Example 36

| Example | Structure | LC-MS analysis |
|---------|-----------|----------------|
| | 5-(4-((1-ethyl-1H-1,2,3-triazol-4-yl)sulfonyl)-1-isobutylpiperazin-2-yl)-1-(4-fluorophenyl)-6-methyl-1H-indazole | |
| 64 | 1-(4-fluorophenyl)-5-(1-isobutyl-4-((1-methyl-1H-pyrazol-4-yl)sulfonyl)piperazin-2-yl)-6-methyl-1H-indazole Or | $R^t$ 1.82 min (Method 9); m/z 511.5 $(M + H)^+$ $(ES^+)$ |

Examples 65-67

TABLE 5

The examples shown in the table below were prepared by similar methods to those described in Example 34 using Intermediate H.

| Example | Structure | LC-MS analysis |
|---|---|---|
| 65 | 1-(3-(1-(4-fluorophenyl)-6-methyl-1H-indazol-5-yl)-4-isobutylpiperazin-1-yl)-2-hydroxypropan-1-one | R$^t$ 1.41 min (Method 9); m/z 439.2 (M + H)$^+$ (ES$^+$) |
| 66 | 1-(3-(1-(4-fluorophenyl)-6-methyl-1H-indazol-5-yl)-4-isobutylpiperazin-1-yl)ethan-1-one | R$^t$ 1.42 min (Method 9); m/z 409.2 (M + H)$^+$ (ES$^+$) |
| 67 | (3-(1-(4-fluorophenyl)-6-methyl-1H-indazol-5-yl)-4-isobutylpiperazin-1-yl)(2-methyl-2H-1,2,3-triazol-4-yl)methanone | R$^t$ 1.60 min (Method 9); m/z 476.2 (M + H)$^+$ (ES$^+$) |

Example 68: 1-(4-fluorophenyl)-6-methyl-5-(4-((2-methyl-2H-1,2,3-triazol-4-yl)sulfonyl)-1-(4,4,4-trifluorobutyl)piperazin-2-yl)-1H-indazole)

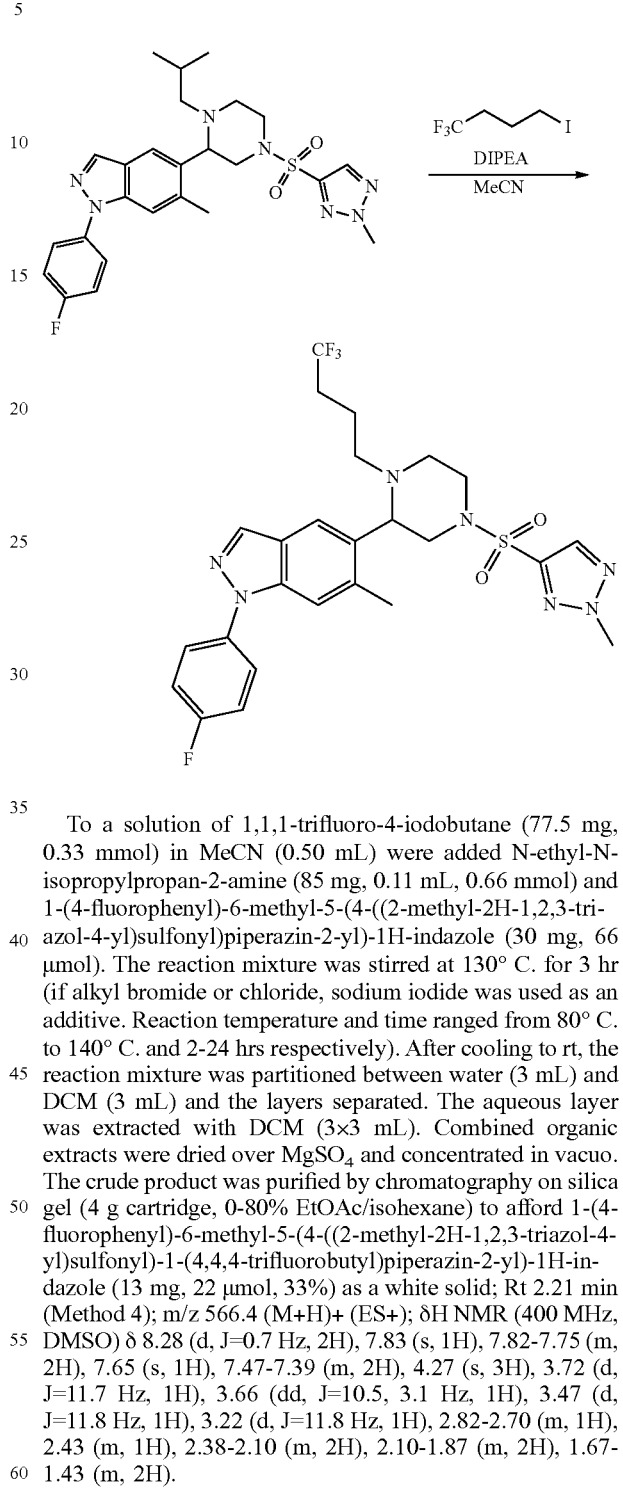

To a solution of 1,1,1-trifluoro-4-iodobutane (77.5 mg, 0.33 mmol) in MeCN (0.50 mL) were added N-ethyl-N-isopropylpropan-2-amine (85 mg, 0.11 mL, 0.66 mmol) and 1-(4-fluorophenyl)-6-methyl-5-(4-((2-methyl-2H-1,2,3-triazol-4-yl)sulfonyl)piperazin-2-yl)-1H-indazole (30 mg, 66 μmol). The reaction mixture was stirred at 130° C. for 3 hr (if alkyl bromide or chloride, sodium iodide was used as an additive. Reaction temperature and time ranged from 80° C. to 140° C. and 2-24 hrs respectively). After cooling to rt, the reaction mixture was partitioned between water (3 mL) and DCM (3 mL) and the layers separated. The aqueous layer was extracted with DCM (3×3 mL). Combined organic extracts were dried over MgSO$_4$ and concentrated in vacuo. The crude product was purified by chromatography on silica gel (4 g cartridge, 0-80% EtOAc/isohexane) to afford 1-(4-fluorophenyl)-6-methyl-5-(4-((2-methyl-2H-1,2,3-triazol-4-yl)sulfonyl)-1-(4,4,4-trifluorobutyl)piperazin-2-yl)-1H-indazole (13 mg, 22 μmol, 33%) as a white solid; Rt 2.21 min (Method 4); m/z 566.4 (M+H)+ (ES+); δH NMR (400 MHz, DMSO) δ 8.28 (d, J=0.7 Hz, 2H), 7.83 (s, 1H), 7.82-7.75 (m, 2H), 7.65 (s, 1H), 7.47-7.39 (m, 2H), 4.27 (s, 3H), 3.72 (d, J=11.7 Hz, 1H), 3.66 (dd, J=10.5, 3.1 Hz, 1H), 3.47 (d, J=11.8 Hz, 1H), 3.22 (d, J=11.8 Hz, 1H), 2.82-2.70 (m, 1H), 2.43 (m, 1H), 2.38-2.10 (m, 2H), 2.10-1.87 (m, 2H), 1.67-1.43 (m, 2H).

Examples 69-83

TABLE 6

The examples shown in the table below were prepared by similar methods to those described in Example 68.

| Example | Structure | LC-MS analysis |
|---|---|---|
| 69 | 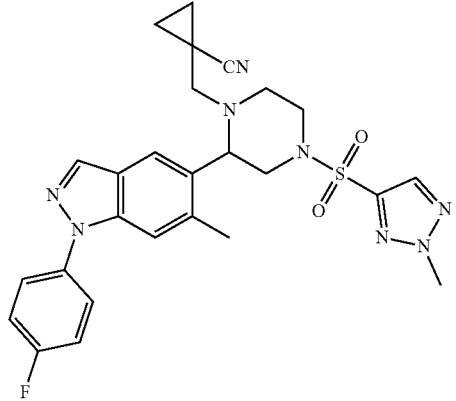 [SMILES: Cc1cc2c(cnn2-c2ccc(F)cc2)cc1C1CN(S(=O)(=O)c2cnn(C)n2)CCN1CC1(C#N)CC1]<br>1-((2-(1-(4-fluorophenyl)-6-methyl-1H-indazol-5-yl)-4-((2-methyl-2H-1,2,3-triazol-4-yl)sulfonyl)piperazin-1-yl)methyl)cyclopropane-1-carbonitrile | R$^t$ 2.09 min (Method 7); m/z 535.2 (M + H)$^+$ (ES$^+$) |
| 70 | 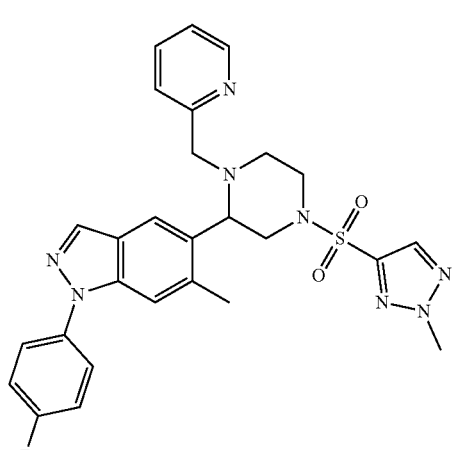<br>1-(4-fluorophenyl)-6-methyl-5-(4-((2-methyl-2H-1,2,3-triazol-4-yl)sulfonyl)-1-(pyridin-2-ylmethyl)piperazin-2-yl)-1H-indazole | R$^t$ 1.64 min (Method 9); m/z 547.2 (M + H)$^+$ (ES$^+$) |

TABLE 6-continued

The examples shown in the table below were prepared by similar methods to those described in Example 68.

| Example | Structure | LC-MS analysis |
|---------|-----------|----------------|
| 71 | 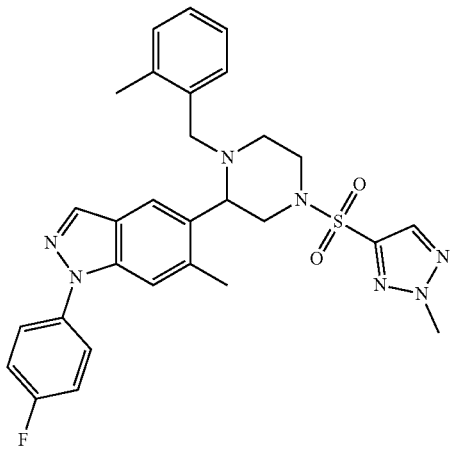 1-(4-fluorophenyl)-6-methyl-5-(4-((2-methyl-2H-1,2,3-triazol-4-yl)sulfonyl)-1-(2-methylbenzyl)piperazin-2-yl)-1H-indazole | $R^t$ 2.40 min (Method 9); m/z 560.2 $(M + H)^+$ $(ES^+)$ |
| 72 | 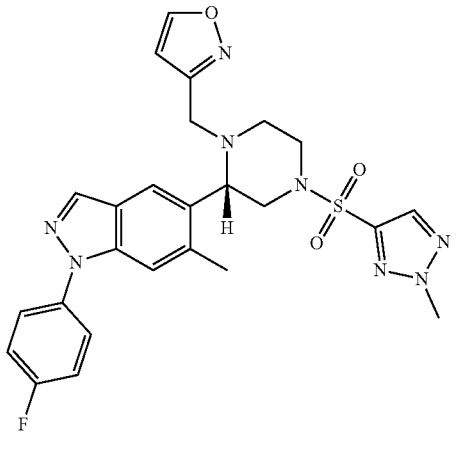 Or 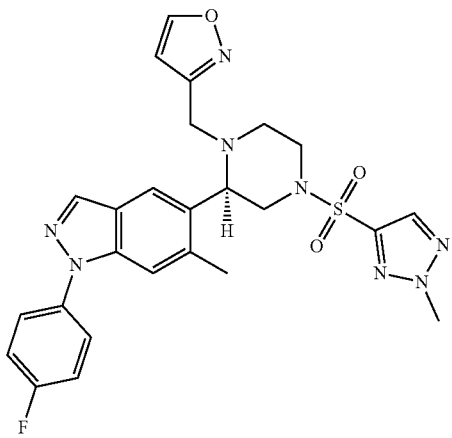 [SMILES: Cc1cc2c(cnn2-c2ccc(F)cc2)cc1[C@@H]1CN(S(=O)(=O)c2cnn(C)n2)CCN1Cc1ccon1] 3-((2-(1-(4-fluorophenyl)-6-methyl-1H-indazol-5-yl)-4-((2-methyl-2H-1,2,3-triazol-4-yl)sulfonyl)piperazin-1-yl)methyl)isoxazole | $R^t$ 2.06 min (Method 7); m/z 537.4 $(M + H)^+$ $(ES^+)$ |

TABLE 6-continued
The examples shown in the table below were prepared by similar methods to those described in Example 68.
| Example | Structure | LC-MS analysis |
|---|---|---|
| 73 | 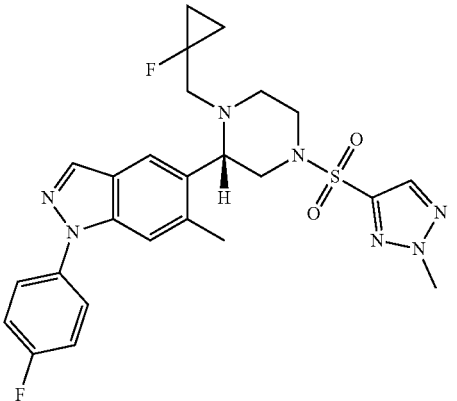 Or 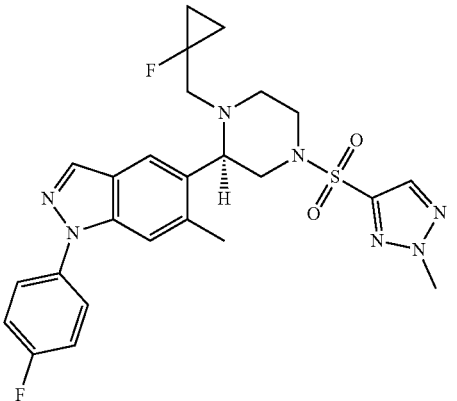 [SMILES: Cc1cc2c(cnn2-c2ccc(F)cc2)cc1[C@@H]1CN(S(=O)(=O)c2cnn(C)n2)CCN1CC1(F)CC1] 5-(1-((1-fluorocyclopropyl)methyl)-4-((2-methyl-2H-1,2,3-triazol-4-yl)sulfonyl)piperazin-2-yl)-1-(4-fluorophenyl)-6-methyl-1H-indazole | $R^t$ 2.13 min (Method 9); m/z 528.2 $(M + H)^+$ $(ES^+)$ |
| 74 | 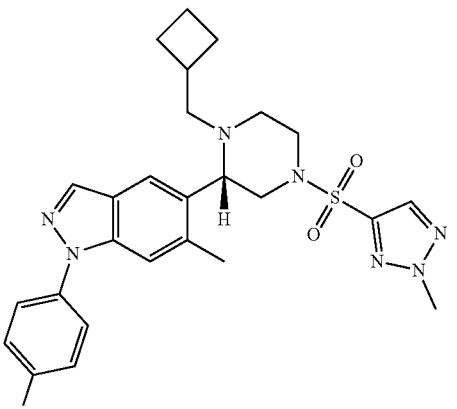 Or | $R^t$ 1.82 min (Method 9); m/z 524.2 $(M + H)^+$ $(ES^+)$ |

TABLE 6-continued

The examples shown in the table below were prepared by similar methods to those described in Example 68.

| Example | Structure | LC-MS analysis |
|---------|-----------|----------------|
|  | 5-(1-(cyclobutylmethyl)-4-((2-methyl-2H-1,2,3-triazol-4-yl)sulfonyl)piperazin-2-yl)-1-(4-fluorophenyl)-6-methyl-1H-indazole |  |
| 75 | Or<br><br>5-(1-((3,3-difluorocyclobutyl)methyl)-4-((2-methyl-2H-1,2,3-triazol-4-yl)sulfonyl)piperazin-2-yl)-1-(4-fluorophenyl)-6-methyl-1H-indazole | $R^t$ 2.11 min (Method 9); m/z 560.2 (M + H)$^+$ (ES$^+$) |

TABLE 6-continued
The examples shown in the table below were prepared by similar methods to those described in Example 68.
| Example | Structure | LC-MS analysis |
|---|---|---|
| 76 | 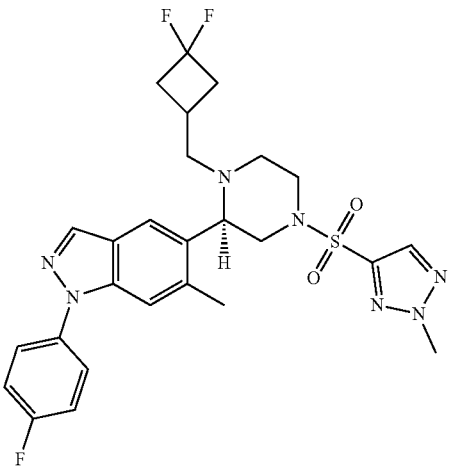 Or <br> 5-(1-(((3,3-difluorocyclobutyl)methyl)-4-((2-methyl-2H-1,2,3-triazol-4-yl)sulfonyl)piperazin-2-yl)-1-(4-fluorophenyl)-6-methyl-1H-indazole | $R^t$ 2.12 min (Method 7); m/z 560.4 $(M + H)^+$ $(ES^+)$ |
| 77 | 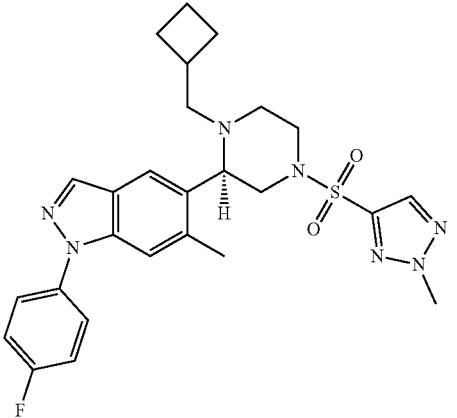 [SMILES: Cc1cc2c(cnn2-c2ccc(F)cc2)cc1[C@@H]1CN(S(=O)(=O)c2cnn(C)n2)CCN1CC1CCC1] Or | $R^t$ 1.80 min (Method 7); m/z 524.5 $(M + H)^+$ $(ES^+)$ |

TABLE 6-continued

The examples shown in the table below were prepared by similar methods to those described in Example 68.

| Example | Structure | LC-MS analysis |
|---------|-----------|----------------|
|  | 5-(1-(cyclobutylmethyl)-4-((2-methyl-2H-1,2,3-triazol-4-yl)sulfonyl)piperazin-2-yl)-1-(4-fluorophenyl)-6-methyl-1H-indazole |  |
| 78 | 5-(1-(cyclopentylmethyl)-4-((2-methyl-2H-1,2,3-triazol-4-yl)sulfonyl)piperazin-2-yl)-1-(4-fluorophenyl)-6-methyl-1H-indazole | R$^t$ 2.05 min (Method 7); m/z 538.4 (M + H)$^+$ (ES$^+$) |

Or

TABLE 6-continued
The examples shown in the table below were prepared by similar methods to those described in Example 68.
| Example | Structure | LC-MS analysis |
|---|---|---|
| 79 | 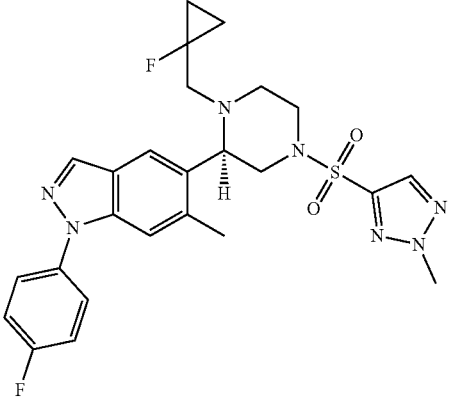 | R$^t$ 2.14 min (Method 9); m/z 528.2 (M + H)$^+$ (ES$^+$) |
| | 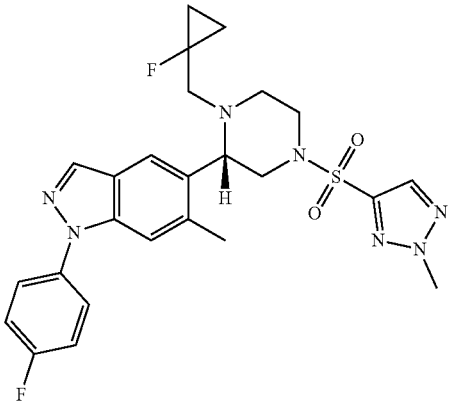 [SMILES: Cc1cc2c(cnn2-c2ccc(F)cc2)cc1[C@H]1CN(S(=O)(=O)c2cnn(C)n2)CCN1CC1(F)CC1] Or<br>5-(1-((1-fluorocyclopropyl)methyl)-4-((2-methyl-2H-1,2,3-triazol-4-yl)sulfonyl)piperazin-2-yl)-1-(4-fluorophenyl)-6-methyl-1H-indazole | |
| 80 | 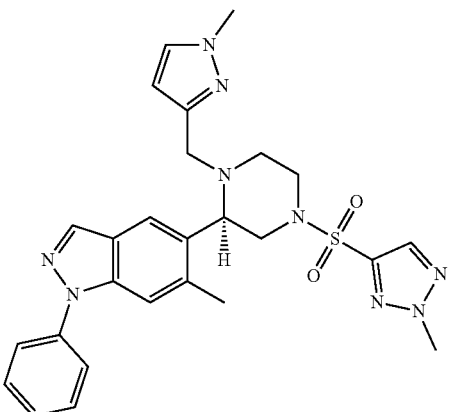 Or | R$^t$ 1.76 min (Method 7); m/z 550.6 (M + H)$^+$ (ES$^+$) |

TABLE 6-continued

The examples shown in the table below were prepared by similar methods to those described in Example 68.

| Example | Structure | LC-MS analysis |
|---------|-----------|----------------|
|  | 1-(4-fluorophenyl)-6-methyl-5-(1-((1-methyl-1H-pyrazol-3-yl)methyl)-4-((2-methyl-2H-1,2,3-triazol-4-yl)sulfonyl)piperazin-2-yl)-1H-indazole |  |
| 81 | 3-((2-(1-(4-fluorophenyl)-6-methyl-1H-indazol-5-yl)-4-((2-methyl-2H-1,2,3-triazol-4-yl)sulfonyl)piperazin-1-yl)methyl)isoxazole | R$^t$ 2.06 min (Method 7); m/z 537.4 (M + H)$^+$ (ES$^+$) |

Or

TABLE 6-continued
The examples shown in the table below were prepared by similar methods to those described in Example 68.
| Example | Structure | LC-MS analysis |
|---|---|---|
| 82 | 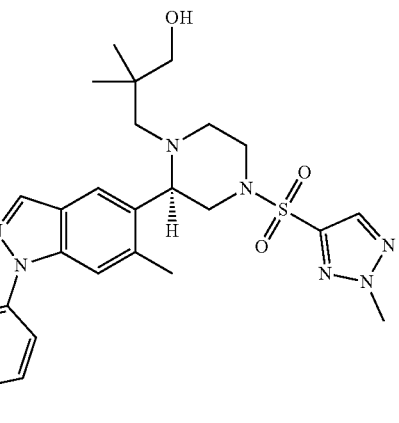 Or 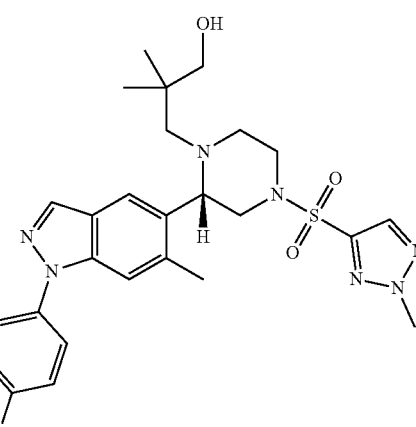<br>3-(2-(1-(4-fluorophenyl)-6-methyl-1H-indazol-5-yl)-4-((2-methyl-2H-1,2,3-triazol-4-yl)sulfonyl)piperazin-1-yl)-2,2-dimethylpropan-1-ol | $R^t$ 1.57 min (Method 7); m/z 542.4 $(M + H)^+$ $(ES^+)$ |
| 83 | 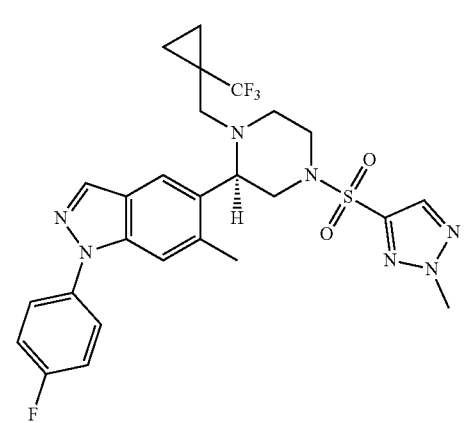 Or | $R^t$ 2.38 min (Method 7); m/z 578.4 $(M + H)^+$ $(ES^+)$ |

TABLE 6-continued

The examples shown in the table below were prepared by similar methods to those described in Example 68.

| Example | Structure | LC-MS analysis |
|---------|-----------|----------------|
| | 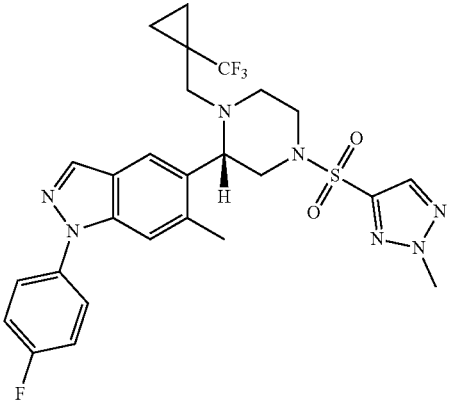 [SMILES: Cc1cc2c(cnn2-c2ccc(F)cc2)cc1[C@H]1CN(S(=O)(=O)c2cnn(C)n2)CCN1CC1(C(F)(F)F)CC1]<br>1-(4-fluorophenyl)-6-methyl-5-(4-((2-methyl-2H-1,2,3-triazol-4-yl)sulfonyl)-1-((1-(trifluoromethyl)cyclopropyl)methyl)piperazin-2-yl)-1H-indazole | |

Example 84: 1-(4-fluorophenyl)-6-methyl-5-(4-((2-methyl-2H-1,2,3-triazol-4-yl)sulfonyl)-1-(3,3,3-trifluoropropyl)piperazin-2-yl)-1H-indazole Intermediate AZ: 1-(4-fluorophenyl)-6-methyl-5-(4-((2-methyl-2H-1,2,3-triazol-4-yl)sulfonyl)piperazin-2-yl)-1H-indazole

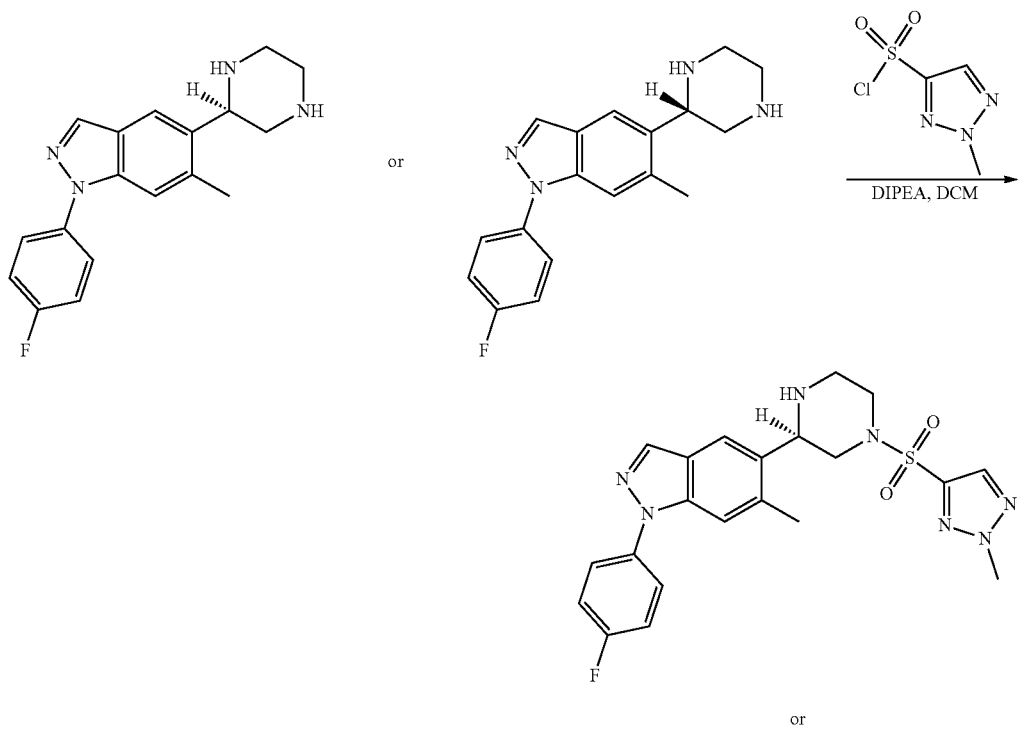

or

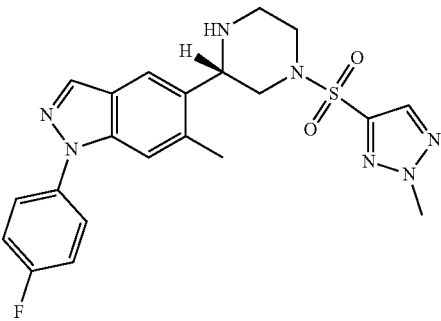

DCM (3.6 L) was charged to an agitated reactor under nitrogen at room temperature followed by the addition of 1-(4-fluorophenyl)-6-methyl-5-(piperazin-2-yl)-1H-indazole (120 g, 0.39 mol) and N-ethyl-N-isopropylpropan-2-amine (151 g, 1.17 mol). The reaction mixture was cooled to 0° C. and a solution of 2-methyl-2H-1,2,3-triazole-4-sulfonyl chloride (212 g, 1.17 mol) in DCM (750 ml) was added at a controlled rate and following complete addition the resultant mixture was stirred for at least 2 h at 0° C. The reaction mixture was then quenched by the addition of sat. aq. NaHCO$_3$ (1500 ml). The phases were separated and the aqueous phase extracted with DCM (2×750 ml). The combined organic phases were concentrated in vacuo and the residue purified by silica chromatography to provide 1-(4-fluorophenyl)-6-methyl-5-(4-((2-methyl-2H-1,2,3-triazol-4-yl)sulfonyl)piperazin-2-yl)-1H-indazole as an off-white solid in 70% yield and a purity of >98% by HPLC. m/z 456.2 (M+H)$^+$ (ES$^+$).

Example 84: 1-(4-fluorophenyl)-6-methyl-5-(4-((2-methyl-2H-1,2,3-triazol-4-yl)sulfonyl)-1-(3,3,3-trifluoropropyl)piperazin-2-yl)-1H-indazole

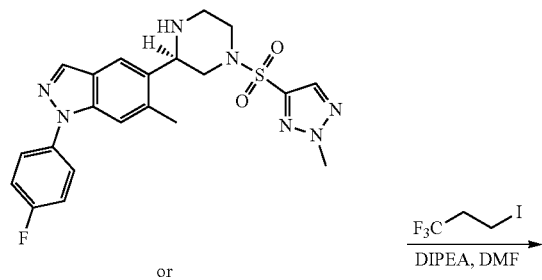

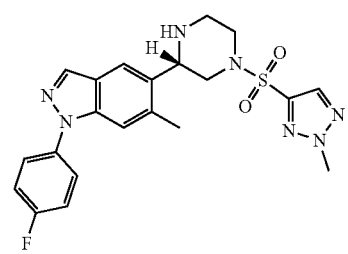

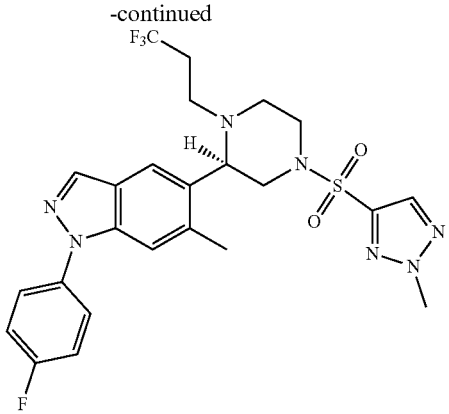

or

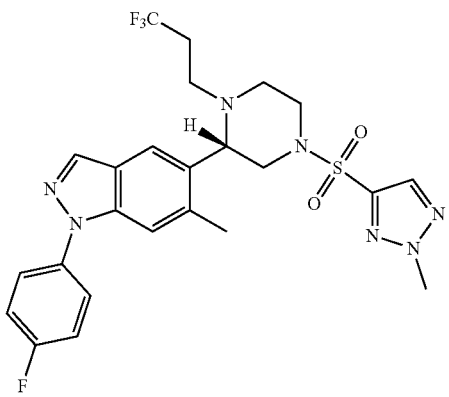

To a solution of (R)-1-(4-fluorophenyl)-6-methyl-5-(4-((2-methyl-2H-1,2,3-triazol-4-yl)sulfonyl)piperazin-2-yl)-1H-indazole (2.50 g, 1 Eq, 5.49 mmol) in MeCN (10.0 mL) were added 1,1,1-trifluoro-3-iodopropane (9.83 g, 8 Eq, 43.9 mmol) and N-ethyl-N-isopropylpropan-2-amine (7.09 g, 10 Eq, 54.9 mmol). The reaction mixture was heated in the microwave at 150° C. for 3 hrs. Power 150; Pressure 125. The reaction was concentrated under vacuum and partitioned between water (40 mL) and DCM (2×100 mL) the combined organic layers were dried using sodium sulfate and concentrated under vacuum to give a tan gum. The crude product was purified by chromatography on silica gel (80 g cartridge, 0-50% EtOAc/isohexane) to afford (R)-1-(4-fluorophenyl)-6-methyl-5-(4-((2-methyl-2H-1,2,3-triazol-4-yl)sulfonyl)-1-(3,3,3-trifluoropropyl)piperazin-2-yl)-1H-indazole (1.98 g, 3.54 mmol, 64.5%, 98.6% Purity) as a colourless glass. m/z 552.2 (M+H)⁺ (ES⁺). δH NMR (300 MHz, DMSO) δ 8.31-8.28 (m, 2H), 7.87 (s, 1H), 7.84-7.78 (m, 2H), 7.68 (s, 1H), 7.48-7.39 (m, 2H), 4.29 (s, 3H), 3.77-3.74 (m, 2H), 3.54-3.50 (m, 1H), 3.35-3.28 (m, 1H), 2.79-2.65 (m, 2H), 2.51-2.34 (m, 4H), 2.27-2.12 (m, 1H)— Indazole CH₃ obscured by DMSO. R$^t$ 2.35 min (Method 7).

Example 85: 1-(4-fluorophenyl)-6-methyl-5-(4-((2-methyl-2H-1,2,3-triazol-4-yl)sulfonyl)-1-((tetrahydrofuran-3-yl)methyl)piperazin-2-yl)-1H-indazole

TABLE 7

The example shown in the table below were prepared by similar methods to those described in Example 68.

| Example | Structure | LC-MS analysis |
|---|---|---|
| 85 | 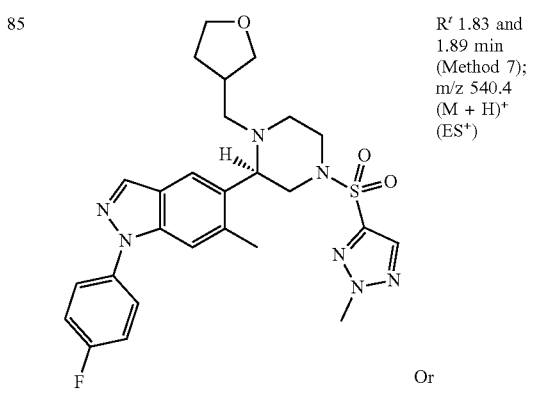 Or 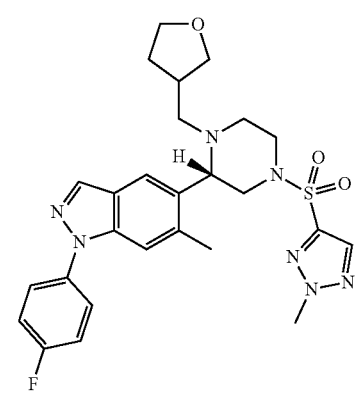 [SMILES: Cc1cc2c(cnn2-c2ccc(F)cc2)cc1[C@H]1CN(S(=O)(=O)c2cnn(C)n2)CCN1CC1CCOC1] 1-(4-fluorophenyl)-6-methyl-5-(4-((2-methyl-2H-1,2,3-triazol-4-yl)sulfonyl)-1-((tetrahydrofuran-3-yl)methyl)piperazin-2-yl)-1H-indazole | R$^t$ 1.83 and 1.89 min (Method 7); m/z 540.4 (M + H)⁺ (ES⁺) |

Example 86: 1-(4-fluorophenyl)-6-methyl-5-(4-((2-methyl-2H-1,2,3-triazol-4-yl)sulfonyl)-1-phenylpiperazin-2-yl)-1H-indazole

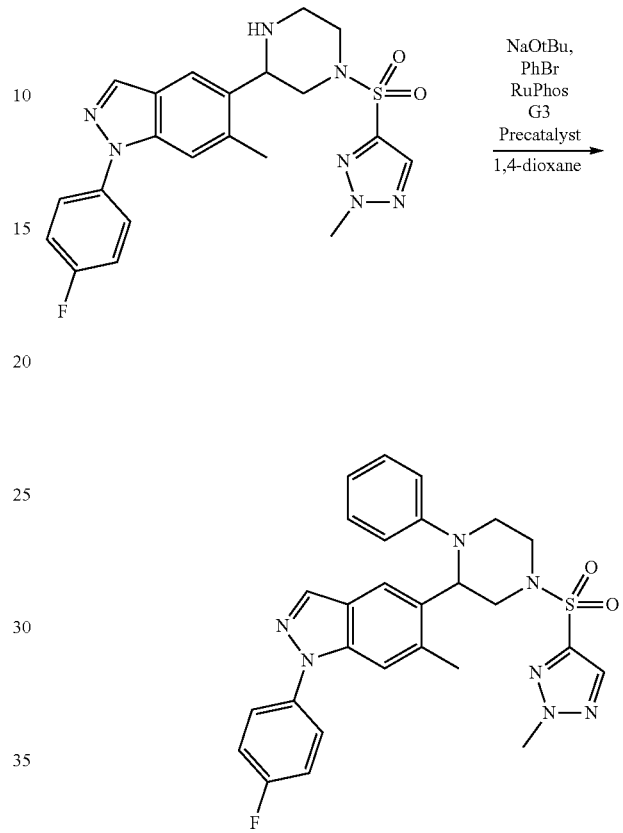

A solution of 1-(4-fluorophenyl)-6-methyl-5-(4-((2-methyl-2H-1,2,3-triazol-4-yl)sulfonyl)piperazin-2-yl)-1H-indazole (50 mg, 0.11 mmol) (prepared using similar methods to Example 1) and bromobenzene (34 mg, 23 µL, 0.22 mmol) in 1,4-dioxane (1.50 mL) was degassed with bubbling nitrogen for 10 mins. RuPhos G3 Precatalyst (9.2 mg, 11 µmol) and sodium tert-butoxide (2M in THF) (63 mg, 0.33 mL, 2 molar, 0.66 mmol) were then added and the reaction mixture stirred at 90° C. for 3 hours before being left to stand at rt overnight. After cooling to rt, the reaction mixture was quenched with MeOH (1 mL) and filtered through celite, washing with DCM (10 mL). The filtrate was then concentrated in vacuo. The crude product was purified by chromatography on silica gel (4 g cartridge, 0-100% EtOAc/isohexane) to afford 1-(4-fluorophenyl)-6-methyl-5-(4-((2-methyl-2H-1,2,3-triazol-4-yl)sulfonyl)-1-phenylpiperazin-2-yl)-1H-indazole (27 mg, 48 µmol, 44%) as a white solid; Rt 2.23 min (Method 4); m/z 532.2 (M+H)+ (ES+); δH NMR (400 MHz, DMSO) δ 8.28 (s, 1H), 8.15 (d, J=0.9 Hz, 1H), 7.78-7.69 (m, 3H), 7.59 (s, 1H), 7.45-7.35 (m, 2H), 7.16-7.06 (m, 2H), 6.93-6.84 (m, 2H), 6.82-6.73 (m, 1H), 4.69 (dd, J=8.8, 3.5 Hz, 1H), 4.21 (s, 3H), 3.66 (d, J=9.7 Hz, 3H), 3.25 (t, J=9.8 Hz, 1H), 3.15 (t, J=9.4 Hz, 1H), 2.81 (dd, J=12.3, 8.8 Hz, 1H), 2.58 (s, 3H).

Example 87: 1-(4-fluorophenyl)-5-(1-isobutyl-6-methyl-4-((2-methyl-2H-1,2,3-triazol-4-yl)sulfonyl)piperazin-2-yl)-6-methyl-1H-indazole Intermediate I: 1-(4-fluorophenyl)-6-methyl-5-(6-methylpyrazin-2-yl)-1H-indazole

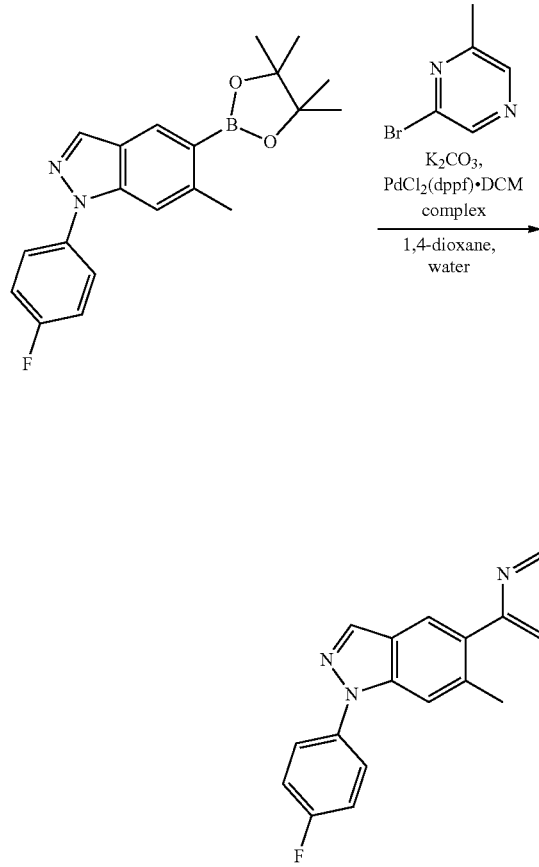

A solution of 1-(4-fluorophenyl)-6-methyl-5-(4,4,5,5-tetramethyl-1,3,2-dioxaborolan-2-yl)-1H-indazole (1.00 g, 2.84 mmol), 2-bromo-6-methylpyrazine (589 mg, 3.41 mmol) and potassium carbonate (589 mg, 4.26 mmol) in 1,4-dioxane (24.0 mL) and water (6.00 mL) was degassed (bubbling nitrogen) for 20 mins. PdCl$_2$(dppf)·DCM complex (232 mg, 284 μmol) was then added and the reaction mixture stirred at 90° C. for 4 hours. After cooling to rt, the reaction mixture was partitioned between water (10 mL), brine (10 mL) and EtOAc (20 mL). The layers were separated, and the aqueous layer extracted with EtOAc (3×10 mL). Combined organic extracts were dried over MgSO$_4$ and concentrated in vacuo. The crude product was purified by chromatography on silica gel (24 g cartridge, 0-50% EtOAc/isohexane) to afford 1-(4-fluorophenyl)-6-methyl-5-(6-methylpyrazin-2-yl)-1H-indazole (850 mg, 2.3 mmol, 82%) as a white solid; Rt 1.96 min (Method 4); m/z 319.2 (M+H)+ (ES+). δH NMR (400 MHz, DMSO) δ 8.66 (s, 1H), 8.55 (s, 1H), 8.39 (d, J=0.9 Hz, 1H), 7.96 (s, 1H), 7.89-7.80 (m, 2H), 7.76 (m, 1H), 7.51-7.40 (m, 2H), 2.57 (s, 3H), 2.47 (d, J=0.9 Hz, 3H).

Example 87: 1-(4-fluorophenyl)-5-(1-isobutyl-6-methyl-4-((2-methyl-2H-1,2,3-triazol-4-yl)sulfonyl)piperazin-2-yl)-6-methyl-1H-indazole

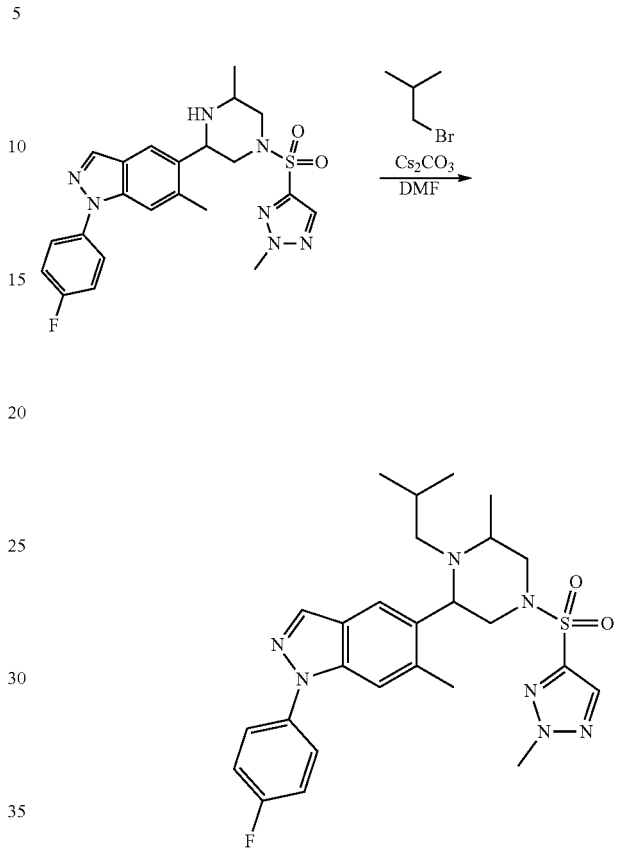

To a solution of 1-(4-fluorophenyl)-6-methyl-5-(6-methyl-4-((2-methyl-2H-1,2,3-triazol-4-yl)sulfonyl)piperazin-2-yl)-1H-indazole (50 mg, 0.11 mmol) (prepared using a similar method to those described for Example 1) in DMF (1 mL) were added cesium carbonate (0.28 g, 0.85 mmol) and 1-bromo-2-methylpropane (567 mg, 450 μL, 4.14 mmol). The reaction mixture was stirred at 90° C. for 6 days. After cooling to rt, the reaction mixture was quenched with water (3 mL) and DCM (3 mL) and the layers separated. The aqueous was extracted with further DCM (3×3 mL). Combined organic extracts were washed with half-saturated brine (2×5 mL), dried over MgSO$_4$, and concentrated in vacuo. The crude product was purified by chromatography on silica gel (4 g cartridge, 0-100% EtOAc/isohexane) to afford 1-(4-fluorophenyl)-5-(1-isobutyl-6-methyl-4-((2-methyl-2H-1,2,3-triazol-4-yl)sulfonyl)piperazin-2-yl)-6-methyl-1H-indazole (10 mg, 18 μmol, 17%) as a white solid; Rt 1.79 min (Method 4); m/z 526.2 (M+H)+ (ES+). δH NMR (400 MHz, DMSO) δ 8.30 (s, 1H), 8.28 (d, J=0.9 Hz, 1H), 7.84 (s, 1H), 7.81-7.75 (m, 2H), 7.64 (s, 1H), 7.46-7.38 (m, 2H), 4.29 (s, 3H), 3.97 (dd, J=10.7, 3.2 Hz, 1H), 3.59 (d, J=11.6 Hz, 1H), 3.42 (d, J=12.2 Hz, 1H), 2.82 (m, 1H), 2.62 (t, J=11.3 Hz, 1H), 2.44 (d, J=11.1 Hz, 1H), 1.30 (dt, J=13.4, 6.6 Hz, 1H), 1.13 (d, J=6.2 Hz, 3H), 0.54 (dd, J=6.7, 4.6 Hz, δH).

Examples 88-89

TABLE 8

The examples shown in the table below were prepared by similar methods to those described in Example 87 and Example 1.

| Example | Structure | LC-MS analysis |
|---|---|---|
| 88 | 1-(4-fluorophenyl)-5-(1-isobutyl-3-methyl-4-((2-methyl-2H-1,2,3-triazol-4-yl)sulfonyl)piperazin-2-yl)-6-methyl-1H-indazole | $R^t$ 2.23 min and 2.25 min (Method 9); m/z 526.2 (M + H)$^+$ (ES$^+$) |
| 89 | 1-(4-fluorophenyl)-5-(1-isobutyl-5-methyl-4-((2-methyl-2H-1,2,3-triazol-4-yl)sulfonyl)piperazin-2-yl)-6-methyl-1H-indazole | $R^t$ 2.55 min (Method 9); m/z 526.2 (M + H)$^+$ (ES$^+$) |

Example 92: 1-(4-fluorophenyl)-5-(1-isobutyl-4-((1-methyl-1H-1,2,4-triazol-3-yl)sulfonyl)piperazin-2-yl)-6-methyl-1H-indazole

Intermediate J: 3-((4-methoxybenzyl)thio)-1-methyl-1H-1,2,4-triazole

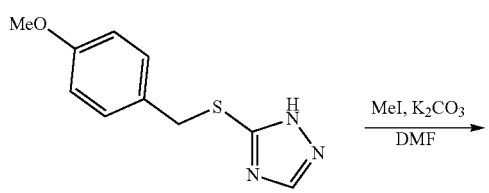

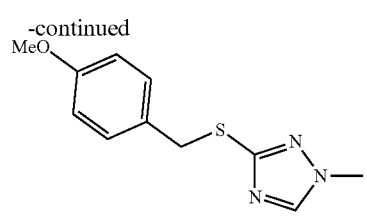

To a stirred solution of 5-((4-methoxybenzyl)thio)-1H-1,2,4-triazole (2.46 g, 11.1 mmol) and potassium carbonate (4.61 g, 33.4 mmol) in dry DMF (11.1 mL) under a nitrogen atmosphere at 0° C. was added iodomethane (1.97 g, 869 μL, 13.9 mmol) dropwise. The reaction mixture was stirred 20° C. for 48 hours. The reaction mixture was diluted with EtOAc (50 mL) and transferred into a separating funnel. The organic layer was extracted. The aqueous layer was washed with EtOAc (1×100 mL). The combined organic layers were collected, washed with brine (100 ml), dried over magnesium sulfate, filtered and adsorbed onto silica in vacuo. The crude product was purified by chromatography on silica gel (40 g cartridge, 0-100% EtOAc/isohexane) to afford 3-((4-methoxybenzyl)thio)-1-methyl-1H-1,2,4-triazole (0.80 g, 3.4 mmol, 31%) as a clear yellow oil; Rt 1.38 min (Method 7); m/z 236.2 (M+H)+ (ES+). δH (CDCl$_3$, 400 MHz) δ 7.96 (s, 1H), 7.54-7.25 (m, 2H), 6.86-6.65 (m, 2H), 4.31 (s, 2H), 3.86 (d, J=1.0 Hz, 3H), 3.78 (d, J=0.8 Hz, 3H).

Example 92: 1-(4-fluorophenyl)-5-(1-isobutyl-4-((1-methyl-1H-1,2,4-triazol-3-yl)sulfonyl)piperazin-2-yl)-6-methyl-1H-indazole

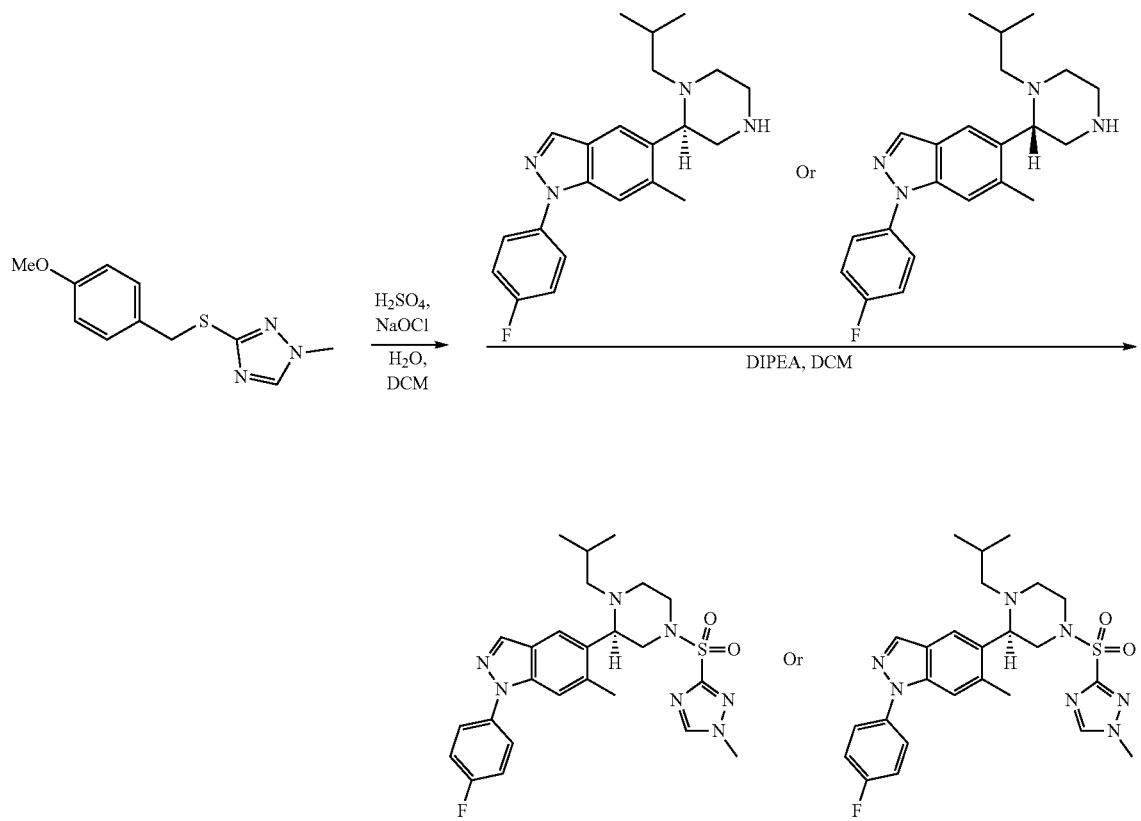

To a stirred solution of 3-((4-methoxybenzyl)thio)-1-methyl-1H-1,2,4-triazole Intermediate J (0.28 g, 1.2 mmol) in DCM (4.00 mL) and water (1.00 mL) was added Cl$_2$ gas, generated by the dropwise addition of 2M H$_2$SO$_4$ (2.3 g, 1.3 mL, 24 mmol) into sodium hypochlorite (15 g, 12 mL, 12% Wt, 24 mmol). The solution of 3-((4-methoxybenzyl)thio)-1-methyl-1H-1,2,4-triazole (0.28 g, 1.2 mmol) was contacted with Cl$_2$ for 2 min at 20° C., until the reaction mixture took on a green colour. The reaction mixture was then stirred for an additional 5 min prior to a further charge of distilled water (5 mL) being added and the was reaction transferred to a phase separator. The organic layer was used without further purification or analysis.

To a stirred solution of 1-(4-fluorophenyl)-5-(1-isobutylpiperazin-2-yl)-6-methyl-1H-indazole (20.0 mg, 54.6 µmol) and DIPEA (742 mg, 1.00 mL, 5.74 mmol) in dry DCM (1.00 mL) under a nitrogen atmosphere at 20° C. was added 1-methyl-1H-1,2,4-triazole-3-sulfonyl chloride as a solution in DCM (39.6 mg, 6.00 mL, 218 µmol). The reaction mixture was stirred at 20° C. for 3 hours. The reaction mixture was diluted with sat. NH$_4$Cl (3 mL) and transferred into a phase separator. The organic layer was washed with NaHCO$_3$ (1×2 mL). The organic layers were collected and concentrated in vacuo. The material was dissolved in 2 mL DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH C18 ODB prep column, 130 Å, 5 µm, 30 mm×100 mm, flow rate 40 mL min-1 eluting with a 0.1% formic acid in water-MeCN gradient over 8.5 mins using UV across all wavelengths with PDA as well as a QDA and ELS detector. At-column dilution pump gives 2 mL min-1 methanol over the entire method, which is included in the following MeCN percentages. Gradient information: 0.0-0.5 min, 42.5% MeCN; 0.5-5.5 min, ramped from 42.5% MeCN to 72.5% MeCN; 5.5-5.6 min, ramped from 72.5% MeCN to 100% MeCN; 5.6-8.5 min, held at 100% MeCN. The clean fractions were evaporated in a Genevac and azeotropically dried with acetonitrile. to afford 1-(4-fluorophenyl)-5-(1-isobutyl-4-((1-methyl-1H-1,2,4-triazol-3-yl)sulfonyl)piperazin-2-yl)-6-methyl-1H-indazole Example 92 (1.80 mg, 3.3 µmol, 6.1%); Rt 1.80 min (Method 7); m/z 512.4 (M+H)+ (ES+). δH (MeOD, 400 MHz) δ 8.59 (s, 1H), 8.17 (s, 1H), 7.94 (s, 1H), 7.82-7.69 (m, 2H), 7.57 (s, 1H), 7.36 (t, J=8.7 Hz, 2H), 4.04 (s, 3H), 3.90 (d, J=12.1 Hz, 1H), 3.73-3.57 (m, 2H), 3.30 (d, J=11.9 Hz, 1H), 3.08 (td, J=12.1, 2.8 Hz, 1H), 2.79 (t, J=11.1 Hz, 1H), 2.56 (s, 3H), 2.35-2.22 (m, 1H), 2.13 (t, J=12.2 Hz, 1H), 1.92-1.80 (m, 2H), 0.88 (d, J=6.3 Hz, 3H), 0.72 (d, J=6.3 Hz, 3H).

Example 93: 5-(4-((2,5-dimethyl-2H-1,2,3-triazol-4-yl)sulfonyl)-1-isobutylpiperazin-2-yl)-1-(4-fluorophenyl)-6-methyl-1H-indazole

Intermediate K: 4-(benzylthio)-2,5-dimethyl-2H-1,2,3-triazole

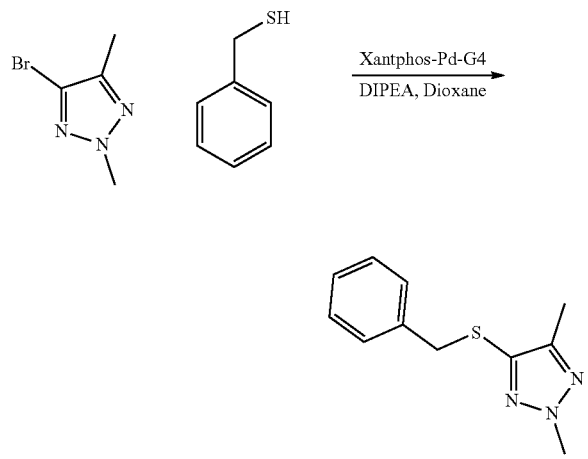

A solution of 4-bromo-2,5-dimethyl-2H-1,2,3-triazole (0.20 g, 1.1 mmol), phenylmethanethiol (0.28 g, 0.27 mL, 2.3 mmol) and DIPEA (0.29 g, 0.40 mL, 2.3 mmol) in 1,4-dioxane (2.3 mL) was prepared and added to xantphos-Pd-G4 (0.10 g, 0.11 mmol) in a vial that was sealed and sparged for 5 min prior to being heated to 90° C. and stirred for 16 hours. The reaction mixture was then adsorbed onto silica gel. The crude product was purified by chromatography on silica gel (12 g cartridge, 0-100% EtOAc/isohexane) to afford 4-(benzylthio)-2,5-dimethyl-2H-1,2,3-triazole Intermediate K (43.0 mg, 196 µmol, 17%) as a clear orange oil; Rt 1.76 min (Method 7); m/z 220.1 (M+H)$^+$ (ES$^+$).

Intermediate L: 2,5-dimethyl-2H-1,2,3-triazole-4-sulfonyl chloride

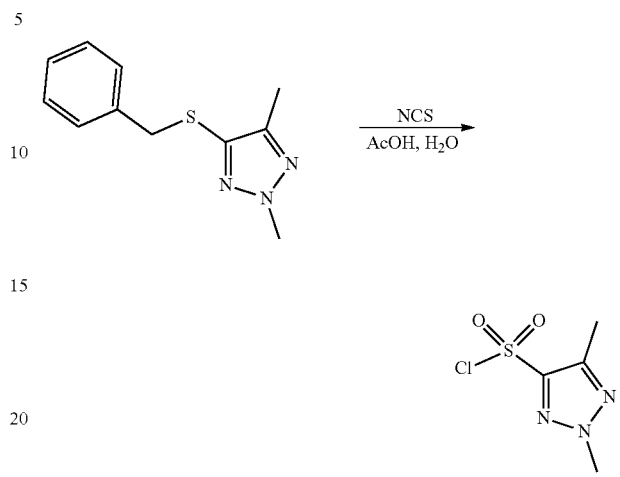

To a stirred solution of 4-(benzylthio)-2,5-dimethyl-2H-1,2,3-triazole (43.0 mg, 196 µmol) in AcOH (1.00 mL) and water (500 µL) under a nitrogen atmosphere at 20° C. was added N-chlorosuccinamide (NCS) (105 mg, 784 µmol). The reaction mixture was then stirred for 1 hour at room temperature. The reaction mixture was diluted with distilled water (2 mL) and transferred into a phase separator. The solution was washed with DCM (1×2 mL). The DCM layer was then washed with water (2 mL) and then NaHCO$_3$ (sat aq, 2 mL) to afford 2,5-dimethyl-2H-1,2,3-triazole-4-sulfonyl chloride Intermediate L as a solution in DCM. A sample of the organic layer was then quenched with a 10 vol % morpholine/methanol solution and analysed by LCMS; Rt 1.14 min (Method 7); m/z 247.1 (M+H)+ (ES+) (morpholine adduct).

TABLE 9

The example shown in the table below was prepared by similar methods to those described in Example 36 using Intermediate L.

| Example | Structure | LC-MS analysis |
|---|---|---|
| 93 | 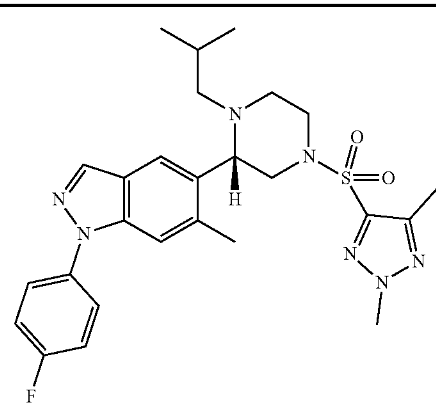 | R$^t$ 2.11 min (Method 7); m/z 526.4 (M + H)$^+$ (ES$^+$) |

Or

TABLE 9-continued

The example shown in the table below was prepared by similar methods to those described in Example 36 using Intermediate L.

| Example | Structure | LC-MS analysis |
|---|---|---|
| | 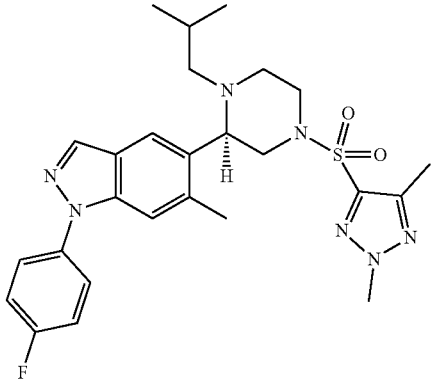 [SMILES: Cc1cc2c(cnn2-c2ccc(F)cc2)cc1[C@@H]1CN(S(=O)(=O)c2nn(C)nc2C)CCN1CC(C)C]<br>5-(4-((2,5-dimethyl-2H-1,2,3-triazol-4-yl)sulfonyl)-1-isobutylpiperazin-2-yl)-1-(4-fluorophenyl)-6-methyl-1H-indazole | |

Example 94: 1-(4-fluorophenyl)-5-(1-isobutyl-4-((4-methyl-4H-1,2,4-triazol-3-yl)sulfonyl)piperazin-2-yl)-6-methyl-1H-indazole

TABLE 10

The example shown in the table below was prepared by similar methods to those described in Example 93

| Example | Structure | LC-MS analysis |
|---|---|---|
| 94 | 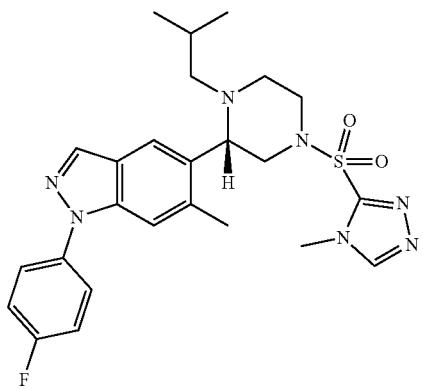 [SMILES: Cc1cc2c(cnn2-c2ccc(F)cc2)cc1[C@@H]1CN(S(=O)(=O)c2nncn2C)CCN1CC(C)C] | $R^t$ 1.77 min (Method 7); m/z 512.4 $(M + H)^+$ $(ES^+)$ |

Or

TABLE 10-continued

The example shown in the table below was prepared by similar methods to those described in Example 93

| Example | Structure | LC-MS analysis |
|---|---|---|
| | 1-(4-fluorophenyl)-5-(1-isobutyl-4-((4-methyl-4H-1,2,4-triazol-3-yl)sulfonyl)piperazin-2-yl)-6-methyl-1H-indazole | |

Example 95: 1-(4-fluorophenyl)-5-(1-isobutyl-4-((2-(2,2,2-trifluoroethyl)-2H-1,2,3-triazol-4-yl)sulfonyl)piperazin-2-yl)-6-methyl-1H-indazole Intermediate M: 4-(benzylthio)-2H-1,2,3-triazole To a stirred solution of 2H-1,2,3-triazole-4-thiol, sodium (5.00 g, 40.3 mmol) in dry DMF (30.0 mL) under a nitrogen atmosphere at 20° C. was added benzyl bromide (6.89 g, 4.79 mL, 40.3 mmol). The reaction mixture was stirred for 3 hours. The reaction mixture was quenched into ice water (500 mL) producing a slurry that was stirred overnight. Precipitate was collected under vacuum and azeotroped twice with toluene 50 mL to afford 4-(benzylthio)-2H-1,2,3-triazole Intermediate M (6.43 g, 26 mmol, 65%) as a yellow solid; Rt 1.39 min (Method 7); m/z 192.2 (M+H)+ (ES+).

Intermediate N: 4-(benzylthio)-2-(2,2,2-trifluoroethyl)-2H-1,2,3-triazole

To a stirred solution of 4-(benzylthio)-2H-1,2,3-triazole (6.40 g, 33.5 mmol) in dry DMF (66.9 mL) under a nitrogen atmosphere at 20° C. was added potassium carbonate (11.6 g, 83.7 mmol) (pulverised) and 1,1,1-trifluoro-2-iodoethane (15.8 g, 7.36 mL, 75.3 mmol). The reaction mixture was stirred for 18 hours, and then at 50° C. for a further 24 hours. The reaction mixture was diluted with EtOAc (100 mL) and transferred into a separating funnel. The organic layer was washed with half saturated brine (100 mL) and the brine layer extracted with EtOAc (2×100 mL) The combined organic layers were collected, dried over magnesium sulfate, filtered and concentrated in vacuo. The crude product was purified by chromatography on silica gel (120 g cartridge, 10-100% EtOAc/isohexane) to afford 3 main bands. The first band was concentrated in vacuo to afford 4-(benzylthio)-2-(2,2,2-trifluoroethyl)-2H-1,2,3-triazole (2.10 g, 6.5 mmol, 20%) as an off-white solid; Rt 0.94 min (Method 9); m/z 274.0 (M+H)+ (ES+).

TABLE 11

The example shown in the table below was prepared by similar methods to those described in Example 93 using Intermediate N

| Example | Structure | LC-MS analysis |
|---|---|---|
| 95 | 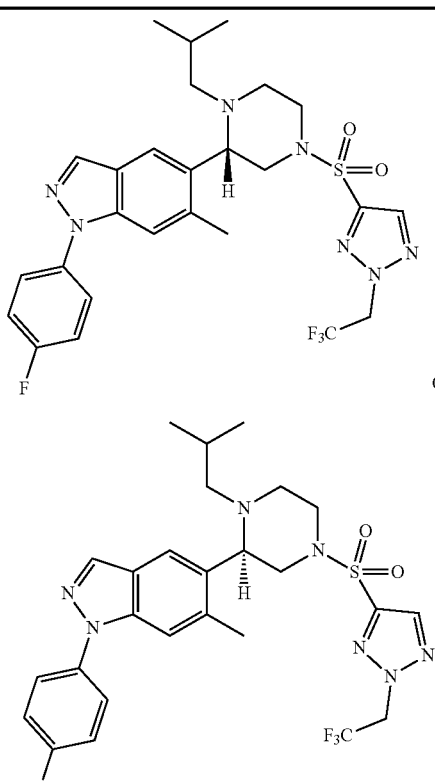 <br>1-(4-fluorophenyl)-5-(1-isobutyl-4-((2-(2,2,2-trifluoroethyl)-2H-1,2,3-triazol-4-yl)sulfonyl)piperazin-2-yl)-6-methyl-1H-indazole | $R^t$ 2.34 min (Method 7); m/z 580.4 (M + H)$^+$ (ES$^+$) |

Examples 96-117

TABLE 12

The examples shown in the table below were prepared by similar methods to those described in Example 36

| Example | Structure | LC-MS analysis |
|---|---|---|
| 96 | 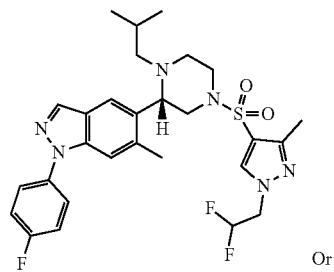 [SMILES: Cc1cc2c(cnn2-c2ccc(F)cc2)cc1[C@H]1CN(S(=O)(=O)c2cn(CC(F)F)nc2C)CCN1CC(C)C] | $R^t$ 2.03 min (Method 7); m/z 575.4 (M + H)$^+$ (ES$^+$) |

TABLE 12-continued

The examples shown in the table below were prepared by similar methods to those described in Example 36

| Example | Structure | LC-MS analysis |
|---------|-----------|----------------|
|  | 5-(4-((1-(2,2-difluoroethyl)-3-methyl-1H-pyrazol-4-yl)sulfonyl)-1-isobutylpiperazin-2-yl)-1-(4-fluorophenyl)-6-methyl-1H-indazole |  |
| 97 | Or<br><br>1-(4-fluorophenyl)-5-(1-isobutyl-4-(pyridin-3-ylsulfonyl)piperazin-2-yl)-6-methyl-1H-indazole | R$^t$ 2.02 min (Method 7); m/z 508.4 (M + H)$^+$ (ES$^+$) |
| 98 | Or | R$^t$ 2.31 min (Method 7); m/z 532.4 (M + H)$^+$ (ES$^+$) |

TABLE 12-continued

The examples shown in the table below were prepared by similar methods to those described in Example 36

| Example | Structure | LC-MS analysis |
|---|---|---|
| | 4-((3-(1-(4-fluorophenyl)-6-methyl-1H-indazol-5-yl)-4-isobutylpiperazin-1-yl)sulfonyl)benzonitrile | |
| 99 | Or | $R^t$ 1.98 min (Method 9); m/z 528.2 (M + H)$^+$ (ES$^+$) |
| | 4-((3-(1-(4-fluorophenyl)-6-methyl-1H-indazol-5-yl)-4-isobutylpiperazin-1-yl)sulfonyl)-2-methylthiazole | |
| 100 | Or | $R^t$ 2.19 min (Method 7); m/z 526.3 (M + H)$^+$ (ES$^+$) |

TABLE 12-continued

The examples shown in the table below were prepared by similar methods to those described in Example 36

| Example | Structure | LC-MS analysis |
|---------|-----------|----------------|

5-(4-((1,4-dimethyl-1H-1,2,3-triazol-5-yl)sulfonyl)-1-isobutylpiperazin-2-yl)-1-(4-fluorophenyl)-6-methyl-1H-indazole

| 101 | | $R^t$ 1.85 min (Method 9); m/z 512.2 (M + H)⁺ (ES⁺) |

Or 1-(4-fluorophenyl)-5-(1-isobutyl-4-((1-methyl-1H-1,2,3-triazol-4-yl)sulfonyl)piperazin-2-yl)-6-methyl-1H-indazole

| 102 | | $R^t$ 2.45 min (Method 9); m/z 576.2 (M + H)⁺ (ES⁺) |

Or

TABLE 12-continued

The examples shown in the table below were prepared by similar methods to those described in Example 36

| Example | Structure | LC-MS analysis |
|---------|-----------|----------------|
| | 1-(4-fluorophenyl)-5-(1-isobutyl-4-((6-(trifluoromethyl)pyridin-3-yl)sulfonyl)piperazin-2-yl)-6-methyl-1H-indazole | |
| 103 | 1-(4-fluorophenyl)-5-(1-isobutyl-4-((6-methoxypyridin-3-yl)sulfonyl)piperazin-2-yl)-6-methyl-1H-indazole Or | $R^t$ 2.25 min (Method 9); m/z 538.2 (M + H)$^+$ (ES$^+$) |
| 104 | Or | $R^t$ 2.07 min (Method 9); m/z 522.2 (M + H)$^+$ (ES$^+$) |

TABLE 12-continued

The examples shown in the table below were prepared by similar methods to those described in Example 36

| Example | Structure | LC-MS analysis |
|---|---|---|
| | 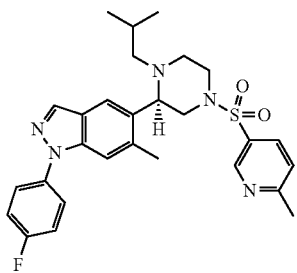 [SMILES: Cc1ccc(S(=O)(=O)N2CCN(CC(C)C)[C@H](c3cc4cnn(-c5ccc(F)cc5)c4cc3C)C2)cn1]<br>1-(4-fluorophenyl)-5-(1-isobutyl-4-((6-methylpyridin-3-yl)sulfonyl)piperazin-2-yl)-6-methyl-1H-indazole | |
| 105 | 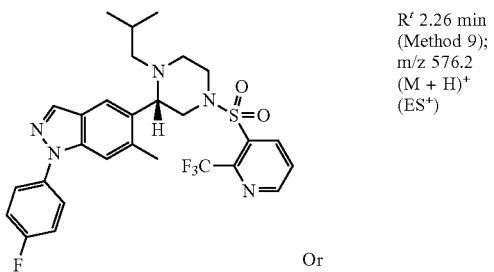    Or<br>1-(4-fluorophenyl)-5-(1-isobutyl-4-((2-(trifluoromethyl)pyridin-3-yl)sulfonyl)piperazin-2-yl)-6-methyl-1H-indazole | R$^t$ 2.26 min (Method 9); m/z 576.2 (M + H)$^+$ (ES$^+$) |
| | 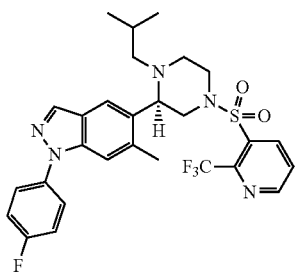 [SMILES: Cc1cc2c(cnn2-c2ccc(F)cc2)cc1[C@@H]1CN(S(=O)(=O)c2cccnc2C(F)(F)F)CCN1CC(C)C] | |
| 106 | 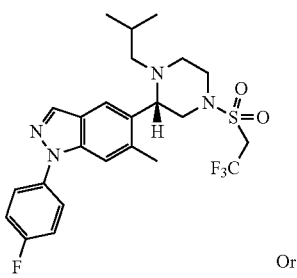 [SMILES: Cc1cc2c(cnn2-c2ccc(F)cc2)cc1[C@H]1CN(S(=O)(=O)CC(F)(F)F)CCN1CC(C)C]    Or | R$^t$ 2.22 min (Method 9); m/z 513.2 (M + H)$^+$ (ES$^+$) |

TABLE 12-continued

The examples shown in the table below were prepared by similar methods to those described in Example 36

| Example | Structure | LC-MS analysis |
|---|---|---|
| | 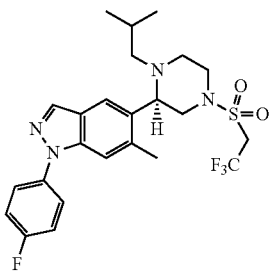 [SMILES: Cc1cc2c(cnn2-c2ccc(F)cc2)cc1[C@@H]1CN(S(=O)(=O)CC(F)(F)F)CCN1CC(C)C]<br>1-(4-fluorophenyl)-5-(1-isobutyl-4-((2,2,2-trifluoroethyl)sulfonyl)piperazin-2-yl)-6-methyl-1H-indazole | |
| 107 | 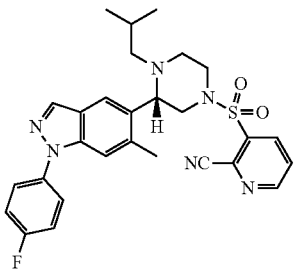<br>Or<br>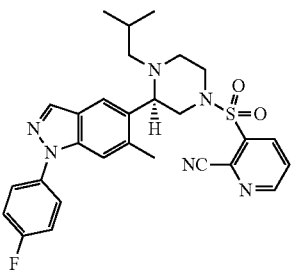 [SMILES: Cc1cc2c(cnn2-c2ccc(F)cc2)cc1[C@@H]1CN(S(=O)(=O)c2cccnc2C#N)CCN1CC(C)C]<br>3-((3-(1-(4-fluorophenyl)-6-methyl-1H-indazol-5-yl)-4-isobutylpiperazin-1-yl)sulfonyl)picolinonitrile | $R^t$ 2.22 min (Method 7); m/z 533.4 $(M + H)^+$ $(ES^+)$ |
| 108 | 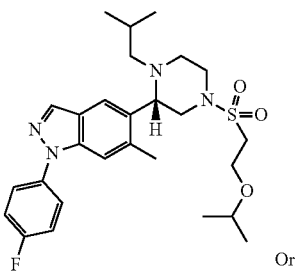 [SMILES: Cc1cc2c(cnn2-c2ccc(F)cc2)cc1[C@H]1CN(S(=O)(=O)CCOC(C)C)CCN1CC(C)C]<br>Or | $R^t$ 1.96 min (Method 7); m/z 517.5 $(M + H)^+$ $(ES^+)$ |

TABLE 12-continued

The examples shown in the table below were prepared by similar methods to those described in Example 36

| Example | Structure | LC-MS analysis |
|---------|-----------|----------------|
| | 1-(4-fluorophenyl)-5-(1-isobutyl-4-((2-isopropoxyethyl)sulfonyl)piperazin-2-yl)-6-methyl-1H-indazole | |
| 109 | 2-((3-(1-(4-fluorophenyl)-6-methyl-1H-indazol-5-yl)-4-isobutylpiperazin-1-yl)sulfonyl)thiazole Or | R$^t$ 2.30 min (Method 9); m/z 514.1 (M + H)$^+$ (ES$^+$) |
| 110 | Or | R$^t$ 2.12 min (Method 7); m/z 579.4 (M + H)$^+$ (ES$^+$) |

TABLE 12-continued

The examples shown in the table below were prepared by similar methods to those described in Example 36

| Example | Structure | LC-MS analysis |
|---|---|---|
| | 1-(4-fluorophenyl)-5-(1-isobutyl-4-((1-(2,2,2-trifluoroethyl)-1H-pyrazol-4-yl)sulfonyl)piperazin-2-yl)-6-methyl-1H-indazole | |
| 111 | 1-(4-fluorophenyl)-5-(1-isobutyl-4-(oxetan-3-ylsulfonyl)piperazin-2-yl)-6-methyl-1H-indazole Or | $R^t$ 1.74 min (Method 9); m/z 487.2 (M + H)$^+$ (ES$^+$) |
| 112 | Or | $R^t$ 2.01 min (Method 9); m/z 522.2 (M + H)$^+$ (ES$^+$) |

TABLE 12-continued

The examples shown in the table below were prepared by similar methods to those described in Example 36

| Example | Structure | LC-MS analysis |
|---|---|---|
| | 1-(4-fluorophenyl)-5-(1-isobutyl-4-((4-methylpyridin-3-yl)sulfonyl)piperazin-2-yl)-6-methyl-1H-indazole | |
| 114 | 4-(((3-(1-(4-fluorophenyl)-6-methyl-1H-indazol-5-yl)-4-isobutylpiperazin-1-yl)sulfonyl)methyl)benzonitrile Or | $R^t$ 1.99 min (Method 7); m/z 546.4 (M + H)$^+$ (ES$^+$) |
| 115 | Or | $R^t$ 1.89 min (Method 7); m/z 508.4 (M + H)$^+$ (ES$^+$) |

TABLE 12-continued
The examples shown in the table below were prepared by similar methods to those described in Example 36
| Example | Structure | LC-MS analysis |
|---|---|---|
| | 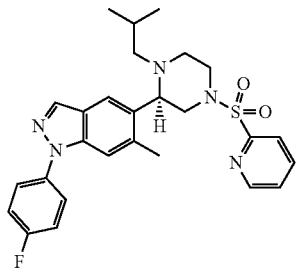 [SMILES: Cc1cc2c(cnn2-c2ccc(F)cc2)cc1[C@@H]1CN(S(=O)(=O)c2ccccn2)CCN1CC(C)C]<br>1-(4-fluorophenyl)-5-(1-isobutyl-4-(pyridin-2-ylsulfonyl)piperazin-2-yl)-6-methyl-1H-indazole | |
| 116 | 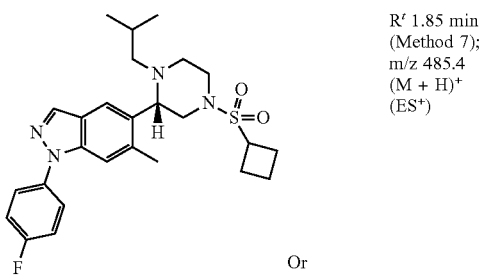<br>Or<br>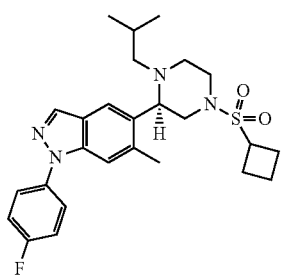 [SMILES: Cc1cc2c(cnn2-c2ccc(F)cc2)cc1[C@@H]1CN(S(=O)(=O)C2CCC2)CCN1CC(C)C]<br>5-(4-(cyclobutylsulfonyl)-1-isobutylpiperazin-2-yl)-1-(4-fluorophenyl)-6-methyl-1H-indazole | $R^t$ 1.85 min (Method 7); m/z 485.4 (M + H)$^+$ (ES$^+$) |

TABLE 12-continued

The examples shown in the table below were prepared by similar methods to those described in Example 36

| Example | Structure | LC-MS analysis |
|---|---|---|
| 117 | 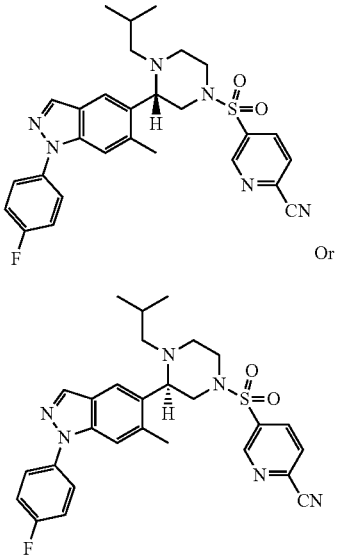<br><br>Or<br><br>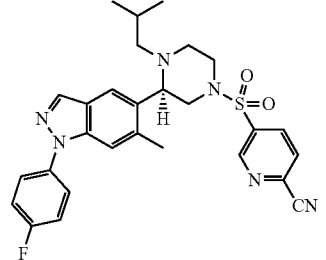 [SMILES: Cc1cc2c(cnn2-c2ccc(F)cc2)cc1[C@@H]1CN(S(=O)(=O)c2ccc(C#N)nc2)CCN1CC(C)C]<br><br>5-((3-(1-(4-fluorophenyl)-6-methyl-1H-indazol-5-yl)-4-isobutylpiperazin-1-yl)sulfonyl)picolinonitrile | R$^t$ 2.24 min (Method 9); m/z 533.2 (M + H)$^+$ (ES$^+$) |

Examples 118-125

TABLE 13

The examples shown in the table below were prepared by similar methods to those described in Example 68

| Example | Structure | LC-MS analysis |
|---|---|---|
| 118 | 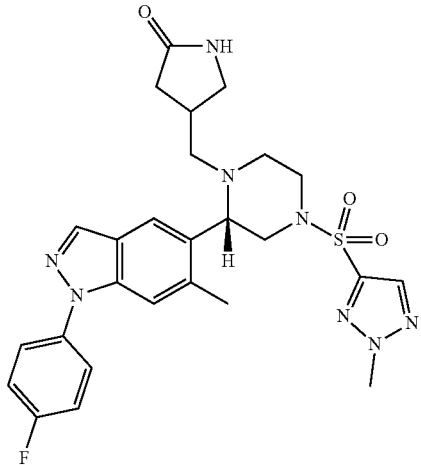<br><br>Or | R$^t$ 1.69 min (Method 9); m/z 553.2 (M + H)$^+$ (ES$^+$) |

TABLE 13-continued

The examples shown in the table below were prepared by similar methods to those described in Example 68

| Example | Structure | LC-MS analysis |
|---|---|---|
| | 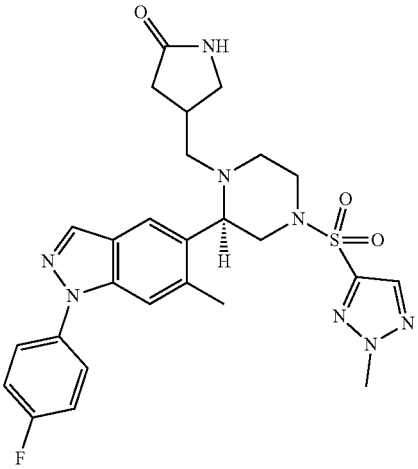 [SMILES: Cc1cc2c(cnn2-c2ccc(F)cc2)cc1[C@@H]1CN(S(=O)(=O)c2cnn(C)n2)CCN1CC1CNC(=O)C1]  4-((2-(1-(4-fluorophenyl)-6-methyl-1H-indazol-5-yl)-4-((2-methyl-2H-1,2,3-triazol-4-yl)sulfonyl)piperazin-1-yl)methyl)pyrrolidin-2-one | |
| 119 | 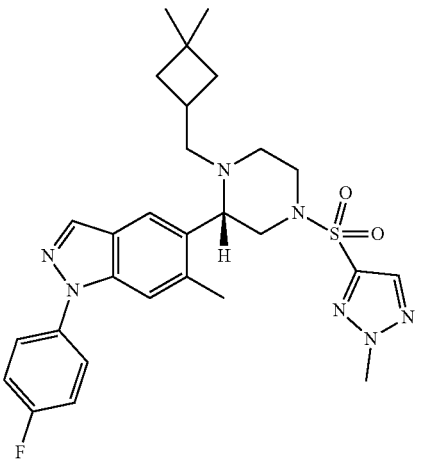  Or  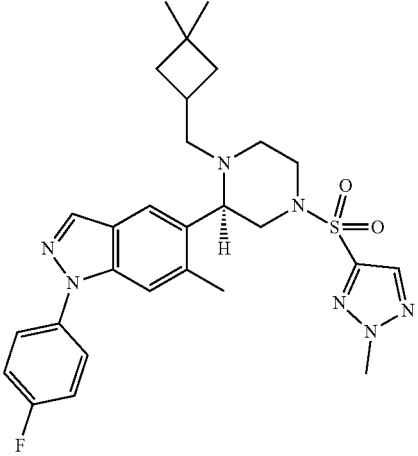 [SMILES: Cc1cc2c(cnn2-c2ccc(F)cc2)cc1[C@@H]1CN(S(=O)(=O)c2cnn(C)n2)CCN1CC1CC(C)(C)C1]  5-(1-((3,3-dimethylcyclobutyl)methyl)-4-((2-methyl-2H-1,2,3-triazol-4-yl)sulfonyl)piperazin-2-yl)-1-(4-fluorophenyl)-6-methyl-1H-indazole | $R^t$ 2.03 min (Method 9); m/z 552.2 (M + H)$^+$ (ES$^+$) |

TABLE 13-continued
The examples shown in the table below were prepared by similar methods to those described in Example 68
| Example | Structure | LC-MS analysis |
|---------|-----------|----------------|
| 120 | 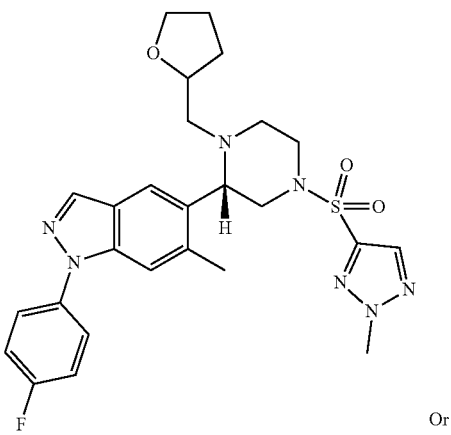 [SMILES: Cc1cc2c(cnn2-c2ccc(F)cc2)cc1[C@H]1CN(S(=O)(=O)c2cnn(C)n2)CCN1CC1CCCO1] | R$^t$ 1.76 and 1.86 min (Method 9); m/z 540.2 (M + H)$^+$ (ES$^+$) |
| | 1-(4-fluorophenyl)-6-methyl-5-(4-((2-methyl-2H-1,2,3-triazol-4-yl)sulfonyl)-1-((tetrahydrofuran-2-yl)methyl)piperazin-2-yl)-1H-indazole | |
| 121 | 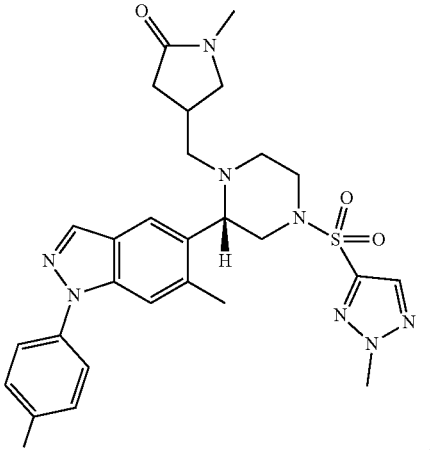 | R$^t$ 1.76 min (Method 7); m/z 567.4 (M + H)$^+$ (ES$^+$) |

TABLE 13-continued

The examples shown in the table below were prepared by similar methods to those described in Example 68

| Example | Structure | LC-MS analysis |
|---|---|---|
| | 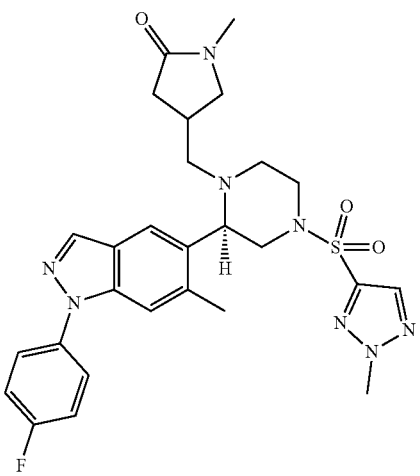 [SMILES: Cc1cc2c(cnn2-c2ccc(F)cc2)cc1[C@@H]1CN(S(=O)(=O)c2cnn(C)n2)CCN1CC1CC(=O)N(C)C1]<br>4-((2-(1-(4-fluorophenyl)-6-methyl-1H-indazol-5-yl)-4-((2-methyl-2H-1,2,3-triazol-4-yl)sulfonyl)piperazin-1-yl)methyl)-1-methylpyrrolidin-2-one | |
| 122 | 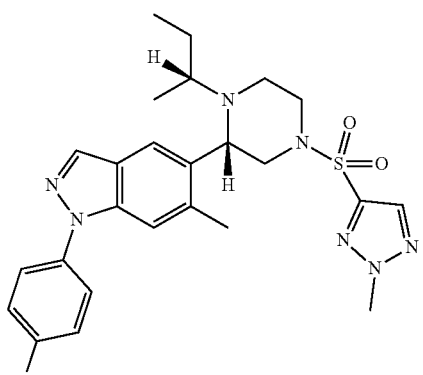<br>Or<br>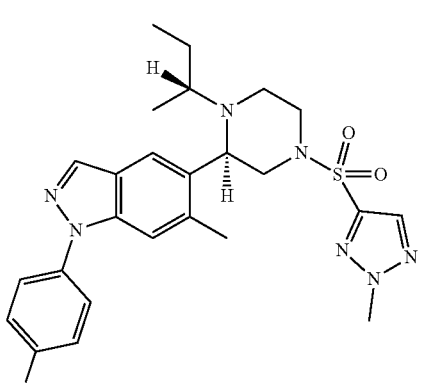<br>5-(1-(sec-butyl)-4-((2-methyl-2H-1,2,3-triazol-4-yl)sulfonyl)piperazin-2-yl)-1-(4-fluorophenyl)-6-methyl-1H-indazole | $R^t$ 1.66 min (Method 9); m/z 512.2 (M + H)$^+$ (ES$^+$) |

TABLE 13-continued
The examples shown in the table below were prepared by similar methods to those described in Example 68
| Example | Structure | LC-MS analysis |
|---------|-----------|----------------|
| 123 | 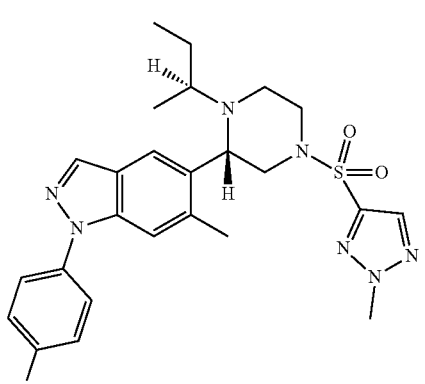 Or 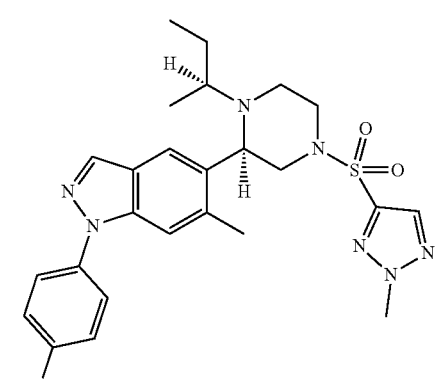<br>5-(1-(sec-butyl)-4-((2-methyl-2H-1,2,3-triazol-4-yl)sulfonyl)piperazin-2-yl)-1-(4-fluorophenyl)-6-methyl-1H-indazole | R$^t$ 1.81 min (Method 9); m/z 512.2 (M + H)$^+$ (ES$^+$) |
| 124 | 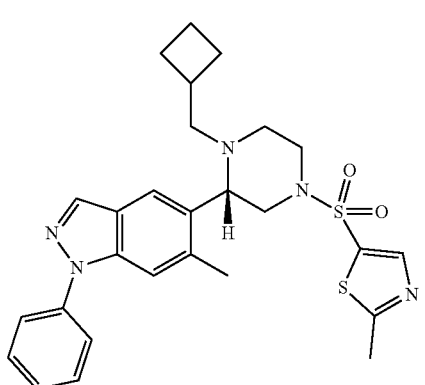 Or | R$^t$ 2.26 and 2.29 min (Method 7 m/z 579.5 (M + H)$^+$ (ES$^+$) |

TABLE 13-continued

The examples shown in the table below were prepared by similar methods to those described in Example 68

| Example | Structure | LC-MS analysis |
|---------|-----------|----------------|
|  | 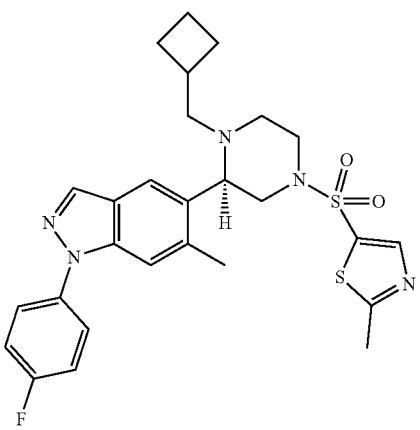 [SMILES: Cc1ncc(S(=O)(=O)N2CCN(CC3CCC3)[C@H](c3cc4cnn(-c5ccc(F)cc5)c4cc3C)C2)s1] 5-((4-(cyclobutylmethyl)-3-(1-(4-fluorophenyl)-6-methyl-1H-indazol-5-yl)piperazin-1-yl)sulfonyl)-2-methylthiazole |  |
| 125 | 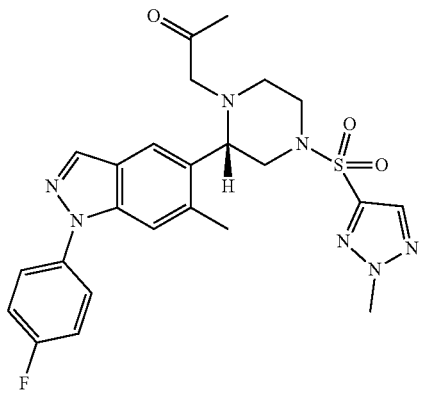 Or 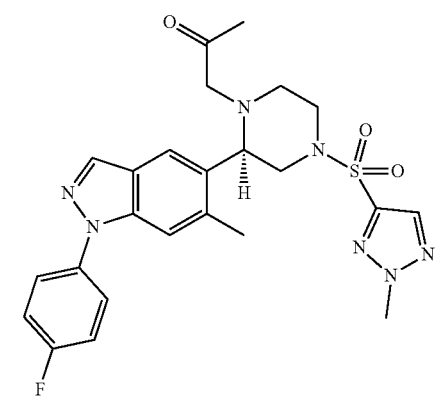 [SMILES: CC(=O)CN1CCN(S(=O)(=O)c2cnn(C)n2)C[C@H]1c1cc2cnn(-c3ccc(F)cc3)c2cc1C] 1-(2-(1-(4-fluorophenyl)-6-methyl-1H-indazol-5-yl)-4-((2-methyl-2H-1,2,3-triazol-4-yl)sulfonyl)piperazin-1-yl)propan-2-one | $R^t$ 1.95 min (Method 7); m/z 512.3 $(M + H)^+$ $(ES^+)$ |

Example 126 and 127: 1-(4-fluorophenyl)-5-(4-isobutyl-5-methyl-1-((2-methyl-2H-1,2,3-triazol-4-yl)sulfonyl)piperidin-3-yl)-6-methyl-1H-indazole 1-(4-fluorophenyl)-5-(4-isobutyl-5-methyl-1-((2-methyl-2H-1,2,3-triazol-4-yl)sulfonyl)piperidin-3-yl)-6-methyl-1H-indazole Example 87 was dissolved in MeOH (1.5 ml), filtered and was then separated by chiral SFC on a Waters prep 100 with a PDA and a QDA detectors, 40° C., 120 bar. The column was a Chiralpak 11H, 5 µM, 21 mm×250 mm; flow rate 65 mL/min of 25% MeOH (no buffer), 75% CO$_2$. The clean fractions were pooled, rinsed with methanol and concentrated to dryness using a rotary evaporator. The residues were re-dissolved in methanol transferred into final vials and evaporated on a Biotage V10. The samples were then further dried in a vacuum oven at 30° C./5 mbar over night to afford 1-(4-fluorophenyl)-5-(4-isobutyl-5-methyl-1-((2-methyl-2H-1,2,3-triazol-4-yl)sulfonyl)piperidin-3-yl)-6-methyl-1H-indazole Example 126 and 1-(4-fluorophenyl)-5-(4-isobutyl-5-methyl-1-((2-methyl-2H-1,2,3-triazol-4-yl)sulfonyl)piperidin-3-yl)-6-methyl-1H-indazole Example 127 as white solids.

TABLE 14

Examples 126 and 127

| Example | Structure | LC-MS analysis |
|---|---|---|
| 126 | 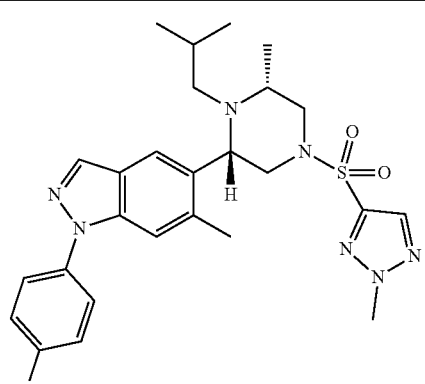 1-(4-fluorophenyl)-5-(4-isobutyl-5-methyl-1-((2-methyl-2H-1,2,3-triazol-4-yl)sulfonyl)piperidin-3-yl)-6-methyl-1H-indazole 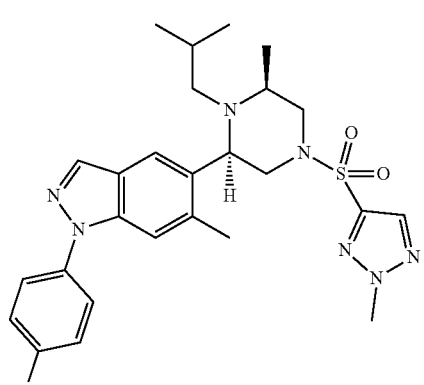 Or | $R^t$ 1.82 min (Method 9); m/z 526.2 (M + H)$^+$ (ES$^+$) |
| 127 | 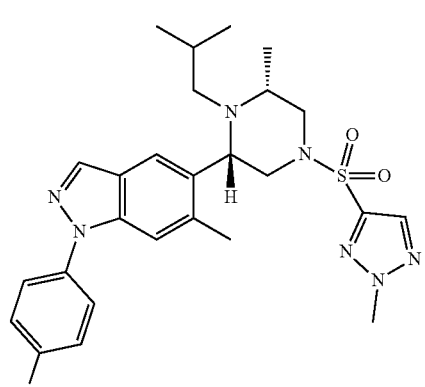 Or | $R^t$ 1.82 min (Method 9); m/z 526.2 (M + H)$^+$ (ES$^+$) |

TABLE 14-continued

Examples 126 and 127

| Example | Structure | LC-MS analysis |
|---|---|---|
| | 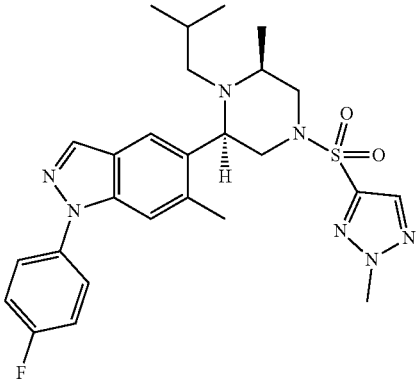 [SMILES: Cc1cc2c(cnn2-c2ccc(F)cc2)cc1[C@@H]1CN(S(=O)(=O)c2cnn(C)n2)C[C@H](C)N1CC(C)C]<br>1-(4-fluorophenyl)-5-(4-isobutyl-5-methyl-1-((2-methyl-2H-1,2,3-triazol-4-yl)sulfonyl)piperidin-3-yl)-6-methyl-1H-indazole | |

Example 128: 1-(4-fluorophenyl)-6-methyl-5-(4-((1-methyl-1H-pyrazol-4-yl)sulfonyl)-1-(3,3,3-trifluoropropyl)piperazin-2-yl)-1H-indazole Intermediate O: tert-butyl 3-(1-(4-fluorophenyl)-6-methyl-1H-indazol-5-yl)piperazine-1-carboxylate

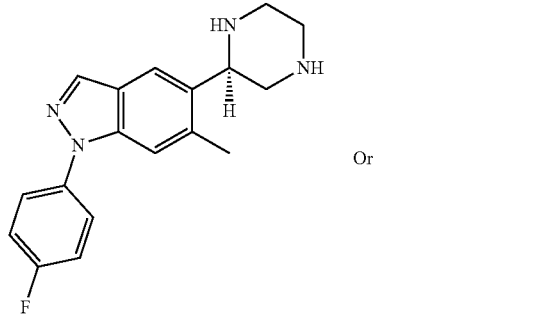

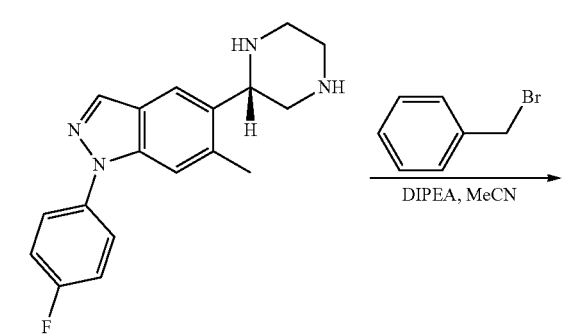

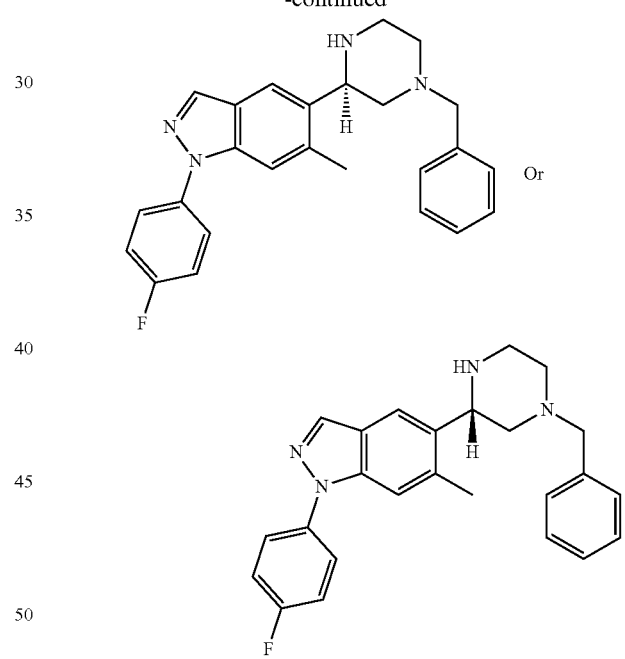

A solution of 1-(4-fluorophenyl)-6-methyl-5-(piperazin-2-yl)-1H-indazole (1.00 g, 3.22 mmol) in MeCN (10.0 mL) was cooled to 0° C. and treated with N-ethyl-N-isopropyl-propan-2-amine (833 mg, 1.12 mL, 6.44 mmol) and (bromomethyl)benzene (661 mg, 459 µL, 3.87 mmol). The reaction was warmed to RT and stirred for 48 hrs. The reaction was quenched with water (10 mL), diluted with EtOAc (2×30 mL) and the phases separated. The bulked organic extracts were dried using sodium sulfate and concentrated under vacuum.

The crude product was purified by chromatography on silica gel (24 g cartridge, 0-5% (0.7 M Ammonia/MeOH)/DCM) to afford 5-(4-benzylpiperazin-2-yl)-1-(4-fluorophenyl)-6-methyl-1H-indazole Intermediate O (850 mg, 2.12 mmol, 65.9%) as a tan foam; Rt 1.35 min (Method 7); m/z 401.5 (M+H)+ (ES+).

Intermediate P: 5-(4-benzyl-1-(3,3,3-trifluoropropyl)piperazin-2-yl)-1-(4-fluorophenyl)-6-methyl-1H-indazole

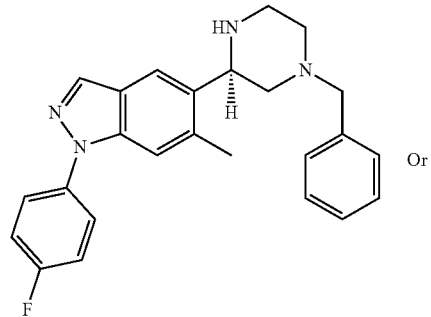

Or

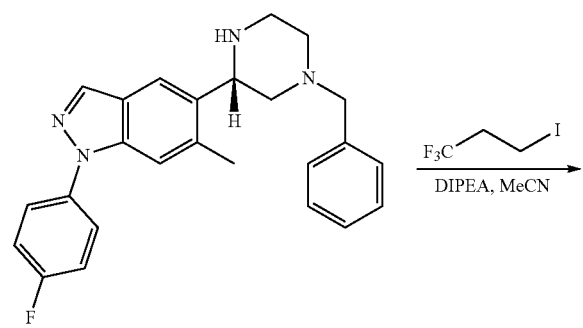

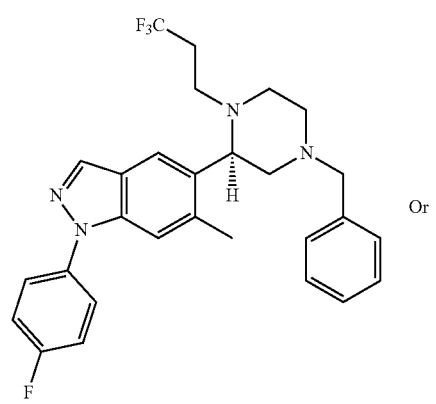

Or

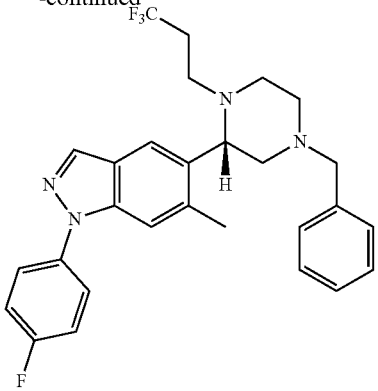

To a solution of 5-(4-benzylpiperazin-2-yl)-1-(4-fluorophenyl)-6-methyl-1H-indazole (320 mg, 799 µmol) in MeCN (2.00 mL) were added 1,1,1-trifluoro-3-iodopropane (1.79 g, 937 µL, 7.99 mmol) and N-ethyl-N-isopropylpropan-2-amine (1.03 g, 1.39 mL, 7.99 mmol). The reaction mixture was heated in the microwave at 150° C. for 2 hrs. The reaction was quenched with water (15 mL) and the organics extracted with DCM (2×15 mL) through a phase separator cartridge and concentrated in vacuo. The crude product was purified by chromatography on silica gel (24 g cartridge, 0-5% (0.7 M ammonia/MeOH)/DCM) to afford the product as a brown solid. The crude product was repurified by chromatography on silica gel (12 g cartridge, 0-50% EtOAc/isohexane containing 1% DIPEA) to afford 5-(4-benzyl-1-(3,3,3-trifluoropropyl)piperazin-2-yl)-1-(4-fluorophenyl)-6-methyl-1H-indazole (350 mg, 0.65 mmol, 81%, 92%) Intermediate P as a clear colourless gum; Rt 1.53 min (Method 7); m/z 497.4 (M+H)+ (ES+).

Intermediate Q: 1-(4-fluorophenyl)-6-methyl-5-(1-(3,3,3-trifluoropropyl)piperazin-2-yl)-1H-indazole

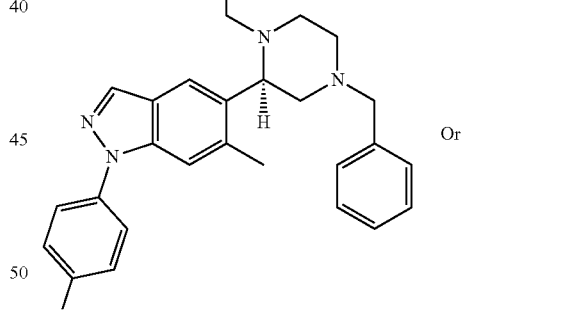

Or

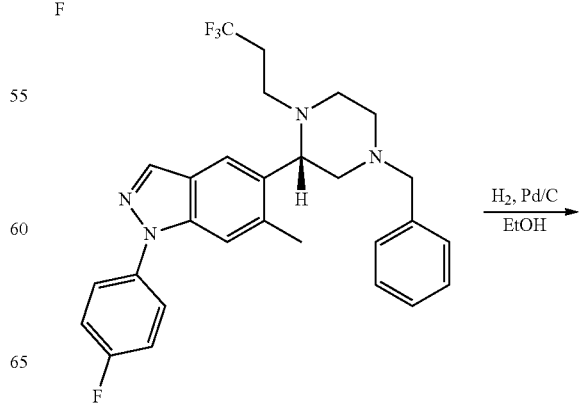

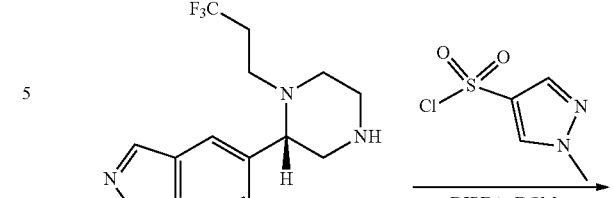

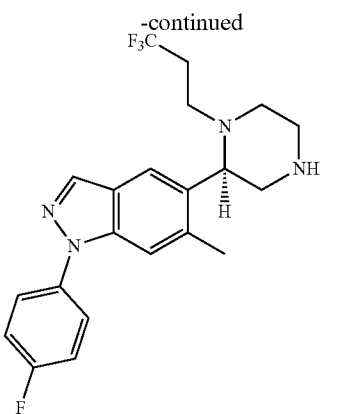

Or

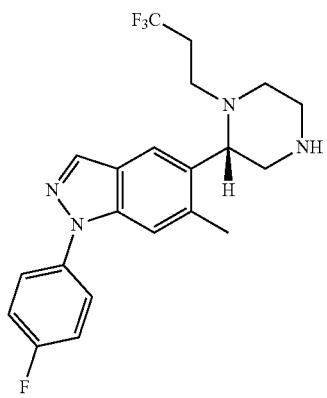

5-(4-benzyl-1-(3,3,3-trifluoropropyl)piperazin-2-yl)-1-(4-fluorophenyl)-6-methyl-1H-indazole Intermediate P (300 mg, 604 μmol) was dissolved in EtOH (5 mL) and treated with 10% palladium on carbon (12.9 mg, 121 μmol). The mixture was purged with nitrogen (×3) then hydrogen (×3) before being hydrogenated at 5 atm at 40° C. overnight. The catalyst was removed by filtration, washing with MeOH/EtOAc (1:1) (20 mL). The solvent was removed in vacuo. The crude product was purified by chromatography on silica gel (12 g cartridge, 0-100% EtOAc/isohexane containing 1% DIPEA) to afford 1-(4-fluorophenyl)-6-methyl-5-(1-(3,3,3-trifluoropropyl)piperazin-2-yl)-1H-indazole Intermediate Q (170 mg, 0.41 mmol, 68%) as a clear colourless gum; Rt 1.36 min (Method 7); m/z 407.4 (M+H)+(ES+).

Example 128: 1-(4-fluorophenyl)-6-methyl-5-(4-((1-methyl-1H-pyrazol-4-yl)sulfonyl)-1-(3,3,3-trifluoropropyl)piperazin-2-yl)-1H-indazole

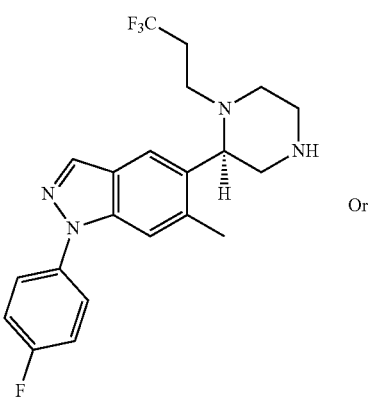

Or

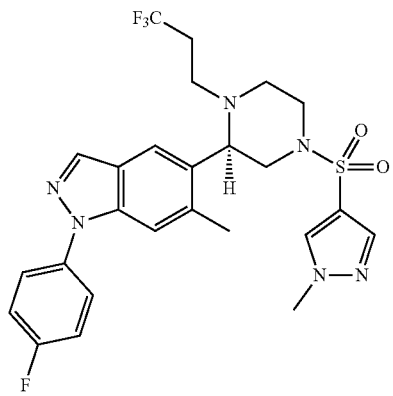

Or

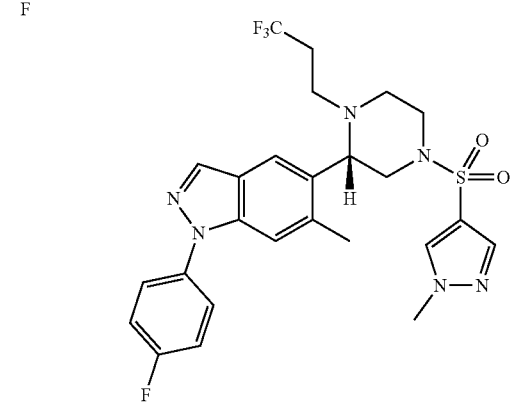

To a solution of 1-(4-fluorophenyl)-6-methyl-5-(1-(3,3,3-trifluoropropyl)piperazin-2-yl)-1H-indazole Intermediate Q (15.0 mg, 36.9 μmol) in DCM (1.00 mL) were added N-ethyl-N-isopropylpropan-2-amine (14.3 mg, 19.2 μL, 111 μmol) and 1-methyl-1H-pyrazole-4-sulfonyl chloride (9.33 mg, 51.7 μmol). The reaction mixture was stirred for 2 hours at rt before being quenched with sat. aq. NaHCO₃ (1 mL) and passed through a phase separator cartridge. The organics were removed in vacuo. The crude product was purified by chromatography on silica gel (4 g cartridge, 0-100% EtOAc/isohexane) to afford 1-(4-fluorophenyl)-6-methyl-5-(4-((1-methyl-1H-pyrazol-4-yl)sulfonyl)-1-(3,3,3-trifluoropropyl)piperazin-2-yl)-1H-indazole (12.5 mg, 21.7 mol, 58.9%); Rt 2.14 min (Method 7); m/z 551.4 (M+H)+ (ES+). δH (DMSO-d6, 400 MHz) δ 8.31 (s, 1H), 8.26 (s, 1H), 7.84-7.73 (m, 4H), 7.66 (s, 1H), 7.43 (t, J=8.8 Hz, 2H), 3.88 (s, 3H), 3.80-3.70 (m, 1H), 3.62 (d, J=8.7 Hz, 1H), 3.40 (d, J=11.6 Hz, 1H), 3.30-3.25 (m, 1H), 2.71-2.60 (m, 1H), 2.51 (s, 3H), 2.43 (m, 4H), 2.20 (dt, J=12.8, 6.6 Hz, 1H), 2.08 (s, 1H). Indazole Me obscured by DMSO.

Examples 129-140
TABLE 15
The examples shown in the table below were prepared by similar methods to those described for Example 128
| Example | Structure | LC-MS analysis |
|---|---|---|
| 129 | 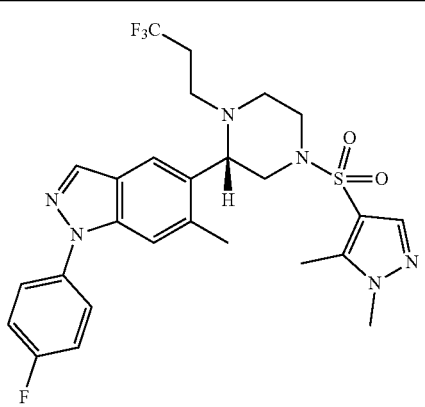<br><br>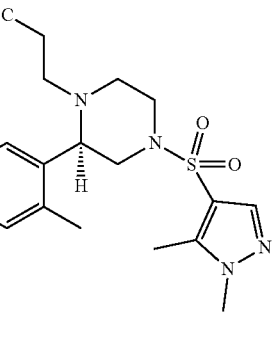<br>5-(4-((1,5-dimethyl-1H-pyrazol-4-yl)sulfonyl)-1-(3,3,3-trifluoropropyl)piperazin-2-yl)-1-(4-fluorophenyl)-6-methyl-1H-indazole | R$^t$ 2.16 min (Method 7); m/z 565.4 (M + H)$^+$ (ES$^+$) |
| 130 | 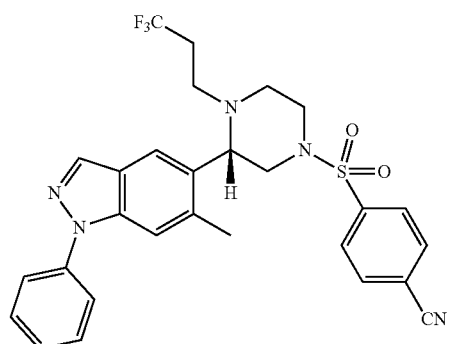 Or | R$^t$ 2.33 min (Method 9); m/z 572.4 (M + H)$^+$ (ES$^+$) |

TABLE 15-continued

The examples shown in the table below were prepared by similar methods to those described for Example 128

| Example | Structure | LC-MS analysis |
|---------|-----------|----------------|
| | 4-((3-(1-(4-fluorophenyl)-6-methyl-1H-indazol-5-yl)-4-(3,3,3-trifluoropropyl)piperazin-1-yl)sulfonyl)benzonitrile | |
| 131 | 5-(4-((1-ethyl-1H-pyrazol-4-yl)sulfonyl)-1-(3,3,3-trifluoropropyl)piperazin-2-yl)-1-(4-fluorophenyl)-6-methyl-1H-indazole | $R^t$ 2.21 min (Method 7); m/z 565.4 (M + H)$^+$ (ES$^+$) |

Or

TABLE 15-continued
The examples shown in the table below were prepared by similar methods to those described for Example 128
| Example | Structure | LC-MS analysis |
|---------|-----------|----------------|
| 132 | 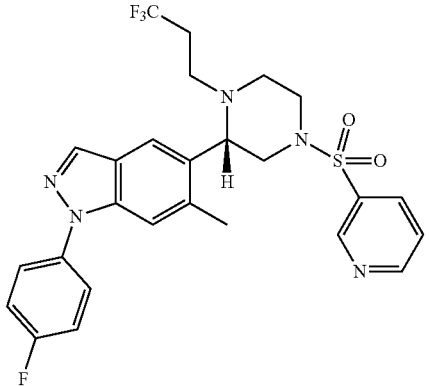<br><br>Or<br><br>1-(4-fluorophenyl)-6-methyl-5-(4-(pyridin-3-ylsulfonyl)-1-(3,3,3-trifluoropropyl)piperazin-2-yl)-1H-indazole | $R^t$ 2.20 min (Method 7); m/z 548.3 (M + H)$^+$ (ES$^+$) |
| 133 | 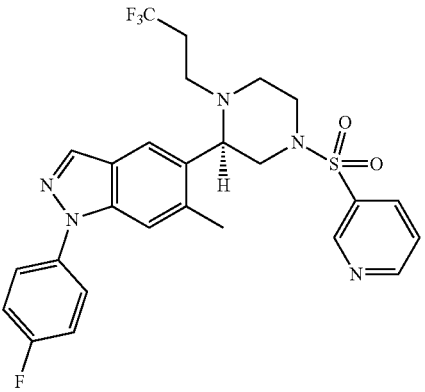<br><br>Or<br><br>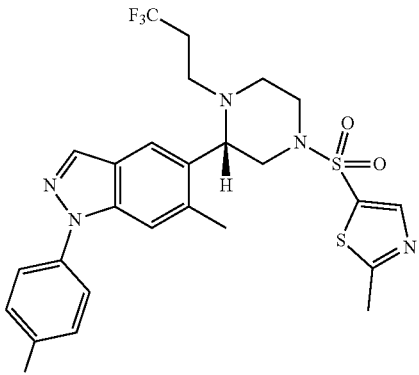 | $R^t$ 2.31 min (Method 9); m/z 568.2 (M + H)$^+$ (ES$^+$) |

TABLE 15-continued

The examples shown in the table below were prepared by similar methods to those described for Example 128

| Example | Structure | LC-MS analysis |
|---|---|---|
| | 5-((3-(1-(4-fluorophenyl)-6-methyl-1H-indazol-5-yl)-4-(3,3,3-trifluoropropyl)piperazin-1-yl)sulfonyl)-2-methylthiazole | |
| 134 | *(structure)* Or *(structure)* 4-((3-(1-(4-fluorophenyl)-6-methyl-1H-indazol-5-yl)-4-(3,3,3-trifluoropropyl)piperazin-1-yl)sulfonyl)-2-methylthiazole | R$^t$ 2.26 min (Method 7); m/z 568.4 (M + H)$^+$ (ES$^+$) |

TABLE 15-continued
The examples shown in the table below were prepared by similar methods to those described for Example 128
| Example | Structure | LC-MS analysis |
|---|---|---|
| 135 | 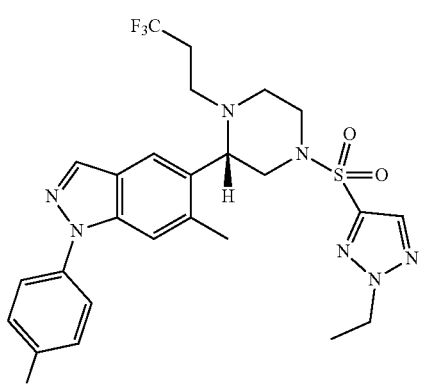<br>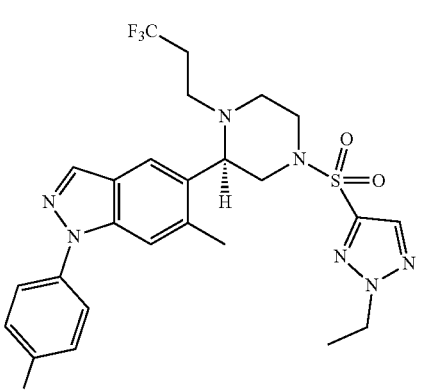<br>5-(4-((2-ethyl-2H-1,2,3-triazol-4-yl)sulfonyl)-1-(3,3,3-trifluoropropyl)piperazin-2-yl)-1-(4-fluorophenyl)-6-methyl-1H-indazole | $R^t$ 2.29 min (Method 9); m/z 566.2 (M + H)$^+$ (ES$^+$) |
| 136 | 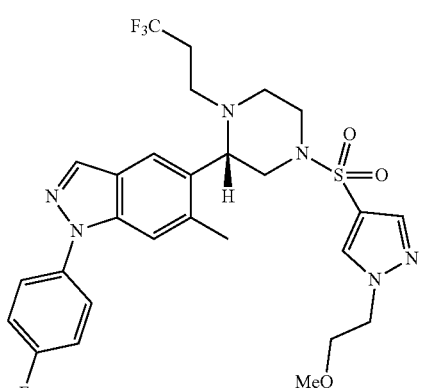 Or | $R^t$ 2.16 min (Method 9); m/z 595.2 (M + H)$^+$ (ES$^+$) |

TABLE 15-continued

The examples shown in the table below were prepared by similar methods to those described for Example 128

| Example | Structure | LC-MS analysis |
|---|---|---|
| | 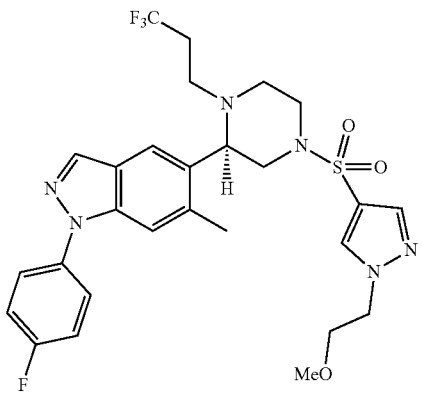 [SMILES: COCCn1cc(S(=O)(=O)N2CCN(CCC(F)(F)F)[C@H](c3cc4cnn(-c5ccc(F)cc5)c4cc3C)C2)cn1]<br>1-(4-fluorophenyl)-5-(4-((1-(2-methoxyethyl)-1H-pyrazol-4-yl)sulfonyl)-1-(3,3,3-trifluoropropyl)piperazin-2-yl)-6-methyl-1H-indazole | |
| 137 | 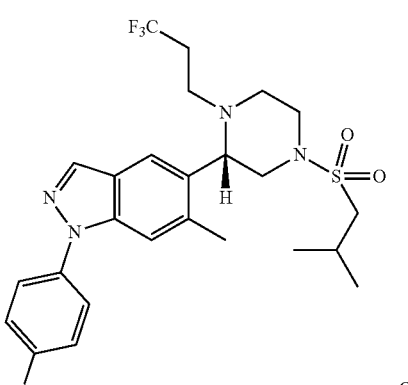<br>Or<br>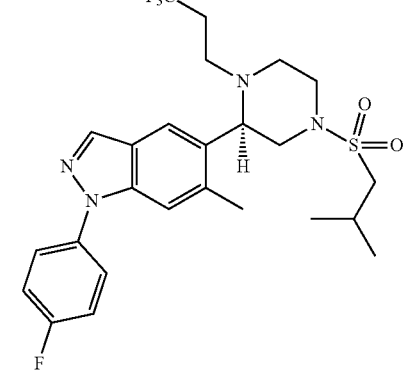<br>1-(4-fluorophenyl)-5-(4-(isobutylsulfonyl)-1-(3,3,3-trifluoropropyl)piperazin-2-yl)-6-methyl-1H-indazole | R$^t$ 2.35 min (Method 9); m/z 527.2 (M + H)$^+$ (ES$^+$) |

TABLE 15-continued
The examples shown in the table below were prepared by similar methods to those described for Example 128
| Example | Structure | LC-MS analysis |
|---|---|---|
| 138 | 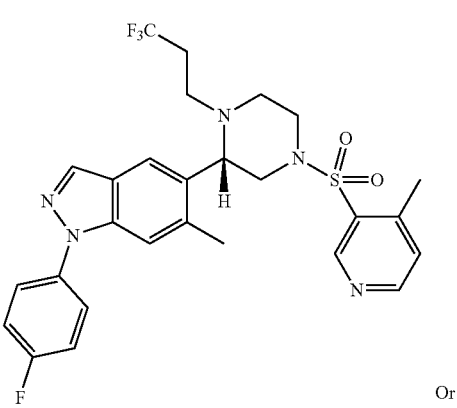 [SMILES: Cc1cc2c(cnn2-c2ccc(F)cc2)cc1[C@H]1CN(S(=O)(=O)c2cnccc2C)CCN1CCC(F)(F)F]<br>1-(4-fluorophenyl)-6-methyl-5-(4-((4-methylpyridin-3-yl)sulfonyl)-1-(3,3,3-trifluoropropyl)piperazin-2-yl)-1H-indazole | R$^t$ 2.25 min (Method 9); m/z 562.2 (M + H)$^+$ (ES$^+$) |
| 139 | 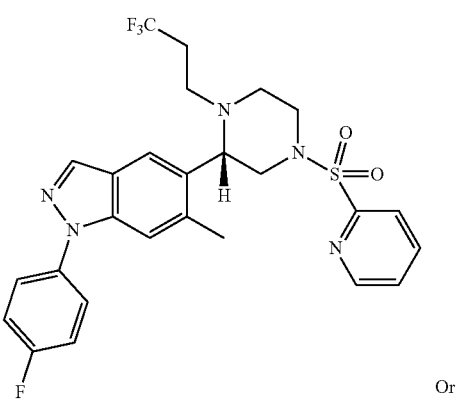 [SMILES: Cc1cc2c(cnn2-c2ccc(F)cc2)cc1[C@H]1CN(S(=O)(=O)c2ccccn2)CCN1CCC(F)(F)F] | R$^t$ 2.23 min (Method 7); m/z 548.3 (M + H)$^+$ (ES$^+$) |

TABLE 15-continued

The examples shown in the table below were prepared by similar methods to those described for Example 128

| Example | Structure | LC-MS analysis |
|---|---|---|
| | 1-(4-fluorophenyl)-6-methyl-5-(4-(pyridin-2-ylsulfonyl)-1-(3,3,3-trifluoropropyl)piperazin-2-yl)-1H-indazole | |
| 140 | 5-(4-(cyclobutylsulfonyl)-1-(3,3,3-trifluoropropyl)piperazin-2-yl)-1-(4-fluorophenyl)-6-methyl-1H-indazole | R$^t$ 2.29 min (Method 7); m/z 525.4 (M + H)$^+$ (ES$^+$) |

Or

Example 141: 1-(4-fluorophenyl)-6-methyl-5-(4-((1-methyl-1H-pyrazol-4-yl)sulfonyl)-1-(3,3,3-trifluoro-2-methylpropyl)piperazin-2-yl)-1H-indazole Intermediate R: 5-(4-benzyl-1-(3,3,3-trifluoro-2-methylpropyl)piperazin-2-yl)-1-(4-fluorophenyl)-6-methyl-1H-indazole

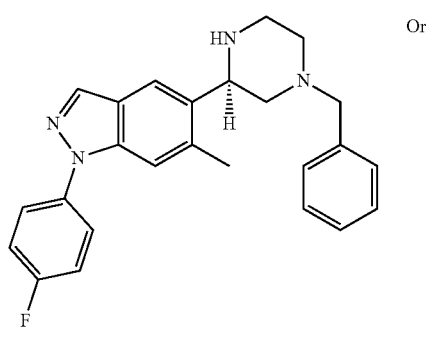

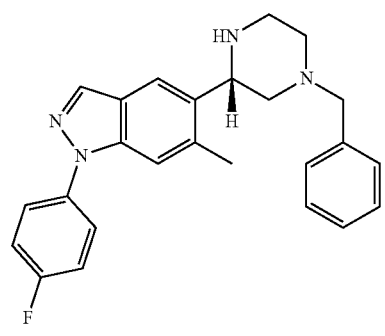

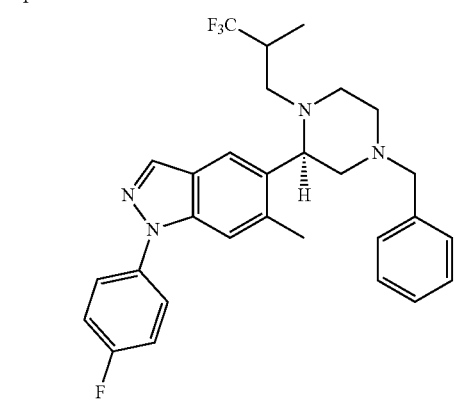

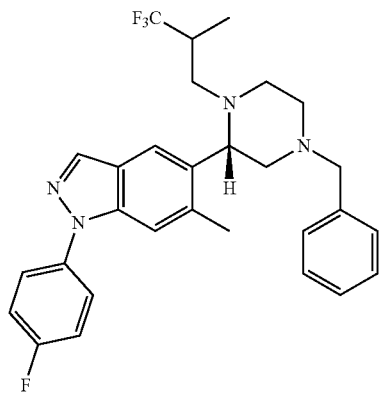

To a solution of 5-(4-benzylpiperazin-2-yl)-1-(4-fluorophenyl)-6-methyl-1H-indazole (500 mg, 1.25 mmol) in DCM (5.00 mL) were added 3,3,3-trifluoro-2-methylpropanal (236 mg, 1.87 mmol) and acetic acid (90.0 mg, 85.7 μL, 1.50 mmol). The reaction mixture was stirred at rt for 45 mins before the addition of sodium triacetoxyhydroborate (794 mg, 3.75 mmol). The reaction mixture was then stirred for a further 2 days at rt before being quenched with sat. aq. NaHCO₃ (8 mL). The layers were separated, and the aqueous layer extracted with DCM (3×15 mL). Combined organic extracts were dried over MgSO₄ and concentrated in vacuo. The crude product was purified by chromatography on silica gel (12 g cartridge, 0-100% EtOAc/isohexane) to afford 5-(4-benzyl-1-(3,3,3-trifluoro-2-methylpropyl)piperazin-2-yl)-1-(4-fluorophenyl)-6-methyl-1H-indazole Intermediate R (350 mg, 685 μmol, 54.9%) as a white solid; Rt 1.64 and 1.65 min (Method 7); m/z 511.5 (M+H)+ (ES+).

Intermediate S: 1-(4-fluorophenyl)-6-methyl-5-(1-(3,3,3-trifluoro-2-methylpropyl)piperazin-2-yl)-1H-indazole

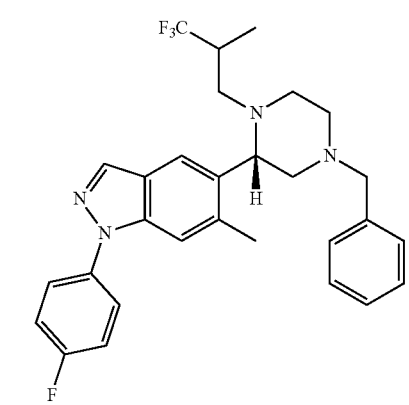

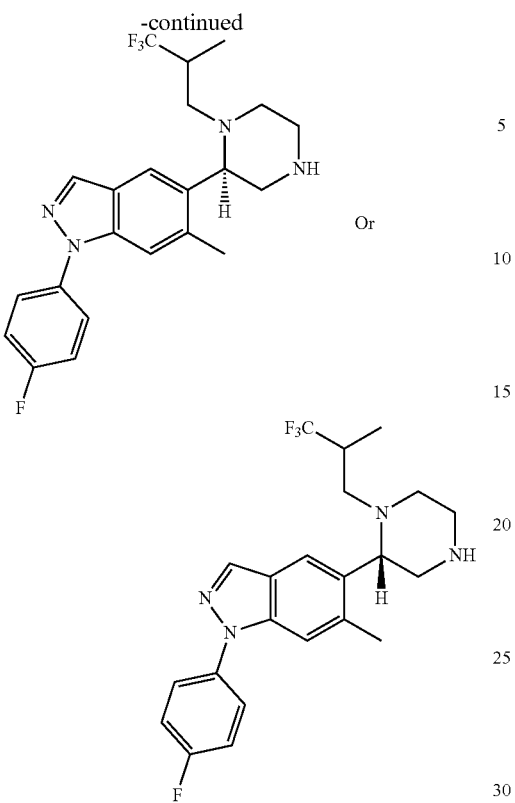

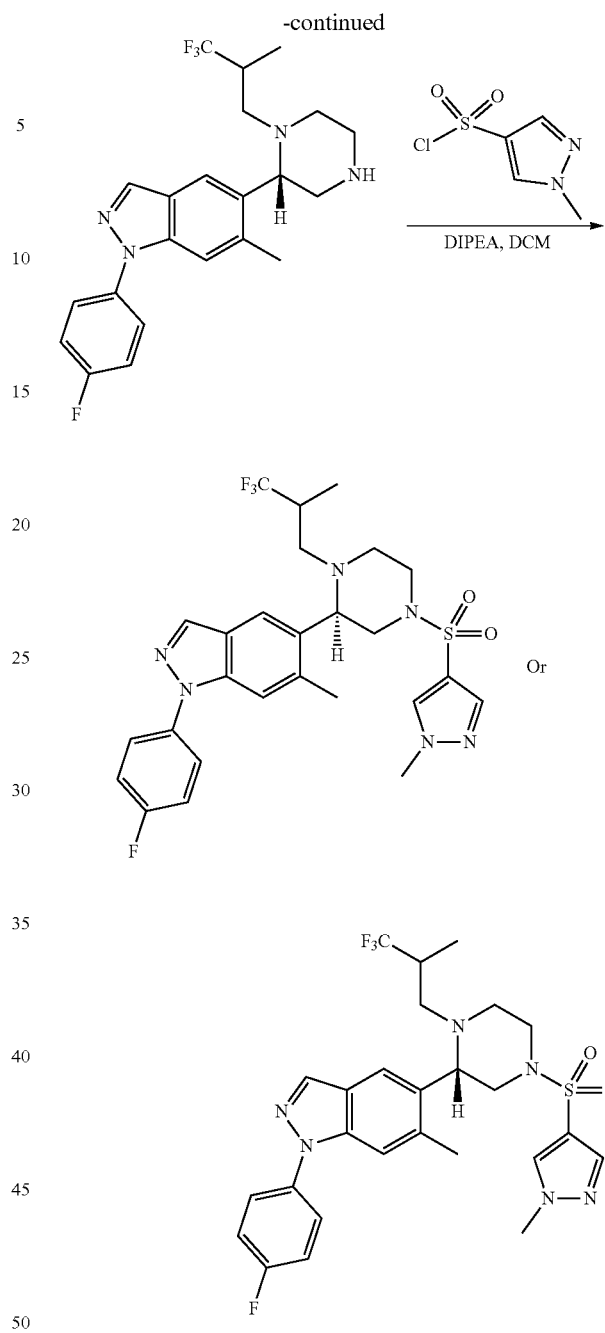

5-(4-benzyl-1-(3,3,3-trifluoro-2-methylpropyl)piperazin-2-yl)-1-(4-fluorophenyl)-6-methyl-1H-indazole Intermediate R (350 mg, 685 μmol) was dissolved in EtOH (5 mL) and treated with 10% palladium on carbon (14.6 mg, 137 μmol). The mixture was purged with nitrogen (×3) then hydrogen (×3) before being hydrogenated at 5 atm overnight 40° C. The catalyst was removed by filtration, washing with MeOH/EtOAc (1:1) (20 mL). The solvent was removed in vacuo to give 1-(4-fluorophenyl)-6-methyl-5-(1-(3,3,3-trifluoro-2-methylpropyl)piperazin-2-yl)-1H-indazole Intermediate S (300 mg, 0.66 mmol, 96%) as a cloudy glass, which was used without further purification; Rt 1.43 and 1.48 min (Method 7); m/z 421.4 (M+H)+ (ES+).

Example 141: 1-(4-fluorophenyl)-6-methyl-5-(4-((1-methyl-1H-pyrazol-4-yl)sulfonyl)-1-(3,3,3-trifluoro-2-methylpropyl)piperazin-2-yl)-1H-indazole

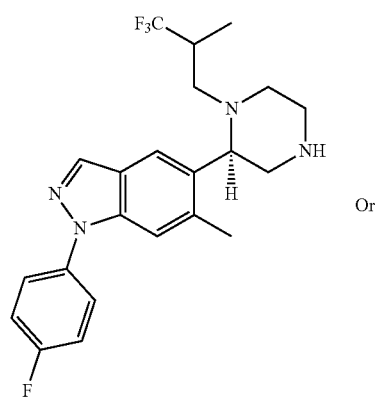

To a solution of 1-(4-fluorophenyl)-6-methyl-5-(1-(3,3,3-trifluoro-2-methylpropyl)piperazin-2-yl)-1H-indazole Intermediate S (15.0 mg, 35.7 μmol) in DCM (1.00 mL) were added N-ethyl-N-isopropylpropan-2-amine (13.8 mg, 18.6 μL, 107 μmol) and 1-methyl-1H-pyrazole-4-sulfonyl chloride (9.02 mg, 49.9 μmol). The reaction mixture was stirred for 2 hours at rt before being quenched with sat. aq. NaHCO₃ (1 mL) and passed through a phase separator cartridge. The organics were removed in vacuo. The crude product was purified by chromatography on silica gel (4 g cartridge, 0-100% EtOAc/isohexane) to afford 1-(4-fluorophenyl)-6-methyl-5-(4-((1-methyl-1H-pyrazol-4-yl)sulfonyl)-1-(3,3,3-trifluoro-2-methylpropyl)piperazin-2-yl)-1H-indazole Example 141; Rt 2.22 and 2.26 min (Method 7); m/z 565.5 (M+H)+ (ES+).

Examples 142-151
TABLE 16
The examples shown in the table below were prepared by similar methods to those described for Example 141
| Example | Structure | LC-MS analysis |
|---|---|---|
| 142 | 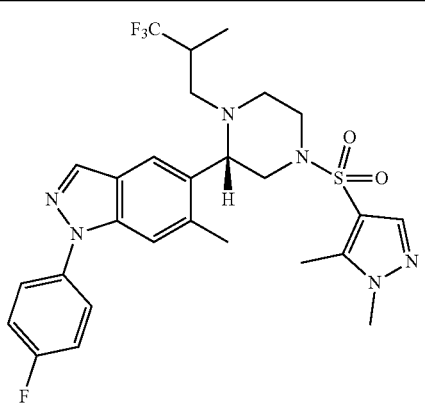  Or  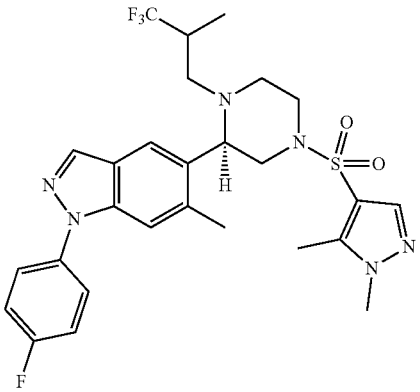 [SMILES: Cc1cc2c(cnn2-c2ccc(F)cc2)cc1[C@@H]1CN(S(=O)(=O)c2cnn(C)c2C)CCN1CC(C)C(F)(F)F]  5-(4-((1,5-dimethyl-1H-pyrazol-4-yl)sulfonyl)-1-(3,3,3-trifluoro-2-methylpropyl)piperazin-2-yl)-1-(4-fluorophenyl)-6-methyl-1H-indazole | $R^t$ 2.26 and 2.29 min (Method 7 m/z 579.5 $(M + H)^+$ $(ES^+)$ |
| 143 | 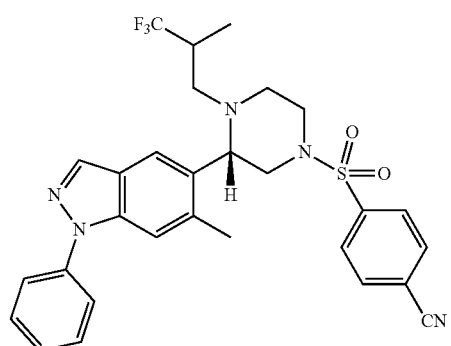  Or | $R^t$ 2.41 and 2.43 min (Method 7); m/z 586.3 $(M + H)^+$ $(ES^+)$ |

TABLE 16-continued

The examples shown in the table below were prepared by similar methods to those described for Example 141

| Example | Structure | LC-MS analysis |
|---|---|---|
| | 4-((3-(1-(4-fluorophenyl)-6-methyl-1H-indazol-5-yl)-4-(3,3,3-trifluoro-2-methylpropyl)piperazin-1-yl)sulfonyl)benzonitrile | |
| 144 | 5-(4-((1-ethyl-1H-pyrazol-4-yl)sulfonyl)-1-(3,3,3-trifluoro-2-methylpropyl)piperazin-2-yl)-1-(4-fluorophenyl)-6-methyl-1H-indazole | $R^t$ 2.30 and 2.33 min (Method 7); m/z 579.4 (M + H)$^+$ (ES$^+$) |

Or

TABLE 16-continued
The examples shown in the table below were prepared by similar methods to those described for Example 141
| Example | Structure | LC-MS analysis |
|---------|-----------|----------------|
| 145 | 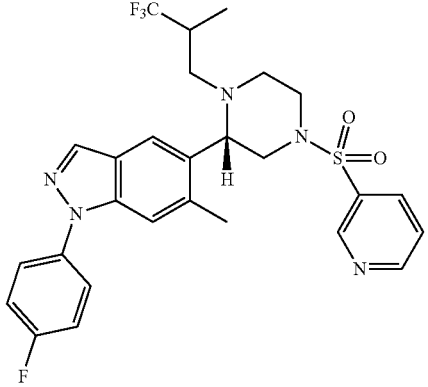 Or 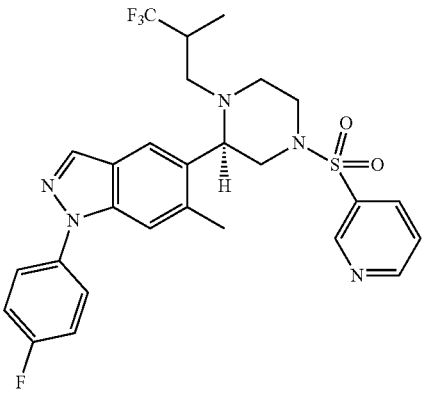 [SMILES: Cc1cc2c(cnn2-c2ccc(F)cc2)cc1[C@@H]1CN(S(=O)(=O)c2cccnc2)CCN1CC(C)C(F)(F)F]<br>1-(4-fluorophenyl)-6-methyl-5-(4-(pyridin-3-ylsulfonyl)-1-(3,3,3-trifluoro-2-methylpropyl)piperazin-2-yl)-1H-indazole | $R^t$ 2.29 and 2.32 min (Method 9); m/z 562.3 $(M + H)^+$ $(ES^+)$ |
| 146 | 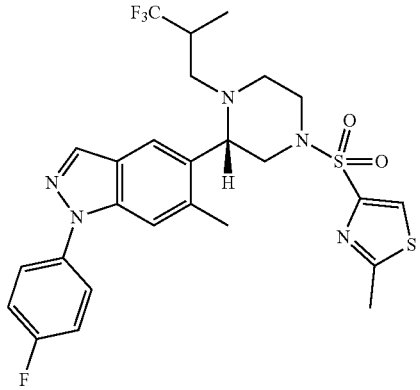 Or | $R^t$ 2.35 and 2.38 min (Method 7); m/z 582.5 $(M + H)^+$ $(ES^+)$ |

TABLE 16-continued

The examples shown in the table below were prepared by similar methods to those described for Example 141

| Example | Structure | LC-MS analysis |
|---|---|---|
| | 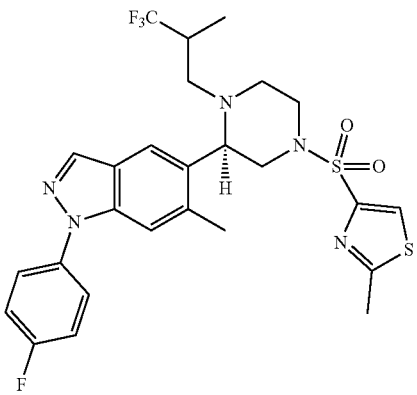 [SMILES: Cc1nc(S(=O)(=O)N2CCN(CC(C)C(F)(F)F)[C@H](c3cc4cnn(-c5ccc(F)cc5)c4cc3C)C2)cs1]<br>4-((3-(1-(4-fluorophenyl)-6-methyl-1H-indazol-5-yl)-4-(3,3,3-trifluoro-2-methylpropyl)piperazin-1-yl)sulfonyl)-2-methylthiazole | |
| 147 | 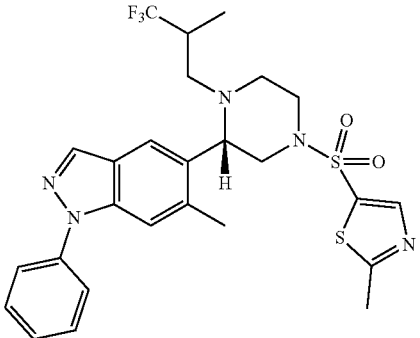<br>Or<br>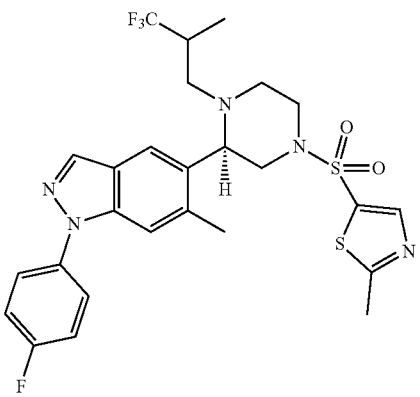 [SMILES: Cc1ncc(S(=O)(=O)N2CCN(CC(C)C(F)(F)F)[C@H](c3cc4cnn(-c5ccc(F)cc5)c4cc3C)C2)s1]<br>5-((3-(1-(4-fluorophenyl)-6-methyl-1H-indazol-5-yl)-4-(3,3,3-trifluoro-2-methylpropyl)piperazin-1-yl)sulfonyl)-2-methylthiazole | $R^t$ 2.39 and 2.42 min (Method 7); m/z 582.5 $(M + H)^+$ $(ES^+)$ |

TABLE 16-continued
The examples shown in the table below were prepared by similar methods to those described for Example 141
| Example | Structure | LC-MS analysis |
|---------|-----------|----------------|
| 148 | 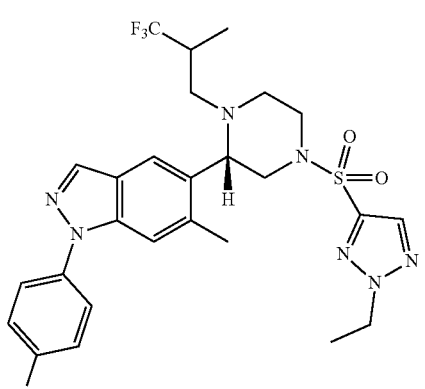<br>Or<br>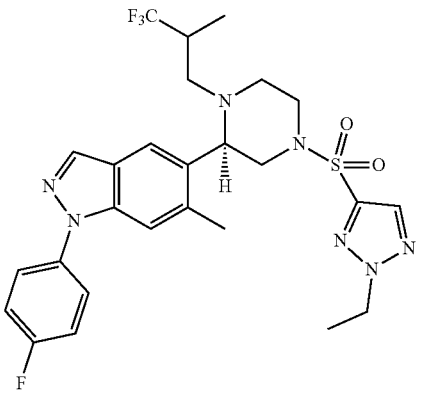<br>5-(4-((2-ethyl-2H-1,2,3-triazol-4-yl)sulfonyl)-1-(3,3,3-trifluoro-2-methylpropyl)piperazin-2-yl)-1-(4-fluorophenyl)-6-methyl-1H-indazole | $R^t$ 2.37 and 2.40 min (Method 9); m/z 580.2 (M + H)$^+$ (ES$^+$) |
| 149 | 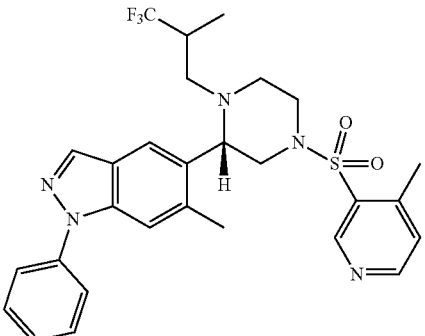<br>Or | $R^t$ 2.34 and 2.37 min (Method 9); m/z 576.2 (M + H)$^+$ (ES$^+$) |

TABLE 16-continued

The examples shown in the table below were prepared by similar methods to those described for Example 141

| Example | Structure | LC-MS analysis |
|---|---|---|
| | 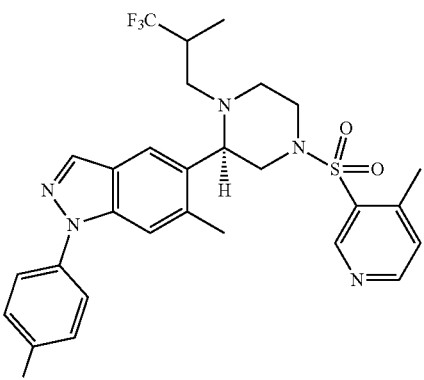 1-(4-fluorophenyl)-6-methyl-5-(4-((4-methylpyridin-3-yl)sulfonyl)-1-(3,3,3-trifluoro-2-methylpropyl)piperazin-2-yl)-1H-indazole | |
| 150 | 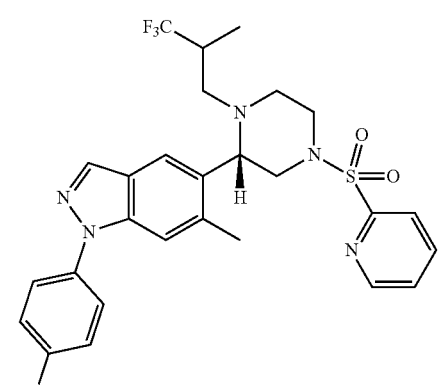<br>Or<br>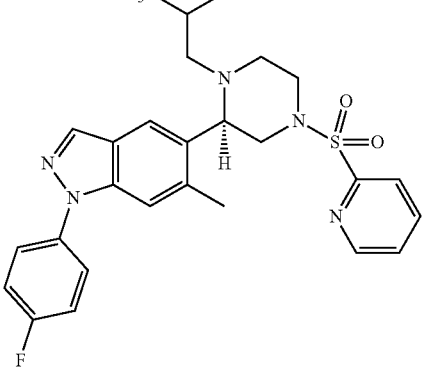<br>1-(4-fluorophenyl)-6-methyl-5-(4-(pyridin-2-ylsulfonyl)-1-(3,3,3-trifluoro-2-methylpropyl)piperazin-2-yl)-1H-indazole | $R^t$ 2.32 and 2.35 min (Method 7); m/z 562.4 (M + H)$^+$ (ES$^+$) |

TABLE 16-continued

The examples shown in the table below were prepared by similar methods to those described for Example 141

| Example | Structure | LC-MS analysis |
|---|---|---|
| 151 | 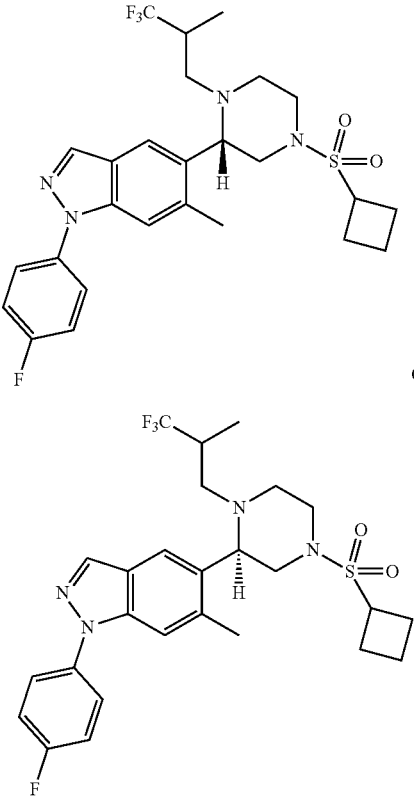<br>Or<br>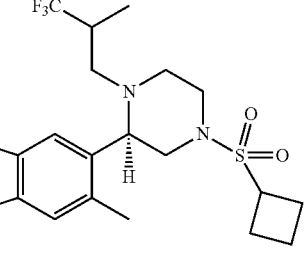<br>5-(4-(cyclobutylsulfonyl)-1-(3,3,3-trifluoro-2-methylpropyl)piperazin-2-yl)-1-(4-fluorophenyl)-6-methyl-1H-indazole | R$^t$ 2.38 and 2.41 min (Method 7); m/z 539.4 (M + H)$^+$ (ES$^+$) |

Example 152: 3-(1-(4-fluorophenyl)-6-methyl-1H-indazol-5-yl)-4-isobutyl-1-((2-methyl-2H-1,2,3-triazol-4-yl)sulfonyl)piperazin-2-one Intermediate T: 1-(4-fluorophenyl)-5-(3-methoxypyrazin-2-yl)-6-methyl-1H-indazole

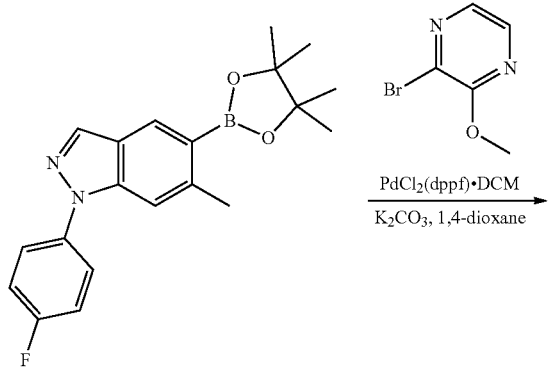

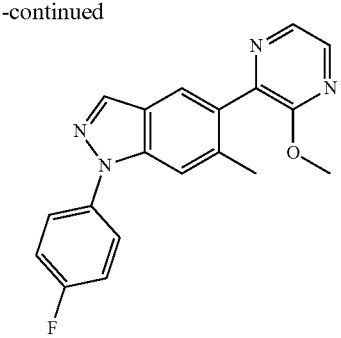

A solution of 1-(4-fluorophenyl)-6-methyl-5-(4,4,5,5-tetramethyl-1,3,2-dioxaborolan-2-yl)-1H-indazole (0.80 g, 2.3 mmol), 2-bromo-3-methoxypyrazine (0.52 g, 2.7 mmol) and potassium carbonate (0.47 g, 3.4 mmol) in 1,4-dioxane (20 mL) and water (5 mL) was degassed (bubbling N$_2$) for 2 mins. PdCl$_2$(dppf)·DCM complex (0.19 g, 0.23 mmol) was then added and the reaction mixture stirred at 90° C. for 2 hours. The reaction mixture was diluted with DCM (50 mL) and transferred into a separating funnel. The organic layer was washed with half saturated brine (1×50 mL). The combined organic layers were collected, dried over MgSO₄, filtered and concentrated in vacuo. The crude product was purified by chromatography on silica gel (12 g cartridge, 5-100 EtOAc/isohexane) to afford 1-(4-fluorophenyl)-5-(3-methoxypyrazin-2-yl)-6-methyl-1H-indazole Intermediate T (0.38 g, 1.1 mmol, 50%) as a flocculent white solid; Rt 1.98 min (Method 9); m/z 335.0 (M+H)+ (ES+).

Intermediate U: 3-(1-(4-fluorophenyl)-6-methyl-1H-indazol-5-yl)piperazin-2-one

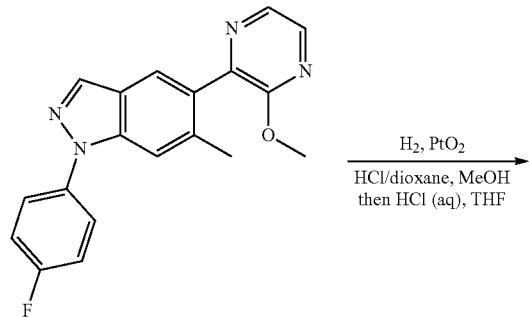

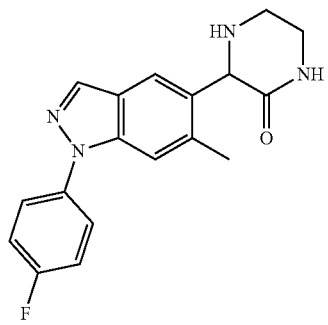

To a solution of 1-(4-fluorophenyl)-5-(3-methoxypyrazin-2-yl)-6-methyl-1H-indazole Intermediate T (150 mg, 449 μmol) in MeOH (10.0 mL) were added HCl (4 M in 1,4-dioxane) (327 mg, 2.24 mL, 4 molar, 8.97 mmol) and platinum(IV) oxide (10.2 mg, 44.9 μmol). The reaction mixture was subjected to hydrogenation at 5 bar at 50° C. for 20 hours. The reaction mixture was then concentrated in vacuo before being redissolved in THF (5 mL) and 1 M HCl (aq., 5 mL) added. The mixture was stirred overnight and then quenched with sat. aq. NaHCO₃ (15 mL). DCM (10 mL) was added, and the layers separated. The aqueous was extracted with DCM (3×5 mL). Combined organic extracts were dried over MgSO₄ and concentrated in vacuo. The crude product was purified by chromatography on silica gel (12 g cartridge, 0-10% (0.7 M ammonia/MeOH)/DCM) to afford 3-(1-(4-fluorophenyl)-6-methyl-1H-indazol-5-yl)piperazin-2-one Intermediate U (52.0 mg, 0.10 mmol, 23%) as a flocculent white solid; Rt 0.74 min (Method 9); m/z 325.2 (M+H)+ (ES+). δH (DMSO-d6, 400 MHz) δ 8.28 (d, J=0.9 Hz, 1H), 7.85-7.75 (m, 3H), 7.71 (s, 1H), 7.58 (s, 1H), 7.42 (t, J=8.8 Hz, 2H), 4.57 (s, 1H), 3.36 (d, J=7.8 Hz, 1H), 3.18 (dd, J=12.7, 7.7 Hz, 1H), 2.98 (s, 1H), 2.88 (s, 2H), 2.52 (s, 3H).

Intermediate V: 3-(1-(4-fluorophenyl)-6-methyl-1H-indazol-5-yl)-4-isobutylpiperazin-2-one

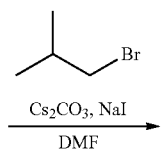

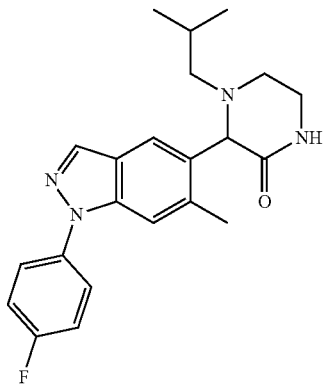

To a solution of 3-(1-(4-fluorophenyl)-6-methyl-1H-indazol-5-yl)piperazin-2-one Intermediate U (42.0 mg, 129 μmol) in DMF (2.00 mL) were added 1-bromo-2-methylpropane (710 mg, 563 μL, 5.18 mmol), cesium carbonate (338 mg, 1.04 mmol) and sodium iodide (77.6 mg, 518 μmol). The reaction mixture was stirred at 100° C. for 2 hours. After cooling to rt, the reaction mixture was quenched with water (10 mL) and brine (10 mL) and the organics extracted with EtOAc (3×8 mL). Combined organics were dried over MgSO₄ and concentrated in vacuo. The crude product was purified by chromatography on silica gel (4 g cartridge, 0-100% EtOAc/isohexane) to afford 3-(1-(4-fluorophenyl)-6-methyl-1H-indazol-5-yl)-4-isobutylpiperazin-2-one Intermediate V (28.0 mg, 34 μmol, 26%) as an off-white solid; Rt 1.90 min (Method 9); m/z 381.2 (M+H)+ (ES+).

Example 152: 3-(1-(4-fluorophenyl)-6-methyl-1H-indazol-5-yl)-4-isobutyl-1-((2-methyl-2H-1,2,3-triazol-4-yl)sulfonyl)piperazin-2-one

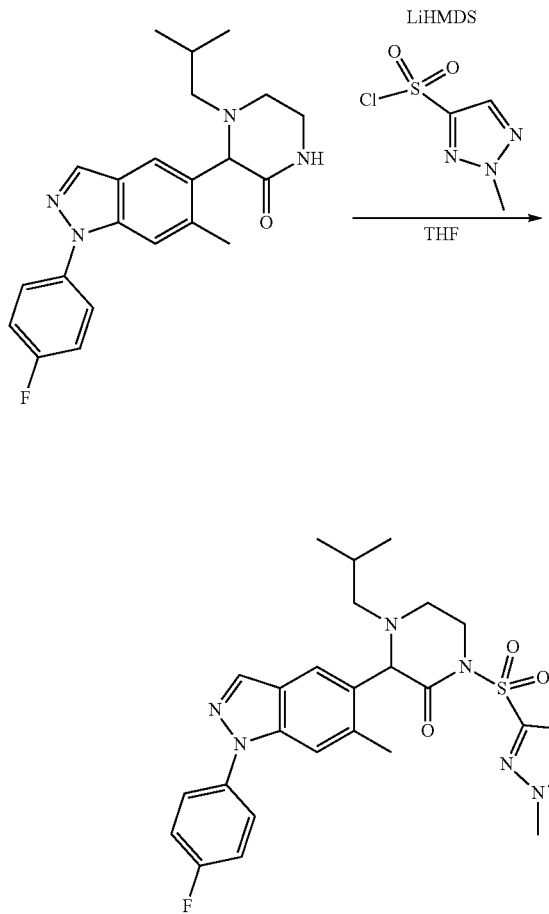

To a solution of 3-(1-(4-fluorophenyl)-6-methyl-1H-indazol-5-yl)-4-isobutylpiperazin-2-one Intermediate V (28.0 mg, 46% Wt, 33.9 μmol) in THF (1.00 mL) at −78° C. was added LiHMDS (1 M in THF) (17.0 mg, 102 μL, 1.00 molar, 102 μmol) and the reaction mixture stirred for 30 mins at −78° C. 2-Methyl-2H-1,2,3-triazole-4-sulfonyl chloride (18.4 mg, 102 μmol) (as a solution in THF (0.30 mL)) was then added and the reaction mixture stirred for 90 mins, warming to rt. The reaction mixture was quenched with sat. aq. NaHCO₃ (3 mL) and EtOAc (5 mL). The layers were separated, and the aqueous layer extracted with EtOAc (3×5 mL). Combined organic extracts were dried over MgSO₄ and concentrated in vacuo. The crude product was purified by chromatography on silica gel (4 g cartridge, 0-100% EtOAc/isohexane) to afford the product at ~88%. This material was then submitted for reverse phase purification to afford 3-(1-(4-fluorophenyl)-6-methyl-1H-indazol-5-yl)-4-isobutyl-1-((2-methyl-2H-1,2,3-triazol-4-yl)sulfonyl)piperazin-2-one Example 152 (6.00 mg, 11 μmol, 32%, 95% Purity) as a white solid; Rt 2.27 min (Method 9); m/z 526.2 (M+H)+ (ES+). δH (DMSO-d6, 400 MHz) δ 8.37 (s, 1H), 8.30 (d, J=0.9 Hz, 1H), 7.84-7.75 (m, 2H), 7.74 (s, 1H), 7.55 (s, 1H), 7.45-7.37 (m, 2H), 4.32 (s, 1H), 4.27 (s, 3H), 4.15 (d, J=11.7 Hz, 1H), 3.91 (td, J=11.6, 3.7 Hz, 1H), 3.37 (d, J=12.7 Hz, 1H), 2.61 (t, J=10.6 Hz, 1H), 2.07 (dd, J=12.2, 4.0 Hz, 1H), 1.84 (t, J=11.4 Hz, 1H), 1.68 (d, J=6.2 Hz, 1H), 0.65 (d, J=6.5 Hz, 3H), 0.62 (d, J=6.4 Hz, 3H). 3H obscured by DMSO peak.

Example 153: 3-(1-(4-fluorophenyl)-6-methyl-1H-indazol-5-yl)-4-isobutyl-1-((2-methyl-2H-1,2,3-triazol-4-yl)sulfinyl)piperazin-2-one Intermediate W: 1-(4-fluorophenyl)-5-(6-methoxypyrazin-2-yl)-6-methyl-1H-indazole

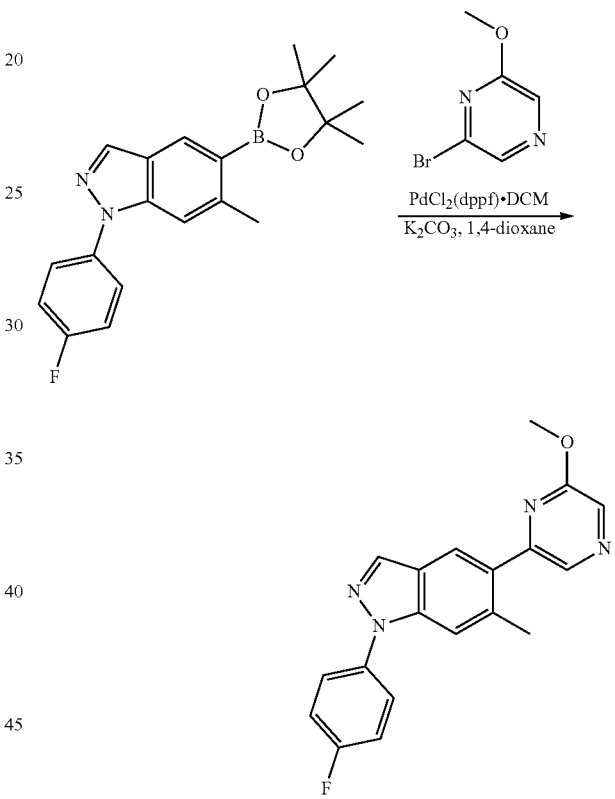

A solution of 1-(4-fluorophenyl)-6-methyl-5-(4,4,5,5-tetramethyl-1,3,2-dioxaborolan-2-yl)-1H-indazole (0.80 g, 2.3 mmol), 2-bromo-6-methoxypyrazine (0.52 g, 2.7 mmol) and potassium carbonate (0.47 g, 3.4 mmol) in 1,4-dioxane (20 mL) and water (5 mL) was degassed (bubbling N2) for 20 mins. PdCl2(dppf)·DCM complex (0.19 g, 0.23 mmol) was then added and the reaction mixture stirred at 90° C. for 2 hours. The reaction mixture was diluted with EtOAc (50 mL) and transferred into a separating funnel. The organic layer was washed with half saturated brine (1×50 mL). The combined organic layers were collected, dried over MgSO₄, filtered and concentrated in vacuo. The crude product was purified by chromatography on silica gel (12 g cartridge, 5-100 EtOAc/isohexane) to afford 1-(4-fluorophenyl)-5-(6-methoxypyrazin-2-yl)-6-methyl-1H-indazole Intermediate W (0.46 g, 1.3 mmol, 59%) as a flocculent white solid; Rt 2.24 min (Method 9); m/z 335.1 (M+H)+(ES+).

Intermediate X: 6-(1-(4-fluorophenyl)-6-methyl-1H-indazol-5-yl)piperazin-2-one

Intermediate Y

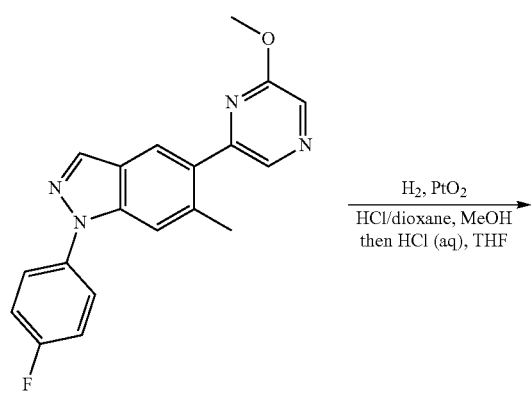

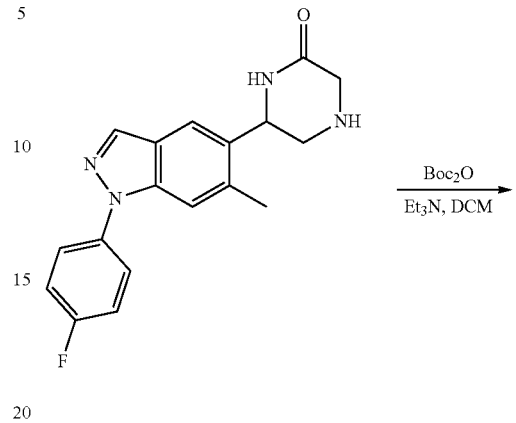

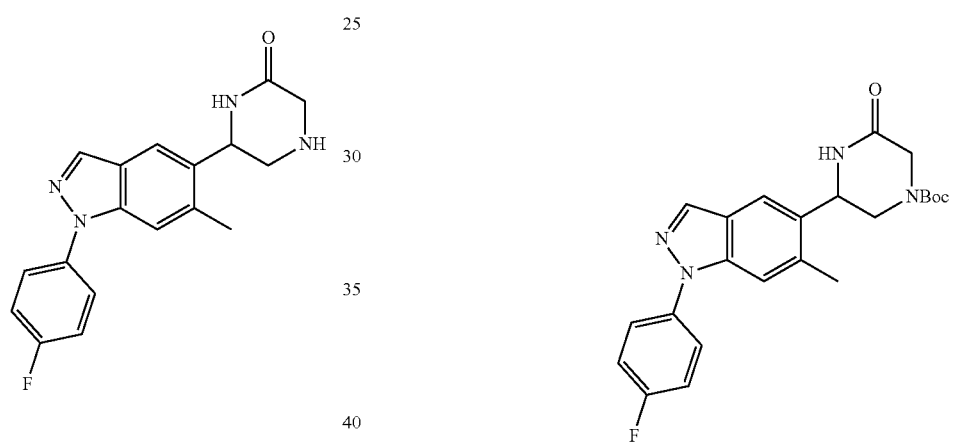

To a suspension of 1-(4-fluorophenyl)-5-(6-methoxypyrazin-2-yl)-6-methyl-1H-indazole Intermediate W (410 mg, 1.23 mmol) in MeOH (40 mL) were added HCl (4 M in dioxane) (894 mg, 6.13 mL, 4 molar, 24.5 mmol) and platinum(IV) oxide (27.8 mg, 123 μmol). The reaction mixture was stirred at 50° C. for 16 hours under an atmosphere of H₂ (5 bar). After cooling to rt, the reaction mixture was filtered through a glass microfibre pad, washing with EtOAc (50 mL). The filtrate was concentrated in vacuo and redissolved in EtOAc (50 mL). NaHCO₃ (100 mL) was added, and the layers separated. The aqueous was extracted with EtOAc (3×30 mL). Combined organic extracts were dried over MgSO₄ and concentrated in vacuo. The crude product was purified by chromatography on silica gel (12 g cartridge, 0-10% (0.7 M ammonia/MeOH)/DCM) to afford 6-(1-(4-fluorophenyl)-6-methyl-1H-indazol-5-yl)piperazin-2-one Intermediate X (220 mg, 0.58 mmol, 47%, 85%) as a white solid; Rt 0.90 min (Method 9); m/z 325.2 (M+H)+ (ES+). δH (DMSO-d6, 400 MHz) δ 8.33 (d, J=0.9 Hz, 1H), 7.91 (s, 1H), 7.83-7.75 (m, 3H), 7.62 (s, 1H), 7.46-7.38 (m, 2H), 4.83 (s, 1H), 3.30 (obscured m, 3H), 3.21-3.11 (m, 1H), 2.56 (m, 1H), 2.46 (s, 3H).

To a solution of 6-(1-(4-fluorophenyl)-6-methyl-1H-indazol-5-yl)piperazin-2-one Intermediate X (40.0 mg, 123 μmol) in DCM (1.50 mL) were added triethylamine (21.8 mg, 30.0 μL, 216 μmol) and Boc anhydride (32.3 mg, 34.0 μL, 148 μmol). The reaction mixture was stirred at rt for 1 hour before being quenched with sat. aq. NaHCO₃ (2 mL). The layers were separated, and the aqueous layer extracted with DCM (3×2 mL). Combined organic extracts were dried over MgSO₄ and concentrated in vacuo. The crude product was purified by chromatography on silica gel (4 g cartridge, 0-100% EtOAc/isohexane then isocratic 25% EtOH/EtOAc) to afford tert-butyl 3-(1-(4-fluorophenyl)-6-methyl-1H-indazol-5-yl)-5-oxopiperazine-1-carboxylate Intermediate Y (47.0 mg, 0.11 mmol, 85%) as a white solid; Rt 1.80 min (Method 9); m/z 425.2 (M+H)+ (ES+). δH (DMSO-d6, 400 MHz) δ 8.40 (d, J=3.3 Hz, 1H), 8.33 (s, 1H), 7.77 (s, 2H), 7.61 (m, 2H), 7.43 (t, J=8.6 Hz, 2H), 4.88 (q, J=3.8 Hz, 1H), 4.33-4.06 (m, 1H), 3.90 (m, 1H), 3.70 (M, 2H), 1.09 (m, 9H). 3H obscured under DMSO peak.

409

Intermediate Z: tert-butyl 4-benzyl-3-(1-(4-fluorophenyl)-6-methyl-1H-indazol-5-yl)-5-oxopiperazine-1-carboxylate

410

Intermediate AA: 1-benzyl-6-(1-(4-fluorophenyl)-6-methyl-1H-indazol-5-yl)piperazin-2-one

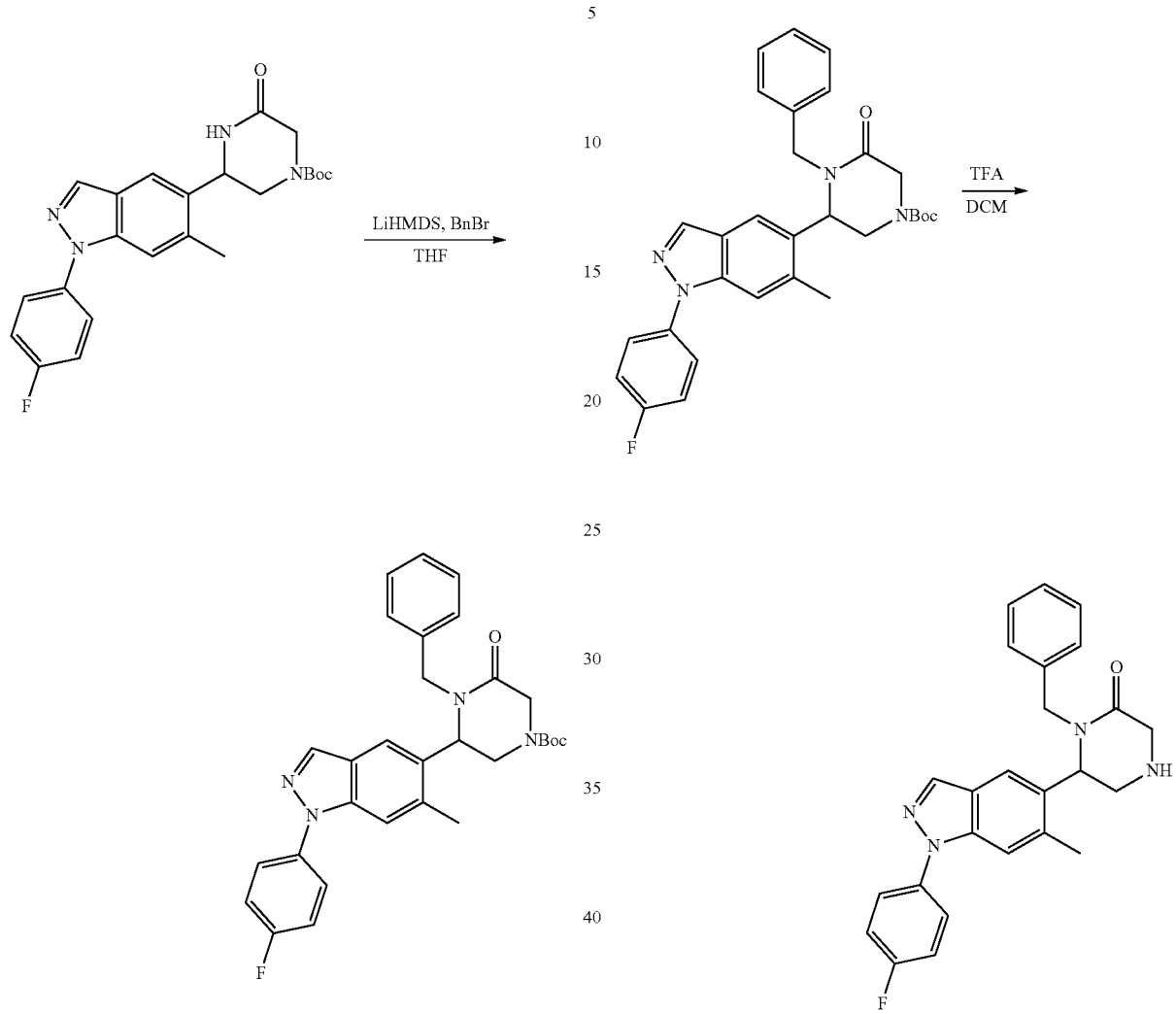

To a solution of tert-butyl 3-(1-(4-fluorophenyl)-6-methyl-1H-indazol-5-yl)-5-oxopiperazine-1-carboxylate Intermediate Y (35.0 mg, 82.5 μmol) in THF (1.50 mL) at 0° C. was added lithium bis(trimethylsilyl)amide (1 M in toluene) (27.6 mg, 165 μL, 1.00 molar, 165 μmol). The reaction mixture was stirred at 0° C. for 20 mins before the addition of (bromomethyl)benzene (42.3 mg, 29.4 μL, 247 μmol). The reaction mixture was then stirred at 60° C. for 3 hours. After cooling to rt, the reaction mixture was quenched with sat. aqueous NH$_4$Cl (5 mL) and diluted with EtOAc (5 mL). The layers were separated, and the aqueous layer extracted with EtOAc (3×5 mL). Combined organic extracts were dried over MgSO$_4$ and concentrated in vacuo. The crude product was purified by chromatography on silica gel (4 g cartridge, 0-100% EtOAc/isohexane) to afford tert-butyl 4-benzyl-3-(1-(4-fluorophenyl)-6-methyl-1H-indazol-5-yl)-5-oxopiperazine-1-carboxylate Intermediate Z (41.0 mg, 53 μmol, 53%) as a pale tan solid; Rt 2.19 min (Method 9); m/z 515.2 (M+H)$^+$ (ES$^+$). δH (DMSO-d6, 400 MHz) δ 8.32 (s, 1H), 7.73 (m, 3H), 7.56-7.15 (m, 8H), 5.31 (m, 1H), 4.71 (d, J=3.1 Hz, 1H), 4.55 (m, 1H), 4.21-3.81 (m, 2H), 3.56 (m, 2H), 2.34 (s, 3H), 0.98 (m, 9H).

To a solution of tert-butyl 4-benzyl-3-(1-(4-fluorophenyl)-6-methyl-1H-indazol-5-yl)-5-oxopiperazine-1-carboxylate Intermediate Z (39.0 mg, 66% Wt, 50.0 μmol) in DCM (1.00 mL) was added 2,2,2-trifluoroacetic acid (149 mg, 100 μL, 1.31 mmol). The reaction mixture was stirred at rt for 2 hours before being diluted with toluene (2 mL) and concentrated in vacuo. The residue was dissolved in DCM (5 mL) and basified with sat. aq. NaHCO$_3$ (5 mL). The mixture was dried through a phase separator and the organics concentrated in vacuo. The crude product was purified by chromatography on silica gel (4 g cartridge, 0-10% (0.7 M Ammonia/MeOH)/DCM) to afford 1-benzyl-6-(1-(4-fluorophenyl)-6-methyl-1H-indazol-5-yl)piperazin-2-one Intermediate AA (15.0 mg, 34 μmol, 69%) as a flocculent white solid; Rt 1.46 min (Method 9); m/z 415.2 (M+H)$^+$ (ES$^+$). δH (DMSO-d6, 400 MHz) δ 8.34 (d, J=0.9 Hz, 1H), 7.84-7.76 (m, 2H), 7.69 (s, 1H), 7.63 (s, 1H), 7.43 (t, J=8.8 Hz, 2H), 7.36-7.21 (m, 3H), 7.17-7.05 (m, 2H), 5.36 (d, J=15.0 Hz, 1H), 4.62 (t, J=4.5 Hz, 1H), 3.54 (q, J=17.1 Hz, 2H), 3.19 (d, J=13.0 Hz, 1H), 2.80 (d, J=13.5 Hz, 1H), 2.19 (s, 3H). 2H obscured under DMSO.

Example 153: 3-(1-(4-fluorophenyl)-6-methyl-1H-indazol-5-yl)-4-isobutyl-1-((2-methyl-2H-1,2,3-triazol-4-yl)sulfinyl)piperazin-2-one

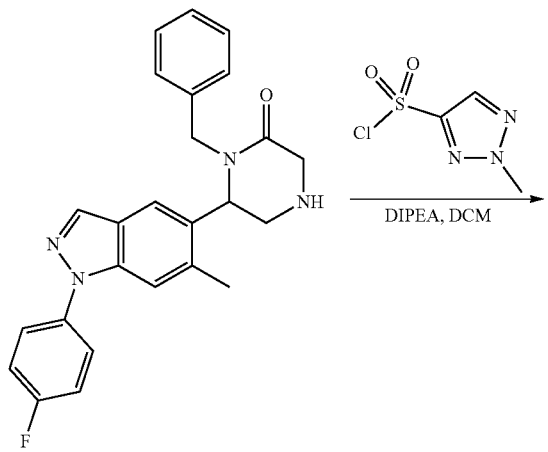

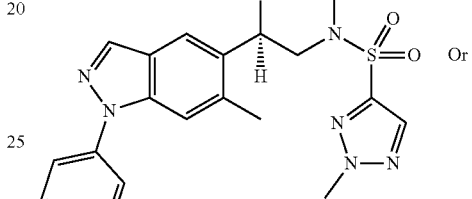

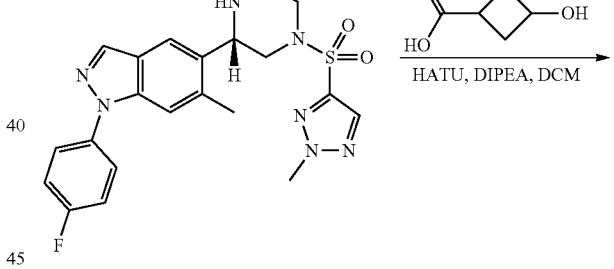

To a solution of 1-benzyl-6-(1-(4-fluorophenyl)-6-methyl-1H-indazol-5-yl)piperazin-2-one Intermediate AA (14.0 mg, 133.8 μmol) in DCM (0.50 mL) were added 2-methyl-2H-1,2,3-triazole-4-sulfonyl chloride (9.20 mg, 50.7 μmol) and N-ethyl-N-isopropylpropan-2-amine (13.1 mg, 17.7 μL, 101 μmol). The reaction mixture was stirred at rt for 4 hours, before being quenched with sat. aq. NaHCO₃ (2 mL). The mixture was transferred to a phase separator and extracted with DCM (5 mL). Combined organic extracts were concentrated in vacuo. The crude product was purified by chromatography on silica gel (4 g cartridge, 0-100% EtOAc/isohexane) to afford the product at ~88% purity. This material was then further purified by reverse phase HPLC to afford 1-benzyl-6-(1-(4-fluorophenyl)-6-methyl-1H-indazol-5-yl)-4-((2-methyl-2H-1,2,3-triazol-4-yl)sulfonyl)piperazin-2-one Example 153 (6.20 mg, 11 μmol, 31%, 95% Purity) as a white solid; Rt 2.07 min (Method 9); m/z 560.2 (M+H)+ (ES+). δH (DMSO-d6, 400 MHz) δ 8.36 (s, 1H), 8.25 (s, 1H), 7.82 (dd, J=8.9, 4.9 Hz, 2H), 7.67 (s, 1H), 7.63 (s, 1H), 7.44 (t, J=8.6 Hz, 2H), 7.28 (m, 3H), 7.11 (d, J=7.2 Hz, 2H), 5.24 (m, 1H), 4.77 (s, 1H), 4.19 (m, 4H), 3.89 (d, J=16.3 Hz, 1H), 3.55 (d, J=12.6 Hz, 1H), 3.47 (m, 2H), 2.26 (s, 3H).

Example 154: 3-((2-(1-(4-fluorophenyl)-6-methyl-1H-indazol-5-yl)-4-((2-methyl-2H-1,2,3-triazol-4-yl)sulfonyl)piperazin-1-yl)methyl)cyclobutan-1-ol Intermediate AB: (2-(1-(4-fluorophenyl)-6-methyl-1H-indazol-5-yl)-4-((2-methyl-2H-1,2,3-triazol-4-yl)sulfonyl)piperazin-1-yl)(3-hydroxycyclobutyl)methanone

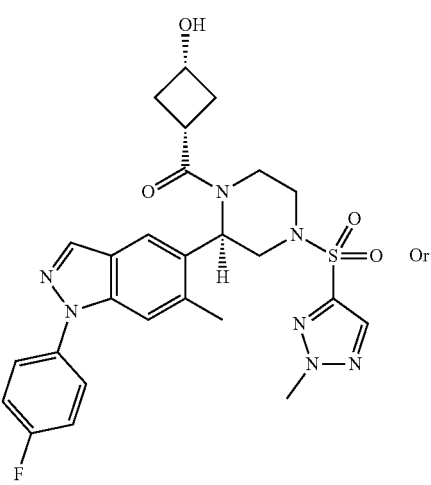

413

-continued

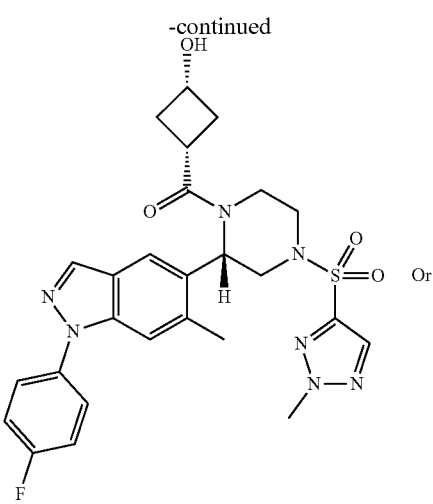

Or

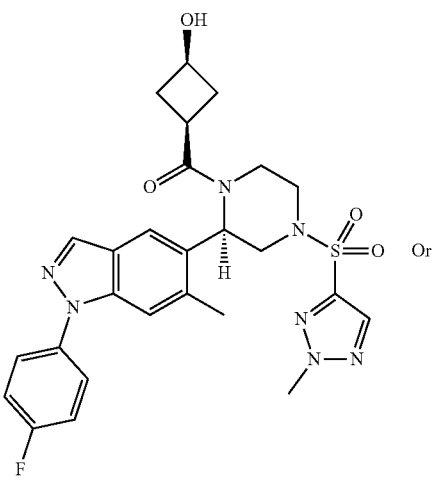

Or

To a solution of 3-hydroxycyclobutane-1-carboxylic acid (38.2 mg, 329 μmol) in DCM (3.00 mL) were added N-ethyl-N-isopropylpropan-2-amine (85.1 mg, 114 μL, 659 μmol) and 2-(3H-[1,2,3]triazolo[4,5-b]pyridin-3-yl)-1,1,3,3-tetramethylisouronium hexafluorophosphate(V) (125 mg, 329 μmol). The reaction mixture was stirred for 10 mins before the addition of 1-(4-fluorophenyl)-6-methyl-5-(4-((2-methyl-2H-1,2,3-triazol-4-yl)sulfonyl)piperazin-2-yl)-1H-indazole (100 mg, 220 μmol). The reaction mixture was then stirred at rt for 16 hours. The reaction mixture was then quenched with 1 M aq HCl (5 mL). The mixture was transferred to a phase separator and the aqueous layer extracted with DCM (2×4 mL). Combined organics were concentrated in vacuo. The crude product was purified by chromatography on silica gel (4 g cartridge, 0-100% EtOAc/isohexane) to afford (2-(1-(4-fluorophenyl)-6-methyl-1H-indazol-5-yl)-4-((2-methyl-2H-1,2,3-triazol-4-yl)sulfonyl)piperazin-1-yl)(3-hydroxycyclobutyl)methanone Intermediate AB (120 mg, 0.13 mmol, 59%, 60%) as a white solid; Rt 1.71 min (Method 9); m/z 554.2 (M+H)+ (ES+).

Example 154: 3-((2-(1-(4-fluorophenyl)-6-methyl-1H-indazol-5-yl)-4-((2-methyl-2H-1,2,3-triazol-4-yl)sulfonyl)piperazin-1-yl)methyl)cyclobutan-1-ol

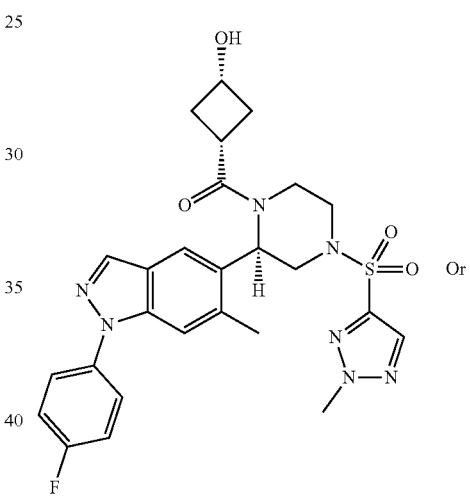

Or

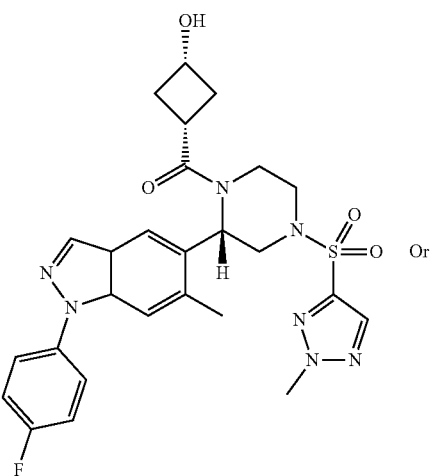

Or

415
-continued

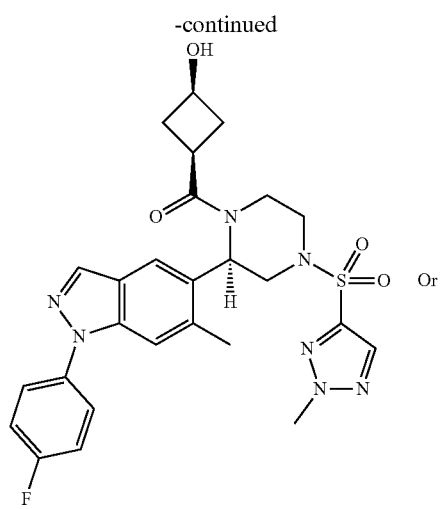

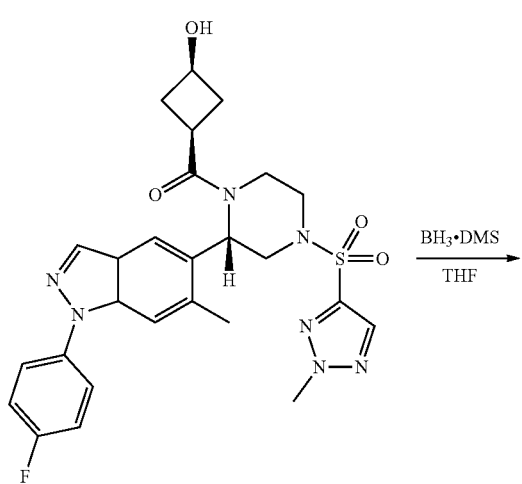

BH₃·DMS
THF

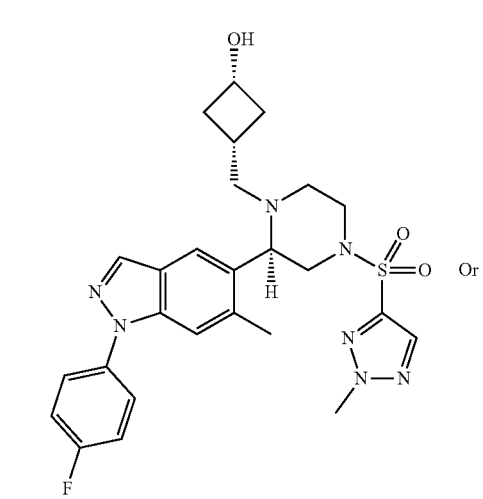

416
-continued

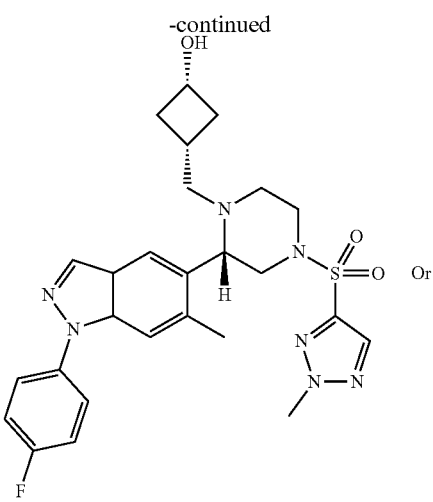

To a solution of (2-(1-(4-fluorophenyl)-6-methyl-1H-indazol-5-yl)-4-((2-methyl-2H-1,2,3-triazol-4-yl)sulfonyl)piperazin-1-yl)(3-hydroxycyclobutyl)methanone Intermediate AB (120 mg, 70% Wt, 152 μmol) in THF (2.00 mL) was added borane-methyl sulfide complex (2M in THF) (69.2 mg, 455 μL, 2.00 molar, 910 μmol). The reaction mixture was stirred at 40° C. for 3 hours. Additional borane-methyl sulfide complex (2M in THF) (45.6 mg, 300 μL, 2.00 molar, 600 μmol) was then added and the reaction mixture stirred at 40° C. for a further 2 hours. After cooling to rt, the reaction mixture was quenched with MeOH (1 mL), water (1 mL) and sat. aq. NH₄Cl (2 mL). DCM (5 mL) was added, and the layers separated. The aqueous layer was extracted with DCM (2×3 mL). Combined organic extracts were dried over MgSO₄ and concentrated in vacuo. The crude product was purified by chromatography on silica gel (2×4 g cartridge, 0-100% EtOAc/isohexane) to afford 3-((2-(1-(4-fluorophenyl)-6-methyl-1H-indazol-5-yl)-4-((2-methyl-2H-1,2,3-triazol-4-yl)sulfonyl)piperazin-1-yl)methyl)cyclobutan-1-ol Example 154 (7.00 mg, 12 µmol, 8.1%, 95% Purity) as a white solid as an 8:1 mixture of diastereomers; Rt 1.48 and 1.53 min (Method 9); m/z 540.2 (M+H)+ (ES+). δH (DMSO-d6, 400 MHz) δ 8.29 (s, 1H), 8.27 (s, 1H), 7.84 (s, 1H), 7.79 (dd, J=9.0, 4.8 Hz, 2H), 7.65 (s, 1H), 7.43 (t, J=8.8 Hz, 2H), 4.79 (d, J=6.8 Hz, 1H), 4.26 (s, 3H), 3.80 (q, J=7.4 Hz, 1H), 3.70 (d, J=11.7 Hz, 1H), 3.60 (dd, J=10.2, 3.1 Hz, 1H), 3.45 (d, J=11.9 Hz, 1H), 3.16 (d, J=11.9 Hz, 1H), 2.68 (d, J=11.2 Hz, 1H), 2.48 (obscured s, 3H), 2.41-2.27 (m, 3H), 2.20 (dq, J=16.0, 7.5 Hz, 1H), 1.77 (dd, J=14.8, 8.3 Hz, 2H), 1.17 (td, J=19.9, 10.1 Hz, 2H). OH proton not observed.

Example 155: 1-(4-fluorophenyl)-5-(1-(((3-methoxycyclobutyl)methyl)-4-((2-methyl-2H-1,2,3-triazol-4-yl)sulfonyl)piperazin-2-yl)-6-methyl-1H-indazole

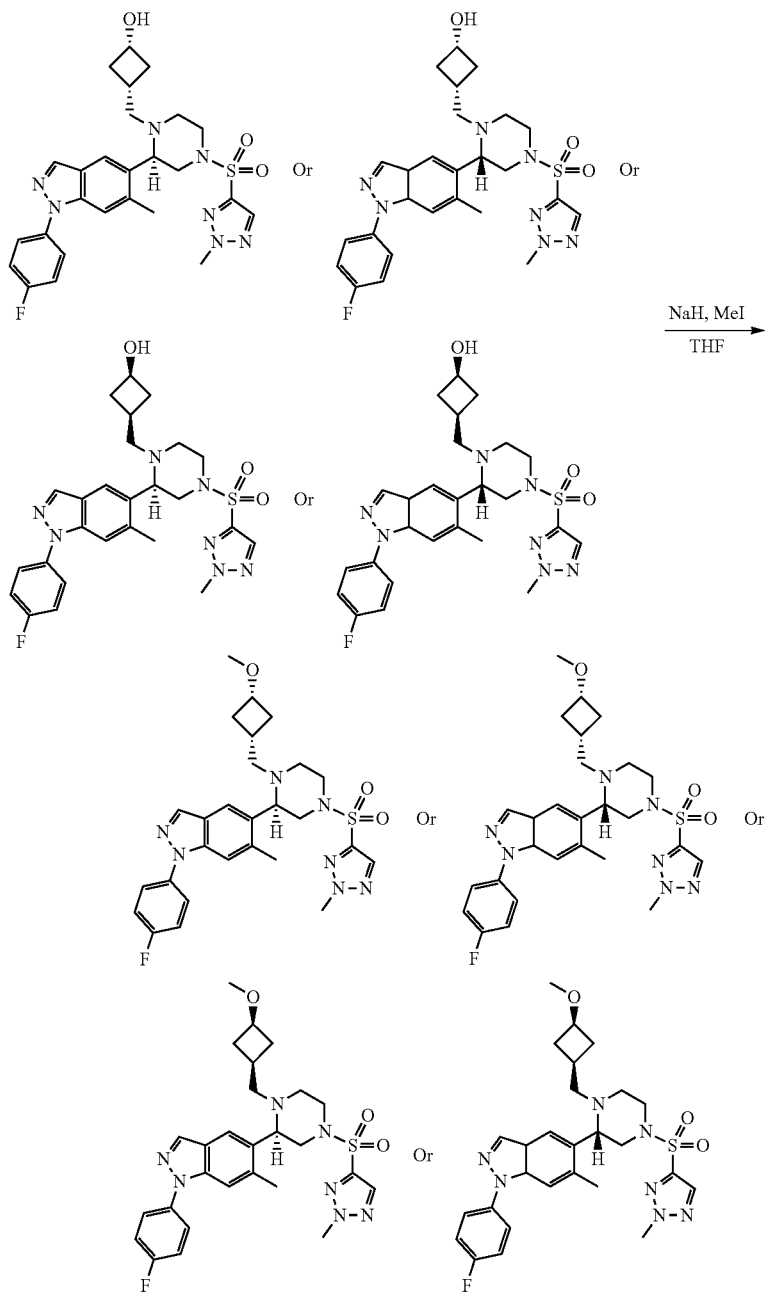

To a solution of 3-((2-(1-(4-fluorophenyl)-6-methyl-1H-indazol-5-yl)-4-((2-methyl-2H-1,2,3-triazol-4-yl)sulfonyl)piperazin-1-yl)methyl)cyclobutan-1-ol Example 154 (32.0 mg, 59.3 µmol) in THF (1.00 mL) at 0° C. was added sodium hydride (60 wt % in mineral oil) (4.7 mg, 60% Wt, 119 μmol) and the reaction mixture stirred for 30 mins. iodomethane (25.3 mg, 11.1 μL, 178 μmol) was then added and the reaction mixture stirred at rt for 18 hours. Additional sodium hydride (24 mg, 60% Wt, 593 μmol) and iodomethane (126 mg, 55.4 μL, 889 μmol) were added and the reaction mixture stirred for a further 30 mins before being quenched with MeOH (1 mL) and sat. aq. NH₄Cl (2 mL). The crude product was purified by chromatography on silica gel (4 g cartridge, 0-100% EtOAc/isohexane) to afford 1-(4-fluorophenyl)-5-(1-((3-methoxycyclobutyl)methyl)-4-((2-methyl-2H-1,2,3-triazol-4-yl)sulfonyl)piperazin-2-yl)-6-methyl-1H-indazole Example 155 (11.0 mg, 19 μmol, 32%) as a white solid; Rt 1.72 min (Method 9); m/z 554.2 (M+H)+ (ES+). δH (DMSO-d6, 400 MHz) δ 8.29 (s, 1H), 8.27 (s, 1H), 7.83 (s, 1H), 7.82-7.75 (m, 2H), 7.65 (s, 1H), 7.43 (t, J=8.8 Hz, 2H), 4.26 (s, 3H), 3.70 (d, J=11.5 Hz, 1H), 3.65-3.52 (m, 2H), 3.45 (d, J=12.0 Hz, 1H), 3.17 (d, J=11.6 Hz, 1H), 2.98 (s, 3H), 2.72-2.63 (m, 1H), 2.48 (s, 3H), 2.37 (dd, J=12.5, 8.6 Hz, 2H), 2.29-2.16 (m, 2H), 2.05 (dd, J=12.6, 5.6 Hz, 1H), 1.92 (t, J=7.6 Hz, 1H), 1.24-1.08 (m, 3H).

Example 156: 5-(1-((3-fluorocyclobutyl)methyl)-4-((2-methyl-2H-1,2,3-triazol-4-yl)sulfonyl)piperazin-2-yl)-1-(4-fluorophenyl)-6-methyl-1H-indazole

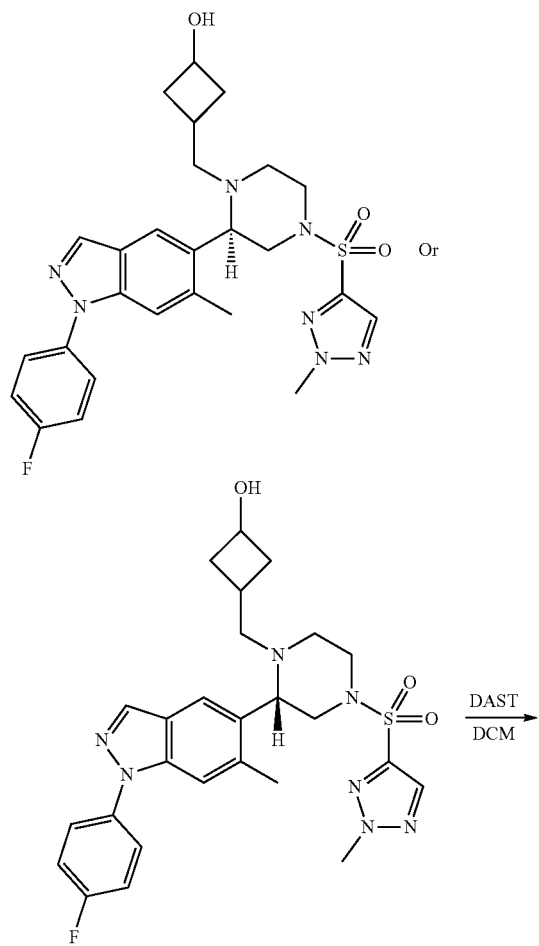

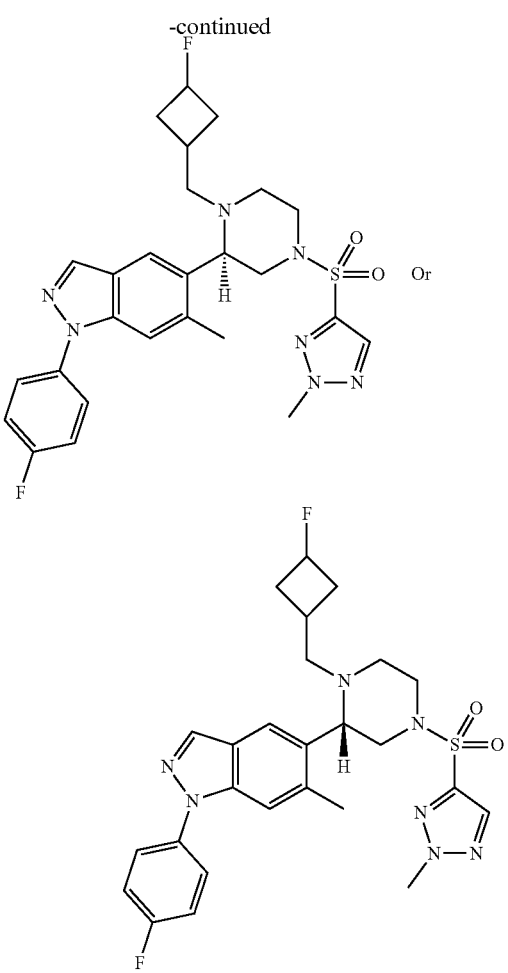

To a solution of 3-((2-(1-(4-fluorophenyl)-6-methyl-1H-indazol-5-yl)-4-((2-methyl-2H-1,2,3-triazol-4-yl)sulfonyl)piperazin-1-yl)methyl)cyclobutan-1-ol (15.0 mg, 27.8 μmol) in DCM (0.30 mL) at −78° C. was added DAST (8.96 mg, 7.35 μL, 55.6 μmol). The reaction mixture was stirred for 2 hours, warming to rt, before being quenched with sat. aq. NaHCO₃ (1 mL) and diluted with DCM (1 mL). The layers were separated, and the aqueous layer extracted with DCM (3×1 mL). Combined organic extracts were dried over MgSO₄ and concentrated in vacuo to an orange solid. The crude mixture was dissolved in 0.9 mL with DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH C18 ODB prep column, 130 Å, 5 μm, 30 mm×100 mm, flow rate 40 mL min-1 eluting with a 0.1% Formic acid in water-MeCN gradient over 12.5 mins using UV across all wavelengths with PDA as well as a QDA and ELS detector. At-column dilution pump gives 2 mL min-1 methanol over the entire method, which is included in the following MeCN percentages. Gradient information: 0.0-0.5 min, 50% MeCN; 0.5-10.5 min, ramped from 50% MeCN to 80% MeCN; 10.5-10.6 min, ramped from 80% MeCN to 100% MeCN; 10.6-12.5 min, held at 100% MeCN to afford 5-(1-((3-fluorocyclobutyl)methyl)-4-((2-methyl-2H-1,2,3-triazol-4-yl)sulfonyl)piperazin-2-yl)-1-(4-fluorophenyl)-6-methyl-1H-indazole (1.50 mg, 2.6 μmol, 9.5%, 95% Purity) was isolated as a mixture of isomers as an off-white solid; Rt 2.19, 2.21 and 2.24 min (Method 9); m/z 542.2 (M+H)+ (ES+).

Example 157: 5-(1-(2,2-difluoropropyl)-4-((2-methyl-2H-1,2,3-triazol-4-yl)sulfonyl)piperazin-2-yl)-1-(4-fluorophenyl)-6-methyl-1H-indazole

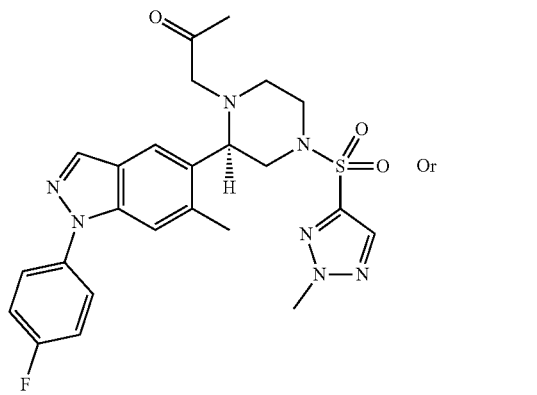

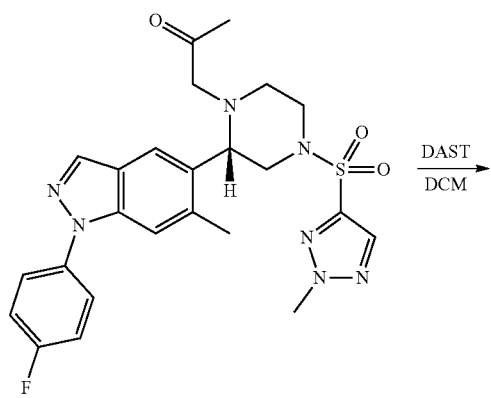

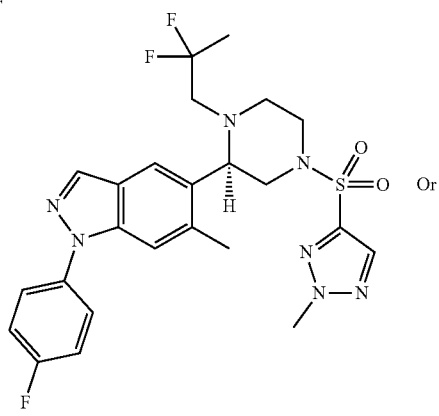

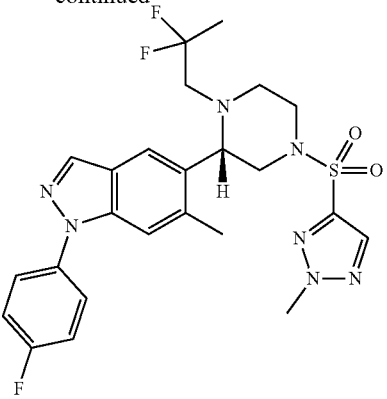

To a stirred solution of (R)-1-(2-(1-(4-fluorophenyl)-6-methyl-1H-indazol-5-yl)-4-((2-methyl-2H-1,2,3-triazol-4-yl)sulfonyl)piperazin-1-yl)propan-2-one (75.0 mg, 1 Eq, 147 μmol) Example 125 in dry DCM (1.00 mL) under a nitrogen atmosphere at −20° C. was added DAST (122 mg, 100 μL, 5.16 Eq, 757 μmol). The reaction mixture was stirred for 30 minutes and then raised to 20° C. for 2 days. The reaction mixture was quenched with 2M NaOH (2 mL) and transferred to a phase separator. The DCM layer was drawn off and adsorbed onto silica gel. The crude product was purified by chromatography on silica gel (4 g cartridge, 10-50% EtOAc/isohexane) to afford 5-(1-(2,2-difluoropropyl)-4-((2-methyl-2H-1,2,3-triazol-4-yl)sulfonyl)piperazin-2-yl)-1-(4-fluorophenyl)-6-methyl-1H-indazole Example 157 (34.0 mg, 61 μmol, 41%) as a white solid; Rt 2.24 min (Method 7); m/z 534.2 (M+H)+ (ES+). δH (DMSO-d6, 400 MHz) δ 8.36-8.18 (m, 2H), 7.88 (s, 1H), 7.83-7.74 (m, 2H), 7.66 (d, J=1.1 Hz, 1H), 7.48-7.31 (m, 2H), 4.28 (s, 3H), 3.86 (dd, J=10.4, 3.1 Hz, 1H), 3.70 (d, J=11.7 Hz, 1H), 3.49 (d, J=11.8 Hz, 1H), 3.29 (s, 1H), 2.88-2.76 (m, 1H), 2.70-2.60 (m, 2H), 2.59-2.52 (m, 2H), 2.51 (s, 3H), 1.47 (t, J=19.2 Hz, 3H).

Example 158: 1-(4-fluorophenyl)-5-(1-(2-fluoropropyl)-4-((2-methyl-2H-1,2,3-triazol-4-yl)sulfonyl)piperazin-2-yl)-6-methyl-1H-indazole Intermediate AC: 1-(2-(1-(4-fluorophenyl)-6-methyl-1H-indazol-5-yl)-4-((2-methyl-2H-1,2,3-triazol-4-yl)sulfonyl)piperazin-1-yl)propan-2-ol

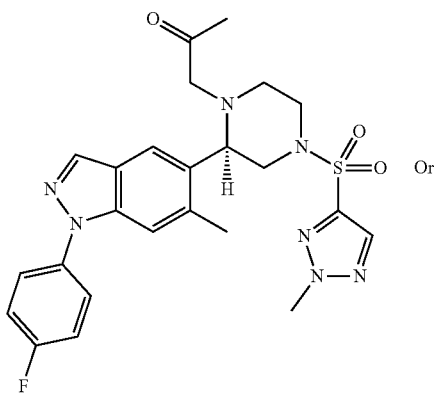

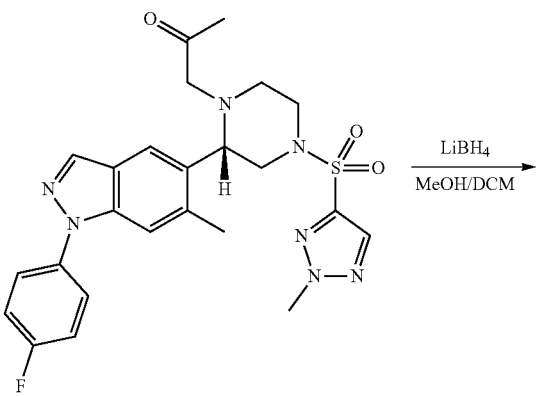

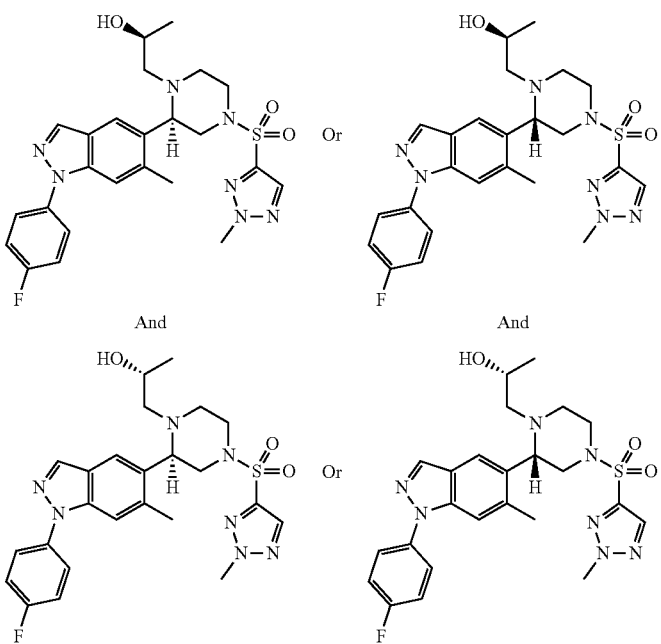

To a solution of 1-(2-(1-(4-fluorophenyl)-6-methyl-1H-indazol-5-yl)-4-((2-methyl-2H-1,2,3-triazol-4-yl)sulfonyl)piperazin-1-yl)propan-2-one Example 125 (50.0 mg, 97.7 μmol) in MeOH (977 μL) and DCM (977 μL) was added LiBH₄ (4.26 mg, 48.9 μL, 4.00 molar in THF, 195 μmol). The reaction mixture was stirred at 20° C. for 1 hour and then the volatiles were removed in vacuo. The residue was dissolved in DCM (2 mL) and transferred into a phase separator. The organic layer was washed with sat NH₄Cl (1×2 mL), water (2 mL) and then brine (2 mL). The organic layers was concentrated in vacuo to afford 1-(2-(1-(4-fluorophenyl)-6-methyl-1H-indazol-5-yl)-4-((2-methyl-2H-1,2,3-triazol-4-yl)sulfonyl)piperazin-1-yl)propan-2-ol Intermediate AC (46.0 mg, 89.6 μmol, 92%) as a flocculent white solid; Rt 1.52 min (Method 7); m/z 514.4 (M+H)+ (ES+).

Example 158: 1-(4-fluorophenyl)-5-(1-(2-fluoropropyl)-4-((2-methyl-2H-1,2,3-triazol-4-yl)sulfonyl)piperazin-2-yl)-6-methyl-1H-indazole

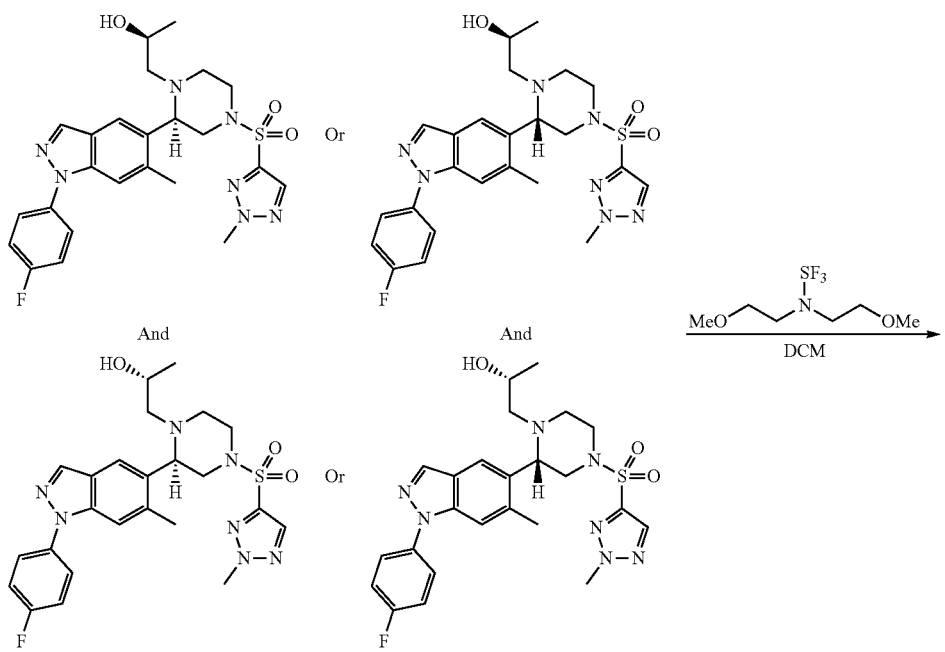

-continued

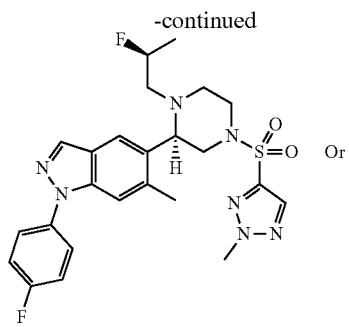

Or

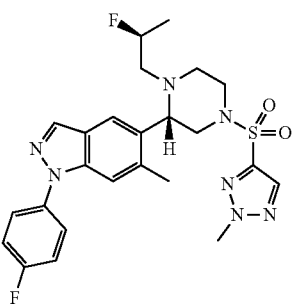

And

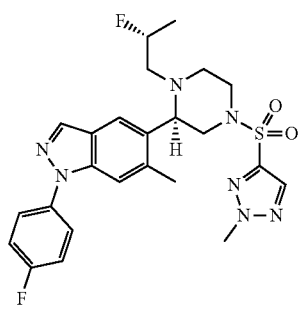

Or

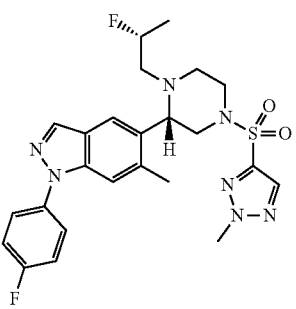

To a stirred solution of 1-(2-(1-(4-fluorophenyl)-6-methyl-1H-indazol-5-yl)-4-((2-methyl-2H-1,2,3-triazol-4-yl)sulfonyl)piperazin-1-yl)propan-2-ol Intermediate AC (46.0 mg, 89.6 µmol) in dry DCM (1.00 mL) under a nitrogen atmosphere at −10° C. was added deoxofluor (86.7 mg, 100 µL, 50% Wt, 196 µmol). The reaction mixture was stirred for 30 minutes and then raised to 20° C. and held for 18 hours. The reaction mixture was quenched with 2M NaOH (2 mL) and transferred into a phase separator. The organic layer was extracted and washed with brine. The organic layer was then adsorbed onto silica gel. The crude product was purified by chromatography on silica gel (4 g cartridge, 0-100% EtOAc/isohexane) to afford 1-(4-fluorophenyl)-5-(1-(2-fluoropropyl)-4-((2-methyl-2H-1,2,3-triazol-4-yl)sulfonyl)piperazin-2-yl)-6-methyl-1H-indazole Example 158 (15.8 mg, 29 µmol, 33%) as a white solid; Rt 2.09 and 2.10 min (Method 7); m/z 516.3 (M+H)+ (ES+).

Example 159: 6-fluoro-1-(4-fluorophenyl)-5-(1-isobutyl-4-((2-methyl-2H-1,2,3-triazol-4-yl)sulfonyl)piperazin-2-yl)-1H-indazole

TABLE 17

The example shown in the table below was prepared by similar methods to those described in Example 1

| Example | Structure | LC-MS analysis |
|---|---|---|
| 159 | 6-fluoro-1-(4-fluorophenyl)-5-(1-isobutyl-4-((2-methyl-2H-1,2,3-triazol-4-yl)sulfonyl)piperazin-2-yl)-1H-indazole | R$^t$ 2.03 min (Method 7); m/z 575.4 (M + H)$^+$ (ES$^+$) |

Example 160: 5-(1-((2,2-difluorocyclopropyl)methyl)-4-((2-methyl-2H-1,2,3-triazol-4-yl)sulfonyl)piperazin-2-yl)-1-(4-fluorophenyl)-6-methyl-1H-indazole Intermediate AD: (2,2-difluorocyclopropyl)(2-(1-(4-fluorophenyl)-6-methyl-1H-indazol-5-yl)-4-((2-methyl-2H-1,2,3-triazol-4-yl)sulfonyl)piperazin-1-yl)methanone

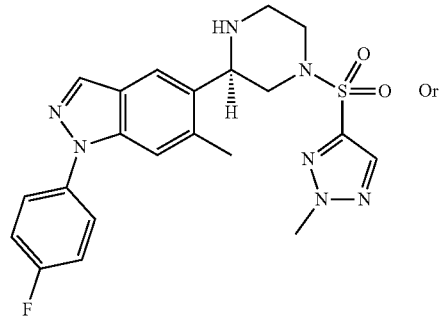

Or

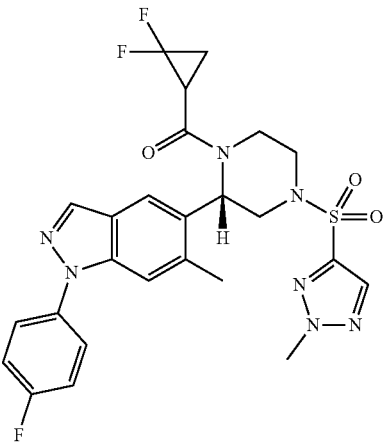

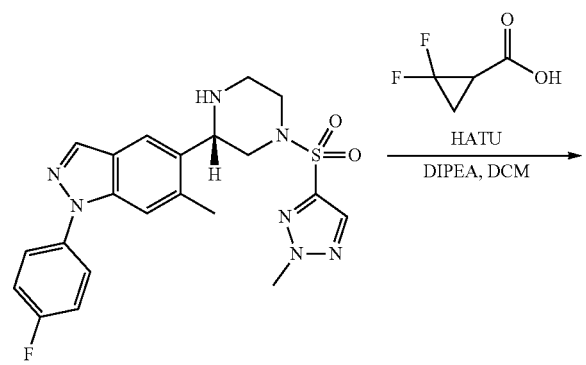

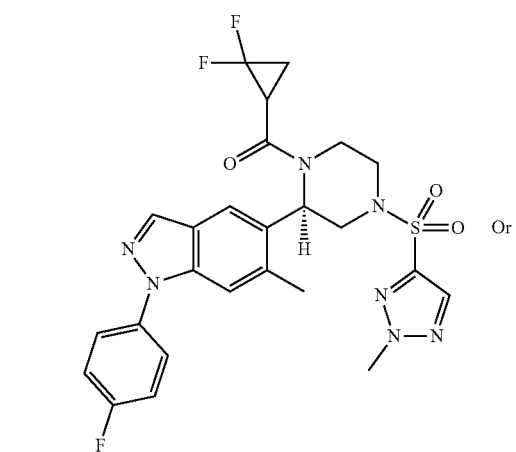

Or

To a solution of 1-(4-fluorophenyl)-6-methyl-5-(4-((2-methyl-2H-1,2,3-triazol-4-yl)sulfonyl)piperazin-2-yl)-1H-indazole (100 mg, 220 μmol) in DCM (3.00 mL) were added 2,2-difluorocyclopropane-1-carboxylic acid (40.2 mg, 329 μmol), DIPEA (85.1 mg, 115 μL, 659 μmol) and HATU (125 mg, 329 μmol). The reaction mixture was stirred for 3 hours at rt before being quenched with sat. aq. NaHCO$_3$ (5 mL). The layers were separated, and the aqueous layer extracted with DCM (3×5 mL). Combined organic extracts were washed with brine (10 mL), dried over MgSO$_4$ and concentrated in vacuo. The crude product was purified by chromatography on silica gel (4 g cartridge, 0-100% EtOAc/isohexane) to afford (2,2-difluorocyclopropyl)(2-(1-(4-fluorophenyl)-6-methyl-1H-indazol-5-yl)-4-((2-methyl-2H-1,2,3-triazol-4-yl)sulfonyl)piperazin-1-yl)methanone Intermediate AD (95 mg, 0.15 mmol, 70%) as a mixture of diastereomers as an off-white solid; Rt 1.96 and 1.99 min (Method 9); m/z 560.2 (M+H)+ (ES+).

TABLE 18

The example shown in the table below was prepared by similar methods to those described in Example 154 using Intermediate AD

| Example | Structure | LC-MS analysis |
|---|---|---|
| 160 | 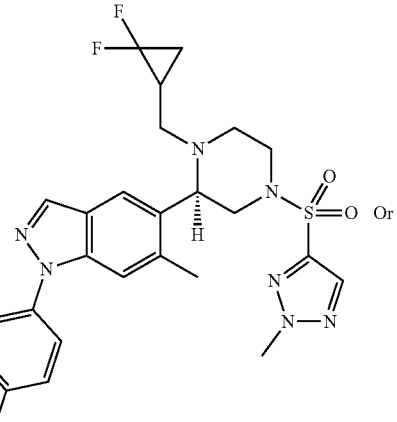<br>5-(1-((2,2-difluorocyclopropyl)methyl)-4-((2-methyl-2H-1,2,3-triazol-4-yl)sulfonyl)piperazin-2-yl)-1-(4-fluorophenyl)-6-methyl-1H-indazole | $R^t$ 2.13 and 2.16 min (Method 9); m/z 546.2 $(M + H)^+$ $(ES^+)$ |

Example 161: 1-(4-fluorophenyl)-6-methyl-5-(4-((2-methyl-2H-1,2,3-triazol-4-yl)sulfonyl)-1-neopentylpiperazin-2-yl)-1H-indazole Intermediate AE: 1-(2-(1-(4-fluorophenyl)-6-methyl-1H-indazol-5-yl)-4-((2-methyl-2H-1,2,3-triazol-4-yl)sulfonyl)piperazin-1-yl)-2,2-dimethyl-propan-1-one

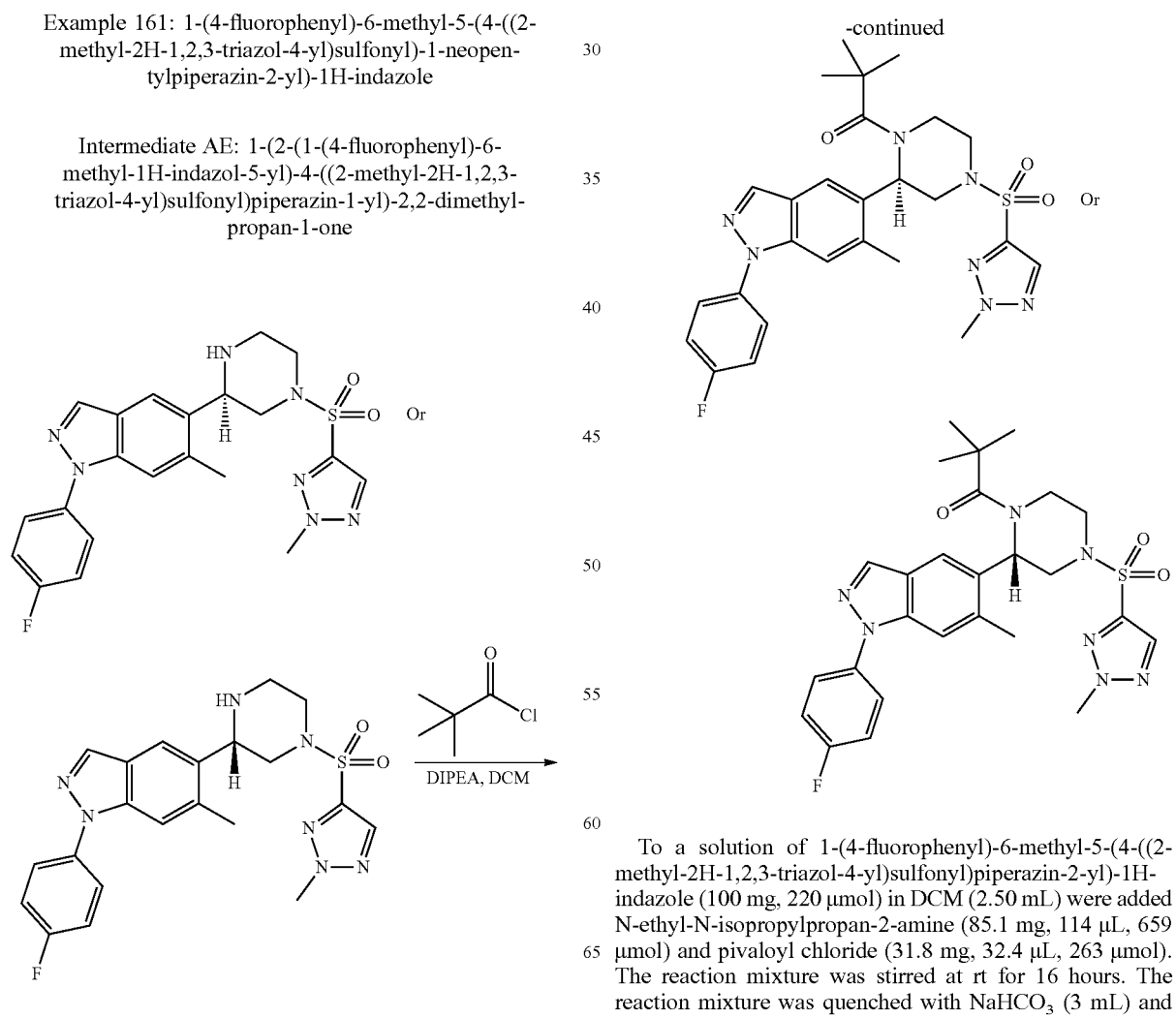

To a solution of 1-(4-fluorophenyl)-6-methyl-5-(4-((2-methyl-2H-1,2,3-triazol-4-yl)sulfonyl)piperazin-2-yl)-1H-indazole (100 mg, 220 µmol) in DCM (2.50 mL) were added N-ethyl-N-isopropylpropan-2-amine (85.1 mg, 114 µL, 659 µmol) and pivaloyl chloride (31.8 mg, 32.4 µL, 263 µmol). The reaction mixture was stirred at rt for 16 hours. The reaction mixture was quenched with NaHCO₃ (3 mL) and the mixture transferred to a phase separator, where the aqueous was further extracted with DCM (2×3 mL). Combined organics were concentrated in vacuo. The crude product was purified by chromatography on silica gel (4 g cartridge, 0-100% EtOAc/isohexane) to afford 1-(2-(1-(4-fluorophenyl)-6-methyl-1H-indazol-5-yl)-4-((2-methyl-2H-1,2,3-triazol-4-yl)sulfonyl)piperazin-1-yl)-2,2-dimethylpropan-1-one Intermediate AE (89.0 mg, 0.16 mmol, 71%, 95% Purity) as a flocculent white solid; Rt 2.06 min (Method 9); m/z 540.2 (M+H)+ (ES+). δH (DMSO-d6, 400 MHz) δ 8.33 (s, 1H), 8.31 (d, J=0.9 Hz, 1H), 7.93 (s, 1H), 7.81-7.75 (m, 2H), 7.60 (s, 1H), 7.47-7.39 (m, 2H), 5.57 (t, J=5.6 Hz, 1H), 4.25 (m, 4H), 3.83 (dd, J=13.4, 6.1 Hz, 1H), 3.74-3.53 (m, 2H), 3.31-3.26 (m, 1H), 3.12-2.95 (m, 1H), 2.37 (s, 3H), 1.15 (s, 9H).

Example 161: 1-(4-fluorophenyl)-6-methyl-5-(4-((2-methyl-2H-1,2,3-triazol-4-yl)sulfonyl)-1-neopentylpiperazin-2-yl)-1H-indazole

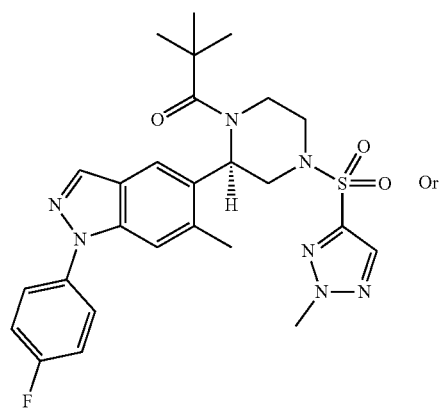

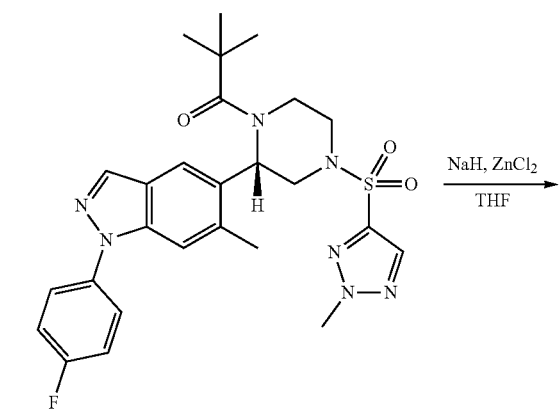

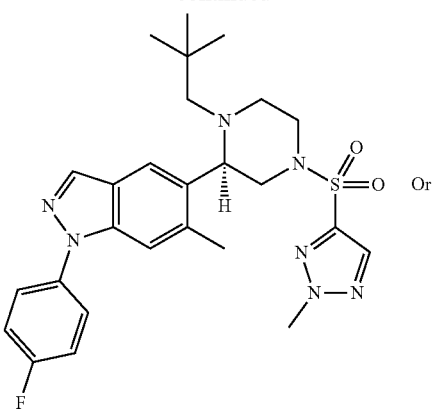 Or

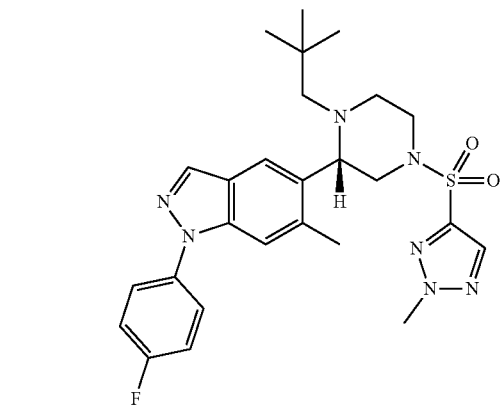

To a suspension of sodium hydride (60% in paraffin oil) (8.0 mg, 60% Wt, 200 μmol) in THF (0.20 mL) was added zinc(II) chloride (0.5 M in THF) (13.6 mg, 200 μL, 0.50 molar, 100 μmol). The suspension was stirred at rt for 15 mins before the addition of 1-(2-(1-(4-fluorophenyl)-6-methyl-1H-indazol-5-yl)-4-((2-methyl-2H-1,2,3-triazol-4-yl)sulfonyl)piperazin-1-yl)-2,2-dimethylpropan-1-one Intermediate AE (20.0 mg, 37.1 μmol) (as a solution in THF (0.50 mL)). The reaction mixture was stirred at rt for 2 hours, at 40° C. for 2 hours and then at 50° C. for 18 hours. The reaction mixture was quenched with MeOH (0.5 mL) and water (3 mL). DCM (5 mL) was added, and the mixture transferred to a phase separator. The aqueous was further extracted with DCM (2×2 mL). Combined organic extracts were concentrated in vacuo. The crude product was purified by chromatography on silica gel (4 g cartridge, 0-100% EtOAc/isohexane) to afford 1-(4-fluorophenyl)-6-methyl-5-(4-((2-methyl-2H-1,2,3-triazol-4-yl)sulfonyl)-1-neopentylpiperazin-2-yl)-1H-indazole Example 161 (1.60 mg, 2.9 μmol, 7.8%) as a white solid; Rt 2.12 min (Method 9); m/z 526.2 (M+H)+ (ES+). δH (MeOD, 400 MHz) δ 8.17 (d, J=0.9 Hz, 1H), 8.05 (s, 1H), 7.93 (s, 1H), 7.81-7.71 (m, 2H), 7.58 (s, 1H), 7.36 (t, J=8.7 Hz, 2H), 4.33 (s, 3H), 3.76 (dd, J=10.6, 3.3 Hz, 2H), 3.67-3.56 (m, 1H), 3.45 (d, J=12.2 Hz, 1H), 2.94 (td, J=11.9, 2.7 Hz, 1H), 2.77 (dd, J=11.9, 10.5 Hz, 1H), 2.56 (s, 3H), 2.50 (td, J=12.1, 3.0 Hz, 1H), 2.25 (d, J=13.4 Hz, 1H), 1.90 (d, J=13.4 Hz, 1H), 0.75 (s, 9H).

Example 162: 1-(2-(1-(4-fluorophenyl)-6-methyl-1H-indazol-5-yl)-4-((2-methyl-2H-1,2,3-triazol-4-yl)sulfonyl)piperazin-1-yl)-2-methylpropan-2-ol

TABLE 19

The example shown in the table below was prepared by similar methods to those described in Example 161

| Example | Structure | LC-MS analysis |
|---------|-----------|----------------|
| 162 | 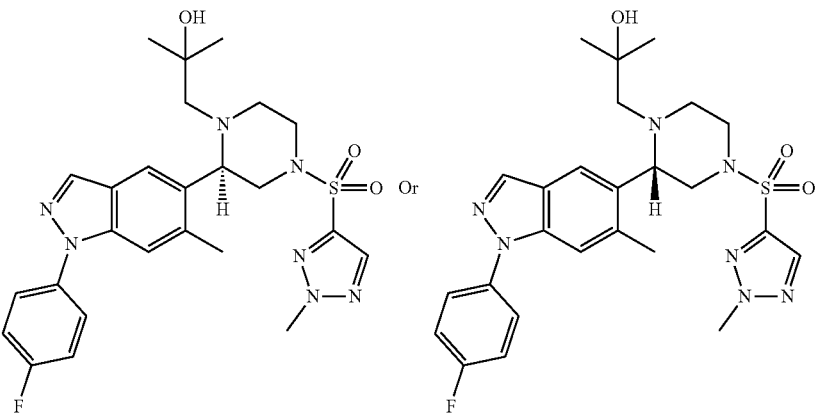 [SMILES: Cc1cc2c(cnn2-c2ccc(F)cc2)cc1[C@@H]1CN(S(=O)(=O)c2cnn(C)n2)CCN1CC(C)(C)O ; Cc1cc2c(cnn2-c2ccc(F)cc2)cc1[C@H]1CN(S(=O)(=O)c2cnn(C)n2)CCN1CC(C)(C)O] 1-(2-(1-(4-fluorophenyl)-6-methyl-1H-indazol-5-yl)-4-((2-methyl-2H-1,2,3-triazol-4-yl)sulfonyl)piperazin-1-yl)-2-methylpropan-2-ol | $R^t$ 1.49 min (Method 9); m/z 528.2 $(M + H)^+$ $(ES^+)$ |

Example 162a: 5-(1-(2-fluoro-2-methylpropyl)-4-((2-methyl-2H-1,2,3-triazol-4-yl)sulfonyl)piperazin-2-yl)-1-(4-fluorophenyl)-6-methyl-1H-indazole Intermediate AF: 2-fluoro-1-(2-(1-(4-fluorophenyl)-6-methyl-1H-indazol-5-yl)-4-((2-methyl-2H-1,2,3-triazol-4-yl)sulfonyl)piperazin-1-yl)-2-methylpropan-1-one

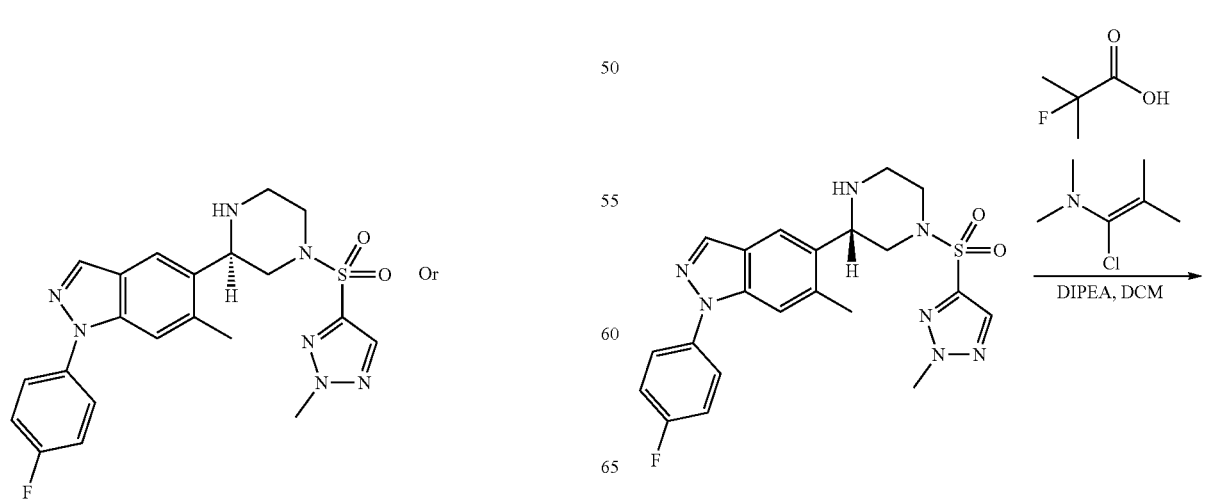

435
-continued

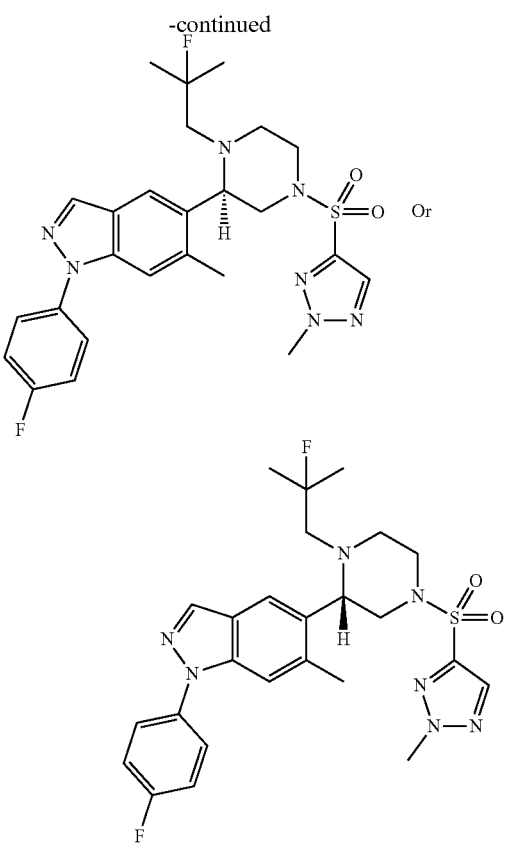

To a solution of 2-fluoro-2-methylpropanoic acid (34.9 mg, 329 μmol) in DCM (1.00 mL) were added 1-chloro-N,N,2-trimethylprop-1-en-1-amine (88.0 mg, 87.1 μL, 659 μmol) and DMF (2 drops). The reaction mixture was stirred at rt for 2 hours and then at 50° C. for 4 hours before being cooled to rt. In a separate vial, 1-(4-fluorophenyl)-6-methyl-5-(4-((2-methyl-2H-1,2,3-triazol-4-yl)sulfonyl)piperazin-2-yl)-1H-indazole (30.0 mg, 65.9 μmol) was dissolved in DCM (1.00 mL) and treated with N-ethyl-N-isopropylpropan-2-amine (128 mg, 172 μL, 988 μmol). The solution of acid chloride generated was then added dropwise and the reaction mixture stirred at rt for 16 hours. The reaction mixture was then quenched with water (8 mL) and diluted with DCM (5 mL). The layers were separated, and the aqueous layer extracted with DCM (2×5 mL). Combined organic extracts were dried over MgSO$_4$ and concentrated in vacuo. The crude product was purified by chromatography on silica gel (4 g cartridge, 0-100% EtOAc/isohexane) to afford 2-fluoro-1-(2-(1-(4-fluorophenyl)-6-methyl-1H-indazol-5-yl)-4-((2-methyl-2H-1,2,3-triazol-4-yl)sulfonyl)piperazin-1-yl)-2-methylpropan-1-one Intermediate AF (33.0 mg, 49 μmol, 74%) as an off-white solid; Rt 2.04 min (Method 9); m/z 544.2 (M+H)+ (ES+).

TABLE 20

The example shown in the table below was prepared by similar methods to those described in Example 154 using Intermediate AF

| Example | Structure | LC-MS analysis |
| --- | --- | --- |
| 162a | 5-(1-(2-fluoro-2-methylpropyl)-4-((2-methyl-2H-1,2,3-triazol-4-yl)sulfonyl)piperazin-2-yl)-1-(4-fluorophenyl)-6-methyl-1H-indazole | R$^r$ 2.27 min (Method 9); m/z 530.2 (M + H)$^+$ (ES$^+$) |

Example 163: 1-(4-fluorophenyl)-6-methyl-5-(4-((2-methyl-2H-1,2,3-triazol-4-yl)sulfonyl)-1-(3,3,3-trifluoro-2,2-dimethylpropyl)piperazin-2-yl)-1H-indazole Intermediate AG: 3,3,3-trifluoro-1-(2-(1-(4-fluorophenyl)-6-methyl-1H-indazol-5-yl)-4-((2-methyl-2H-1,2,3-triazol-4-yl)sulfonyl)piperazin-1-yl)-2,2-dimethylpropan-1-one To a solution of 3,3,3-trifluoro-2,2-dimethylpropanoic acid (34.3 mg, 220 µmol) in DCM (1.00 mL) were added 1-(chloro(pyrrolidin-1-yl)methylene)pyrrolidin-1-ium hexafluorophosphate(V) (87.6 mg, 263 µmol) and N-ethyl-N-isopropylpropan-2-amine (85.1 mg, 114 µL, 3 Eq, 659 µmol). The reaction mixture was stirred for 5 min at rt. 1-(4-fluorophenyl)-6-methyl-5-(4-((2-methyl-2H-1,2,3-triazol-4-yl)sulfonyl)piperazin-2-yl)-1H-indazole (100 mg, 220 µmol) was then added and the reaction mixture heated in the microwave (150 W) at 100° C. for 10 hours. The reaction mixture was diluted with DCM (2 mL) and transferred into a phase separator. The organic layer was washed with 2M NaOH (1×2 mL). The combined organic layers were collected and adsorbed onto silica gel. The crude product was purified by chromatography on silica gel (4 g cartridge, 25-100% EtOAc/isohexane) to afford 3,3,3-trifluoro-1-(2-(1-(4-fluorophenyl)-6-methyl-1H-indazol-5-yl)-4-((2-methyl-2H-1,2,3-triazol-4-yl)sulfonyl)piperazin-1-yl)-2,2-dimethylpropan-1-one Intermediate AG (100 mg, 0.16 mmol, 71%) as a clear colourless solid; Rt 2.13 min (Method 7); m/z 594.5 (M+H)+ (ES+).

Example 163: 1-(4-fluorophenyl)-6-methyl-5-(4-((2-methyl-2H-1,2,3-triazol-4-yl)sulfonyl)-1-(3,3,3-trifluoro-2,2-dimethylpropyl)piperazin-2-yl)-1H-indazole

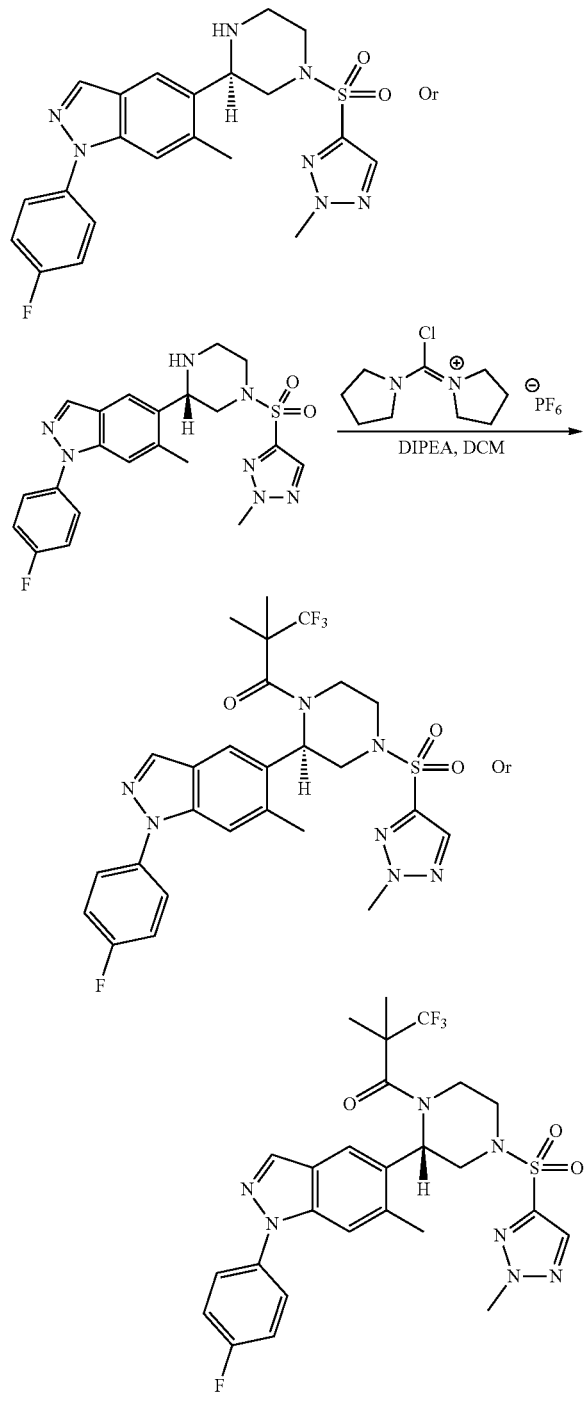
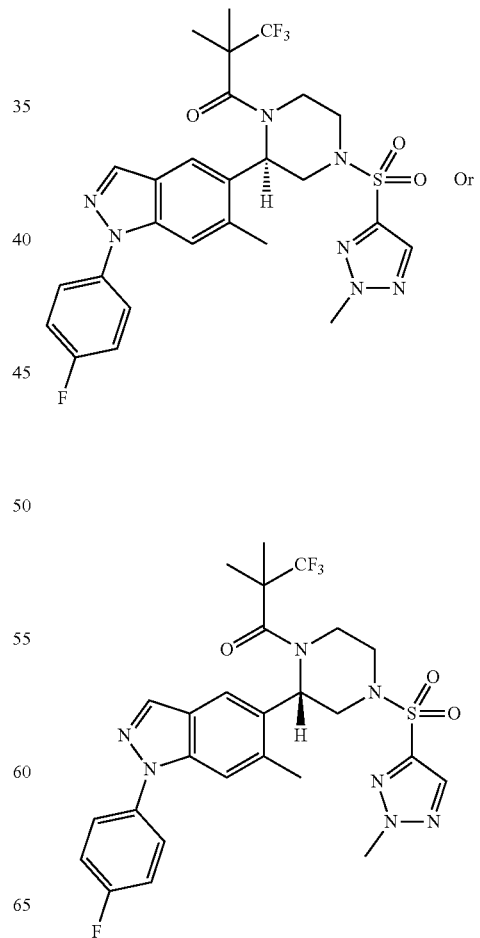

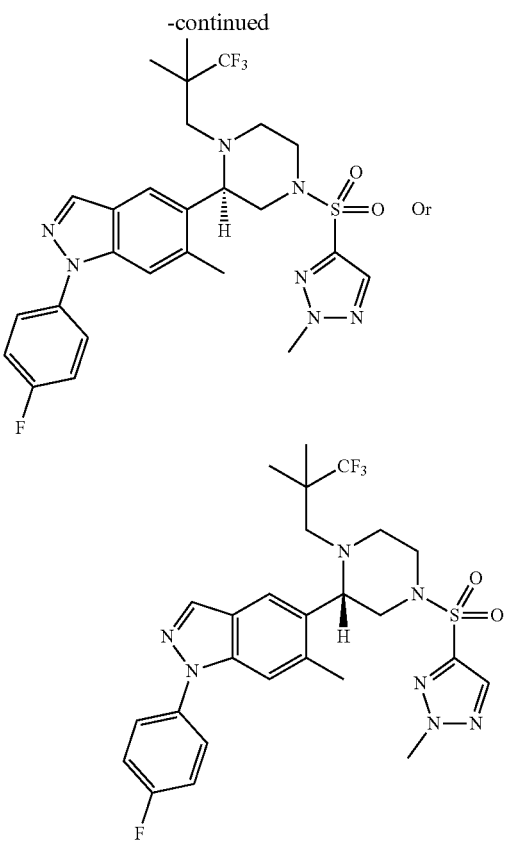

A suspension of 3,3,3-trifluoro-1-(2-(1-(4-fluorophenyl)-6-methyl-1H-indazol-5-yl)-4-((2-methyl-2H-1,2,3-triazol-4-yl)sulfonyl)piperazin-1-yl)-2,2-dimethylpropan-1-one Intermediate AG (40.0 mg, 67.4 μmol) was dosed with borane tetrahydrofuran complex (57.9 mg, 674 μL, 1.00 molar, 674 μmol) and the reaction mixture heated to 65° C. for 18 hours. An additional charge of borane tetrahydrofuran complex (57.9 mg, 674 μL, 1.00 molar, 674 μmol) was made and the reaction mixture heated for a further 5 hours. The reaction mixture was quenched with 2M NaOH and transferred into a phase separator. The cloudy solution was washed with DCM (5 mL). The organic layer was extracted and concentrated in vacuo. The concentrate was dissolved in 1.4 mL with DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH C18 ODB prep column, 130 Å, 5 μm, 30 mm×100 mm, flow rate 40 mL min-1 eluting with a 0.1% formic acid in water-MeCN gradient over 12.5 mins using UV across all wavelengths with PDA as well as a QDA and ELS detector. At-column dilution pump gives 2 mL min-1 methanol over the entire method, which is included in the following MeCN percentages. Gradient information: 0.0-0.5 min, 57.5% MeCN; 0.5-10.5 min, ramped from 57.5% MeCN to 87.5% MeCN; 10.5-10.6 min, ramped from 87.5% MeCN to 100% MeCN; 10.6-12.5 min, held at 100% MeCN. The clean fractions were evaporated in a Genevac prior to azeotroping with MeCN to afford 1-(4-fluorophenyl)-6-methyl-5-(4-((2-methyl-2H-1,2,3-triazol-4-yl)sulfonyl)-1-(3,3,3-trifluoro-2,2-dimethylpropyl) piperazin-2-yl)-1H-indazole Example 163 (3.80 mg, 6.2 μmol, 9.2%) as a white solid; Rt 2.49 min (Method 7); m/z 580.2 (M+H)+ (ES+).

Example 164: 1-(4-fluorophenyl)-5-(1-isobutyl-4-((2-methyl-2H-1,2,3-triazol-4-yl)sulfonyl)piperazin-2-yl)-6-(trifluoromethyl)-1H-indazole Intermediate AH:
5-nitro-6-(trifluoromethyl)-1H-indazole

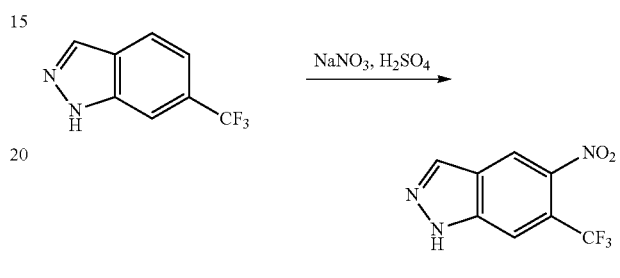

6-(Trifluoromethyl)-1H-indazole (4400 mg, 23.64 mmol) was suspended in sulfuric acid (27.82 g, 15.12 mL, 50% Wt, 141.8 mmol) and the mixture was stirred for 5 mins before the addition of sodium nitrate (2.813 g, 33.09 mmol). Stirring continued for 60 mins before pouring the reaction mixture over ice and neutralising with 0.88 ammonia. The solid precipitate was collected by filtration, washed with water and dried in vac oven to give 5-nitro-6-(trifluoromethyl)-1H-indazole Intermediate AH (4.20 g, 18.2 mmol, 76.9%, 100% Purity) as a cream coloured solid; Rt 1.54 min (Method 7); m/z 232.4 (M+H)+ (ES+).

Intermediate AI:
6-(trifluoromethyl)-1H-indazol-5-amine

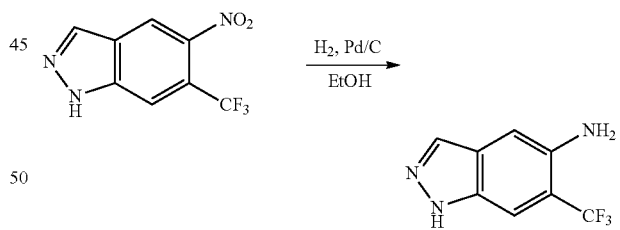

5-Nitro-6-(trifluoromethyl)-1H-indazole Intermediate AH (4.50 g, 19.5 mmol) was dissolved in EtOH (50.0 mL) and treated with palladium on carbon (207 mg, 1.95 mmol). The mixture was purged with nitrogen (×3) then hydrogen (×3) before being hydrogenated at 5 atm overnight at 40° C. The catalyst was removed by filtration, washing with MeOH (2×20 mL). The solvent was removed in vacuo to give a pale yellow solid. The crude product was purified by chromatography on silica gel (120 g cartridge, 0-100% EtOAc/isohexane) to afford 6-(trifluoromethyl)-1H-indazol-5-amine Intermediate AI (3.60 g, 17.2 mmol, 88%) as an off white solid; Rt 1.03 min (Method 7); m/z 201.8 (M+H)+ (ES+).

Intermediate AJ: 5-bromo-6-(trifluoromethyl)-1H-indazole

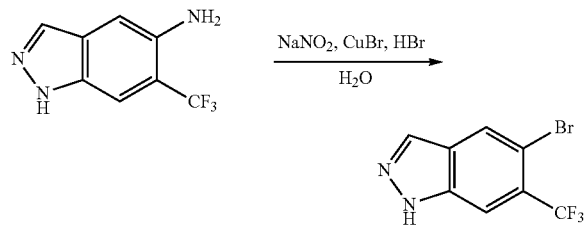

6-(Trifluoromethyl)-1H-indazol-5-amine Intermediate AI (4770 mg, 23.71 mmol) was dissolved in HBr (25.3 g, 17.0 mL, 48% Wt, 150 mmol) and water (54.0 mL). The resulting solution was cooled to 0° C. and treated dropwise with a solution of sodium nitrite (1.800 g, 6.09 mmol) in water (68.0 mL). The reaction was stirred at 0° C. for 15 mins. This solution was then added dropwise into a stirring solution of copper(I) bromide (10.21 g, 3 Eq, 71.14 mmol) in HBr (50.7 g, 34.0 mL, 48% Wt, 12.7 Eq, 301 mmol) and water (70.0 mL) at room temperature and the reaction stirred overnight. The reaction was cooled to 0° C. and basified using concentrated ammonium hydroxide. The aqueous was extracted with DCM (3×100 mL), the bulked organic extracts were dried using sodium sulfate and concentrated in vacuo to give 5-bromo-6-(trifluoromethyl)-1H-indazole Intermediate AJ (5.05 g, 17 mmol, 72%) as a mustard solid; Rt 1.74 min (Method 7); m/z 264.8/266.7 (M+H)+ (ES+).

Intermediate AK: 5-bromo-1-(4-fluorophenyl)-6-(trifluoromethyl)-1H-indazole

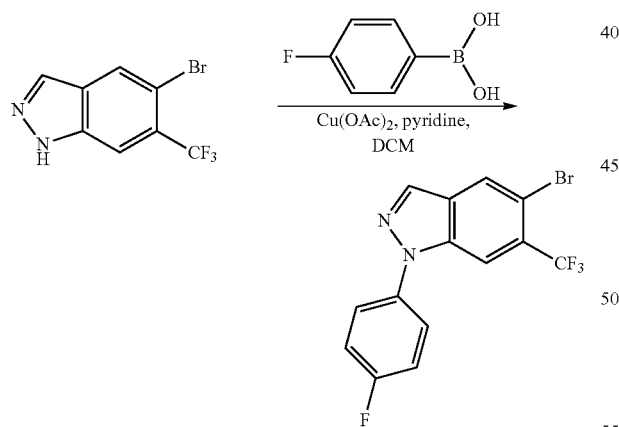

Pyridine (2.98 g, 3.04 mL, 37.7 mmol) was added to a solution of 5-bromo-6-(trifluoromethyl)-1H-indazole Intermediate AJ (5.00 g, 18.9 mmol), (4-fluorophenyl)boronic acid (5.28 g, 37.7 mmol) and copper (II) acetate (3.43 g, 18.9 mmol) in DCM (50.0 mL). The reaction mixture was stirred at 20° C. for 48 hours. The reaction mixture was absorbed onto silica and the crude product was purified by chromatography on silica gel (220 g cartridge, 5-30% EtOAc/isohexane) to afford 5-bromo-1-(4-fluorophenyl)-6-(trifluoromethyl)-1H-indazole (5.01 g, 12 mmol, 64%) as a cream solid; Rt 2.32 min (Method 7); m/z 359.2/361.0 (M+H)+ (ES+). δH (DMSO-d6, 400 MHz) δ 8.51 (d, J=0.9 Hz, 1H), 8.48 (s, 1H), 8.11 (s, 1H), 7.89-7.80 (m, 2H), 7.54-7.43 (m, 2H).

TABLE 21

The example shown in the table below was prepared by similar methods to those described in Example 1 using Intermediate AK

| Example | Structure | LC-MS analysis |
|---|---|---|
| 164 | 1-(4-fluorophenyl)-5-(1-isobutyl-4-((2-methyl-2H-1,2,3-triazol-4-yl)sulfonyl)piperazin-2-yl)-6-(trifluoromethyl)-1H-indazole | R' 2.48 min (Method 7); m/z 566.4 (M + H)+ (ES+) |

Example 165: 1-methyl-5-(6-methyl-5-(4-((2-methyl-2H-1,2,3-triazol-4-yl)sulfonyl)-1-(3,3,3-trifluoropropyl)piperazin-2-yl)-1H-indazol-1-yl)pyridin-2(1H)-one

Intermediate AL: 5-bromo-6-methyl-1-(tetrahydro-2H-pyran-2-yl)-1H-indazole

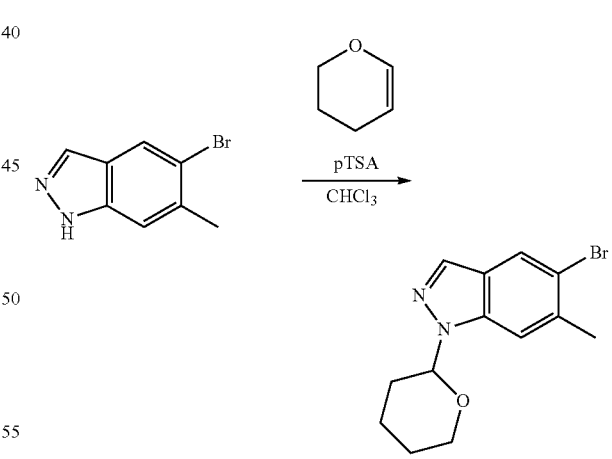

To a solution of 5-bromo-6-methyl-1H-indazole (25.00 g, 118.4 mmol) and dihydropyran (19.93 g, 21.5 mL, 236.9 mmol) in chloroform (400 mL) was added p-toluenesulfonic acid monohydrate (2.50 g, 13.1 mmol). The brown suspension was stirred at room temperature for 16 hours and then heated at reflux for 2 hours. The reaction mixture was washed with sodium bicarbonate (2×200 mL) and then brine, (200 mL), the organic layer was dried using magnesium sulfate and the solvent was removed under reduced pressure to give 5-bromo-6-methyl-1-(tetrahydro-2H-pyran- 2-yl)-1H-indazole Intermediate AL (40.7 g, 0.10 mol, 87%) as a brown oil; Rt 2.05 min (Method 7); m/z 295.2/297.2 (M+H)+ (ES+).

Intermediate AM: 6-methyl-1-(tetrahydro-2H-pyran-2-yl)-5-(4,4,5,5-tetramethyl-1,3,2-dioxaborolan-2-yl)-1H-indazole

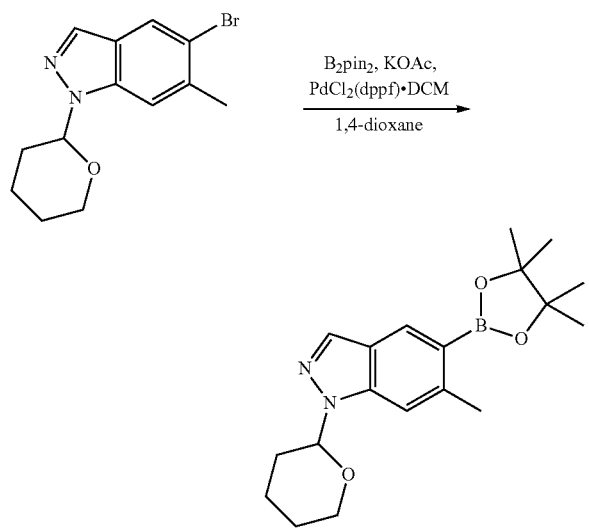

To a mixture of 5-bromo-6-methyl-1-(tetrahydro-2H-pyran-2-yl)-1H-indazole Intermediate AL (40.7 g, 138 mmol), potassium acetate (50.0 g, 509 mmol) and 4,4,4',4',5,5,5',5'-octamethyl-2,2'-bi(1,3,2-dioxaborolane) (53.6 g, 211 mmol) in dry 1,4-dioxane (689 mL) was added PdCl₂(dppf)-CH₂Cl₂ adduct (11.3 g, 13.8 mmol). The reaction mixture was stirred for 18 hours at 90° C. The reaction mixture was filtered and the filtrate was concentrated in vacuo. The residue was taken up in EtOAc (400 mL). The solution was washed with 1:1 brine:distilled water (500 mL) and the organic layer extracted. The organic layer was washed with NaHCO₃ (1×500 mL). The combined organic layers were collected, dried over magnesium sulfate, filtered and concentrated in vacuo to afford 6-methyl-1-(tetrahydro-2H-pyran-2-yl)-5-(4,4,5,5-tetramethyl-1,3,2-dioxaborolan-2-yl)-1H-indazole Intermediate AM (52.0 g, 0.12 mol, 87%) as a brown oil; Rt 2.28 min (Method 7); m/z 343.5 (M+H)+ (ES+).

Intermediate AN: 6-methyl-5-(pyrazin-2-yl)-1-(tetrahydro-2H-pyran-2-yl)-1H-indazole

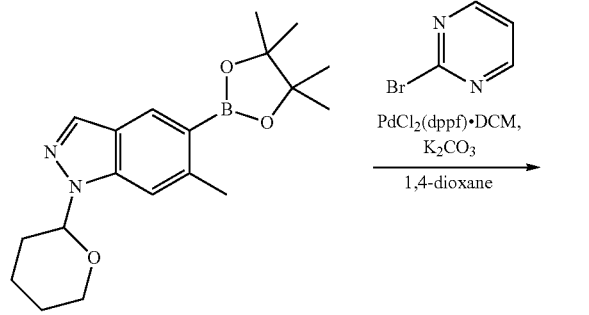

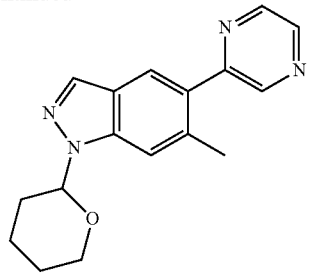

To a stirred solution of 6-methyl-1-(tetrahydro-2H-pyran-2-yl)-5-(4,4,5,5-tetramethyl-1,3,2-dioxaborolan-2-yl)-1H-indazole Intermediate AM (52.0 g, 50% Wt, 76.0 mmol) in dry 1,4-dioxane (304 mL) and water (76.0 mL) was added potassium carbonate (21.0 g, 152 mmol) and 2-bromopyrazine (19.5 g, 123 mmol). The reaction mixture was sparged for 5 mins with N₂ prior to the addition of Pd(dppf)Cl₂·DCM (6.20 g, 0.1 Eq, 7.60 mmol). The reaction mixture was then heated to 90° C. and stirred for 16 hours. The reaction mixture was concentrated in vacuo and partitioned between DCM (400 mL) and water (400 mL). The DCM layer was drawn off and washed twice more with brine (2×400 mL). The organic layer was then concentrated in vacuo to afford 52 g of crude brown oil. The crude product was purified by chromatography in 2 passes on silica gel (220 g cartridge, 20-100 EtOAc/isohexane) to afford 6-methyl-5-(pyrazin-2-yl)-1-(tetrahydro-2H-pyran-2-yl)-1H-indazole Intermediate AN (8.61 g, 27 mmol, 36%) as a light yellow solid. The batches were combined for analysis. Rt 1.57 min (Method 7); m/z 295.3 (M+H)+ (ES+). δH (DMSO-d6, 400 MHz) δ 8.85 (d, J=1.5 Hz, 1H), 8.74 (dd, J=2.6, 1.5 Hz, 1H), 8.64 (d, J=2.6 Hz, 1H), 8.13 (d, J=0.9 Hz, 1H), 7.86 (s, 1H), 7.70 (d, J=1.0 Hz, 1H), 5.87 (dd, J=9.7, 2.6 Hz, 1H), 4.01-3.86 (m, 1H), 3.76 (ddd, J=13.7, 7.1, 5.0 Hz, 1H), 2.46 (s, 3H), 2.44-2.35 (m, 1H), 2.14-1.93 (m, 2H), 1.84-1.67 (m, 1H), 1.66-1.55 (m, 2H).

Intermediate AO: 6-methyl-5-(piperazin-2-yl)-1-(tetrahydro-2H-pyran-2-yl)-1H-indazole

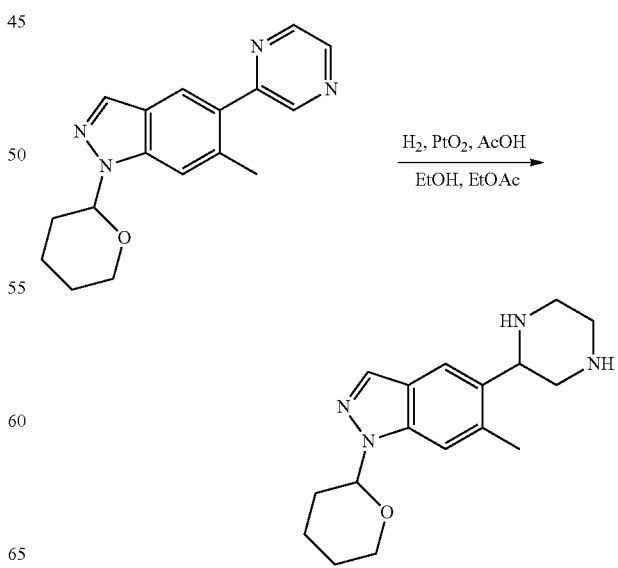

To a suspension of 6-methyl-5-(pyrazin-2-yl)-1-(tetrahydro-2H-pyran-2-yl)-1H-indazole (4.11 g, 98% Wt, 13.7 mmol) Intermediate AN in EtOH (230 mL) and acetic acid (24.7 g, 23.5 mL, 410 mmol) and EtOAc (50.0 mL) was added platinum(IV) oxide (500 mg, 2.20 mmol). The reaction mixture was stirred under an atmosphere of $H_2$ (5 bar) at 60° C. for 3 hours. The reaction mixture was then filtered and concentrated in vacuo. The residue was dissolved in EtOAc (250 mL) and washed with 2M NaOH (100 mL). The organic layer was then washed in brine. The combined aqueous layers were back-extracted with more EtOAc (250 mL). Concentration of the organic layers afforded minimal product, which had preferentially partitioned into the aqueous layer. The crude product was loaded onto a column of SCX (50 g) in water. The column was washed with distilled water (200 mL), MeOH (250 mL) and then the product was eluted with 0.7 M ammonia in MeOH. The resultant mixture was concentrated and azeotroped with MeCN in vacuo to afford 6-methyl-5-(piperazin-2-yl)-1-(tetrahydro-2H-pyran-2-yl)-1H-indazole (2.90 g, 8.7 mmol, 63%, 90% Purity) Intermediate AO as a sticky yellow oil; Rt 0.26 min (Method 7); m/z 301.4 (M+H)+ (ES+). δH (MeOD, 400 MHz) δ 7.99 (s, 1H), 7.85 (s, 1H), 7.51 (s, 1H), 5.77 (dt, J=9.9, 2.1 Hz, 1H), 4.14-4.04 (m, 1H), 4.07-3.95 (m, 1H), 3.90-3.75 (m, 1H), 3.16-3.07 (m, 1H), 3.06-2.93 (m, 4H), 2.92-2.81 (m, 1H), 2.65 (dd, J=12.5, 10.4 Hz, 1H), 2.58 (s, 3H), 2.55-2.47 (m, 1H), 2.18-2.08 (m, 1H), 2.05-1.97 (m, 1H), 1.91-1.76 (m, 1H), 1.76-1.62 (m, 2H). 1 exchangeable NH not accounted for.

Intermediate AP: 6-methyl-5-(4-((2-methyl-2H-1,2,3-triazol-4-yl)sulfonyl)piperazin-2-yl)-1-(tetrahydro-2H-pyran-2-yl)-1H-indazole

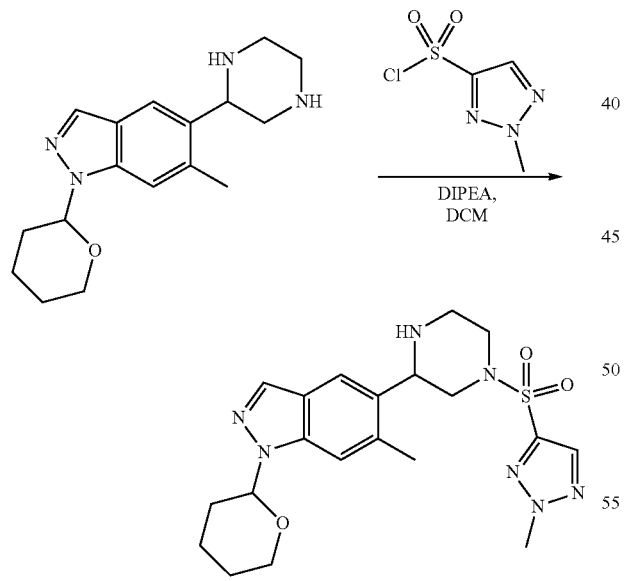

To a stirred solution of 6-methyl-5-(piperazin-2-yl)-1-(tetrahydro-2H-pyran-2-yl)-1H-indazole Intermediate AO (2.90 g, 90% Wt, 8.69 mmol) and DIPEA (3.37 g, 4.54 mL, 26.1 mmol) in dry DCM (86.9 mL) under a nitrogen atmosphere at −3° C. (bath T) was added 2-methyl-2H-1,2,3-triazole-4-sulfonyl chloride (1.66 g, 9.12 mmol) dropwise over 10 minutes, as a DCM solution. The reaction mixture was stirred for 1 hour. The reaction mixture was quenched with sat. NaHCO₃ (50 mL) and transferred into a separating funnel. The organic layer was extracted, and the aqueous layer washed with DCM (25 mL). The combined organic layers were collected, dried over magnesium sulfate, filtered and adsorbed onto silica in vacuo. The crude product was purified by chromatography on silica gel (80 g cartridge, 0-50% (0.7 M ammonia/MeOH)/DCM) and the clean fractions azeotroped in MeCN twice to afford 6-methyl-5-(4-((2-methyl-2H-1,2,3-triazol-4-yl)sulfonyl)piperazin-2-yl)-1-(tetrahydro-2H-pyran-2-yl)-1H-indazole Intermediate AP (3.55 g, 6.4 mmol, 73%) as a sticky yellow solid; Rt 1.33 and 1.36 min (Method 7); m/z 446.1 (M+H)+ (ES+). δH (MeOD, 400 MHz) δ 8.05 (d, J=0.8 Hz, 1H), 7.97 (d, J=0.9 Hz, 1H), 7.81 (s, 1H), 7.54 (s, 1H), 5.78 (dd, J=10.0, 2.7 Hz, 1H), 4.29 (s, 3H), 4.15 (dd, J=10.5, 2.9 Hz, 1H), 4.05-3.97 (m, 2H), 3.90-3.75 (m, 4H), 3.21 (ddd, J=12.5, 3.3, 1.9 Hz, 1H), 3.12-3.00 (m, 1H), 2.90-2.70 (m, 1H), 2.50 (ddd, J=12.0, 8.1, 5.1 Hz, 2H), 2.26-2.09 (m, 2H), 2.02 (dd, J=12.0, 8.9 Hz, 2H), 1.85-1.62 (m, 3H).

Intermediate AQ: 6-methyl-5-(4-((2-methyl-2H-1,2,3-triazol-4-yl)sulfonyl)-1-(3,3,3-trifluoropropyl)piperazin-2-yl)-1-(tetrahydro-2H-pyran-2-yl)-1H-indazole

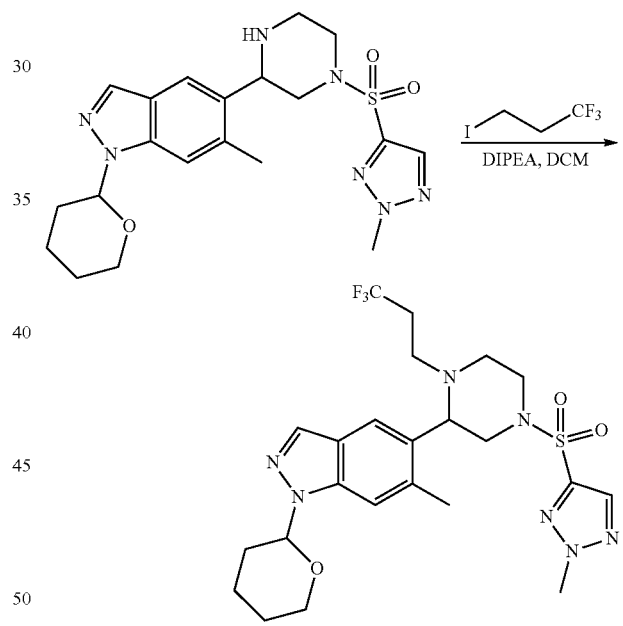

To a solution of 6-methyl-5-(4-((2-methyl-2H-1,2,3-triazol-4-yl)sulfonyl)piperazin-2-yl)-1-(tetrahydro-2H-pyran-2-yl)-1H-indazole Intermediate AP (3.55 g, 7.97 mmol) in MeCN (10.0 mL) were added N-ethyl-N-isopropylpropan-2-amine (6.18 g, 8.33 mL, 47.8 mmol) and 1,1,1-trifluoro-3-iodopropane (8.92 g, 4.67 mL, 39.8 mmol). The reaction mixture was then stirred at 150° C. for 1 hour in a CEM microwave (Pressure 300 psi, Power 150 W). Partial conversion was observed and so reaction was continued for an additional 5 hours at 150° C. The reaction mixture was diluted with EtOAc (25 mL) and transferred into a separating funnel. The organic layer was washed with distilled water (1×50 mL) and then brine (1×50 mL) and then extracted. The combined aqueous layers were then back-extracted with EtOAc (1×50 mL). The combined organic Intermediate AR: 6-methyl-5-(4-((2-methyl-2H-1,2,3-triazol-4-yl)sulfonyl)-1-(3,3,3-trifluoropropyl)piperazin-2-yl)-1H-indazole

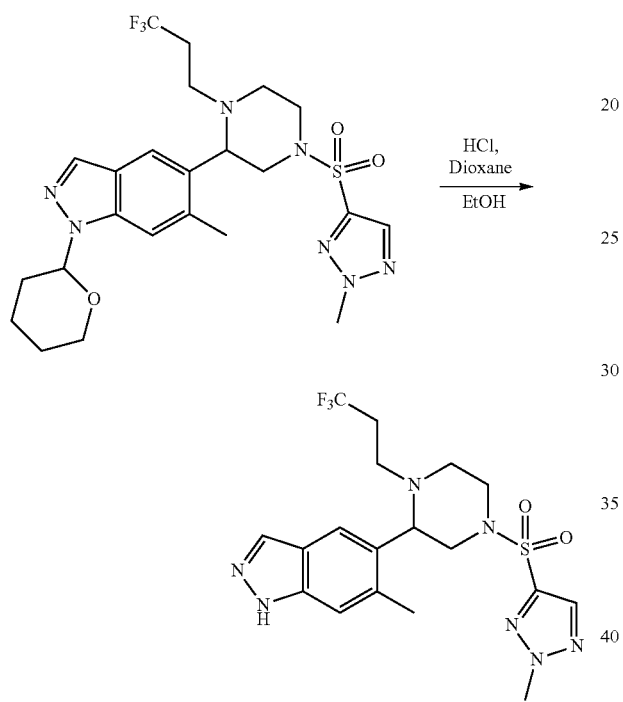

To a solution of 6-methyl-5-(4-((2-methyl-2H-1,2,3-triazol-4-yl)sulfonyl)-1-(3,3,3-trifluoropropyl)piperazin-2-yl)-1-(tetrahydro-2H-pyran-2-yl)-1H-indazole Intermediate AQ (1.70 g, 70% Wt, 2.20 mmol) in EtOH (5.00 mL) was added HCl (in dioxane) (10.5 g, 10.0 mL, 4 molar, 40.0 mmol). The reaction mixture was stirred at 20° C. for 16 hours prior to being loaded onto an SCX column. The crude product was loaded onto a column of SCX (25 g) in MeOH. The column was washed with MeOH and then the product was eluted with 0.7 M ammonia in MeOH. The resultant mixture was concentrated in vacuo to afford 1.6 g material that was concentrated, dissolved in 10 vol % MeOH/DCM and loaded onto silica gel. The crude product was purified by chromatography on silica gel (24 g cartridge, 0-20% (0.7 M Ammonia/MeOH)/DCM) to afford 6-methyl-5-(4-((2-methyl-2H-1,2,3-triazol-4-yl)sulfonyl)-1-(3,3,3-trifluoropropyl)piperazin-2-yl)-1H-indazole Intermediate AR (630 mg, 1.2 mmol, 56%) as a sticky yellow solid; Rt 1.42 min (Method 8); m/z 458.3 (M+H)+ (ES+). δH (DMSO-d6, 400 MHz) δ 8.29 (s, 1H), 7.96 (s, 1H), 7.74 (s, 1H), 7.37 (s, 1H), 4.27 (s, 3H), 3.80-3.62 (m, 2H), 3.58-3.17 (m, 2H), 2.81-2.59 (m, 1H), 2.46 (m, 10H).

Example 165: 1-methyl-5-(6-methyl-5-(4-((2-methyl-2H-1,2,3-triazol-4-yl)sulfonyl)-1-(3,3,3-trifluoropropyl)piperazin-2-yl)-1H-indazol-1-yl)pyridin-2(1H)-one

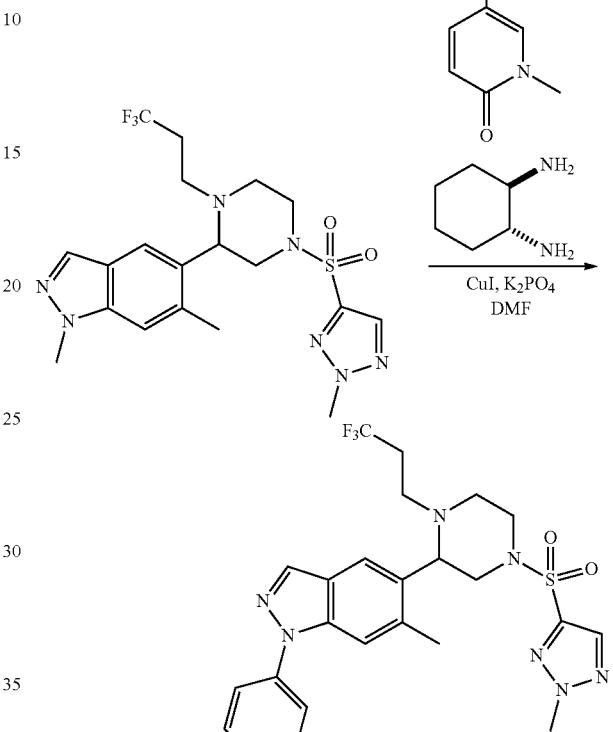

A suspension of 6-methyl-5-(4-((2-methyl-2H-1,2,3-triazol-4-yl)sulfonyl)-1-(3,3,3-trifluoropropyl)piperazin-2-yl)-1H-indazole Intermediate AR (75.0 mg, 90% Wt, 148 μmol), 5-bromo-1-methylpyridin-2(1H)-one (41.6 mg, 221 μmol), copper(I) iodide (14.1 mg, 73.8 μmol) and potassium phosphate (62.6 mg, 295 μmol) was degassed under vacuum 3 times prior to being suspended in DMF (1.50 mL) and (1R,2R)-cyclohexane-1,2-diamine (16.8 mg, 17.7 μL, 148 μmol) being added. The suspension was sparged with N2 for 2 mins and the reaction mixture was then heated to 120° C. for 24 hours. The filtrate mixture was diluted with EtOAc (10 mL) and transferred into a separating funnel. The layer was washed with 5 wt % LiCl (3×25 mL). The organic layer was collected, dried over magnesium sulfate, filtered and concentrated in vacuo. The concentrate was dissolved in DMSO (2.1 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters XBridge BEH C18 ODB prep column, 130 Å, 5 μm, 30 mm×100 mm, flow rate 40 mL min-1 eluting with a 0.3% ammonia in water-MeCN gradient over 12.5 mins using UV across all wavelengths with PDA as well as a QDA and ELS detector. At-column dilution pump gives 2 mL min-1 methanol over the entire method, which is included in the following MeCN percentages. Gradient information: 0.0-0.5 min, 32.5% MeCN; 0.5-10.5 min, ramped from 32.5% MeCN to 62.5% MeCN; 10.5-10.6 min, ramped from 62.5% MeCN to 100% MeCN; 10.6-12.5 min, held at 100% MeCN. Clean fractions were concentrated in vacuo to give 1-methyl-5-(6-methyl-5-(4-((2-methyl-2H-1,2,3-triazol-4-yl)sulfonyl)-1-(3,3,3-trifluoropropyl)piperazin-2-yl)-1H-indazol-1-yl)pyridin-2(1H)-one Example 165 (23.0 mg, 39 μmol, 26%) as a yellow solid; Rt 1.71 min (Method 7); m/z 565.5 (M+H)$^+$ (ES$^+$). δH (DMSO-d6, 400 MHz) δ 8.28 (s, 1H), 8.25-8.17 (m, 2H), 7.81 (s, 1H), 7.74 (dd, J=9.6, 3.0 Hz, 1H), 7.53 (s, 1H), 6.56 (d, J=9.6 Hz, 1H), 4.26 (s, 3H), 3.79-3.65 (m, 2H), 3.47 (d, J=11.8 Hz, 1H), 3.28-3.11 (m, 1H), 2.78-2.60 (m, 2H), 2.49-2.47 (m, 5H), 2.46-2.31 (m, 5H), 2.28-2.14 (m, 1H).

Examples 166-170

TABLE 22

The examples shown in the table below were prepared by similar methods to those described in Example 165 using Intermediate AR

| Example | Structure | LC-MS analysis |
|---------|-----------|----------------|
| 166 | 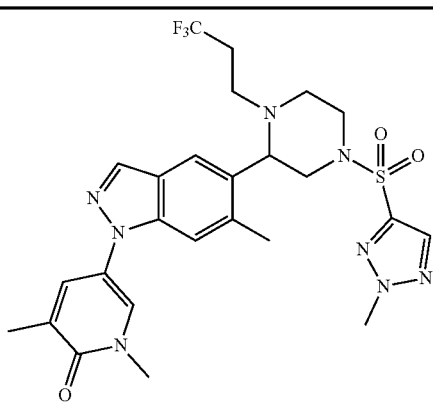<br>1-(4-fluorophenyl)-5-(1-isobutyl-4-((2-methyl-2H-1,2,3-triazol-4-yl)sulfonyl)piperazin-2-yl)-6-(trifluoromethyl)-1H-indazole | R$^t$ 1.95 min (Method 7); m/z 579.1 (M + H)$^+$ (ES$^+$) |
| 167 | 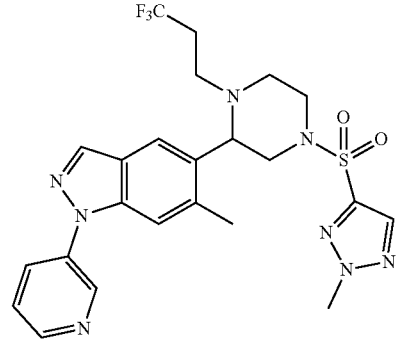 [SMILES: Cc1cc2c(cnn2-c2cccnc2)cc1C1CN(S(=O)(=O)c2cnn(C)n2)CCN1CCC(F)(F)F]<br>6-methyl-5-(4-((2-methyl-2H-1,2,3-triazol-4-yl)sulfonyl)-1-(3,3,3-trifluoropropyl)piperazin-2-yl)-1-(pyridin-3-yl)-1H-indazole | R$^t$ 1.88 min (Method 7); m/z 535.3 (M + H)$^+$ (ES$^+$) |
| 168 | 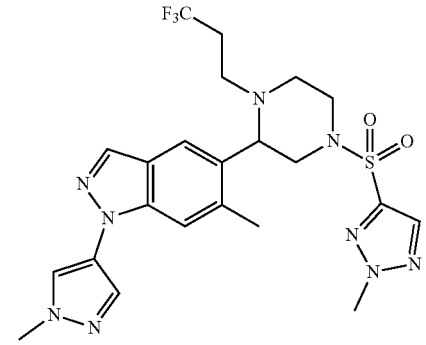 [SMILES: Cc1cc2c(cnn2-c2cnn(C)c2)cc1C1CN(S(=O)(=O)c2cnn(C)n2)CCN1CCC(F)(F)F]<br>6-methyl-1-(1-methyl-1H-pyrazol-4-yl)-5-(4-((2-methyl-2H-1,2,3-triazol-4-yl)sulfonyl)-1-(3,3,3-trifluoropropyl)piperazin-2-yl)-1H-indazole | R$^t$ 1.83 min (Method 7); m/z 538.3 (M + H)$^+$ (ES$^+$) |

TABLE 22-continued

The examples shown in the table below were prepared by similar methods to those described in Example 165 using Intermediate AR

| Example | Structure | LC-MS analysis |
|---|---|---|
| 169 | 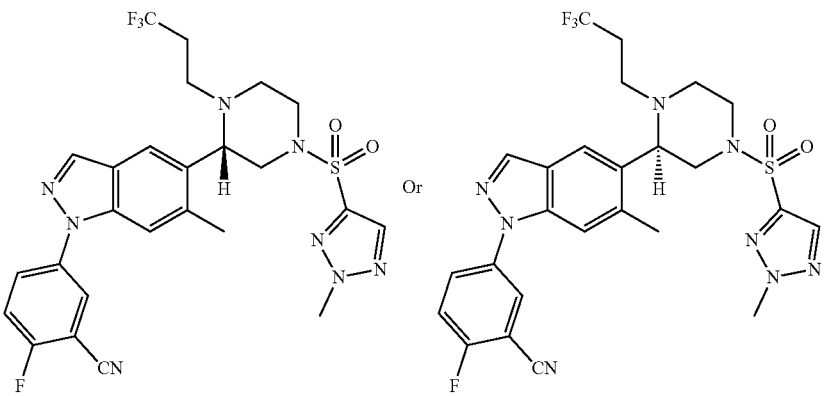 [SMILES: Cc1cc2c(cnn2-c2ccc(F)c(C#N)c2)cc1[C@H]1CN(S(=O)(=O)c2cnn(C)n2)CCN1CCC(F)(F)F ; Cc1cc2c(cnn2-c2ccc(F)c(C#N)c2)cc1[C@@H]1CN(S(=O)(=O)c2cnn(C)n2)CCN1CCC(F)(F)F] 2-fluoro-5-(6-methyl-5-(4-((2-methyl-2H-1,2,3-triazol-4-yl)sulfonyl)-1-(3,3,3-trifluoropropyl)piperazin-2-yl)-1H-indazol-1-yl)benzonitrile | $R^t$ 2.19 min (Method 7); m/z 577.2 $(M + H)^+$ $(ES^+)$ |
| 170 | 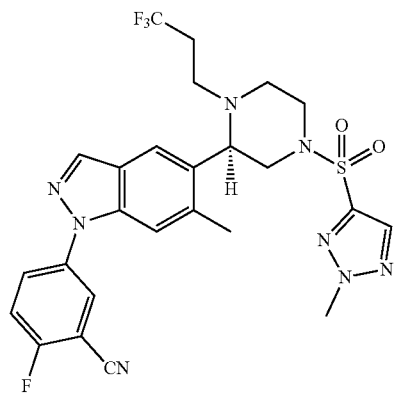 2-fluoro-5-(6-methyl-5-(4-((2-methyl-2H-1,2,3-triazol-4-yl)sulfonyl)-1-(3,3,3-trifluoropropyl)piperazin-2-yl)-1H-indazol-1-yl)benzonitrile | $R^t$ 2.18 min (Method 7); m/z 577.4 $(M + H)^+$ $(ES^+)$ |

Examples 171-172

Intermediate AS: (4-benzyl-2-(1-(4-fluorophenyl)-6-methyl-1H-indazol-5-yl)piperazin-1-yl)-3-methoxycyclobutyl)methanone

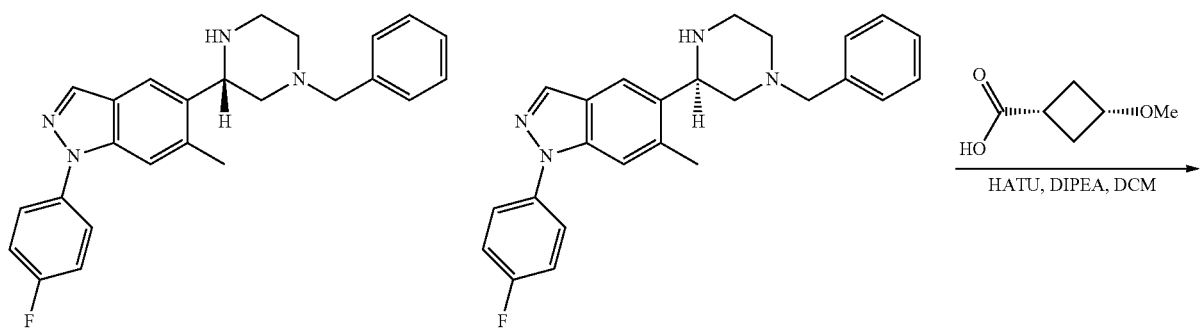

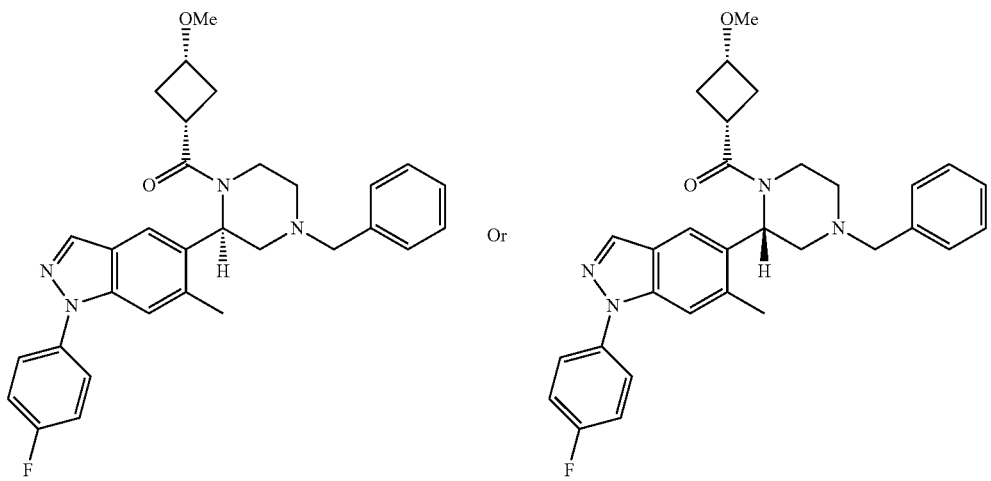

To a solution of (1s,3s)-3-methoxycyclobutane-1-carboxylic acid (390 mg, 3.00 mmol) in DCM (12.0 mL) were added DIPEA (968 mg, 1.30 mL, 7.49 mmol) and HATU (1.14 g, 1.2 Eq, 3.00 mmol). The reaction mixture was stirred at rt for 20 mins before the addition of 5-(4-benzylpiperazin-2-yl)-1-(4-fluorophenyl)-6-methyl-1H-indazole (1.00 g, 2.50 mmol) (as a solution in DCM (12.0 mL)). The reaction mixture was stirred for a further 16 hours at rt, before being quenched with water (20 mL) and sat. aq. NaHCO$_3$ (20 mL). The layers were separated, and the aqueous layer extracted with DCM (3×20 mL). Combined organic extracts were dried over MgSO$_4$ and concentrated in vacuo. The crude product was purified by chromatography on silica gel (40 g cartridge, 0-100% EtOAc/isohexane) to afford (4-benzyl-2-(1-(4-fluorophenyl)-6-methyl-1H-indazol-5-yl)piperazin-1-yl)-3-methoxycyclobutyl)methanone Intermediate AS (1.18 g, 2.1 mmol, 83%) as a white solid; Rt 1.72 min (Method 9); m/z 513.2 (M+H)+ (ES+). δH (DMSO-d6, 400 MHz) δ 8.57 (s, 1H), 8.35 (d, J=0.9 Hz, 1H), 7.86-7.69 (m, 2H), 7.56 (s, 1H), 7.41 (m, 7H), 5.75 (s, 1H), 3.87-3.65 (m, 1H), 3.63-3.41 (m, 3H), 3.14 (d, J=29.9 Hz, 5H), 2.91 (d, J=11.5 Hz, 2H), 2.44-2.29 (m, δH), 2.04-1.88 (s, 3H).

Intermediate AT: 5-(4-benzyl-1-((3-methoxycyclobutyl)methyl)piperazin-2-yl)-1-(4-fluorophenyl)-6-methyl-1H-indazole

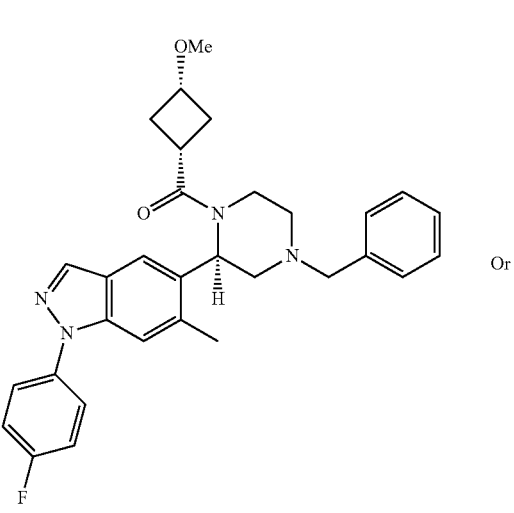

-continued

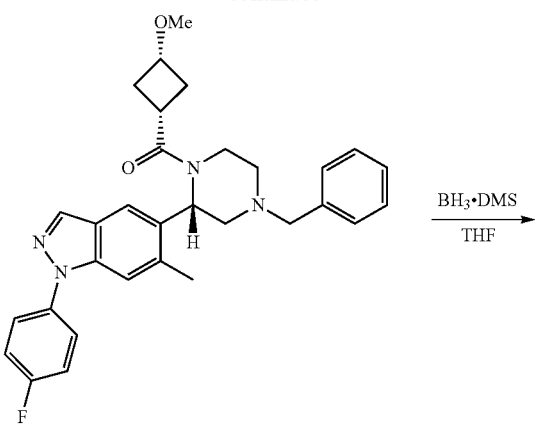

BH₃·DMS
THF

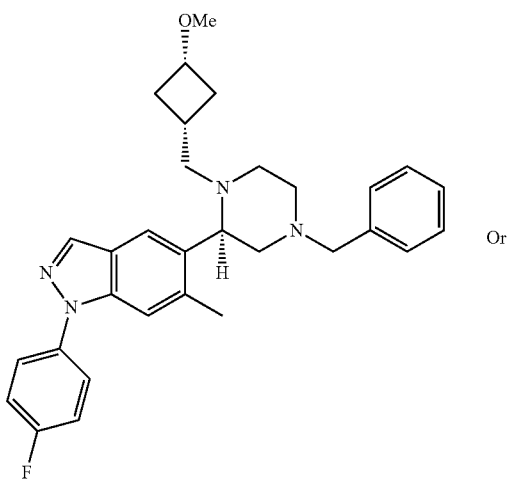

Or

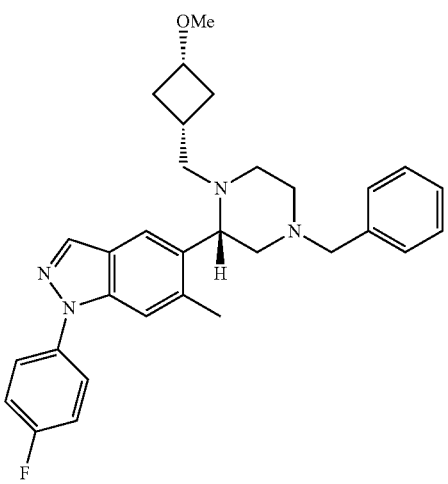

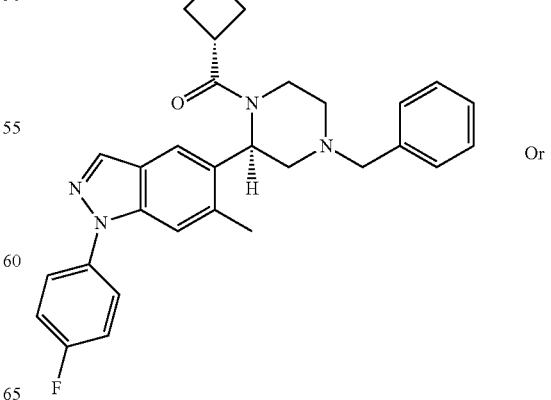

Or

To a solution of 4-benzyl-2-(1-(4-fluorophenyl)-6-methyl-1H-indazol-5-yl)piperazin-1-yl)-3-methoxycyclobutyl)methanone Intermediate AS (1.18 g, 2.30 mmol) in THF (24.0 mL) was added borane-methyl sulfide complex (2 M in THF) (699 mg, 4.60 mL, 2.00 molar, 9.21 mmol) and the reaction mixture stirred at 40° C. for 16 hours. After cooling to rt, the reaction mixture was quenched with MeOH (3 mL) and then sat. aq. NH₄Cl (15 mL). EtOAc (30 mL) was added, and the layers separated. The aqueous layer was extracted with EtOAc (3×20 mL). Combined organic extracts were washed with water (15 mL) and then brine (5 mL) and then dried over MgSO₄ before being concentrated in vacuo. The crude product was purified by chromatography on silica gel (24 g cartridge, 0-100% EtOAc/isohexane), but LCMS of the major fraction showed multiple peaks of the same m/z. This material was dissolved in THF (20 mL) and 1M aq HCl (20 mL) added. The solution was stirred vigorously for 1 hour before being diluted with water (30 mL) and EtOAc (30 mL). The layers were separated, and the aqueous layer extracted with EtOAc (3×10 mL). Combined organic extracts were dried over MgSO₄ and concentrated in vacuo to afford 5-(4-benzyl-1-((3-methoxycyclobutyl)methyl)piperazin-2-yl)-1-(4-fluorophenyl)-6-methyl-1H-indazole Intermediate AT (502 mg, 0.86 mmol, 37%) as an off-white solid; Rt 1.63 min (Method 9); m/z 499.2 (M+H)⁺ (ES⁺). δH (DMSO-d6, 400 MHz) δ 8.30 (s, 1H), 7.91 (s, 1H), 7.86-7.72 (m, 2H), 7.57 (s, 1H), 7.48-7.34 (m, 2H), 7.34-7.18 (m, 5H), 3.47 (m, 3H), 3.11-3.02 (m, 1H), 2.99 (s, 3H), 2.83 (d, J=10.3 Hz, 1H), 2.66 (d, J=11.4 Hz, 1H), 2.46-2.14 (m, 8H), 2.05-1.80 (m, 3H), 1.36 (s, 1H), 1.30-1.11 (m, 2H).

Intermediate AU: 1-(4-fluorophenyl)-5-(1-((3-methoxycyclobutyl)methyl)piperazin-2-yl)-6-methyl-1H-indazole 457
-continued

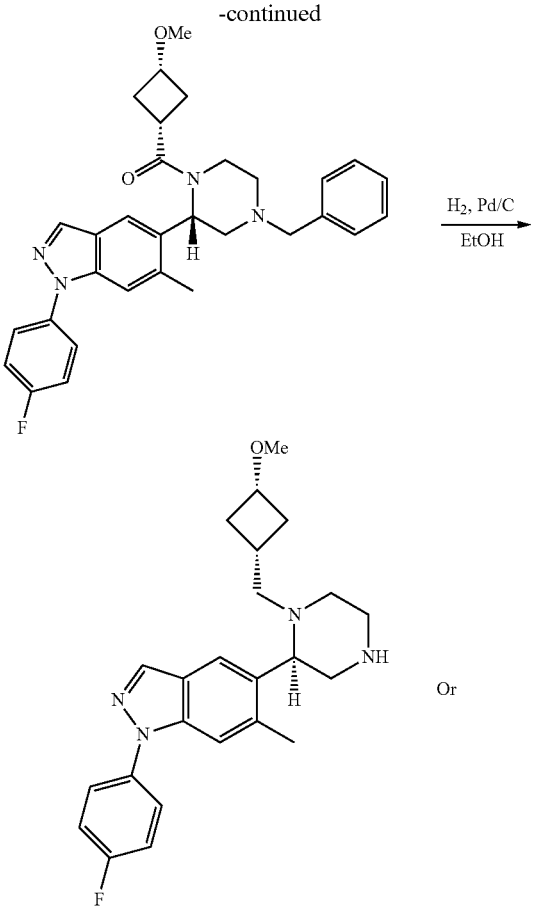

H₂, Pd/C
EtOH

Or

458
-continued

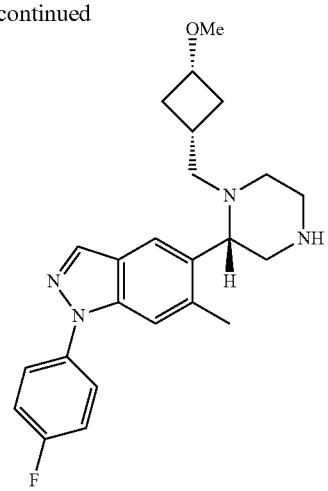

To a solution of 5-(4-benzyl-1-((3-methoxycyclobutyl)methyl)piperazin-2-yl)-1-(4-fluorophenyl)-6-methyl-1H-indazole Intermediate AT (375 mg, 752 µmol) in EtOH (15.0 mL) was added palladium (120 mg, 10% Wt, 113 µmol) and the reaction mixture stirred at 70° C. for 16 hours. The reaction mixture was filtered through glass microfibre filter pad and concentrated in vacuo. The residue was azeotroped in toluene 3 times to remove residual EtOH to afford 280 mgs of crude material as yellow oil. 100 mgs of this material was purified chromatography on silica gel (4 g cartridge, 0-100% 0.7M ammonia in MeOH/DCM) to afford 1-(4-fluorophenyl)-5-(1-((3-methoxycyclobutyl)methyl)piperazin-2-yl)-6-methyl-1H-indazole Intermediate AU (40 mg, 91 µmol, 12%) as a colourless oil; Rt 1.25 min (Method 7); m/z 409.4 (M+H)⁺ (ES⁺).

TABLE 23

The examples shown in the table below were prepared by similar methods to those described in Example 36 using Intermediate AU

| Example | Structure | LC-MS analysis |
|---|---|---|
| 171 | [Structure: OMe-cyclobutyl-CH₂-piperazine-indazole(6-methyl,1-(4-fluorophenyl))-sulfonyl-2-methylthiazole] Or [enantiomer]<br><br>4-((3-(1-(4-fluorophenyl)-6-methyl-1H-indazol-5-yl)-4-((3-methoxycyclobutyl)methyl)piperazin-1-yl)sulfonyl)-2-methylthiazole | Rᵗ 1.79 min (Method 7); m/z 570.1 (M + H)⁺ (ES⁺) |

TABLE 23-continued

The examples shown in the table below were prepared by similar methods to those described in Example 36 using Intermediate AU

| Example | Structure | LC-MS analysis |
|---|---|---|
| 172 | 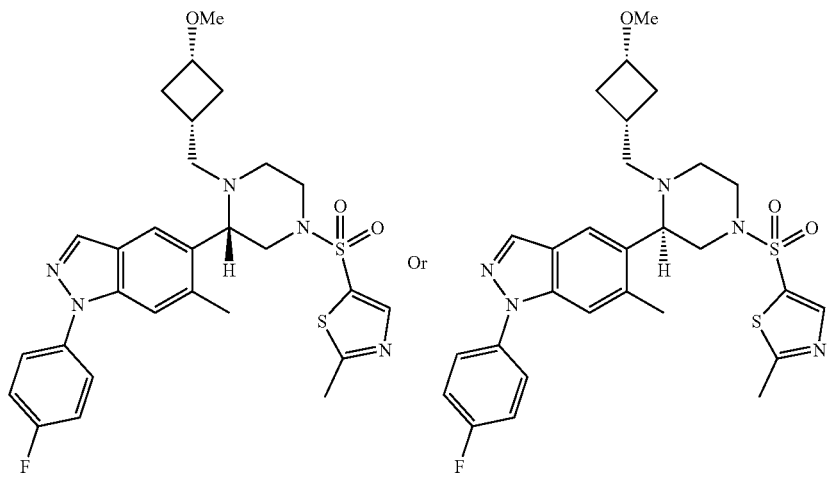 [SMILES: CO[C@H]1C[C@@H](CN2CCN(S(=O)(=O)c3cnc(C)s3)C[C@@H]2c2cc3cnn(-c4ccc(F)cc4)c3cc2C)C1 ; CO[C@H]1C[C@@H](CN2CCN(S(=O)(=O)c3cnc(C)s3)C[C@H]2c2cc3cnn(-c4ccc(F)cc4)c3cc2C)C1]
5-((3-(1-(4-fluorophenyl)-6-methyl-1H-indazol-5-yl)-4-((3-methoxycyclobutyl)methyl)piperazin-1-yl)sulfonyl)-2-methylthiazole | R' 1.76 min (Method 7); m/z 570.4 (M + H)+ (ES+) |

Example 173: 1-(4-fluorophenyl)-6-methyl-5-(4-(2-methyltriazol-4-yl)sulfonyl-1-(3,3,3-trifluoropropyl)-1,4-diazepan-2-yl)indazole Intermediate BA: tert-butyl 3-(1-(4-fluorophenyl)-6-methyl-indazol-5-yl)-1,4-diazepane-1-carboxylate

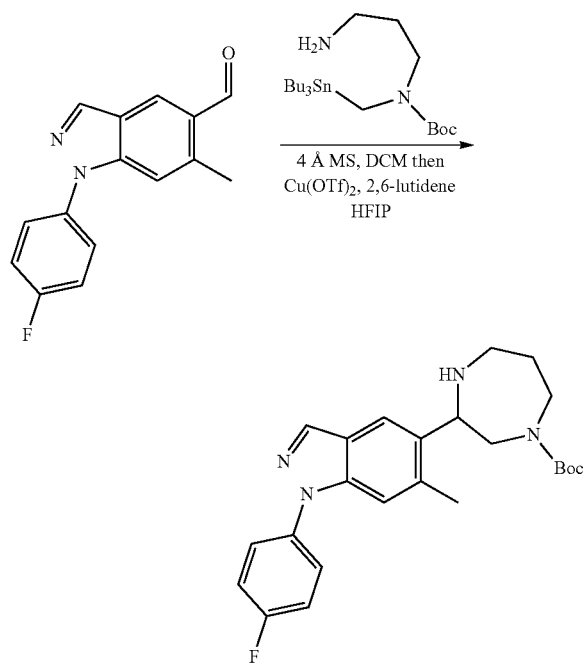

To a solution of 1-(4-fluorophenyl)-6-methyl-indazole-5-carbaldehyde (245 mg, 0.960 mmol) in DCM (5.0 mL) at rt was added tert-butyl N-(3-aminopropyl)-N-(tributylstannyl-methyl)carbamate (460 mg, 0.960 mmol), followed by 4 Å molecular sieves (4 pellets). The resulting mixture was maintained at rt for 4 hours, then diluted with further DCM (16.0 mL). Simultaneously, Cu(OTf)$_2$ (349 mg, 0.960 mmol) and 2,6-lutidine (112 µL, 0.960 mmol) were stirred in hexafluoro isopropanol (HFIP) (4.0 mL) for 4 hours. To the resulting homogeneous suspension was added the pre-formed solution of imine at rt and the mixture was maintained at rt for 60 hours. The crude mixture was diluted with DCM (20.0 mL) and 10% aq NH$_3$:brine (1:1, 20.0 mL) and vigorously stirred for 15 minutes. The biphasic mixture that formed was separated, the aqueous phase extracted with further DCM (2×20.0 mL) and the combined organic extracts dried (phase separator) and evaporated in vacuo. The residue thus obtained was purified by flash column chromatography (25 g cartridge, 0-2.5% 2 M NH$_3$ in MeOH in DCM) to afford tert-butyl 3-(1-(4-fluorophenyl)-6-methyl-indazol-5-yl)-1,4-diazepane-1-carboxylate (180 mg, 0.420 mmol, 44%) as a yellow gum; R' 1.48 min (Method 12); m/z 369.2 (M+H-tBu)+ (ES+); δH NMR (400 MHz, Chloroform-d) δ 8.08 (d, J=6.3 Hz, 1H), 7.94 (d, J=3.9 Hz, 1H), 7.71-7.61 (m, 2H), 7.45 (s, 1H), 7.26-7.18 (m, 2H), 4.16-3.82 (m, 3H), 3.36-3.18 (m, 2H), 2.92-2.70 (m, 2H), 2.59 (d, J=17.2 Hz, 3H), 2.18-1.95 (m, 1H), 1.95-1.82 (m, 1H), 1.50 (d, J=1.9 Hz, 9H). NH not observed.

Intermediate BB: tert-butyl 3-(1-(4-fluorophenyl)-6-methyl-indazol-5-yl)-4-(3,3,3-trifluoropropyl)-1,4-diazepane-1-carboxylate

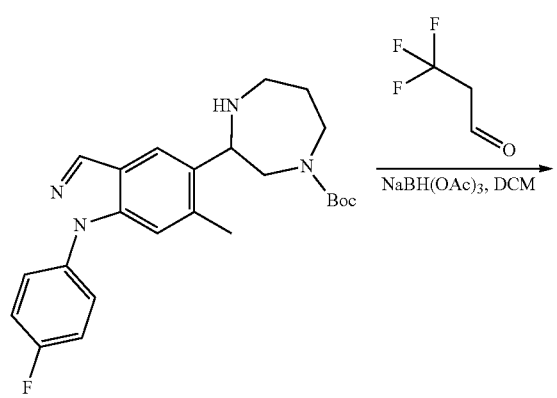

Intermediate BC: 1-(4-fluorophenyl)-6-methyl-5-(1-(3,3,3-trifluoropropyl)-1,4-diazepan-2-yl)indazole hydrochloride

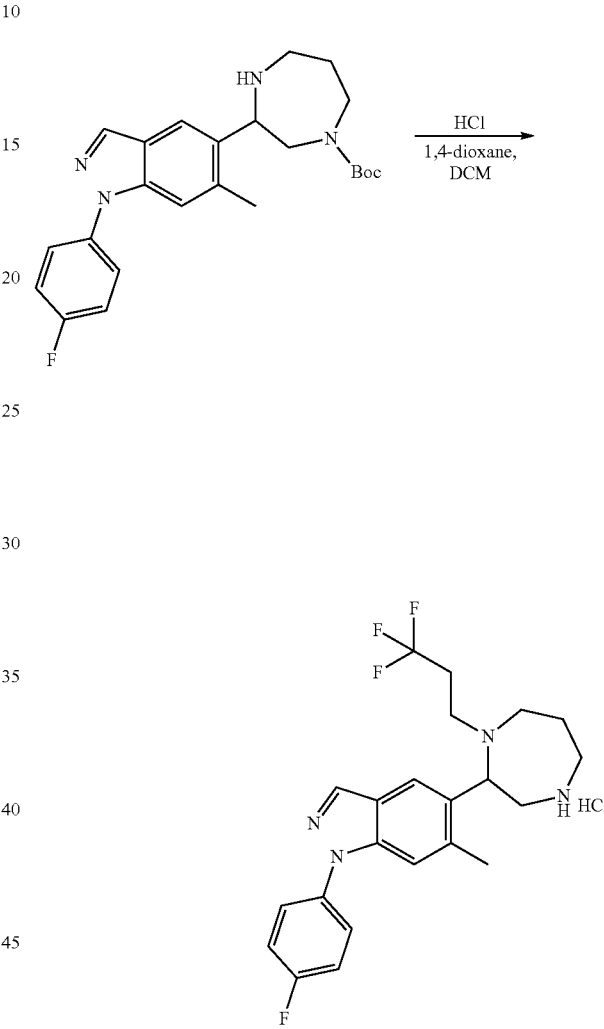

To a solution of tert-butyl 3-(1-(4-fluorophenyl)-6-methyl-indazol-5-yl)-1,4-diazepane-1-carboxylate (180 mg, 0.420 mmol) in DCM (5.0 mL) at rt was 3,3,3-trifluoropropanal (73 µL, 0.850 mmol), followed by NaBH(OAc)$_3$ (270 mg, 1.27 mmol). The resulting mixture was maintained at rt for 18 hours, then diluted with sat aq NaHCO$_3$ and EtOAc. The biphasic mixture was separated, and the organic extracts washed with further EtOAc. The combined organic layers were washed with further sat aq NaHCO$_3$, dried (Na$_2$SO$_4$) and evaporated in vacuo. The residue thus obtained was purified by flash column chromatography (10 g cartridge, 0-20% EtOAc in heptane) to afford tert-butyl 3-(1-(4-fluorophenyl)-6-methyl-indazol-5-yl)-4-(3,3,3-trifluoropropyl)-1,4-diazepane-1-carboxylate (174 mg, 0.330 mmol, 79%) as a colourless gum; R$^t$ 2.10 min (Method 12); m/z 465.2 (M+H-tBu)$^+$ (ES$^+$); δH NMR (400 MHz, Chloroform-d) δ 8.10 (apparent d, 1H), 7.89 (apparent d, 1H), 7.72-7.63 (m, 2H), 7.45 (s, 1H), 7.23 (apparent m, 2H, obscured by solvent), 4.04-3.69 (over-lapping m, 3H), 3.25-2.94 (over-lapping m, 2.5H), 3.01 (dd, J=14.8, 10.0 Hz, 0.5H), 2.84-2.65 (m, 2H), 2.65-2.48 (over-lapping m+2×s, 4H), 2.23-1.85 (over-lapping m, 4H), 1.49 (s, 4.5H), 1.43 (s, 4.5H). Restricted rotation observed.

To a solution of tert-butyl 3-(1-(4-fluorophenyl)-6-methyl-indazol-5-yl)-4-(3,3,3-trifluoropropyl)-1,4-diazepane-1-carboxylate (174 mg, 0.330 mmol) in DCM (1.0 mL) at rt was added HCl (3.7-4.2 N in 1,4-dioxane, 2.0 mL, 0.330 mmol). The resulting mixture was maintained at rt for 4 hours and then evaporated in vacuo. The residue obtained was azeotroped with DCM (×4) and dried in vacuo to give 1-(4-fluorophenyl)-6-methyl-5-(1-(3,3,3-trifluoropropyl)-1,4-diazepan-2-yl)indazole hydrochloride (172 mg) as a white solid; R$^t$ 1.47 min (Method 12); m/z 421.2 (M+H)$^+$ (ES$^+$). This material was used in the subsequent step without further purification.

Example 173: 1-(4-fluorophenyl)-6-methyl-5-(4-(2-methyltriazol-4-yl)sulfonyl-1-(3,3,3-trifluoropropyl)-1,4-diazepan-2-yl)indazole

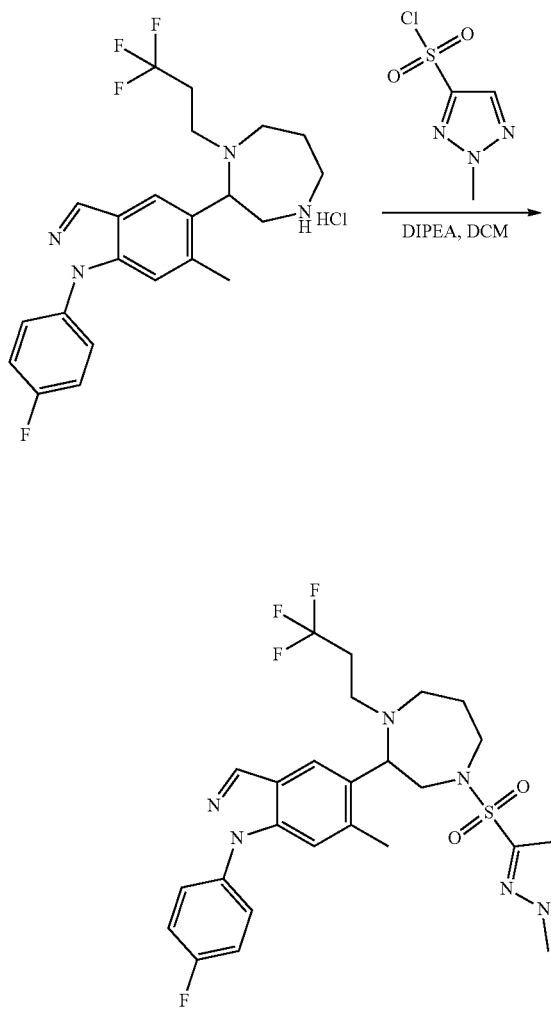

To a solution of 1-(4-fluorophenyl)-6-methyl-5-(1-(3,3,3-trifluoropropyl)-1,4-diazepan-2-yl)indazole hydrochloride (54.0 mg, 0.120 mmol) and DIPEA (82 µL, 0.470 mmol) in DCM (2.0 mL) at rt was added 2-methyltriazole-4-sulfonyl chloride (25.8 mg, 0.140 mmol) dropwise. The resulting mixture was maintained at rt for 18 hours and then dry loaded onto silica and purified by flash column chromatography (10 g cartridge, 0-50% EtOAc in heptane) to afford 1-(4-fluorophenyl)-6-methyl-5-(4-(2-methyltriazol-4-yl)sulfonyl-1-(3,3,3-trifluoro propyl)-1,4-diazepan-2-yl)indazole (38.7 mg, 0.0700 mmol, 56%) as a white solid; R$^t$ 2.92 min (Method 11); m/z 566.2 (M+H)$^+$ (ES$^+$); δH NMR (400 MHz, DMSO-d6) δ 8.29 (d, J=0.9 Hz, 1H), 8.25 (s, 1H), 7.92 (s, 1H), 7.83-7.77 (m, 2H), 7.65 (q, J=0.9 Hz, 1H), 7.46-7.39 (m, 2H), 4.20 (s, 3H), 4.00 (dd, J=9.8, 2.8 Hz, 1H), 3.57-3.52 (m, 1H), 3.48 (dd, J=15.5, 2.5 Hz, 1H), 3.24-3.18 (m, 2H), 3.07 (dt, J=11.2, 5.2 Hz, 1H), 2.74 (dd, J=13.9, 8.7 Hz, 1H), 2.66-2.57 (m, 1H), 2.54 (d, J=1.0 Hz, 3H), 2.53-2.50 (m, assume 1H, obscured by solvent), 2.40-2.24 (m, 2H), 2.14-2.01 (m, 1H), 1.98-1.87 (m, 1H).

Example 174: 5-(5-(4-(1-ethylpyrazol-4-yl)sulfonyl-1-(3,3,3-trifluoropropyl)piperazin-2-yl)-6-methyl-indazol-1-yl)-1,3-dimethyl-pyridin-2-one

Intermediate CA: 6-methyl-1-tetrahydropyran-2-yl-indazole-5-carbaldehyde

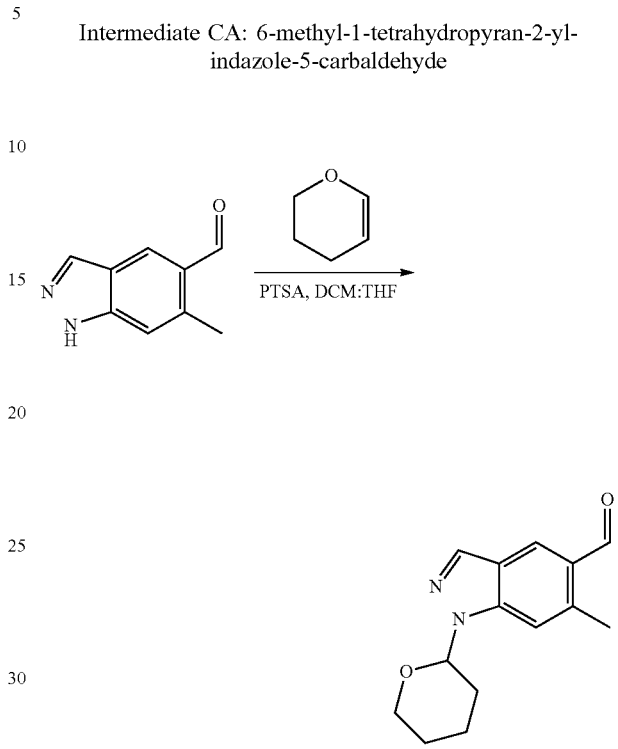

To a suspension of 6-methyl-1H-indazole-5-carbaldehyde (940 mg, 5.87 mmol) in THF:DCM (1:1, 20 mL) at rt was added 3,4-dihydro-2H-pyran (1.61 mL, 17.6 mmol) and PTSA monohydrate (223 mg, 1.17 mmol). The resulting mixture was maintained at rt for 20 hours and then evaporated in vacuo. The residue thus obtained was purified by flash column chromatography (50 g cartridge, 0-25% EtOAc in heptane) to afford 6-methyl-1-tetrahydropyran-2-yl-indazole-5-carbaldehyde (992 mg, 4.06 mmol, 69%) as an off-white gum; δH NMR (400 MHz, Chloroform-d) δ 10.22 (s, 1H), 8.20 (s, 1H), 8.12 (d, J=0.9 Hz, 1H), 7.41 (s, 1H), 5.72 (dd, J=9.4, 2.8 Hz, 1H), 4.09-4.00 (m, 1H), 3.82-3.72 (m, 1H), 2.80 (d, J=0.9 Hz, 3H), 2.62-2.44 (m, 1H), 2.23-2.03 (m, 2H), 1.85-1.63 (over-lapping m, 3H).

Intermediate CB: tert-butyl 3-(6-methyl-1-tetrahydropyran-2-yl-indazol-5-yl)piperazine-1-carboxylate

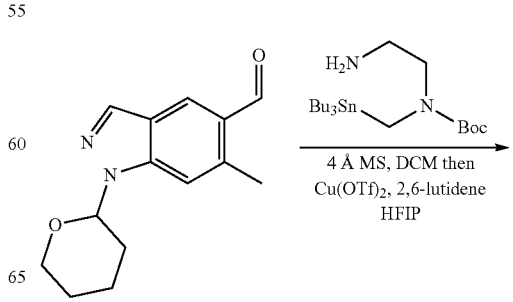

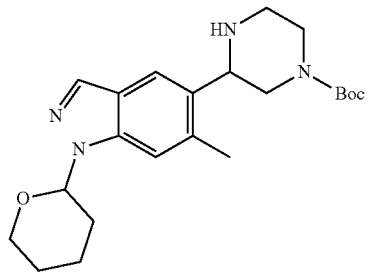

To a solution of 6-methyl-1-tetrahydropyran-2-yl-indazole-5-carbaldehyde (0.990 g, 4.05 mmol) in DCM (18.0 mL) at rt was added tert-butyl N-(2-aminoethyl)-N-(tributylstannylmethyl)carbamate (1.88 g, 4.05 mmol), followed by 4 Å molecular sieves (20 pellets). The resulting mixture was maintained at rt for 4 hours, then diluted with further DCM (60.0 mL). Simultaneously, Cu(OTf)$_2$ (1.47 g, 4.05 mmol) and 2,6-lutidine (472 μL, 4.05 mmol) were stirred in HFIP (16.6 mL) for 4 hours. To the resulting homogeneous suspension was added the pre-formed solution of imine at rt and the mixture was maintained at rt for 72 hours. The crude mixture was diluted with DCM (20.0 mL) and 10% aq NH$_3$:brine (1:1, 60.0 mL) and vigorously stirred for 15 minutes. The biphasic mixture that formed was separated, the aqueous phase extracted with further DCM (2×20.0 mL) and the combined organic extracts dried (Na$_2$SO$_4$) and evaporated in vacuo. The residue thus obtained was purified by flash column chromatography (120 g cartridge, 0-4% 2 M NH$_3$ in MeOH in DCM) to afford tert-butyl 3-(6-methyl-1-tetrahydropyran-2-yl-indazol-5-yl)piperazine-1-carboxylate (0.88 g, 0.208 mmol, 51%) as a light yellow gum; R$^t$ 1.36 min (Method 12); m/z 345.2 (M+H-tBu)$^+$ (ES$^+$); δH NMR (400 MHz, Chloroform-d) δ 7.95 (br d, 1H), 7.93 (s, 1H), 7.38 (s, 1H), 5.68 (dt, J=9.5, 2.5 Hz, 1H), 4.21-3.96 (over-lapping br s+dd, 3H), 3.96-3.89 (m, 1H), 3.80-3.69 (m, 1H), 3.18-3.05 (m, 1H), 3.04-2.86 (m, 2H), 2.71-2.48 (over-lapping m+s, 5H), 2.21-2.11 (m, 1H), 2.06 (d, J=13.6 Hz, 1H), 1.83-1.59 (m, 4H), 1.48 (s, 9H).

Intermediate CC: tert-butyl 3-(6-methyl-1-tetrahydropyran-2-yl-indazol-5-yl)-4-(3,3,3-trifluoropropyl)piperazine-1-carboxylate

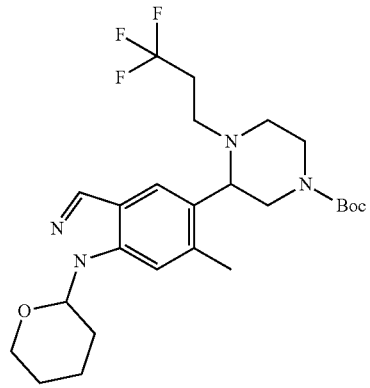

To a solution of tert-butyl 3-(6-methyl-1-tetrahydropyran-2-yl-indazol-5-yl)piperazine-1-carboxylate (875 mg, 2.18 mmol) in DCM (15.0 mL) at rt was added 3,3,3-trifluoropropanal (377 μL, 4.37 mmol), followed by NaBH(OAc)$_3$ (1.39 g, 6.55 mmol). The resulting mixture was maintained at rt for 18 hours, then diluted with sat aq NaHCO$_3$ and DCM and stirred for 10 minutes. The biphasic mixture was separated, and the organic extracts washed with further DCM. The combined organic layers were dried (Na$_2$SO$_4$) and evaporated in vacuo. The residue thus obtained was purified by flash column chromatography (50 g cartridge, 0-25% EtOAc in heptane) to afford tert-butyl 3-(6-methyl-1-tetrahydropyran-2-yl-indazol-5-yl)-4-(3,3,3-trifluoropropyl)piperazine-1-carboxylate (803 mg, 1.62 mmol, 74%) as a colourless gum; R$^t$ 2.03 min (Method 12); m/z 441.2 (M+H-tBu)$^+$ (ES$^+$); δH NMR (400 MHz, Chloroform-d) δ 7.95 (s, 1H), 7.84 (s, 1H), 7.39 (s, 1H), 5.74-5.60 (m, 1H), 4.27-3.83 (over-lapping m, 3H), 3.83-3.71 (m, 1H), 3.52-3.34 (m, 1H), 3.19-2.89 (over-lapping m, 2H), 2.91-2.54 (over-lapping m, 3H), 2.52 (s, 3H), 2.33-2.04 (over-lapping m, δH), 1.85-1.60 (over-lapping m, 3H), 1.46 (s, 9H).

Intermediate CD: 6-methyl-5-[1-(3,3,3-trifluoropropyl)piperazin-2-yl]-1H-indazole hydrochloride

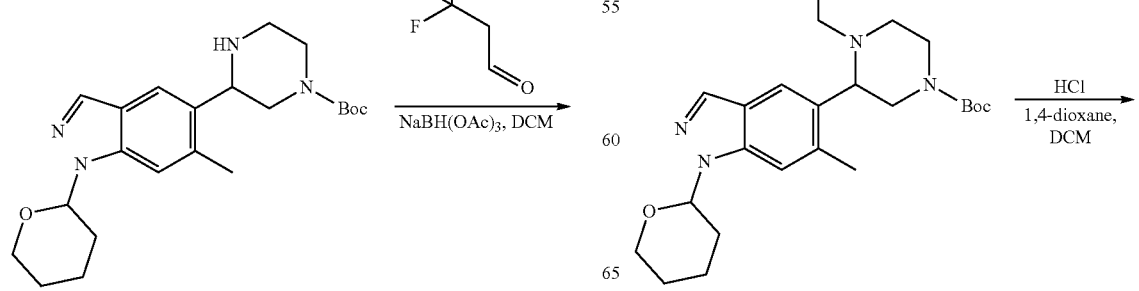

-continued

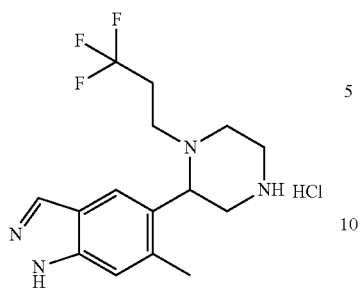

A solution of tert-butyl 3-(6-methyl-1-tetrahydropyran-2-yl-indazol-5-yl)-4-(3,3,3-trifluoropropyl)piperazine-1-carboxylate (802 mg, 1.62 mmol) and HCl (1.25 M in ethanol, 8.0 mL, 10.0 mmol) was stirred at rt for 1 hour. The mixture was heated to 50° C., maintained at this temperature for 4 hours and then evaporated in vacuo to give 6-methyl-5-(1-(3,3,3-trifluoropropyl)piperazin-2-yl)-1H-indazole hydrochloride (647 mg) as a white solid; $R^t$ 1.19 min (Method 12); m/z 313.2 (M+H)$^+$ (ES$^+$). This material was used in the subsequent step without further purification.

Intermediate CE: 5-(4-(1-ethylpyrazol-4-yl)sulfonyl-1-(3,3,3-trifluoropropyl)piperazin-2-yl)-6-methyl-1H-indazole

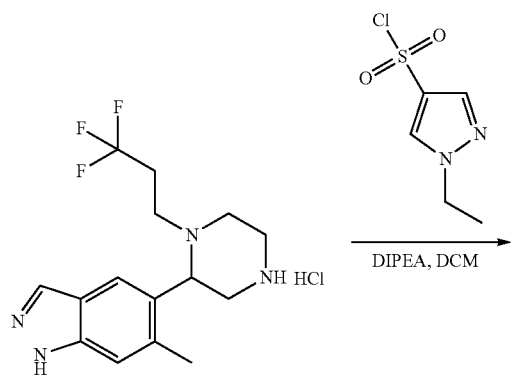

-continued

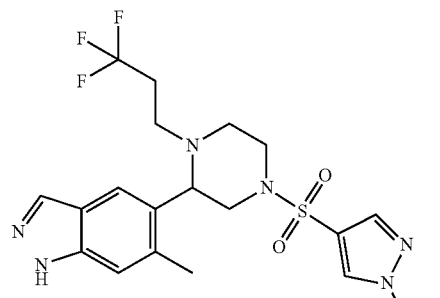

To a solution of 6-methyl-5-(1-(3,3,3-trifluoropropyl)piperazin-2-yl)-1H-indazole hydrochloride (69.0 mg, 0.180 mmol) and DIPEA (125 μL, 0.716 mmol) in DCM (2.0 mL) at rt was added a solution of 1-ethylpyrazole-4-sulfonyl chloride (33.1 mg, 0.170 mmol) in DCM (0.5 mL) dropwise. The resulting mixture was maintained at rt for 30 minutes and then diluted with water. The resulting biphasic mixture was separated and the organic extracts dry loaded onto silica and purified by flash column chromatography (12 g cartridge, 0-3% MeOH in DCM) to afford 5-(4-(1-ethylpyrazol-4-yl)sulfonyl-1-(3,3,3-trifluoropropyl) piperazin-2-yl)-6-methyl-1H-indazole (75.0 mg, 0.159 mmol, 89%) as a white solid; $R^t$ 1.69 min (Method 12); m/z 471.2 (M+H)$^+$ (ES$^+$); δH NMR (400 MHz, Chloroform-d) δ 9.97 (br s, 1H), 7.99 (s, 1H), 7.75 (br s, J=17.7 Hz, 1H), 7.71 (s, 1H), 7.68 (d, J=0.7 Hz, 1H), 7.32 (br s, 1H), 4.20 (q, J=7.3 Hz, 2H), 3.84-3.68 (over-lapping m, 2H), 3.64-3.56 (m, 1H), 3.26-3.10 (m, 1H), 2.91-2.72 (m, 1H), 2.68-2.46 (over-lapping m+s, 5H), 2.36-2.06 (over-lapping m, 4H), 1.51 (t, J=7.3 Hz, 3H).

Example 174: 5-(5-(4-(1-ethylpyrazol-4-yl)sulfonyl-1-(3,3,3-trifluoropropyl)piperazin-2-yl)-6-methyl-indazol-1-yl)-1,3-dimethyl-pyridin-2-one

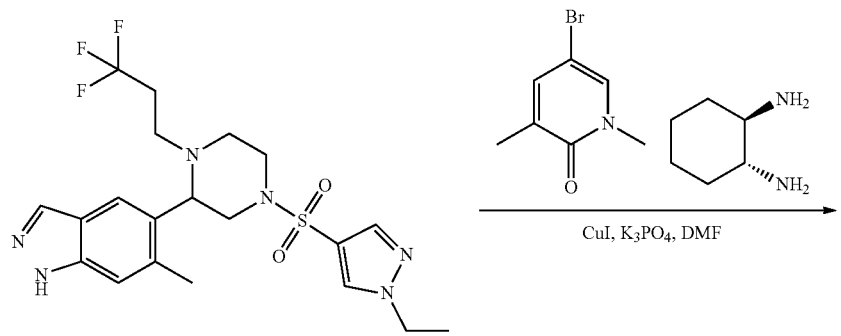

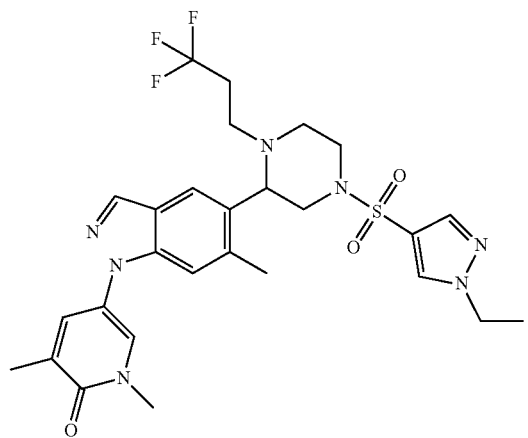

A suspension of 5-(4-(1-ethylpyrazol-4-yl)sulfonyl-1-(3,3,3-trifluoropropyl)piperazin-2-yl)-6-methyl-1H-indazole (75.0 mg, 0.159 mmol), 5-bromo-1,3-dimethyl-pyridin-2-one (48.3 mg, 0.239 mmol), CuI (15.2 mg, 0.0797 mmol) and K$_3$PO$_4$ (67.7 mg, 0.319 mmol) in DMF (2.0 mL) was degassed for 10 minutes and then treated with a solution of (1R,2R)-cyclohexane-1,2-diamine (18.4 mg, 0.160 mmol) in DMF (0.5 mL). The resulting mixture was degassed for a further 5 minutes and then heated at 120° C. for 18 hours. Further (1R,2R)-cyclohexane-1,2-diamine (18.4 mg, 0.160 mmol), CuI (15.2 mg, 0.0797 mmol) and K$_3$PO$_4$ (67.7 mg, 0.319 mmol) were added, and the reaction mixture heated at 120° C. for 4 hours. After cooling to rt the mixture was diluted with EtOAc and filtered through a pad celite. The filtrate was partitioned with water and the phases separated. The aqueous layer was diluted with brine and extracted with further EtOAc (×3). The combined organic extracts were washed with brine (×2), dried (Na$_2$SO$_4$), and evaporated in vacuo. The residue thus obtained was purified by flash column chromatography (12 g cartridge, 0-3% MeOH/DCM). Further purification by preparative HPLC (Method AA) afforded 5-(5-(4-(1-ethylpyrazol-4-yl)sulfonyl-1-(3,3,3-trifluoropropyl)piperazin-2-yl)-6-methyl-indazol-1-yl)-1,3-dimethyl-pyridin-2-one (28.1 mg, 0.0467 mmol, 29%) as a white solid; R$^t$ 2.45 min (Method 11); m/z 592.2 (M+H)$^+$ (ES$^+$); δH NMR (400 MHz, DMSO-d6) δ 8.36 (s, 1H), 8.19 (d, J=1.0 Hz, 1H), 8.06 (dd, J=3.0, 0.8 Hz, 1H), 7.81-7.76 (over-lapping d+s, 2H), 7.68-7.58 (m, 1H), 7.52 (s, 1H), 4.18 (q, J=7.3 Hz, 2H), 3.72 (dd, J=10.3, 3.0 Hz, 1H), 3.66-3.59 (m, 1H), 3.54 (s, 3H), 3.43-3.35 (m, 1H), 3.29-3.20 (m, 1H), 2.71-2.59 (m, 1H), 2.48 (s, 3H), 2.46-2.36 (over-lapping m, 4H), 2.24-2.06 (over-lapping m+s, 5H), 1.37 (t, J=7.3 Hz, 3H).

Example 175: 2,4-dimethyl-6-(6-methyl-5-(4-(2-methyltriazol-4-yl)sulfonyl-1-(3,3,3-trifluoropropyl)piperazin-2-yl)indazol-1-yl)pyridazin-3-one Intermediate DA: 6-methyl-5-(4-(2-methyltriazol-4-yl)sulfonyl-1-(3,3,3-trifluoropropyl) piperazin-2-yl)-1H-indazole

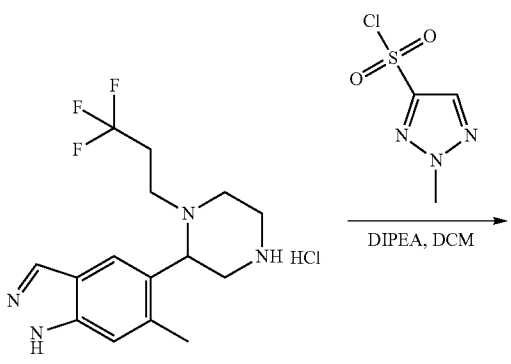

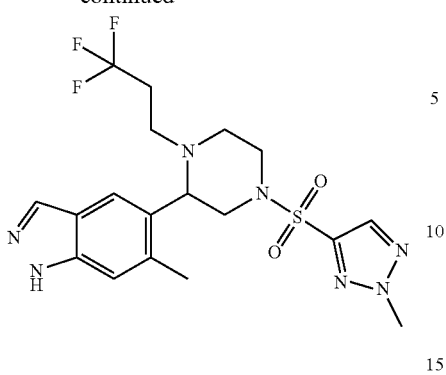

To a solution of 6-methyl-5-(1-(3,3,3-trifluoropropyl)piperazin-2-yl)-1H-indazole hydrochloride (523 mg, 1.36 mmol) and DIPEA (946 μL, 5.43 mmol) in DCM (13.6 mL) at rt was added a solution of 2-methyltriazole-4-sulfonyl chloride (234 mg, 1.29 mmol) in DCM (2.0 mL) dropwise. The resulting mixture was maintained at rt for 30 minutes and then diluted with water. The resulting biphasic mixture was separated, and the organic extracts evaporated in vacuo. The residue thus obtained was purified by flash column chromatography (24 g cartridge, 0-2% MeOH in DCM) to afford 6-methyl-5-[4-(2-methyltriazol-4-yl)sulfonyl-1-(3,3,3-trifluoropropyl)piperazin-2-yl]-1H-indazole (543 mg, 1.19 mmol, 87%) as a white solid; $R^r$ 1.71 min (Method 12); m/z 458.0 (M+H)$^+$ (ES$^+$); δH NMR (400 MHz, DMSO-d6) δ 12.92 (s, 1H), 8.28 (s, 1H), 7.95 (s, 1H), 7.71 (s, 1H), 7.36 (s, 1H), 4.26 (s, 3H), 3.72 (dd, J=11.5, 1.9 Hz, 1H), 3.66 (dd, J=10.4, 3.1 Hz, 1H), 3.46 (dt, J=11.8, 2.6 Hz, 1H), 3.25 (apparent d, 1H), 2.76-2.60 (m, 2H), 2.45 (s, 3H), 2.43-2.26 (over-lapping m, 4H), 2.17 (ddd, J=13.2, 8.2, 5.3 Hz, 1H).

Example 175: 2,4-dimethyl-6-(6-methyl-5-(4-(2-methyltriazol-4-yl)sulfonyl-1-(3,3,3-trifluoropropyl)piperazin-2-yl)indazol-1-yl)pyridazin-3-one

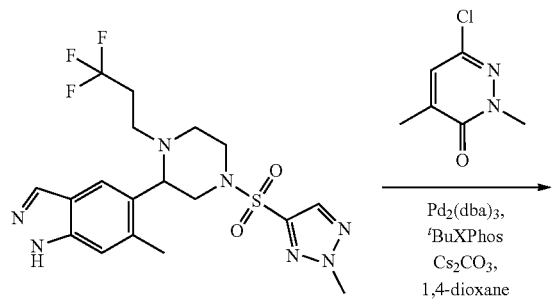

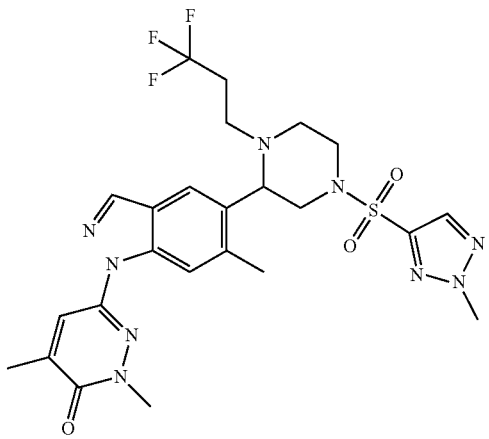

A suspension of 6-methyl-5-(4-(2-methyltriazol-4-yl)sulfonyl-1-(3,3,3-trifluoropropyl) piperazin-2-yl)-1H-indazole (50.0 mg, 0.109 mmol), 6-chloro-2,4-dimethylpyridazin-3-one (17.3 mg, 0.109 mmol), Pd$_2$(dba)$_3$ (3.14 mg, 0.00550 mmol), $^t$BuXPhos (4.64 mg, 0.0109 mmol) and Cs$_2$CO$_3$ (53.4 mg, 0.164 mmol) in 1,4-dioxane (0.5 mL) was degassed for 5 minutes and then heated at 105° C. for 18 hours. After cooling to rt the mixture was partitioned between water (10 mL) and EtOAc (10 mL). The organic phase was separated, dried (phase separator) and evaporated in vacuo. The residue thus obtained was purified by flash column chromatography (4 g cartridge, 0-80% EtOAc in heptane). The white solid so obtained was taken up into DCM and subjected to SCX capture and release. After evaporation in vacuo the resulting white solid was taken up in DCM (2.0 mL) and washed with water (2.0 mL). The biphasic mixture was passed through a phase separator and the organic extracts evaporated in vacuo to afford 2,4-dimethyl-6-(6-methyl-5-(4-(2-methyltriazol-4-yl)sulfonyl-1-(3,3,3-trifluoropropyl)piperazin-2-yl)indazol-1-yl)pyridazin-3-one (26.0 mg, 0.0426 mmol, 39%) as a white solid; $R^r$ 2.68 min (Method 11); m/z 580.2 (M+H)$^+$ (ES$^+$); δH NMR (400 MHz, DMSO-d6) δ 8.35 (d, J=0.9 Hz, 1H), 8.29 (s, 1H), 8.22 (s, 1H), 8.08 (q, J=1.2 Hz, 1H), 7.86 (s, 1H), 4.27 (s, 3H), 3.79 (s, 3H), 3.77-3.70 (m, 2H), 3.51 (dt, J=12.0, 2.5 Hz, 1H), 3.27 (apparent d, 1H), 2.73 (td, J=11.5, 2.6 Hz, 1H), 2.67-2.58 (m, 1H), 2.55 (s, 3H), 2.47-2.31 (over-lapping m, 4H), 2.22 (d, J=1.3 Hz, 3H), 2.27-2.17 (m, 1H).

Example 176: 1-(4-fluorophenyl)-6-methyl-5-(4-pyridazin-3-ylsulfonyl-1-(3,3,3-trifluoro propyl) piperazin-2-yl)indazole (Route D)

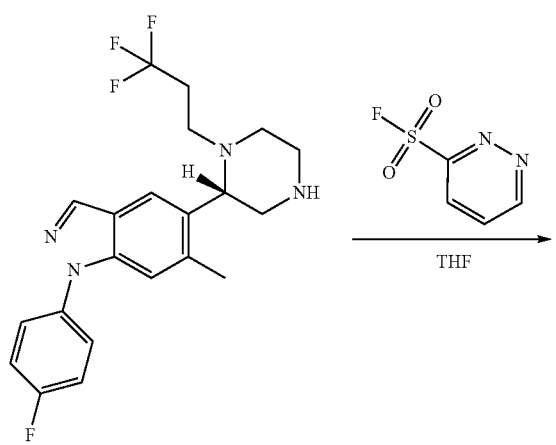

Or

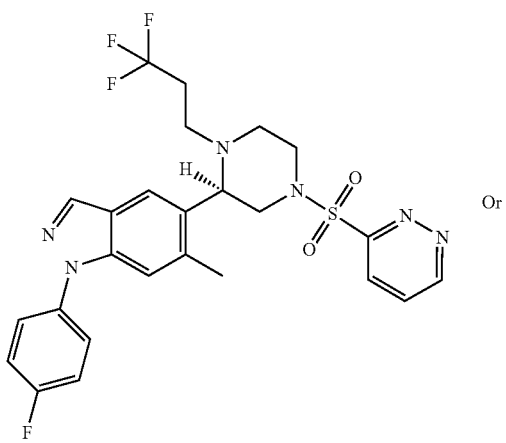

Or

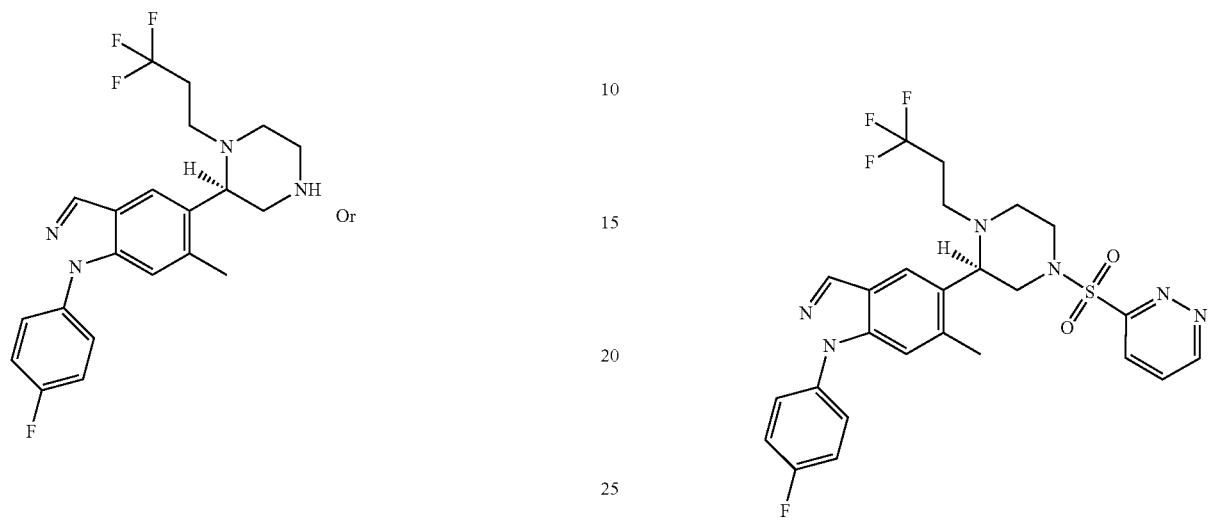

To a solution of pyridazine-3-sulfonyl fluoride (22.5 mg, 0.132 mmol) in THF (0.7 mL) at 0° C. was added a solution of 1-(4-fluorophenyl)-6-methyl-5-[1-(3,3,3-trifluoropropyl)piperazin-2-yl]indazole (67.5 mg, 0.166 mmol) in THF (0.3 mL). The resulting mixture was warmed to rt and maintained at this temperature for 48 hours, then partitioned between water (2 mL) and DCM (5 mL). The layers were separated and the aqueous extracted with further DCM (2×5 mL). The combined organic extracts were dried (phase separator) and evaporated in vacuo. The residue thus obtained was purified by flash column chromatography (4 g cartridge, 0-4% MeOH in DCM) to afford 1-(4-fluorophenyl)-6-methyl-5-(4-pyridazin-3-ylsulfonyl-1-(3,3,3-trifluoropropyl)piperazin-2-yl)indazole (34.1 mg, 0.0609 mmol, 46%) as a white solid; R$^t$ 2.81 min (Method 11); m/z 549.0 (M+H)$^+$ (ES$^+$); δH NMR (400 MHz, DMSO-d6) δ 9.50 (dd, J=5.1, 1.5 Hz, 1H), 8.26 (d, J=0.9 Hz, 1H), 8.20 (dd, J=8.6, 1.6 Hz, 1H), 8.02 (dd, J=8.6, 5.1 Hz, 1H), 7.86 (s, 1H), 7.82-7.76 (m, 2H), 7.65 (s, 1H), 7.46-7.37 (m, 2H), 3.88 (d, J=12.1 Hz, 1H), 3.72 (dd, J=10.3, 3.2 Hz, 1H), 3.65 (d, J=12.4 Hz, 1H), 3.27 (d, J=12.3 Hz, 1H), 3.06-2.97 (m, 1H), 2.77-2.60 (m, 2H), 2.47-2.31 (m, 3H), 2.24-2.12 (m, 1H). Methyl signal obscured by solvent but presence confirmed by 2D NMR.

Examples 177-215

TABLE 24

The examples shown in the table below were prepared by method in the Example indicated for the synthesis method

| Ex. | Structure | LC-MS analysis | Synthesis Method |
|---|---|---|---|
| 177 | 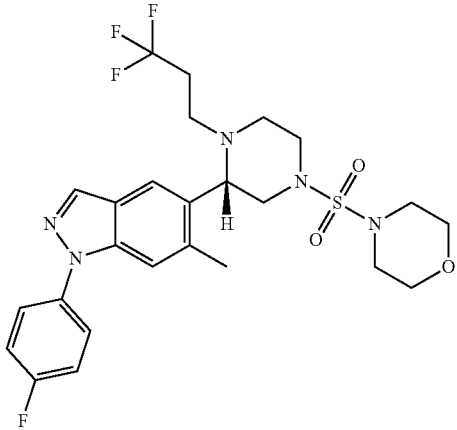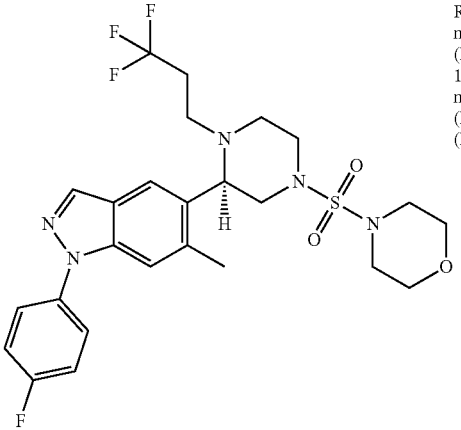<br>4-(3-(1-(4-fluorophenyl)-6-methyl-indazol-5-yl)-4-(3,3,3-trifluoropropyl)piperazin-1-yl)sulfonylmorpholine | R$^t$ 2.91 min (Method 11); m/z 556.2 (M + H)$^+$ (ES$^+$) | 1 |
| 178 | 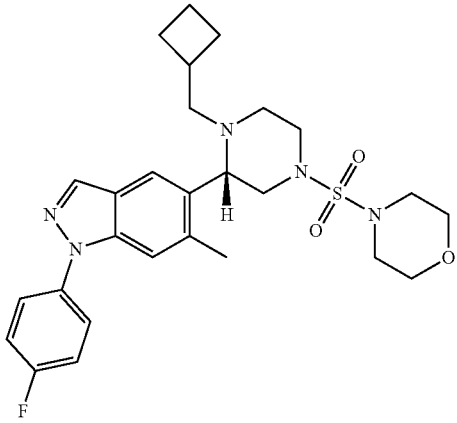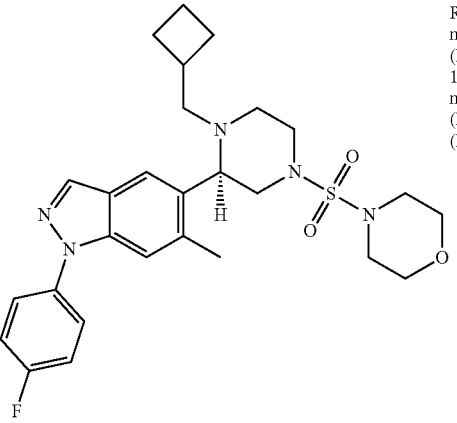<br>4-(4-(cyclobutylmethyl)-3-[1-(4-fluorophenyl)-6-methyl-indazol-5-yl]piperazin-1-yl)sulfonylmorpholine | R$^t$ 2.16 min (Method 11); m/z 528.2 (M + H)$^+$ (ES$^+$) | 1 |

TABLE 24-continued

The examples shown in the table below were prepared by method in the Example indicated for the synthesis method

| Ex. | Structure | LC-MS analysis | Synthesis Method |
|---|---|---|---|
| 179 | 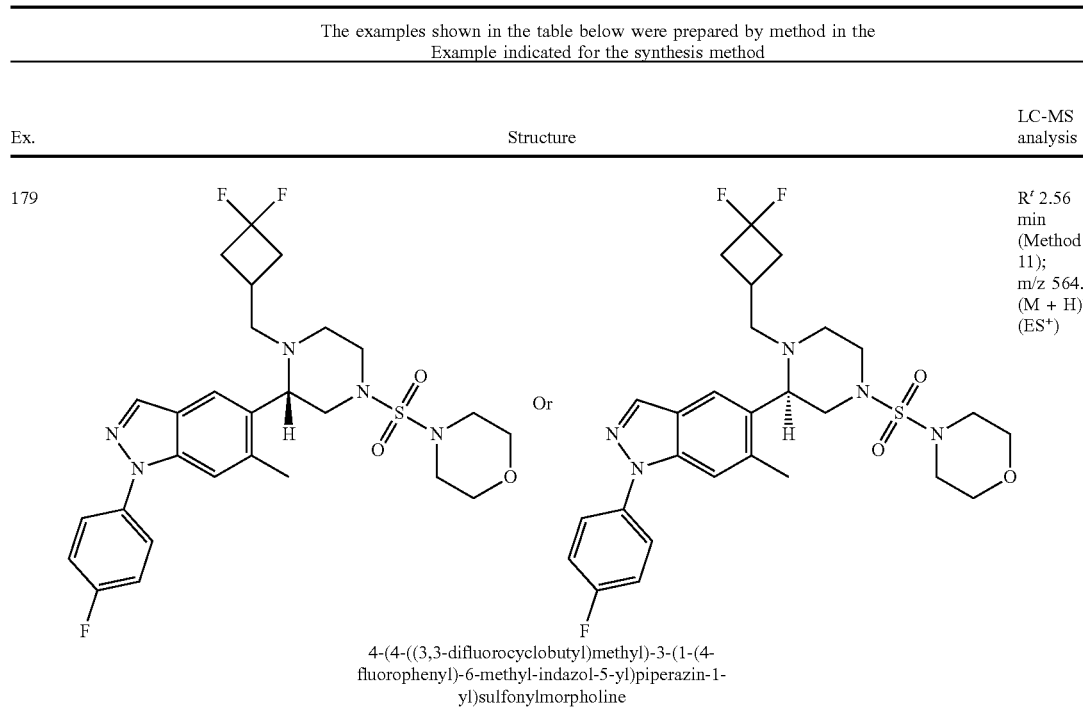  4-(4-((3,3-difluorocyclobutyl)methyl)-3-(1-(4-fluorophenyl)-6-methyl-indazol-5-yl)piperazin-1-yl)sulfonylmorpholine | $R^t$ 2.56 min (Method 11); m/z 564.2 $(M + H)^+$ $(ES^+)$ | 1 |
| 180 | 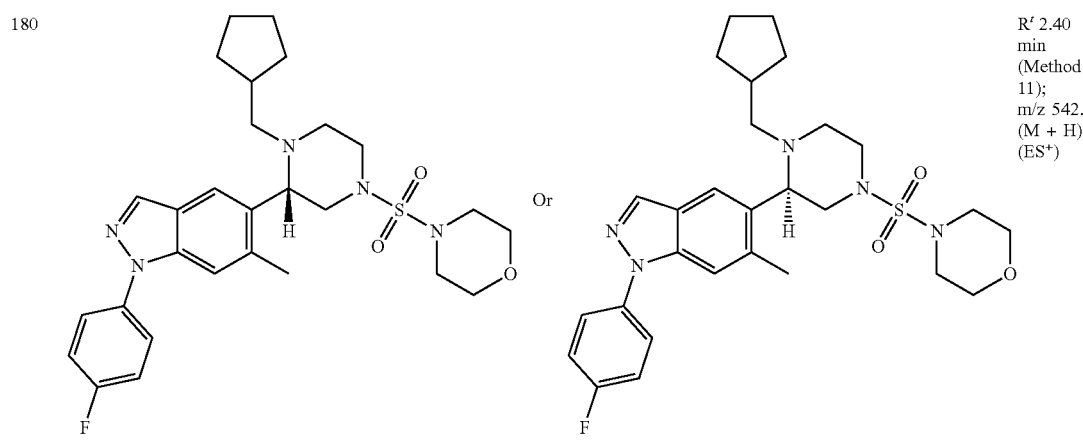  4-(4-(cyclopentylmethyl)-3-(1-(4-fluorophenyl)-6-methyl-indazol-5-yl)piperazin-1-yl)sulfonylmorpholine | $R^t$ 2.40 min (Method 11); m/z 542.2 $(M + H)^+$ $(ES^+)$ | 1 |
| 181 | 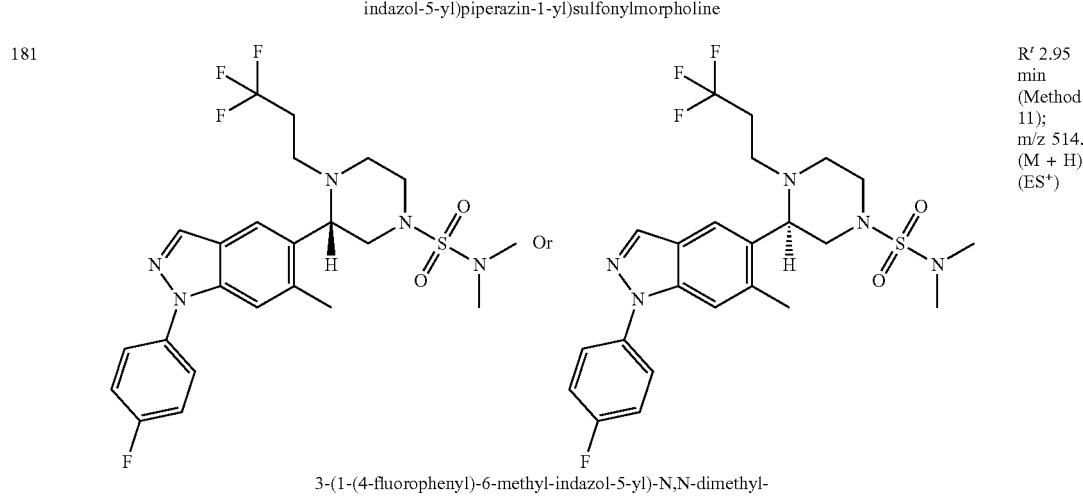  3-(1-(4-fluorophenyl)-6-methyl-indazol-5-yl)-N,N-dimethyl-4-(3,3,3-trifluoropropyl)piperazine-1-sulfonamide | $R^t$ 2.95 min (Method 11); m/z 514.1 $(M + H)^+$ $(ES^+)$ | 1 |

TABLE 24-continued

The examples shown in the table below were prepared by method in the
Example indicated for the synthesis method

| Ex. | Structure | LC-MS analysis | Synthesis Method |
|---|---|---|---|
| 182 | 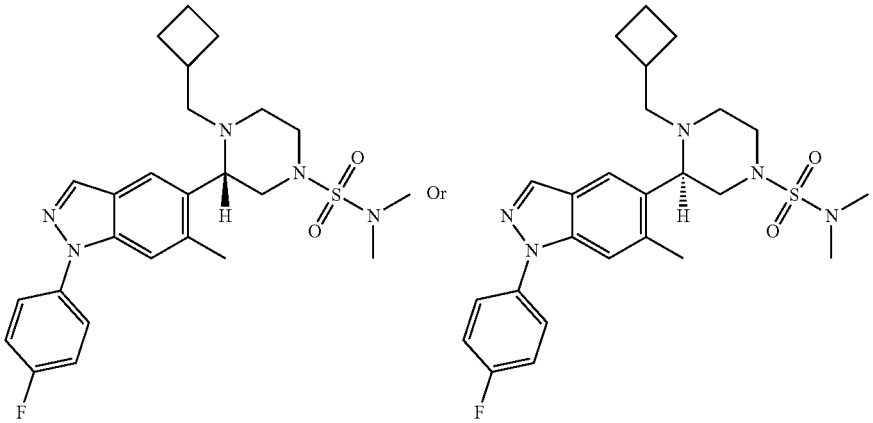 [SMILES: Cc1cc2c(cnn2-c2ccc(F)cc2)cc1[C@H]1CN(S(=O)(=O)N(C)C)CCN1CC1CCC1 ; Cc1cc2c(cnn2-c2ccc(F)cc2)cc1[C@@H]1CN(S(=O)(=O)N(C)C)CCN1CC1CCC1] 4-(cyclobutylmethyl)-3-(1-(4-fluorophenyl)-6-methyl-indazol-5-yl)-N,N-dimethyl-piperazine-1-sulfonamide | R$^t$ 2.15 min (Method 11); m/z 486.2 (M + H)$^+$ (ES$^+$) | 1 |
| 183 | 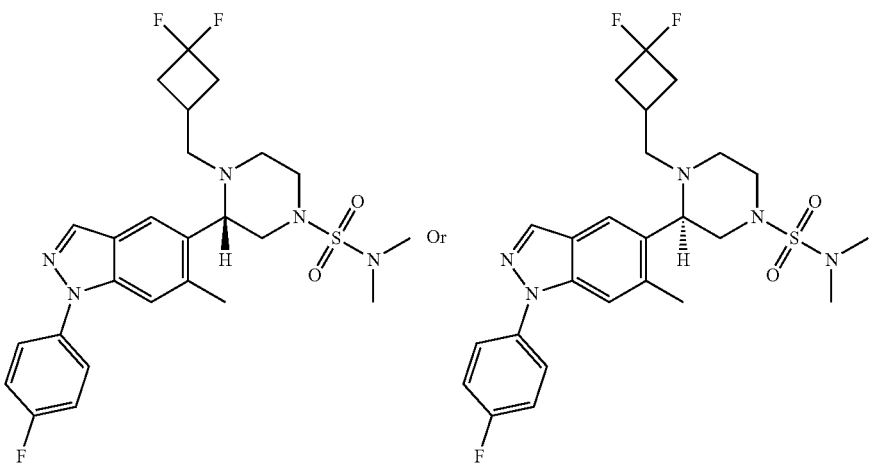 [SMILES: Cc1cc2c(cnn2-c2ccc(F)cc2)cc1[C@H]1CN(S(=O)(=O)N(C)C)CCN1CC1CC(F)(F)C1 ; Cc1cc2c(cnn2-c2ccc(F)cc2)cc1[C@@H]1CN(S(=O)(=O)N(C)C)CCN1CC1CC(F)(F)C1] 4-((3,3-difluorocyclobutyl)methyl)-3-(1-(4-fluorophenyl)-6-methyl-indazol-5-yl)-N,N-dimethyl-piperazine-1-sulfonamide | R$^t$ 2.56 min (Method 11); m/z 522.2 (M + H)$^+$ (ES$^+$) | 1 |
| 184 | 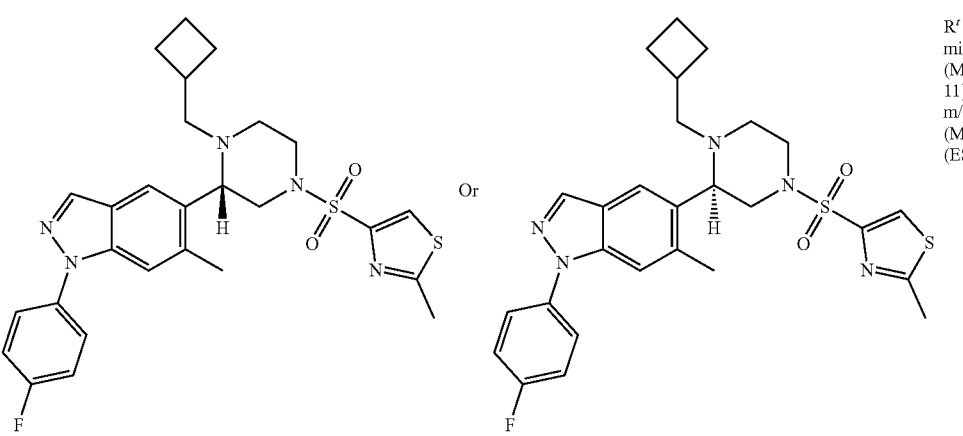 4-(4-(cyclobutylmethyl)-3-(1-(4-fluorophenyl)-6-methyl-indazol-5-yl)piperazin-1-yl)sulfonyl-2-methyl-thiazole | R$^t$ 2.36 min (Method 11); m/z 540.2 (M + H)$^+$ (ES$^+$) | 1 |

TABLE 24-continued

The examples shown in the table below were prepared by method in the Example indicated for the synthesis method

| Ex. | Structure | LC-MS analysis | Synthesis Method |
|---|---|---|---|
| 185 | 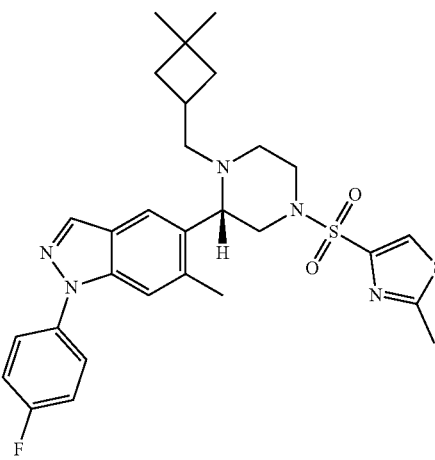 Or 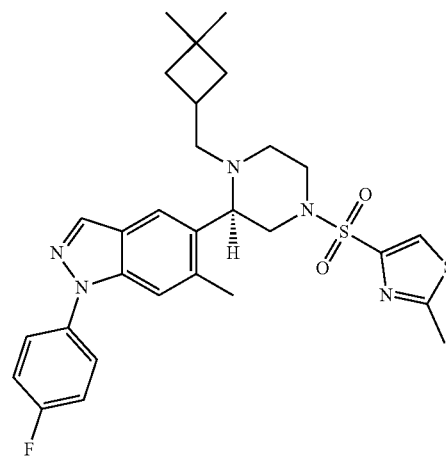  4-(4-((3,3-dimethylcyclobutyl)methyl)-3-(1-(4-fluorophenyl)-6-methyl-indazol-5-yl)piperazin-1-yl)sulfonyl-2-methyl-thiazole | R$^t$ 2.60 min (Method 11); m/z 568.2 (M + H)$^+$ (ES$^+$) | 1 |
| 186 | 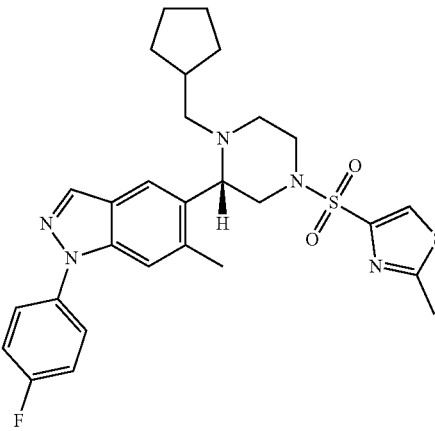 Or 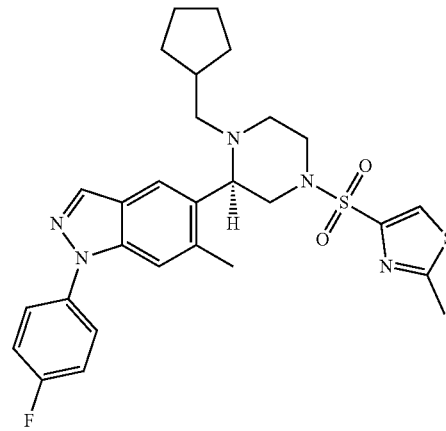  4-(4-(cyclopentylmethyl)-3-(1-(4-fluorophenyl)-6-methyl-indazol-5-yl)piperazin-1-yl)sulfonyl-2-methyl-thiazole | R$^t$ 2.60 min (Method 11); m/z 554.2 (M + H)$^+$ (ES$^+$) | 1 |
| 187 | 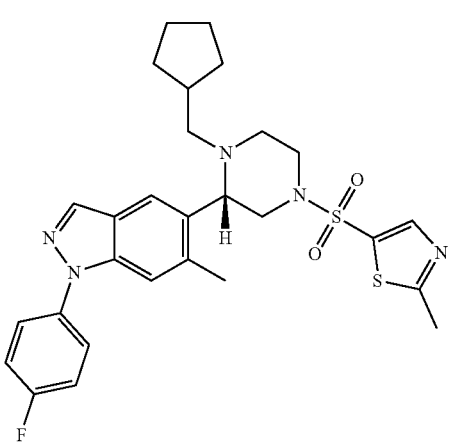 Or 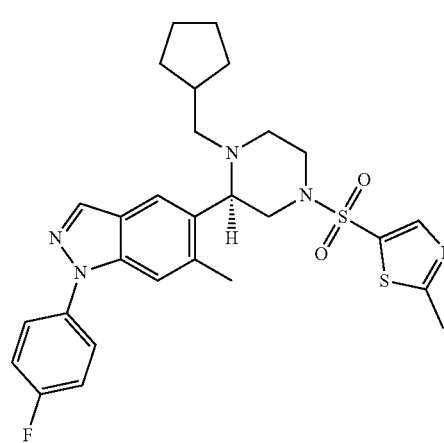  5-(4-(cyclopentylmethyl)-3-(1-(4-fluorophenyl)-6-methyl-indazol-5-yl)piperazin-1-yl)sulfonyl-2-methyl-thiazole | R$^t$ 2.86 min (Method 11); m/z 554.2 (M + H)$^+$ (ES$^+$) | 1 |

TABLE 24-continued

The examples shown in the table below were prepared by method in the Example indicated for the synthesis method

| Ex. | Structure | LC-MS analysis | Synthesis Method |
|---|---|---|---|
| 188 | 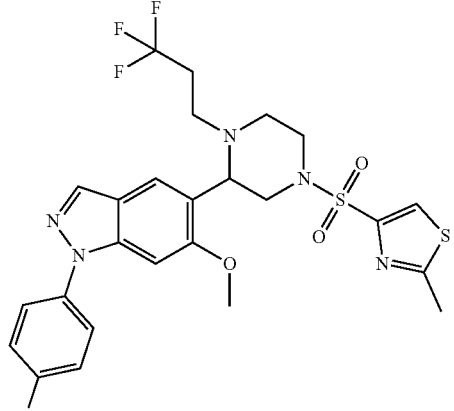 4-(3-(1-(4-fluorophenyl)-6-methoxy-indazol-5-yl)-4-(3,3,3-trifluoropropyl)piperazin-1-yl)sulfonyl-2-methyl-thiazole | $R^t$ 2.84 min (Method 11); m/z 584.0 $(M + H)^+$ $(ES^+)$ | 1 |
| 189 | 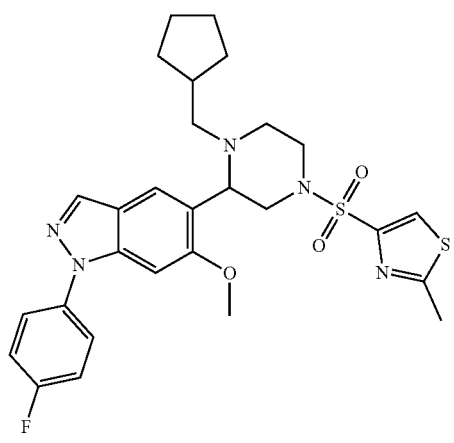 [SMILES: COc1cc2c(cnn2-c2ccc(F)cc2)cc1C1CN(S(=O)(=O)c2csc(C)n2)CCN1CC1CCCC1] 4-(4-(cyclopentylmethyl)-3-(1-(4-fluorophenyl)-6-methoxy-indazol-5-yl)piperazin-1-yl)sulfonyl-2-methyl-thiazole | $R^t$ 2.17 min (Method 11); m/z 570.2 $(M + H)^+$ $(ES^+)$ | 1 |
| 190 | 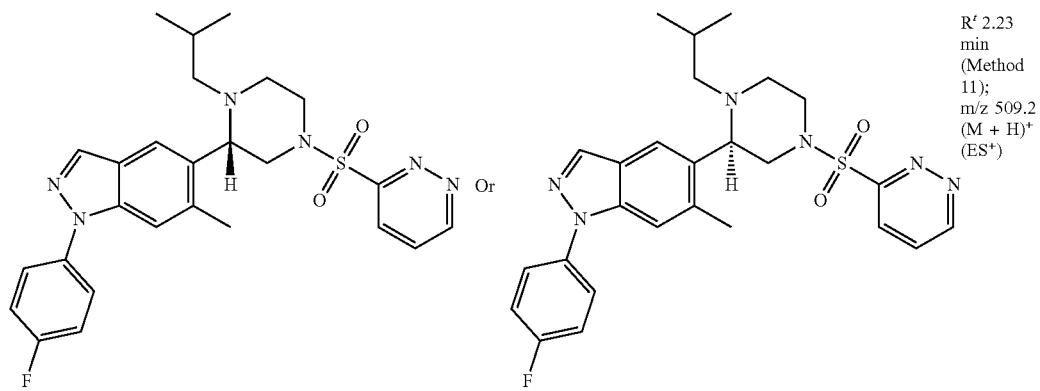 1-(4-fluorophenyl)-5-(1-isobutyl-4-pyridazin-3-ylsulfonyl-piperazin-2-yl)-6-methyl-indazole | $R^t$ 2.23 min (Method 11); m/z 509.2 $(M + H)^+$ $(ES^+)$ | 176 |

TABLE 24-continued

The examples shown in the table below were prepared by method in the Example indicated for the synthesis method

| Ex. | Structure | LC-MS analysis | Synthesis Method |
|---|---|---|---|
| 191 | 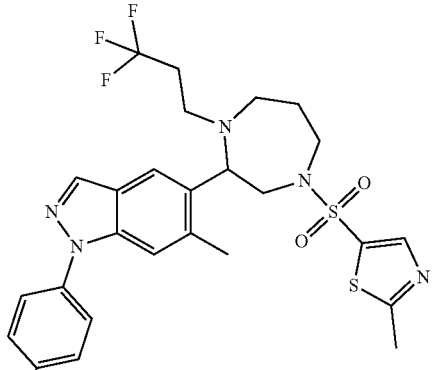 5-((3-(1-(4-fluorophenyl)-6-methyl-indazol-5-yl)-4-(3,3,3-trifluoropropyl)-1,4-diazepan-1-yl)sulfonyl)-2-methyl-thiazole | $R^t$ 3.01 min (Method 11); m/z 582.2 $(M + H)^+$ $(ES^+)$ | 173 |
| 192 | 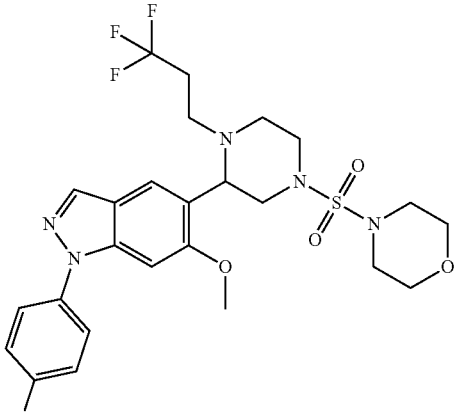 4-(3-(1-(4-fluorophenyl)-6-methoxy-indazol-5-yl)-4-(3,3,3-trifluoropropyl)piperazin-1-yl)sulfonylmorpholine | $R^t$ 2.70 min (Method 11); m/z 572.2 $(M + H)^+$ $(ES^+)$ | 1 |
| 193 | 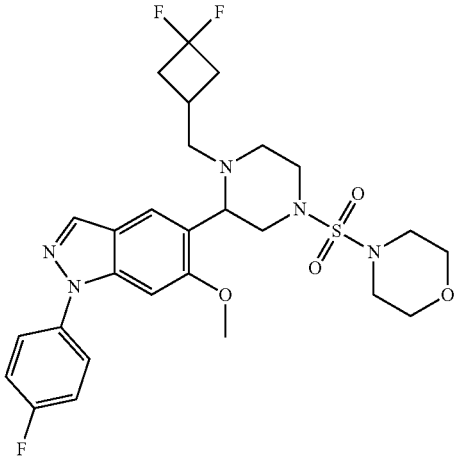 [SMILES: COc1cc2c(cnn2-c2ccc(F)cc2)cc1C1CN(S(=O)(=O)N2CCOCC2)CCN1CC1CC(F)(F)C1] 4-(4-((3,3-difluorocyclobutyl)methyl)-3-(1-(4-fluorophenyl)-6-methoxy-indazol-5-yl)piperazin-1-yl)sulfonylmorpholine | $R^t$ 2.16 min (Method 11); m/z 580.2 $(M + H)^+$ $(ES^+)$ | 1 |

TABLE 24-continued

The examples shown in the table below were prepared by method in the
Example indicated for the synthesis method

| Ex. | Structure | LC-MS analysis | Synthesis Method |
|---|---|---|---|
| 194 | 1,3-dimethyl-5-(6-methyl-5-(4-(3-pyridylsulfonyl)-1-(3,3,3-trifluoropropyl)piperazin-2-yl)indazol-1-yl)pyridin-2-one | R$^t$ 2.43 min (Method 11); m/z 575.2 (M + H)$^+$ (ES$^+$) | 174 |
| 195 | 1,3-dimethyl-5-(6-methyl-5-(4-(2-pyridylsulfonyl)-1-(3,3,3-trifluoropropyl)piperazin-2-yl)indazol-1-yl)pyridin-2-one | R$^t$ 2.47 min (Method 11); m/z 575.2 (M + H)$^+$ (ES$^+$) | 174 |
| 196 | 3-(1-(1,5-dimethyl-6-oxo-3-pyridyl)-6-methyl-indazol-5-yl)-N,N-dimethyl-4-(3,3,3-trifluoropropyl)piperazine-1-sulfonamide | R$^t$ 2.44 min (Method 11); m/z 541.2 (M + H)$^+$ (ES$^+$) | 174 |

TABLE 24-continued

The examples shown in the table below were prepared by method in the Example indicated for the synthesis method

| Ex. | Structure | LC-MS analysis | Synthesis Method |
|---|---|---|---|
| 197 | 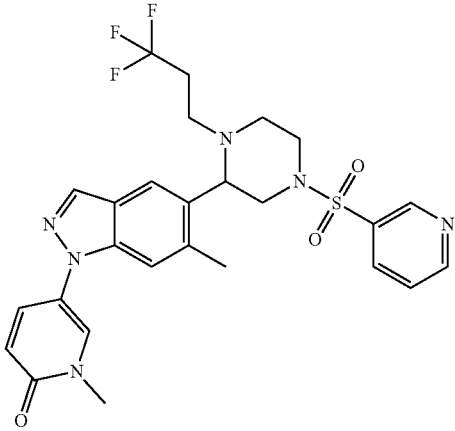 [SMILES: Cc1cc2c(cnn2-c2ccc(=O)n(C)c2)cc1C1CN(S(=O)(=O)c2cccnc2)CCN1CCC(F)(F)F]<br>1-methyl-5-(6-methyl-5-(4-(3-pyridylsulfonyl)-1-(3,3,3-trifluoropropyl)piperazin-2-yl)indazol-1-yl)pyridin-2-one | R$^t$ 2.31 min (Method 11); m/z 561.2 (M + H)$^+$ (ES$^+$) | 174 |
| 198 | 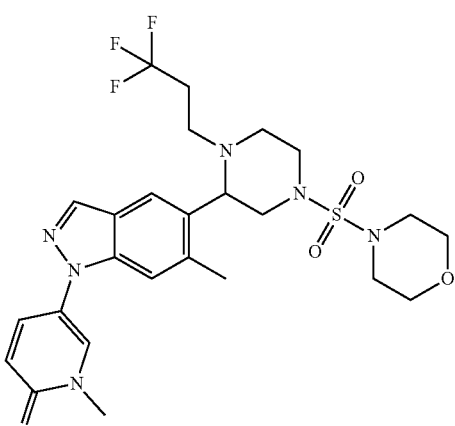<br>1-methyl-5-(6-methyl-5-(4-morpholinosulfonyl-1-(3,3,3-trifluoropropyl)piperazin-2-yl)indazol-1-yl)pyridin-2-one | R$^t$ 2.28 min (Method 11); m/z 569.2 (M + H)$^+$ (ES$^+$) | 174 |
| 199 | 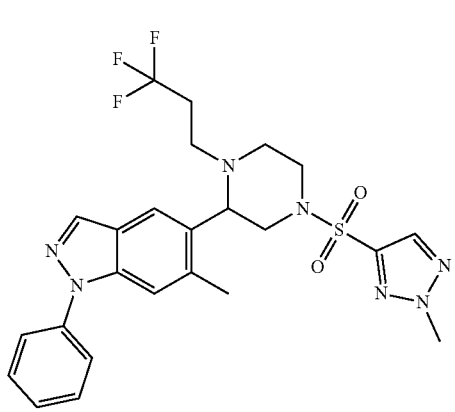 [SMILES: Cc1cc2c(cnn2-c2ccccc2)cc1C1CN(S(=O)(=O)c2cnn(C)n2)CCN1CCC(F)(F)F]<br>6-methyl-5-(4-(2-methyltriazol-4-yl)sulfonyl-1-(3,3,3-trifluoropropyl)piperazin-2-yl)-1-phenyl-indazole | R$^t$ 2.91 min (Method 11); m/z 534.0 (M + H)$^+$ (ES$^+$) | 174 |

TABLE 24-continued

The examples shown in the table below were prepared by method in the Example indicated for the synthesis method

| Ex. | Structure | LC-MS analysis | Synthesis Method |
|---|---|---|---|
| 200 | 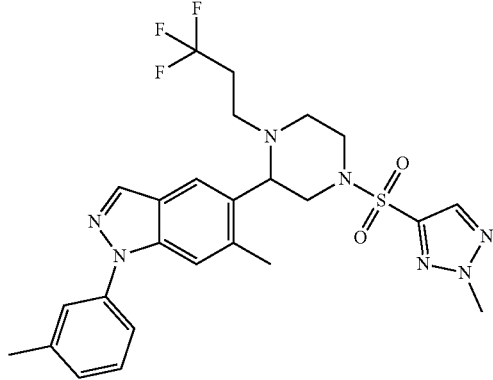 [SMILES: Cc1cccc(-n2ncc3cc(C4CN(S(=O)(=O)c5cnn(C)n5)CCN4CCC(F)(F)F)c(C)cc32)c1]<br>6-methyl-5-(4-(2-methyltriazol-4-yl)sulfonyl-1-(3,3,3-trifluoropropyl)piperazin-2-yl)-1-(m-tolyl)indazole | $R^t$ 3.01 min (Method 11); m/z 548.0 (M + H)⁺ (ES⁺) | 174 |
| 201 | 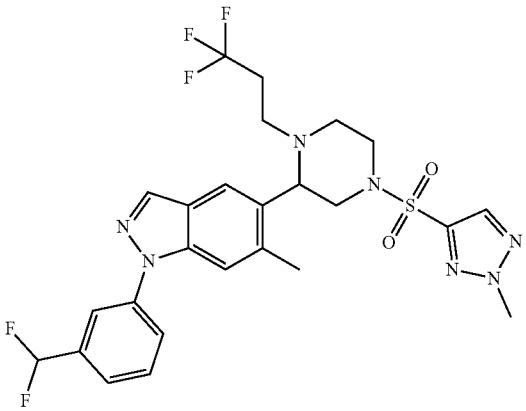 [SMILES: Cc1cc2c(cnn2-c2cccc(C(F)F)c2)cc1C1CN(S(=O)(=O)c2cnn(C)n2)CCN1CCC(F)(F)F]<br>1-(3-(difluoromethyl)phenyl)-6-methyl-5-(4-(2-methyltriazol-4-yl)sulfonyl-1-(3,3,3-trifluoropropyl)piperazin-2-yl)indazole | $R^t$ 2.98 min (Method 11); m/z 584.1 (M + H)⁺ (ES⁺) | 174 |
| 202 | 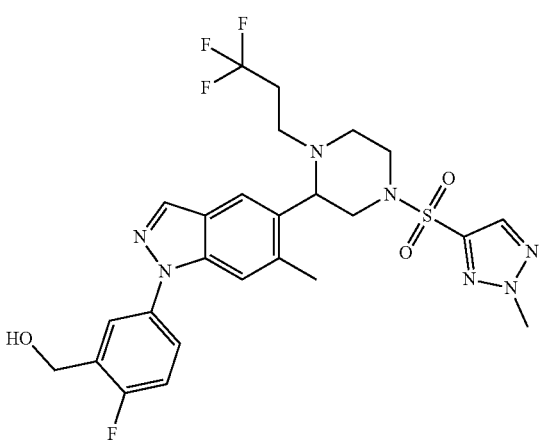 [SMILES: Cc1cc2c(cnn2-c2ccc(F)c(CO)c2)cc1C1CN(S(=O)(=O)c2cnn(C)n2)CCN1CCC(F)(F)F]<br>(2-fluoro-5-(6-methyl-5-(4-(2-methyltriazol-4-yl)sulfonyl-1-(3,3,3-trifluoropropyl)piperazin-2-yl)indazol-1-yl)phenyl)methanol | $R^t$ 2.67 min (Method 11); m/z 582.2 (M + H)⁺ (ES⁺) | 174 |

TABLE 24-continued

The examples shown in the table below were prepared by method in the Example indicated for the synthesis method

| Ex. | Structure | LC-MS analysis | Synthesis Method |
|---|---|---|---|
| 203 | 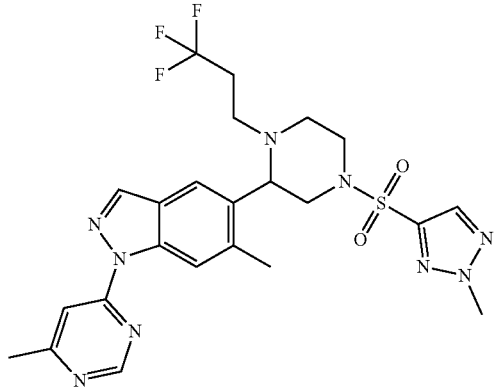 [SMILES: Cc1cc(-n2ncc3cc(C4CN(S(=O)(=O)c5cnn(C)n5)CCN4CCC(F)(F)F)c(C)cc32)ncn1]<br>6-methyl-1-(6-methylpyrimidin-4-yl)-5-(4-(2-methyltriazol-4-yl)sulfonyl-1-(3,3,3-trifluoropropyl)piperazin-2-yl)indazole | $R^t$ 2.77 min (Method 11); m/z 550.0 (M + H)$^+$ (ES$^+$) | 174 |
| 204 | 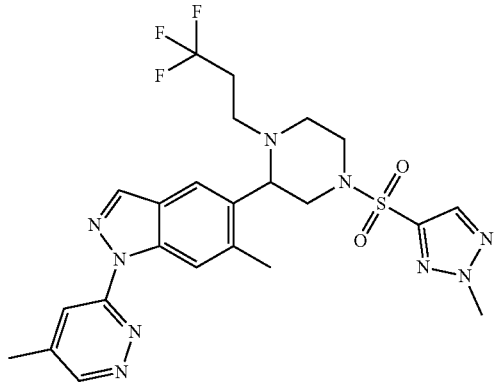 [SMILES: Cc1cnnc(-n2ncc3cc(C4CN(S(=O)(=O)c5cnn(C)n5)CCN4CCC(F)(F)F)c(C)cc32)c1]<br>6-methyl-1-(5-methylpyridazin-3-yl)-5-(4-(2-methyltriazol-4-yl)sulfonyl-1-(3,3,3-trifluoropropyl)piperazin-2-yl)indazole | $R^t$ 2.69 min (Method 11); m/z 550.2 (M + H)$^+$ (ES$^+$) | 174 |
| 205 | 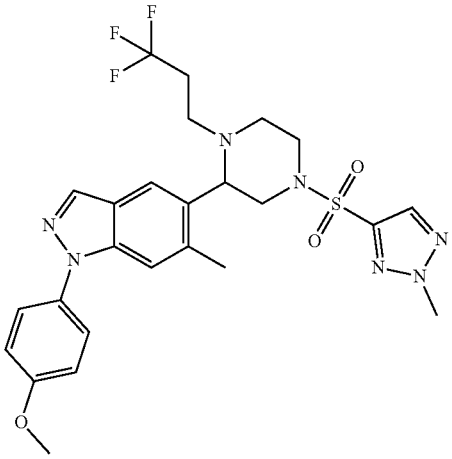 [SMILES: COc1ccc(-n2ncc3cc(C4CN(S(=O)(=O)c5cnn(C)n5)CCN4CCC(F)(F)F)c(C)cc32)cc1]<br>1-(4-methoxyphenyl)-6-methyl-5-(4-(2-methyltriazol-4-yl)sulfonyl-1-(3,3,3-trifluoropropyl)piperazin-2-yl)indazole | $R^t$ 2.87 min (Method 11); m/z 564.2 (M + H)$^+$ (ES$^+$) | 174 |

TABLE 24-continued

The examples shown in the table below were prepared by method in the
Example indicated for the synthesis method

| Ex. | Structure | LC-MS analysis | Synthesis Method |
|---|---|---|---|
| 206 | 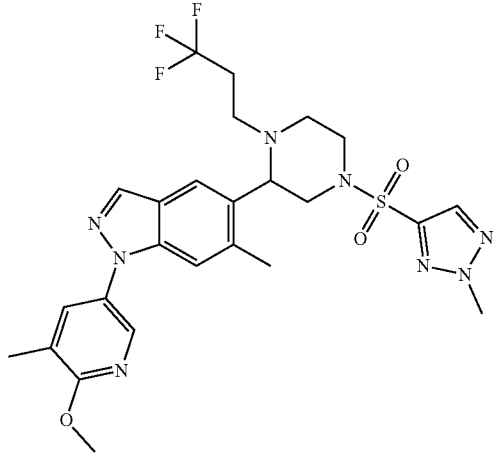 [SMILES: COc1ncc(-n2ncc3cc(C4CN(S(=O)(=O)c5cnn(C)n5)CCN4CCC(F)(F)F)c(C)cc32)cc1C]<br>1-(6-methoxy-5-methyl-3-pyridyl)-6-methyl-5-(4-(2-methyltriazol-4-yl)sulfonyl-1-(3,3,3-trifluoropropyl)piperazin-2-yl)indazole | $R^t$ 2.97 min (Method 11); m/z 579.2 (M + H)$^+$ (ES$^+$) | 174 |
| 207 | 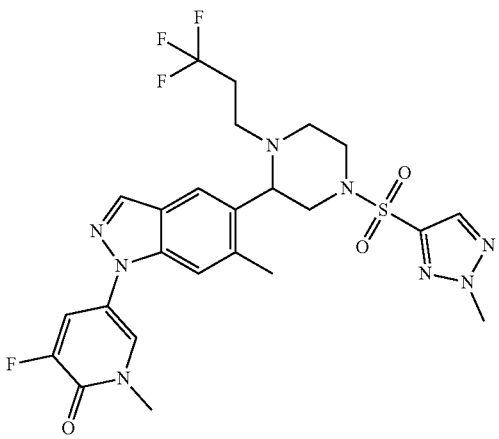 [SMILES: Cc1cc2c(cnn2-c2cc(F)c(=O)n(C)c2)cc1C1CN(S(=O)(=O)c2cnn(C)n2)CCN1CCC(F)(F)F]<br>3-fluoro-1-methyl-5-(6-methyl-5-(4-(2-methyltriazol-4-yl)sulfonyl-1-(3,3,3-trifluoropropyl)piperazin-2-yl)indazol-1-yl)pyridin-2-one | $R^t$ 2.40 min (Method 11); m/z 583.0 (M + H)$^+$ (ES$^+$) | 174 |
| 209 | 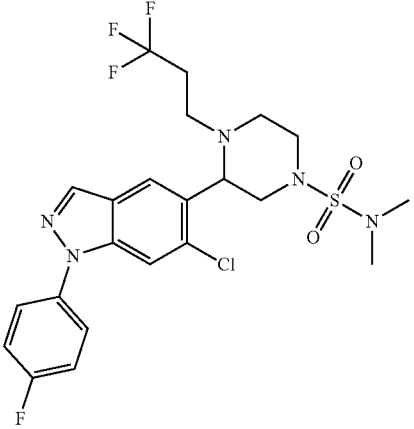 [SMILES: CN(C)S(=O)(=O)N1CCN(CCC(F)(F)F)C(c2cc3cnn(-c4ccc(F)cc4)c3cc2Cl)C1]<br>3-(6-chloro-1-(4-fluorophenyl)indazol-5-yl)-N,N-dimethyl-4-(3,3,3-trifluoropropyl)piperazine-1-sulfonamide | $R^t$ 3.01 min (Method 11); m/z 534.1 (M + H)$^+$ (ES$^+$) | 174 |

TABLE 24-continued

The examples shown in the table below were prepared by method in the
Example indicated for the synthesis method

| Ex. | Structure | LC-MS analysis | Synthesis Method |
|---|---|---|---|
| 210 | 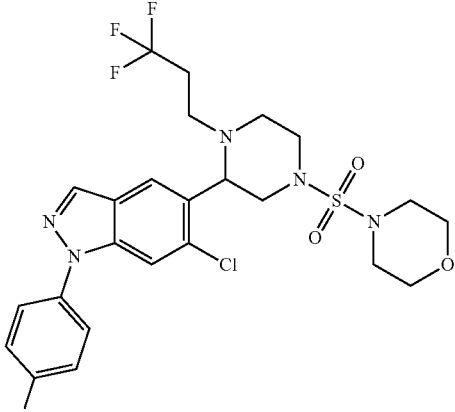<br>4-(3-(6-chloro-1-(4-fluorophenyl)indazol-5-yl)-4-(3,3,3-trifluoropropyl)piperazin-1-yl)sulfonylmorpholine | R$^t$ 2.51 min (Method 11); m/z 603.2 (M + H)$^+$ (ES$^+$) | 174 |
| 211 | 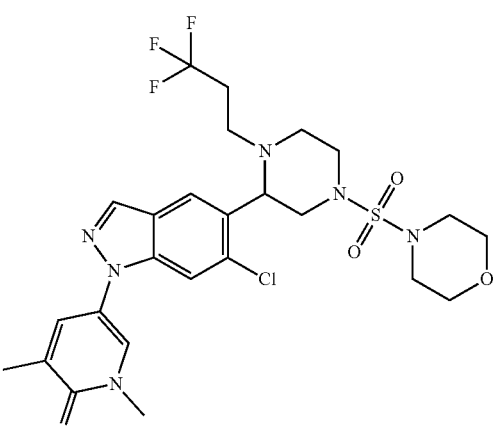<br>5-(6-chloro-5-(4-morpholinosulfonyl-1-(3,3,3-trifluoropropyl)piperazin-2-yl)indazol-1-yl)-1,3-dimethyl-pyridin-2-one | R$^t$ 2.51 min (Method 11); m/z 603.2 (M + H)$^+$ (ES$^+$) | 174 |
| 212 | 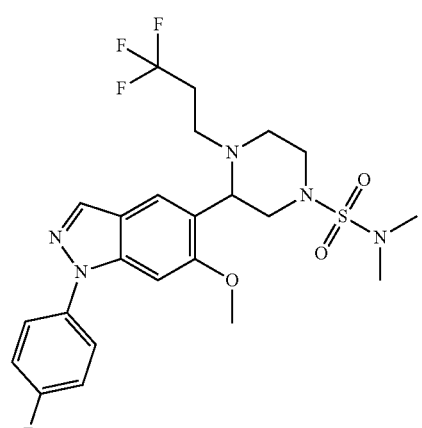<br>3-(1-(4-fluorophenyl)-6-methoxy-indazol-5-yl)-N,N-dimethyl-4-(3,3,3-trifluoropropyl)piperazine-1-sulfonamide | R$^t$ 2.60 min (Method 11); m/z 530.2 (M + H)$^+$ (ES$^+$) | 1 |

TABLE 24-continued

The examples shown in the table below were prepared by method in the Example indicated for the synthesis method

| Ex. | Structure | LC-MS analysis | Synthesis Method |
|---|---|---|---|
| 213 | 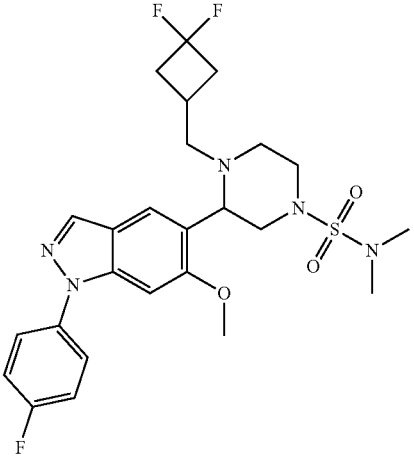 [SMILES: COc1cc2c(cnn2-c2ccc(F)cc2)cc1C1CN(S(=O)(=O)N(C)C)CCN1CC1CC(F)(F)C1] 4-((3,3-difluorocyclobutyl)methyl)-3-(1-(4-fluorophenyl)-6-methoxy-indazol-5-yl)-N,N-dimethyl-piperazine-1-sulfonamide | $R^t$ 2.09 min (Method 11); m/z 538.2 (M + H)$^+$ (ES$^+$) | 1 |
| 214 | 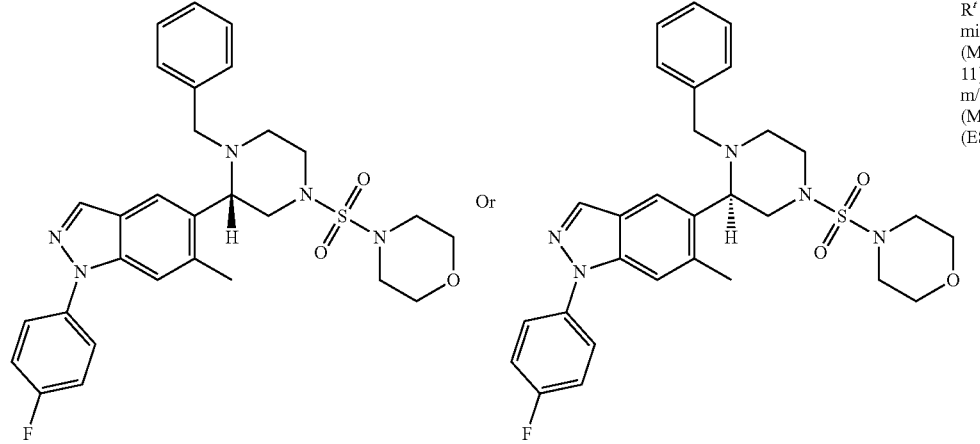 4-(4-benzyl-3-(1-(4-fluorophenyl)-6-methyl-indazol-5-yl)piperazin-1-yl)sulfonylmorpholine | $R^t$ 2.75 min (Method 11); m/z 550.2 (M + H)$^+$ (ES$^+$) | 1 |

TABLE 24-continued

The examples shown in the table below were prepared by method in the Example indicated for the synthesis method

| Ex. | Structure | LC-MS analysis | Synthesis Method |
|---|---|---|---|
| 215 | 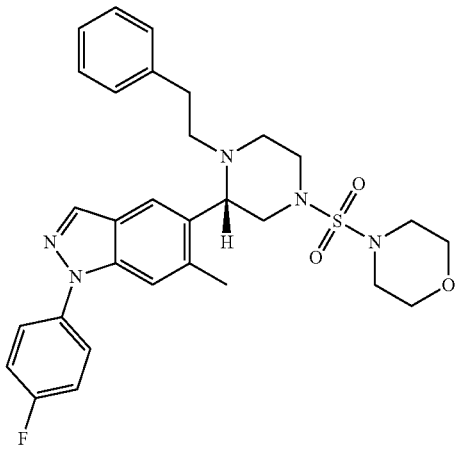 Or 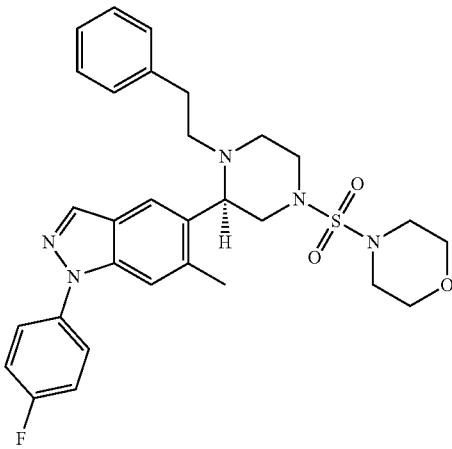<br>4-(3-(1-(4-fluorophenyl)-6-methyl-indazol-5-yl)-4-(2-phenylethyl)piperazin-1-yl)sulfonylmorpholine | $R^t$ 2.51 min (Method 11); m/z 564.2 $(M + H)^+$ $(ES^+)$ | 1 |

VII. Biological Examples

Example 1: GR Binding Assay

Binding of test compounds to the glucocorticoid receptor (GR) is determined using a fluorescence polarisation (FP) assay utilising a recombinant ligand binding domain (LBD) of GR. The test compounds are assessed by their ability to displace a fluorescently tagged ligand and detection of the resulting decrease in fluorescence polarisation. Fluorescence polarisation values are converted to % inhibition using the high (1% DMSO only) and low (1 µM) controls and $IC_{50}$ values are calculated from non-linear regression curves fitted using Dotmatics software.

Example 2: Hep G2 TAT Ki

Glucocorticoid mediated activation of TAT occurs by transactivation of glucocorticoid response elements in the TAT promoter by glucocorticoid receptor-agonist complex. The following protocol describes an assay for measuring induction of TAT by dexamethasone in HepG2 cells (a human liver hepatocellular carcinoma cell line; ECACC, UK).

TAT activity was measured as outlined in the literature by A. Ali et al., J. Med. Chem., 2004, 47, 2441-2452. Dexamethasone induced TAT production with an average $EC_{50}$ value (half-maximal effect) of 20 nM.

HepG2 cells were cultured using MEME media supplemented with 10% (v/v) foetal bovine serum; 2 mM L-glutamine and 1% (v/v) NEAA at 37° C., 5%/95% (v/v) $CO_2$/air. The HepG2 cells were counted and adjusted to yield a density of $0.2 \times 10^6$ cells/ml in RPMI 1640 without phenol red, 10% (v/v) charcoal stripped FBS, 2 mM L-glutamine and seeded at 40,000 cells/well in 200 µl into 96 well, sterile, tissue culture micro titre plates, and incubated at 37° C., 5% $CO_2$ for 24 hours Growth media was removed and replaced with assay media {RPMI 1640 without phenol red, 2 mM L-glutamine+ 10 µM forskolin}. Test compounds were screened against a challenge of 100 nM dexamethasone. Compounds were serially half log diluted in 100% (v/v) dimethylsulphoxide from a 10 mM stock. Then an 8-point half-log dilution curve was generated followed by a 1:100 dilution into assay media to give a 10× final assay [compound]: this resulted in final assay [compound] that ranged 10 to 0.003 µM in 0.1% (v/v) dimethylsulfoxide.

100 nM of dexamethasone was added to the test compounds which were then subsequently incubated for 18-24 hr at 37° C., 5/95 (v/v) $CO_2$/air to allow optimal TAT induction.

HepG2 cells were then lysed with 30 µl of cell lysis buffer containing a protease inhibitor cocktail for 15 minutes at 4° C. 155 µl of substrate mixture was then added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction was terminated by the addition of 15 µl of 10M aqueous potassium hydroxide solution, and the plates incubated for a further 30 minutes at 37° C. The TAT activity product was measured by absorbance at k 340 nm.

$IC_{50}$ values were calculated by plotting % inhibition (normalised to 100 nM dexamethasone TAT stimulation) v. [compound] and fitting the data to a 4 parameter logistic equation. $IC_{50}$ values were converted to Ki (equilibrium dissociation constant) using the Cheng and Prusoff equation, assuming the antagonists were competitive inhibitors with respect to dexamethasone.

TABLE 25

Activity Data

| Example No. | HepG2 TAT Ki (nM) |
|---|---|
| 1 | 35 |
| 2 | 81 |
| 3 | 85 |
| 4 | 41 |
| 5 | 420 |
| 6 | 46 |
| 7 | 62 |
| 8 | 66 |
| 9 | 72 |
| 10 | 430 |
| 11 | 20 |
| 12 | 68 |
| 13 | 97 |
| 14 | 62 |
| 15 | 260 |
| 16 | 520 |
| 17 | 110 |
| 18 | 330 |
| 19 | 140 |
| 20 | 130 |
| 21 | 120 |
| 22 | 57 |
| 23 | 13 |
| 24 | 73 |
| 25 | 77 |
| 26 | 180 |
| 27 | 47 |
| 28 | 230 |
| 29 | 74 |
| 30 | 90 |
| 31 | 11 |
| 32 | 19 |
| 33 | 11 |
| 34 | 430 |
| 35 | 770 |
| 36 | 50 |
| 37 | 76 |
| 38 | 46 |
| 39 | 57 |
| 40 | 53 |
| 41 | 60 |
| 42 | 40 |
| 43 | 76 |
| 44 | 93 |
| 45 | 510 |
| 46 | 310 |
| 47 | 23 |
| 48 | 23 |
| 49 | 31 |
| 50 | 64 |
| 51 | 28 |
| 52 | 24 |
| 53 | 41 |
| 54 | 31 |
| 55 | 19 |
| 56 | 65 |
| 57 | 19 |
| 58 | 15 |
| 59 | 22 |
| 60 | 28 |
| 61 | 64 |
| 62 | 44 |
| 63 | 20 |
| 64 | 50 |
| 65 | 370 |
| 66 | 260 |
| 67 | 390 |
| 68 | 58 |
| 69 | 180 |
| 70 | 170 |
| 71 | 160 |
| 72 | 330 |
| 73 | 170 |
| 74 | 160 |
| 75 | 140 |
| 76 | 22 |
| 77 | 13 |
| 78 | 13 |
| 79 | 29 |
| 80 | 150 |
| 81 | 73 |
| 82 | 43 |
| 83 | 33 |
| 84 | 14 |
| 85 | 29 |
| 86 | 180 |
| 87 | 54 |
| 88 | 35 |
| 89 | 34 |
| 92 | 86 |
| 93 | 36 |
| 94 | 74 |
| 95 | 100 |
| 96 | 43 |
| 97 | 23 |
| 98 | 25 |
| 99 | 19 |
| 100 | 42 |
| 101 | 28 |
| 102 | 39 |
| 103 | 35 |
| 104 | 19 |
| 105 | 46 |
| 106 | 33 |
| 107 | 22 |
| 108 | 44 |
| 109 | 12 |
| 110 | 27 |
| 111 | 65 |
| 112 | 36 |
| 113 | |
| 114 | 55 |
| 115 | 24 |
| 116 | 25 |
| 117 | 38 |
| 118 | 190 |
| 119 | 19 |
| 120 | 65 |
| 121 | 270 |
| 122 | 110 |
| 123 | 71 |
| 124 | 14 |
| 125 | 87 |
| 126 | 62 |
| 127 | 22 |
| 128 | 14 |
| 129 | 13 |
| 130 | 7.7 |
| 131 | 13 |
| 132 | 13 |
| 133 | 11 |
| 134 | 6.5 |
| 135 | 23 |
| 136 | 57 |
| 137 | 33 |
| 138 | 35 |
| 139 | 37 |
| 140 | 47 |
| 141 | 14 |
| 142 | 13 |
| 143 | 25 |
| 144 | 15 |
| 145 | 8.5 |
| 146 | 7.5 |
| 147 | 11 |
| 148 | 38 |
| 149 | 56 |
| 150 | 19 |
| 151 | 35 |
| 152 | 120 |

TABLE 25-continued

Activity Data

| Example No. | HepG2 TAT Ki (nM) |
|---|---|
| 153 | 380 |
| 154 | 24 |
| 155 | 11 |
| 156 | 28 |
| 157 | 43 |
| 158 | 45 |
| 159 | 220 |
| 160 | 32 |
| 161 | 57 |
| 162 | 260 |
| 162a | 57 |
| 163 | 44 |
| 164 | 170 |
| 165 | 81 |
| 166 | 28 |
| 167 | 59 |
| 168 | 100 |
| 169 | 66 |
| 170 | 91 |
| 171 | 24 |
| 172 | 36 |

Example 3: Hep G2 TAT IC50

Glucocorticoid mediated activation of TAT occurs by transactivation of glucocorticoid response elements in the TAT promoter by glucocorticoid receptor/agonist complex. The following protocol describes an assay for measuring induction of TAT by dexamethasone in HepG2 cells (a human liver hepatocellular carcinoma cell line; ATCC, cat. HB-8065, UK).

TAT activity was measured as outlined in the literature by A. Ali et al., J. Med. Chem., 2004, 47, 2441-2452. Dexamethasone induced TAT production with an average $EC_{50}$ value (half-maximal effect) of 20 nM.

HepG2 cells were cultured using MEME media supplemented with 10% (v/v) foetal bovine serum, 2 mM L-glutamine, 1% (v/v) NEAA, and 1% (v/v) penstrep, at 37° C., 5%/95% (v/v) $CO_2$/air. The HepG2 cells were counted and adjusted to yield a density of $0.5 \times 10^6$ cells/mL in RPMI 1640 without phenol red, 10% (v/v) charcoal stripped FBS, 2 mM L-glutamine, and 1% (v/v) penstrep and seeded at 10,000 cells/well in 20 µL into a 384 well, sterile, tissue culture micro titre plates, and incubated at 37° C., 5% $CO_2$ for 24 hours.

Growth media was removed and replaced with assay media {RPMI 1640 without phenol red, 2 mM L-glutamine, 1% (v/v) penstrep+10 µM forskolin}. Test compounds were screened against a challenge of 100 nM dexamethasone. Compounds were diluted from a 10 mM stock via an Echo Acoustic liquid handler into 10 µL assay media to generate a 10-point half-log dilution curve. After the compound was dispensed, an additional 30 µL of assay media was added to give 2× the final compound concentration: this resulted in a final assay compound concentration that ranged from 30 to 0.001 µM in 0.3% (v/v) dimethylsulfoxide.

100 nM of dexamethasone was added to the test compounds which were then subsequently incubated for 18-22 hours at 37° C., 5/95 (v/v) $CO_2$/air to allow optimal TAT induction.

HepG2 cells were then lysed with 8 µL of cell lysis buffer containing a protease inhibitor cocktail for 15 minutes at 25° C. 39 µL of substrate mixture was then added, containing 5.4 mM tyrosine sodium salt, 10.8 mM alpha ketoglutarate and 0.06 mM pyridoxal 5' phosphate in 0.1 M potassium phosphate buffer (pH 7.5). After a 2-hour incubation at 37° C. the reaction was terminated by the addition of 8 µL of 5 M aqueous potassium hydroxide solution, and the plates incubated for a further 30 minutes at 37° C.

$IC_{50}$ values were calculated by plotting % inhibition (normalised to 100 nM dexamethasone TAT stimulation) v. [compound] and fitting the data to a 4-parameter logistic equation.

TABLE 26

Activity Data

| Example | HepG2 TAT IC50 (nM) |
|---|---|
| 173 | 2750 |
| 174 | 191 |
| 175 | 1245 |
| 176 | 841 |
| 177 | 2455 |
| 178 | 3428 |
| 179 | 2018 |
| 180 | 2089 |
| 181 | 1660 |
| 182 | 3589 |
| 183 | 2661 |
| 184 | 1161 |
| 185 | 1216 |
| 186 | 2399 |
| 187 | 1660 |
| 188 | 1318 |
| 189 | 1660 |
| 190 | 1072 |
| 191 | 4027 |
| 192 | 3162 |
| 193 | 2786 |
| 194 | 443 |
| 195 | 253 |
| 196 | 284 |
| 197 | 1000 |
| 198 | 1279 |
| 199 | 1318 |
| 200 | 4012 |
| 201 | 3846 |
| 202 | 1035 |
| 203 | 9333 |
| 204 | 3846 |
| 205 | 2884 |
| 206 | 6119 |
| 207 | 933 |
| 209 | 3126 |
| 210 | 2541 |
| 211 | 589 |
| 212 | 1445 |
| 213 | 2239 |
| 214 | 2754 |
| 215 | 3981 |

Although the foregoing invention has been described in some detail by way of illustration and Examples for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A compound of Formula J:

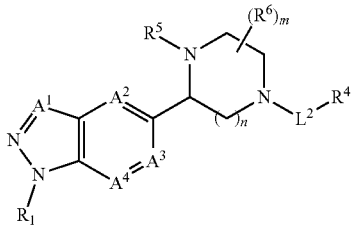

or a pharmaceutically acceptable salt thereof, wherein
R$^1$ is heterocycloalkyl having 3 to 12 ring members and 1 to 4 heteroatoms each N, O or S, or heteroaryl having 5 to 10 ring members and 1 to 5 heteroatoms each N, O or S, each independently substituted with 0 to 5 R$^{1a}$ groups;
each R$^{1a}$ is independently C$_{1-6}$ alkyl, C$_{1-6}$ alkoxy, C$_{1-6}$ alkoxyalkyl, C$_{1-6}$ hydroxyalkyl, halogen, C$_{1-6}$ haloalkyl, C$_{1-6}$ haloalkoxy, —OH, oxo, —CN, —C(O)N(R$^{1b}$)(R$^{1c}$), C$_{3-10}$ cycloalkyl, or heterocycloalkyl having 3 to 12 ring members and 1 to 4 heteroatoms each N, O or S;
each R$^{1b}$ and R$^{1c}$ is independently hydrogen, C$_{1-6}$ alkyl or a 3 to 8 membered heterocycloalkyl having 1 to 3 heteroatoms each independently N, O or S;
A$^1$, A$^2$, A$^3$ and A$^4$ are each independently =CR$^2$— or =N—;
each R$^2$ is independently hydrogen, C$_{1-6}$ alkyl, C$_{1-6}$ alkoxy, C$_{2-6}$ alkoxyalkyl, halogen, C$_{1-6}$ haloalkyl, C$_{1-6}$ haloalkoxy, hydroxy or —CN;
L$^2$ is —C(O)—, —C(O)O—, —C(O)N(R$^3$)—, —S(O)$_2$— or —S(O)$_2$N(R$^3$)—;
R$^3$ is hydrogen, or C$_{1-6}$ alkyl;
R$^4$ is C$_{1-6}$ alkyl, C$_{2-6}$ alkenyl, C$_{2-6}$ alkynyl, C$_{2-6}$ alkoxyalkyl, C$_{1-6}$ hydroxyalkyl, C$_{1-6}$ haloalkyl, C$_{3-8}$ cycloalkyl, C$_{1-6}$ alkyl-C$_{3-8}$ cycloalkyl, heterocycloalkyl, C$_{1-6}$ alkyl-heterocycloalkyl, C$_{6-12}$ aryl, C$_{1-6}$ alkyl-C$_{6-12}$ aryl, —O—C$_{6-12}$ aryl, heteroaryl, or C$_{1-6}$ alkyl-heteroaryl,
wherein each heterocycloalkyl independently has 3 to 12 ring members and 1 to 3 heteroatoms each independently N, O or S,
wherein each heteroaryl independently has 5 to 10 ring members and 1 to 4 heteroatoms each independently N, O or S, and
wherein the cycloalkyl, heterocycloalkyl, aryl and heteroaryl are each independently substituted with 0 to 5 R$^{4a}$ groups;
alternatively, R$^3$ and R$^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 C$_{1-6}$ alkyl groups;
each R$^{4a}$ is independently C$_{1-6}$ alkyl, C$_{2-6}$ alkenyl, C$_{2-6}$ alkynyl, C$_{1-6}$ alkoxy, C$_{2-6}$ alkoxyalkyl, C$_{1-6}$ hydroxyalkyl, halogen, C$_{1-6}$ haloalkyl, C$_{1-6}$ haloalkoxy, —CN, —OH, oxo, —C(O)R$^{4b}$, —C(O)OR$^{4b}$, —OC(O)R$^{4b}$, —OC(O)OR$^{4b}$, —C(O)N(R$^{4b}$)(R$^{4c}$), —N(R$^{4b}$)C(O)R$^{4c}$, —OC(O)N(R$^{4b}$)(R$^{4c}$), —N(R$^{4b}$)C(O)OR$^{4c}$, —S(O)$_2$R$^{4b}$, —S(O)$_2$N(R$^{4b}$)(R$^{4c}$), —N(R$^{4b}$)S(O)$_2$R$^{4c}$, C$_{3-8}$ cycloalkyl, C$_{1-6}$ alkyl-C$_{3-8}$ cycloalkyl, heterocycloalkyl, C$_{1-6}$ alkyl-heterocycloalkyl, C$_{6-12}$ aryl, C$_{1-6}$ alkyl-C$_{6-12}$ aryl, —O—C$_{6-12}$ aryl, heteroaryl, or C$_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 C$_{1-6}$ alkyl groups;
each R$^{4b}$ and R$^{4c}$ is hydrogen or C$_{1-6}$ alkyl;
R$^5$ is C$_{1-6}$ alkyl, C$_{2-6}$ alkenyl, C$_{2-6}$ alkynyl, C$_{2-6}$ alkoxyalkyl, C$_{1-6}$ hydroxyalkyl, C$_{1-6}$ haloalkyl, C$_{1-6}$ alkyl-OR$^{5a}$, —C(O)R$^{5a}$, C$_{1-6}$ alkyl-C(O)R$^{5a}$, —C(O)OR$^{5a}$, —C(O)N(R$^{5a}$)(R$^{5b}$), —S(O)$_2$R$^{5a}$, —S(O)$_2$N(R$^{5a}$)(R$^{5b}$), C$_{3-8}$ cycloalkyl, C$_{1-6}$ alkyl-C$_{3-8}$ cycloalkyl, heterocycloalkyl, C$_{1-6}$ alkyl-heterocycloalkyl, C$_{6-12}$ aryl, C$_{1-6}$ alkyl-C$_{6-12}$ aryl, heteroaryl, or C$_{1-6}$ alkyl-heteroaryl,
wherein each heterocycloalkyl independently has 3 to 12 ring members and 1 to 3 heteroatoms each independently N, O or S,
wherein each heteroaryl independently has 5 to 10 ring members and 1 to 4 heteroatoms each independently N, O or S, and
wherein each cycloalkyl, heterocycloalkyl, aryl and heteroaryl is independently substituted with 0 to 4 R$^{5c}$ groups;
each R$^{5a}$ and R$^{5b}$ is independently hydrogen, C$_{1-6}$ alkyl, C$_{2-6}$ alkenyl, C$_{2-6}$ alkynyl, C$_{2-6}$ alkoxyalkyl, hydroxy, C$_{1-6}$ hydroxyalkyl, C$_{1-6}$ haloalkyl, C$_{1-6}$ haloalkoxy, C$_{3-8}$ cycloalkyl, C$_{1-6}$ alkyl-C$_{3-8}$ cycloalkyl, heterocycloalkyl, C$_{1-6}$ alkyl-heterocycloalkyl, C$_{6-12}$ aryl, C$_{1-6}$ alkyl-C$_{6-12}$ aryl, heteroaryl, or C$_{1-6}$ alkyl-heteroaryl,
wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 R$^{5d}$ groups;
alternatively, R$^{5a}$ and R$^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 C$_{1-6}$ alkyl groups;
each R$^{5c}$ is independently C$_{1-6}$ alkyl, C$_{2-6}$ alkenyl, C$_{2-6}$ alkynyl, C$_{1-6}$ alkoxy, C$_{2-6}$ alkoxyalkyl, C$_{1-6}$ hydroxyalkyl, halogen, C$_{1-6}$ haloalkyl, C$_{1-6}$ haloalkoxy, —CN, oxo, —OH, —C(O)R$^{5c1}$, —C(O)OR$^{5c1}$, —OC(O)R$^{5c1}$, —OC(O)OR$^{5c1}$, —C(O)N(R$^{5c1}$)(R$^{5c2}$), —N(R$^{5c1}$)C(O)R$^{5c2}$, —OC(O)N(R$^{5c1}$)(R$^{5c2}$), —N(R$^{5c1}$)C(O)OR$^{5c2}$, —S(O)$_2$R$^{5c1}$, —S(O)$_2$N(R$^{5c1}$)(R$^{5c2}$), —N(R$^{5c1}$)S(O)$_2$R$^{5c2}$, C$_{3-8}$ cycloalkyl, C$_{1-6}$ alkyl-C$_{3-8}$ cycloalkyl, heterocycloalkyl, C$_{1-6}$ alkyl-heterocycloalkyl, C$_{6-12}$ aryl, C$_{1-6}$ alkyl-C$_{6-12}$ aryl, heteroaryl, or C$_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 C$_{1-6}$ alkyl groups;
each R$^{5c1}$ and R$^{5c2}$ is independently hydrogen, C$_{1-6}$ alkyl, C$_{2-6}$ alkenyl, C$_{2-6}$ alkynyl, C$_{2-6}$ alkoxyalkyl, C$_{1-6}$ hydroxyalkyl, C$_{1-6}$ haloalkyl, C$_{3-8}$ cycloalkyl, C$_{1-6}$ alkyl-C$_{3-8}$ cycloalkyl, heterocycloalkyl, C$_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently hydrogen, $C_{1-6}$ alkyl, halogen, $C_{1-6}$ haloalkyl, or oxo;

subscript m is 0, 1, 2, 3, 4, or 5; and subscript n is 1 or 2.

2. The compound of claim 1, or a pharmaceutically acceptable salt thereof, wherein $R^1$ is

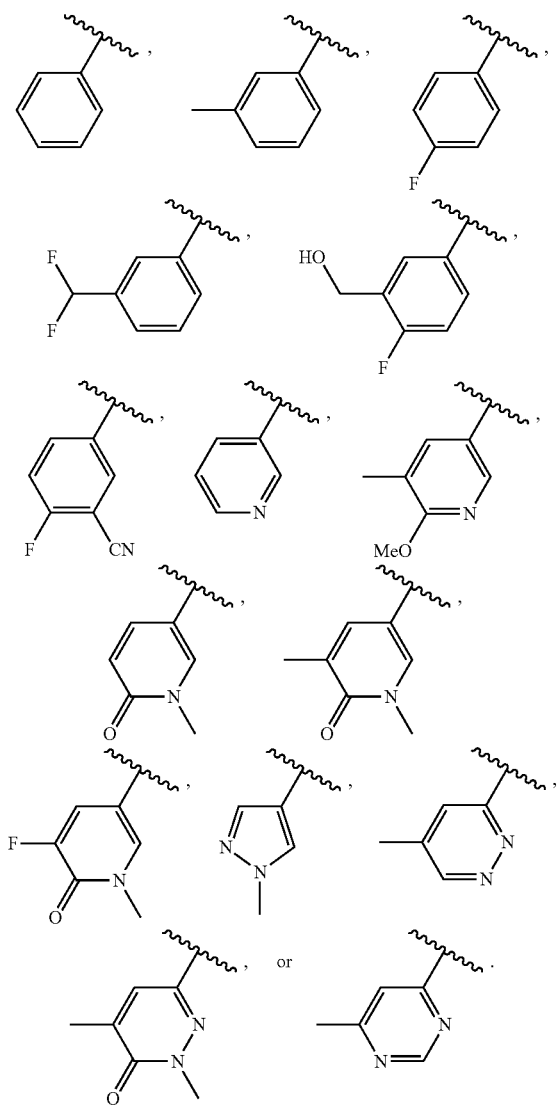

3. The compound of claim 1, or a pharmaceutically acceptable salt thereof, wherein $A^1$, $A^2$ and $A^4$ are each =CH—; and $A^3$ is =C(Me)-, =C(OMe)-, =C(F)—, =C(Cl)—, or =C(CF$_3$)—.

4. The compound of claim 1, or a pharmaceutically acceptable salt thereof, wherein $A^1$, $A^2$ and $A^4$ are each =CH—; and $A^3$ is =C(Me)-.

5. The compound of claim 1, or a pharmaceutically acceptable salt thereof, wherein $L^2$ is —C(O)—, —S(O)$_2$— or —S(O)$_2$N(Me)-.

6. The compound of claim 1, or a pharmaceutically acceptable salt thereof, wherein $L^2$ is —S(O)$_2$—.

7. The compound of claim 1, or a pharmaceutically acceptable salt thereof, having the structure of Formula Ic:

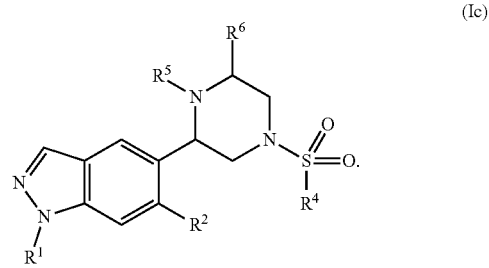

(Ic)

8. The compound of claim 1, or a pharmaceutically acceptable salt thereof, wherein $R^4$ is pyridine, pyrazole, thiazole, or triazole, each substituted with 0 to 2 $R^{4a}$ groups; and each $R^{4a}$ is independently methyl, ethyl, n-propyl, isopropyl, methoxy, methoxyethyl, fluoro, —CHF$_2$, —CF$_3$, —CH$_2$CHF$_2$, —CH$_2$CF$_3$, —CN, or tetrahydropyran.

9. The compound of claim 1, or a pharmaceutically acceptable salt thereof, wherein $R^4$ is methyl, n-propyl, iso-butyl, —CH(OH)CH$_3$, methoxyethyl, isopropoxyethyl, CH$_2$CF$_3$,

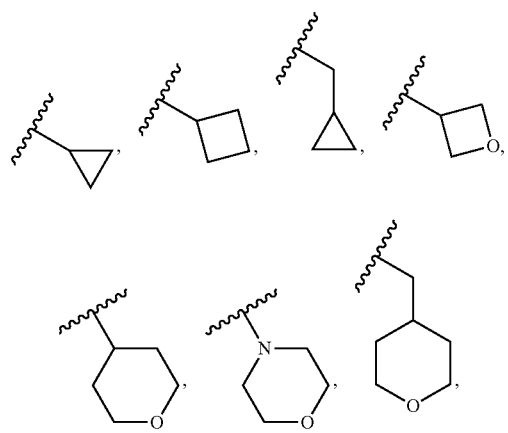

511
-continued
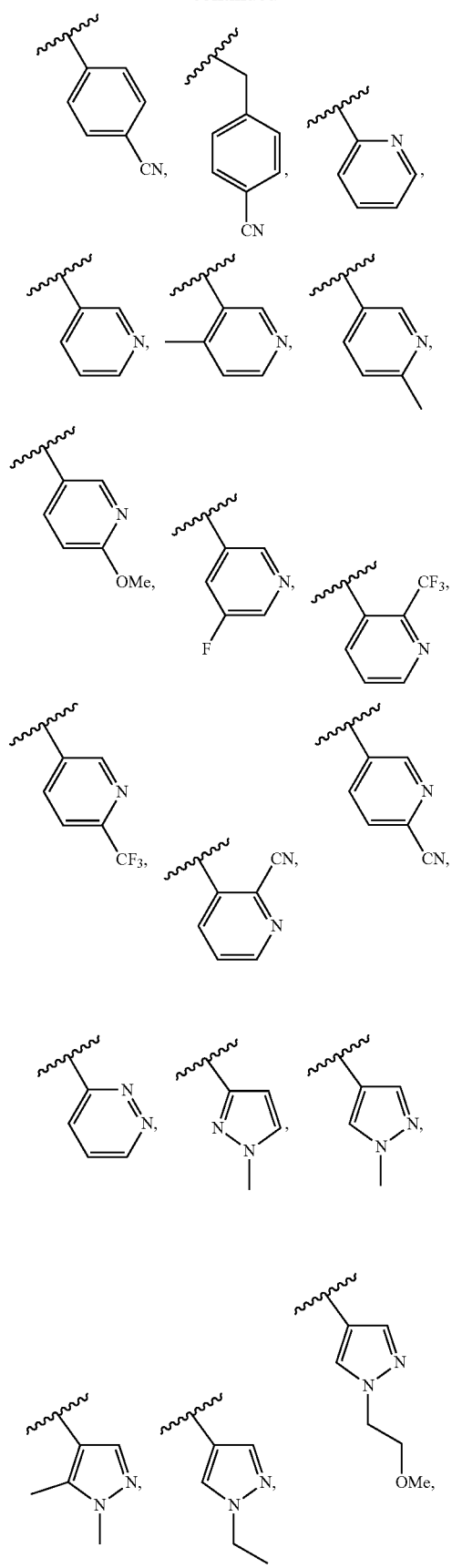
512
-continued
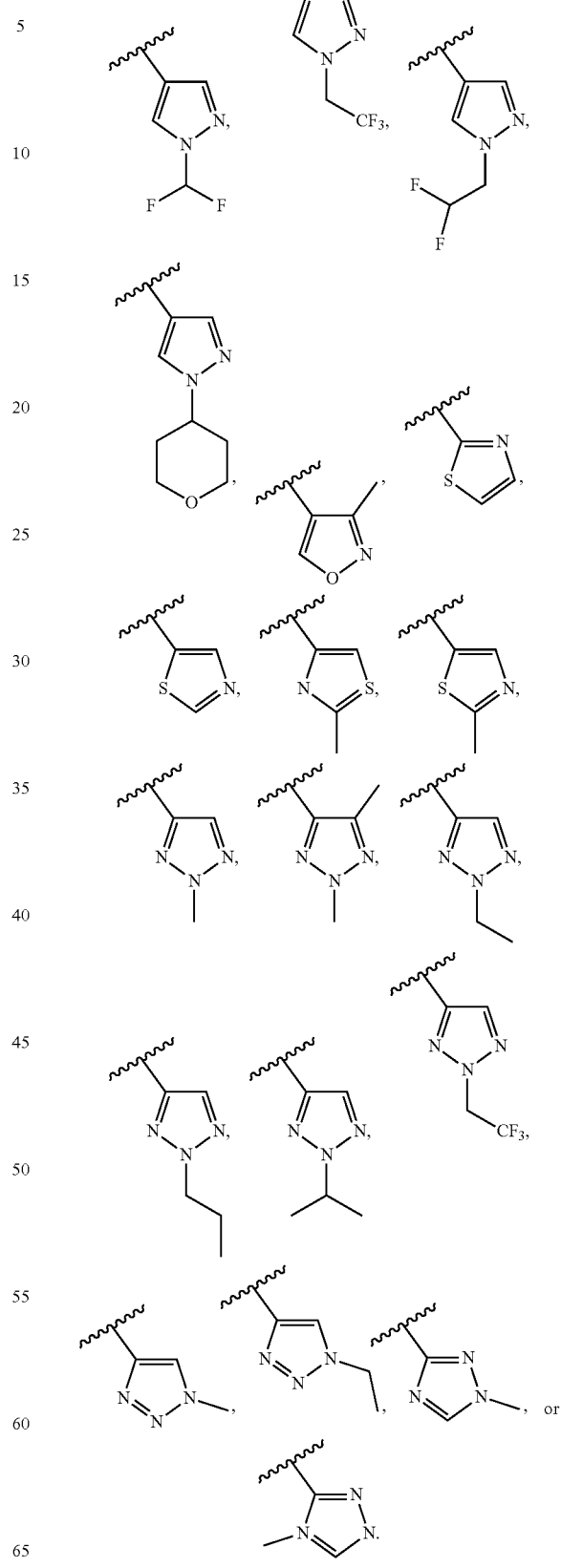

10. The compound of claim 1, or a pharmaceutically acceptable salt thereof, wherein R⁵ is ethyl, iso-propyl, iso-butyl,

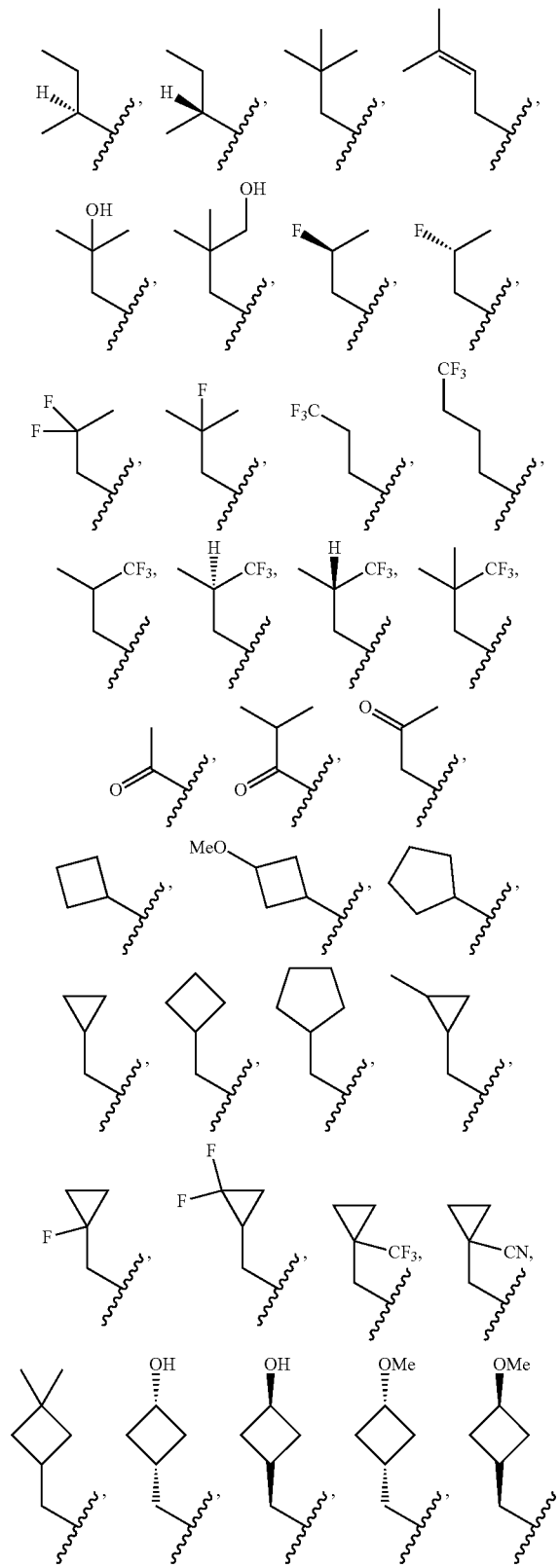

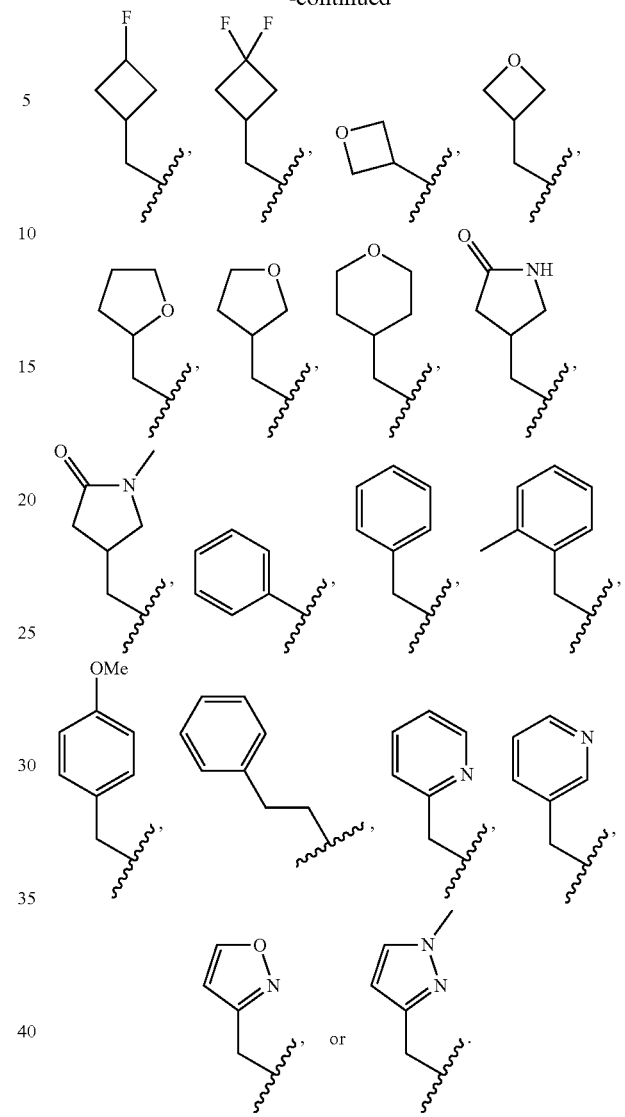

11. The compound of claim 1, or a pharmaceutically acceptable salt thereof, wherein R¹ is

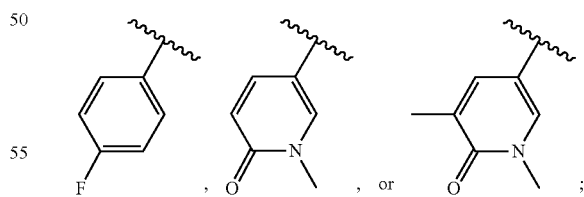

A¹, A² and A⁴ are each =CH—;
A³ is =C(Me)-;
L² is —S(O)₂—;
R⁴ is pyridine, pyrazole, thiazole, or triazole, each substituted with 0 to 2 R⁴ᵃ groups;
each R⁴ᵃ is independently methyl, ethyl, n-propyl, iso-propyl, methoxy, methoxyethyl, fluoro, —CHF₂, —CF₃, —CH₂CHF₂, —CH₂CF₃, —CN, or tetrahydropyran;

$R^5$ is $C_{1-6}$ alkyl, $C_{1-6}$ haloalkyl, or $C_{1-2}$ alkyl-$C_{3-6}$ cycloalkyl, wherein each cycloalkyl is independently substituted with 0 to 2 $R^{5c}$ groups;

each $R^{5c}$ is independently $C_{1-3}$ alkyl, $C_{1-3}$ alkoxy, halogen, $C_{1-3}$ haloalkyl, —CN, oxo or —OH;

subscript m is 0; and subscript n is 1.

12. The compound of claim 1, or a pharmaceutically acceptable salt thereof, wherein $R^1$ is

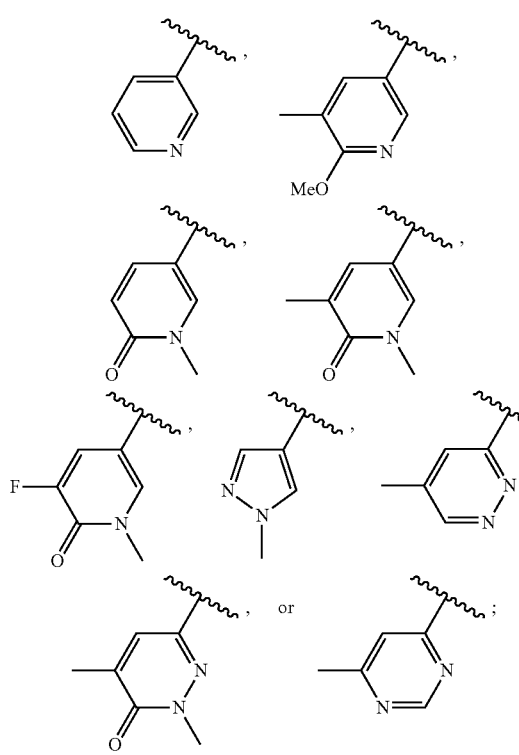

$A^1$, $A^2$ and $A^4$ are each =CH—;

$A^3$ is =C(Me)-, =C(OMe)-, =C(F)—, =C(Cl)—, or =C(CF$_3$)—;

$L^2$ is —C(O)—, —S(O)$_2$— or —S(O)$_2$N(Me)-;

$R^4$ is methyl, n-propyl, iso-butyl, —CH(OH)CH$_3$, methoxyethyl, isopropoxyethyl, CH$_2$CF$_3$,

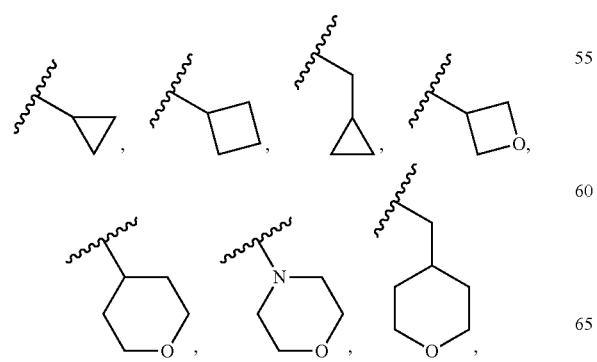

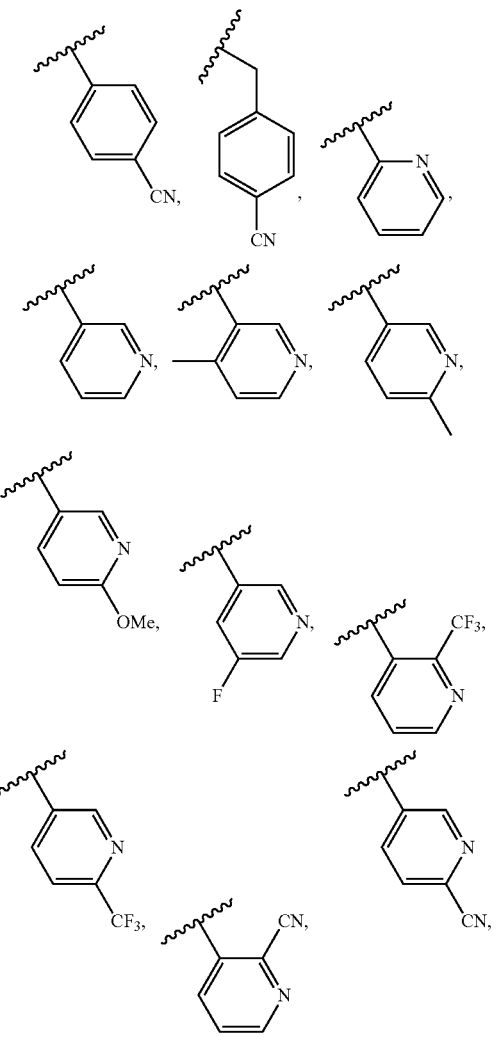

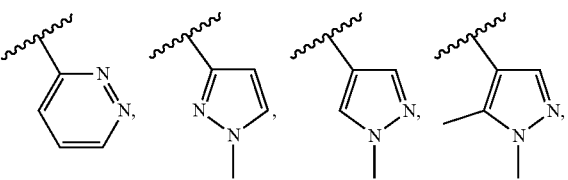

517
-continued
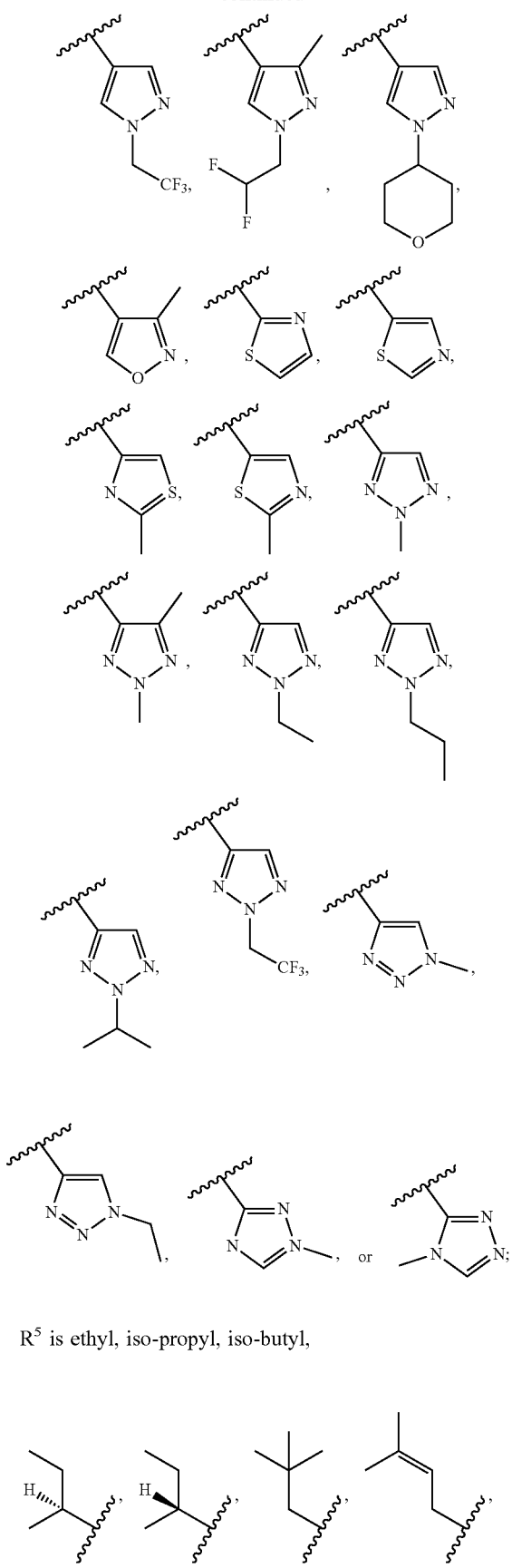
R⁵ is ethyl, iso-propyl, iso-butyl,
518
-continued
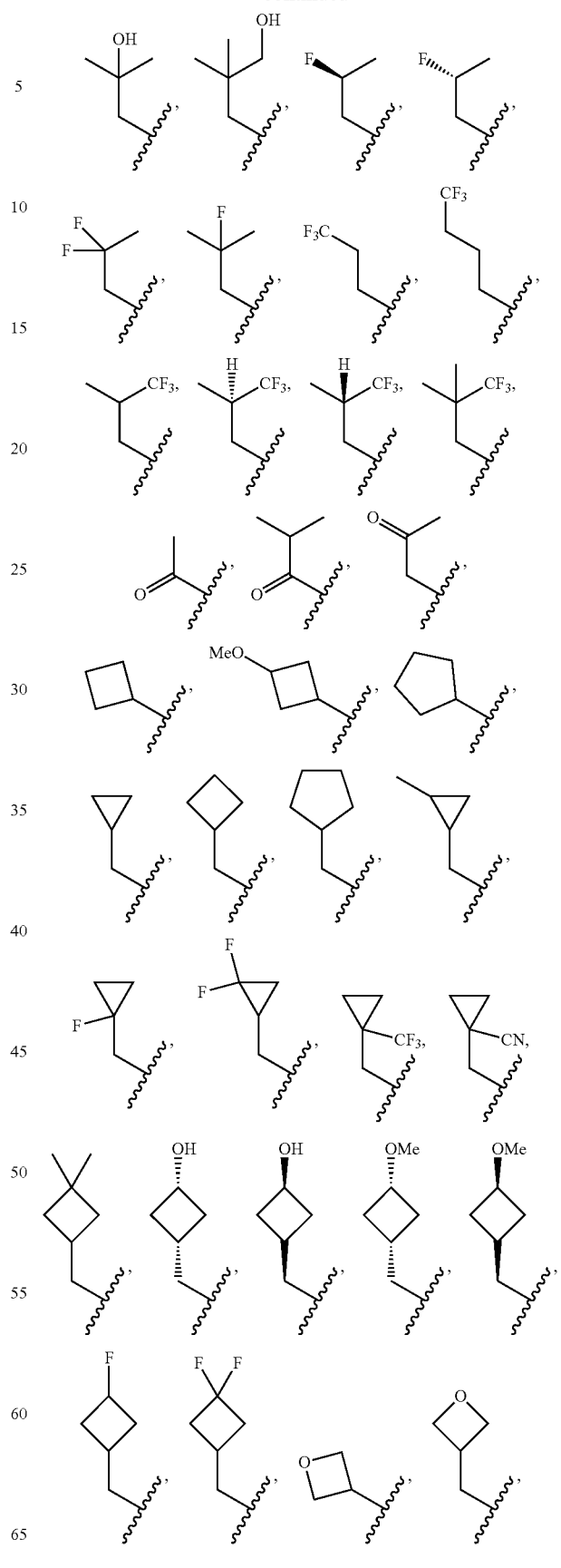

519
-continued
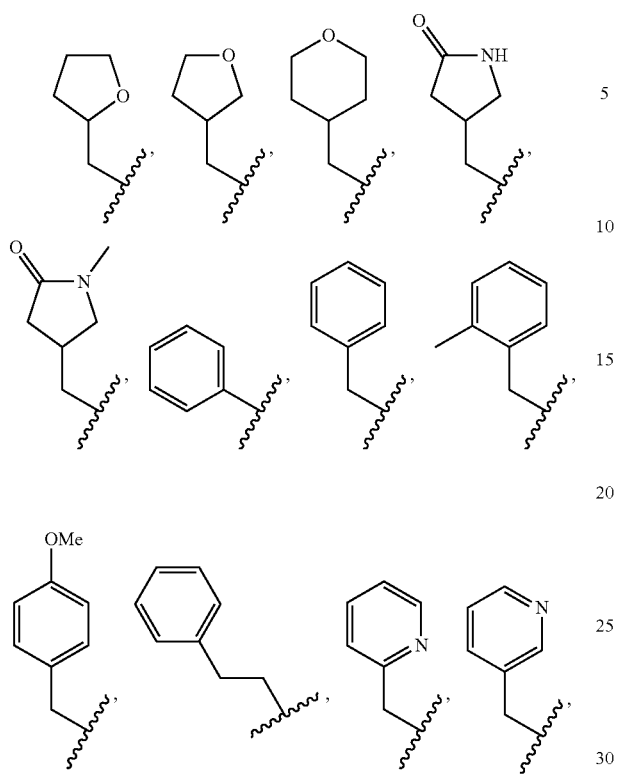
$R^6$ is hydrogen, methyl, or oxo; and
subscript m is 0, 1 or 2.
13. The compound of claim 1, or a pharmaceutically acceptable salt thereof, is selected from the group consisting of:
520
-continued
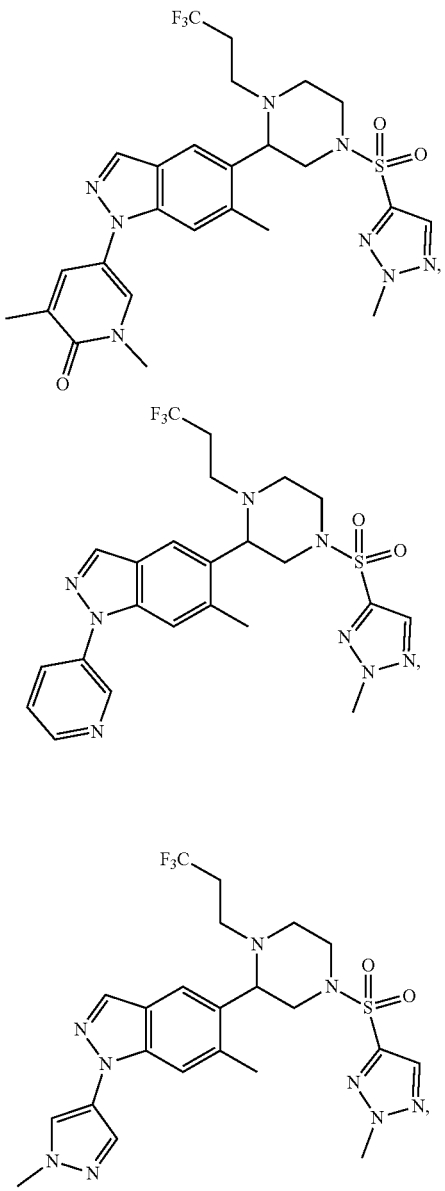
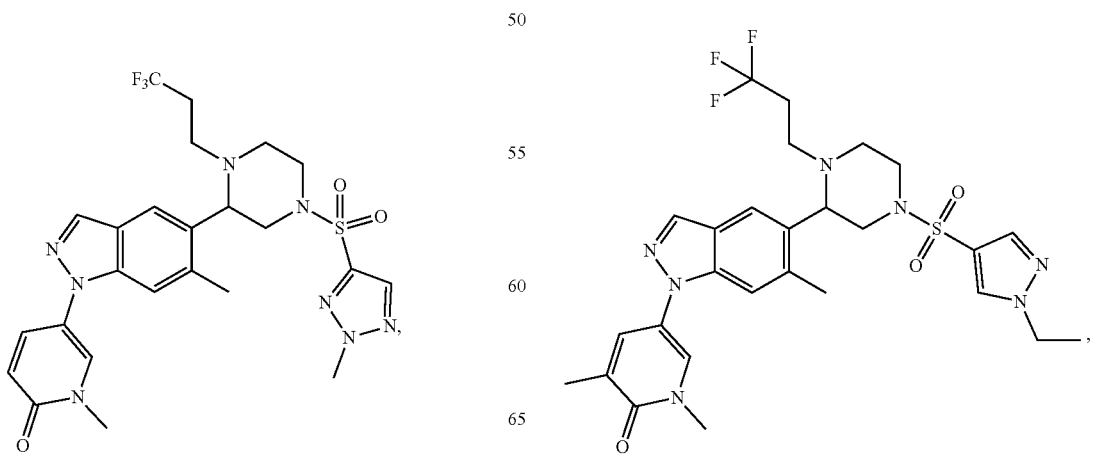

521
-continued
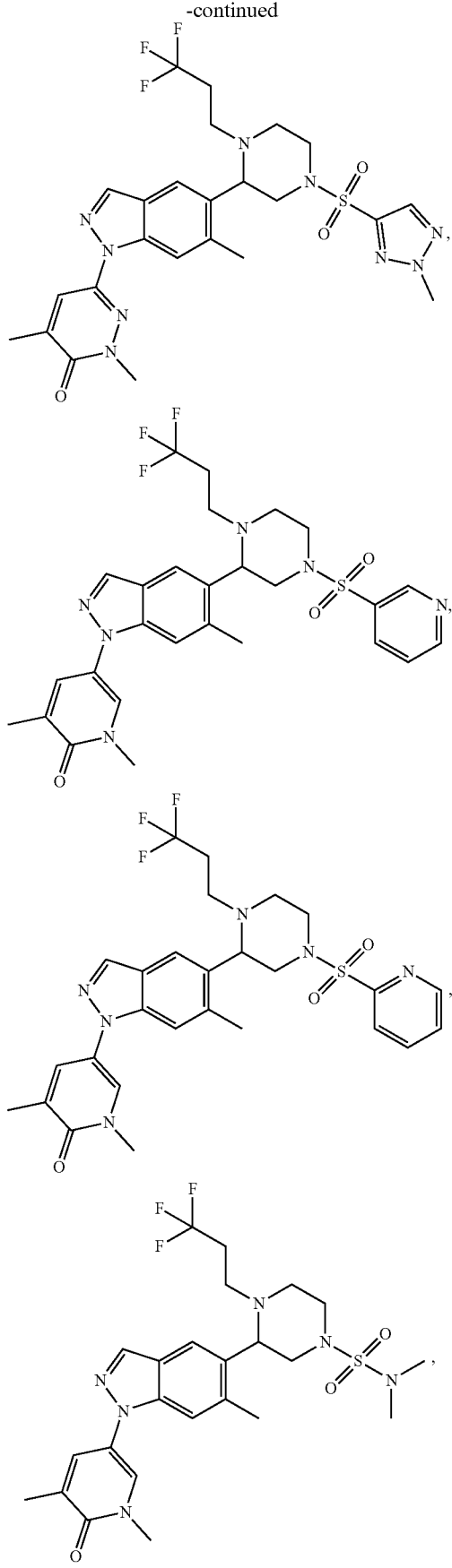
522
-continued
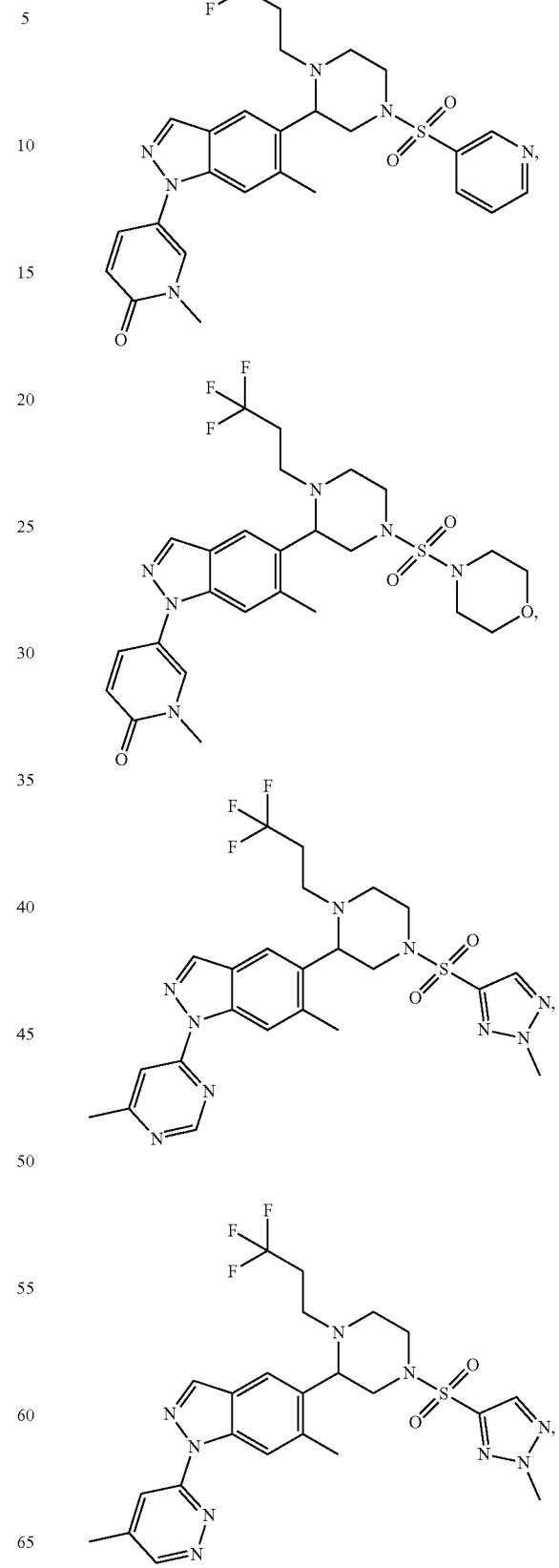

523
-continued
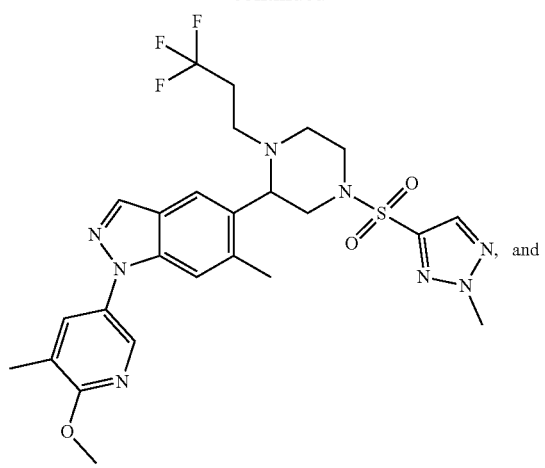
, and
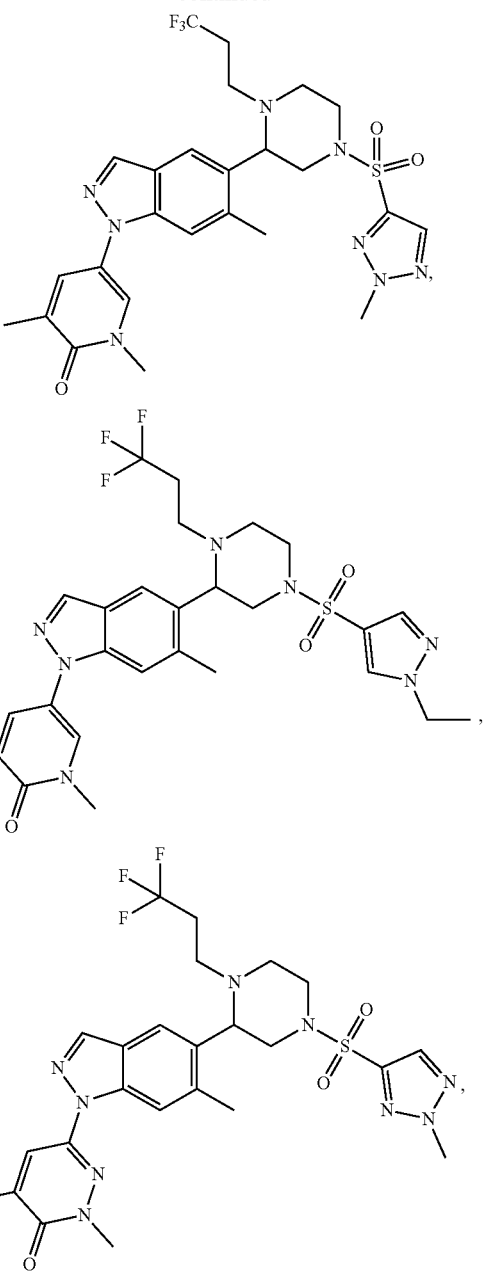
14. The compound of claim 1, or a pharmaceutically acceptable salt thereof, is the compound having the structure:
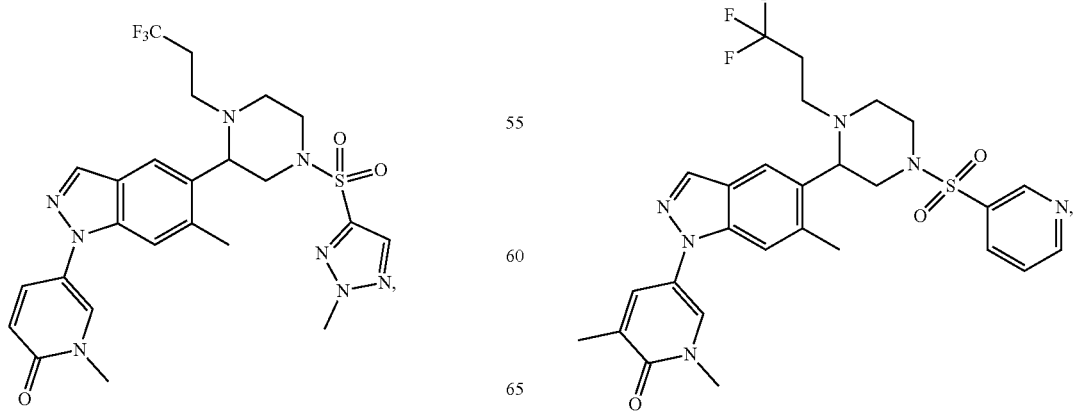

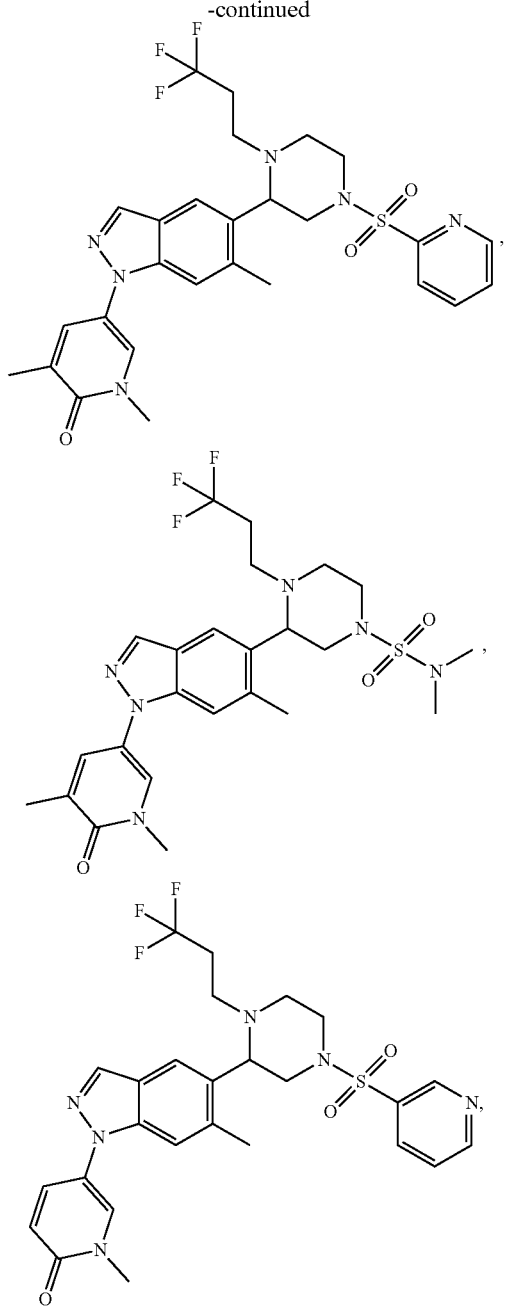
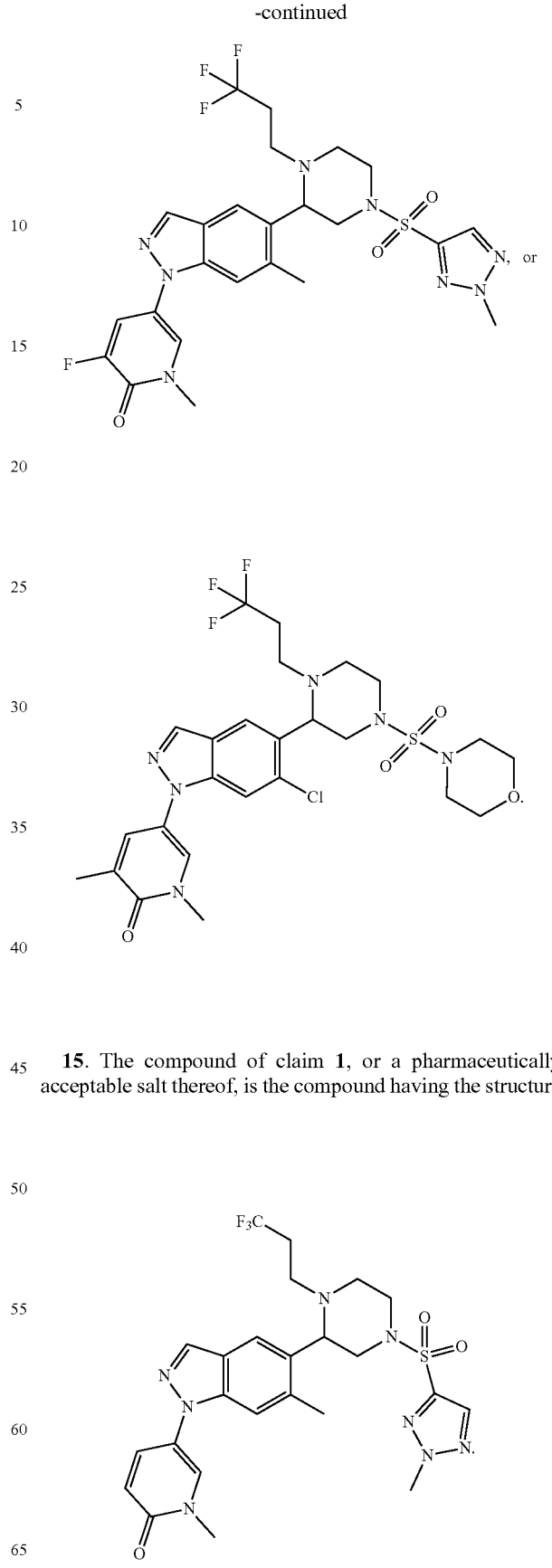
15. The compound of claim 1, or a pharmaceutically acceptable salt thereof, is the compound having the structure

16. The compound of claim 1, or a pharmaceutically acceptable salt thereof, is the compound having the structure

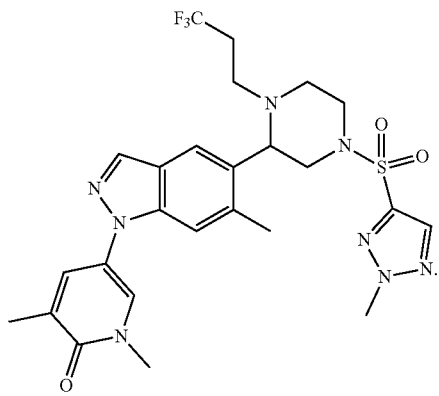 [SMILES: Cc1cc2c(cnn2-c2cc(C)c(=O)n(C)c2)cc1C1CN(S(=O)(=O)c2cnn(C)n2)CCN1CCC(F)(F)F]

17. The compound of claim 1, or a pharmaceutically acceptable salt thereof, is the compound having the structure

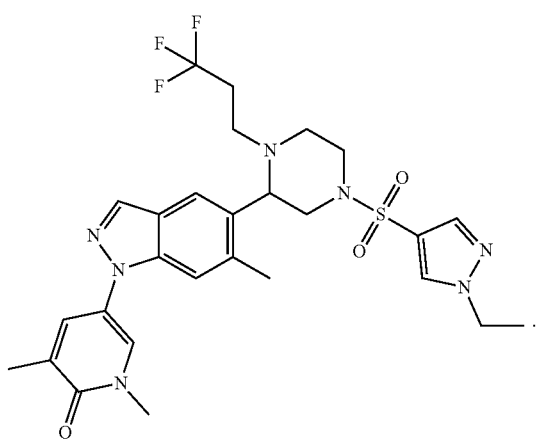 [SMILES: CCn1cc(S(=O)(=O)N2CCN(CCC(F)(F)F)C(c3cc4cnn(-c5cc(C)c(=O)n(C)c5)c4cc3C)C2)cn1]

18. The compound of claim 1, or a pharmaceutically acceptable salt thereof, is the compound having the structure

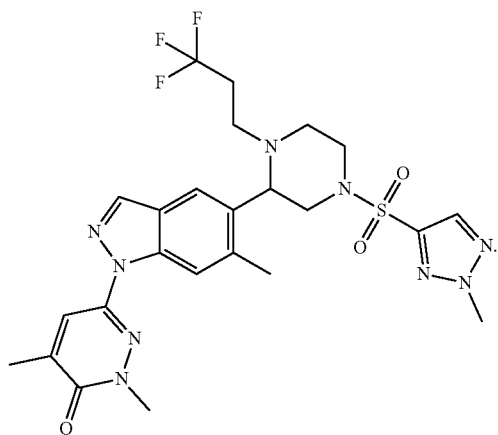 [SMILES: Cc1cc2c(cnn2-c2cc(C)c(=O)n(C)n2)cc1C1CN(S(=O)(=O)c2cnn(C)n2)CCN1CCC(F)(F)F]

19. The compound of claim 1, or a pharmaceutically acceptable salt thereof, is the compound having the structure

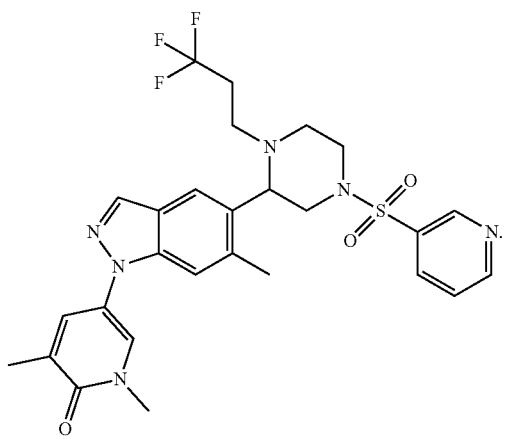 [SMILES: Cc1cc2c(cnn2-c2cc(C)c(=O)n(C)c2)cc1C1CN(S(=O)(=O)c2cccnc2)CCN1CCC(F)(F)F]

20. The compound of claim 1, or a pharmaceutically acceptable salt thereof, is the compound having the structure

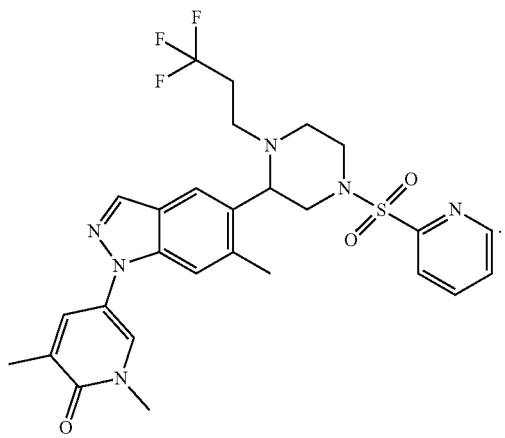 [SMILES: Cc1cc2c(cnn2-c2cc(C)c(=O)n(C)c2)cc1C1CN(S(=O)(=O)c2ccccn2)CCN1CCC(F)(F)F]

21. The compound of claim 1, or a pharmaceutically acceptable salt thereof, is the compound having the structure

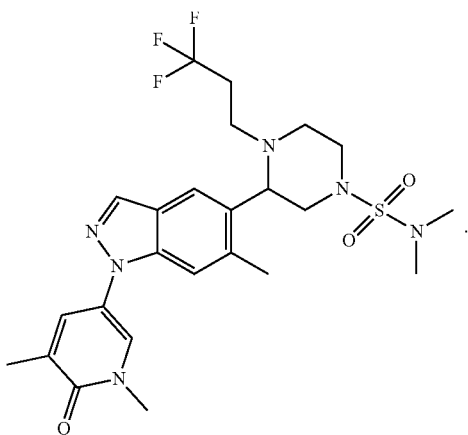

22. The compound of claim 1, or a pharmaceutically acceptable salt thereof, is the compound having the structure

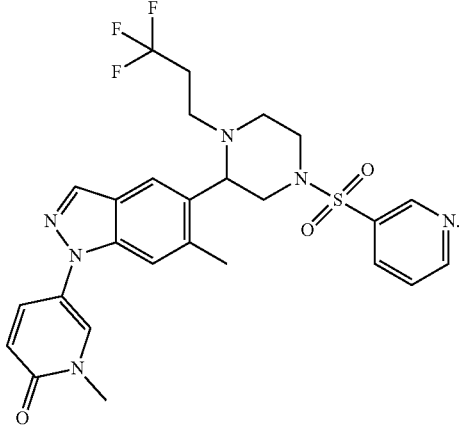 [SMILES: Cc1cc2c(cnn2-c2ccc(=O)n(C)c2)cc1C1CN(S(=O)(=O)c2cccnc2)CCN1CCC(F)(F)F]

23. The compound of claim 1, or a pharmaceutically acceptable salt thereof, is the compound having the structure

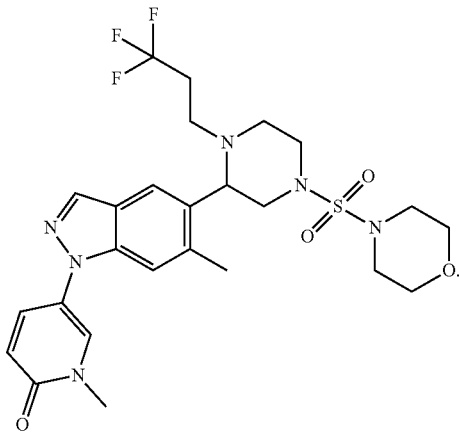 [SMILES: Cc1cc2c(cnn2-c2ccc(=O)n(C)c2)cc1C1CN(S(=O)(=O)N2CCOCC2)CCN1CCC(F)(F)F]

24. The compound of claim 1, or a pharmaceutically acceptable salt thereof, is the compound having the structure

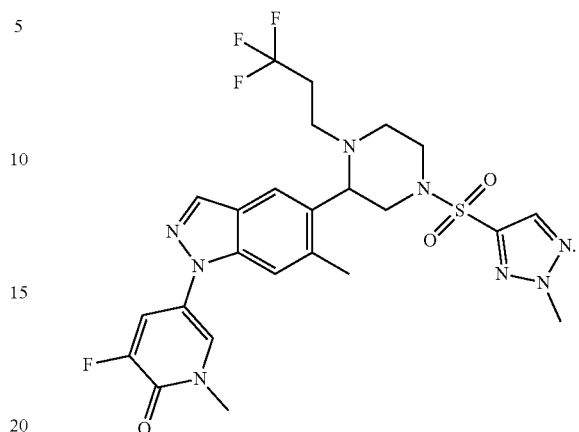

25. The compound of claim 1, or a pharmaceutically acceptable salt thereof, is the compound having the structure

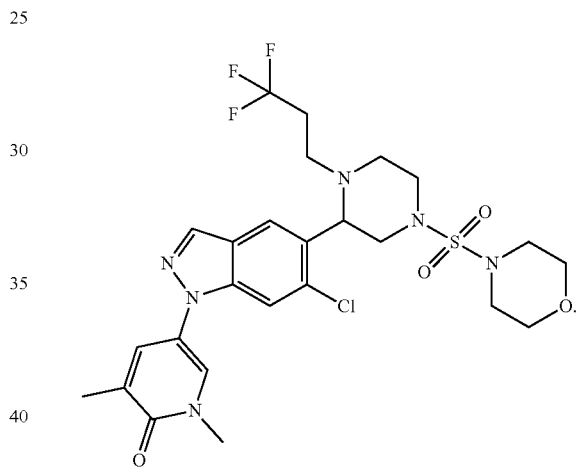

26. A pharmaceutical composition comprising a compound of claim 1, or a pharmaceutically acceptable salt thereof, and a pharmaceutically acceptable excipient.

27. A method of treating a disorder or condition through modulating a glucocorticoid receptor, the method comprising administering to a subject in need of such treatment, a therapeutically effective amount of a compound of claim 1, or a pharmaceutically acceptable salt thereof, thereby treating the disorder or condition.

28. A method of treating a disorder or condition through antagonizing a glucocorticoid receptor, the method comprising administering to a subject in need of such treatment, an effective amount of the compound of claim 1, or a pharmaceutically acceptable salt thereof.

* * * * *